US009387232B2

(12) United States Patent
Pedersen et al.

(10) Patent No.: US 9,387,232 B2
(45) Date of Patent: *Jul. 12, 2016

(54) SORCS1 FOR THE TREATMENT OF OBESITY

(75) Inventors: Karen-Marie Pedersen, Tjele (DK); Anders Nykjaer, Risskov (DK); Mads Fuglsang Kjolby, Risskov (DK)

(73) Assignee: Aarhus Universitet (DK)

( * ) Notice: Subject to any disclaimer, the term of this patent is extended or adjusted under 35 U.S.C. 154(b) by 792 days.

This patent is subject to a terminal disclaimer.

(21) Appl. No.: 13/327,234

(22) Filed: Dec. 15, 2011

(65) Prior Publication Data

US 2012/0207721 A1 Aug. 16, 2012

Related U.S. Application Data

(63) Continuation-in-part of application No. 13/377,277, filed as application No. PCT/DK2010/050131 on Jun. 10, 2010.

(60) Provisional application No. 61/213,455, filed on Jun. 10, 2009.

(30) Foreign Application Priority Data

Jun. 10, 2009 (DK) .................................. 2009 70024

(51) Int. Cl.
| A61K 38/17 | (2006.01) |
| A61K 38/00 | (2006.01) |
| C07K 14/705 | (2006.01) |
| A01K 67/027 | (2006.01) |
| A61K 48/00 | (2006.01) |

(52) U.S. Cl.
CPC ........... *A61K 38/177* (2013.01); *A01K 67/0276* (2013.01); *A61K 48/005* (2013.01); *C07K 14/705* (2013.01); *A01K 2217/056* (2013.01); *A01K 2227/105* (2013.01); *A01K 2267/0362* (2013.01); *A61K 38/00* (2013.01); *A61K 48/00* (2013.01); *C12N 2799/022* (2013.01); *C12N 2799/025* (2013.01)

(58) Field of Classification Search
None
See application file for complete search history.

(56) References Cited

FOREIGN PATENT DOCUMENTS

| WO | 03/027223 | 4/2003 |
| WO | 2004/022719 | 3/2004 |
| WO | WO 2004022719 A2 * | 3/2004 |
| WO | 2006/042002 | 4/2006 |
| WO | 2007/141346 | 12/2007 |
| WO | 2010/069331 | 6/2010 |

OTHER PUBLICATIONS

Kolchanov, 1988, Journal of Molecular Evolution, vol. 27, pp. 154-162.*
Pasquo, 2012, PLoS ONE, vol. 7, Issue 2, e32555.*
Bork, 2000, Genome Research 10:398-400.*
Bork et al., 1996, Trends in Genetics 12:425-427.*
Andersen, O.M., et al. "Neuronal sorting protein-related receptor SorLA/LR11 regulates processing of the amyloid precursor protein". 2005, Proc. Natl. Acad. Sci. USA. 102(38) pp. 13461-13466.
Champe, P.C. and Harvey, R.A. "Diabetes Mellitus". 2005, Biochemistry 3rd Chapter 25.
Clee, S.M. , et al. "Positional of SorCS1, a type 2 diabetes quantitative trait locus" 2006, Nature genetics 6 pp. 688-693.
Database UniProt (Online) Dec. 13, 2002, "SORC1_HUMAN" (XP-002564765)—Database accesion No. Q8WY21 the whole document.
FASTA alignment display.
Goodarzi, M.O., et al., "SorCS1: A novel human type 2 diabetes susceptibility gene suggested by the mouse" 2007, Diabetes 56(7) pp. 1922-1929.
Graham, I.E. and Kahn, B.B. "Tissue-specific alterations of glucose transport and molecular mechanisms of intertissue communication in obesity and type 2 diabetes". 2007, Horm. Metab. Res. 39 pp. 717-721.
Granhall et al; High-resolution quantitative trait locus analysis reveals multiple diabetes susceptibility loci mapped to intervals < 800kb in the species-conserved Niddm1: of the GK rat Genetics 2006, vol. 174, No. 3. pp. 1565-1572.
Guerra, C., et al. "Brown adipose tissue-specific insulin receptor knockout shows diabetic phenotype without insulin resistance". 2001, J. Clin. Invest. 108(8) pp. 1205-1213.
Guido Hermey at al; "Characterization of SorCS1, an Alternatively Spliced Receptor with Completely Different Cytoplasmic, Domains that Mediate Different Trafficking in Cells". Journal of Biological Chemistry, vol. 278, No. 9, Issue of Feb. 28. 2003 pp. 7390-7396, 2003 (XP-002976994).
Herman, M.A. and Kahn. B.B. "Glucose transport and sensing in them maintenance of glucose homeostasis and metabolic harmony". 2006, J. Cli. Invest. 116 pp. 1767-1775.
Hermey G et al. "Characterization of SorCS1, an alternatively spliced receptor with completely different cytoplasmic domains that mediate different trafficking in cells". 2003, J. Biol.Chem. 278 pp. 7390-7396.
Hermey, G., and Schaller, H.C. "Alternative splicing of murine SorCS leads to two forms of the receptor that differ completely in their cytoplasmic tails". 2000, Biochim. Biophys. Acta 1491(1-3) pp. 350-354.
Hermey, G., et al. "Identification and characterization of SorCS, a third member of a novel receptor family". 1999, Biochem. Biophys. Res. Commun. 266(2) pp. 347-351.

(Continued)

*Primary Examiner* — Christine J Saoud
*Assistant Examiner* — Jegatheesan Seharaseyon
(74) *Attorney, Agent, or Firm* — Sunstein Kann Murphy & Timbers LLP

(57) ABSTRACT

The present invention relates to SorCS1-like agents, including SorCS1, nucleic acid molecule encoding expression of SorCS1 and fragments thereof, as well as vectors containing said nucleic acid and to cells expressing SorCS1 and said fragments, for the treatment of obesity.

19 Claims, 36 Drawing Sheets

(56) References Cited

OTHER PUBLICATIONS

Hou, J.C. and Pessin, J.E. "Ins (endocytosis) and outs (exocytosis) of GLUT4 trafficking". 2007, Cur. Opin. Cell. Biol. 19 pp. 466-473.

Koren, S. and Fantus, G. "Inhibition of the protein tyrosine phosphatase PTP1B: potential therapy for obesity, insulin resistance and type-2 diabetes mellitus". 2007, Prac. Res. Clin. Endo. Meta. 21(4) pp. 621-640.

Morris, N.J., et al. "Sortilin is the major 110-kDa protein in GLUT4 vesicles from adipocytes". 1998, J.Biol.Chem. 273(6) pp. 3582-3587.

Nielsen, M.S., et al. "Different motifs regulate trafficking of SorCS1 isoforms". 2008, Traffic 9 pp. 980-994.

Nykjær, A., et al. "Sortilin is essential for proNGF-induced neuronal death". 2004, Nature 427(6977) pp. 843-848.

Pedersen et al; From gene to function: conditional knockout of four splice variants of the murine SorCS1 gene; Danish Med Builitin 2007, vol. 54, No. 2, pp. 183.

Plum, L. et al. "Transgenic and knockout mice in diabetes research: Novel insights into pathophysiology, limitations, and perspectives". 2004, Physiology 20 pp. 152-161.

Shi, J., and Kandror, V. "Sortilin is essential and sufficient for the formation of Glut4 storage vesicles in 3T3-L1 adipocytes". 2005, Dev. Cell 9 pp. 99-108.

Srinivasan, K., and Ramarao, P. "Animal models in type 2 diabetes research: An overview". 2007, Indian J. Med. Res. 125, pp. 451-472.

Zimmet, P., et al. "The Metabolic Syndrome: A global public health problem and a new definition" Journal of Atherosclerosis and Thrombosis, vol. 12, No. 6, pp. 295-300, 2005.

Australian Patent Office, Patent Examination Report No. 1—Application No. 2010257887, dated Jun. 14, 2012 (3 pages).

Australian Patent Office, Patent Examination Report No. 2—Application No. 2010257887, dated Sep. 21, 2012 (3 pages).

Australian Patent Office, Notice of Acceptance—Application No. 2010257887, dated Oct. 29, 2013 (2 pages).

International Searching Authority, International Search Report—International Application NO. PCT/DK2010/050131, dated Sep. 9, 2010, 6 pages.

International Preliminary Examining Authority, International Application No. PCT/DK2010/050131, dated Oct. 10, 2011, 11 pages.

Nørgaard, Jens Viktor, Response to Written Opinion for PCT Internationa Application No. PCT/DK2010/050131, dated Jan. 19, 2011, 7 pages.

The State Intellectual Property Office of The People's Republic of China, The First Office Action—Application No. 201080035738.1. dated May 31, 2013 (9 pages).

The State Intellectual Property Office of The People's Republic of China, The First Office Action—Application No. 201080035738.1, dated May 31, 2013 (9 pages) [English Translation].

The State Intellectual Property Office of The People's Republic of China, The Second Office Action—Application No. 201080035738.1, dated Jan. 27, 2014 (6 pages).

The State Intellectual Property Office of The People's Republic of China, The Second Office Action—Application No. 201080035738.1, dated Jan. 27, 2014 (7 pages) [English Translation].

European Patent Office, Communication pursuant to Article 94(E) EPC—Application No. 10 785 771.6-1405, dated Nov. 8, 2013 (5 pages).

European Patent Office, Extended European Search Report for Application No. 10785771.6-1405/2440233 dated Feb. 14, 2013, 12 pages.

Invitek Incorporation, "Standard Protocol for Diabetes, Study with db/db Mice", Aug. 10, 2008, 2 pages.

\* cited by examiner

* $P < 0.05$ wt vs SorCS1 KO

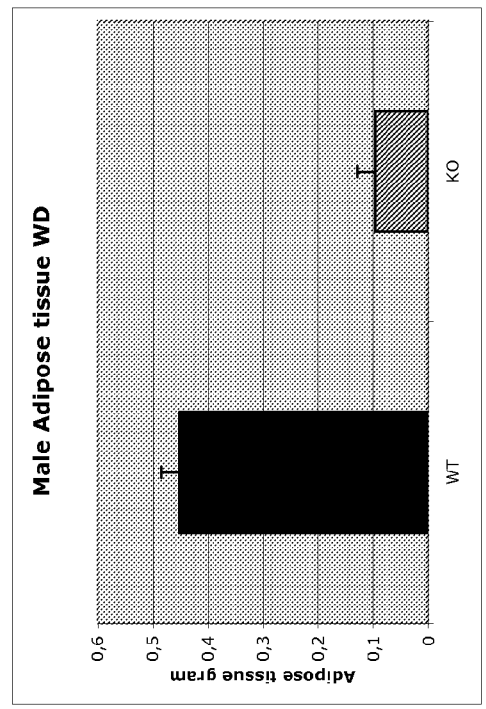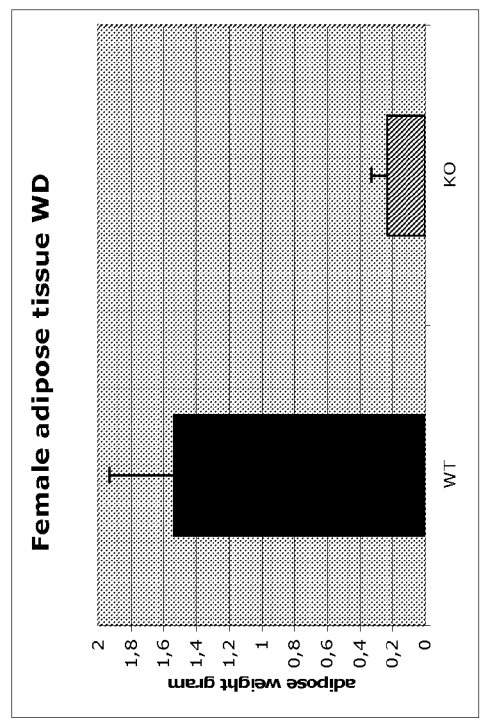
Fig. 9

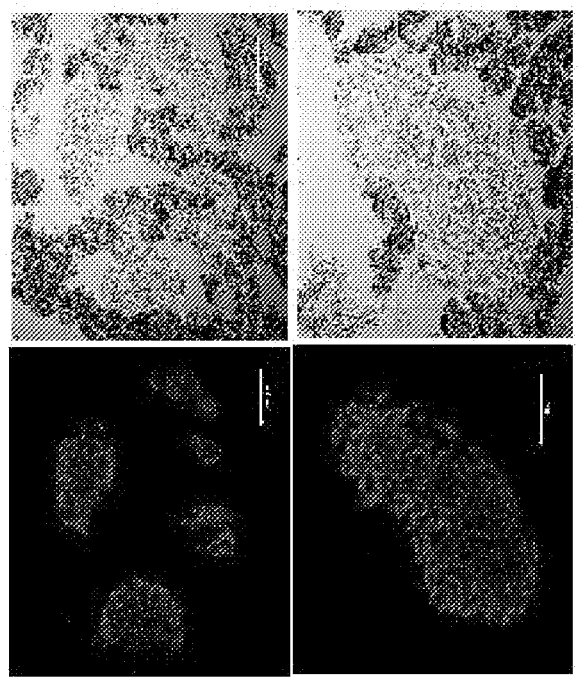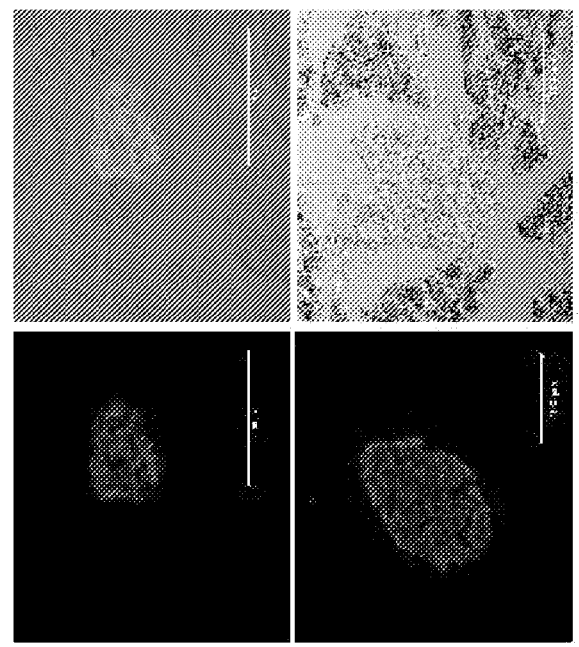
Fig. 15

Alignment of the SorCS1 protein from different species

Sequence 1: gi|61743975|ref|NP_001013049.1    1198 aa    Human (homo sapiens)
Sequence 2: gi|114632730|ref|XP_508026.2|     1361 aa    Chimpanzee (Pan troglodytes)
Sequence 3: gi|119917739|ref|XP_001253082.    1196 aa    Cow (Bos Taurus)
Sequence 4: gi|12025518|ref|NP_067352.1|      1167 aa    Mouse (Mus musculus)
Sequence 5: gi|109460253|ref|XP_220080.4|     1369 aa    Rat (Rattus norvegicus)
Sequence 6: gi|73998824|ref|XP_535010.2|       997 aa    Dog (Canis lupus familiaris)
Sequence 7: gi|118093020|ref|XP_421750.2|     1258 aa    Chicken (Gallus gallus)

```
Human (homo sapiens)            ------------------------------------------                   -
Chimpanzee (Pan troglodytes)    --------MTGRFPPRNRKLPTHRPLREPGVDRPRGQGARTQRMDPRPRG         42
Cow (Bos taurus)                ------------------------------------------                   -
Mouse (Mus musculus)            ------------------------------------------                   -
Rat (Rattus norvegicus)         MRAQVFLQQSGLSEKKHTDGIPTVPSINVIPERSKELLVPRGRVLMLLAG         50
Dog (Canis lupus familiaris)    ------------------------------------------                   -
Chicken (Gallus gallus)         ------------------------------------------                   -

Human (homo sapiens)            ------------------------------------------                   -
Chimpanzee (Pan troglodytes)    RRVGGGERRGEAAAAPARPRGSRRRRLQRPETRARARSASDFSSAPPPRG         92
Cow (Bos taurus)                ------------------------------------------                   -
Mouse (Mus musculus)            ------------------------------------------                   -
Rat (Rattus norvegicus)         TLRSLGRVGDSTARARLPVHSAARRRDAAPGALAEPALPPASPRRRRRW         100
Dog (Canis lupus familiaris)    ------------------------------------------                   -
Chicken (Gallus gallus)         ------------------------------------------                   -

Human (homo sapiens)            ------------------------------------------                   -
Chimpanzee (Pan troglodytes)    GGSLRPDPRSAQAQPGRAAATCPAPPPPAPTAAQLGWSWGPERRPPTAAS        142
Cow (Bos taurus)                ------------------------------------------                   -
Mouse (Mus musculus)            ------------------------------------------                   -
Rat (Rattus norvegicus)         LAAPSQPARSSQAQPGRAAGTCPAPPRAPPPPNLDGVVVLSAHPAAVSP         150
Dog (Canis lupus familiaris)    ------------------------------------------                   -
Chicken (Gallus gallus)         ---------------------------------------MEKV                  4
```

Fig. 16

```
Human (homo sapiens)          ------------------------------MGKVGAGGGSQARLSALLAGAGLLILCAP  29
Chimpanzee (Pan troglodytes)  AELRAATFVLGPLSPLLFAPAMGKVGAGGGSQARLSALLAGAGLLILCAP 192
Cow (Bos taurus)              ------------------------------MGKVGAGGVSPAGLSALLAGAGLLVLCAP  29
Mouse (Mus musculus)          ------------------------------MGKVGAGDGSSAGLSALLAGAGLLMLLAP  29
Rat (Rattus norvegicus)       VPRSAACLRFGTPSPLLSAPEMGKVGAGDGSSAALSALITGAGLLMLLAP 200
Dog (Canis lupus familiaris)  ----------------------------------------------------------
Chicken (Gallus gallus)       AGWYPAWHVALLYWTWLFLFTFGFTGAEITCRSCHSQVNPQQQHPQQGLP  54

Human (homo sapiens)          GVCGGGSCCPSPHPSSAPRSASTPRGFSHQGRPGRAPATPLPLVVRPLFS  79
Chimpanzee (Pan troglodytes)  GVCGGGSCCPPPHPSSAPRSASTPRGFSHQGRPGRAPATPLPLVVRPLFS 242
Cow (Bos taurus)              GSCGGGSCCPPRHPSAAPRWAPTPGGLPHQGPRGRAPATPLPQLGRPLFA  79
Mouse (Mus musculus)          GVCSSLSCCPPQHPSSTPRRTLTPRGFPHPGPLGRAPATPPPLFMRPLFA  79
Rat (Rattus norvegicus)       GICSSLSCCPPQHPSSTPRWTLTPRGFSYPGPLGRAPATPPPLFMRPLFA 250
Dog (Canis lupus familiaris)  ----------------------------------------------------------
Chicken (Gallus gallus)       MHLKTDRGEKERWRIPGEQGGERGRGAGMDTEDAELQAPFDPALAGTKFS 104

Human (homo sapiens)          -VAPGDRALSLERARGTGASMAVAARSGRR-RRSGADQEKAERGEGASRS 127
Chimpanzee (Pan troglodytes)  -VAPGDRALSLERARGTGASMAVAARSGRR-RRSGADQEKAERGEGASRS 290
Cow (Bos taurus)              -VAPGDRALSLERAPGTGASVAVAPRSGRK-RRSGEDQEKAERGEGTSRS 127
Mouse (Mus musculus)          -VAPGDRALFLERAGGSRVSVATAARSGRR-RRSGTEPEKIEPGEGASRS 127
Rat (Rattus norvegicus)       -VAPGDRALFLERAGGSRVSVATASRSGRR-RRSGMDPEKTEPGEGTSRS 298
Dog (Canis lupus familiaris)  ----------------------------------------------------------
Chicken (Gallus gallus)       GWETRSWASEPEKAPGDSRPGAAAAPTGEYPQRGQAGGRRNSARRRRGRS 154

Human (homo sapiens)          PRGVLRDGGQQEPGTRERDPDKATRFRMEELRLTSTTFALTGDSAHNQAM 177
Chimpanzee (Pan troglodytes)  PRGVLRDGGQQEPGTLERDPDKATRFRMEELRLTSTTFALTGDSAHNQAM 340
Cow (Bos taurus)              PRGVLRDRGQLEPGTLERDPDKATRFRLEELKLTSTTFALTGDSAHNQAM 177
Mouse (Mus musculus)          RRDMLKDGGQQGLGTGARDPGKATRFRMEELRLTSTTFALTGDSAHNQAM 177
Rat (Rattus norvegicus)       RRDMLRDGGQQGPGTGARDPDKATRFRMEELRLITSTTFALTGDSAHNQAM 348
Dog (Canis lupus familiaris)  ---------------------------MRKVS--------------EIM   8
Chicken (Gallus gallus)       PRGTAGPGGAAG---REPGGSGAARFGLEELRLGSTTFALTGSTTFALTGDSAHNQAM 201
                                                        :   :      *                *
```

Fig. 16, continued

| | | |
|---|---|---|
| Human (homo sapiens) | VHWSGHNSSVILILTKLYDYNLGSITESSLWRSTDYGTTYEKLNDKVGLK | 227 |
| Chimpanzee (Pan troglodytes) | VHWSGHNSSVILILTKLYDYNLGSITESSLWRSTDYGTTYEKLNDKVGLK | 390 |
| Cow (Bos taurus) | VHWSGHNSSVILILKLFDYNLGSITESSLWRSTDYGTTYEKLNDKVGLK | 227 |
| Mouse (Mus musculus) | VHWSGHNSSVILILTKLYDYNLGSITESSLWRSTDYGTTYEKLNDKVGLK | 227 |
| Rat (Rattus norvegicus) | VHWSGHNSSVILILTKLYDYNLGSITESSLWRSTDYGTTYEKLNDKVGLK | 398 |
| Dog (Canis lupus familiaris) | VLRSWH--SVILILTKLYDYNLGSITESSLWRSTDYGTTYEKLNDKVGLK | 56 |
| Chicken (Gallus gallus) | VHWSGQNSSVILILTKLYDYNLGSITESSLWRSTDYGTTYEKLNDKIGLK | 251 |
| | * * :  ******:.******************.:* | |
| | | |
| Human (homo sapiens) | TILSYLYVCPTNKRKIMLLTDPEIESSLLISSDEGATYQKYRLNFYIQSL | 277 |
| Chimpanzee (Pan troglodytes) | TILSYLYVCPTNKRKIMLLTDPEIESSLLISSDEGATYQKYRLNFYIQSL | 440 |
| Cow (Bos taurus) | TILSYLYVCPTNKRKIMLLTDPEIESSLLISSDEGATYQKYRLNFYIQSL | 277 |
| Mouse (Mus musculus) | TILSYLYVCPTNKCKIMLLTDPEIESSLLISSDEGATYQKYRLNFYLQSL | 277 |
| Rat (Rattus norvegicus) | TILSYLYVCPTNKRKIMLLTDPEIESSLLISSDEGATYQKYRLNFYIQSL | 448 |
| Dog (Canis lupus familiaris) | TILSYLYVCPTNKRKIMLLTDPESSLLISSDEGATYQKYRLNFYIQSL | 106 |
| Chicken (Gallus gallus) | TILSYLYVCPTNKRKIMLLTDPEVSSLLISTDEGATYQKYRLNFYIHSL | 301 |
| | *********** ****:.***:*:*******:. | |
| | | |
| Human (homo sapiens) | LFHPKQEDWILAYSQDQKLYSSAEFGRRWQLIQEGVVPNRFYWSVMGSNK | 327 |
| Chimpanzee (Pan troglodytes) | LFHPKQEDWILAYSQDQKLYSSAEFGRRWQLIQEGVVPNRFYWSVMGSNK | 490 |
| Cow (Bos taurus) | LFHPKQEDWILAYSQDQKLYSSAEFGRRWQLIQEAVVPNRFYWSVMGSNK | 327 |
| Mouse (Mus musculus) | LFHPKQEDWILAYSQDQKLYSSAEFGRRWQLIQESVVPNRFYWSVMGSSK | 327 |
| Rat (Rattus norvegicus) | LFHPKQEDWILAYSQDQKLYSSAEFGRRWQLIQEAVVPNRFYWSVMGSNK | 498 |
| Dog (Canis lupus familiaris) | LFHPKQEDWILAYSQDQKLYSSAEFGRRWQLIQEGVVPNRFYWSVLGSNK | 156 |
| Chicken (Gallus gallus) | LFHPKQEDWILAYSQDQKLFSSVEFGRRWLLHEGVAPNRFYWSMMVSGR | 351 |
| | ****************:. .*******  *::*.*.********:: *.: | |
| | | |
| Human (homo sapiens) | EPDLVHLEARTVDGHSHYLTCRMQNCTEANRNQPFPGYIDPDSLIVQDHY | 377 |
| Chimpanzee (Pan troglodytes) | EPDLVHLEARTVDGHSHYLTCRMQNCTEANRNQPFPGYIDPDSLIVQDHY | 540 |
| Cow (Bos taurus) | EPDLVHLEARTVDGHSQYLTCRMQNCTEANRNKPFPGYIDPDSLIVQDDY | 377 |
| Mouse (Mus musculus) | EPDLVHLEARTVDGHSQYLTCRMQNCTEANRNKPFPGYIDPDSLIVQDDY | 377 |
| Rat (Rattus norvegicus) | EPDLVHLEARTVDGHSIYLTCRMQNCTEANRNKPFPGYIDPDSLIVQDDY | 548 |
| Dog (Canis lupus familiaris) | EPDLVHLEARTVDGHSQYLTCRMQNCTEANRNKPFPGYIDPDSLIVQDDY | 206 |
| Chicken (Gallus gallus) | EPDLVHLEAKTVDGHAQYITCKMQNCSEASQNKPFPGYIDHNSLIVQDDY | 401 |
| | *******:****:  *::::.*:****:.***.* | |

Fig. 16, continued

```
Human (homo sapiens)          VFVQLTSGGRPHYYVSYRRNAFAQMKLPKYALPKDMHVISTDENQVFAAV 427
Chimpanzee (Pan troglodytes)  VFVQLTSGGRPHYYVSYRRNAFAQMKLPKYALPKDMHVISTDENQVFAAV 590
Cow (Bos taurus)              VFVQLTSGGRPHYYVSYRRNAFAQMKLPKYALPKDMHVISTDENQVFAAV 427
Mouse (Mus musculus)          VFVQLTSGGRPHYYVSYRRSPFAQMKLPKYALPKDMHVISTDENQVFAAV 427
Rat (Rattus norvegicus)       VFVQLTSGGRPHYYVSYRRNPFAQMKLPKYALPKDMHVISTDENQVFAAV 598
Dog (Canis lupus familiaris)  VFVQLTSGGRPHYYVSYRRNAFAQMKLPKYALPKDMHVISTDENQVFAAV 256
Chicken (Gallus gallus)       VFVQLTSGGRPHYYVSYRRNAFTPIKLPKYSLPKDMHVISTDESQVFAAV 451
                              ***************** .*: :******:***************:******

Human (homo sapiens)          QEWNQNDTYNLYISDTRGVYFTLALENVQSRGPEGNIMIDLYEVAGIKG 477
Chimpanzee (Pan troglodytes)  QEWNQNDTYNLYISDTRGVYFTLALENVQSRGPEGNIMIDLYEVAGIKG 640
Cow (Bos taurus)              QEWNQNDTYNLYISDTRGVYFTLALENVQSSRGPEGNVMIDLYEVAGIKG 477
Mouse (Mus musculus)          QEWNQNDTYNLYISDTRGVYFTLALENVRSSRGPEGNVMIDLYEVAGIKG 477
Rat (Rattus norvegicus)       QEWNQNDTYNLYISDTRGVYFTLALENVQSSRGPEGNVMIDLYEVAGIKG 648
Dog (Canis lupus familiaris)  QEWNQNDTYNLYISDTRGVYFTLALENVQSSRGPEGNIMIDLYEVAGIKG 306
Chicken (Gallus gallus)       QEWNQNDTYNLYISDTRGVYFTLALENVKSSQGLDGNVMIDLYEVAGIKG 501
                              ***************************.:** :***:***********

Human (homo sapiens)          MFLANKKIDNQVKTFITYNKGRDWRLLQAPDTDLRGDPVHCLLPYCSLHL 527
Chimpanzee (Pan troglodytes)  MFLANKKIDNQVKTFITYNKGRDWRLLQAPDTDLRGDPVHCLLPYCSLHL 690
Cow (Bos taurus)              MFLANKKIDNQVKTFITYNKGRDWRLLQAPDTDLRGDPVHCVLPYCSLHL 527
Mouse (Mus musculus)          MFLANKKIDNQVKTFITYNKGRDWRLLQAPDADLRGDPVHCLLPYCSLHL 527
Rat (Rattus norvegicus)       MFLANKKIDNQVKTFITYNKGRDWRLLQAPDADLRGDPVHCLLPYCSLHL 698
Dog (Canis lupus familiaris)  MFLANKKIDNQVKTFITYNKGRDWRLLQAPDTDLRGDPVHCLLPYCSLHL 356
Chicken (Gallus gallus)       MFLANKKIDNQVKTFITYNKGRDWNLLQAPDTDLKGNPVHCLLPYCSLHL 551
                              ************************ ****** **.:*** ********

Human (homo sapiens)          HLKVSENPYTSGIIASKDTAPSIIVASGNIGSELSDTDISMFVSSDAGNT 577
Chimpanzee (Pan troglodytes)  HLKVSENPYTSGIIASKDTAPSIIVASGNIGSELSDTDISMFVSSDAGNT 740
Cow (Bos taurus)              HLKVSENPYTSGIIASRDTAPSIIVASGNIGSELSDSDISMFVSSDAGNT 577
Mouse (Mus musculus)          HLKVSENPYTSGIIASRDTAPSIIVASGNIGSELSDSDISMFVSSDAGNT 577
Rat (Rattus norvegicus)       HLKVSENPYTSGIIASRDTAPSIIVASGNIGSELSDSDISMFVSSDAGNT 748
Dog (Canis lupus familiaris)  HLKVSENPYTSGIIASRDTAPSIIVASGNIGSELSDSDISMFVSSDAGNT 406
Chicken (Gallus gallus)       HLKVSENPYTSGNIASRDTAPSIIVASGNIGPELSDNDISMFVSSDAGNT 601
                              ************ ***:****************.****.**********
```

Fig. 16, continued

```
Human (homo sapiens)          WRQIFEEEHSVLYLDQGGVLIVAMKHTSLPIRHLWLSFDEGRSWSKYSFTS 627
Chimpanzee (Pan troglodytes)  WRQIFEEEHSVLYLDQGGVLIVAMKHTSLPIRHLWLSFDEGRSWSKYSFTS 790
Cow (Bos taurus)              WRQIFEEEHSVLYLDQGGVLIVAMKHTSLPIRHLWLSFDEGRSWSKYSFTS 627
Mouse (Mus musculus)          WRQIFEEEHSILYLDQGGVLIVAMKHTSLPIRHLWLSFDEGRSWSKYSFTS 627
Rat (Rattus norvegicus)       WRQIFEEEHSILYLDQGGVLIVAMKHTSLPIRHLWLSFDEGRSWSKYSFTS 798
Dog (Canis lupus familiaris)  WRQIFEEEHSVLYLDQGGVLIVAMKHTSLPIRHLWLSFDEGRSWSKYSFTS 456
Chicken (Gallus gallus)       WRQIFEEEHSVLYLDQGGVLIVAIKHTSLPIRHLWLSFDEGKSWSKYSFTS 651
                              ***********:*****************************:********

Human (homo sapiens)          IPLFVDGVLGEPGEETLIMTVFGHFSHRSEWQLVKVDYKSIFDRRCAEED  677
Chimpanzee (Pan troglodytes)  IPLFVDGVLGEPGEETLIMTVFGHFSHRSEWQLVKVDYKSIFDRRCAEED  840
Cow (Bos taurus)              IPLFVDGVLGEPGEETLIMTLLDHS--HSDWLVTALQPCCLFLLGNEWED  675
Mouse (Mus musculus)          IPLFVDGVLGEPGEETLIMTVFGHFSHRSEWQLVKVDYKSIFDRRCAEED  677
Rat (Rattus norvegicus)       IPLFVDGVLGEPGEETLIMTVFGHFSHRSEWQLVKVDYKSIFDRRCAEED  848
Dog (Canis lupus familiaris)  IPLFVDGVLGEPGEETLIMTVFGHFSHRSEWQLVKVDYKSIFDRRCAEED  506
Chicken (Gallus gallus)       LPLFVDGILGEPGEETLIMTVFGHFSHRSEWQLVKIDYKSIFDRRCAEED  701
                              :******.************    ::      ::    *      **

Human (homo sapiens)          YRPWQLHSQGEACIMGAKRIYKKRKSERKCMQGKYAGAMESEPCVCTEAD  727
Chimpanzee (Pan troglodytes)  YRPWQLHSQGEACIMGAKRIYKKKRKSERKCMQGKYAGAMESEPCVCTEAD 890
Cow (Bos taurus)              KIAWKPQDQGEACIMGAKRIYKKRKSERKCMQGKYAGAMESEPCVCTEAD  725
Mouse (Mus musculus)          YRPWQLHSQGEACIMGAKRIYKKKRKSERKCMQ-KYAGAMESEPCVCTEAD 726
Rat (Rattus norvegicus)       YRPWQLHSQGEACIMGAKRIYKKRKSERKCMQGTYAGAMESEPCVCTEAD  898
Dog (Canis lupus familiaris)  YRPWQLHSQGEACIMGAKRIYKKRKSERKCMQGKYAGAMESEPCVCTEAD  556
Chicken (Gallus gallus)       YWTWQLHSQGEACIMGAKRIYRKRKSEKKCMQGKYAGAMTSEPCVCTDAD  751
                              :  :****************::.****** . ****** *********:**

Human (homo sapiens)          FDCDYGYERHSNGQCLPAFWFNPSSLSKDCSLGQSYLNSTGYRKVVSNNC  777
Chimpanzee (Pan troglodytes)  FDCDYGYERHSNGQCLPAFWFNPSSLSKDCSLGQSYLNSTGYRKVVSNNC  940
Cow (Bos taurus)              FDCDYGYERHSNGQCLPAFWFNPSSLSKDCSLGQSYLNSTGYRKVVSNNC  775
Mouse (Mus musculus)          FDCDYGYERHSNGQCLPAFWFNPSSLSKDCSLGQSYLNSAGYRKVVSNNC  776
Rat (Rattus norvegicus)       FDCDYGYERHSNGQCLPAFWFNPSSLSKDCSLGQSYLNSTGYRKVVSNNC  948
Dog (Canis lupus familiaris)  FDCDYGYERHSNGQCLPAFWFNPSSLSKDCSLGQSYLNSTGYRKVVSNNC  606
Chicken (Gallus gallus)       FDCDYGYERHRNGQCLPAFWYNPSSLSKDCSLGQSYLNSTGYRKVVSNNC  801
                              **********.*********:******************:**********
```

Fig. 16, continued

| | | |
|---|---|---|
| Human (homo sapiens) | TDGVREQYTAKPQKCPGKAPRGLRIVTADGKLTAEQGHNVTLMVQLEEGD | 827 |
| Chimpanzee (Pan troglodytes) | TDGVREQYTAKPQKCPGKAPRGLRIVTADGKLTAEQGHNVTLMVQLEEGD | 990 |
| Cow (Bos taurus) | TDGVREQYTAKPQKCPGKAPRGLRIVTADGKLTAEQGHNVTLMVQLEEGD | 825 |
| Mouse (Mus musculus) | TDGVREQYTAKPQKCPGKAPRGLRIVTADGKLTAEQGHNVTLMVQLEEGD | 826 |
| Rat (Rattus norvegicus) | TDGVREQYTAKPQKCPGKAPRGLRIVTADGKLTAEQGHNVTLMVQLEEGD | 998 |
| Dog (Canis lupus familiaris) | TDGVREQYTAKPQKCPGKAPRGLRIVTADGKLTAEQGHNVTLMVQLEEGD | 656 |
| Chicken (Gallus gallus) | TDGVREQYTAKPQQCPGKAPQGLRIITSDGKLTAEQGHNVTFLVQLEEGD | 851 |
| | **************:.***:.:.****************** | |
| Human (homo sapiens) | VQRTLIQVDFGDGIAVSYVNLSSMEDGIKHVYQNVGIFRVTVQVDNSLGS | 877 |
| Chimpanzee (Pan troglodytes) | VQRTLIQVDFGDGIAVSYVNLSSMEDGIKHVYQNVGIFRVTVQVDNSLGS | 1040 |
| Cow (Bos taurus) | VQRTLIQVDFGDGIAVSYVNLSSMEDGIKHVYHNVGIFRVTVQVDNSLGS | 875 |
| Mouse (Mus musculus) | VQRTLIQVDFGDGIAVSYVNLSSMEDGIKHVYQNVGIFRVTVQVDNSLGS | 876 |
| Rat (Rattus norvegicus) | VQRTLIQVDFGDGIAVSYVNLSSMEDGIKHVYQNVGIFRVTVQVDNSLGS | 1048 |
| Dog (Canis lupus familiaris) | VQRTLIQVDFGDGIAVSYVNLSSMEDGIKHVYHNVGIFRVTVQVDNSLGS | 706 |
| Chicken (Gallus gallus) | LQRSLIQVDFGDGTAVSYANLSSTEDGIKHTYQNVGIFRVTVLVENSLGS | 901 |
| | ::*****....***.*:*********** *:****** | |
| Human (homo sapiens) | DSAVLYLHVTCPLEHVHLSLPFVTTKNKEVNATAVLWPSQVGTLTYVWWY | 927 |
| Chimpanzee (Pan troglodytes) | DSAVLYLHVTCPLEHVHLSLPFVTTKNKEVNATAVLWPSQVGTLTYVWWY | 1090 |
| Cow (Bos taurus) | DSAVLYLHVTCPLEHVHLSLPFVTTKNKEVNATAVLWPSQVGTLTYVWWY | 925 |
| Mouse (Mus musculus) | DSAVLYLHVTCPLEHVHLSLPFVTTKNKEVNATAVLWPSQVGTLTYVWWY | 926 |
| Rat (Rattus norvegicus) | DSAVLYLHVTCPLEHVHLSLPFVTTKNKEVNATAVLWPSQVGTLTYVWWY | 1098 |
| Dog (Canis lupus familiaris) | DSAVLYLHVTCPLEHVHLSLPFVTTKNKEVNATAVLWPSQVGTLTYVWWY | 756 |
| Chicken (Gallus gallus) | DNAVLYLHVTCPLEHVHLSLPFVTTKNKEVNATAVLWPSQVGTLTYVWWF | 951 |
| | *.************************************************: | |
| Human (homo sapiens) | GNNTEPLITLEGSISFRFTSEGMNTITVQVSAGNAILQDTKTIAVYEEFR | 977 |
| Chimpanzee (Pan troglodytes) | GNNTEPLITLEGSISFRFTSEGMNTITVQVSAGNAILQDTKTIAVYEEFR | 1140 |
| Cow (Bos taurus) | GNNTEPLITLEGSIAFKFTSEGMNTITVQVSAGNAILQDTKTIAVYEEFR | 975 |
| Mouse (Mus musculus) | GNNTEPLITLEGSISFKFTSEGMNTITVQVSAGNAILQDTKTIAVYEEFR | 976 |
| Rat (Rattus norvegicus) | GNNTEPLITLEGSISFKFTSEGMNTITVQVSAGNAILQDTKTIAVYEEFR | 1148 |
| Dog (Canis lupus familiaris) | GNNTEPLITLEGSISFKFTSEGMNTITVQVSAGNAILQDTKTIAVYEEFR | 806 |
| Chicken (Gallus gallus) | GNNTEPLITLEGSITFTFSVEGMNTITVQVSAGNTILQDTKTIAVYEQFR | 1001 |
| | **************:* *: ************ :*******: | |

Fig. 16, continued

| | | |
|---|---|---|
| Human (homo sapiens) | SLRLSFSPNLDDYNPDIPEWRRDIGRVIKKSLVEATGVPGQHILVAVLPG | 1027 |
| Chimpanzee (Pan troglodytes) | SLRLSFSPNLDDYNPDIPEWRRDIGRVIKKSLVEATGVPGQHILVAVLPG | 1190 |
| Cow (Bos taurus) | SLRLSFSPNLDDYNPDIPEWRRDVSRVIKKALVEATGVPGQHILVAVLPG | 1025 |
| Mouse (Mus musculus) | SLRLAFSPNLDDYNPDIPEWRRDISRVIKKSLVEATGIPSQHILVAVLPG | 1026 |
| Rat (Rattus norvegicus) | SLRLAFSPNLDDYNPDIPEWRRDISRVIKKSLVEATGIPSQHILVAVLPG | 1198 |
| Dog (Canis lupus familiaris) | SLRLSFSPNLDDYNPDIPEWRRDISRVIKKSLVEATGVPGQHILVAVLPG | 856 |
| Chicken (Gallus gallus) | SLRLSFSPNLDDYNPDIPEWRRDISRVVKRALVEATGISSKHILVAVLPG | 1051 |
| | **:***************:.:*::*****:.:.:******* | |
| Human (homo sapiens) | LPTTAELFVLPYQDPAGENKRSTDDLEQISELLIHTLNQNSVHFELKPGV | 1077 |
| Chimpanzee (Pan troglodytes) | LPTTAELFVLPYQDPAGENKRSTDDLEQISELLIHTLNQNSVHFELKPGV | 1240 |
| Cow (Bos taurus) | LPTAAELFVLPHQDPTGENKRPAEDLEQISELMIHKLNQNSVHFELKPGV | 1075 |
| Mouse (Mus musculus) | LPTAAELFVLPYQDGTRENKRSPEDLEQISEVLIHKLNQNLVHFELKPGV | 1076 |
| Rat (Rattus norvegicus) | LPTAAELFVLPYQDGARENKRSPEDLEQISEVLIHKLNQNLVHFELKPGV | 1248 |
| Dog (Canis lupus familiaris) | LPTAAELFVLPYQDPTGENKRSAEDLEQISELLIHKLNQNSVHFELKPGV | 906 |
| Chicken (Gallus gallus) | LPTSAELFILPYQDATGGNKR-TEDLEQISEILIQKLNQNFVHFELKPGV | 1100 |
| | *.:::  :  *  .:********:::*:.** ******* | |
| Human (homo sapiens) | RVLVHAAHLTAAPLVDLTPTHSGSAMLMLLSVVFVGLAVFVIYKFKRKIP | 1127 |
| Chimpanzee (Pan troglodytes) | RVLVHAAHLTAAPLVDLTPTHSGSAMLMLLSVVFVGLAVFVIYKFKRKIP | 1290 |
| Cow (Bos taurus) | QVLVHAAHLTAAPLVDLTPTHSGSAMLMLLSVVFVGLAVFVIYKFKRKIP | 1125 |
| Mouse (Mus musculus) | QVLVHAAHLTAAPLVDLTPTHSGSAMLMLLSVVFVGLAVFVIYKFKRRVA | 1126 |
| Rat (Rattus norvegicus) | QVLVHAAHLTAAPLVDLTPTHSGSAMLMLLSVVFVGLAVFVIYKFKRKIP | 1298 |
| Dog (Canis lupus familiaris) | QILVHAAHLTAAPLVDLTPSHSGSAMLMLLSVVFVGLAVFVIYKFKRRVA | 956 |
| Chicken (Gallus gallus) | RVLVHAAHLTAAPLVDLTPSHSGSAMLMLLSVVFVGLAVFVIYKFKRKIP | 1150 |
| | :******************:****************:::. | |
| Human (homo sapiens) | GINVYAQMQNEKEQEMISPVSHSESRPNVPQTELRRPGQLIDEKVESQLI | 1177 |
| Chimpanzee (Pan troglodytes) | GINVYAQMQNEKEQEMISPVSHFESRPSVPQTELRRPGQLIDEKVESQLI | 1340 |
| Cow (Bos taurus) | GINVYAQMQNEKEQEMVSRVSHPESRPYVPQTELRRPGQLIDEKVESQLI | 1175 |
| Mouse (Mus musculus) | LPSPPSPSAQPGDSSLR----LQRPRPATPPSSPKRGSAGAQFAI------ | 1167 |
| Rat (Rattus norvegicus) | GINVYAQMQNEKEQELINPVSHTESRPTAPHPDLRRPGQIVDEKVESHLL | 1348 |
| Dog (Canis lupus familiaris) | LPSPPSPSTQPGDSSLR----LQRARHATPPSTPKRGSAGAQFAI------ | 997 |
| Chicken (Gallus gallus) | GLNIYAQMQNEKDQEMVSPVSQRESIPNVPQSELMSPEQLVDEKLDVQPI | 1200 |
| | : . :   :    :    *    . | |

Fig. 16, continued

| | | |
|---|---|---|
| Human (homo sapiens) | GSISIVAENQSTKEIPTYVNV------------------------------- | 1198 |
| Chimpanzee (Pan troglodytes) | GSISIVAENQSTKEIPTYVNV------------------------------- | 1361 |
| Cow (Bos taurus) | GSISIVAENQSTKEIPTYVNV------------------------------- | 1196 |
| Mouse (Mus musculus) | ----------------------------------------------------- | |
| Rat (Rattus norvegicus) | GSISIVAENQSTKEIPTYVNV------------------------------- | 1369 |
| Dog (Canis lupus familiaris) | ----------------------------------------------------- | |
| Chicken (Gallus gallus) | EQPQATVQNPRKGNAAKVVWTEDFQKACGSPRGFKPRPGAEVFPQLLSPR | 1250 |

| | | |
|---|---|---|
| Human (homo sapiens) | --------- | |
| Chimpanzee (Pan troglodytes) | --------- | |
| Cow (Bos taurus) | --------- | |
| Mouse (Mus musculus) | | |
| Rat (Rattus norvegicus) | --------- | |
| Dog (Canis lupus familiaris) | --------- | |
| Chicken (Gallus gallus) | AQKKSLPM | 1258 |

Fig. 16, continued

| | |
|---|---|
| 34-36: | KDLFPNLTVIRGSRLFFNYAL (aa 100-120) |
| 43-46: | HLK ELGLYNLMNTRGSVRIEKNN (aa 127-150) |
| 95-99: | SFCQDLHHKCKNSRRQGCHQYVIHNNK (aa 284-310) |
| 121-122: | VINGSLIINIRGGNNLAA (aa 362-379) |
| 198-199: | VKTLVTFSDERRTYGAKS (aa 593-610) |
| 210-213: | ISVSNSSSQIILKWKPPSDPNGNI (aa 629-652) |
| 250-253: | GTGAEDPRPSRKRRSLGDVGNVTV (aa 749-772) |

Fig. 23A

Insulin signalling
(adipose tissue SorCS1 KO >< wildtype)

| Gene | Fold regulation | p-value |
|---|---|---|
| Aebp1 (AE binding protein 1) | -5.93 | 0.406 |
| Dok1 (docking protein 1) | 7.24 | 0.188 |
| Igf1r (insulin-like growth factor 1 receptor) | 3.30 | 0.00008 |
| Irs2 (Insulin receptor substrate 2) | -2.95 | 0.100 |
| Pik3cb (phosphoinositide-3-kinase, catalytic, beta polypeptide) | -5.65 | 0.196 |
| Ucp1 (uncoupling protein 1) | -25.35 | 0.085 |

| Gene | Function |
|---|---|
| Aebp1 | A transcriptional repressor with carboxypeptidase activity. Binds promotor of adipose P2 gene. |
| Dok1 | A member of the IRS family. Function as a scaffolding protein that recruits signalling molecules (ras-GTP, Nck). |
| Igf1r | Binds IGF1 with high affinity. Has tyrosine kinase activity. Plays a critical role in transformation events. |
| Irs2 | A cytoplasmic signaling molecule that mediates effects of insulin, insulin-like growth factor 1, and other cytokines by acting as a molecular adaptor between diverse receptor tyrosine kinases and downstream effectors. |
| Pik3cb | PI3k phosphorylate the inositol ring in inositol lipids. Is a participant in signalling pathways regulating cell growth |
| Ucp1 | Plays a role in heat production by uncoupling oxidative phosphorylation from the respiratory chain |

Fig. 24A

**Lipoprotein signalling and Cholesterol metabolism
(Adipose tissue SorCS1 KO >< wildtype)**

| Gene | Fold reg. | p-value |
|---|---|---|
| Akr1d1 (aldo-keto reductase family1, member D1) | 8.06 | 0.042 |
| Colec12 (collectin sub-family member 12) | 3.12 | 0.046 |
| Dhcr7 (7-dehydrocholestrol reductase) | 3.82 | 0.040 |
| Hmgcs2 (3-hydroxy-3-methylglutaryl-Coenzyme A synthase 2) | 6.01 | 0.013 |
| Lcat (Lecithin cholesterol acyltransferase) | 3.37 | 0.008 |
| Ldlr (Low density protein receptor) | 3.44 | 0.014 |
| Mvd (mevalonate (diphospho) decarboxylase) | 3.48 | 0.039 |
| Nr1h4 (Nuclear receptor subfamily 1, group H, member 4) | 3.49 | 0.041 |
| Osbpl5 (Oxysterol binding protein-like 5) | 3.61 | 0.048 |
| Prkag2 (Protein kinase, AMP-activated, gamma 2 non-catalytic) | 5.27 | 0.007 |
| Soat1 (Sterol O-acyltransferase 1) | 11.75 | 0.020 |
| Vldlr (very low density lipoprotein receptor) | 4.53 | 0.018 |

| Gene | Function |
|---|---|
| Akr1d1 | Catalysis of the 5-beta-reduction of bile acid intermediates and steroid hormones. |
| Colec12 | A scavenger receptor for binding to carbohydrate antigens on microorganisms and oxidized phospholipids of oxidatively damaged or apoptotic cells. |
| Dhcr7 | A penultimate enzyme of sterol biosynthesis that converts 7-dehydrocholesterol to cholesterol |
| Hmgcs2 | Mediates the first reaction in ketogenesis, a metabolic pathway that provides lipid-derived energy during carbohydrate deprivation |
| Lcat | An extracellular cholesterol esterifying enzyme. The esterification of cholesterol is required for cholesterol transport. |
| Ldlr | A cell surface protein involved in receptor mediated endocytosis of specific ligands, eg. LDL |
| Mvd | Catalyzes the conversion of mevalonate pyrophosphate into isopentyl pyrophosphate – one of the early steps in cholesterol biosynthesis |
| Nr1h4 | Regulates the expression of various transport proteins and biosynthetic enzymes crucial to the physiological maintenance of cholesterol and bile acid homeostasis. |
| Osbpl5 | An intracellular lipid receptor – a member of the oxy sterol-binding protein family. |
| Prkag2 | Subunit of AMPK an important energy-sensing enzyme that monitors cellular energy status and functions by inactivating key enzymes involved in regulating de novo biosynthesis of fatty acid and cholesterol |
| Soat1 | Forms cholesterol esters from cholesterol. Accumulation of cholesterol esters as cytoplasmic lipid droplets is a characteristic feature of early stages of atherosclerotic plaques |
| Vldlr | Mediates cholesterol uptake possible in collaboration with ldl |

Fig. 24B

SEQUENCE LISTING

<160> NUMBER OF SEQ ID NOS: 102

<210> SEQ ID NO 1
<211> LENGTH: 1168
<212> TYPE: PRT
<213> ORGANISM: Homo sapiens
<220> FEATURE:
<221> NAME/KEY: MISC_FEATURE
<222> LOCATION: (1)..(1168)
<223> OTHER INFORMATION: preproSorCS1b, Isoform 1

<400> SEQUENCE: 1

```
Met Gly Lys Val Gly Ala Gly Gly Gly Ser Gln Ala Arg Leu Ser Ala
1               5                   10                  15

Leu Leu Ala Gly Ala Gly Leu Leu Ile Leu Cys Ala Pro Gly Val Cys
            20                  25                  30

Gly Gly Gly Ser Cys Cys Pro Ser Pro His Pro Ser Ser Ala Pro Arg
        35                  40                  45

Ser Ala Ser Thr Pro Arg Gly Phe Ser His Gln Gly Arg Pro Gly Arg
    50                  55                  60

Ala Pro Ala Thr Pro Leu Pro Leu Val Val Arg Pro Leu Phe Ser Val
65                  70                  75                  80

Ala Pro Gly Asp Arg Ala Leu Ser Leu Glu Arg Ala Arg Gly Thr Gly
                85                  90                  95

Ala Ser Met Ala Val Ala Ala Arg Ser Gly Arg Arg Arg Ser Gly
            100                 105                 110

Ala Asp Gln Glu Lys Ala Glu Arg Gly Glu Gly Ala Ser Arg Ser Pro
        115                 120                 125

Arg Gly Val Leu Arg Asp Gly Gln Gln Glu Pro Gly Thr Arg Glu
    130                 135                 140

Arg Asp Pro Asp Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                165                 170                 175

Met Val His Trp Ser Gly His Asn Ser Ser Val Ile Leu Ile Leu Thr
            180                 185                 190

Lys Leu Tyr Asp Tyr Asn Leu Gly Ser Ile Thr Glu Ser Ser Leu Trp
        195                 200                 205
```

Arg Ser Thr Asp Tyr Gly Thr Thr Tyr Glu Lys Leu Asn Asp Lys Val
210             215                 220

Gly Leu Lys Thr Ile Leu Ser Tyr Leu Tyr Val Cys Pro Thr Asn Lys
225             230                 235                 240

Arg Lys Ile Met Leu Leu Thr Asp Pro Glu Ile Glu Ser Ser Leu Leu
            245                 250                 255

Ile Ser Ser Asp Glu Gly Ala Thr Tyr Gln Lys Tyr Arg Leu Asn Phe
        260                 265                 270

Tyr Ile Gln Ser Leu Leu Phe His Pro Lys Gln Glu Asp Trp Ile Leu
        275                 280                 285

Ala Tyr Ser Gln Asp Gln Lys Leu Tyr Ser Ser Ala Glu Phe Gly Arg
290                 295                 300

Arg Trp Gln Leu Ile Gln Glu Gly Val Val Pro Asn Arg Phe Tyr Trp
305             310                 315                 320

Ser Val Met Gly Ser Asn Lys Glu Pro Asp Leu Val His Leu Glu Ala
            325                 330                 335

Arg Thr Val Asp Gly His Ser His Tyr Leu Thr Cys Arg Met Gln Asn
            340                 345                 350

Cys Thr Glu Ala Asn Arg Asn Gln Pro Phe Pro Gly Tyr Ile Asp Pro
        355                 360                 365

Asp Ser Leu Ile Val Gln Asp His Tyr Val Phe Val Gln Leu Thr Ser
370                 375                 380

Gly Gly Arg Pro His Tyr Val Ser Tyr Arg Asn Ala Phe Ala
385                 390                 395                 400

Gln Met Lys Leu Pro Lys Tyr Ala Leu Pro Lys Asp Met His Val Ile
                405                 410                 415

Ser Thr Asp Glu Asn Gln Val Phe Ala Ala Val Gln Glu Trp Asn Gln
            420                 425                 430

Asn Asp Thr Tyr Asn Leu Tyr Ile Ser Asp Thr Arg Gly Val Tyr Phe
        435                 440                 445

Thr Leu Ala Leu Glu Asn Val Gln Ser Ser Arg Gly Pro Glu Gly Asn
    450                 455                 460

Ile Met Ile Asp Leu Tyr Glu Val Ala Gly Ile Lys Gly Met Phe Leu
465             470                 475                 480

Ala Asn Lys Lys Ile Asp Asn Gln Val Lys Thr Phe Ile Thr Tyr Asn
            485                 490                 495

Lys Gly Arg Asp Trp Arg Leu Leu Gln Ala Pro Asp Thr Asp Leu Arg
            500                 505                 510

Gly Asp Pro Val His Cys Leu Leu Pro Tyr Cys Ser Leu His Leu His
            515                 520                 525

Leu Lys Val Ser Glu Asn Pro Tyr Thr Ser Gly Ile Ile Ala Ser Lys
    530                 535                 540

Asp Thr Ala Pro Ser Ile Ile Val Ala Ser Gly Asn Ile Gly Ser Glu
545                 550                 555                 560

Leu Ser Asp Thr Asp Ile Ser Met Phe Val Ser Ser Asp Ala Gly Asn
            565                 570                 575

Thr Trp Arg Gln Ile Phe Glu Glu His Ser Val Leu Tyr Leu Asp
            580                 585                 590

Gln Gly Gly Val Leu Val Ala Met Lys His Thr Ser Leu Pro Ile Arg
                595                 600                 605

His Leu Trp Leu Ser Phe Asp Glu Gly Arg Ser Trp Ser Lys Tyr Ser
            610                 615                 620

Phe Thr Ser Ile Pro Leu Phe Val Asp Gly Val Leu Gly Glu Pro Gly

```
            625                 630                 635                 640
Glu Glu Thr Leu Ile Met Thr Val Phe Gly His Phe Ser His Arg Ser
                    645                 650                 655
Glu Trp Gln Leu Val Lys Val Asp Tyr Lys Ser Ile Phe Asp Arg Arg
                660                 665                 670
Cys Ala Glu Glu Asp Tyr Arg Pro Trp Gln Leu His Ser Gln Gly Glu
            675                 680                 685
Ala Cys Ile Met Gly Ala Lys Arg Ile Tyr Lys Lys Arg Lys Ser Glu
        690                 695                 700
Arg Lys Cys Met Gln Gly Lys Tyr Ala Gly Ala Met Glu Ser Glu Pro
705                 710                 715                 720
Cys Val Cys Thr Glu Ala Asp Phe Asp Cys Asp Tyr Gly Tyr Glu Arg
                725                 730                 735
His Ser Asn Gly Gln Cys Leu Pro Ala Phe Trp Phe Asn Pro Ser Ser
                740                 745                 750
Leu Ser Lys Asp Cys Ser Leu Gly Gln Ser Tyr Leu Asn Ser Thr Gly
            755                 760                 765
Tyr Arg Lys Val Val Ser Asn Asn Cys Thr Asp Gly Val Arg Glu Gln
        770                 775                 780
Tyr Thr Ala Lys Pro Gln Lys Cys Pro Gly Lys Ala Pro Arg Gly Leu
785                 790                 795                 800
Arg Ile Val Thr Ala Asp Gly Lys Leu Thr Ala Glu Gln Gly His Asn
                805                 810                 815
Val Thr Leu Met Val Gln Leu Glu Glu Gly Asp Val Gln Arg Thr Leu
                820                 825                 830
Ile Gln Val Asp Phe Gly Asp Gly Ile Ala Val Ser Tyr Val Asn Leu
            835                 840                 845
Ser Ser Met Glu Asp Gly Ile Lys His Val Tyr Gln Asn Val Gly Ile
        850                 855                 860
Phe Arg Val Thr Val Gln Val Asp Asn Ser Leu Gly Ser Asp Ser Ala
865                 870                 875                 880
Val Leu Tyr Leu His Val Thr Cys Pro Leu Glu His Val His Leu Ser
                885                 890                 895
Leu Pro Phe Val Thr Thr Lys Asn Lys Glu Val Asn Ala Thr Ala Val
                900                 905                 910
Leu Trp Pro Ser Gln Val Gly Thr Leu Thr Tyr Val Trp Trp Tyr Gly
            915                 920                 925
Asn Asn Thr Glu Pro Leu Ile Thr Leu Glu Gly Ser Ile Ser Phe Arg
        930                 935                 940
Phe Thr Ser Glu Gly Met Asn Thr Ile Thr Val Gln Val Ser Ala Gly
945                 950                 955                 960
Asn Ala Ile Leu Gln Asp Thr Lys Thr Ile Ala Val Tyr Glu Glu Phe
                965                 970                 975
Arg Ser Leu Arg Leu Ser Phe Ser Pro Asn Leu Asp Asp Tyr Asn Pro
                980                 985                 990
Asp Ile Pro Glu Trp Arg Arg Asp Ile Gly Arg Val Ile Lys Lys Ser
            995                 1000                1005
Leu Val Glu Ala Thr Gly Val Pro Gly Gln His Ile Leu Val Ala
        1010                1015                1020
Val Leu Pro Gly Leu Pro Thr Thr Ala Glu Leu Phe Val Leu Pro
        1025                1030                1035
Tyr Gln Asp Pro Ala Gly Glu Asn Lys Arg Ser Thr Asp Asp Leu
        1040                1045                1050
```

```
Glu Gln Ile Ser Glu Leu Leu Ile His Thr Leu Asn Gln Asn Ser
    1055                1060                1065

Val His Phe Glu Leu Lys Pro Gly Val Arg Val Leu Val His Ala
    1070                1075                1080

Ala His Leu Thr Ala Ala Pro Leu Val Asp Leu Thr Pro Thr His
    1085                1090                1095

Ser Gly Ser Ala Met Leu Met Leu Leu Ser Val Val Phe Val Gly
    1100                1105                1110

Leu Ala Val Phe Val Ile Tyr Lys Phe Lys Arg Arg Val Ala Leu
    1115                1120                1125

Pro Ser Pro Pro Ser Pro Ser Thr Gln Pro Gly Asp Ser Ser Leu
    1130                1135                1140

Arg Leu Gln Arg Ala Arg His Ala Thr Pro Pro Ser Thr Pro Lys
    1145                1150                1155

Arg Gly Ser Ala Gly Ala Gln Tyr Ala Ile
    1160                1165

<210> SEQ ID NO 2
<211> LENGTH: 1197
<212> TYPE: PRT
<213> ORGANISM: Homo sapiens
<220> FEATURE:
<221> NAME/KEY: MISC_FEATURE
<222> LOCATION: (1)..(1197)
<223> OTHER INFORMATION: preproSorCS1, Isoform 2

<400> SEQUENCE: 2

Met Gly Lys Val Gly Ala Gly Gly Gly Ser Gln Ala Arg Leu Ser Ala
1               5                   10                  15

Leu Leu Ala Gly Ala Gly Leu Leu Ile Leu Cys Ala Pro Gly Val Cys
                20                  25                  30

Gly Gly Gly Ser Cys Cys Pro Ser Pro His Pro Ser Ser Ala Pro Arg
            35                  40                  45

Ser Ala Ser Thr Pro Arg Gly Phe Ser His Gln Gly Arg Pro Gly Arg
    50                  55                  60

Ala Pro Ala Thr Pro Leu Pro Leu Val Val Arg Pro Leu Phe Ser Val
65                  70                  75                  80

Ala Pro Gly Asp Arg Ala Leu Ser Leu Glu Arg Ala Arg Gly Thr Gly
                85                  90                  95

Ala Ser Met Ala Val Ala Ala Arg Ser Gly Arg Arg Arg Ser Gly
            100                 105                 110

Ala Asp Gln Glu Lys Ala Glu Arg Gly Glu Gly Ala Ser Arg Ser Pro
    115                 120                 125

Arg Gly Val Leu Arg Asp Gly Gly Gln Gln Glu Pro Gly Thr Arg Glu
    130                 135                 140

Arg Asp Pro Asp Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                165                 170                 175

Met Val His Trp Ser Gly His Asn Ser Ser Val Ile Leu Ile Leu Thr
            180                 185                 190

Lys Leu Tyr Asp Tyr Asn Leu Gly Ser Ile Thr Glu Ser Ser Leu Trp
        195                 200                 205

Arg Ser Thr Asp Tyr Gly Thr Thr Tyr Glu Lys Leu Asn Asp Lys Val
    210                 215                 220
```

```
Gly Leu Lys Thr Ile Leu Ser Tyr Leu Tyr Val Cys Pro Thr Asn Lys
225                 230                 235                 240

Arg Lys Ile Met Leu Leu Thr Asp Pro Glu Ile Glu Ser Ser Leu Leu
            245                 250                 255

Ile Ser Ser Asp Glu Gly Ala Thr Tyr Gln Lys Tyr Arg Leu Asn Phe
        260                 265                 270

Tyr Ile Gln Ser Leu Leu Phe His Pro Lys Gln Glu Asp Trp Ile Leu
    275                 280                 285

Ala Tyr Ser Gln Asp Gln Lys Leu Tyr Ser Ser Ala Glu Phe Gly Arg
290                 295                 300

Arg Trp Gln Leu Ile Gln Glu Gly Val Val Pro Asn Arg Phe Tyr Trp
305                 310                 315                 320

Ser Val Met Gly Ser Asn Lys Glu Pro Asp Leu Val His Leu Glu Ala
            325                 330                 335

Arg Thr Val Asp Gly His Ser His Tyr Leu Thr Cys Arg Met Gln Asn
        340                 345                 350

Cys Thr Glu Ala Asn Arg Gln Pro Phe Pro Gly Tyr Ile Asp Pro Asp
    355                 360                 365

Ser Leu Ile Val Gln Asp His Tyr Val Phe Val Gln Leu Thr Ser Gly
370                 375                 380

Gly Arg Pro His Tyr Tyr Val Ser Tyr Arg Arg Asn Ala Phe Ala Gln
385                 390                 395                 400

Met Lys Leu Pro Lys Tyr Ala Leu Pro Lys Asp Met His Val Ile Ser
            405                 410                 415

Thr Asp Glu Asn Gln Val Phe Ala Ala Val Gln Glu Trp Asn Gln Asn
        420                 425                 430

Asp Thr Tyr Asn Leu Tyr Ile Ser Asp Thr Arg Gly Val Tyr Phe Thr
    435                 440                 445

Leu Ala Leu Glu Asn Val Gln Ser Ser Arg Gly Pro Glu Gly Asn Ile
450                 455                 460

Met Ile Asp Leu Tyr Glu Val Ala Gly Ile Lys Gly Met Phe Leu Ala
465                 470                 475                 480

Asn Lys Lys Ile Asp Asn Gln Val Lys Thr Phe Ile Thr Tyr Asn Lys
            485                 490                 495

Gly Arg Asp Trp Arg Leu Leu Gln Ala Pro Asp Thr Asp Leu Arg Gly
        500                 505                 510

Asp Pro Val His Cys Leu Leu Pro Tyr Cys Ser Leu His Leu His Leu
    515                 520                 525

Lys Val Ser Glu Asn Pro Tyr Thr Ser Gly Ile Ala Ser Lys Asp
530                 535                 540

Thr Ala Pro Ser Ile Ile Val Ala Ser Gly Asn Ile Gly Ser Glu Leu
545                 550                 555                 560

Ser Asp Thr Asp Ile Ser Met Phe Val Ser Ser Asp Ala Gly Asn Thr
            565                 570                 575

Trp Arg Gln Ile Phe Glu Glu His Ser Val Leu Tyr Leu Asp Gln
        580                 585                 590

Gly Gly Val Leu Val Ala Met Lys His Thr Ser Leu Pro Ile Arg His
    595                 600                 605

Leu Trp Leu Ser Phe Asp Glu Gly Arg Ser Trp Ser Lys Tyr Ser Phe
610                 615                 620

Thr Ser Ile Pro Leu Phe Val Asp Gly Val Leu Gly Glu Pro Gly Glu
625                 630                 635                 640

Glu Thr Leu Ile Met Thr Val Phe Gly His Phe Ser His Arg Ser Glu
```

645                 650                 655
Trp Gln Leu Val Lys Val Asp Tyr Lys Ser Ile Phe Asp Arg Arg Cys
            660                 665                 670

Ala Glu Glu Asp Tyr Arg Pro Trp Gln Leu His Ser Gln Gly Glu Ala
            675                 680                 685

Cys Ile Met Gly Ala Lys Arg Ile Tyr Lys Lys Arg Lys Ser Glu Arg
            690                 695                 700

Lys Cys Met Gln Gly Lys Tyr Ala Gly Ala Met Glu Ser Glu Pro Cys
705                 710                 715                 720

Val Cys Thr Glu Ala Asp Phe Asp Cys Asp Tyr Gly Tyr Glu Arg His
                    725                 730                 735

Ser Asn Gly Gln Cys Leu Pro Ala Phe Trp Phe Asn Pro Ser Ser Leu
                    740                 745                 750

Ser Lys Asp Cys Ser Leu Gly Gln Ser Tyr Leu Asn Ser Thr Gly Tyr
                    755                 760                 765

Arg Lys Val Val Ser Asn Asn Cys Thr Asp Gly Val Arg Glu Gln Tyr
            770                 775                 780

Thr Ala Lys Pro Gln Lys Cys Pro Gly Lys Ala Pro Arg Gly Leu Arg
785                 790                 795                 800

Ile Val Thr Ala Asp Gly Lys Leu Thr Ala Glu Gln Gly His Asn Val
                    805                 810                 815

Thr Leu Met Val Gln Leu Glu Glu Gly Asp Val Gln Arg Thr Leu Ile
                    820                 825                 830

Gln Val Asp Phe Gly Asp Gly Ile Ala Val Ser Tyr Val Asn Leu Ser
                    835                 840                 845

Ser Met Glu Asp Gly Ile Lys His Val Tyr Gln Asn Val Gly Ile Phe
            850                 855                 860

Arg Val Thr Val Gln Val Asp Asn Ser Leu Gly Ser Asp Ser Ala Val
865                 870                 875                 880

Leu Tyr Leu His Val Thr Cys Pro Leu Glu His Val His Leu Ser Leu
                    885                 890                 895

Pro Phe Val Thr Thr Lys Asn Lys Glu Val Asn Ala Thr Ala Val Leu
            900                 905                 910

Trp Pro Ser Gln Val Gly Thr Leu Thr Tyr Val Trp Trp Tyr Gly Asn
            915                 920                 925

Asn Thr Glu Pro Leu Ile Thr Leu Glu Gly Ser Ile Ser Phe Arg Phe
            930                 935                 940

Thr Ser Glu Gly Met Asn Thr Ile Thr Val Gln Val Ser Ala Gly Asn
945                 950                 955                 960

Ala Ile Leu Gln Asp Thr Lys Thr Ile Ala Val Tyr Glu Glu Phe Arg
                    965                 970                 975

Ser Leu Arg Leu Ser Phe Ser Pro Asn Leu Asp Asp Tyr Asn Pro Asp
                    980                 985                 990

Ile Pro Glu Trp Arg Arg Asp Ile Gly Arg Val Ile Lys Lys Ser Leu
                    995                 1000                1005

Val Glu Ala Thr Gly Val Pro Gly Gln His Ile Leu Val Ala Val
            1010                1015                1020

Leu Pro Gly Leu Pro Thr Thr Ala Glu Leu Phe Val Leu Pro Tyr
            1025                1030                1035

Gln Asp Pro Ala Gly Glu Asn Lys Arg Ser Thr Asp Asp Leu Glu
            1040                1045                1050

Gln Ile Ser Glu Leu Leu Ile His Thr Leu Asn Gln Asn Ser Val
            1055                1060                1065

-continued

```
His Phe Glu Leu Lys Pro Gly Val Arg Val Leu Val His Ala Ala
    1070            1075                1080

His Leu Thr Ala Ala Pro Leu Val Asp Leu Thr Pro Thr His Ser
    1085            1090                1095

Gly Ser Ala Met Leu Met Leu Leu Ser Val Val Phe Val Gly Leu
    1100            1105                1110

Ala Val Phe Val Ile Tyr Lys Phe Lys Arg Lys Ile Pro Gly Ile
    1115            1120                1125

Asn Val Tyr Ala Gln Met Gln Asn Glu Lys Glu Gln Glu Met Ile
    1130            1135                1140

Ser Pro Val Ser His Ser Glu Ser Arg Pro Asn Val Pro Gln Thr
    1145            1150                1155

Glu Leu Arg Arg Pro Gly Gln Leu Ile Asp Glu Lys Val Glu Ser
    1160            1165                1170

Gln Leu Ile Gly Ser Ile Ser Ile Val Ala Glu Asn Gln Ser Thr
    1175            1180                1185

Lys Glu Ile Pro Thr Tyr Val Asn Val
    1190            1195
```

<210> SEQ ID NO 3
<211> LENGTH: 1179
<212> TYPE: PRT
<213> ORGANISM: Homo sapiens
<220> FEATURE:
<221> NAME/KEY: MISC_FEATURE
<222> LOCATION: (1)..(1179)
<223> OTHER INFORMATION: preproSorCS1c, Isoform 3

<400> SEQUENCE: 3

```
Met Gly Lys Val Gly Ala Gly Gly Ser Gln Ala Arg Leu Ser Ala
1                5                  10                 15

Leu Leu Ala Gly Ala Gly Leu Leu Ile Leu Cys Ala Pro Gly Val Cys
        20                  25                  30

Gly Gly Gly Ser Cys Cys Pro Ser Pro His Pro Ser Ser Ala Pro Arg
            35                  40                  45

Ser Ala Ser Thr Pro Arg Gly Phe Ser His Gln Gly Pro Gly Arg
        50                  55                  60

Ala Pro Ala Thr Pro Leu Pro Leu Val Val Arg Pro Leu Phe Ser Val
65                  70                  75                  80

Ala Pro Gly Asp Arg Ala Leu Ser Leu Glu Arg Ala Arg Gly Thr Gly
            85                  90                  95

Ala Ser Met Ala Val Ala Ala Arg Ser Gly Arg Arg Arg Ser Gly
            100                 105                 110

Ala Asp Gln Glu Lys Ala Glu Arg Gly Glu Gly Ala Ser Arg Ser Pro
        115                 120                 125

Arg Gly Val Leu Arg Asp Gly Gly Gln Gln Glu Pro Gly Thr Arg Glu
    130                 135                 140

Arg Asp Pro Asp Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
            165                 170                 175

Met Val His Trp Ser Gly His Asn Ser Ser Val Ile Leu Ile Leu Thr
        180                 185                 190

Lys Leu Tyr Asp Tyr Asn Leu Gly Ser Ile Thr Glu Ser Ser Leu Trp
    195                 200                 205
```

```
Arg Ser Thr Asp Tyr Gly Thr Thr Tyr Glu Lys Leu Asn Asp Lys Val
    210                 215                 220

Gly Leu Lys Thr Ile Leu Ser Tyr Leu Tyr Val Cys Pro Thr Asn Lys
225                 230                 235                 240

Arg Lys Ile Met Leu Leu Thr Asp Pro Glu Ile Glu Ser Ser Leu Leu
                245                 250                 255

Ile Ser Ser Asp Glu Gly Ala Thr Tyr Gln Lys Tyr Arg Leu Asn Phe
            260                 265                 270

Tyr Ile Gln Ser Leu Leu Phe His Pro Lys Gln Glu Asp Trp Ile Leu
        275                 280                 285

Ala Tyr Ser Gln Asp Gln Lys Leu Tyr Ser Ser Ala Glu Phe Gly Arg
290                 295                 300

Arg Trp Gln Leu Ile Gln Glu Gly Val Val Pro Asn Arg Phe Tyr Trp
305                 310                 315                 320

Ser Val Met Gly Ser Asn Lys Glu Pro Asp Leu Val His Leu Glu Ala
                325                 330                 335

Arg Thr Val Asp Gly His Ser His Tyr Leu Thr Cys Arg Met Gln Asn
            340                 345                 350

Cys Thr Glu Ala Asn Arg Asn Gln Pro Phe Pro Gly Tyr Ile Asp Pro
        355                 360                 365

Asp Ser Leu Ile Val Gln Asp His Tyr Val Phe Val Gln Leu Thr Ser
370                 375                 380

Gly Gly Arg Pro His Tyr Val Ser Tyr Arg Arg Asn Ala Phe Ala
385                 390                 395                 400

Gln Met Lys Leu Pro Lys Tyr Ala Leu Pro Lys Asp Met His Val Ile
                405                 410                 415

Ser Thr Asp Glu Asn Gln Val Phe Ala Ala Val Gln Glu Trp Asn Gln
            420                 425                 430

Asn Asp Thr Tyr Asn Leu Tyr Ile Ser Asp Thr Arg Gly Val Tyr Phe
        435                 440                 445

Thr Leu Ala Leu Glu Asn Val Gln Ser Ser Arg Gly Pro Glu Gly Asn
450                 455                 460

Ile Met Ile Asp Leu Tyr Glu Val Ala Gly Ile Lys Gly Met Phe Leu
465                 470                 475                 480

Ala Asn Lys Lys Ile Asp Asn Gln Val Lys Thr Phe Ile Thr Tyr Asn
                485                 490                 495

Lys Gly Arg Asp Trp Arg Leu Leu Gln Ala Pro Asp Thr Asp Leu Arg
            500                 505                 510

Gly Asp Pro Val His Cys Leu Leu Pro Tyr Cys Ser Leu His Leu His
        515                 520                 525

Leu Lys Val Ser Glu Asn Pro Tyr Thr Ser Gly Ile Ile Ala Ser Lys
530                 535                 540

Asp Thr Ala Pro Ser Ile Ile Val Ala Ser Gly Asn Ile Gly Ser Glu
545                 550                 555                 560

Leu Ser Asp Thr Asp Ile Ser Met Phe Val Ser Ser Asp Ala Gly Asn
                565                 570                 575

Thr Trp Arg Gln Ile Phe Glu Glu His Ser Val Leu Tyr Leu Asp
            580                 585                 590

Gln Gly Gly Val Leu Val Ala Met Lys His Thr Ser Leu Pro Ile Arg
        595                 600                 605

His Leu Trp Leu Ser Phe Asp Glu Gly Arg Ser Trp Ser Lys Tyr Ser
610                 615                 620

Phe Thr Ser Ile Pro Leu Phe Val Asp Gly Val Leu Gly Glu Pro Gly
```

-continued

```
        625                 630                 635                 640
    Glu Glu Thr Leu Ile Met Thr Val Phe Gly His Phe Ser His Arg Ser
                        645                 650                 655
    Glu Trp Gln Leu Val Lys Val Asp Tyr Lys Ser Ile Phe Asp Arg Arg
                660                 665                 670
    Cys Ala Glu Glu Asp Tyr Arg Pro Trp Gln Leu His Ser Gln Gly Glu
            675                 680                 685
    Ala Cys Ile Met Gly Ala Lys Arg Ile Tyr Lys Lys Arg Lys Ser Glu
        690                 695                 700
    Arg Lys Cys Met Gln Gly Lys Tyr Ala Gly Ala Met Glu Ser Glu Pro
    705                 710                 715                 720
    Cys Val Cys Thr Glu Ala Asp Phe Asp Cys Asp Tyr Gly Tyr Glu Arg
                    725                 730                 735
    His Ser Asn Gly Gln Cys Leu Pro Ala Phe Trp Phe Asn Pro Ser Ser
                740                 745                 750
    Leu Ser Lys Asp Cys Ser Leu Gly Gln Ser Tyr Leu Asn Ser Thr Gly
            755                 760                 765
    Tyr Arg Lys Val Val Ser Asn Asn Cys Thr Asp Gly Val Arg Glu Gln
        770                 775                 780
    Tyr Thr Ala Lys Pro Gln Lys Cys Pro Gly Lys Ala Pro Arg Gly Leu
    785                 790                 795                 800
    Arg Ile Val Thr Ala Asp Gly Lys Leu Thr Ala Glu Gln Gly His Asn
                    805                 810                 815
    Val Thr Leu Met Val Gln Leu Glu Gly Asp Val Gln Arg Thr Leu
                820                 825                 830
    Ile Gln Val Asp Phe Gly Asp Gly Ile Ala Val Ser Tyr Val Asn Leu
            835                 840                 845
    Ser Ser Met Glu Asp Gly Ile Lys His Val Tyr Gln Asn Val Gly Ile
        850                 855                 860
    Phe Arg Val Thr Val Gln Val Asp Asn Ser Leu Gly Ser Asp Ser Ala
    865                 870                 875                 880
    Val Leu Tyr Leu His Val Thr Cys Pro Leu Glu His Val His Leu Ser
                    885                 890                 895
    Leu Pro Phe Val Thr Thr Lys Asn Lys Glu Val Asn Ala Thr Ala Val
                900                 905                 910
    Leu Trp Pro Ser Gln Val Gly Thr Leu Thr Tyr Val Trp Trp Tyr Gly
            915                 920                 925
    Asn Asn Thr Glu Pro Leu Ile Thr Leu Glu Gly Ser Ile Ser Phe Arg
        930                 935                 940
    Phe Thr Ser Glu Gly Met Asn Thr Ile Thr Val Gln Val Ser Ala Gly
    945                 950                 955                 960
    Asn Ala Ile Leu Gln Asp Thr Lys Thr Ile Ala Val Tyr Glu Glu Phe
                    965                 970                 975
    Arg Ser Leu Arg Leu Ser Phe Ser Pro Asn Leu Asp Asp Tyr Asn Pro
                980                 985                 990
    Asp Ile Pro Glu Trp Arg Arg Asp  Ile Gly Arg Val Ile Lys Lys Ser
            995                 1000                1005
    Leu Val  Glu Ala Thr Gly Val  Pro Gly Gln His Ile  Leu Val Ala
        1010                1015                1020
    Val Leu  Pro Gly Leu Pro Thr  Thr Ala Glu Leu Phe  Val Leu Pro
        1025                1030                1035
    Tyr Gln  Asp Pro Ala Gly Glu  Asn Lys Arg Ser Thr  Asp Asp Leu
        1040                1045                1050
```

```
Glu Gln Ile Ser Glu Leu Leu Ile His Thr Leu Asn Gln Asn Ser
    1055                1060                1065

Val His Phe Glu Leu Lys Pro Gly Val Arg Val Leu Val His Ala
    1070                1075                1080

Ala His Leu Thr Ala Ala Pro Leu Val Asp Leu Thr Pro Thr His
    1085                1090                1095

Ser Gly Ser Ala Met Leu Met Leu Leu Ser Val Val Phe Val Gly
    1100                1105                1110

Leu Ala Val Phe Val Ile Tyr Lys Phe Lys Arg Lys Ile Pro Gly
    1115                1120                1125

Ile Asn Val Tyr Ala Gln Met Gln Asn Glu Lys Glu Gln Glu Met
    1130                1135                1140

Ile Ser Pro Val Ser His Ser Glu Ser Arg Pro Asn Val Pro Gln
    1145                1150                1155

Thr Glu Leu Arg Arg Pro Gly Gln Leu Ile Asp Glu Lys Val Glu
    1160                1165                1170

Ser Gln Leu Ile Gly Lys
    1175

<210> SEQ ID NO 4
<211> LENGTH: 1159
<212> TYPE: PRT
<213> ORGANISM: Homo sapiens
<220> FEATURE:
<221> NAME/KEY: MISC_FEATURE
<222> LOCATION: (1)..(1159)
<223> OTHER INFORMATION: preproSorCS1a, Isoform 4

<400> SEQUENCE: 4

Met Gly Lys Val Gly Ala Gly Gly Ser Gln Ala Arg Leu Ser Ala
1                   5                   10                  15

Leu Leu Ala Gly Ala Gly Leu Leu Ile Leu Cys Ala Pro Gly Val Cys
                20                  25                  30

Gly Gly Gly Ser Cys Cys Pro Ser Pro His Pro Ser Ser Ala Pro Arg
                35                  40                  45

Ser Ala Ser Thr Pro Arg Gly Phe Ser His Gln Gly Pro Gly Arg
    50                  55                  60

Ala Pro Ala Thr Pro Leu Pro Leu Val Val Arg Pro Leu Phe Ser Val
65                  70                  75                  80

Ala Pro Gly Asp Arg Ala Leu Ser Leu Glu Arg Ala Arg Gly Thr Gly
                85                  90                  95

Ala Ser Met Ala Val Ala Ala Arg Ser Gly Arg Arg Arg Ser Gly
                100                 105                 110

Ala Asp Gln Glu Lys Ala Glu Arg Gly Glu Gly Ala Ser Arg Ser Pro
                115                 120                 125

Arg Gly Val Leu Arg Asp Gly Gly Gln Gln Glu Pro Gly Thr Arg Glu
    130                 135                 140

Arg Asp Pro Asp Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                165                 170                 175

Met Val His Trp Ser Gly His Asn Ser Ser Val Ile Leu Ile Leu Thr
                180                 185                 190

Lys Leu Tyr Asp Tyr Asn Leu Gly Ser Ile Thr Glu Ser Ser Leu Trp
                195                 200                 205
```

```
Arg Ser Thr Asp Tyr Gly Thr Thr Tyr Glu Lys Leu Asn Asp Lys Val
    210                 215                 220

Gly Leu Lys Thr Ile Leu Ser Tyr Leu Tyr Val Cys Pro Thr Asn Lys
225                 230                 235                 240

Arg Lys Ile Met Leu Leu Thr Asp Pro Glu Ile Glu Ser Ser Leu Leu
                245                 250                 255

Ile Ser Ser Asp Glu Gly Ala Thr Tyr Gln Lys Tyr Arg Leu Asn Phe
                260                 265                 270

Tyr Ile Gln Ser Leu Leu Phe His Pro Lys Gln Glu Asp Trp Ile Leu
            275                 280                 285

Ala Tyr Ser Gln Asp Gln Lys Leu Tyr Ser Ser Ala Glu Phe Gly Arg
    290                 295                 300

Arg Trp Gln Leu Ile Gln Glu Gly Val Val Pro Asn Arg Phe Tyr Trp
305                 310                 315                 320

Ser Val Met Gly Ser Asn Lys Glu Pro Asp Leu Val His Leu Glu Ala
                325                 330                 335

Arg Thr Val Asp Gly His Ser His Tyr Leu Thr Cys Arg Met Gln Asn
                340                 345                 350

Cys Thr Glu Ala Asn Arg Asn Gln Pro Phe Pro Gly Tyr Ile Asp Pro
            355                 360                 365

Asp Ser Leu Ile Val Gln Asp His Tyr Val Phe Val Gln Leu Thr Ser
    370                 375                 380

Gly Gly Arg Pro His Tyr Val Ser Tyr Arg Arg Asn Ala Phe Ala
385                 390                 395                 400

Gln Met Lys Leu Pro Lys Tyr Ala Leu Pro Lys Asp Met His Val Ile
                405                 410                 415

Ser Thr Asp Glu Asn Gln Val Phe Ala Ala Val Gln Glu Trp Asn Gln
                420                 425                 430

Asn Asp Thr Tyr Asn Leu Tyr Ile Ser Asp Thr Arg Gly Val Tyr Phe
            435                 440                 445

Thr Leu Ala Leu Glu Asn Val Gln Ser Ser Arg Gly Pro Glu Gly Asn
    450                 455                 460

Ile Met Ile Asp Leu Tyr Glu Val Ala Gly Ile Lys Gly Met Phe Leu
465                 470                 475                 480

Ala Asn Lys Lys Ile Asp Asn Gln Val Lys Thr Phe Ile Thr Tyr Asn
                485                 490                 495

Lys Gly Arg Asp Trp Arg Leu Leu Gln Ala Pro Asp Thr Asp Leu Arg
                500                 505                 510

Gly Asp Pro Val His Cys Leu Leu Pro Tyr Cys Ser Leu His Leu His
            515                 520                 525

Leu Lys Val Ser Glu Asn Pro Tyr Thr Ser Gly Ile Ile Ala Ser Lys
    530                 535                 540

Asp Thr Ala Pro Ser Ile Ile Val Ala Ser Gly Asn Ile Gly Ser Glu
545                 550                 555                 560

Leu Ser Asp Thr Asp Ile Ser Met Phe Val Ser Ser Asp Ala Gly Asn
                565                 570                 575

Thr Trp Arg Gln Ile Phe Glu Glu His Ser Val Leu Tyr Leu Asp
                580                 585                 590

Gln Gly Gly Val Leu Val Ala Met Lys His Thr Ser Leu Pro Ile Arg
            595                 600                 605

His Leu Trp Leu Ser Phe Asp Glu Gly Arg Ser Trp Ser Lys Tyr Ser
    610                 615                 620

Phe Thr Ser Ile Pro Leu Phe Val Asp Gly Val Leu Gly Glu Pro Gly
```

-continued

```
            625                 630                 635                 640
        Glu Glu Thr Leu Ile Met Thr Val Phe Gly His Phe Ser His Arg Ser
                        645                 650                 655
        Glu Trp Gln Leu Val Lys Val Asp Tyr Lys Ser Ile Phe Asp Arg Arg
                        660                 665                 670
        Cys Ala Glu Glu Asp Tyr Arg Pro Trp Gln Leu His Ser Gln Gly Glu
                        675                 680                 685
        Ala Cys Ile Met Gly Ala Lys Arg Ile Tyr Lys Lys Arg Lys Ser Glu
                        690                 695                 700
        Arg Lys Cys Met Gln Gly Lys Tyr Ala Gly Ala Met Glu Ser Glu Pro
        705                 710                 715                 720
        Cys Val Cys Thr Glu Ala Asp Phe Asp Cys Asp Tyr Gly Tyr Glu Arg
                        725                 730                 735
        His Ser Asn Gly Gln Cys Leu Pro Ala Phe Trp Phe Asn Pro Ser Ser
                        740                 745                 750
        Leu Ser Lys Asp Cys Ser Leu Gly Gln Ser Tyr Leu Asn Ser Thr Gly
                        755                 760                 765
        Tyr Arg Lys Val Val Ser Asn Asn Cys Thr Asp Gly Val Arg Glu Gln
                        770                 775                 780
        Tyr Thr Ala Lys Pro Gln Lys Cys Pro Gly Lys Ala Pro Arg Gly Leu
        785                 790                 795                 800
        Arg Ile Val Thr Ala Asp Gly Lys Leu Thr Ala Glu Gln Gly His Asn
                        805                 810                 815
        Val Thr Leu Met Val Gln Leu Glu Gly Asp Val Gln Arg Thr Leu
                        820                 825                 830
        Ile Gln Val Asp Phe Gly Asp Gly Ile Ala Val Ser Tyr Val Asn Leu
                        835                 840                 845
        Ser Ser Met Glu Asp Gly Ile Lys His Val Tyr Gln Asn Val Gly Ile
                        850                 855                 860
        Phe Arg Val Thr Val Gln Val Asp Asn Ser Leu Gly Ser Asp Ser Ala
        865                 870                 875                 880
        Val Leu Tyr Leu His Val Thr Cys Pro Leu Glu His Val His Leu Ser
                        885                 890                 895
        Leu Pro Phe Val Thr Thr Lys Asn Lys Glu Val Asn Ala Thr Ala Val
                        900                 905                 910
        Leu Trp Pro Ser Gln Val Gly Thr Leu Thr Tyr Val Trp Trp Tyr Gly
                        915                 920                 925
        Asn Asn Thr Glu Pro Leu Ile Thr Leu Glu Gly Ser Ile Ser Phe Arg
                        930                 935                 940
        Phe Thr Ser Glu Gly Met Asn Thr Ile Thr Val Gln Val Ser Ala Gly
        945                 950                 955                 960
        Asn Ala Ile Leu Gln Asp Thr Lys Thr Ile Ala Val Tyr Glu Glu Phe
                        965                 970                 975
        Arg Ser Leu Arg Leu Ser Phe Ser Pro Asn Leu Asp Asp Tyr Asn Pro
                        980                 985                 990
        Asp Ile Pro Glu Trp Arg Arg Asp Ile Gly Arg Val Ile Lys Lys Ser
                        995                 1000                1005
        Leu Val Glu Ala Thr Gly Val Pro Gly Gln His Ile Leu Val Ala
                        1010                1015                1020
        Val Leu Pro Gly Leu Pro Thr Thr Ala Glu Leu Phe Val Leu Pro
                        1025                1030                1035
        Tyr Gln Asp Pro Ala Gly Glu Asn Lys Arg Ser Thr Asp Asp Leu
                        1040                1045                1050
```

Glu Gln Ile Ser Glu Leu Leu Ile His Thr Leu Asn Gln Asn Ser
    1055                1060                1065

Val His Phe Glu Leu Lys Pro Gly Val Arg Val Leu Val His Ala
    1070                1075                1080

Ala His Leu Thr Ala Ala Pro Leu Val Asp Leu Thr Pro Thr His
    1085                1090                1095

Ser Gly Ser Ala Met Leu Met Leu Leu Ser Val Val Phe Val Gly
    1100                1105                1110

Leu Ala Val Phe Val Ile Tyr Lys Phe Lys Arg Cys Val Ser Leu
    1115                1120                1125

Tyr Pro Arg Ser Pro Thr Pro Asp Leu Phe Leu Leu Pro Asp Arg
    1130                1135                1140

Phe Arg Ser Met Cys Tyr Ser Asp Val His Ser Ser Asp Gly Phe
    1145                1150                1155

Tyr

<210> SEQ ID NO 5
<211> LENGTH: 1100
<212> TYPE: PRT
<213> ORGANISM: Homo sapiens
<220> FEATURE:
<221> NAME/KEY: MISC_FEATURE
<222> LOCATION: (1)..(1100)
<223> OTHER INFORMATION: Soluble preproSorCS1

<400> SEQUENCE: 5

Met Gly Lys Val Gly Ala Gly Gly Ser Gln Ala Arg Leu Ser Ala
1               5                   10                  15

Leu Leu Ala Gly Ala Gly Leu Leu Ile Leu Cys Ala Pro Gly Val Cys
                20                  25                  30

Gly Gly Gly Ser Cys Cys Pro Ser Pro His Pro Ser Ser Ala Pro Arg
                35                  40                  45

Ser Ala Ser Thr Pro Arg Gly Phe Ser His Gln Gly Arg Pro Gly Arg
    50                  55                  60

Ala Pro Ala Thr Pro Leu Pro Leu Val Val Arg Pro Leu Phe Ser Val
65                  70                  75                  80

Ala Pro Gly Asp Arg Ala Leu Ser Leu Glu Arg Ala Arg Gly Thr Gly
                85                  90                  95

Ala Ser Met Ala Val Ala Ala Arg Ser Gly Arg Arg Arg Ser Gly
                100                 105                 110

Ala Asp Gln Glu Lys Ala Glu Arg Gly Glu Gly Ala Ser Arg Ser Pro
                115                 120                 125

Arg Gly Val Leu Arg Asp Gly Gly Gln Gln Glu Pro Gly Thr Arg Glu
    130                 135                 140

Arg Asp Pro Asp Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                165                 170                 175

Met Val His Trp Ser Gly His Asn Ser Ser Val Ile Leu Ile Leu Thr
                180                 185                 190

Lys Leu Tyr Asp Tyr Asn Leu Gly Ser Ile Thr Glu Ser Ser Leu Trp
                195                 200                 205

Arg Ser Thr Asp Tyr Gly Thr Thr Tyr Glu Lys Leu Asn Asp Lys Val
    210                 215                 220

Gly Leu Lys Thr Ile Leu Ser Tyr Leu Tyr Val Cys Pro Thr Asn Lys

-continued

```
                225                 230                 235                 240
Arg Lys Ile Met Leu Leu Thr Asp Pro Glu Ile Glu Ser Ser Leu Leu
                245                 250                 255
Ile Ser Ser Asp Glu Gly Ala Thr Tyr Gln Lys Tyr Arg Leu Asn Phe
                260                 265                 270
Tyr Ile Gln Ser Leu Leu Phe His Pro Lys Gln Glu Asp Trp Ile Leu
                275                 280                 285
Ala Tyr Ser Gln Asp Gln Lys Leu Tyr Ser Ser Ala Glu Phe Gly Arg
                290                 295                 300
Arg Trp Gln Leu Ile Gln Glu Gly Val Val Pro Asn Arg Phe Tyr Trp
305                 310                 315                 320
Ser Val Met Gly Ser Asn Lys Glu Pro Asp Leu Val His Leu Glu Ala
                325                 330                 335
Arg Thr Val Asp Gly His Ser His Tyr Leu Thr Cys Arg Met Gln Asn
                340                 345                 350
Cys Thr Glu Ala Asn Arg Asn Gln Pro Phe Pro Gly Tyr Ile Asp Pro
                355                 360                 365
Asp Ser Leu Ile Val Gln Asp His Tyr Val Phe Val Gln Leu Thr Ser
                370                 375                 380
Gly Gly Arg Pro His Tyr Val Ser Tyr Arg Arg Asn Ala Phe Ala
385                 390                 395                 400
Gln Met Lys Leu Pro Lys Tyr Ala Leu Pro Lys Asp Met His Val Ile
                405                 410                 415
Ser Thr Asp Glu Asn Gln Val Phe Ala Ala Val Gln Glu Trp Asn Gln
                420                 425                 430
Asn Asp Thr Tyr Asn Leu Tyr Ile Ser Asp Thr Arg Gly Val Tyr Phe
                435                 440                 445
Thr Leu Ala Leu Glu Asn Val Gln Ser Ser Arg Gly Pro Glu Gly Asn
                450                 455                 460
Ile Met Ile Asp Leu Tyr Glu Val Ala Gly Ile Lys Gly Met Phe Leu
465                 470                 475                 480
Ala Asn Lys Lys Ile Asp Asn Gln Val Lys Thr Phe Ile Thr Tyr Asn
                485                 490                 495
Lys Gly Arg Asp Trp Arg Leu Leu Gln Ala Pro Asp Thr Asp Leu Arg
                500                 505                 510
Gly Asp Pro Val His Cys Leu Leu Pro Tyr Cys Ser Leu His Leu His
                515                 520                 525
Leu Lys Val Ser Glu Asn Pro Tyr Thr Ser Gly Ile Ile Ala Ser Lys
                530                 535                 540
Asp Thr Ala Pro Ser Ile Ile Val Ala Ser Gly Asn Ile Gly Ser Glu
545                 550                 555                 560
Leu Ser Asp Thr Asp Ile Ser Met Phe Val Ser Ser Asp Ala Gly Asn
                565                 570                 575
Thr Trp Arg Gln Ile Phe Glu Glu His Ser Val Leu Tyr Leu Asp
                580                 585                 590
Gln Gly Gly Val Leu Val Ala Met Lys His Thr Ser Leu Pro Ile Arg
                595                 600                 605
His Leu Trp Leu Ser Phe Asp Glu Gly Arg Ser Trp Ser Lys Tyr Ser
                610                 615                 620
Phe Thr Ser Ile Pro Leu Phe Val Asp Gly Val Leu Gly Glu Pro Gly
625                 630                 635                 640
Glu Glu Thr Leu Ile Met Thr Val Phe Gly His Phe Ser His Arg Ser
                645                 650                 655
```

-continued

```
Glu Trp Gln Leu Val Lys Val Asp Tyr Lys Ser Ile Phe Asp Arg Arg
            660             665             670

Cys Ala Glu Glu Asp Tyr Arg Pro Trp Gln Leu His Ser Gln Gly Glu
            675             680             685

Ala Cys Ile Met Gly Ala Lys Arg Ile Tyr Lys Arg Lys Ser Glu
690             695             700

Arg Lys Cys Met Gln Gly Lys Tyr Ala Gly Ala Met Glu Ser Glu Pro
705             710             715             720

Cys Val Cys Thr Glu Ala Asp Phe Asp Cys Asp Tyr Gly Tyr Glu Arg
            725             730             735

His Ser Asn Gly Gln Cys Leu Pro Ala Phe Trp Phe Asn Pro Ser Ser
            740             745             750

Leu Ser Lys Asp Cys Ser Leu Gly Gln Ser Tyr Leu Asn Ser Thr Gly
            755             760             765

Tyr Arg Lys Val Val Ser Asn Asn Cys Thr Asp Gly Val Arg Glu Gln
            770             775             780

Tyr Thr Ala Lys Pro Gln Lys Cys Pro Gly Lys Ala Pro Arg Gly Leu
785             790             795             800

Arg Ile Val Thr Ala Asp Gly Lys Leu Thr Ala Glu Gln Gly His Asn
            805             810             815

Val Thr Leu Met Val Gln Leu Glu Gly Asp Val Gln Arg Thr Leu
            820             825             830

Ile Gln Val Asp Phe Gly Asp Gly Ile Ala Val Ser Tyr Val Asn Leu
            835             840             845

Ser Ser Met Glu Asp Gly Ile Lys His Val Tyr Gln Asn Val Gly Ile
            850             855             860

Phe Arg Val Thr Val Gln Val Asp Asn Ser Leu Gly Ser Asp Ser Ala
865             870             875             880

Val Leu Tyr Leu His Val Thr Cys Pro Leu Glu His Val His Leu Ser
            885             890             895

Leu Pro Phe Val Thr Thr Lys Asn Lys Glu Val Asn Ala Thr Ala Val
            900             905             910

Leu Trp Pro Ser Gln Val Gly Thr Leu Thr Tyr Val Trp Trp Tyr Gly
            915             920             925

Asn Asn Thr Glu Pro Leu Ile Thr Leu Glu Gly Ser Ile Ser Phe Arg
            930             935             940

Phe Thr Ser Glu Gly Met Asn Thr Ile Thr Val Gln Val Ser Ala Gly
945             950             955             960

Asn Ala Ile Leu Gln Asp Thr Lys Thr Ile Ala Val Tyr Glu Glu Phe
            965             970             975

Arg Ser Leu Arg Leu Ser Phe Ser Pro Asn Leu Asp Asp Tyr Asn Pro
            980             985             990

Asp Ile Pro Glu Trp Arg Arg Asp Ile Gly Arg Val Ile Lys Lys Ser
            995            1000            1005

Leu Val Glu Ala Thr Gly Val Pro Gly Gln His Ile Leu Val Ala
        1010            1015            1020

Val Leu Pro Gly Leu Pro Thr Thr Ala Glu Leu Phe Val Leu Pro
        1025            1030            1035

Tyr Gln Asp Pro Ala Gly Glu Asn Lys Arg Ser Thr Asp Asp Leu
        1040            1045            1050

Glu Gln Ile Ser Glu Leu Leu Ile His Thr Leu Asn Gln Asn Ser
        1055            1060            1065
```

Val His Phe Glu Leu Lys Pro Gly Val Arg Val Leu Val His Ala
1070                1075                1080

Ala His Leu Thr Ala Ala Pro Leu Val Asp Leu Thr Pro Thr His
1085                1090                1095

Ser Gly
1100

<210> SEQ ID NO 6
<211> LENGTH: 1134
<212> TYPE: PRT
<213> ORGANISM: Homo sapiens
<220> FEATURE:
<221> NAME/KEY: MISC_FEATURE
<222> LOCATION: (1)..(1134)
<223> OTHER INFORMATION: proSorCS1b, Isoform 1

<400> SEQUENCE: 6

Gly Gly Ser Cys Cys Pro Ser Pro His Pro Ser Ser Ala Pro Arg Ser
1               5                   10                  15

Ala Ser Thr Pro Arg Gly Phe Ser His Gln Gly Arg Pro Gly Arg Ala
            20                  25                  30

Pro Ala Thr Pro Leu Pro Leu Val Val Arg Pro Leu Phe Ser Val Ala
        35                  40                  45

Pro Gly Asp Arg Ala Leu Ser Leu Glu Arg Ala Arg Gly Thr Gly Ala
    50                  55                  60

Ser Met Ala Val Ala Ala Arg Ser Gly Arg Arg Arg Ser Gly Ala
65                  70                  75                  80

Asp Gln Glu Lys Ala Glu Arg Gly Glu Gly Ala Ser Arg Ser Pro Arg
                85                  90                  95

Gly Val Leu Arg Asp Gly Gly Gln Gln Glu Pro Gly Thr Arg Glu Arg
            100                 105                 110

Asp Pro Asp Lys Ala Thr Arg Phe Arg Met Glu Glu Leu Arg Leu Thr
        115                 120                 125

Ser Thr Thr Phe Ala Leu Thr Gly Asp Ser Ala His Asn Gln Ala Met
    130                 135                 140

Val His Trp Ser Gly His Asn Ser Ser Val Ile Leu Ile Leu Thr Lys
145                 150                 155                 160

Leu Tyr Asp Tyr Asn Leu Gly Ser Ile Thr Glu Ser Ser Leu Trp Arg
                165                 170                 175

Ser Thr Asp Tyr Gly Thr Thr Tyr Glu Lys Leu Asn Asp Lys Val Gly
            180                 185                 190

Leu Lys Thr Ile Leu Ser Tyr Leu Tyr Val Cys Pro Thr Asn Lys Arg
        195                 200                 205

Lys Ile Met Leu Leu Thr Asp Pro Glu Ile Glu Ser Ser Leu Leu Ile
    210                 215                 220

Ser Ser Asp Glu Gly Ala Thr Tyr Gln Lys Tyr Arg Leu Asn Phe Tyr
225                 230                 235                 240

Ile Gln Ser Leu Leu Phe His Pro Lys Gln Glu Asp Trp Ile Leu Ala
                245                 250                 255

Tyr Ser Gln Asp Gln Lys Leu Tyr Ser Ser Ala Glu Phe Gly Arg Arg
            260                 265                 270

Trp Gln Leu Ile Gln Glu Gly Val Pro Asn Arg Phe Tyr Trp Ser
        275                 280                 285

Val Met Gly Ser Asn Lys Glu Pro Asp Leu Val His Leu Glu Ala Arg
    290                 295                 300

Thr Val Asp Gly His Ser His Tyr Leu Thr Cys Arg Met Gln Asn Cys

```
        305                 310                 315                 320
Thr Glu Ala Asn Arg Asn Gln Pro Phe Pro Gly Tyr Ile Asp Pro Asp
                    325                 330                 335
Ser Leu Ile Val Gln Asp His Tyr Val Phe Val Gln Leu Thr Ser Gly
                    340                 345                 350
Gly Arg Pro His Tyr Tyr Val Ser Tyr Arg Arg Asn Ala Phe Ala Gln
                    355                 360                 365
Met Lys Leu Pro Lys Tyr Ala Leu Pro Lys Asp Met His Val Ile Ser
            370                 375                 380
Thr Asp Glu Asn Gln Val Phe Ala Ala Val Gln Glu Trp Asn Gln Asn
385                 390                 395                 400
Asp Thr Tyr Asn Leu Tyr Ile Ser Asp Thr Arg Gly Val Tyr Phe Thr
                    405                 410                 415
Leu Ala Leu Glu Asn Val Gln Ser Ser Arg Gly Pro Glu Gly Asn Ile
                    420                 425                 430
Met Ile Asp Leu Tyr Glu Val Ala Gly Ile Lys Gly Met Phe Leu Ala
            435                 440                 445
Asn Lys Lys Ile Asp Asn Gln Val Lys Thr Phe Ile Thr Tyr Asn Lys
            450                 455                 460
Gly Arg Asp Trp Arg Leu Leu Gln Ala Pro Asp Thr Asp Leu Arg Gly
465                 470                 475                 480
Asp Pro Val His Cys Leu Leu Pro Tyr Cys Ser Leu His Leu His Leu
                    485                 490                 495
Lys Val Ser Glu Asn Pro Tyr Thr Ser Gly Ile Ile Ala Ser Lys Asp
                    500                 505                 510
Thr Ala Pro Ser Ile Ile Val Ala Ser Gly Asn Ile Gly Ser Glu Leu
            515                 520                 525
Ser Asp Thr Asp Ile Ser Met Phe Val Ser Ser Asp Ala Gly Asn Thr
            530                 535                 540
Trp Arg Gln Ile Phe Glu Glu His Ser Val Leu Tyr Leu Asp Gln
545                 550                 555                 560
Gly Gly Val Leu Val Ala Met Lys His Thr Ser Leu Pro Ile Arg His
                    565                 570                 575
Leu Trp Leu Ser Phe Asp Glu Gly Arg Ser Trp Ser Lys Tyr Ser Phe
                    580                 585                 590
Thr Ser Ile Pro Leu Phe Val Asp Gly Val Leu Gly Glu Pro Gly Glu
            595                 600                 605
Glu Thr Leu Ile Met Thr Val Phe Gly His Phe Ser His Arg Ser Glu
            610                 615                 620
Trp Gln Leu Val Lys Val Asp Tyr Lys Ser Ile Phe Asp Arg Arg Cys
625                 630                 635                 640
Ala Glu Glu Asp Tyr Arg Pro Trp Gln Leu His Ser Gln Gly Glu Ala
                    645                 650                 655
Cys Ile Met Gly Ala Lys Arg Ile Tyr Lys Lys Arg Lys Ser Glu Arg
                    660                 665                 670
Lys Cys Met Gln Gly Lys Tyr Ala Gly Ala Met Glu Ser Glu Pro Cys
            675                 680                 685
Val Cys Thr Glu Ala Asp Phe Asp Cys Asp Tyr Gly Tyr Glu Arg His
            690                 695                 700
Ser Asn Gly Gln Cys Leu Pro Ala Phe Trp Phe Asn Pro Ser Ser Leu
705                 710                 715                 720
Ser Lys Asp Cys Ser Leu Gly Gln Ser Tyr Leu Asn Ser Thr Gly Tyr
                    725                 730                 735
```

```
Arg Lys Val Val Ser Asn Asn Cys Thr Asp Gly Val Arg Glu Gln Tyr
            740                 745                 750

Thr Ala Lys Pro Gln Lys Cys Pro Gly Lys Ala Pro Arg Gly Leu Arg
            755                 760                 765

Ile Val Thr Ala Asp Gly Lys Leu Thr Ala Glu Gln Gly His Asn Val
            770                 775                 780

Thr Leu Met Val Gln Leu Glu Glu Gly Asp Val Gln Arg Thr Leu Ile
785                 790                 795                 800

Gln Val Asp Phe Gly Asp Gly Ile Ala Val Ser Tyr Val Asn Leu Ser
            805                 810                 815

Ser Met Glu Asp Gly Ile Lys His Val Tyr Gln Asn Val Gly Ile Phe
            820                 825                 830

Arg Val Thr Val Gln Val Asp Asn Ser Leu Gly Ser Asp Ser Ala Val
            835                 840                 845

Leu Tyr Leu His Val Thr Cys Pro Leu Glu His Val His Leu Ser Leu
    850                 855                 860

Pro Phe Val Thr Thr Lys Asn Lys Glu Val Asn Ala Thr Ala Val Leu
865                 870                 875                 880

Trp Pro Ser Gln Val Gly Thr Leu Thr Tyr Val Trp Trp Tyr Gly Asn
            885                 890                 895

Asn Thr Glu Pro Leu Ile Thr Leu Glu Gly Ser Ile Ser Phe Arg Phe
            900                 905                 910

Thr Ser Glu Gly Met Asn Thr Ile Thr Val Gln Val Ser Ala Gly Asn
            915                 920                 925

Ala Ile Leu Gln Asp Thr Lys Thr Ile Ala Val Tyr Glu Glu Phe Arg
            930                 935                 940

Ser Leu Arg Leu Ser Phe Ser Pro Asn Leu Asp Asp Tyr Asn Pro Asp
945                 950                 955                 960

Ile Pro Glu Trp Arg Arg Asp Ile Gly Arg Val Ile Lys Lys Ser Leu
            965                 970                 975

Val Glu Ala Thr Gly Val Pro Gly Gln His Ile Leu Val Ala Val Leu
            980                 985                 990

Pro Gly Pro Thr Thr Ala Glu Leu Phe Val Leu Pro Tyr Gln Asp Pro
            995                 1000                1005

Ala Gly Glu Asn Lys Arg Ser Thr Asp Asp Leu Glu Gln Ile Ser
    1010                1015                1020

Glu Leu Leu Ile His Thr Leu Asn Gln Asn Ser Val His Phe Glu
    1025                1030                1035

Leu Lys Pro Gly Val Arg Val Leu Val His Ala Ala His Leu Thr
    1040                1045                1050

Ala Ala Pro Leu Val Asp Leu Thr Pro Thr His Ser Gly Ser Ala
    1055                1060                1065

Met Leu Met Leu Leu Ser Val Val Phe Val Gly Leu Ala Val Phe
    1070                1075                1080

Val Ile Tyr Lys Phe Lys Arg Arg Val Ala Leu Pro Ser Pro Pro
    1085                1090                1095

Ser Pro Ser Thr Gln Pro Gly Asp Ser Ser Leu Arg Leu Gln Arg
    1100                1105                1110

Ala Arg His Ala Thr Pro Pro Ser Thr Pro Lys Arg Gly Ser Ala
    1115                1120                1125

Gly Ala Gln Tyr Ala Ile
    1130
```

```
<210> SEQ ID NO 7
<211> LENGTH: 1164
<212> TYPE: PRT
<213> ORGANISM: Homo sapiens
<220> FEATURE:
<221> NAME/KEY: MISC_FEATURE
<222> LOCATION: (1)..(1164)
<223> OTHER INFORMATION: proSorCS1, Isoform 2

<400> SEQUENCE: 7

Gly Gly Ser Cys Cys Pro Ser Pro His Pro Ser Ser Ala Pro Arg Ser
1               5                   10                  15

Ala Ser Thr Pro Arg Gly Phe Ser His Gln Gly Arg Pro Gly Arg Ala
            20                  25                  30

Pro Ala Thr Pro Leu Pro Leu Val Val Arg Pro Leu Phe Ser Val Ala
        35                  40                  45

Pro Gly Asp Arg Ala Leu Ser Leu Glu Arg Ala Arg Gly Thr Gly Ala
    50                  55                  60

Ser Met Ala Val Ala Ala Arg Ser Gly Arg Arg Arg Ser Gly Ala
65                  70                  75                  80

Asp Gln Glu Lys Ala Glu Arg Gly Glu Gly Ala Ser Arg Ser Pro Arg
                85                  90                  95

Gly Val Leu Arg Asp Gly Gly Gln Gln Glu Pro Gly Thr Arg Glu Arg
            100                 105                 110

Asp Pro Asp Lys Ala Thr Arg Phe Arg Met Glu Glu Leu Arg Leu Thr
        115                 120                 125

Ser Thr Thr Phe Ala Leu Thr Gly Asp Ser Ala His Asn Gln Ala Met
130                 135                 140

Val His Trp Ser Gly His Asn Ser Ser Val Ile Leu Ile Leu Thr Lys
145                 150                 155                 160

Leu Tyr Asp Tyr Asn Leu Gly Ser Ile Thr Glu Ser Ser Leu Trp Arg
                165                 170                 175

Ser Thr Asp Tyr Gly Thr Thr Tyr Glu Lys Leu Asn Asp Lys Val Gly
            180                 185                 190

Leu Lys Thr Ile Leu Ser Tyr Leu Tyr Val Cys Pro Thr Asn Lys Arg
        195                 200                 205

Lys Ile Met Leu Leu Thr Asp Pro Glu Ile Glu Ser Ser Leu Leu Ile
    210                 215                 220

Ser Ser Asp Glu Gly Ala Thr Tyr Gln Lys Tyr Arg Leu Asn Phe Tyr
225                 230                 235                 240

Ile Gln Ser Leu Leu Phe His Pro Lys Gln Glu Asp Trp Ile Leu Ala
                245                 250                 255

Tyr Ser Gln Asp Gln Lys Leu Tyr Ser Ser Ala Glu Phe Gly Arg Arg
            260                 265                 270

Trp Gln Leu Ile Gln Glu Gly Val Val Pro Asn Arg Phe Tyr Trp Ser
        275                 280                 285

Val Met Gly Ser Asn Lys Glu Pro Asp Leu Val His Leu Glu Ala Arg
    290                 295                 300

Thr Val Asp Gly His Ser His Tyr Leu Thr Cys Arg Met Gln Asn Cys
305                 310                 315                 320

Thr Glu Ala Asn Arg Gln Pro Phe Pro Gly Tyr Ile Asp Pro Asp Ser
                325                 330                 335

Leu Ile Val Gln Asp His Tyr Val Phe Val Gln Leu Thr Ser Gly Gly
            340                 345                 350

Arg Pro His Tyr Tyr Val Ser Tyr Arg Arg Asn Ala Phe Ala Gln Met
```

```
            355                 360                 365
Lys Leu Pro Lys Tyr Ala Leu Pro Lys Asp Met His Val Ile Ser Thr
370                 375                 380

Asp Glu Asn Gln Val Phe Ala Val Gln Glu Trp Asn Gln Asn Asp
385                 390                 395                 400

Thr Tyr Asn Leu Tyr Ile Ser Asp Thr Arg Gly Val Tyr Phe Thr Leu
                405                 410                 415

Ala Leu Glu Asn Val Gln Ser Ser Arg Gly Pro Glu Gly Asn Ile Met
                420                 425                 430

Ile Asp Leu Tyr Glu Val Ala Gly Ile Lys Gly Met Phe Leu Ala Asn
                435                 440                 445

Lys Lys Ile Asp Asn Gln Val Lys Thr Phe Ile Thr Tyr Asn Lys Gly
            450                 455                 460

Arg Asp Trp Arg Leu Leu Gln Ala Pro Asp Thr Asp Leu Arg Gly Asp
465                 470                 475                 480

Pro Val His Cys Leu Leu Pro Tyr Cys Ser Leu His Leu His Leu Lys
                485                 490                 495

Val Ser Glu Asn Pro Tyr Thr Ser Gly Ile Ile Ala Ser Lys Asp Thr
                500                 505                 510

Ala Pro Ser Ile Ile Val Ala Ser Gly Asn Ile Gly Ser Glu Leu Ser
            515                 520                 525

Asp Thr Asp Ile Ser Met Phe Val Ser Ser Asp Ala Gly Asn Thr Trp
            530                 535                 540

Arg Gln Ile Phe Glu Glu His Ser Val Leu Tyr Leu Asp Gln Gly Gly
545                 550                 555                 560

Gly Val Leu Val Ala Met Lys His Thr Ser Leu Pro Ile Arg His Leu
                565                 570                 575

Trp Leu Ser Phe Asp Glu Gly Arg Ser Trp Ser Lys Tyr Ser Phe Thr
                580                 585                 590

Ser Ile Pro Leu Phe Val Asp Gly Val Leu Gly Glu Pro Gly Glu Glu
            595                 600                 605

Thr Leu Ile Met Thr Val Phe Gly His Phe Ser His Arg Ser Glu Trp
610                 615                 620

Gln Leu Val Lys Val Asp Tyr Lys Ser Ile Phe Asp Arg Arg Cys Ala
625                 630                 635                 640

Glu Glu Asp Tyr Arg Pro Trp Gln Leu His Ser Gln Gly Glu Ala Cys
                645                 650                 655

Ile Met Gly Ala Lys Arg Ile Tyr Lys Lys Arg Lys Ser Glu Arg Lys
                660                 665                 670

Cys Met Gln Gly Lys Tyr Ala Gly Ala Met Glu Ser Glu Pro Cys Val
            675                 680                 685

Cys Thr Glu Ala Asp Phe Asp Cys Asp Tyr Gly Tyr Glu Arg His Ser
            690                 695                 700

Asn Gly Gln Cys Leu Pro Ala Phe Trp Phe Asn Pro Ser Ser Leu Ser
705                 710                 715                 720

Lys Asp Cys Ser Leu Gly Gln Ser Tyr Leu Asn Ser Thr Gly Tyr Arg
                725                 730                 735

Lys Val Val Ser Asn Asn Cys Thr Asp Gly Val Arg Glu Gln Tyr Thr
                740                 745                 750

Ala Lys Pro Gln Lys Cys Pro Gly Lys Ala Pro Arg Gly Leu Arg Ile
            755                 760                 765

Val Thr Ala Asp Gly Lys Leu Thr Ala Glu Gln Gly His Asn Val Thr
            770                 775                 780
```

Leu Met Val Gln Leu Glu Glu Gly Asp Val Gln Arg Thr Leu Ile Gln
785                 790                 795                 800

Val Asp Phe Gly Asp Gly Ile Ala Val Ser Tyr Val Asn Leu Ser Ser
                805                 810                 815

Met Glu Asp Gly Ile Lys His Val Tyr Gln Asn Val Gly Ile Phe Arg
            820                 825                 830

Val Thr Val Gln Val Asp Asn Ser Leu Gly Ser Asp Ser Ala Val Leu
        835                 840                 845

Tyr Leu His Val Thr Cys Pro Leu Glu His Val His Leu Ser Leu Pro
850                 855                 860

Phe Val Thr Thr Lys Asn Lys Glu Val Asn Ala Thr Ala Val Leu Trp
865                 870                 875                 880

Pro Ser Gln Val Gly Thr Leu Thr Tyr Val Trp Trp Tyr Gly Asn Asn
                885                 890                 895

Thr Glu Pro Leu Ile Thr Leu Glu Gly Ser Ile Ser Phe Arg Phe Thr
                900                 905                 910

Ser Glu Gly Met Asn Thr Ile Thr Val Gln Val Ser Ala Gly Asn Ala
            915                 920                 925

Ile Leu Gln Asp Thr Lys Thr Ile Ala Val Tyr Glu Glu Phe Arg Ser
930                 935                 940

Leu Arg Leu Ser Phe Ser Pro Asn Leu Asp Asp Tyr Asn Pro Asp Ile
945                 950                 955                 960

Pro Glu Trp Arg Arg Asp Ile Gly Arg Val Ile Lys Lys Ser Leu Val
                965                 970                 975

Glu Ala Thr Gly Val Pro Gly Gln His Ile Leu Val Ala Val Leu Pro
            980                 985                 990

Gly Leu Pro Thr Thr Ala Glu Leu Phe Val Leu Pro Tyr Gln Asp Pro
        995                 1000                1005

Ala Gly Glu Asn Lys Arg Ser Thr Asp Asp Leu Glu Gln Ile Ser
    1010                1015                1020

Glu Leu Leu Ile His Thr Leu Asn Gln Asn Ser Val His Phe Glu
    1025                1030                1035

Leu Lys Pro Gly Val Arg Val Leu Val His Ala Ala His Leu Thr
    1040                1045                1050

Ala Ala Pro Leu Val Asp Leu Thr Pro Thr His Ser Gly Ser Ala
    1055                1060                1065

Met Leu Met Leu Leu Ser Val Phe Val Gly Leu Ala Val Phe
    1070                1075                1080

Val Ile Tyr Lys Phe Lys Arg Lys Ile Pro Gly Ile Asn Val Tyr
    1085                1090                1095

Ala Gln Met Gln Asn Glu Lys Glu Gln Glu Met Ile Ser Pro Val
    1100                1105                1110

Ser His Ser Glu Ser Arg Pro Asn Val Pro Gln Thr Glu Leu Arg
    1115                1120                1125

Arg Pro Gly Gln Leu Ile Asp Glu Lys Val Glu Ser Gln Leu Ile
    1130                1135                1140

Gly Ser Ile Ser Ile Val Ala Glu Asn Gln Ser Thr Lys Glu Ile
    1145                1150                1155

Pro Thr Tyr Val Asn Val
    1160

<210> SEQ ID NO 8
<211> LENGTH: 1146

<212> TYPE: PRT
<213> ORGANISM: Homo sapiens
<220> FEATURE:
<221> NAME/KEY: MISC_FEATURE
<222> LOCATION: (1)..(1146)
<223> OTHER INFORMATION: proSorCS1c, Isoform 3

<400> SEQUENCE: 8

```
Gly Gly Ser Cys Cys Pro Ser Pro His Pro Ser Ala Pro Arg Ser
1               5                   10                  15

Ala Ser Thr Pro Arg Gly Phe Ser His Gln Gly Arg Pro Gly Arg Ala
            20                  25                  30

Pro Ala Thr Pro Leu Pro Leu Val Val Arg Pro Leu Phe Ser Val Ala
            35                  40                  45

Pro Gly Asp Arg Ala Leu Ser Leu Glu Arg Ala Arg Gly Thr Gly Ala
50                  55                  60

Ser Met Ala Val Ala Ala Arg Ser Gly Arg Arg Arg Ser Gly Ala
65                  70                  75                  80

Asp Gln Glu Lys Ala Glu Arg Gly Glu Gly Ala Ser Arg Ser Pro Arg
                85                  90                  95

Gly Val Leu Arg Asp Gly Gly Gln Gln Glu Pro Gly Thr Arg Glu Arg
            100                 105                 110

Asp Pro Asp Lys Ala Thr Arg Phe Arg Met Glu Glu Leu Arg Leu Thr
            115                 120                 125

Ser Thr Thr Phe Ala Leu Thr Gly Asp Ser Ala His Asn Gln Ala Met
130                 135                 140

Val His Trp Ser Gly His Asn Ser Ser Val Ile Leu Ile Leu Thr Lys
145                 150                 155                 160

Leu Tyr Asp Tyr Asn Leu Gly Ser Ile Thr Glu Ser Ser Leu Trp Arg
                165                 170                 175

Ser Thr Asp Tyr Gly Thr Thr Tyr Glu Lys Leu Asn Asp Lys Val Gly
            180                 185                 190

Leu Lys Thr Ile Leu Ser Tyr Leu Tyr Val Cys Pro Thr Asn Lys Arg
            195                 200                 205

Lys Ile Met Leu Leu Thr Asp Pro Glu Ile Glu Ser Ser Leu Leu Ile
210                 215                 220

Ser Ser Asp Glu Gly Ala Thr Tyr Gln Lys Tyr Arg Leu Asn Phe Tyr
225                 230                 235                 240

Ile Gln Ser Leu Leu Phe His Pro Lys Gln Glu Asp Trp Ile Leu Ala
                245                 250                 255

Tyr Ser Gln Asp Gln Lys Leu Tyr Ser Ser Ala Glu Phe Gly Arg Arg
            260                 265                 270

Trp Gln Leu Ile Gln Glu Gly Val Val Pro Asn Arg Phe Tyr Trp Ser
            275                 280                 285

Val Met Gly Ser Asn Lys Glu Pro Asp Leu Val His Leu Glu Ala Arg
290                 295                 300

Thr Val Asp Gly His Ser His Tyr Leu Thr Cys Arg Met Gln Asn Cys
305                 310                 315                 320

Thr Glu Ala Asn Arg Asn Gln Pro Phe Pro Gly Tyr Ile Asp Pro Asp
                325                 330                 335

Ser Leu Ile Val Gln Asp His Tyr Val Phe Val Gln Leu Thr Ser Gly
            340                 345                 350

Gly Arg Pro His Tyr Tyr Val Ser Tyr Arg Arg Asn Ala Phe Ala Gln
            355                 360                 365

Met Lys Leu Pro Lys Tyr Ala Leu Pro Lys Asp Met His Val Ile Ser
```

```
             370             375              380
Thr Asp Glu Asn Gln Val Phe Ala Ala Val Gln Glu Trp Asn Gln Asn
385                 390                 395                 400

Asp Thr Tyr Asn Leu Tyr Ile Ser Asp Thr Arg Gly Val Tyr Phe Thr
            405                 410                 415

Leu Ala Leu Glu Asn Val Gln Ser Ser Arg Gly Pro Glu Gly Asn Ile
                420                 425                 430

Met Ile Asp Leu Tyr Glu Val Ala Gly Ile Lys Gly Met Phe Leu Ala
            435                 440                 445

Asn Lys Lys Ile Asp Asn Gln Val Lys Thr Phe Ile Thr Tyr Asn Lys
450                 455                 460

Gly Arg Asp Trp Arg Leu Leu Gln Ala Pro Asp Thr Asp Leu Arg Gly
465                 470                 475                 480

Asp Pro Val His Cys Leu Leu Pro Tyr Cys Ser Leu His Leu His Leu
                485                 490                 495

Lys Val Ser Glu Asn Pro Tyr Thr Ser Gly Ile Ile Ala Ser Lys Asp
                500                 505                 510

Thr Ala Pro Ser Ile Ile Val Ala Ser Gly Asn Ile Gly Ser Glu Leu
            515                 520                 525

Ser Asp Thr Asp Ile Ser Met Phe Val Ser Ser Asp Ala Gly Asn Thr
530                 535                 540

Trp Arg Gln Ile Phe Glu Glu His Ser Val Leu Tyr Leu Asp Gln
545                 550                 555                 560

Gly Gly Val Leu Val Ala Met Lys His Thr Ser Leu Pro Ile Arg His
                565                 570                 575

Leu Trp Leu Ser Phe Asp Glu Gly Arg Ser Trp Ser Lys Tyr Ser Phe
                580                 585                 590

Thr Ser Ile Pro Leu Phe Val Asp Gly Val Leu Gly Glu Pro Gly Glu
            595                 600                 605

Glu Thr Leu Ile Met Thr Val Phe Gly His Phe Ser His Arg Ser Glu
            610                 615                 620

Trp Gln Leu Val Lys Val Asp Tyr Lys Ser Ile Phe Asp Arg Arg Cys
625                 630                 635                 640

Ala Glu Glu Asp Tyr Arg Pro Trp Gln Leu His Ser Gln Gly Glu Ala
                645                 650                 655

Cys Ile Met Gly Ala Lys Arg Ile Tyr Lys Lys Arg Lys Ser Glu Arg
                660                 665                 670

Lys Cys Met Gln Gly Lys Tyr Ala Gly Ala Met Glu Ser Glu Pro Cys
            675                 680                 685

Val Cys Thr Glu Ala Asp Phe Asp Cys Asp Tyr Gly Tyr Glu Arg His
            690                 695                 700

Ser Asn Gly Gln Cys Leu Pro Ala Phe Trp Phe Asn Pro Ser Ser Leu
705                 710                 715                 720

Ser Lys Asp Cys Ser Leu Gly Gln Ser Tyr Leu Asn Ser Thr Gly Tyr
                725                 730                 735

Arg Lys Val Val Ser Asn Asn Cys Thr Asp Gly Val Arg Glu Gln Tyr
                740                 745                 750

Thr Ala Lys Pro Gln Lys Cys Pro Gly Lys Ala Pro Arg Gly Leu Arg
            755                 760                 765

Ile Val Thr Ala Asp Gly Lys Leu Thr Ala Glu Gln Gly His Asn Val
            770                 775                 780

Thr Leu Met Val Gln Leu Glu Glu Gly Asp Val Gln Arg Thr Leu Ile
785                 790                 795                 800
```

Gln Val Asp Phe Gly Asp Gly Ile Ala Val Ser Tyr Val Asn Leu Ser
                805                 810                 815

Ser Met Glu Asp Gly Ile Lys His Val Tyr Gln Asn Val Gly Ile Phe
                820                 825                 830

Arg Val Thr Val Gln Val Asp Asn Ser Leu Gly Ser Asp Ser Ala Val
            835                 840                 845

Leu Tyr Leu His Val Thr Cys Pro Leu Glu His Val His Leu Ser Leu
        850                 855                 860

Pro Phe Val Thr Thr Lys Asn Lys Glu Val Asn Ala Thr Ala Val Leu
865                 870                 875                 880

Trp Pro Ser Gln Val Gly Thr Leu Thr Tyr Val Trp Trp Tyr Gly Asn
                885                 890                 895

Asn Thr Glu Pro Leu Ile Thr Leu Glu Gly Ser Ile Ser Phe Arg Phe
                900                 905                 910

Thr Ser Glu Gly Met Asn Thr Ile Thr Val Gln Val Ser Ala Gly Asn
            915                 920                 925

Ala Ile Leu Gln Asp Thr Lys Thr Ile Ala Val Tyr Glu Glu Phe Arg
        930                 935                 940

Ser Leu Arg Leu Ser Phe Ser Pro Asn Leu Asp Asp Tyr Asn Pro Asp
945                 950                 955                 960

Ile Pro Glu Trp Arg Arg Asp Ile Gly Arg Val Ile Lys Lys Ser Leu
                965                 970                 975

Val Glu Ala Thr Gly Val Pro Gly Gln His Ile Leu Val Ala Val Leu
            980                 985                 990

Pro Gly Leu Pro Thr Thr Ala Glu Leu Phe Val Leu Pro Tyr Gln Asp
                995                1000                1005

Pro Ala Gly Glu Asn Lys Arg Ser Thr Asp Asp Leu Glu Gln Ile
        1010                1015                1020

Ser Glu Leu Leu Ile His Thr Leu Asn Gln Asn Ser Val His Phe
        1025                1030                1035

Glu Leu Lys Pro Gly Val Arg Val Leu Val His Ala Ala His Leu
        1040                1045                1050

Thr Ala Ala Pro Leu Val Asp Leu Thr Pro Thr His Ser Gly Ser
        1055                1060                1065

Ala Met Leu Met Leu Leu Ser Val Val Phe Val Gly Leu Ala Val
        1070                1075                1080

Phe Val Ile Tyr Lys Phe Lys Arg Lys Ile Pro Gly Ile Asn Val
        1085                1090                1095

Tyr Ala Gln Met Gln Asn Glu Lys Glu Gln Glu Met Ile Ser Pro
        1100                1105                1110

Val Ser His Ser Glu Ser Arg Pro Asn Val Pro Gln Thr Glu Leu
        1115                1120                1125

Arg Arg Pro Gly Gln Leu Ile Asp Glu Lys Val Glu Ser Gln Leu
        1130                1135                1140

Ile Gly Lys
    1145

<210> SEQ ID NO 9
<211> LENGTH: 1125
<212> TYPE: PRT
<213> ORGANISM: Homo sapiens
<220> FEATURE:
<221> NAME/KEY: MISC_FEATURE
<222> LOCATION: (1)..(1125)
<223> OTHER INFORMATION: proSorCS1a, Isoform 4

<400> SEQUENCE: 9

```
Gly Gly Ser Cys Cys Pro Ser Pro His Pro Ser Ser Ala Pro Arg Ser
1               5                   10                  15

Ala Ser Thr Pro Arg Gly Phe Ser His Gln Gly Arg Pro Gly Arg Ala
            20                  25                  30

Pro Ala Thr Pro Leu Pro Leu Val Val Arg Pro Leu Phe Ser Val Ala
        35                  40                  45

Pro Gly Asp Arg Ala Leu Ser Leu Glu Arg Ala Arg Gly Thr Gly Ala
    50                  55                  60

Ser Met Ala Val Ala Ala Arg Ser Gly Arg Arg Arg Ser Gly Ala
65                  70                  75                  80

Asp Gln Glu Lys Ala Glu Arg Gly Glu Gly Ala Ser Arg Ser Pro Arg
                85                  90                  95

Gly Val Leu Arg Asp Gly Gly Gln Gln Glu Pro Gly Thr Arg Glu Arg
                100                 105                 110

Asp Pro Asp Lys Ala Thr Arg Phe Arg Met Glu Glu Leu Arg Leu Thr
            115                 120                 125

Ser Thr Thr Phe Ala Leu Thr Gly Asp Ser Ala His Asn Gln Ala Met
130                 135                 140

Val His Trp Ser Gly His Asn Ser Ser Val Ile Leu Ile Leu Thr Lys
145                 150                 155                 160

Leu Tyr Asp Tyr Asn Leu Gly Ser Ile Thr Glu Ser Ser Leu Trp Arg
                165                 170                 175

Ser Thr Asp Tyr Gly Thr Thr Tyr Glu Lys Leu Asn Asp Lys Val Gly
            180                 185                 190

Leu Lys Thr Ile Leu Ser Tyr Leu Tyr Val Cys Pro Thr Asn Lys Arg
        195                 200                 205

Lys Ile Met Leu Leu Thr Asp Pro Glu Ile Glu Ser Ser Leu Leu Ile
    210                 215                 220

Ser Ser Asp Glu Gly Ala Thr Tyr Gln Lys Tyr Arg Leu Asn Phe Tyr
225                 230                 235                 240

Ile Gln Ser Leu Leu Phe His Pro Lys Gln Glu Asp Trp Ile Leu Ala
                245                 250                 255

Tyr Ser Gln Asp Gln Lys Leu Tyr Ser Ser Ala Glu Phe Gly Arg Arg
            260                 265                 270

Trp Gln Leu Ile Gln Glu Gly Val Val Pro Asn Arg Phe Tyr Trp Ser
        275                 280                 285

Val Met Gly Ser Asn Lys Glu Pro Asp Leu Val His Leu Glu Ala Arg
    290                 295                 300

Thr Val Asp Gly His Ser His Tyr Leu Thr Cys Arg Met Gln Asn Cys
305                 310                 315                 320

Thr Glu Ala Asn Arg Asn Gln Pro Phe Pro Gly Tyr Ile Asp Pro Asp
                325                 330                 335

Ser Leu Ile Val Gln Asp His Tyr Val Phe Val Gln Leu Thr Ser Gly
            340                 345                 350

Gly Arg Pro His Tyr Tyr Val Ser Tyr Arg Arg Asn Ala Phe Ala Gln
        355                 360                 365

Met Lys Leu Pro Lys Tyr Ala Leu Pro Lys Asp Met His Val Ile Ser
    370                 375                 380

Thr Asp Glu Asn Gln Val Phe Ala Ala Val Gln Glu Trp Asn Gln Asn
385                 390                 395                 400

Asp Thr Tyr Asn Leu Tyr Ile Ser Asp Thr Arg Gly Val Tyr Phe Thr
```

```
            405                 410                 415
Leu Ala Leu Glu Asn Val Gln Ser Ser Arg Gly Pro Glu Gly Asn Ile
            420                 425                 430

Met Ile Asp Leu Tyr Glu Val Ala Gly Ile Lys Gly Met Phe Leu Ala
            435                 440                 445

Asn Lys Lys Ile Asp Asn Gln Val Lys Thr Phe Ile Thr Tyr Asn Lys
            450                 455                 460

Gly Arg Asp Trp Arg Leu Leu Gln Ala Pro Asp Thr Asp Leu Arg Gly
465                 470                 475                 480

Asp Pro Val His Cys Leu Leu Pro Tyr Cys Ser Leu His Leu His Leu
                    485                 490                 495

Lys Val Ser Glu Asn Pro Tyr Thr Ser Gly Ile Ala Ser Lys Asp Thr
            500                 505                 510

Ala Pro Ser Ile Ile Val Ala Ser Gly Asn Ile Gly Ser Glu Leu Ser
            515                 520                 525

Asp Thr Asp Ile Ser Met Phe Val Ser Asp Ala Gly Asn Thr Trp
            530                 535                 540

Arg Gln Ile Phe Glu Glu His Ser Val Leu Tyr Leu Asp Gln Gly
545                 550                 555                 560

Gly Val Leu Val Ala Met Lys His Thr Ser Leu Pro Ile Arg His Leu
                    565                 570                 575

Trp Leu Ser Phe Asp Glu Gly Arg Ser Trp Ser Lys Tyr Ser Phe Thr
                    580                 585                 590

Ser Ile Pro Leu Phe Val Asp Gly Val Leu Gly Glu Pro Gly Glu Glu
            595                 600                 605

Thr Leu Ile Met Thr Val Phe Gly His Phe Ser His Arg Ser Glu Trp
            610                 615                 620

Gln Leu Val Lys Val Asp Tyr Lys Ser Ile Phe Asp Arg Arg Cys Ala
625                 630                 635                 640

Glu Glu Asp Tyr Arg Pro Trp Gln Leu His Ser Gln Gly Glu Ala Cys
                    645                 650                 655

Ile Met Gly Ala Lys Arg Ile Tyr Lys Lys Arg Lys Ser Glu Arg Lys
            660                 665                 670

Cys Met Gln Gly Lys Tyr Ala Gly Ala Met Glu Ser Glu Pro Cys Val
            675                 680                 685

Cys Thr Glu Ala Asp Phe Asp Cys Asp Tyr Gly Tyr Glu Arg His Ser
            690                 695                 700

Asn Gly Gln Cys Leu Pro Ala Phe Trp Phe Asn Pro Ser Ser Leu Ser
705                 710                 715                 720

Lys Asp Cys Ser Leu Gly Gln Ser Tyr Leu Asn Ser Thr Gly Tyr Arg
            725                 730                 735

Lys Val Val Ser Asn Asn Cys Thr Asp Gly Val Arg Glu Gln Tyr Thr
            740                 745                 750

Ala Lys Pro Gln Lys Cys Pro Gly Lys Ala Pro Arg Gly Leu Arg Ile
            755                 760                 765

Val Thr Ala Asp Gly Lys Leu Thr Ala Glu Gln Gly His Asn Val Thr
            770                 775                 780

Leu Met Val Gln Leu Glu Glu Gly Asp Val Gln Arg Thr Leu Ile Gln
785                 790                 795                 800

Val Asp Phe Gly Asp Gly Ile Ala Val Ser Tyr Val Asn Leu Ser Ser
                    805                 810                 815

Met Glu Asp Gly Ile Lys His Val Tyr Gln Asn Val Gly Ile Phe Arg
            820                 825                 830
```

```
Val Thr Val Gln Val Asp Asn Ser Leu Gly Ser Asp Ser Ala Val Leu
        835                 840                 845

Tyr Leu His Val Thr Cys Pro Leu Glu His Val His Leu Ser Leu Pro
    850                 855                 860

Phe Val Thr Thr Lys Asn Lys Glu Val Asn Ala Thr Ala Val Leu Trp
865                 870                 875                 880

Pro Ser Gln Val Gly Thr Leu Thr Tyr Val Trp Trp Tyr Gly Asn Asn
                885                 890                 895

Thr Glu Pro Leu Ile Thr Leu Glu Gly Ser Ile Ser Phe Arg Phe Thr
            900                 905                 910

Ser Glu Gly Met Asn Thr Ile Thr Val Gln Val Ser Ala Gly Asn Ala
        915                 920                 925

Ile Leu Gln Asp Thr Lys Thr Ile Ala Val Tyr Glu Glu Phe Arg Ser
    930                 935                 940

Leu Arg Leu Ser Phe Ser Pro Asn Leu Asp Asp Tyr Asn Pro Asp Ile
945                 950                 955                 960

Pro Glu Trp Arg Arg Asp Ile Gly Arg Val Ile Lys Lys Ser Leu Val
                965                 970                 975

Glu Ala Thr Gly Val Pro Gly Gln His Ile Leu Val Ala Val Leu Pro
            980                 985                 990

Gly Leu Pro Thr Thr Ala Glu Leu Phe Val Leu Pro Tyr Gln Asp Pro
        995                 1000                1005

Ala Gly Glu Asn Lys Arg Ser Thr Asp Asp Leu Glu Gln Ile Ser
    1010                1015                1020

Glu Leu Leu Ile His Thr Leu Asn Gln Asn Ser Val His Phe Glu
    1025                1030                1035

Leu Lys Pro Gly Val Arg Val Leu Val His Ala Ala His Leu Thr
    1040                1045                1050

Ala Ala Pro Leu Val Asp Leu Thr Pro Thr His Ser Gly Ser Ala
    1055                1060                1065

Met Leu Met Leu Leu Ser Val Val Phe Val Gly Leu Ala Val Phe
    1070                1075                1080

Val Ile Tyr Lys Phe Lys Arg Cys Val Ser Leu Tyr Pro Arg Ser
    1085                1090                1095

Pro Thr Pro Asp Leu Phe Leu Leu Pro Asp Arg Phe Arg Ser Met
    1100                1105                1110

Cys Tyr Ser Asp Val His Ser Asp Gly Phe Tyr
    1115                1120                1125
```

<210> SEQ ID NO 10
<211> LENGTH: 1046
<212> TYPE: PRT
<213> ORGANISM: Homo sapiens
<220> FEATURE:
<221> NAME/KEY: MISC_FEATURE
<222> LOCATION: (1)..(1046)
<223> OTHER INFORMATION: Soluble proSorCS1

<400> SEQUENCE: 10

```
Gly Phe Ser His Gln Gly Arg Pro Gly Arg Ala Pro Ala Thr Pro Leu
1               5                   10                  15

Pro Leu Val Val Arg Pro Leu Phe Ser Val Ala Pro Gly Asp Arg Ala
                20                  25                  30

Leu Ser Leu Glu Arg Ala Arg Gly Thr Gly Ala Ser Met Ala Val Ala
            35                  40                  45
```

```
Ala Arg Ser Gly Arg Arg Arg Ser Gly Ala Asp Gln Glu Lys Ala
    50                  55                  60
Glu Arg Gly Glu Gly Ala Ser Arg Ser Pro Arg Gly Val Leu Arg Asp
65                  70                  75                  80
Gly Gly Gln Gln Glu Pro Gly Thr Arg Glu Arg Asp Pro Asp Lys Ala
                85                  90                  95
Thr Arg Phe Arg Met Glu Glu Leu Arg Leu Thr Ser Thr Thr Phe Ala
                100                 105                 110
Leu Thr Gly Asp Ser Ala His Asn Gln Ala Met Val His Trp Ser Gly
                115                 120                 125
His Asn Ser Ser Val Ile Leu Ile Leu Thr Lys Leu Tyr Asp Tyr Asn
130                 135                 140
Leu Gly Ser Ile Thr Glu Ser Ser Leu Trp Arg Ser Thr Asp Tyr Gly
145                 150                 155                 160
Thr Thr Tyr Glu Lys Leu Asn Asp Lys Val Gly Leu Lys Thr Ile Leu
                165                 170                 175
Ser Tyr Leu Tyr Val Cys Pro Thr Asn Lys Arg Lys Ile Met Leu Leu
                180                 185                 190
Thr Asp Pro Glu Ile Glu Ser Ser Leu Leu Ile Ser Ser Asp Glu Gly
                195                 200                 205
Ala Thr Tyr Gln Lys Tyr Arg Leu Asn Phe Tyr Ile Gln Ser Leu Leu
210                 215                 220
Phe His Pro Lys Gln Glu Asp Trp Ile Leu Ala Tyr Ser Gln Asp Gln
225                 230                 235                 240
Lys Leu Tyr Ser Ser Ala Glu Phe Gly Arg Arg Trp Gln Leu Ile Gln
                245                 250                 255
Glu Gly Val Val Pro Asn Arg Phe Tyr Trp Ser Val Met Gly Ser Asn
                260                 265                 270
Lys Glu Pro Asp Leu Val His Leu Glu Ala Arg Thr Val Asp Gly His
                275                 280                 285
Ser His Tyr Leu Thr Cys Arg Met Gln Asn Cys Thr Glu Ala Asn Arg
                290                 295                 300
Asn Gln Pro Phe Pro Gly Tyr Ile Asp Pro Asp Ser Leu Ile Val Gln
305                 310                 315                 320
Asp His Tyr Val Phe Val Gln Leu Thr Ser Gly Gly Arg Pro His Tyr
                325                 330                 335
Tyr Val Ser Tyr Arg Arg Asn Ala Phe Ala Gln Met Lys Leu Pro Lys
                340                 345                 350
Tyr Ala Leu Pro Lys Asp Met His Val Ile Ser Thr Asp Glu Asn Gln
                355                 360                 365
Val Phe Ala Ala Val Gln Glu Trp Asn Gln Asn Asp Thr Tyr Asn Leu
370                 375                 380
Tyr Ile Ser Asp Thr Arg Gly Val Tyr Phe Thr Leu Ala Leu Glu Asn
385                 390                 395                 400
Val Gln Ser Ser Arg Gly Pro Glu Gly Asn Ile Met Ile Asp Leu Tyr
                405                 410                 415
Glu Val Ala Gly Ile Lys Gly Met Phe Leu Ala Asn Lys Lys Ile Asp
                420                 425                 430
Asn Gln Val Lys Thr Phe Ile Thr Tyr Asn Lys Gly Arg Asp Trp Arg
                435                 440                 445
Leu Leu Gln Ala Pro Asp Thr Asp Leu Arg Gly Asp Pro Val His Cys
450                 455                 460
Leu Leu Pro Tyr Cys Ser Leu His Leu His Leu Lys Val Ser Glu Asn
```

```
465                 470                 475                 480
Pro Tyr Thr Ser Gly Ile Ile Ala Ser Lys Asp Thr Ala Pro Ser Ile
                485                 490                 495

Ile Val Ala Ser Gly Asn Ile Gly Ser Glu Leu Ser Asp Thr Asp Ile
                500                 505                 510

Ser Met Phe Val Ser Ser Asp Ala Gly Asn Thr Trp Arg Gln Ile Phe
                515                 520                 525

Glu Glu Glu His Ser Val Leu Tyr Leu Asp Gln Gly Val Leu Val
            530                 535                 540

Ala Met Lys His Thr Ser Leu Pro Ile Arg His Leu Trp Leu Ser Phe
545                 550                 555                 560

Asp Glu Gly Arg Ser Trp Ser Lys Tyr Ser Phe Thr Ser Ile Pro Leu
                565                 570                 575

Phe Val Asp Gly Val Leu Gly Glu Pro Gly Glu Thr Leu Ile Met
                580                 585                 590

Thr Val Phe Gly His Phe Ser His Arg Ser Glu Trp Gln Leu Val Lys
                595                 600                 605

Val Asp Tyr Lys Ser Ile Phe Asp Arg Arg Cys Ala Glu Asp Tyr
            610                 615                 620

Arg Pro Trp Gln Leu His Ser Gln Gly Glu Ala Cys Ile Met Gly Ala
625                 630                 635                 640

Lys Arg Ile Tyr Lys Lys Arg Lys Ser Glu Arg Lys Cys Met Gln Gly
                645                 650                 655

Lys Tyr Ala Gly Ala Met Glu Ser Glu Pro Cys Val Cys Thr Glu Ala
                660                 665                 670

Asp Phe Asp Cys Asp Tyr Gly Tyr Glu Arg His Ser Asn Gly Gln Cys
            675                 680                 685

Leu Pro Ala Phe Trp Phe Asn Pro Ser Ser Leu Ser Lys Asp Cys Ser
                690                 695                 700

Leu Gly Gln Ser Tyr Leu Asn Ser Thr Gly Tyr Arg Lys Val Val Ser
705                 710                 715                 720

Asn Asn Cys Thr Asp Gly Val Arg Glu Gln Tyr Thr Ala Lys Pro Gln
                725                 730                 735

Lys Cys Pro Gly Lys Ala Pro Arg Gly Leu Arg Ile Val Thr Ala Asp
                740                 745                 750

Gly Lys Leu Thr Ala Glu Gln Gly His Asn Val Thr Leu Met Val Gln
                755                 760                 765

Leu Glu Glu Gly Asp Val Gln Arg Thr Leu Ile Gln Val Asp Phe Gly
                770                 775                 780

Asp Gly Ile Ala Val Ser Tyr Val Asn Leu Ser Ser Met Glu Asp Gly
785                 790                 795                 800

Ile Lys His Val Tyr Gln Asn Val Gly Ile Phe Arg Val Thr Val Gln
                805                 810                 815

Val Asp Asn Ser Leu Gly Ser Asp Ser Ala Val Leu Tyr Leu His Val
                820                 825                 830

Thr Cys Pro Leu Glu His Val His Leu Ser Leu Pro Phe Val Thr Thr
                835                 840                 845

Lys Asn Lys Glu Val Asn Ala Thr Ala Val Leu Trp Pro Ser Gln Val
                850                 855                 860

Gly Thr Leu Thr Tyr Val Trp Trp Tyr Gly Asn Asn Thr Glu Pro Leu
865                 870                 875                 880

Ile Thr Leu Glu Gly Ser Ile Ser Phe Arg Phe Thr Ser Glu Gly Met
                885                 890                 895
```

```
Asn Thr Ile Thr Val Gln Val Ser Ala Gly Asn Ala Ile Leu Gln Asp
                900                 905                 910

Thr Lys Thr Ile Ala Val Tyr Glu Glu Phe Arg Ser Leu Arg Leu Ser
        915                 920                 925

Phe Ser Pro Asn Leu Asp Asp Tyr Asn Pro Asp Ile Pro Glu Trp Arg
    930                 935                 940

Arg Asp Ile Gly Arg Val Ile Lys Lys Ser Leu Val Glu Ala Thr Gly
945                 950                 955                 960

Val Pro Gly Gln His Ile Leu Val Ala Val Leu Pro Gly Leu Pro Thr
                965                 970                 975

Thr Ala Glu Leu Phe Val Leu Pro Tyr Gln Asp Pro Ala Gly Glu Asn
            980                 985                 990

Lys Arg Ser Thr Asp Asp Leu Glu Gln Ile Ser Glu Leu Leu Ile His
        995                 1000                1005

Thr Leu Asn Gln Asn Ser Val His Phe Glu Leu Lys Pro Gly Val
    1010                1015                1020

Arg Val Leu Val His Ala Ala His Leu Thr Ala Ala Pro Leu Val
    1025                1030                1035

Asp Leu Thr Pro Thr His Ser Gly
    1040                1045

<210> SEQ ID NO 11
<211> LENGTH: 1058
<212> TYPE: PRT
<213> ORGANISM: Homo sapiens
<220> FEATURE:
<221> NAME/KEY: MISC_FEATURE
<222> LOCATION: (1)..(1058)
<223> OTHER INFORMATION: Mature SorCS1b, Isoform 1

<400> SEQUENCE: 11

Ser Gly Ala Asp Gln Glu Lys Ala Glu Arg Gly Glu Gly Ala Ser Arg
1               5                   10                  15

Ser Pro Arg Gly Val Leu Arg Asp Gly Gly Gln Gln Glu Pro Gly Thr
            20                  25                  30

Arg Glu Arg Asp Pro Asp Lys Ala Thr Arg Phe Arg Met Glu Glu Leu
        35                  40                  45

Arg Leu Thr Ser Thr Thr Phe Ala Leu Thr Gly Asp Ser Ala His Asn
    50                  55                  60

Gln Ala Met Val His Trp Ser Gly His Asn Ser Ser Val Ile Leu Ile
65                  70                  75                  80

Leu Thr Lys Leu Tyr Asp Tyr Asn Leu Gly Ser Ile Thr Glu Ser Ser
                85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
        115                 120                 125

Asn Lys Arg Lys Ile Met Leu Leu Thr Asp Pro Glu Ile Glu Ser Ser
    130                 135                 140

Leu Leu Ile Ser Ser Asp Glu Gly Ala Thr Tyr Gln Lys Tyr Arg Leu
145                 150                 155                 160

Asn Phe Tyr Ile Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190
```

```
Gly Arg Arg Trp Gln Leu Ile Gln Glu Gly Val Val Pro Asn Arg Phe
            195                 200                 205

Tyr Trp Ser Val Met Gly Ser Asn Lys Glu Pro Asp Leu Val His Leu
210                 215                 220

Glu Ala Arg Thr Val Asp Gly His Ser His Tyr Leu Thr Cys Arg Met
225                 230                 235                 240

Gln Asn Cys Thr Glu Ala Asn Arg Asn Gln Pro Phe Pro Gly Tyr Ile
                245                 250                 255

Asp Pro Asp Ser Leu Ile Val Gln Asp His Tyr Val Phe Val Gln Leu
            260                 265                 270

Thr Ser Gly Gly Arg Pro His Tyr Tyr Val Ser Tyr Arg Arg Asn Ala
        275                 280                 285

Phe Ala Gln Met Lys Leu Pro Lys Tyr Ala Leu Pro Lys Asp Met His
290                 295                 300

Val Ile Ser Thr Asp Glu Asn Gln Val Phe Ala Ala Val Gln Glu Trp
305                 310                 315                 320

Asn Gln Asn Asp Thr Tyr Asn Leu Tyr Ile Ser Asp Thr Arg Gly Val
                325                 330                 335

Tyr Phe Thr Leu Ala Leu Glu Asn Val Gln Ser Ser Arg Gly Pro Glu
            340                 345                 350

Gly Asn Ile Met Ile Asp Leu Tyr Glu Val Ala Gly Ile Lys Gly Met
        355                 360                 365

Phe Leu Ala Asn Lys Lys Ile Asp Asn Gln Val Lys Thr Phe Ile Thr
370                 375                 380

Tyr Asn Lys Gly Arg Asp Trp Arg Leu Leu Gln Ala Pro Asp Thr Asp
385                 390                 395                 400

Leu Arg Gly Asp Pro Val His Cys Leu Leu Pro Tyr Cys Ser Leu His
                405                 410                 415

Leu His Leu Lys Val Ser Glu Asn Pro Tyr Thr Ser Gly Ile Ile Ala
            420                 425                 430

Ser Lys Asp Thr Ala Pro Ser Ile Ile Val Ala Ser Gly Asn Ile Gly
        435                 440                 445

Ser Glu Leu Ser Asp Thr Asp Ile Ser Met Phe Val Ser Ser Asp Ala
450                 455                 460

Gly Asn Thr Trp Arg Gln Ile Phe Glu Glu His Ser Val Leu Tyr
465                 470                 475                 480

Leu Asp Gln Gly Gly Val Leu Val Ala Met Lys His Thr Ser Leu Pro
                485                 490                 495

Ile Arg His Leu Trp Leu Ser Phe Asp Glu Gly Arg Ser Trp Ser Lys
            500                 505                 510

Tyr Ser Phe Thr Ser Ile Pro Leu Phe Val Asp Gly Val Leu Gly Glu
        515                 520                 525

Pro Gly Glu Glu Thr Leu Ile Met Thr Val Phe Gly His Phe Ser His
530                 535                 540

Arg Ser Glu Trp Gln Leu Val Lys Val Asp Tyr Lys Ser Ile Phe Asp
545                 550                 555                 560

Arg Arg Cys Ala Glu Glu Asp Tyr Arg Pro Trp Gln Leu His Ser Gln
                565                 570                 575

Gly Glu Ala Cys Ile Met Gly Ala Lys Arg Ile Tyr Lys Lys Arg Lys
            580                 585                 590

Ser Glu Arg Lys Cys Met Gln Gly Lys Tyr Ala Gly Ala Met Glu Ser
        595                 600                 605

Glu Pro Cys Val Cys Thr Glu Ala Asp Phe Asp Cys Asp Tyr Gly Tyr
```

-continued

```
            610                 615                 620
Glu Arg His Ser Asn Gly Gln Cys Leu Pro Ala Phe Trp Phe Asn Pro
625                 630                 635                 640

Ser Ser Leu Ser Lys Asp Cys Ser Leu Gly Gln Ser Tyr Leu Asn Ser
                645                 650                 655

Thr Gly Tyr Arg Lys Val Val Ser Asn Cys Thr Asp Gly Val Arg
                    660                 665                 670

Glu Gln Tyr Thr Ala Lys Pro Gln Lys Cys Pro Gly Lys Ala Pro Arg
                675                 680                 685

Gly Leu Arg Ile Val Thr Ala Asp Gly Lys Leu Thr Ala Glu Gln Gly
                690                 695                 700

His Asn Val Thr Leu Met Val Gln Leu Glu Glu Gly Asp Val Gln Arg
705                 710                 715                 720

Thr Leu Ile Gln Val Asp Phe Gly Asp Gly Ile Ala Val Ser Tyr Val
                725                 730                 735

Asn Leu Ser Ser Met Glu Asp Gly Ile Lys His Val Tyr Gln Asn Val
                740                 745                 750

Gly Ile Phe Arg Val Thr Val Gln Val Asp Asn Ser Leu Gly Ser Asp
                755                 760                 765

Ser Ala Val Leu Tyr Leu His Val Thr Cys Pro Leu Glu His Val His
770                 775                 780

Leu Ser Leu Pro Phe Val Thr Thr Lys Asn Lys Glu Val Asn Ala Thr
785                 790                 795                 800

Ala Val Leu Trp Pro Ser Gln Val Gly Thr Leu Thr Tyr Val Trp Trp
                805                 810                 815

Tyr Gly Asn Asn Thr Glu Pro Leu Ile Thr Leu Glu Gly Ser Ile Ser
                820                 825                 830

Phe Arg Phe Thr Ser Glu Gly Met Asn Thr Ile Thr Val Gln Val Ser
                835                 840                 845

Ala Gly Asn Ala Ile Leu Gln Asp Thr Lys Thr Ile Ala Val Tyr Glu
                850                 855                 860

Glu Phe Arg Ser Leu Arg Leu Ser Phe Ser Pro Asn Leu Asp Asp Tyr
865                 870                 875                 880

Asn Pro Asp Ile Pro Glu Trp Arg Arg Asp Ile Gly Arg Val Ile Lys
                885                 890                 895

Lys Ser Leu Val Glu Ala Thr Gly Val Pro Gly Gln His Ile Leu Val
                900                 905                 910

Ala Val Leu Pro Gly Leu Pro Thr Thr Ala Glu Leu Phe Val Leu Pro
                915                 920                 925

Tyr Gln Asp Pro Ala Gly Glu Asn Lys Arg Ser Thr Asp Asp Leu Glu
930                 935                 940

Gln Ile Ser Glu Leu Leu Ile His Thr Leu Asn Gln Asn Ser Val His
945                 950                 955                 960

Phe Glu Leu Lys Pro Gly Val Arg Val Leu Val His Ala Ala His Leu
                965                 970                 975

Thr Ala Ala Pro Leu Val Asp Leu Thr Pro Thr His Ser Gly Ser Ala
                980                 985                 990

Met Leu Met Leu Leu Ser Val Val Phe Val Gly Leu Ala Val Phe Val
                995                 1000                1005

Ile Tyr Lys Phe Lys Arg Arg Val Ala Leu Pro Ser Pro Pro Ser
    1010                1015                1020

Pro Ser Thr Gln Pro Gly Asp Ser Ser Leu Arg Leu Gln Arg Ala
    1025                1030                1035
```

-continued

Arg His Ala Thr Pro Pro Ser Thr Pro Lys Arg Gly Ser Ala Gly
    1040                1045                1050

Ala Gln Tyr Ala Ile
    1055

<210> SEQ ID NO 12
<211> LENGTH: 1087
<212> TYPE: PRT
<213> ORGANISM: Homo sapiens
<220> FEATURE:
<221> NAME/KEY: MISC_FEATURE
<222> LOCATION: (1)..(1087)
<223> OTHER INFORMATION: Mature SorCS1, Isoform 2

<400> SEQUENCE: 12

Ser Gly Ala Asp Gln Glu Lys Ala Glu Arg Gly Glu Gly Ala Ser Arg
1               5                   10                  15

Ser Pro Arg Gly Val Leu Arg Asp Gly Gly Gln Gln Glu Pro Gly Thr
            20                  25                  30

Arg Glu Arg Asp Pro Asp Lys Ala Thr Arg Phe Arg Met Glu Glu Leu
        35                  40                  45

Arg Leu Thr Ser Thr Thr Phe Ala Leu Thr Gly Asp Ser Ala His Asn
    50                  55                  60

Gln Ala Met Val His Trp Ser Gly His Asn Ser Ser Val Ile Leu Ile
65                  70                  75                  80

Leu Thr Lys Leu Tyr Asp Tyr Asn Leu Gly Ser Ile Thr Glu Ser Ser
                85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
        115                 120                 125

Asn Lys Arg Lys Ile Met Leu Leu Thr Asp Pro Glu Ile Glu Ser Ser
    130                 135                 140

Leu Leu Ile Ser Ser Asp Glu Gly Ala Thr Tyr Gln Lys Tyr Arg Leu
145                 150                 155                 160

Asn Phe Tyr Ile Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Gly Val Val Pro Asn Arg Phe
        195                 200                 205

Tyr Trp Ser Val Met Gly Ser Asn Lys Glu Pro Asp Leu Val His Leu
    210                 215                 220

Glu Ala Arg Thr Val Asp Gly His Ser His Tyr Leu Thr Cys Arg Met
225                 230                 235                 240

Gln Asn Cys Thr Glu Ala Asn Arg Gln Pro Phe Pro Gly Tyr Ile Asp
                245                 250                 255

Pro Asp Ser Leu Ile Val Gln Asp His Tyr Val Phe Val Gln Leu Thr
            260                 265                 270

Ser Gly Gly Arg Pro His Tyr Tyr Val Ser Tyr Arg Arg Asn Ala Phe
        275                 280                 285

Ala Gln Met Lys Leu Pro Lys Tyr Ala Leu Pro Lys Asp Met His Val
    290                 295                 300

Ile Ser Thr Asp Glu Asn Gln Val Phe Ala Ala Val Gln Glu Trp Asn
305                 310                 315                 320

-continued

Gln Asn Asp Thr Tyr Asn Leu Tyr Ile Ser Asp Thr Arg Gly Val Tyr
              325                 330                 335

Phe Thr Leu Ala Leu Glu Asn Val Gln Ser Ser Arg Gly Pro Glu Gly
          340                 345                 350

Asn Ile Met Ile Asp Leu Tyr Glu Val Ala Gly Ile Lys Gly Met Phe
          355                 360                 365

Leu Ala Asn Lys Lys Ile Asp Asn Gln Val Lys Thr Phe Ile Thr Tyr
    370                 375                 380

Asn Lys Gly Arg Asp Trp Arg Leu Leu Gln Ala Pro Asp Thr Asp Leu
385                 390                 395                 400

Arg Gly Asp Pro Val His Cys Leu Leu Pro Tyr Cys Ser Leu His Leu
              405                 410                 415

His Leu Lys Val Ser Glu Asn Pro Tyr Thr Ser Gly Ile Ile Ala Ser
          420                 425                 430

Lys Asp Thr Ala Pro Ser Ile Ile Val Ala Ser Gly Asn Ile Gly Ser
          435                 440                 445

Glu Leu Ser Asp Thr Asp Ile Ser Met Phe Val Ser Ser Asp Ala Gly
    450                 455                 460

Asn Thr Trp Arg Gln Ile Phe Glu Gly Glu His Ser Val Leu Tyr Leu
465                 470                 475                 480

Asp Gln Gly Gly Val Leu Val Ala Met Lys His Thr Ser Leu Pro Ile
              485                 490                 495

Arg His Leu Trp Leu Ser Phe Asp Glu Gly Arg Ser Trp Ser Lys Tyr
          500                 505                 510

Ser Phe Thr Ser Ile Pro Leu Phe Val Asp Gly Val Leu Gly Glu Pro
          515                 520                 525

Gly Glu Glu Thr Leu Ile Met Thr Val Phe Gly His Phe Ser His Arg
    530                 535                 540

Ser Glu Trp Gln Leu Val Lys Val Asp Tyr Lys Ser Ile Phe Asp Arg
545                 550                 555                 560

Arg Cys Ala Glu Glu Asp Tyr Arg Pro Trp Gln Leu His Ser Gln Gly
              565                 570                 575

Glu Ala Cys Ile Met Gly Ala Lys Arg Ile Tyr Lys Lys Arg Lys Ser
          580                 585                 590

Glu Arg Lys Cys Met Gln Gly Lys Tyr Ala Gly Ala Met Glu Ser Glu
    595                 600                 605

Pro Cys Val Cys Thr Glu Ala Asp Phe Asp Cys Asp Tyr Gly Tyr Glu
    610                 615                 620

Arg His Ser Asn Gly Gln Cys Leu Pro Ala Phe Trp Phe Asn Pro Ser
625                 630                 635                 640

Ser Leu Ser Lys Asp Cys Ser Leu Gly Gln Ser Tyr Leu Asn Ser Thr
              645                 650                 655

Gly Tyr Arg Lys Val Val Ser Asn Asn Cys Thr Asp Gly Val Arg Glu
          660                 665                 670

Gln Tyr Thr Ala Lys Pro Gln Lys Cys Pro Gly Lys Ala Pro Arg Gly
          675                 680                 685

Leu Arg Ile Val Thr Ala Asp Gly Lys Leu Thr Ala Glu Gln Gly His
    690                 695                 700

Asn Val Thr Leu Met Val Gln Leu Glu Glu Gly Asp Val Gln Arg Thr
705                 710                 715                 720

Leu Ile Gln Val Asp Phe Gly Asp Gly Ile Ala Val Ser Tyr Val Asn
              725                 730                 735

Leu Ser Ser Met Glu Asp Gly Ile Lys His Val Tyr Gln Asn Val Gly 740                 745                 750
Ile Phe Arg Val Thr Val Gln Val Asp Asn Ser Leu Gly Ser Asp Ser
            755                 760                 765

Ala Val Leu Tyr Leu His Val Thr Cys Pro Leu Glu His Val His Leu
        770                 775                 780

Ser Leu Pro Phe Val Thr Lys Asn Lys Glu Val Asn Ala Thr Ala
785                 790                 795                 800

Val Leu Trp Pro Ser Gln Val Gly Thr Leu Thr Tyr Val Trp Trp Tyr
                805                 810                 815

Gly Asn Asn Thr Glu Pro Leu Ile Thr Leu Glu Gly Ser Ile Ser Phe
            820                 825                 830

Arg Phe Thr Ser Glu Gly Met Asn Thr Ile Thr Val Gln Val Ser Ala
        835                 840                 845

Gly Asn Ala Ile Leu Gln Asp Thr Lys Thr Ile Ala Val Tyr Glu Glu
    850                 855                 860

Phe Arg Ser Leu Arg Leu Ser Phe Ser Pro Asn Leu Asp Asp Tyr Asn
865                 870                 875                 880

Pro Asp Ile Pro Glu Trp Arg Arg Asp Ile Gly Arg Val Ile Lys Lys
                885                 890                 895

Ser Leu Val Glu Ala Thr Gly Val Pro Gly Gln His Ile Leu Val Ala
            900                 905                 910

Val Leu Pro Gly Leu Pro Thr Thr Ala Glu Leu Phe Val Leu Pro Tyr
        915                 920                 925

Gln Asp Pro Ala Gly Glu Asn Lys Arg Ser Thr Asp Asp Leu Glu Gln
    930                 935                 940

Ile Ser Glu Leu Leu Ile His Thr Leu Asn Gln Asn Ser Val His Phe
945                 950                 955                 960

Glu Leu Lys Pro Gly Val Arg Val Leu Val His Ala Ala His Leu Thr
                965                 970                 975

Ala Ala Pro Leu Val Asp Leu Thr Pro Thr His Ser Gly Ser Ala Met
            980                 985                 990

Leu Met Leu Leu Ser Val Val Phe Val Gly Leu Ala Val Phe Val Ile
        995                 1000                1005

Tyr Lys Phe Lys Arg Lys Ile Pro Gly Ile Asn Val Tyr Ala Gln
    1010                1015                1020

Met Gln Asn Glu Lys Glu Glu Met Ile Ser Pro Val Ser His
    1025                1030                1035

Ser Glu Ser Arg Pro Asn Val Pro Gln Thr Glu Leu Arg Arg Pro
    1040                1045                1050

Gly Gln Leu Ile Asp Glu Lys Val Glu Ser Gln Leu Ile Gly Ser
    1055                1060                1065

Ile Ser Ile Val Ala Glu Asn Gln Ser Thr Lys Glu Ile Pro Thr
    1070                1075                1080

Tyr Val Asn Val
    1085

<210> SEQ ID NO 13
<211> LENGTH: 1069
<212> TYPE: PRT
<213> ORGANISM: Homo sapiens
<220> FEATURE:
<221> NAME/KEY: MISC_FEATURE
<222> LOCATION: (1)..(1069)
<223> OTHER INFORMATION: Mature SorCS1c, Isoform 3

<400> SEQUENCE: 13

```
Ser Gly Ala Asp Gln Glu Lys Ala Glu Arg Gly Gly Ala Ser Arg
  1               5                  10                 15

Ser Pro Arg Gly Val Leu Arg Asp Gly Gln Gln Glu Pro Gly Thr
             20                  25                 30

Arg Glu Arg Asp Pro Asp Lys Ala Thr Arg Phe Arg Met Glu Glu Leu
         35                  40                  45

Arg Leu Thr Ser Thr Thr Phe Ala Leu Thr Gly Asp Ser Ala His Asn
     50                  55                  60

Gln Ala Met Val His Trp Ser Gly His Asn Ser Ser Val Ile Leu Ile
 65                  70                  75                  80

Leu Thr Lys Leu Tyr Asp Tyr Asn Leu Gly Ser Ile Thr Glu Ser Ser
                 85                  90                  95

Leu Trp Arg Ser Thr Asp Tyr Gly Thr Thr Tyr Glu Lys Leu Asn Asp
             100                 105                 110

Lys Val Gly Leu Lys Thr Ile Leu Ser Tyr Leu Tyr Val Cys Pro Thr
             115                 120                 125

Asn Lys Arg Lys Ile Met Leu Leu Thr Asp Pro Glu Ile Glu Ser Ser
130                 135                 140

Leu Leu Ile Ser Ser Asp Glu Gly Ala Thr Tyr Gln Lys Tyr Arg Leu
145                 150                 155                 160

Asn Phe Tyr Ile Gln Ser Leu Leu Phe His Pro Lys Gln Glu Asp Trp
                 165                 170                 175

Ile Leu Ala Tyr Ser Gln Asp Gln Lys Leu Tyr Ser Ser Ala Glu Phe
             180                 185                 190

Gly Arg Arg Trp Gln Leu Ile Gln Glu Gly Val Val Pro Asn Arg Phe
             195                 200                 205

Tyr Trp Ser Val Met Gly Ser Asn Lys Glu Pro Asp Leu Val His Leu
             210                 215                 220

Glu Ala Arg Thr Val Asp Gly His Ser His Tyr Leu Thr Cys Arg Met
225                 230                 235                 240

Gln Asn Cys Thr Glu Ala Asn Arg Asn Gln Pro Phe Pro Gly Tyr Ile
             245                 250                 255

Asp Pro Asp Ser Leu Ile Val Gln Asp His Tyr Val Phe Val Gln Leu
             260                 265                 270

Thr Ser Gly Gly Arg Pro His Tyr Tyr Val Ser Tyr Arg Arg Asn Ala
             275                 280                 285

Phe Ala Gln Met Lys Leu Pro Lys Tyr Ala Leu Pro Lys Asp Met His
             290                 295                 300

Val Ile Ser Thr Asp Glu Asn Gln Val Phe Ala Val Gln Glu Trp
305                 310                 315                 320

Asn Gln Asn Asp Thr Tyr Asn Leu Tyr Ile Ser Asp Thr Arg Gly Val
             325                 330                 335

Tyr Phe Thr Leu Ala Leu Glu Asn Val Gln Ser Ser Arg Gly Pro Glu
             340                 345                 350

Gly Asn Ile Met Ile Asp Leu Tyr Glu Val Ala Gly Ile Lys Gly Met
             355                 360                 365

Phe Leu Ala Asn Lys Lys Ile Asp Asn Gln Val Lys Thr Phe Ile Thr
             370                 375                 380

Tyr Asn Lys Gly Arg Asp Trp Arg Leu Leu Gln Ala Pro Asp Thr Asp
385                 390                 395                 400

Leu Arg Gly Asp Pro Val His Cys Leu Leu Pro Tyr Cys Ser Leu His
             405                 410                 415
```

-continued

```
Leu His Leu Lys Val Ser Glu Asn Pro Tyr Thr Ser Gly Ile Ile Ala
            420                 425                 430

Ser Lys Asp Thr Ala Pro Ser Ile Ile Val Ala Ser Gly Asn Ile Gly
            435                 440                 445

Ser Glu Leu Ser Asp Thr Asp Ile Ser Met Phe Val Ser Ser Asp Ala
            450                 455                 460

Gly Asn Thr Trp Arg Gln Ile Phe Glu Glu His Ser Val Leu Tyr
465                 470                 475                 480

Leu Asp Gln Gly Gly Val Leu Val Ala Met Lys His Thr Ser Leu Pro
                    485                 490                 495

Ile Arg His Leu Trp Leu Ser Phe Asp Glu Gly Arg Ser Trp Ser Lys
            500                 505                 510

Tyr Ser Phe Thr Ser Ile Pro Leu Phe Val Asp Gly Val Leu Gly Glu
            515                 520                 525

Pro Gly Glu Glu Thr Leu Ile Met Thr Val Phe Gly His Phe Ser His
530                 535                 540

Arg Ser Glu Trp Gln Leu Val Lys Val Asp Tyr Lys Ser Ile Phe Asp
545                 550                 555                 560

Arg Arg Cys Ala Glu Glu Asp Tyr Arg Pro Trp Gln Leu His Ser Gln
            565                 570                 575

Gly Glu Ala Cys Ile Met Gly Ala Lys Arg Ile Tyr Lys Lys Arg Lys
            580                 585                 590

Ser Glu Arg Lys Cys Met Gln Gly Lys Tyr Ala Gly Ala Met Glu Ser
            595                 600                 605

Glu Pro Cys Val Cys Thr Glu Ala Asp Phe Asp Cys Asp Tyr Gly Tyr
610                 615                 620

Glu Arg His Ser Asn Gly Gln Cys Leu Pro Ala Phe Trp Phe Asn Pro
625                 630                 635                 640

Ser Ser Leu Ser Lys Asp Cys Ser Leu Gly Gln Ser Tyr Leu Asn Ser
            645                 650                 655

Thr Gly Tyr Arg Lys Val Val Ser Asn Asn Cys Thr Asp Gly Val Arg
            660                 665                 670

Glu Gln Tyr Thr Ala Lys Pro Gln Lys Cys Pro Gly Lys Ala Pro Arg
            675                 680                 685

Gly Leu Arg Ile Val Thr Ala Asp Gly Lys Leu Thr Ala Glu Gln Gly
690                 695                 700

His Asn Val Thr Leu Met Val Gln Leu Glu Glu Gly Asp Val Gln Arg
705                 710                 715                 720

Thr Leu Ile Gln Val Asp Phe Gly Asp Gly Ile Ala Val Ser Tyr Val
            725                 730                 735

Asn Leu Ser Ser Met Glu Asp Gly Ile Lys His Val Tyr Gln Asn Val
            740                 745                 750

Gly Ile Phe Arg Val Thr Val Gln Val Asp Asn Ser Leu Gly Ser Asp
            755                 760                 765

Ser Ala Val Leu Tyr Leu His Val Thr Cys Pro Leu Glu His Val His
770                 775                 780

Leu Ser Leu Pro Phe Val Thr Thr Lys Asn Lys Glu Val Asn Ala Thr
785                 790                 795                 800

Ala Val Leu Trp Pro Ser Gln Val Gly Thr Leu Thr Tyr Val Trp Trp
                    805                 810                 815

Tyr Gly Asn Asn Thr Glu Pro Leu Ile Thr Leu Glu Gly Ser Ile Ser
            820                 825                 830

Phe Arg Phe Thr Ser Glu Gly Met Asn Thr Ile Thr Val Gln Val Ser
```

```
                835                 840                 845
Ala Gly Asn Ala Ile Leu Gln Asp Thr Lys Thr Ile Ala Val Tyr Glu
            850                 855                 860
Glu Phe Arg Ser Leu Arg Leu Ser Phe Ser Pro Asn Leu Asp Asp Tyr
865                 870                 875                 880
Asn Pro Asp Ile Pro Glu Trp Arg Arg Asp Ile Gly Arg Val Ile Lys
                885                 890                 895
Lys Ser Leu Val Glu Ala Thr Gly Val Pro Gly Gln His Ile Leu Val
            900                 905                 910
Ala Val Leu Pro Gly Leu Pro Thr Thr Ala Glu Leu Phe Val Leu Pro
            915                 920                 925
Tyr Gln Asp Pro Ala Gly Glu Asn Lys Arg Ser Thr Asp Asp Leu Glu
            930                 935                 940
Gln Ile Ser Glu Leu Leu Ile His Thr Leu Asn Gln Asn Ser Val His
945                 950                 955                 960
Phe Glu Leu Lys Pro Gly Val Arg Val Leu Val His Ala Ala His Leu
                965                 970                 975
Thr Ala Ala Pro Leu Val Asp Leu Thr Pro Thr His Ser Gly Ser Ala
            980                 985                 990
Met Leu Met Leu Leu Ser Val Val  Phe Val Gly Leu Ala  Val Phe Val
            995                 1000                1005
Ile Tyr  Lys Phe Lys Arg  Lys  Ile Pro Gly Ile Asn  Val Tyr Ala
            1010                1015                1020
Gln Met  Gln Asn Glu Lys Glu  Gln Glu Met Ile Ser  Pro Val Ser
            1025                1030                1035
His Ser  Glu Ser Arg Pro Asn  Val Pro Gln Thr Glu  Leu Arg Arg
            1040                1045                1050
Pro Gly  Gln Leu Ile Asp Glu  Lys Val Glu Ser Gln  Leu Ile Gly
            1055                1060                1065
Lys

<210> SEQ ID NO 14
<211> LENGTH: 1048
<212> TYPE: PRT
<213> ORGANISM: Homo sapiens
<220> FEATURE:
<221> NAME/KEY: MISC_FEATURE
<222> LOCATION: (1)..(1048)
<223> OTHER INFORMATION: Mature SorCS1a, Isoform 4

<400> SEQUENCE: 14

Ser Gly Ala Asp Gln Glu Lys Ala Glu Arg Gly Glu Gly Ala Ser Arg
1               5                   10                  15
Ser Pro Arg Gly Val Leu Arg Asp Gly Gln Gln Gly Pro Gly Thr
            20                  25                  30
Arg Glu Arg Asp Pro Asp Lys Ala Thr Arg Phe Arg Met Glu Glu Leu
        35                  40                  45
Arg Leu Thr Ser Thr Thr Phe Ala Leu Thr Gly Asp Ser Ala His Asn
    50                  55                  60
Gln Ala Met Val His Trp Ser Gly His Asn Ser Ser Val Ile Leu Ile
65                  70                  75                  80
Leu Thr Lys Leu Tyr Asp Tyr Asn Leu Gly Ser Ile Thr Glu Ser Ser
                85                  90                  95
Leu Trp Arg Ser Thr Asp Tyr Gly Thr Thr Tyr Glu Lys Leu Asn Asp
            100                 105                 110
```

```
Lys Val Gly Leu Lys Thr Ile Leu Ser Tyr Leu Tyr Val Cys Pro Thr
            115                 120                 125

Asn Lys Arg Lys Ile Met Leu Leu Thr Asp Pro Glu Ile Glu Ser Ser
130                 135                 140

Leu Leu Ile Ser Ser Asp Glu Gly Ala Thr Tyr Gln Lys Tyr Arg Leu
145                 150                 155                 160

Asn Phe Tyr Ile Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Gly Val Val Pro Asn Arg Phe
            195                 200                 205

Tyr Trp Ser Val Met Gly Ser Asn Lys Glu Pro Asp Leu Val His Leu
210                 215                 220

Glu Ala Arg Thr Val Asp Gly His Ser His Tyr Leu Thr Cys Arg Met
225                 230                 235                 240

Gln Asn Cys Thr Glu Ala Asn Arg Asn Gln Pro Phe Pro Gly Tyr Ile
                245                 250                 255

Asp Pro Asp Ser Leu Ile Val Gln Asp His Tyr Val Phe Val Gln Leu
            260                 265                 270

Thr Ser Gly Gly Arg Pro His Tyr Tyr Val Ser Tyr Arg Arg Asn Ala
            275                 280                 285

Phe Ala Gln Met Lys Leu Pro Lys Tyr Ala Leu Pro Lys Asp Met His
            290                 295                 300

Val Ile Ser Thr Asp Glu Asn Gln Val Phe Ala Ala Val Gln Glu Trp
305                 310                 315                 320

Asn Gln Asn Asp Thr Tyr Asn Leu Tyr Ile Ser Asp Thr Arg Gly Val
                325                 330                 335

Tyr Phe Thr Leu Ala Leu Glu Asn Val Gln Ser Ser Arg Gly Pro Glu
            340                 345                 350

Gly Asn Ile Met Ile Asp Leu Tyr Glu Val Ala Gly Ile Lys Gly Met
            355                 360                 365

Phe Leu Ala Asn Lys Lys Ile Asp Asn Gln Val Lys Thr Phe Ile Thr
370                 375                 380

Tyr Asn Lys Gly Arg Asp Trp Arg Leu Leu Gln Ala Pro Asp Thr Asp
385                 390                 395                 400

Leu Arg Gly Asp Pro Val His Cys Leu Leu Pro Tyr Cys Ser Leu His
                405                 410                 415

Leu His Leu Lys Val Ser Glu Asn Pro Tyr Thr Ser Gly Ile Ala Ser
            420                 425                 430

Lys Asp Thr Ala Pro Ser Ile Ile Val Ala Ser Gly Asn Ile Gly Ser
            435                 440                 445

Glu Leu Ser Asp Thr Asp Ile Ser Met Phe Val Ser Ser Asp Ala Gly
            450                 455                 460

Asn Thr Trp Arg Gln Ile Phe Glu Glu His Ser Val Leu Tyr Leu
465                 470                 475                 480

Asp Gln Gly Gly Val Leu Val Ala Met Lys His Thr Ser Leu Pro Ile
                485                 490                 495

Arg His Leu Trp Leu Ser Phe Asp Glu Gly Arg Ser Trp Ser Lys Tyr
            500                 505                 510

Ser Phe Thr Ser Ile Pro Leu Phe Val Asp Gly Val Leu Gly Glu Pro
            515                 520                 525

Gly Glu Glu Thr Leu Ile Met Thr Val Phe Gly His Phe Ser His Arg
```

```
                530             535             540
Ser Glu Trp Gln Leu Val Lys Val Asp Tyr Lys Ser Ile Phe Asp Arg
545                 550                 555                 560

Arg Cys Ala Glu Glu Asp Tyr Arg Pro Trp Gln Leu His Ser Gln Gly
                565                 570                 575

Glu Ala Cys Ile Met Gly Ala Lys Arg Ile Tyr Lys Lys Arg Lys Ser
                580                 585                 590

Glu Arg Lys Cys Met Gln Gly Lys Tyr Ala Gly Ala Met Glu Ser Glu
                595                 600                 605

Pro Cys Val Cys Thr Glu Ala Asp Phe Asp Cys Asp Tyr Gly Tyr Glu
                610                 615                 620

Arg His Ser Asn Gly Gln Cys Leu Pro Ala Phe Trp Phe Asn Pro Ser
625                 630                 635                 640

Ser Leu Ser Lys Asp Cys Ser Leu Gly Gln Ser Tyr Leu Asn Ser Thr
                645                 650                 655

Gly Tyr Arg Lys Val Val Ser Asn Asn Cys Thr Asp Gly Val Arg Glu
                660                 665                 670

Gln Tyr Thr Ala Lys Pro Gln Lys Cys Pro Gly Lys Ala Pro Arg Gly
                675                 680                 685

Leu Arg Ile Val Thr Ala Asp Gly Lys Leu Thr Ala Glu Gln Gly His
690                 695                 700

Asn Val Thr Leu Met Val Gln Leu Glu Glu Gly Asp Val Gln Arg Thr
705                 710                 715                 720

Leu Ile Gln Val Asp Phe Gly Asp Gly Ile Ala Val Ser Tyr Val Asn
                725                 730                 735

Leu Ser Ser Met Glu Asp Gly Ile Lys His Val Tyr Gln Asn Val Gly
                740                 745                 750

Ile Phe Arg Val Thr Val Gln Val Asp Asn Ser Leu Gly Ser Asp Ser
                755                 760                 765

Ala Val Leu Tyr Leu His Val Thr Cys Pro Leu Glu His Val His Leu
770                 775                 780

Ser Leu Pro Phe Val Thr Thr Lys Asn Lys Glu Val Asn Ala Thr Ala
785                 790                 795                 800

Val Leu Trp Pro Ser Gln Val Gly Thr Leu Thr Tyr Val Trp Trp Tyr
                805                 810                 815

Gly Asn Asn Thr Glu Pro Leu Ile Thr Leu Glu Gly Ser Ile Ser Phe
                820                 825                 830

Arg Phe Thr Ser Glu Gly Met Asn Thr Ile Thr Val Gln Val Ser Ala
                835                 840                 845

Gly Asn Ala Ile Leu Gln Asp Thr Lys Thr Ile Ala Val Tyr Glu Glu
850                 855                 860

Phe Arg Ser Leu Arg Leu Ser Phe Ser Pro Asn Leu Asp Asp Tyr Asn
865                 870                 875                 880

Pro Asp Ile Pro Glu Trp Arg Arg Asp Ile Gly Arg Val Ile Lys Lys
                885                 890                 895

Ser Leu Val Glu Ala Thr Gly Val Pro Gly Gln His Ile Leu Val Ala
                900                 905                 910

Val Leu Pro Gly Leu Pro Thr Thr Ala Glu Leu Phe Val Leu Pro Tyr
                915                 920                 925

Gln Asp Pro Ala Gly Glu Asn Lys Arg Ser Thr Asp Asp Leu Glu Gln
                930                 935                 940

Ile Ser Glu Leu Leu Ile His Thr Leu Asn Gln Asn Ser Val His Phe
945                 950                 955                 960
```

```
Glu Leu Lys Pro Gly Val Arg Val Leu Val His Ala Ala His Leu Thr
            965                 970                 975
Ala Ala Pro Leu Val Asp Leu Thr Pro Thr His Ser Gly Ser Ala Met
            980                 985                 990
Leu Met Leu Leu Ser Val Val Phe Val Gly Leu Ala Val Phe Val Ile
            995                1000                1005
Tyr Lys Phe Lys Arg Cys Val Ser Leu Tyr Pro Arg Ser Pro Thr
       1010                1015                1020
Pro Asp Leu Phe Leu Leu Pro Asp Arg Phe Arg Ser Met Cys Tyr
       1025                1030                1035
Ser Asp Val His Ser Ser Asp Gly Phe Tyr
       1040                1045

<210> SEQ ID NO 15
<211> LENGTH: 990
<212> TYPE: PRT
<213> ORGANISM: Homo sapiens
<220> FEATURE:
<221> NAME/KEY: MISC_FEATURE
<222> LOCATION: (1)..(990)
<223> OTHER INFORMATION: Soluble mature SorCS1

<400> SEQUENCE: 15

Ser Gly Ala Asp Gln Glu Lys Ala Glu Arg Gly Glu Gly Ala Ser Arg
1               5                  10                  15
Ser Pro Arg Gly Val Leu Arg Asp Gly Gly Gln Gln Glu Pro Gly Thr
            20                  25                  30
Arg Glu Arg Asp Pro Asp Lys Ala Thr Arg Phe Arg Met Glu Glu Leu
        35                  40                  45
Arg Leu Thr Ser Thr Thr Phe Ala Leu Thr Gly Asp Ser Ala His Asn
    50                  55                  60
Gln Ala Met Val His Trp Ser Gly His Asn Ser Ser Val Ile Leu Ile
65                  70                  75                  80
Leu Thr Lys Leu Tyr Asp Tyr Asn Leu Gly Ser Ile Thr Glu Ser Ser
                85                  90                  95
Leu Trp Arg Ser Thr Asp Tyr Gly Thr Thr Tyr Glu Lys Leu Asn Asp
            100                 105                 110
Lys Val Gly Leu Lys Thr Ile Leu Ser Tyr Leu Tyr Val Cys Pro Thr
        115                 120                 125
Asn Lys Arg Lys Ile Met Leu Leu Thr Asp Pro Glu Ile Glu Ser Ser
    130                 135                 140
Leu Leu Ile Ser Ser Asp Glu Gly Ala Thr Tyr Gln Lys Tyr Arg Leu
145                 150                 155                 160
Asn Phe Tyr Ile Gln Ser Leu Leu Phe His Pro Lys Gln Glu Asp Trp
                165                 170                 175
Ile Leu Ala Tyr Ser Gln Asp Gln Lys Leu Tyr Ser Ser Ala Glu Phe
            180                 185                 190
Gly Arg Arg Trp Gln Leu Ile Gln Glu Gly Val Val Pro Asn Arg Phe
        195                 200                 205
Tyr Trp Ser Val Met Gly Ser Asn Lys Glu Pro Asp Leu Val His Leu
    210                 215                 220
Glu Ala Arg Thr Val Asp Gly His Ser His Tyr Leu Thr Cys Arg Met
225                 230                 235                 240
Gln Asn Cys Thr Glu Ala Asn Arg Asn Gln Pro Phe Pro Gly Tyr Ile
                245                 250                 255
```

```
Asp Pro Asp Ser Leu Ile Val Gln Asp His Tyr Val Phe Val Gln Leu
            260                 265                 270

Thr Ser Gly Gly Arg Pro His Tyr Tyr Val Ser Tyr Arg Arg Asn Ala
        275                 280                 285

Phe Ala Gln Met Lys Leu Pro Lys Tyr Ala Leu Pro Lys Asp Met His
    290                 295                 300

Val Ile Ser Thr Asp Glu Asn Gln Val Phe Ala Ala Val Gln Glu Trp
305                 310                 315                 320

Asn Gln Asn Asp Thr Tyr Asn Leu Tyr Ile Ser Asp Thr Arg Gly Val
                325                 330                 335

Tyr Phe Thr Leu Ala Leu Glu Asn Val Gln Ser Ser Arg Gly Pro Glu
            340                 345                 350

Gly Asn Ile Met Ile Asp Leu Tyr Glu Val Ala Gly Ile Lys Gly Met
        355                 360                 365

Phe Leu Ala Asn Lys Lys Ile Asp Asn Gln Val Lys Thr Phe Ile Thr
    370                 375                 380

Tyr Asn Lys Gly Arg Asp Trp Arg Leu Leu Gln Ala Pro Asp Thr Asp
385                 390                 395                 400

Leu Arg Gly Asp Pro Val His Cys Leu Leu Pro Tyr Cys Ser Leu His
                405                 410                 415

Leu His Leu Lys Val Ser Glu Asn Pro Tyr Thr Ser Gly Ile Ile Ala
            420                 425                 430

Ser Lys Asp Thr Ala Pro Ser Ile Val Ala Ser Gly Asn Ile Gly
        435                 440                 445

Ser Glu Leu Ser Asp Thr Asp Ile Ser Met Phe Val Ser Ser Asp Ala
    450                 455                 460

Gly Asn Thr Trp Arg Gln Ile Phe Glu Glu Glu His Ser Val Leu Tyr
465                 470                 475                 480

Leu Asp Gln Gly Gly Val Leu Val Ala Met Lys His Thr Ser Leu Pro
                485                 490                 495

Ile Arg His Leu Trp Leu Ser Phe Asp Glu Gly Arg Ser Trp Ser Lys
            500                 505                 510

Tyr Ser Phe Thr Ser Ile Pro Leu Phe Val Asp Gly Val Leu Gly Glu
        515                 520                 525

Pro Gly Glu Glu Thr Leu Ile Met Thr Val Phe Gly His Phe Ser His
    530                 535                 540

Arg Ser Glu Trp Gln Leu Val Lys Val Asp Tyr Lys Ser Ile Phe Asp
545                 550                 555                 560

Arg Arg Cys Ala Glu Glu Asp Tyr Arg Pro Trp Gln Leu His Ser Gln
                565                 570                 575

Gly Glu Ala Cys Ile Met Gly Ala Lys Arg Ile Tyr Lys Lys Arg Lys
            580                 585                 590

Ser Glu Arg Lys Cys Met Gln Gly Lys Tyr Ala Gly Ala Met Glu Ser
        595                 600                 605

Glu Pro Cys Val Cys Thr Glu Ala Asp Phe Asp Cys Asp Tyr Gly Tyr
    610                 615                 620

Glu Arg His Ser Asn Gly Gln Cys Leu Pro Ala Phe Trp Phe Asn Pro
625                 630                 635                 640

Ser Ser Leu Ser Lys Asp Cys Ser Leu Gly Gln Ser Tyr Leu Asn Ser
                645                 650                 655

Thr Gly Tyr Arg Lys Val Val Ser Asn Asn Cys Thr Asp Gly Val Arg
            660                 665                 670

Glu Gln Tyr Thr Ala Lys Pro Gln Lys Cys Pro Gly Lys Ala Pro Arg
```

675                 680                 685

Gly Leu Arg Ile Val Thr Ala Asp Gly Lys Leu Thr Ala Glu Gln Gly
            690                 695                 700

His Asn Val Thr Leu Met Val Gln Leu Glu Glu Gly Asp Val Gln Arg
705                 710                 715                 720

Thr Leu Ile Gln Val Asp Phe Gly Asp Gly Ile Ala Val Ser Tyr Val
                725                 730                 735

Asn Leu Ser Ser Met Glu Asp Gly Ile Lys His Val Tyr Gln Asn Val
            740                 745                 750

Gly Ile Phe Arg Val Thr Val Gln Val Asp Asn Ser Leu Gly Ser Asp
        755                 760                 765

Ser Ala Val Leu Tyr Leu His Val Thr Cys Pro Leu Glu His Val His
770                 775                 780

Leu Ser Leu Pro Phe Val Thr Lys Asn Lys Glu Val Asn Ala Thr
785                 790                 795                 800

Ala Val Leu Trp Pro Ser Gln Val Gly Thr Leu Thr Tyr Val Trp Trp
                805                 810                 815

Tyr Gly Asn Asn Thr Glu Pro Leu Ile Thr Leu Glu Gly Ser Ile Ser
            820                 825                 830

Phe Arg Phe Thr Ser Glu Gly Met Asn Thr Ile Thr Val Gln Val Ser
        835                 840                 845

Ala Gly Asn Ala Ile Leu Gln Asp Thr Lys Thr Ile Ala Val Tyr Glu
850                 855                 860

Glu Phe Arg Ser Leu Arg Leu Ser Phe Ser Pro Asn Leu Asp Asp Tyr
865                 870                 875                 880

Asn Pro Asp Ile Pro Glu Trp Arg Arg Asp Ile Gly Arg Val Ile Lys
                885                 890                 895

Lys Ser Leu Val Glu Ala Thr Gly Val Pro Gly Gln His Ile Leu Val
            900                 905                 910

Ala Val Leu Pro Gly Leu Pro Thr Thr Ala Glu Leu Phe Val Leu Pro
        915                 920                 925

Tyr Gln Asp Pro Ala Gly Glu Asn Lys Arg Ser Thr Asp Asp Leu Glu
930                 935                 940

Gln Ile Ser Glu Leu Leu Ile His Thr Leu Asn Gln Asn Ser Val His
945                 950                 955                 960

Phe Glu Leu Lys Pro Gly Val Arg Val Leu Val His Ala Ala His Leu
                965                 970                 975

Thr Ala Ala Pro Leu Val Asp Leu Thr Pro Thr His Ser Gly
            980                 985                 990

<210> SEQ ID NO 16
<211> LENGTH: 1167
<212> TYPE: PRT
<213> ORGANISM: Mus musculus
<220> FEATURE:
<221> NAME/KEY: MISC_FEATURE
<222> LOCATION: (1)..(1167)
<223> OTHER INFORMATION: preproSorCS1b, isoform 1

<400> SEQUENCE: 16

Met Gly Lys Val Gly Ala Gly Asp Gly Ser Ser Ala Gly Leu Ser Ala
1               5                   10                  15

Leu Leu Ala Gly Ala Gly Leu Leu Met Leu Leu Ala Pro Gly Val Cys
            20                  25                  30

Ser Ser Leu Ser Cys Cys Pro Pro Gln His Pro Ser Ser Thr Pro Arg
        35                  40                  45

```
Arg Thr Leu Thr Pro Arg Gly Phe Pro His Pro Gly Pro Leu Gly Arg
    50                  55                  60

Ala Pro Ala Thr Pro Pro Leu Phe Met Arg Pro Leu Phe Ala Val
65              70                  75                  80

Ala Pro Gly Asp Arg Ala Leu Phe Leu Glu Arg Ala Gly Gly Ser Arg
                85                  90                  95

Val Ser Val Ala Thr Ala Ala Arg Ser Gly Arg Arg Arg Ser Gly
            100                 105                 110

Thr Glu Pro Glu Lys Ile Glu Pro Gly Glu Gly Ala Ser Arg Ser Arg
                115                 120                 125

Arg Asp Met Leu Lys Asp Gly Gly Gln Gln Gly Leu Gly Thr Gly Ala
    130                 135                 140

Arg Asp Pro Gly Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                165                 170                 175

Met Val His Trp Ser Gly His Asn Ser Ser Val Ile Leu Ile Leu Thr
                180                 185                 190

Lys Leu Tyr Asp Tyr Asn Leu Gly Ser Ile Thr Glu Ser Ser Leu Trp
            195                 200                 205

Arg Ser Thr Asp Tyr Gly Thr Thr Tyr Glu Lys Leu Asn Asp Lys Val
    210                 215                 220

Gly Leu Lys Thr Ile Leu Ser Tyr Leu Tyr Val Cys Pro Thr Asn Lys
225                 230                 235                 240

Cys Lys Ile Met Leu Leu Thr Asp Pro Glu Ile Glu Ser Ser Leu Leu
                245                 250                 255

Ile Ser Ser Asp Glu Gly Ala Thr Tyr Gln Lys Tyr Arg Leu Asn Phe
                260                 265                 270

Tyr Leu Gln Ser Leu Leu Phe His Pro Lys Gln Glu Asp Trp Ile Leu
            275                 280                 285

Ala Tyr Ser Gln Asp Gln Lys Leu Tyr Ser Ser Ala Glu Phe Gly Arg
    290                 295                 300

Arg Trp Gln Leu Ile Gln Glu Ser Val Val Pro Asn Arg Phe Tyr Trp
305                 310                 315                 320

Ser Val Met Gly Ser Ser Lys Glu Pro Asp Leu Val His Leu Glu Ala
                325                 330                 335

Arg Thr Val Asp Gly His Ser Ile Tyr Leu Thr Cys Arg Met Gln Asn
                340                 345                 350

Cys Thr Glu Ala Asn Arg Asn Lys Pro Phe Pro Gly Tyr Ile Asp Pro
            355                 360                 365

Asp Ser Leu Ile Val Gln Asp Asp Tyr Val Phe Val Gln Leu Thr Ser
    370                 375                 380

Gly Gly Arg Pro His Tyr Tyr Val Ser Tyr Arg Arg Ser Pro Phe Ala
385                 390                 395                 400

Gln Met Lys Leu Pro Lys Tyr Ala Leu Pro Lys Asp Met His Val Ile
                405                 410                 415

Ser Thr Asp Glu Asn Gln Val Phe Ala Ala Val Gln Glu Trp Asn Gln
            420                 425                 430

Asn Asp Thr Tyr Asn Leu Tyr Ile Ser Asp Thr Arg Gly Val Tyr Phe
    435                 440                 445

Thr Leu Ala Leu Glu Asn Val Arg Ser Ser Arg Gly Pro Glu Gly Asn
    450                 455                 460
```

```
Val Met Ile Asp Leu Tyr Glu Val Ala Gly Ile Lys Gly Met Phe Leu
465                 470                 475                 480

Ala Asn Lys Lys Ile Asp Asn Gln Val Lys Thr Phe Ile Thr Tyr Asn
                485                 490                 495

Lys Gly Arg Asp Trp Arg Leu Leu Gln Ala Pro Asp Ala Asp Leu Arg
            500                 505                 510

Gly Asp Pro Val His Cys Leu Leu Pro Tyr Cys Ser Leu His Leu His
            515                 520                 525

Leu Lys Val Ser Glu Asn Pro Tyr Thr Ser Gly Ile Ile Ala Ser Arg
530                 535                 540

Asp Thr Ala Pro Ser Ile Ile Val Ala Ser Gly Asn Ile Gly Ser Glu
545                 550                 555                 560

Leu Ser Asp Ser Asp Ile Ser Met Phe Val Ser Asp Ala Gly Asn
                565                 570                 575

Thr Trp Arg Gln Ile Phe Glu Glu His Ser Ile Leu Tyr Leu Asp
            580                 585                 590

Gln Gly Gly Val Leu Val Ala Met Lys His Thr Ser Leu Pro Ile Arg
            595                 600                 605

His Leu Trp Leu Ser Phe Asp Glu Gly Arg Ser Trp Ser Lys Tyr Ser
    610                 615                 620

Phe Thr Ser Ile Pro Leu Phe Val Asp Gly Val Leu Gly Glu Pro Gly
625                 630                 635                 640

Glu Glu Thr Leu Ile Met Thr Val Phe Gly His Phe Ser His Arg Ser
                645                 650                 655

Glu Trp Gln Leu Val Lys Val Asp Tyr Lys Ser Ile Phe Asp Arg Arg
            660                 665                 670

Cys Ala Glu Glu Asp Tyr Arg Pro Trp Gln Leu His Ser Gln Gly Glu
            675                 680                 685

Ala Cys Ile Met Gly Ala Lys Arg Ile Tyr Lys Lys Arg Lys Ser Glu
            690                 695                 700

Arg Lys Cys Met Gln Lys Tyr Ala Gly Ala Met Glu Ser Glu Pro Cys
705                 710                 715                 720

Val Cys Thr Glu Ala Asp Phe Asp Cys Asp Tyr Gly Tyr Glu Arg His
                725                 730                 735

Ser Asn Gly Gln Cys Leu Pro Ala Phe Trp Phe Asn Pro Ser Ser Leu
            740                 745                 750

Ser Lys Asp Cys Ser Leu Gly Gln Ser Tyr Leu Asn Ser Ala Gly Tyr
    755                 760                 765

Arg Lys Val Val Ser Asn Asn Cys Thr Asp Gly Val Arg Glu Gln Tyr
770                 775                 780

Thr Ala Lys Pro Gln Lys Cys Pro Gly Lys Ala Pro Arg Gly Leu Arg
785                 790                 795                 800

Ile Val Thr Ala Asp Gly Lys Leu Thr Ala Glu Gln Gly His Asn Val
                805                 810                 815

Thr Leu Met Val Gln Leu Glu Glu Gly Asp Val Gln Arg Thr Leu Ile
            820                 825                 830

Gln Val Asp Phe Gly Asp Gly Ile Ala Val Ser Tyr Val Asn Leu Ser
            835                 840                 845

Ser Met Glu Asp Gly Ile Lys His Val Tyr Gln Asn Val Gly Ile Phe
    850                 855                 860

Arg Val Thr Val Gln Val Asp Asn Ser Leu Gly Ser Asp Ser Ala Val
865                 870                 875                 880

Leu Tyr Leu His Val Thr Cys Pro Leu Glu His Val His Leu Ser Leu
```

```
                885                 890                 895

Pro Phe Val Thr Thr Lys Asn Lys Glu Val Asn Ala Thr Ala Val Leu
            900                 905                 910

Trp Pro Ser Gln Val Gly Thr Leu Thr Tyr Val Trp Trp Tyr Gly Asn
        915                 920                 925

Asn Thr Glu Pro Leu Ile Thr Leu Glu Gly Ser Ile Ser Phe Lys Phe
    930                 935                 940

Thr Ser Glu Gly Met Asn Thr Ile Thr Val Gln Val Ser Ala Gly Asn
945                 950                 955                 960

Ala Ile Leu Gln Asp Thr Lys Thr Ile Ala Val Tyr Glu Gln Phe Arg
            965                 970                 975

Ser Leu Arg Leu Ala Phe Ser Pro Asn Leu Asp Asp Tyr Asn Pro Asp
        980                 985                 990

Ile Pro Glu Trp Arg Arg Asp Ile Ser Arg Val Ile Lys Lys Ser Leu
    995                1000                1005

Val Glu Ala Thr Gly Ile Pro Ser Gln His Ile Leu Val Ala Val
1010                1015                1020

Leu Pro Gly Leu Pro Thr Ala Ala Glu Leu Phe Val Leu Pro Tyr
    1025                1030                1035

Gln Asp Gly Thr Arg Glu Asn Lys Arg Ser Pro Glu Asp Leu Glu
    1040                1045                1050

Gln Ile Ser Glu Val Leu Ile His Lys Leu Asn Gln Asn Leu Val
    1055                1060                1065

His Phe Glu Leu Lys Pro Gly Val Gln Val Leu Val His Ala Ala
    1070                1075                1080

His Leu Thr Ala Ala Pro Leu Val Asp Leu Thr Pro Thr His Ser
    1085                1090                1095

Gly Ser Ala Met Leu Met Leu Leu Ser Val Val Phe Val Gly Leu
    1100                1105                1110

Ala Val Phe Val Ile Tyr Lys Phe Lys Arg Arg Val Ala Leu Pro
    1115                1120                1125

Ser Pro Pro Ser Pro Ser Ala Gln Pro Gly Asp Ser Ser Leu Arg
    1130                1135                1140

Leu Gln Arg Pro Arg Pro Ala Thr Pro Ser Ser Pro Lys Arg
    1145                1150                1155

Gly Ser Ala Gly Ala Gln Phe Ala Ile
    1160                1165

<210> SEQ ID NO 17
<211> LENGTH: 1147
<212> TYPE: PRT
<213> ORGANISM: Mus musculus
<220> FEATURE:
<221> NAME/KEY: MISC_FEATURE
<222> LOCATION: (1)..(1147)
<223> OTHER INFORMATION: preproSorCS1b, isoform 2

<400> SEQUENCE: 17

Met Gly Lys Val Gly Ala Gly Asp Gly Ser Ser Ala Gly Leu Ser Ala
1               5                  10                  15

Leu Leu Ala Gly Ala Gly Leu Leu Met Leu Leu Ala Pro Gly Val Cys
            20                  25                  30

Ser Ser Leu Ser Cys Cys Pro Pro Gln His Pro Ser Ser Thr Pro Arg
        35                  40                  45

Arg Thr Leu Thr Pro Arg Gly Phe Pro His Pro Gly Pro Leu Gly Arg
    50                  55                  60
```

```
Ala Pro Ala Thr Pro Pro Leu Phe Met Arg Pro Leu Phe Ala Val
65                  70                  75                  80

Ala Pro Gly Asp Arg Ala Leu Phe Leu Glu Arg Ala Gly Gly Ser Arg
            85                  90                  95

Val Ser Val Ala Thr Ala Ala Arg Ser Gly Arg Arg Arg Ser Gly
            100                 105                 110

Thr Glu Pro Glu Lys Ile Glu Pro Gly Glu Gly Ala Ser Arg Ser Arg
            115                 120                 125

Arg Asp Met Leu Lys Asp Gly Gln Gln Gly Leu Gly Thr Gly Ala
130                 135                 140

Arg Asp Pro Gly Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
            165                 170                 175

Met Val His Trp Ser Gly His Asn Ser Ser Val Ile Leu Ile Leu Thr
            180                 185                 190

Lys Leu Tyr Asp Tyr Asn Leu Gly Ser Ile Thr Glu Ser Ser Leu Trp
            195                 200                 205

Arg Ser Thr Asp Tyr Gly Thr Thr Tyr Glu Lys Leu Asn Asp Lys Val
210                 215                 220

Gly Leu Lys Thr Ile Leu Ser Tyr Leu Tyr Val Cys Pro Thr Asn Lys
225                 230                 235                 240

Cys Lys Ile Met Leu Leu Thr Asp Pro Glu Ile Glu Ser Ser Leu Leu
            245                 250                 255

Ile Ser Ser Asp Glu Gly Ala Thr Tyr Gln Lys Tyr Arg Leu Asn Phe
            260                 265                 270

Tyr Leu Gln Ser Leu Leu Phe His Pro Lys Gln Glu Asp Trp Ile Leu
            275                 280                 285

Ala Tyr Ser Gln Asp Gln Lys Leu Tyr Ser Ser Ala Glu Phe Gly Arg
290                 295                 300

Arg Trp Gln Leu Ile Gln Glu Ser Val Val Pro Asn Arg Phe Tyr Trp
305                 310                 315                 320

Ser Val Met Gly Ser Ser Lys Glu Pro Asp Leu Val His Leu Glu Ala
            325                 330                 335

Arg Thr Val Asp Gly His Ser Ile Tyr Leu Thr Cys Arg Met Gln Asn
            340                 345                 350

Cys Thr Glu Ala Asn Arg Asn Lys Pro Phe Pro Gly Tyr Ile Asp Pro
            355                 360                 365

Asp Ser Leu Ile Val Gln Asp Asp Tyr Val Phe Val Gln Leu Thr Ser
            370                 375                 380

Gly Gly Arg Pro His Tyr Tyr Val Ser Tyr Arg Arg Ser Pro Phe Ala
385                 390                 395                 400

Gln Met Lys Leu Pro Lys Tyr Ala Leu Pro Lys Asp Met His Val Ile
            405                 410                 415

Ser Thr Asp Glu Asn Gln Val Phe Ala Ala Val Gln Glu Trp Asn Gln
            420                 425                 430

Asn Asp Thr Tyr Asn Leu Tyr Ile Ser Asp Thr Arg Gly Val Tyr Phe
            435                 440                 445

Thr Leu Ala Leu Glu Asn Val Arg Ser Ser Arg Gly Pro Glu Gly Asn
            450                 455                 460

Val Met Ile Asp Leu Tyr Glu Val Ala Gly Ile Lys Gly Met Phe Leu
465                 470                 475                 480
```

```
Ala Asn Lys Lys Ile Asp Asn Gln Val Lys Thr Phe Ile Thr Tyr Asn
            485                 490                 495

Lys Gly Arg Asp Trp Arg Leu Leu Gln Ala Pro Asp Ala Asp Leu Arg
        500                 505                 510

Gly Asp Pro Val His Cys Leu Leu Pro Tyr Cys Ser Leu His Leu His
        515                 520                 525

Leu Lys Val Ser Glu Asn Pro Tyr Thr Ser Gly Ile Ile Ala Ser Arg
        530                 535                 540

Asp Thr Ala Pro Ser Ile Ile Val Ala Ser Gly Asn Ile Gly Ser Glu
545                 550                 555                 560

Leu Ser Asp Ser Asp Ile Ser Met Phe Val Ser Ser Asp Ala Gly Asn
                565                 570                 575

Thr Trp Arg Gln Ile Phe Glu Glu His Ser Ile Leu Tyr Leu Asp
        580                 585                 590

Gln Gly Gly Val Leu Val Ala Met Lys His Thr Ser Leu Pro Ile Arg
        595                 600                 605

His Leu Trp Leu Ser Phe Asp Glu Gly Arg Ser Trp Ser Lys Tyr Ser
        610                 615                 620

Phe Thr Ser Ile Pro Leu Phe Val Asp Gly Val Leu Gly Glu Pro Gly
625                 630                 635                 640

Glu Glu Thr Leu Ile Met Thr Val Phe Gly His Phe Ser His Arg Ser
                645                 650                 655

Glu Trp Gln Leu Val Lys Val Asp Tyr Lys Ser Ile Phe Asp Arg Arg
            660                 665                 670

Cys Ala Glu Glu Asp Tyr Arg Pro Trp Gln Leu His Ser Gln Gly Glu
        675                 680                 685

Ala Cys Ile Met Gly Ala Lys Arg Ile Tyr Lys Lys Arg Lys Ser Glu
        690                 695                 700

Arg Lys Cys Met Gln Lys Tyr Ala Gly Ala Met Glu Ser Glu Pro Cys
705                 710                 715                 720

Val Cys Thr Glu Ala Asp Phe Asp Cys Asp Tyr Gly Tyr Glu Arg His
                725                 730                 735

Ser Asn Gly Gln Cys Leu Pro Ala Phe Trp Phe Asn Pro Ser Ser Leu
            740                 745                 750

Ser Lys Asp Cys Ser Leu Gly Gln Ser Tyr Leu Asn Ser Ala Gly Tyr
        755                 760                 765

Arg Lys Val Val Ser Asn Asn Cys Thr Asp Gly Val Arg Glu Gln Tyr
        770                 775                 780

Thr Ala Lys Pro Gln Lys Cys Pro Gly Lys Ala Pro Arg Gly Leu Arg
785                 790                 795                 800

Ile Val Thr Ala Asp Gly Lys Leu Thr Ala Glu Gln Gly His Asn Val
                805                 810                 815

Thr Leu Met Val Gln Leu Glu Glu Gly Asp Val Gln Arg Thr Leu Ile
            820                 825                 830

Gln Val Asp Phe Gly Asp Gly Ile Ala Val Ser Tyr Val Asn Leu Ser
        835                 840                 845

Ser Met Glu Asp Gly Ile Lys His Val Tyr Gln Asn Val Gly Ile Phe
        850                 855                 860

Arg Val Thr Val Gln Val Asp Asn Ser Leu Gly Ser Asp Ser Ala Val
865                 870                 875                 880

Leu Tyr Leu His Val Thr Cys Pro Leu Glu His Val His Leu Ser Leu
                885                 890                 895

Pro Phe Val Thr Thr Lys Asn Lys Glu Val Asn Ala Thr Ala Val Leu
```

```
                    900             905             910
Trp Pro Ser Gln Val Gly Thr Leu Thr Tyr Val Trp Trp Tyr Gly Asn
        915             920             925

Asn Thr Glu Pro Leu Ile Thr Leu Glu Gly Ser Ile Ser Phe Lys Phe
        930             935             940

Thr Ser Glu Gly Met Asn Thr Ile Thr Val Gln Val Ser Ala Gly Asn
945             950             955             960

Ala Ile Leu Gln Asp Thr Lys Thr Ile Ala Val Tyr Glu Glu Phe Arg
                965             970             975

Ser Leu Arg Leu Ala Phe Ser Pro Asn Leu Asp Asp Tyr Asn Pro Asp
                980             985             990

Ile Pro Glu Trp Arg Arg Asp Ile Ser Arg Val Ile Lys Lys Ser Leu
        995             1000            1005

Val Glu Ala Thr Gly Ile Pro Ser Gln His Ile Leu Val Ala Val
        1010            1015            1020

Leu Pro Gly Leu Pro Thr Ala Ala Glu Leu Phe Val Leu Pro Tyr
        1025            1030            1035

Gln Asp Gly Thr Arg Glu Asn Lys Arg Ser Pro Glu Asp Leu Glu
        1040            1045            1050

Gln Ile Ser Glu Val Leu Ile His Lys Leu Asn Gln Asn Leu Val
        1055            1060            1065

His Phe Glu Leu Lys Pro Gly Val Gln Val Leu Val His Ala Ala
        1070            1075            1080

His Leu Thr Ala Ala Pro Leu Val Asp Leu Thr Pro Thr His Ser
        1085            1090            1095

Gly Ser Ala Met Leu Met Leu Leu Ser Val Val Phe Val Gly Leu
        1100            1105            1110

Ala Val Phe Val Ile Tyr Lys Phe Lys Arg Cys Val Phe Leu Leu
        1115            1120            1125

Leu Pro Ser Tyr Pro Arg Pro Pro Pro Ser Ser Phe Cys Gln
        1130            1135            1140

Val Gln Lys Gln
        1145

<210> SEQ ID NO 18
<211> LENGTH: 1178
<212> TYPE: PRT
<213> ORGANISM: Mus musculus
<220> FEATURE:
<221> NAME/KEY: MISC_FEATURE
<222> LOCATION: (1)..(1178)
<223> OTHER INFORMATION: preproSorCS1c, isoform 3

<400> SEQUENCE: 18

Met Gly Lys Val Gly Ala Gly Asp Gly Ser Ser Ala Gly Leu Ser Ala
1               5                   10                  15

Leu Leu Ala Gly Ala Gly Leu Leu Met Leu Leu Ala Pro Gly Val Cys
                20                  25                  30

Ser Ser Leu Ser Cys Cys Pro Pro Gln His Pro Ser Ser Thr Pro Arg
            35                  40                  45

Arg Thr Leu Thr Pro Arg Gly Phe Pro His Pro Gly Pro Leu Gly Arg
        50                  55                  60

Ala Pro Ala Thr Pro Pro Leu Phe Met Arg Pro Leu Phe Ala Val
65                  70                  75                  80

Ala Pro Gly Asp Arg Ala Leu Phe Leu Glu Arg Ala Gly Gly Ser Arg
                85                  90                  95
```

```
Val Ser Val Ala Thr Ala Ala Arg Ser Gly Arg Arg Arg Ser Gly
            100                 105                 110

Thr Glu Pro Glu Lys Ile Glu Pro Gly Glu Gly Ala Ser Arg Ser Arg
            115                 120                 125

Arg Asp Met Leu Lys Asp Gly Gly Gln Gln Gly Leu Gly Thr Gly Ala
            130                 135                 140

Arg Asp Pro Gly Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                165                 170                 175

Met Val His Trp Ser Gly His Asn Ser Ser Val Ile Leu Ile Leu Thr
            180                 185                 190

Lys Leu Tyr Asp Tyr Asn Leu Gly Ser Ile Thr Glu Ser Ser Leu Trp
            195                 200                 205

Arg Ser Thr Asp Tyr Gly Thr Thr Tyr Glu Lys Leu Asn Asp Lys Val
            210                 215                 220

Gly Leu Lys Thr Ile Leu Ser Tyr Leu Tyr Val Cys Pro Thr Asn Lys
225                 230                 235                 240

Cys Lys Ile Met Leu Leu Thr Asp Pro Glu Ile Glu Ser Ser Leu Leu
                245                 250                 255

Ile Ser Ser Asp Glu Gly Ala Thr Tyr Gln Lys Tyr Arg Leu Asn Phe
            260                 265                 270

Tyr Leu Gln Ser Leu Leu Phe His Pro Lys Gln Glu Asp Trp Ile Leu
            275                 280                 285

Ala Tyr Ser Gln Asp Gln Lys Leu Tyr Ser Ser Ala Glu Phe Gly Arg
            290                 295                 300

Arg Trp Gln Leu Ile Gln Glu Ser Val Val Pro Asn Arg Phe Tyr Trp
305                 310                 315                 320

Ser Val Met Gly Ser Ser Lys Glu Pro Asp Leu Val His Leu Glu Ala
                325                 330                 335

Arg Thr Val Asp Gly His Ser Ile Tyr Leu Thr Cys Arg Met Gln Asn
            340                 345                 350

Cys Thr Glu Ala Asn Arg Asn Lys Pro Phe Pro Gly Tyr Ile Asp Pro
            355                 360                 365

Asp Ser Leu Ile Val Gln Asp Asp Tyr Val Phe Val Gln Leu Thr Ser
            370                 375                 380

Gly Gly Arg Pro His Tyr Tyr Val Ser Tyr Arg Arg Ser Pro Phe Ala
385                 390                 395                 400

Gln Met Lys Leu Pro Lys Tyr Ala Leu Pro Lys Asp Met His Val Ile
                405                 410                 415

Ser Thr Asp Glu Asn Gln Val Phe Ala Ala Val Gln Glu Trp Asn Gln
            420                 425                 430

Asn Asp Thr Tyr Asn Leu Tyr Ile Ser Asp Thr Arg Gly Val Tyr Phe
            435                 440                 445

Thr Leu Ala Leu Glu Asn Val Arg Ser Ser Arg Gly Pro Glu Gly Asn
            450                 455                 460

Val Met Ile Asp Leu Tyr Glu Val Ala Gly Ile Lys Gly Met Phe Leu
465                 470                 475                 480

Ala Asn Lys Lys Ile Asp Asn Gln Val Lys Thr Phe Ile Thr Tyr Asn
                485                 490                 495

Lys Gly Arg Asp Trp Arg Leu Leu Gln Ala Pro Asp Ala Asp Leu Arg
            500                 505                 510
```

-continued

```
Gly Asp Pro Val His Cys Leu Leu Pro Tyr Cys Ser Leu His Leu His
            515                 520                 525

Leu Lys Val Ser Glu Asn Pro Tyr Thr Ser Gly Ile Ile Ala Ser Arg
530                 535                 540

Asp Thr Ala Pro Ser Ile Ile Val Ala Ser Gly Asn Ile Gly Ser Glu
545                 550                 555                 560

Leu Ser Asp Ser Asp Ile Ser Met Phe Val Ser Ser Asp Ala Gly Asn
                565                 570                 575

Thr Trp Arg Gln Ile Phe Glu Glu His Ser Ile Leu Tyr Leu Asp
            580                 585                 590

Gln Gly Gly Val Leu Val Ala Met Lys His Thr Ser Leu Pro Ile Arg
            595                 600                 605

His Leu Trp Leu Ser Phe Asp Glu Gly Arg Ser Trp Ser Lys Tyr Ser
            610                 615                 620

Phe Thr Ser Ile Pro Leu Phe Val Asp Gly Val Leu Gly Glu Pro Gly
625                 630                 635                 640

Glu Glu Thr Leu Ile Met Thr Val Phe Gly His Phe Ser His Arg Ser
                645                 650                 655

Glu Trp Gln Leu Val Lys Val Asp Tyr Lys Ser Ile Phe Asp Arg Arg
            660                 665                 670

Cys Ala Glu Glu Asp Tyr Arg Pro Trp Gln Leu His Ser Gln Gly Glu
            675                 680                 685

Ala Cys Ile Met Gly Ala Lys Arg Ile Tyr Lys Lys Arg Lys Ser Glu
            690                 695                 700

Arg Lys Cys Met Gln Lys Tyr Ala Gly Ala Met Glu Ser Glu Pro Cys
705                 710                 715                 720

Val Cys Thr Glu Ala Asp Phe Asp Cys Asp Tyr Gly Tyr Glu Arg His
                725                 730                 735

Ser Asn Gly Gln Cys Leu Pro Ala Phe Trp Phe Asn Pro Ser Ser Leu
            740                 745                 750

Ser Lys Asp Cys Ser Leu Gly Gln Ser Tyr Leu Asn Ser Ala Gly Tyr
            755                 760                 765

Arg Lys Val Val Ser Asn Asn Cys Thr Asp Gly Val Arg Glu Gln Tyr
770                 775                 780

Thr Ala Lys Pro Gln Lys Cys Pro Gly Lys Ala Pro Arg Gly Leu Arg
785                 790                 795                 800

Ile Val Thr Ala Asp Gly Lys Leu Thr Ala Glu Gln Gly His Asn Val
                805                 810                 815

Thr Leu Met Val Gln Leu Glu Glu Gly Asp Val Gln Arg Thr Leu Ile
            820                 825                 830

Gln Val Asp Phe Gly Asp Gly Ile Ala Val Ser Tyr Val Asn Leu Ser
            835                 840                 845

Ser Met Glu Asp Gly Ile Lys His Val Tyr Gln Asn Val Gly Ile Phe
850                 855                 860

Arg Val Thr Val Gln Val Asp Asn Ser Leu Gly Ser Asp Ser Ala Val
865                 870                 875                 880

Leu Tyr Leu His Val Thr Cys Pro Leu Glu His Val His Leu Ser Leu
                885                 890                 895

Pro Phe Val Thr Thr Lys Asn Lys Glu Val Asn Ala Thr Ala Val Leu
            900                 905                 910

Trp Pro Ser Gln Val Gly Thr Leu Thr Tyr Val Trp Trp Tyr Gly Asn
            915                 920                 925

Asn Thr Glu Pro Leu Ile Thr Leu Glu Gly Ser Ile Ser Phe Lys Phe
```

```
                    930             935             940
Thr Ser Glu Gly Met Asn Thr Ile Thr Val Gln Val Ser Ala Gly Asn
945             950             955             960

Ala Ile Leu Gln Asp Thr Lys Thr Ile Ala Val Tyr Glu Glu Phe Arg
            965             970             975

Ser Leu Arg Leu Ala Phe Ser Pro Asn Leu Asp Asp Tyr Asn Pro Asp
            980             985             990

Ile Pro Glu Trp Arg Arg Asp Ile Ser Arg Val Ile Lys Lys Ser Leu
            995             1000            1005

Val Glu Ala Thr Gly Ile Pro Ser Gln His Ile Leu Val Ala Val
    1010            1015            1020

Leu Pro Gly Leu Pro Thr Ala Ala Glu Leu Phe Val Leu Pro Tyr
    1025            1030            1035

Gln Asp Gly Thr Arg Glu Asn Lys Arg Ser Pro Glu Asp Leu Glu
    1040            1045            1050

Gln Ile Ser Glu Val Leu Ile His Lys Leu Asn Gln Asn Leu Val
    1055            1060            1065

His Phe Glu Leu Lys Pro Gly Val Gln Val Leu Val His Ala Ala
    1070            1075            1080

His Leu Thr Ala Ala Pro Leu Val Asp Leu Thr Pro Thr His Ser
    1085            1090            1095

Gly Ser Ala Met Leu Met Leu Leu Ser Val Val Phe Val Gly Leu
    1100            1105            1110

Ala Val Phe Val Ile Tyr Lys Phe Lys Arg Lys Ile Pro Gly Ile
    1115            1120            1125

Asn Val Tyr Ala Gln Met Gln Asn Glu Lys Glu Gln Glu Leu Ile
    1130            1135            1140

Asn Pro Val Ser His Ser Glu Ser Arg Pro Ser Val Pro His Pro
    1145            1150            1155

Asp Leu Arg Arg Pro Gly Gln Leu Val Asp Glu Lys Val Glu Ser
    1160            1165            1170

Gln Leu Leu Gly Lys
    1175

<210> SEQ ID NO 19
<211> LENGTH: 1178
<212> TYPE: PRT
<213> ORGANISM: Mus musculus
<220> FEATURE:
<221> NAME/KEY: MISC_FEATURE
<222> LOCATION: (1)..(1178)
<223> OTHER INFORMATION: preproSorCS1c+, isoform 4

<400> SEQUENCE: 19

Met Gly Lys Val Gly Ala Gly Asp Gly Ser Ser Ala Gly Leu Ser Ala
1               5                   10                  15

Leu Leu Ala Gly Ala Gly Leu Leu Met Leu Leu Ala Pro Gly Val Cys
                20                  25                  30

Ser Ser Leu Ser Cys Cys Pro Pro Gln His Pro Ser Ser Thr Pro Arg
            35                  40                  45

Arg Thr Leu Thr Pro Arg Gly Phe Pro His Pro Gly Pro Leu Gly Arg
        50                  55                  60

Ala Pro Ala Thr Pro Pro Leu Phe Met Arg Pro Leu Phe Ala Val
65                  70                  75                  80

Ala Pro Gly Asp Arg Ala Leu Phe Leu Glu Arg Ala Gly Gly Ser Arg
                85                  90                  95
```

```
Val Ser Val Ala Thr Ala Ala Arg Ser Gly Arg Arg Arg Ser Gly
            100                 105                 110

Thr Glu Pro Glu Lys Ile Glu Pro Gly Gly Ala Ser Arg Ser Arg
            115                 120                 125

Arg Asp Met Leu Lys Asp Gly Gln Gln Gly Leu Gly Thr Gly Ala
            130                 135                 140

Arg Asp Pro Gly Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                    165                 170                 175

Met Val His Trp Ser Gly His Asn Ser Ser Val Ile Leu Ile Leu Thr
                180                 185                 190

Lys Leu Tyr Asp Tyr Asn Leu Gly Ser Ile Thr Glu Ser Ser Leu Trp
            195                 200                 205

Arg Ser Thr Asp Tyr Gly Thr Thr Tyr Glu Lys Leu Asn Asp Lys Val
            210                 215                 220

Gly Leu Lys Thr Ile Leu Ser Tyr Leu Tyr Val Cys Pro Thr Asn Lys
225                 230                 235                 240

Cys Lys Ile Met Leu Leu Thr Asp Pro Glu Ile Glu Ser Ser Leu Leu
                    245                 250                 255

Ile Ser Ser Asp Glu Gly Ala Thr Tyr Gln Lys Tyr Arg Leu Asn Phe
                260                 265                 270

Tyr Leu Gln Ser Leu Leu Phe His Pro Lys Gln Glu Asp Trp Ile Leu
            275                 280                 285

Ala Tyr Ser Gln Asp Gln Lys Leu Tyr Ser Ser Ala Glu Phe Gly Arg
            290                 295                 300

Arg Trp Gln Leu Ile Gln Glu Ser Val Val Pro Asn Arg Phe Tyr Trp
305                 310                 315                 320

Ser Val Met Gly Ser Ser Lys Glu Pro Asp Leu Val His Leu Glu Ala
                    325                 330                 335

Arg Thr Val Asp Gly His Ser Ile Tyr Leu Thr Cys Arg Met Gln Asn
                340                 345                 350

Cys Thr Glu Ala Asn Arg Asn Lys Pro Phe Pro Gly Tyr Ile Asp Pro
            355                 360                 365

Asp Ser Leu Ile Val Gln Asp Asp Tyr Val Phe Val Gln Leu Thr Ser
            370                 375                 380

Gly Gly Arg Pro His Tyr Tyr Val Ser Tyr Arg Arg Ser Pro Phe Ala
385                 390                 395                 400

Gln Met Lys Leu Pro Lys Tyr Ala Leu Pro Lys Asp Met His Val Ile
                    405                 410                 415

Ser Thr Asp Glu Asn Gln Val Phe Ala Ala Val Gln Glu Trp Asn Gln
                420                 425                 430

Asn Asp Thr Tyr Asn Leu Tyr Ile Ser Asp Thr Arg Gly Val Tyr Phe
            435                 440                 445

Thr Leu Ala Leu Glu Asn Val Arg Ser Ser Arg Gly Pro Glu Gly Asn
            450                 455                 460

Val Met Ile Asp Leu Tyr Glu Val Ala Gly Ile Lys Gly Met Phe Leu
465                 470                 475                 480

Ala Asn Lys Lys Ile Asp Asn Gln Val Lys Thr Phe Ile Thr Tyr Asn
                    485                 490                 495

Lys Gly Arg Asp Trp Arg Leu Leu Gln Ala Pro Asp Ala Asp Leu Arg
                500                 505                 510
```

-continued

Gly Asp Pro Val His Cys Leu Leu Pro Tyr Cys Ser Leu His Leu His
515                 520                 525

Leu Lys Val Ser Glu Asn Pro Tyr Thr Ser Gly Ile Ile Ala Ser Arg
530                 535                 540

Asp Thr Ala Pro Ser Ile Ile Val Ala Ser Gly Asn Ile Gly Ser Glu
545                 550                 555                 560

Leu Ser Asp Ser Asp Ile Ser Met Phe Val Ser Ser Asp Ala Gly Asn
                565                 570                 575

Thr Trp Arg Gln Ile Phe Glu Glu His Ser Ile Leu Tyr Leu Asp
                580                 585                 590

Gln Gly Gly Val Leu Val Ala Met Lys His Thr Ser Leu Pro Ile Arg
                595                 600                 605

His Leu Trp Leu Ser Phe Asp Glu Gly Arg Ser Trp Ser Lys Tyr Ser
610                 615                 620

Phe Thr Ser Ile Pro Leu Phe Val Asp Gly Val Leu Gly Glu Pro Gly
625                 630                 635                 640

Glu Glu Thr Leu Ile Met Thr Val Phe Gly His Phe Ser His Arg Ser
                645                 650                 655

Glu Trp Gln Leu Val Lys Val Asp Tyr Lys Ser Ile Phe Asp Arg Arg
                660                 665                 670

Cys Ala Glu Glu Asp Tyr Arg Pro Trp Gln Leu His Ser Gln Gly Glu
            675                 680                 685

Ala Cys Ile Met Gly Ala Lys Arg Ile Tyr Lys Lys Arg Lys Ser Glu
            690                 695                 700

Arg Lys Cys Met Gln Lys Tyr Ala Gly Ala Met Glu Ser Glu Pro Cys
705                 710                 715                 720

Val Cys Thr Glu Ala Asp Phe Asp Cys Asp Tyr Gly Tyr Glu Arg His
                725                 730                 735

Ser Asn Gly Gln Cys Leu Pro Ala Phe Trp Phe Asn Pro Ser Ser Leu
            740                 745                 750

Ser Lys Asp Cys Ser Leu Gly Gln Ser Tyr Leu Asn Ser Ala Gly Tyr
            755                 760                 765

Arg Lys Val Val Ser Asn Asn Cys Thr Asp Gly Val Arg Glu Gln Tyr
770                 775                 780

Thr Ala Lys Pro Gln Lys Cys Pro Gly Lys Ala Pro Arg Gly Leu Arg
785                 790                 795                 800

Ile Val Thr Ala Asp Gly Lys Leu Thr Ala Glu Gln Gly His Asn Val
                805                 810                 815

Thr Leu Met Val Gln Leu Glu Glu Gly Asp Val Gln Arg Thr Leu Ile
                820                 825                 830

Gln Val Asp Phe Gly Asp Gly Ile Ala Val Ser Tyr Val Asn Leu Ser
                835                 840                 845

Ser Met Glu Asp Gly Ile Lys His Val Tyr Gln Asn Val Gly Ile Phe
850                 855                 860

Arg Val Thr Val Gln Val Asp Asn Ser Leu Gly Ser Asp Ser Ala Val
865                 870                 875                 880

Leu Tyr Leu His Val Thr Cys Pro Leu Glu His Val His Leu Ser Leu
                885                 890                 895

Pro Phe Val Thr Thr Lys Asn Lys Glu Val Asn Ala Thr Ala Val Leu
                900                 905                 910

Trp Pro Ser Gln Val Gly Thr Leu Thr Tyr Val Trp Trp Tyr Gly Asn
                915                 920                 925

Asn Thr Glu Pro Leu Ile Thr Leu Glu Gly Ser Ile Ser Phe Lys Phe

```
                    930             935             940
        Thr Ser Glu Gly Met Asn Thr Ile Thr Val Gln Val Ser Ala Gly Asn
        945             950             955             960

Ala Ile Leu Gln Asp Thr Lys Thr Ile Ala Val Tyr Glu Glu Phe Arg
                        965             970             975

Ser Leu Arg Leu Ala Phe Ser Pro Asn Leu Asp Asp Tyr Asn Pro Asp
                        980             985             990

Ile Pro Glu Trp Arg Arg Asp Ile Ser Arg Val Ile Lys Lys Ser Leu
                        995            1000            1005

Val Glu Ala Thr Gly Ile Pro Ser Gln His Ile Leu Val Ala Val
                1010            1015            1020

Leu Pro Gly Leu Pro Thr Ala Ala Glu Leu Phe Val Leu Pro Tyr
                1025            1030            1035

Gln Asp Gly Thr Arg Glu Asn Lys Arg Ser Pro Glu Asp Leu Glu
                1040            1045            1050

Gln Ile Ser Glu Val Leu Ile His Lys Leu Asn Gln Asn Leu Val
                1055            1060            1065

His Phe Glu Leu Lys Pro Gly Val Gln Val Leu Val His Ala Ala
                1070            1075            1080

His Leu Thr Ala Ala Pro Leu Val Asp Leu Thr Pro Thr His Ser
                1085            1090            1095

Gly Ser Ala Met Leu Met Leu Leu Ser Val Phe Val Gly Leu
                1100            1105            1110

Ala Val Phe Val Ile Tyr Lys Phe Lys Arg Lys Ile Pro Gly Ile
                1115            1120            1125

Asn Val Tyr Ala Gln Met Gln Asn Glu Lys Glu Gln Glu Leu Ile
                1130            1135            1140

Asn Pro Val Ser His Ser Glu Ser Arg Ser Ser Val Pro His Pro
                1145            1150            1155

Asp Leu Arg Arg Pro Gly Gln Leu Val Asp Glu Lys Val Glu Ser
                1160            1165            1170

Gln Leu Leu Gly Glu
                1175

<210> SEQ ID NO 20
<211> LENGTH: 1191
<212> TYPE: PRT
<213> ORGANISM: Mus musculus
<220> FEATURE:
<221> NAME/KEY: MISC_FEATURE
<222> LOCATION: (1)..(1191)
<223> OTHER INFORMATION: preproSorCS1d

<400> SEQUENCE: 20

Met Gly Lys Val Gly Ala Gly Asp Gly Ser Ser Ala Gly Leu Ser Ala
1               5                   10                  15

Leu Leu Ala Gly Ala Gly Leu Leu Met Leu Leu Ala Pro Gly Val Cys
                20                  25                  30

Ser Ser Leu Ser Cys Cys Pro Pro Gln His Pro Ser Ser Thr Pro Arg
            35                  40                  45

Arg Thr Leu Thr Pro Arg Gly Phe Pro His Pro Gly Pro Leu Gly Arg
        50                  55                  60

Ala Pro Ala Thr Pro Pro Leu Phe Met Arg Pro Leu Phe Ala Val
65                  70                  75                  80

Ala Pro Gly Asp Arg Ala Leu Phe Leu Glu Arg Ala Gly Gly Ser Arg
                85                  90                  95
```

```
Val Ser Val Ala Thr Ala Ala Arg Ser Gly Arg Arg Arg Ser Gly
            100                 105                 110

Thr Glu Pro Glu Lys Ile Glu Pro Gly Gly Ala Ser Arg Ser Arg
            115                 120                 125

Arg Asp Met Leu Lys Asp Gly Gln Gln Gly Leu Gly Thr Gly Ala
            130                 135                 140

Arg Asp Pro Gly Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
            165                 170                 175

Met Val His Trp Ser Gly His Asn Ser Ser Val Ile Leu Ile Leu Thr
            180                 185                 190

Lys Leu Tyr Asp Tyr Asn Leu Gly Ser Ile Thr Glu Ser Ser Leu Trp
            195                 200                 205

Arg Ser Thr Asp Tyr Gly Thr Thr Tyr Glu Lys Leu Asn Asp Lys Val
            210                 215                 220

Gly Leu Lys Thr Ile Leu Ser Tyr Leu Tyr Val Cys Pro Thr Asn Lys
225                 230                 235                 240

Cys Lys Ile Met Leu Leu Thr Asp Pro Glu Ile Glu Ser Ser Leu Leu
            245                 250                 255

Ile Ser Ser Asp Glu Gly Ala Thr Tyr Gln Lys Tyr Arg Leu Asn Phe
            260                 265                 270

Tyr Leu Gln Ser Leu Leu Phe His Pro Lys Gln Glu Asp Trp Ile Leu
            275                 280                 285

Ala Tyr Ser Gln Asp Gln Lys Leu Tyr Ser Ser Ala Glu Phe Gly Arg
            290                 295                 300

Arg Trp Gln Leu Ile Gln Glu Ser Val Val Pro Asn Arg Phe Tyr Trp
305                 310                 315                 320

Ser Val Met Gly Ser Ser Lys Glu Pro Asp Leu Val His Leu Glu Ala
            325                 330                 335

Arg Thr Val Asp Gly His Ser Ile Tyr Leu Thr Cys Arg Met Gln Asn
            340                 345                 350

Cys Thr Glu Ala Asn Arg Asn Lys Pro Phe Pro Gly Tyr Ile Asp Pro
            355                 360                 365

Asp Ser Leu Ile Val Gln Asp Asp Tyr Val Phe Val Gln Leu Thr Ser
            370                 375                 380

Gly Gly Arg Pro His Tyr Tyr Val Ser Tyr Arg Arg Ser Pro Phe Ala
385                 390                 395                 400

Gln Met Lys Leu Pro Lys Tyr Ala Leu Pro Lys Asp Met His Val Ile
            405                 410                 415

Ser Thr Asp Glu Asn Gln Val Phe Ala Ala Val Gln Glu Trp Asn Gln
            420                 425                 430

Asn Asp Thr Tyr Asn Leu Tyr Ile Ser Asp Thr Arg Gly Val Tyr Phe
            435                 440                 445

Thr Leu Ala Leu Glu Asn Val Arg Ser Ser Arg Gly Pro Glu Gly Asn
            450                 455                 460

Val Met Ile Asp Leu Tyr Glu Val Ala Gly Ile Lys Gly Met Phe Leu
465                 470                 475                 480

Ala Asn Lys Lys Ile Asp Asn Gln Val Lys Thr Phe Ile Thr Tyr Asn
            485                 490                 495

Lys Gly Arg Asp Trp Arg Leu Leu Gln Ala Pro Asp Ala Asp Leu Arg
            500                 505                 510
```

```
Gly Asp Pro Val His Cys Leu Leu Pro Tyr Cys Ser Leu His Leu His
            515                 520                 525

Leu Lys Val Ser Glu Asn Pro Tyr Thr Ser Gly Ile Ile Ala Ser Arg
530                 535                 540

Asp Thr Ala Pro Ser Ile Ile Val Ala Ser Gly Asn Ile Gly Ser Glu
545                 550                 555                 560

Leu Ser Asp Ser Asp Ile Ser Met Phe Val Ser Ser Asp Ala Gly Asn
                565                 570                 575

Thr Trp Arg Gln Ile Phe Glu Glu His Ser Ile Leu Tyr Leu Asp
            580                 585                 590

Gln Gly Gly Val Leu Val Ala Met Lys His Thr Ser Leu Pro Ile Arg
            595                 600                 605

His Leu Trp Leu Ser Phe Asp Glu Gly Arg Ser Trp Ser Lys Tyr Ser
            610                 615                 620

Phe Thr Ser Ile Pro Leu Phe Val Asp Gly Val Leu Gly Glu Pro Gly
625                 630                 635                 640

Glu Glu Thr Leu Ile Met Thr Val Phe Gly His Phe Ser His Arg Ser
                645                 650                 655

Glu Trp Gln Leu Val Lys Val Asp Tyr Lys Ser Ile Phe Asp Arg Arg
            660                 665                 670

Cys Ala Glu Glu Asp Tyr Arg Pro Trp Gln Leu His Ser Gln Gly Glu
            675                 680                 685

Ala Cys Ile Met Gly Ala Lys Arg Ile Tyr Lys Lys Arg Lys Ser Glu
            690                 695                 700

Arg Lys Cys Met Gln Lys Tyr Ala Gly Ala Met Glu Ser Glu Pro Cys
705                 710                 715                 720

Val Cys Thr Glu Ala Asp Phe Asp Cys Asp Tyr Gly Tyr Glu Arg His
                725                 730                 735

Ser Asn Gly Gln Cys Leu Pro Ala Phe Trp Phe Asn Pro Ser Ser Leu
            740                 745                 750

Ser Lys Asp Cys Ser Leu Gly Gln Ser Tyr Leu Asn Ser Ala Gly Tyr
            755                 760                 765

Arg Lys Val Val Ser Asn Asn Cys Thr Asp Gly Val Arg Glu Gln Tyr
770                 775                 780

Thr Ala Lys Pro Gln Lys Cys Pro Gly Lys Ala Pro Arg Gly Leu Arg
785                 790                 795                 800

Ile Val Thr Ala Asp Gly Lys Leu Thr Ala Glu Gln Gly His Asn Val
                805                 810                 815

Thr Leu Met Val Gln Leu Glu Glu Gly Asp Val Gln Arg Thr Leu Ile
                820                 825                 830

Gln Val Asp Phe Gly Asp Gly Ile Ala Val Ser Tyr Val Asn Leu Ser
            835                 840                 845

Ser Met Glu Asp Gly Ile Lys His Val Tyr Gln Asn Val Gly Ile Phe
850                 855                 860

Arg Val Thr Val Gln Val Asp Asn Ser Leu Gly Ser Asp Ser Ala Val
865                 870                 875                 880

Leu Tyr Leu His Val Thr Cys Pro Leu Glu His Val His Leu Ser Leu
                885                 890                 895

Pro Phe Val Thr Thr Lys Asn Lys Glu Val Asn Ala Thr Ala Val Leu
                900                 905                 910

Trp Pro Ser Gln Val Gly Thr Leu Thr Tyr Val Trp Trp Tyr Gly Asn
            915                 920                 925

Asn Thr Glu Pro Leu Ile Thr Leu Glu Gly Ser Ile Ser Phe Lys Phe
```

```
                930           935          940
    Thr Ser Glu Gly Met Asn Thr Ile Thr Val Gln Val Ser Ala Gly Asn
    945              950              955              960

Ala Ile Leu Gln Asp Thr Lys Thr Ile Ala Val Tyr Glu Glu Phe Arg
                    965              970              975

Ser Leu Arg Leu Ala Phe Ser Pro Asn Leu Asp Asp Tyr Asn Pro Asp
                    980              985              990

Ile Pro Glu Trp Arg Arg Asp Ile  Ser Arg Val Ile Lys  Lys Ser Leu
            995              1000              1005

Val Glu  Ala Thr Gly Ile Pro  Ser Gln His Ile Leu  Val Ala Val
        1010              1015              1020

Leu Pro  Gly Leu Pro Thr Ala  Ala Glu Leu Phe Val  Leu Pro Tyr
        1025              1030              1035

Gln Asp  Gly Thr Arg Glu Asn  Lys Arg Ser Pro Glu  Asp Leu Glu
        1040              1045              1050

Gln Ile  Ser Glu Val Leu Ile  His Lys Leu Asn Gln  Asn Leu Val
        1055              1060              1065

His Phe  Glu Leu Lys Pro Gly  Val Gln Val Leu Val  His Ala Ala
        1070              1075              1080

His Leu  Thr Ala Ala Pro Leu  Val Asp Leu Thr Pro  Thr His Ser
        1085              1090              1095

Gly Ser  Ala Met Leu Met Leu  Leu Ser Val Val Phe  Val Gly Leu
        1100              1105              1110

Ala Val  Phe Val Ile Tyr Lys  Phe Lys Arg Gly Trp  Arg Asp Arg
        1115              1120              1125

Ser Ala  Val Lys Asn Ile Gly  Cys Ser Cys Arg Gly  Pro Gly Phe
        1130              1135              1140

Asn Ser  Gln His Gln Gln Gly  Gly Ser Gln Ala Ser  Val Thr Ser
        1145              1150              1155

Val Pro  Arg Asp Pro Ser Pro  Ser Ser Asp Leu His  Gly His Gln
        1160              1165              1170

Glu His  Thr Trp Cys Thr Asp  Ile His Pro Gly Lys  Thr Pro Ile
        1175              1180              1185

His Ile  Lys
        1190

<210> SEQ ID NO 21
<211> LENGTH: 1099
<212> TYPE: PRT
<213> ORGANISM: Mus musculus
<220> FEATURE:
<221> NAME/KEY: MISC_FEATURE
<222> LOCATION: (1)..(1099)
<223> OTHER INFORMATION: Soluble preproSorCS1

<400> SEQUENCE: 21

Met Gly Lys Val Gly Ala Gly Asp Gly Ser Ser Ala Gly Leu Ser Ala
1               5                   10                  15

Leu Leu Ala Gly Ala Gly Leu Leu Met Leu Leu Ala Pro Gly Val Cys
                20                  25                  30

Ser Ser Leu Ser Cys Cys Pro Pro Gln His Pro Ser Thr Pro Arg
            35                  40                  45

Arg Thr Leu Thr Pro Arg Gly Phe Pro His Pro Gly Pro Leu Gly Arg
        50                  55                  60

Ala Pro Ala Thr Pro Pro Pro Leu Phe Met Arg Pro Leu Phe Ala Val
65                  70                  75                  80
```

```
Ala Pro Gly Asp Arg Ala Leu Phe Leu Glu Arg Ala Gly Ser Arg
             85                  90                  95

Val Ser Val Ala Thr Ala Ala Arg Ser Gly Arg Arg Arg Ser Gly
            100                 105                 110

Thr Glu Pro Glu Lys Ile Glu Pro Gly Glu Gly Ala Ser Arg Ser Arg
        115                 120                 125

Arg Asp Met Leu Lys Asp Gly Gln Gln Gly Leu Gly Thr Gly Ala
130                 135                 140

Arg Asp Pro Gly Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                165                 170                 175

Met Val His Trp Ser Gly His Asn Ser Ser Val Ile Leu Ile Leu Thr
            180                 185                 190

Lys Leu Tyr Asp Tyr Asn Leu Gly Ser Ile Thr Glu Ser Ser Leu Trp
            195                 200                 205

Arg Ser Thr Asp Tyr Gly Thr Thr Tyr Glu Lys Leu Asn Asp Lys Val
    210                 215                 220

Gly Leu Lys Thr Ile Leu Ser Tyr Leu Tyr Val Cys Pro Thr Asn Lys
225                 230                 235                 240

Cys Lys Ile Met Leu Leu Thr Asp Pro Glu Ile Glu Ser Ser Leu Leu
                245                 250                 255

Ile Ser Ser Asp Glu Gly Ala Thr Tyr Gln Lys Tyr Arg Leu Asn Phe
            260                 265                 270

Tyr Leu Gln Ser Leu Leu Phe His Pro Lys Gln Glu Asp Trp Ile Leu
            275                 280                 285

Ala Tyr Ser Gln Asp Gln Lys Leu Tyr Ser Ser Ala Glu Phe Gly Arg
            290                 295                 300

Arg Trp Gln Leu Ile Gln Glu Ser Val Val Pro Asn Arg Phe Tyr Trp
305                 310                 315                 320

Ser Val Met Gly Ser Ser Lys Glu Pro Asp Leu Val His Leu Glu Ala
                325                 330                 335

Arg Thr Val Asp Gly His Ser Ile Tyr Leu Thr Cys Arg Met Gln Asn
            340                 345                 350

Cys Thr Glu Ala Asn Arg Asn Lys Pro Phe Pro Gly Tyr Ile Asp Pro
            355                 360                 365

Asp Ser Leu Ile Val Gln Asp Tyr Val Phe Val Gln Leu Thr Ser
370                 375                 380

Gly Gly Arg Pro His Tyr Tyr Val Ser Tyr Arg Arg Ser Pro Phe Ala
385                 390                 395                 400

Gln Met Lys Leu Pro Lys Tyr Ala Leu Pro Lys Asp Met His Val Ile
                405                 410                 415

Ser Thr Asp Glu Asn Gln Val Phe Ala Ala Val Gln Glu Trp Asn Gln
            420                 425                 430

Asn Asp Thr Tyr Asn Leu Tyr Ile Ser Asp Thr Arg Gly Val Tyr Phe
            435                 440                 445

Thr Leu Ala Leu Glu Asn Val Arg Ser Ser Arg Gly Pro Glu Gly Asn
450                 455                 460

Val Met Ile Asp Leu Tyr Glu Val Ala Gly Ile Lys Gly Met Phe Leu
465                 470                 475                 480

Ala Asn Lys Lys Ile Asp Asn Gln Val Lys Thr Phe Ile Thr Tyr Asn
                485                 490                 495
```

```
              -continued

Lys Gly Arg Asp Trp Arg Leu Leu Gln Ala Pro Asp Ala Asp Leu Arg
            500                 505                 510

Gly Asp Pro Val His Cys Leu Leu Pro Tyr Cys Ser Leu His Leu His
        515                 520                 525

Leu Lys Val Ser Glu Asn Pro Tyr Thr Ser Gly Ile Ile Ala Ser Arg
    530                 535                 540

Asp Thr Ala Pro Ser Ile Ile Val Ala Ser Gly Asn Ile Gly Ser Glu
545                 550                 555                 560

Leu Ser Asp Ser Asp Ile Ser Met Phe Val Ser Ser Asp Ala Gly Asn
                565                 570                 575

Thr Trp Arg Gln Ile Phe Glu Glu His Ser Ile Leu Tyr Leu Asp
            580                 585                 590

Gln Gly Gly Val Leu Val Ala Met Lys His Thr Ser Leu Pro Ile Arg
        595                 600                 605

His Leu Trp Leu Ser Phe Asp Glu Gly Arg Ser Trp Ser Lys Tyr Ser
    610                 615                 620

Phe Thr Ser Ile Pro Leu Phe Val Asp Val Leu Gly Glu Pro Gly
625                 630                 635                 640

Glu Glu Thr Leu Ile Met Thr Val Phe Gly His Phe Ser His Arg Ser
                645                 650                 655

Glu Trp Gln Leu Val Lys Val Asp Tyr Lys Ser Ile Phe Asp Arg Arg
            660                 665                 670

Cys Ala Glu Glu Asp Tyr Arg Pro Trp Gln Leu His Ser Gln Gly Glu
        675                 680                 685

Ala Cys Ile Met Gly Ala Lys Arg Ile Tyr Lys Lys Arg Lys Ser Glu
    690                 695                 700

Arg Lys Cys Met Gln Lys Tyr Ala Gly Ala Met Glu Ser Glu Pro Cys
705                 710                 715                 720

Val Cys Thr Glu Ala Asp Phe Asp Cys Asp Tyr Gly Tyr Glu Arg His
                725                 730                 735

Ser Asn Gly Gln Cys Leu Pro Ala Phe Trp Phe Asn Pro Ser Ser Leu
            740                 745                 750

Ser Lys Asp Cys Ser Leu Gly Gln Ser Tyr Leu Asn Ser Ala Gly Tyr
        755                 760                 765

Arg Lys Val Val Ser Asn Asn Cys Thr Asp Gly Val Arg Glu Gln Tyr
    770                 775                 780

Thr Ala Lys Pro Gln Lys Cys Pro Gly Lys Ala Pro Arg Gly Leu Arg
785                 790                 795                 800

Ile Val Thr Ala Asp Gly Lys Leu Thr Ala Glu Gln Gly His Asn Val
                805                 810                 815

Thr Leu Met Val Gln Leu Glu Glu Gly Asp Val Gln Arg Thr Leu Ile
            820                 825                 830

Gln Val Asp Phe Gly Asp Gly Ile Ala Val Ser Tyr Val Asn Leu Ser
        835                 840                 845

Ser Met Glu Asp Gly Ile Lys His Val Tyr Gln Asn Val Gly Ile Phe
    850                 855                 860

Arg Val Thr Val Gln Val Asp Asn Ser Leu Gly Ser Asp Ser Ala Val
865                 870                 875                 880

Leu Tyr Leu His Val Thr Cys Pro Leu Glu His Val His Leu Ser Leu
                885                 890                 895

Pro Phe Val Thr Thr Lys Asn Lys Glu Val Asn Ala Thr Ala Val Leu
            900                 905                 910

Trp Pro Ser Gln Val Gly Thr Leu Thr Tyr Val Trp Trp Tyr Gly Asn
```

-continued

```
                915                 920                 925
Asn Thr Glu Pro Leu Ile Thr Leu Glu Gly Ser Ile Ser Phe Lys Phe
    930                 935                 940

Thr Ser Glu Gly Met Asn Thr Ile Thr Val Gln Val Ser Ala Gly Asn
945                 950                 955                 960

Ala Ile Leu Gln Asp Thr Lys Thr Ile Ala Val Tyr Glu Glu Phe Arg
                965                 970                 975

Ser Leu Arg Leu Ala Phe Ser Pro Asn Leu Asp Asp Tyr Asn Pro Asp
            980                 985                 990

Ile Pro Glu Trp Arg Arg Asp Ile Ser Arg Val Ile Lys Lys Ser Leu
        995                 1000                1005

Val Glu Ala Thr Gly Ile Pro Ser Gln His Ile Leu Val Ala Val
    1010                1015                1020

Leu Pro Gly Leu Pro Thr Ala Ala Glu Leu Phe Val Leu Pro Tyr
    1025                1030                1035

Gln Asp Gly Thr Arg Glu Asn Lys Arg Ser Pro Glu Asp Leu Glu
    1040                1045                1050

Gln Ile Ser Glu Val Leu Ile His Lys Leu Asn Gln Asn Leu Val
    1055                1060                1065

His Phe Glu Leu Lys Pro Gly Val Gln Val Leu Val His Ala Ala
    1070                1075                1080

His Leu Thr Ala Ala Pro Leu Val Asp Leu Thr Pro Thr His Ser
    1085                1090                1095

Gly
```

<210> SEQ ID NO 22
<211> LENGTH: 1134
<212> TYPE: PRT
<213> ORGANISM: Mus musculus
<220> FEATURE:
<221> NAME/KEY: MISC_FEATURE
<222> LOCATION: (1)..(1134)
<223> OTHER INFORMATION: proSorCS1b (isoform 1)

<400> SEQUENCE: 22

```
Ser Leu Ser Cys Cys Pro Pro Gln His Pro Ser Thr Pro Arg Arg
1               5                   10                  15

Thr Leu Thr Pro Arg Gly Phe Pro His Pro Gly Pro Leu Gly Arg Ala
            20                  25                  30

Pro Ala Thr Pro Pro Pro Leu Phe Met Arg Pro Leu Phe Ala Val Ala
        35                  40                  45

Pro Gly Asp Arg Ala Leu Phe Leu Glu Arg Ala Gly Ser Arg Val
    50                  55                  60

Ser Val Ala Thr Ala Ala Arg Ser Gly Arg Arg Arg Ser Gly Thr
65                  70                  75                  80

Glu Pro Glu Lys Ile Glu Pro Gly Glu Gly Ala Ser Arg Ser Arg Arg
                85                  90                  95

Asp Met Leu Lys Asp Gly Gly Gln Gln Gly Leu Gly Thr Gly Ala Arg
            100                 105                 110

Asp Pro Gly Lys Ala Thr Arg Phe Arg Met Glu Glu Leu Arg Leu Thr
        115                 120                 125

Ser Thr Thr Phe Ala Leu Thr Gly Asp Ser Ala His Asn Gln Ala Met
    130                 135                 140

Val His Trp Ser Gly His Asn Ser Ser Val Ile Leu Ile Leu Thr Lys
145                 150                 155                 160
```

```
Leu Tyr Asp Tyr Asn Leu Gly Ser Ile Thr Glu Ser Ser Leu Trp Arg
            165                 170                 175

Ser Thr Asp Tyr Gly Thr Thr Tyr Glu Lys Leu Asn Asp Lys Val Gly
        180                 185                 190

Leu Lys Thr Ile Leu Ser Tyr Leu Tyr Val Cys Pro Thr Asn Lys Cys
            195                 200                 205

Lys Ile Met Leu Leu Thr Asp Pro Glu Ile Glu Ser Ser Leu Leu Ile
        210                 215                 220

Ser Ser Asp Glu Gly Ala Thr Tyr Gln Lys Tyr Arg Leu Asn Phe Tyr
225                 230                 235                 240

Leu Gln Ser Leu Leu Phe His Pro Lys Gln Glu Asp Trp Ile Leu Ala
            245                 250                 255

Tyr Ser Gln Asp Gln Lys Leu Tyr Ser Ser Ala Glu Phe Gly Arg Arg
        260                 265                 270

Trp Gln Leu Ile Gln Glu Ser Val Pro Asn Arg Phe Tyr Trp Ser
            275                 280                 285

Val Met Gly Ser Ser Lys Glu Pro Asp Leu Val His Leu Glu Ala Arg
        290                 295                 300

Thr Val Asp Gly His Ser Ile Tyr Leu Thr Cys Arg Met Gln Asn Cys
305                 310                 315                 320

Thr Glu Ala Asn Arg Asn Lys Pro Phe Pro Gly Tyr Ile Asp Pro Asp
            325                 330                 335

Ser Leu Ile Val Gln Asp Asp Tyr Val Phe Val Gln Leu Thr Ser Gly
        340                 345                 350

Gly Arg Pro His Tyr Tyr Val Ser Tyr Arg Arg Ser Pro Phe Ala Gln
            355                 360                 365

Met Lys Leu Pro Lys Tyr Ala Leu Pro Lys Asp Met His Val Ile Ser
        370                 375                 380

Thr Asp Glu Asn Gln Val Phe Ala Ala Val Gln Glu Trp Asn Gln Asn
385                 390                 395                 400

Asp Thr Tyr Asn Leu Tyr Ile Ser Asp Thr Arg Gly Val Tyr Phe Thr
            405                 410                 415

Leu Ala Leu Glu Asn Val Arg Ser Ser Arg Gly Pro Glu Gly Asn Val
        420                 425                 430

Met Ile Asp Leu Tyr Glu Val Ala Gly Ile Lys Gly Met Phe Leu Ala
            435                 440                 445

Asn Lys Lys Ile Asp Asn Gln Val Lys Thr Phe Ile Thr Tyr Asn Lys
        450                 455                 460

Gly Arg Asp Trp Arg Leu Leu Gln Ala Pro Asp Ala Asp Leu Arg Gly
465                 470                 475                 480

Asp Pro Val His Cys Leu Leu Pro Tyr Cys Ser Leu His Leu His Leu
            485                 490                 495

Lys Val Ser Glu Asn Pro Tyr Thr Ser Gly Ile Ile Ala Ser Arg Asp
        500                 505                 510

Thr Ala Pro Ser Ile Val Ala Ser Gly Asn Ile Gly Ser Glu Leu
            515                 520                 525

Ser Asp Ser Asp Ile Ser Met Phe Val Ser Ser Asp Ala Gly Asn Thr
        530                 535                 540

Trp Arg Gln Ile Phe Glu Glu His Ser Ile Leu Tyr Leu Asp Gln
545                 550                 555                 560

Gly Gly Val Leu Val Ala Met Lys His Thr Ser Leu Pro Ile Arg His
            565                 570                 575

Leu Trp Leu Ser Phe Asp Glu Gly Arg Ser Trp Ser Lys Tyr Ser Phe
```

```
                580                 585                 590
Thr Ser Ile Pro Leu Phe Val Asp Gly Val Leu Gly Glu Pro Gly Glu
            595                 600                 605

Glu Thr Leu Ile Met Thr Val Phe Gly His Phe Ser His Arg Ser Glu
            610                 615                 620

Trp Gln Leu Val Lys Val Asp Tyr Lys Ser Ile Phe Asp Arg Arg Cys
625                 630                 635                 640

Ala Glu Glu Asp Tyr Arg Pro Trp Gln Leu His Ser Gln Gly Glu Ala
                645                 650                 655

Cys Ile Met Gly Ala Lys Arg Ile Tyr Lys Lys Arg Lys Ser Glu Arg
                660                 665                 670

Lys Cys Met Gln Lys Tyr Ala Gly Ala Met Glu Ser Glu Pro Cys Val
            675                 680                 685

Cys Thr Glu Ala Asp Phe Asp Cys Asp Tyr Gly Tyr Glu Arg His Ser
            690                 695                 700

Asn Gly Gln Cys Leu Pro Ala Phe Trp Phe Asn Pro Ser Ser Leu Ser
705                 710                 715                 720

Lys Asp Cys Ser Leu Gly Gln Ser Tyr Leu Asn Ser Ala Gly Tyr Arg
                725                 730                 735

Lys Val Val Ser Asn Asn Cys Thr Asp Gly Val Arg Glu Gln Tyr Thr
                740                 745                 750

Ala Lys Pro Gln Lys Cys Pro Gly Lys Ala Pro Arg Gly Leu Arg Ile
                755                 760                 765

Val Thr Ala Asp Gly Lys Leu Thr Ala Glu Gln Gly His Asn Val Thr
            770                 775                 780

Leu Met Val Gln Leu Glu Glu Gly Asp Val Gln Arg Thr Leu Ile Gln
785                 790                 795                 800

Val Asp Phe Gly Asp Gly Ile Ala Val Ser Tyr Val Asn Leu Ser Ser
                805                 810                 815

Met Glu Asp Gly Ile Lys His Val Tyr Gln Asn Val Gly Ile Phe Arg
                820                 825                 830

Val Thr Val Gln Val Asp Asn Ser Leu Gly Ser Asp Ser Ala Val Leu
            835                 840                 845

Tyr Leu His Val Thr Cys Pro Leu Glu His Val His Leu Ser Leu Pro
            850                 855                 860

Phe Val Thr Thr Lys Asn Lys Glu Val Asn Ala Thr Ala Val Leu Trp
865                 870                 875                 880

Pro Ser Gln Val Gly Thr Leu Thr Tyr Val Trp Trp Tyr Gly Asn Asn
                885                 890                 895

Thr Glu Pro Leu Ile Thr Leu Glu Gly Ser Ile Ser Phe Lys Phe Thr
                900                 905                 910

Ser Glu Gly Met Asn Thr Ile Thr Val Gln Val Ser Ala Gly Asn Ala
            915                 920                 925

Ile Leu Gln Asp Thr Lys Thr Ile Ala Val Tyr Glu Glu Phe Arg Ser
            930                 935                 940

Leu Arg Leu Ala Phe Ser Pro Asn Leu Asp Asp Tyr Asn Pro Asp Ile
945                 950                 955                 960

Pro Glu Trp Arg Arg Asp Ile Ser Arg Val Ile Lys Lys Ser Leu Val
                965                 970                 975

Glu Ala Thr Gly Ile Pro Ser Gln His Ile Leu Val Ala Val Leu Pro
            980                 985                 990

Gly Leu Pro Thr Ala Ala Glu Leu  Phe Val Leu Pro Tyr  Gln Asp Gly
            995                 1000                1005
```

```
Thr Arg Glu Asn Lys Arg Ser Pro Glu Asp Leu Glu Gln Ile Ser
1010             1015                 1020

Glu Val Leu Ile His Lys Leu Asn Gln Asn Leu Val His Phe Glu
1025             1030                 1035

Leu Lys Pro Gly Val Gln Val Leu Val His Ala Ala His Leu Thr
1040             1045                 1050

Ala Ala Pro Leu Val Asp Leu Thr Pro Thr His Ser Gly Ser Ala
1055             1060                 1065

Met Leu Met Leu Leu Ser Val Val Phe Val Gly Leu Ala Val Phe
1070             1075                 1080

Val Ile Tyr Lys Phe Lys Arg Arg Val Ala Leu Pro Ser Pro Pro
1085             1090                 1095

Ser Pro Ser Ala Gln Pro Gly Asp Ser Ser Leu Arg Leu Gln Arg
1100             1105                 1110

Pro Arg Pro Ala Thr Pro Pro Ser Ser Pro Lys Arg Gly Ser Ala
1115             1120                 1125

Gly Ala Gln Phe Ala Ile
1130

<210> SEQ ID NO 23
<211> LENGTH: 1114
<212> TYPE: PRT
<213> ORGANISM: Mus musculus
<220> FEATURE:
<221> NAME/KEY: MISC_FEATURE
<222> LOCATION: (1)..(1114)
<223> OTHER INFORMATION: proSorCS1a, isoform 2

<400> SEQUENCE: 23

Ser Leu Ser Cys Cys Pro Pro Gln His Pro Ser Ser Thr Pro Arg Arg
1               5                   10                  15

Thr Leu Thr Pro Arg Gly Phe Pro His Pro Gly Pro Leu Gly Arg Ala
                20                  25                  30

Pro Ala Thr Pro Pro Leu Phe Met Arg Pro Leu Phe Ala Val Ala
            35                  40                  45

Pro Gly Asp Arg Ala Leu Phe Leu Glu Arg Ala Gly Gly Ser Arg Val
        50                  55                  60

Ser Val Ala Thr Ala Ala Arg Ser Gly Arg Arg Arg Ser Gly Thr
65                  70                  75                  80

Glu Pro Glu Lys Ile Glu Pro Gly Gly Ala Ser Arg Ser Arg Arg
                85                  90                  95

Asp Met Leu Lys Asp Gly Gly Gln Gln Gly Leu Gly Thr Gly Ala Arg
                100                 105                 110

Asp Pro Gly Lys Ala Thr Arg Phe Arg Met Glu Glu Leu Arg Leu Thr
            115                 120                 125

Ser Thr Thr Phe Ala Leu Thr Gly Asp Ser Ala His Asn Gln Ala Met
    130                 135                 140

Val His Trp Ser Gly His Asn Ser Ser Val Ile Leu Ile Leu Thr Lys
145                 150                 155                 160

Leu Tyr Asp Tyr Asn Leu Gly Ser Ile Thr Glu Ser Ser Leu Trp Arg
                165                 170                 175

Ser Thr Asp Tyr Gly Thr Thr Tyr Glu Lys Leu Asn Asp Lys Val Gly
            180                 185                 190

Leu Lys Thr Ile Leu Ser Tyr Leu Tyr Val Cys Pro Thr Asn Lys Cys
        195                 200                 205
```

```
Lys Ile Met Leu Leu Thr Asp Pro Glu Ile Glu Ser Ser Leu Leu Ile
            210                 215                 220

Ser Ser Asp Glu Gly Ala Thr Tyr Gln Lys Tyr Arg Leu Asn Phe Tyr
225                 230                 235                 240

Leu Gln Ser Leu Leu Phe His Pro Lys Gln Glu Asp Trp Ile Leu Ala
                245                 250                 255

Tyr Ser Gln Asp Gln Lys Leu Tyr Ser Ser Ala Glu Phe Gly Arg Arg
                260                 265                 270

Trp Gln Leu Ile Gln Glu Ser Val Pro Asn Arg Phe Tyr Trp Ser
            275                 280                 285

Val Met Gly Ser Ser Lys Glu Pro Asp Leu Val His Leu Glu Ala Arg
290                 295                 300

Thr Val Asp Gly His Ser Ile Tyr Leu Thr Cys Arg Met Gln Asn Cys
305                 310                 315                 320

Thr Glu Ala Asn Arg Asn Lys Pro Phe Pro Gly Tyr Ile Asp Pro Asp
                325                 330                 335

Ser Leu Ile Val Gln Asp Tyr Val Phe Val Gln Leu Thr Ser Gly
                340                 345                 350

Gly Arg Pro His Tyr Tyr Val Ser Tyr Arg Arg Ser Pro Phe Ala Gln
                355                 360                 365

Met Lys Leu Pro Lys Tyr Ala Leu Pro Lys Asp Met His Val Ile Ser
370                 375                 380

Thr Asp Glu Asn Gln Val Phe Ala Ala Val Gln Glu Trp Asn Gln Asn
385                 390                 395                 400

Asp Thr Tyr Asn Leu Tyr Ile Ser Asp Thr Arg Gly Val Tyr Phe Thr
                405                 410                 415

Leu Ala Leu Glu Asn Val Arg Ser Ser Arg Gly Pro Glu Gly Asn Val
                420                 425                 430

Met Ile Asp Leu Tyr Glu Val Ala Gly Ile Lys Gly Met Phe Leu Ala
                435                 440                 445

Asn Lys Lys Ile Asp Asn Gln Val Lys Thr Phe Ile Thr Tyr Asn Lys
            450                 455                 460

Gly Arg Asp Trp Arg Leu Leu Gln Ala Pro Asp Ala Asp Leu Arg Gly
465                 470                 475                 480

Asp Pro Val His Cys Leu Leu Pro Tyr Cys Ser Leu His Leu His Leu
                485                 490                 495

Lys Val Ser Glu Asn Pro Tyr Thr Ser Gly Ile Ile Ala Ser Arg Asp
                500                 505                 510

Thr Ala Pro Ser Ile Ile Val Ala Ser Gly Asn Ile Gly Ser Glu Leu
                515                 520                 525

Ser Asp Ser Asp Ile Ser Met Phe Val Ser Ser Asp Ala Gly Asn Thr
530                 535                 540

Trp Arg Gln Ile Phe Glu Glu His Ser Ile Leu Tyr Leu Asp Gln
545                 550                 555                 560

Gly Gly Val Leu Val Ala Met Lys His Thr Ser Leu Pro Ile Arg His
                565                 570                 575

Leu Trp Leu Ser Phe Asp Glu Gly Arg Ser Trp Ser Lys Tyr Ser Phe
                580                 585                 590

Thr Ser Ile Pro Leu Phe Val Asp Gly Val Leu Gly Glu Pro Gly Glu
            595                 600                 605

Glu Thr Leu Ile Met Thr Val Phe Gly His Phe Ser His Arg Ser Glu
            610                 615                 620

Trp Gln Leu Val Lys Val Asp Tyr Lys Ser Ile Phe Asp Arg Arg Cys
```

```
                625                 630                 635                 640
Ala Glu Glu Asp Tyr Arg Pro Trp Gln Leu His Ser Gln Gly Glu Ala
                        645                 650                 655

Cys Ile Met Gly Ala Lys Arg Ile Tyr Lys Lys Arg Lys Ser Glu Arg
                        660                 665                 670

Lys Cys Met Gln Lys Tyr Ala Gly Ala Met Glu Ser Glu Pro Cys Val
                        675                 680                 685

Cys Thr Glu Ala Asp Phe Asp Cys Asp Tyr Gly Tyr Glu Arg His Ser
        690                 695                 700

Asn Gly Gln Cys Leu Pro Ala Phe Trp Phe Asn Pro Ser Ser Leu Ser
705                 710                 715                 720

Lys Asp Cys Ser Leu Gly Gln Ser Tyr Leu Asn Ser Ala Gly Tyr Arg
                        725                 730                 735

Lys Val Val Ser Asn Asn Cys Thr Asp Gly Val Arg Glu Gln Tyr Thr
                740                 745                 750

Ala Lys Pro Gln Lys Cys Pro Gly Lys Ala Pro Arg Gly Leu Arg Ile
                755                 760                 765

Val Thr Ala Asp Gly Lys Leu Thr Ala Glu Gln Gly His Asn Val Thr
    770                 775                 780

Leu Met Val Gln Leu Glu Glu Gly Asp Val Gln Arg Thr Leu Ile Gln
785                 790                 795                 800

Val Asp Phe Gly Asp Gly Ile Ala Val Ser Tyr Val Asn Leu Ser Ser
                    805                 810                 815

Met Glu Asp Gly Ile Lys His Val Tyr Gln Asn Val Gly Ile Phe Arg
                820                 825                 830

Val Thr Val Gln Val Asp Asn Ser Leu Gly Ser Asp Ser Ala Val Leu
            835                 840                 845

Tyr Leu His Val Thr Cys Pro Leu Glu His Val His Leu Ser Leu Pro
        850                 855                 860

Phe Val Thr Thr Lys Asn Lys Glu Val Asn Ala Thr Ala Val Leu Trp
865                 870                 875                 880

Pro Ser Gln Val Gly Thr Leu Thr Tyr Val Trp Trp Tyr Gly Asn Asn
                        885                 890                 895

Thr Glu Pro Leu Ile Thr Leu Glu Gly Ser Ile Ser Phe Lys Phe Thr
                    900                 905                 910

Ser Glu Gly Met Asn Thr Ile Thr Val Gln Val Ser Ala Gly Asn Ala
                915                 920                 925

Ile Leu Gln Asp Thr Lys Thr Ile Ala Val Tyr Glu Glu Phe Arg Ser
        930                 935                 940

Leu Arg Leu Ala Phe Ser Pro Asn Leu Asp Asp Tyr Asn Pro Asp Ile
945                 950                 955                 960

Pro Glu Trp Arg Arg Asp Ile Ser Arg Val Ile Lys Lys Ser Leu Val
                    965                 970                 975

Glu Ala Thr Gly Ile Pro Ser Gln His Ile Leu Val Ala Val Leu Pro
                980                 985                 990

Gly Leu Pro Thr Ala Ala Glu Leu Phe Val Leu Pro Tyr Gln Asp Gly
        995                 1000                1005

Thr Arg Glu Asn Lys Arg Ser Pro Glu Asp Leu Glu Gln Ile Ser
    1010                1015                1020

Glu Val Leu Ile His Lys Leu Asn Gln Asn Leu Val His Phe Glu
    1025                1030                1035

Leu Lys Pro Gly Val Gln Val Leu Val His Ala Ala His Leu Thr
    1040                1045                1050
```

```
Ala Ala Pro Leu Val Asp Leu Thr Pro Thr His Ser Gly Ser Ala
    1055            1060                1065

Met Leu Met Leu Leu Ser Val Val Phe Val Gly Leu Ala Val Phe
    1070            1075                1080

Val Ile Tyr Lys Phe Lys Arg Cys Val Phe Leu Leu Leu Pro Ser
    1085            1090                1095

Tyr Pro Arg Pro Pro Pro Ser Ser Phe Cys Gln Val Gln Lys
    1100            1105                1110

Gln

<210> SEQ ID NO 24
<211> LENGTH: 1145
<212> TYPE: PRT
<213> ORGANISM: Mus musculus
<220> FEATURE:
<221> NAME/KEY: MISC_FEATURE
<222> LOCATION: (1)..(1145)
<223> OTHER INFORMATION: proSorCS1c, isoform 3

<400> SEQUENCE: 24

Ser Leu Ser Cys Cys Pro Pro Gln His Pro Ser Thr Pro Arg Arg
1               5                   10                  15

Thr Leu Thr Pro Arg Gly Phe Pro His Pro Gly Pro Leu Gly Arg Ala
                20                  25                  30

Pro Ala Thr Pro Pro Leu Phe Met Arg Pro Leu Phe Ala Val Ala
            35                  40                  45

Pro Gly Asp Arg Ala Leu Phe Leu Glu Arg Ala Gly Gly Ser Arg Val
        50                  55                  60

Ser Val Ala Thr Ala Ala Arg Ser Gly Arg Arg Arg Ser Gly Thr
65                  70                  75                  80

Glu Pro Glu Lys Ile Glu Pro Gly Gly Ala Ser Arg Ser Arg Arg
                85                  90                  95

Asp Met Leu Lys Asp Gly Gly Gln Gln Gly Leu Gly Thr Gly Ala Arg
                100                 105                 110

Asp Pro Gly Lys Ala Thr Arg Phe Arg Met Glu Glu Leu Arg Leu Thr
            115                 120                 125

Ser Thr Thr Phe Ala Leu Thr Gly Asp Ser Ala His Asn Gln Ala Met
130                 135                 140

Val His Trp Ser Gly His Asn Ser Ser Val Ile Leu Ile Leu Thr Lys
145                 150                 155                 160

Leu Tyr Asp Tyr Asn Leu Gly Ser Ile Thr Glu Ser Ser Leu Trp Arg
                165                 170                 175

Ser Thr Asp Tyr Gly Thr Thr Tyr Glu Lys Leu Asn Asp Lys Val Gly
                180                 185                 190

Leu Lys Thr Ile Leu Ser Tyr Leu Tyr Val Cys Pro Thr Asn Lys Cys
            195                 200                 205

Lys Ile Met Leu Leu Thr Asp Pro Glu Ile Glu Ser Ser Leu Leu Ile
        210                 215                 220

Ser Ser Asp Glu Gly Ala Thr Tyr Gln Lys Tyr Arg Leu Asn Phe Tyr
225                 230                 235                 240

Leu Gln Ser Leu Leu Phe His Pro Lys Gln Glu Asp Trp Ile Leu Ala
                245                 250                 255

Tyr Ser Gln Asp Gln Lys Leu Tyr Ser Ser Ala Glu Phe Gly Arg Arg
                260                 265                 270

Trp Gln Leu Ile Gln Glu Ser Val Val Pro Asn Arg Phe Tyr Trp Ser
```

-continued

```
            275                 280                 285
Val Met Gly Ser Ser Lys Glu Pro Asp Leu Val His Leu Glu Ala Arg
            290                 295                 300
Thr Val Asp Gly His Ser Ile Tyr Leu Thr Cys Arg Met Gln Asn Cys
305                 310                 315                 320
Thr Glu Ala Asn Arg Asn Lys Pro Phe Pro Gly Tyr Ile Asp Pro Asp
                        325                 330                 335
Ser Leu Ile Val Gln Asp Asp Tyr Val Phe Val Gln Leu Thr Ser Gly
                        340                 345                 350
Gly Arg Pro His Tyr Tyr Val Ser Tyr Arg Arg Ser Pro Phe Ala Gln
                        355                 360                 365
Met Lys Leu Pro Lys Tyr Ala Leu Pro Lys Asp Met His Val Ile Ser
            370                 375                 380
Thr Asp Glu Asn Gln Val Phe Ala Ala Val Gln Glu Trp Asn Gln Asn
385                 390                 395                 400
Asp Thr Tyr Asn Leu Tyr Ile Ser Asp Thr Arg Gly Val Tyr Phe Thr
                        405                 410                 415
Leu Ala Leu Glu Asn Val Arg Ser Ser Arg Gly Pro Glu Gly Asn Val
                        420                 425                 430
Met Ile Asp Leu Tyr Glu Val Ala Gly Ile Lys Gly Met Phe Leu Ala
                        435                 440                 445
Asn Lys Lys Ile Asp Asn Gln Val Lys Thr Phe Ile Thr Tyr Asn Lys
            450                 455                 460
Gly Arg Asp Trp Arg Leu Leu Gln Ala Pro Asp Ala Asp Leu Arg Gly
465                 470                 475                 480
Asp Pro Val His Cys Leu Leu Pro Tyr Cys Ser Leu His Leu His Leu
                        485                 490                 495
Lys Val Ser Glu Asn Pro Tyr Thr Ser Gly Ile Ile Ala Ser Arg Asp
                        500                 505                 510
Thr Ala Pro Ser Ile Ile Val Ala Ser Gly Asn Ile Gly Ser Glu Leu
                        515                 520                 525
Ser Asp Ser Asp Ile Ser Met Phe Val Ser Ser Asp Ala Gly Asn Thr
            530                 535                 540
Trp Arg Gln Ile Phe Glu Glu Glu His Ser Ile Leu Tyr Leu Asp Gln
545                 550                 555                 560
Gly Gly Val Leu Val Ala Met Lys His Thr Ser Leu Pro Ile Arg His
                        565                 570                 575
Leu Trp Leu Ser Phe Asp Glu Gly Arg Ser Trp Ser Lys Tyr Ser Phe
                        580                 585                 590
Thr Ser Ile Pro Leu Phe Val Asp Gly Val Leu Gly Glu Pro Gly Glu
                        595                 600                 605
Glu Thr Leu Ile Met Thr Val Phe Gly His Phe Ser His Arg Ser Glu
            610                 615                 620
Trp Gln Leu Val Lys Val Asp Tyr Lys Ser Ile Phe Asp Arg Arg Cys
625                 630                 635                 640
Ala Glu Glu Asp Tyr Arg Pro Trp Gln Leu His Ser Gln Gly Glu Ala
                        645                 650                 655
Cys Ile Met Gly Ala Lys Arg Ile Tyr Lys Arg Lys Ser Glu Arg
                        660                 665                 670
Lys Cys Met Gln Lys Tyr Ala Gly Ala Met Glu Ser Glu Pro Cys Val
            675                 680                 685
Cys Thr Glu Ala Asp Phe Asp Cys Asp Tyr Gly Tyr Glu Arg His Ser
            690                 695                 700
```

Asn Gly Gln Cys Leu Pro Ala Phe Trp Phe Asn Pro Ser Ser Leu Ser
705                 710                 715                 720

Lys Asp Cys Ser Leu Gly Gln Ser Tyr Leu Asn Ser Ala Gly Tyr Arg
            725                 730                 735

Lys Val Val Ser Asn Asn Cys Thr Asp Gly Val Arg Glu Gln Tyr Thr
                740                 745                 750

Ala Lys Pro Gln Lys Cys Pro Gly Lys Ala Pro Arg Gly Leu Arg Ile
            755                 760                 765

Val Thr Ala Asp Gly Lys Leu Thr Ala Glu Gln Gly His Asn Val Thr
                770                 775                 780

Leu Met Val Gln Leu Glu Glu Gly Asp Val Gln Arg Thr Leu Ile Gln
785                 790                 795                 800

Val Asp Phe Gly Asp Gly Ile Ala Val Ser Tyr Val Asn Leu Ser Ser
                805                 810                 815

Met Glu Asp Gly Ile Lys His Val Tyr Gln Asn Val Gly Ile Phe Arg
                820                 825                 830

Val Thr Val Gln Val Asp Asn Ser Leu Gly Ser Asp Ser Ala Val Leu
                835                 840                 845

Tyr Leu His Val Thr Cys Pro Leu Glu His Val His Leu Ser Leu Pro
850                 855                 860

Phe Val Thr Thr Lys Asn Lys Glu Val Asn Ala Thr Ala Val Leu Trp
865                 870                 875                 880

Pro Ser Gln Val Gly Thr Leu Thr Tyr Val Trp Trp Tyr Gly Asn Asn
                885                 890                 895

Thr Glu Pro Leu Ile Thr Leu Glu Gly Ser Ile Ser Phe Lys Phe Thr
                900                 905                 910

Ser Glu Gly Met Asn Thr Ile Thr Val Gln Val Ser Ala Gly Asn Ala
                915                 920                 925

Ile Leu Gln Asp Thr Lys Thr Ile Ala Val Tyr Glu Glu Phe Arg Ser
930                 935                 940

Leu Arg Leu Ala Phe Ser Pro Asn Leu Asp Asp Tyr Asn Pro Asp Ile
945                 950                 955                 960

Pro Glu Trp Arg Arg Asp Ile Ser Arg Val Ile Lys Lys Ser Leu Val
                965                 970                 975

Glu Ala Thr Gly Ile Pro Ser Gln His Ile Leu Val Ala Val Leu Pro
                980                 985                 990

Gly Leu Pro Thr Ala Ala Glu Leu Phe Val Leu Pro Tyr Gln Asp Gly
            995                 1000                1005

Thr Arg Glu Asn Lys Arg Ser Pro Glu Asp Leu Glu Gln Ile Ser
    1010                1015                1020

Glu Val Leu Ile His Lys Leu Asn Gln Asn Leu Val His Phe Glu
    1025                1030                1035

Leu Lys Pro Gly Val Gln Val Leu Val His Ala Ala His Leu Thr
    1040                1045                1050

Ala Ala Pro Leu Val Asp Leu Thr Pro Thr His Ser Gly Ser Ala
    1055                1060                1065

Met Leu Met Leu Leu Ser Val Val Phe Val Gly Leu Ala Val Phe
    1070                1075                1080

Val Ile Tyr Lys Phe Lys Arg Lys Ile Pro Gly Ile Asn Val Tyr
    1085                1090                1095

Ala Gln Met Gln Asn Glu Lys Glu Gln Glu Leu Ile Asn Pro Val
    1100                1105                1110

```
Ser His Ser Glu Ser Arg Pro Ser Val Pro His Pro Asp Leu Arg
    1115                1120                1125

Arg Pro Gly Gln Leu Val Asp Glu Lys Val Glu Ser Gln Leu Leu
    1130                1135                1140

Gly Lys
    1145

<210> SEQ ID NO 25
<211> LENGTH: 1144
<212> TYPE: PRT
<213> ORGANISM: Mus musculus
<220> FEATURE:
<221> NAME/KEY: MISC_FEATURE
<222> LOCATION: (1)..(1144)
<223> OTHER INFORMATION: proSorCS1c+, isoform 4

<400> SEQUENCE: 25

Ser Leu Ser Cys Cys Pro Pro Gln His Pro Ser Ser Thr Pro Arg Arg
1               5                   10                  15

Thr Leu Thr Pro Arg Gly Phe Pro His Pro Gly Pro Leu Gly Arg Ala
            20                  25                  30

Pro Ala Thr Pro Pro Leu Phe Met Arg Pro Leu Phe Ala Val Ala
        35                  40                  45

Pro Gly Asp Arg Ala Leu Phe Leu Glu Arg Ala Gly Gly Ser Arg Val
    50                  55                  60

Ser Val Ala Thr Ala Ala Arg Ser Gly Arg Arg Arg Ser Gly Thr
65                  70                  75                  80

Glu Pro Glu Lys Ile Glu Pro Gly Glu Gly Ala Ser Arg Ser Arg Arg
                85                  90                  95

Asp Met Leu Lys Asp Gly Gly Gln Gln Gly Leu Gly Thr Gly Ala Arg
            100                 105                 110

Asp Pro Gly Lys Ala Thr Arg Phe Arg Met Glu Glu Leu Arg Leu Thr
        115                 120                 125

Ser Thr Thr Phe Ala Leu Thr Gly Asp Ser Ala His Asn Gln Ala Met
    130                 135                 140

Val Trp Ser Gly His Asn Ser Ser Val Ile Leu Ile Leu Thr Lys Leu
145                 150                 155                 160

Tyr Asp Tyr Asn Leu Gly Ser Ile Thr Glu Ser Ser Leu Trp Arg Ser
                165                 170                 175

Thr Asp Tyr Gly Thr Thr Tyr Glu Lys Leu Asn Asp Lys Val Gly Leu
            180                 185                 190

Lys Thr Ile Leu Ser Tyr Leu Tyr Val Cys Pro Thr Asn Lys Cys Lys
        195                 200                 205

Ile Met Leu Leu Thr Asp Pro Glu Ile Glu Ser Ser Leu Leu Ile Ser
    210                 215                 220

Ser Asp Glu Gly Ala Thr Tyr Gln Lys Tyr Arg Leu Asn Phe Tyr Leu
225                 230                 235                 240

Gln Ser Leu Leu Phe His Pro Lys Gln Glu Asp Trp Ile Leu Ala Tyr
                245                 250                 255

Ser Gln Asp Gln Lys Leu Tyr Ser Ser Ala Glu Phe Gly Arg Arg Trp
            260                 265                 270

Gln Leu Ile Gln Glu Ser Val Val Pro Asn Arg Phe Tyr Trp Ser Val
        275                 280                 285

Met Gly Ser Ser Lys Glu Pro Asp Leu Val His Leu Glu Ala Arg Thr
    290                 295                 300

Val Asp Gly His Ser Ile Tyr Leu Thr Cys Arg Met Gln Asn Cys Thr
```

```
305                 310                 315                 320
Glu Ala Asn Arg Asn Lys Pro Phe Pro Gly Tyr Ile Asp Pro Asp Ser
                325                 330                 335
Leu Ile Val Gln Asp Asp Tyr Val Phe Val Gln Leu Thr Ser Gly Gly
                340                 345                 350
Arg Pro His Tyr Tyr Val Ser Tyr Arg Arg Ser Pro Phe Ala Gln Met
                355                 360                 365
Lys Leu Pro Lys Tyr Ala Leu Pro Lys Asp Met His Val Ile Ser Thr
            370                 375                 380
Asp Glu Asn Gln Val Phe Ala Ala Val Gln Glu Trp Asn Gln Asn Asp
385                 390                 395                 400
Thr Tyr Asn Leu Tyr Ile Ser Asp Thr Arg Gly Val Tyr Phe Thr Leu
                405                 410                 415
Ala Leu Glu Asn Val Arg Ser Ser Arg Gly Pro Glu Gly Asn Val Met
                420                 425                 430
Ile Asp Leu Tyr Glu Val Ala Gly Ile Lys Gly Met Phe Leu Ala Asn
            435                 440                 445
Lys Lys Ile Asp Asn Gln Val Lys Thr Phe Ile Thr Tyr Asn Lys Gly
    450                 455                 460
Arg Asp Trp Arg Leu Leu Gln Ala Pro Asp Ala Asp Leu Arg Gly Asp
465                 470                 475                 480
Pro Val His Cys Leu Leu Pro Tyr Cys Ser Leu His Leu His Leu Lys
                485                 490                 495
Val Ser Glu Asn Pro Tyr Thr Ser Gly Ile Ile Ala Ser Arg Asp Thr
                500                 505                 510
Ala Pro Ser Ile Ile Val Ala Ser Gly Asn Ile Gly Ser Glu Leu Ser
            515                 520                 525
Asp Ser Asp Ile Ser Met Phe Val Ser Ser Asp Ala Gly Asn Thr Trp
    530                 535                 540
Arg Gln Ile Phe Glu Glu His Ser Ile Leu Tyr Leu Asp Gln Gly
545                 550                 555                 560
Gly Val Leu Val Ala Met Lys His Thr Ser Leu Pro Ile Arg His Leu
                565                 570                 575
Trp Leu Ser Phe Asp Glu Gly Arg Ser Trp Ser Lys Tyr Ser Phe Thr
                580                 585                 590
Ser Ile Pro Leu Phe Val Asp Gly Val Leu Gly Glu Pro Gly Glu Glu
            595                 600                 605
Thr Leu Ile Met Thr Val Phe Gly His Phe Ser His Arg Ser Glu Trp
        610                 615                 620
Gln Leu Val Lys Val Asp Tyr Lys Ser Ile Phe Asp Arg Arg Cys Ala
625                 630                 635                 640
Glu Glu Asp Tyr Arg Pro Trp Gln Leu His Ser Gln Gly Glu Ala Cys
                645                 650                 655
Ile Met Gly Ala Lys Arg Ile Tyr Lys Lys Arg Lys Ser Glu Arg Lys
                660                 665                 670
Cys Met Gln Lys Tyr Ala Gly Ala Met Glu Ser Glu Pro Cys Val Cys
            675                 680                 685
Thr Glu Ala Asp Phe Asp Cys Asp Tyr Gly Tyr Glu Arg His Ser Asn
        690                 695                 700
Gly Gln Cys Leu Pro Ala Phe Trp Phe Asn Pro Ser Ser Leu Ser Lys
705                 710                 715                 720
Asp Cys Ser Leu Gly Gln Ser Tyr Leu Asn Ser Ala Gly Tyr Arg Lys
                725                 730                 735
```

```
Val Val Ser Asn Asn Cys Thr Asp Gly Val Arg Glu Gln Tyr Thr Ala
            740                 745                 750

Lys Pro Gln Lys Cys Pro Gly Lys Ala Pro Arg Gly Leu Arg Ile Val
            755                 760                 765

Thr Ala Asp Gly Lys Leu Thr Ala Glu Gln Gly His Asn Val Thr Leu
            770                 775                 780

Met Val Gln Leu Glu Glu Gly Asp Val Gln Arg Thr Leu Ile Gln Val
785                 790                 795                 800

Asp Phe Gly Asp Gly Ile Ala Val Ser Tyr Val Asn Leu Ser Ser Met
            805                 810                 815

Glu Asp Gly Ile Lys His Val Tyr Gln Asn Val Gly Ile Phe Arg Val
            820                 825                 830

Thr Val Gln Val Asp Asn Ser Leu Gly Ser Asp Ser Ala Val Leu Tyr
            835                 840                 845

Leu His Val Thr Cys Pro Leu Glu His Val His Leu Ser Leu Pro Phe
            850                 855                 860

Val Thr Thr Lys Asn Lys Glu Val Asn Ala Thr Ala Val Leu Trp Pro
865                 870                 875                 880

Ser Gln Val Gly Thr Leu Thr Tyr Val Trp Trp Tyr Gly Asn Asn Thr
            885                 890                 895

Glu Pro Leu Ile Thr Leu Glu Gly Ser Ile Ser Phe Lys Phe Thr Ser
            900                 905                 910

Glu Gly Met Asn Thr Ile Thr Val Gln Val Ser Ala Gly Asn Ala Ile
            915                 920                 925

Leu Gln Asp Thr Lys Thr Ile Ala Val Tyr Glu Glu Phe Arg Ser Leu
            930                 935                 940

Arg Leu Ala Phe Ser Pro Asn Leu Asp Asp Tyr Asn Pro Asp Ile Pro
945                 950                 955                 960

Glu Trp Arg Arg Asp Ile Ser Arg Val Ile Lys Lys Ser Leu Val Glu
            965                 970                 975

Ala Thr Gly Ile Pro Ser Gln His Ile Leu Val Ala Val Leu Pro Gly
            980                 985                 990

Leu Pro Thr Ala Ala Glu Leu Phe Val Leu Pro Tyr Gln Asp Gly Thr
            995                 1000                1005

Arg Glu Asn Lys Arg Ser Pro Glu Asp Leu Glu Gln Ile Ser Glu
            1010                1015                1020

Val Leu Ile His Lys Leu Asn Gln Asn Leu Val His Phe Glu Leu
            1025                1030                1035

Lys Pro Gly Val Gln Val Leu Val His Ala Ala His Leu Thr Ala
            1040                1045                1050

Ala Pro Leu Val Asp Leu Thr Pro Thr His Ser Gly Ser Ala Met
            1055                1060                1065

Leu Met Leu Leu Ser Val Val Phe Val Gly Leu Ala Val Phe Val
            1070                1075                1080

Ile Tyr Lys Phe Lys Arg Lys Ile Pro Gly Ile Asn Val Tyr Ala
            1085                1090                1095

Gln Met Gln Asn Glu Lys Glu Gln Glu Leu Ile Asn Pro Val Ser
            1100                1105                1110

His Ser Glu Ser Arg Ser Ser Val Pro His Pro Asp Leu Arg Arg
            1115                1120                1125

Pro Gly Gln Leu Val Asp Glu Lys Val Glu Ser Gln Leu Leu Gly
            1130                1135                1140
```

Glu

<210> SEQ ID NO 26
<211> LENGTH: 1158
<212> TYPE: PRT
<213> ORGANISM: Mus musculus
<220> FEATURE:
<221> NAME/KEY: MISC_FEATURE
<222> LOCATION: (1)..(1158)
<223> OTHER INFORMATION: proSorCS1d

<400> SEQUENCE: 26

```
Ser Leu Ser Cys Cys Pro Pro Gln His Pro Ser Thr Pro Arg Arg
1               5                   10                  15

Thr Leu Thr Pro Arg Gly Phe Pro His Pro Gly Pro Leu Gly Arg Ala
            20                  25                  30

Pro Ala Thr Pro Pro Leu Phe Met Arg Pro Leu Phe Ala Val Ala
        35                  40                  45

Pro Gly Asp Arg Ala Leu Phe Leu Glu Arg Ala Gly Gly Ser Arg Val
    50                  55                  60

Ser Val Ala Thr Ala Ala Arg Ser Gly Arg Arg Arg Ser Gly Thr
65                  70                  75                  80

Glu Pro Glu Lys Ile Glu Pro Gly Glu Gly Ala Ser Arg Ser Arg Arg
                85                  90                  95

Asp Met Leu Lys Asp Gly Gly Gln Gln Gly Leu Gly Thr Gly Ala Arg
            100                 105                 110

Asp Pro Gly Lys Ala Thr Arg Phe Arg Met Glu Glu Leu Arg Leu Thr
        115                 120                 125

Ser Thr Thr Phe Ala Leu Thr Gly Asp Ser Ala His Asn Gln Ala Met
    130                 135                 140

Val His Trp Ser Gly His Asn Ser Ser Val Ile Leu Ile Leu Thr Lys
145                 150                 155                 160

Leu Tyr Asp Tyr Asn Leu Gly Ser Ile Thr Glu Ser Ser Leu Trp Arg
                165                 170                 175

Ser Thr Asp Tyr Gly Thr Thr Tyr Glu Lys Leu Asn Asp Lys Val Gly
            180                 185                 190

Leu Lys Thr Ile Leu Ser Tyr Leu Tyr Val Cys Pro Thr Asn Lys Cys
        195                 200                 205

Lys Ile Met Leu Leu Thr Asp Pro Glu Ile Glu Ser Ser Leu Leu Ile
    210                 215                 220

Ser Ser Asp Glu Gly Ala Thr Tyr Gln Lys Tyr Arg Leu Asn Phe Tyr
225                 230                 235                 240

Leu Gln Ser Leu Leu Phe His Pro Lys Gln Glu Asp Trp Ile Leu Ala
                245                 250                 255

Tyr Ser Gln Asp Gln Lys Leu Tyr Ser Ser Ala Glu Phe Gly Arg Arg
            260                 265                 270

Trp Gln Leu Ile Gln Glu Ser Val Val Pro Asn Arg Phe Tyr Trp Ser
        275                 280                 285

Val Met Gly Ser Ser Lys Glu Pro Asp Leu Val His Leu Glu Ala Arg
    290                 295                 300

Thr Val Asp Gly His Ser Ile Tyr Leu Thr Cys Arg Met Gln Asn Cys
305                 310                 315                 320

Thr Glu Ala Asn Arg Asn Lys Pro Phe Pro Gly Tyr Ile Asp Pro Asp
                325                 330                 335

Ser Leu Ile Val Gln Asp Asp Tyr Val Phe Val Gln Leu Thr Ser Gly
            340                 345                 350
```

```
Gly Arg Pro His Tyr Tyr Val Ser Tyr Arg Arg Ser Pro Phe Ala Gln
            355                 360                 365

Met Lys Leu Pro Lys Tyr Ala Leu Pro Lys Asp Met His Val Ile Ser
        370                 375                 380

Thr Asp Glu Asn Gln Val Phe Ala Ala Val Gln Glu Trp Asn Gln Asn
385                 390                 395                 400

Asp Thr Tyr Asn Leu Tyr Ile Ser Asp Thr Arg Gly Val Tyr Phe Thr
                405                 410                 415

Leu Ala Leu Glu Asn Val Arg Ser Arg Gly Pro Glu Gly Asn Val
                420                 425                 430

Met Ile Asp Leu Tyr Glu Val Ala Gly Ile Lys Gly Met Phe Leu Ala
            435                 440                 445

Asn Lys Lys Ile Asp Asn Gln Val Lys Thr Phe Ile Thr Tyr Asn Lys
        450                 455                 460

Gly Arg Asp Trp Arg Leu Leu Gln Ala Pro Asp Ala Asp Leu Arg Gly
465                 470                 475                 480

Asp Pro Val His Cys Leu Leu Pro Tyr Cys Ser Leu His Leu His Leu
                485                 490                 495

Lys Val Ser Glu Asn Pro Tyr Thr Ser Gly Ile Ile Ala Ser Arg Asp
                500                 505                 510

Thr Ala Pro Ser Ile Ile Val Ala Ser Gly Asn Ile Gly Ser Glu Leu
            515                 520                 525

Ser Asp Ser Asp Ile Ser Met Phe Val Ser Ser Asp Ala Gly Asn Thr
        530                 535                 540

Trp Arg Gln Ile Phe Glu Glu His Ser Ile Leu Tyr Leu Asp Gln
545                 550                 555                 560

Gly Gly Val Leu Val Ala Met Lys His Thr Ser Leu Pro Ile Arg His
                565                 570                 575

Leu Trp Leu Ser Phe Asp Glu Gly Arg Ser Trp Ser Lys Tyr Ser Phe
                580                 585                 590

Thr Ser Ile Pro Leu Phe Val Asp Gly Val Leu Gly Glu Pro Gly Glu
            595                 600                 605

Glu Thr Leu Ile Met Thr Val Phe Gly His Phe Ser His Arg Ser Glu
        610                 615                 620

Trp Gln Leu Val Lys Val Asp Tyr Lys Ser Ile Phe Asp Arg Arg Cys
625                 630                 635                 640

Ala Glu Glu Asp Tyr Arg Pro Trp Gln Leu His Ser Gln Gly Glu Ala
                645                 650                 655

Cys Ile Met Gly Ala Lys Arg Ile Tyr Lys Lys Arg Lys Ser Glu Arg
                660                 665                 670

Lys Cys Met Gln Lys Tyr Ala Gly Ala Met Glu Ser Glu Pro Cys Val
            675                 680                 685

Cys Thr Glu Ala Asp Phe Asp Cys Asp Tyr Gly Tyr Glu Arg His Ser
        690                 695                 700

Asn Gly Gln Cys Leu Pro Ala Phe Trp Phe Asn Pro Ser Ser Leu Ser
705                 710                 715                 720

Lys Asp Cys Ser Leu Gly Gln Ser Tyr Leu Asn Ser Ala Gly Tyr Arg
                725                 730                 735

Lys Val Val Ser Asn Asn Cys Thr Asp Gly Val Arg Glu Gln Tyr Thr
                740                 745                 750

Ala Lys Pro Gln Lys Cys Pro Gly Lys Ala Pro Arg Gly Leu Arg Ile
            755                 760                 765
```

Val Thr Ala Asp Gly Lys Leu Thr Ala Glu Gln Gly His Asn Val Thr
770                 775                 780

Leu Met Val Gln Leu Glu Glu Gly Asp Val Gln Arg Thr Leu Ile Gln
785                 790                 795                 800

Val Asp Phe Gly Asp Gly Ile Ala Val Ser Tyr Val Asn Leu Ser Ser
            805                 810                 815

Met Glu Asp Gly Ile Lys His Val Tyr Gln Asn Val Gly Ile Phe Arg
            820                 825                 830

Val Thr Val Gln Val Asp Asn Ser Leu Gly Ser Asp Ser Ala Val Leu
            835                 840                 845

Tyr Leu His Val Thr Cys Pro Leu Glu His Val His Leu Ser Leu Pro
850                 855                 860

Phe Val Thr Thr Lys Asn Lys Glu Val Asn Ala Thr Ala Val Leu Trp
865                 870                 875                 880

Pro Ser Gln Val Gly Thr Leu Thr Tyr Val Trp Trp Tyr Gly Asn Asn
            885                 890                 895

Thr Glu Pro Leu Ile Thr Leu Gly Ser Ile Ser Phe Lys Phe Thr
            900                 905                 910

Ser Glu Gly Met Asn Thr Ile Thr Val Gln Val Ser Ala Gly Asn Ala
            915                 920                 925

Ile Leu Gln Asp Thr Lys Thr Ile Ala Val Tyr Glu Glu Phe Arg Ser
930                 935                 940

Leu Arg Leu Ala Phe Ser Pro Asn Leu Asp Asp Tyr Asn Pro Asp Ile
945                 950                 955                 960

Pro Glu Trp Arg Arg Asp Ile Ser Arg Val Ile Lys Lys Ser Leu Val
            965                 970                 975

Glu Ala Thr Gly Ile Pro Ser Gln His Ile Leu Val Ala Val Leu Pro
            980                 985                 990

Gly Leu Pro Thr Ala Ala Glu Leu Phe Val Leu Pro Tyr Gln Asp Gly
        995                 1000                1005

Thr Arg Glu Asn Lys Arg Ser Pro Glu Asp Leu Glu Gln Ile Ser
    1010                1015                1020

Glu Val Leu Ile His Lys Leu Asn Gln Asn Leu Val His Phe Glu
    1025                1030                1035

Leu Lys Pro Gly Val Gln Val Leu Val His Ala Ala His Leu Thr
    1040                1045                1050

Ala Ala Pro Leu Val Asp Leu Thr Pro Thr His Ser Gly Ser Ala
    1055                1060                1065

Met Leu Met Leu Leu Ser Val Val Phe Val Gly Leu Ala Val Phe
    1070                1075                1080

Val Ile Tyr Lys Phe Lys Arg Gly Trp Arg Asp Arg Ser Ala Val
    1085                1090                1095

Lys Asn Ile Gly Cys Ser Cys Arg Gly Pro Gly Phe Asn Ser Gln
    1100                1105                1110

His Gln Gln Gly Gly Ser Gln Ala Ser Val Thr Ser Val Pro Arg
    1115                1120                1125

Asp Pro Ser Pro Ser Ser Asp Leu His Gly His Gln Glu His Thr
    1130                1135                1140

Trp Cys Thr Asp Ile His Pro Gly Lys Thr Pro Ile His Ile Lys
    1145                1150                1155

<210> SEQ ID NO 27
<211> LENGTH: 1066
<212> TYPE: PRT

```
<213> ORGANISM: Mus musculus
<220> FEATURE:
<221> NAME/KEY: MISC_FEATURE
<222> LOCATION: (1)..(1066)
<223> OTHER INFORMATION: Soluble proSorCS1

<400> SEQUENCE: 27
```

| | | | | | | | | | | | | | | | |
|---|---|---|---|---|---|---|---|---|---|---|---|---|---|---|---|
| Ser | Leu | Ser | Cys | Cys | Pro | Pro | Gln | His | Pro | Ser | Ser | Thr | Pro | Arg | Arg |
| 1 | | | | 5 | | | | | 10 | | | | | 15 | |
| Thr | Leu | Thr | Pro | Arg | Gly | Phe | Pro | His | Pro | Gly | Pro | Leu | Gly | Arg | Ala |
| | | | 20 | | | | | 25 | | | | | 30 | | |
| Pro | Ala | Thr | Pro | Pro | Leu | Phe | Met | Arg | Pro | Leu | Phe | Ala | Val | Ala | |
| | | 35 | | | | | 40 | | | | | 45 | | | |
| Pro | Gly | Asp | Arg | Ala | Leu | Phe | Leu | Glu | Arg | Ala | Gly | Gly | Ser | Arg | Val |
| | 50 | | | | | 55 | | | | | 60 | | | | |
| Ser | Val | Ala | Thr | Ala | Ala | Arg | Ser | Gly | Arg | Arg | Arg | Ser | Gly | Thr | |
| 65 | | | | | 70 | | | | | 75 | | | | | 80 |
| Glu | Pro | Glu | Lys | Ile | Glu | Pro | Gly | Gly | Ala | Ser | Arg | Ser | Arg | Arg | |
| | | | | 85 | | | | | 90 | | | | | 95 | |
| Asp | Met | Leu | Lys | Asp | Gly | Gly | Gln | Gln | Gly | Leu | Gly | Thr | Gly | Ala | Arg |
| | | | 100 | | | | | 105 | | | | | 110 | | |
| Asp | Pro | Gly | Lys | Ala | Thr | Arg | Phe | Arg | Met | Glu | Glu | Leu | Arg | Leu | Thr |
| | | 115 | | | | | 120 | | | | | 125 | | | |
| Ser | Thr | Thr | Phe | Ala | Leu | Thr | Gly | Asp | Ser | Ala | His | Asn | Gln | Ala | Met |
| | 130 | | | | | 135 | | | | | 140 | | | | |
| Val | His | Trp | Ser | Gly | His | Asn | Ser | Ser | Val | Ile | Leu | Ile | Leu | Thr | Lys |
| 145 | | | | | 150 | | | | | 155 | | | | | 160 |
| Leu | Tyr | Asp | Tyr | Asn | Leu | Gly | Ser | Ile | Thr | Glu | Ser | Ser | Leu | Trp | Arg |
| | | | | 165 | | | | | 170 | | | | | 175 | |
| Ser | Thr | Asp | Tyr | Gly | Thr | Thr | Tyr | Glu | Lys | Leu | Asn | Asp | Lys | Val | Gly |
| | | | 180 | | | | | 185 | | | | | 190 | | |
| Leu | Lys | Thr | Ile | Leu | Ser | Tyr | Leu | Tyr | Val | Cys | Pro | Thr | Asn | Lys | Cys |
| | | 195 | | | | | 200 | | | | | 205 | | | |
| Lys | Ile | Met | Leu | Leu | Thr | Asp | Pro | Glu | Ile | Glu | Ser | Ser | Leu | Leu | Ile |
| | 210 | | | | | 215 | | | | | 220 | | | | |
| Ser | Ser | Asp | Glu | Gly | Ala | Thr | Tyr | Gln | Lys | Tyr | Arg | Leu | Asn | Phe | Tyr |
| 225 | | | | | 230 | | | | | 235 | | | | | 240 |
| Leu | Gln | Ser | Leu | Leu | Phe | His | Pro | Lys | Gln | Glu | Asp | Trp | Ile | Leu | Ala |
| | | | | 245 | | | | | 250 | | | | | 255 | |
| Tyr | Ser | Gln | Asp | Gln | Lys | Leu | Tyr | Ser | Ser | Ala | Glu | Phe | Gly | Arg | Arg |
| | | | 260 | | | | | 265 | | | | | 270 | | |
| Trp | Gln | Leu | Ile | Gln | Glu | Ser | Val | Val | Pro | Asn | Arg | Phe | Tyr | Trp | Ser |
| | | 275 | | | | | 280 | | | | | 285 | | | |
| Val | Met | Gly | Ser | Ser | Lys | Glu | Pro | Asp | Leu | Val | His | Leu | Glu | Ala | Arg |
| | 290 | | | | | 295 | | | | | 300 | | | | |
| Thr | Val | Asp | Gly | His | Ser | Ile | Tyr | Leu | Thr | Cys | Arg | Met | Gln | Asn | Cys |
| 305 | | | | | 310 | | | | | 315 | | | | | 320 |
| Thr | Glu | Ala | Asn | Arg | Asn | Lys | Pro | Phe | Pro | Gly | Tyr | Ile | Asp | Pro | Asp |
| | | | | 325 | | | | | 330 | | | | | 335 | |
| Ser | Leu | Ile | Val | Gln | Asp | Asp | Tyr | Val | Phe | Val | Gln | Leu | Thr | Ser | Gly |
| | | | 340 | | | | | 345 | | | | | 350 | | |
| Gly | Arg | Pro | His | Tyr | Tyr | Val | Ser | Tyr | Arg | Arg | Ser | Pro | Phe | Ala | Gln |
| | | 355 | | | | | 360 | | | | | 365 | | | |
| Met | Lys | Leu | Pro | Lys | Tyr | Ala | Leu | Pro | Lys | Asp | Met | His | Val | Ile | Ser |
| | 370 | | | | | 375 | | | | | 380 | | | | |

```
Thr Asp Glu Asn Gln Val Phe Ala Ala Val Gln Glu Trp Asn Gln Asn
385                 390                 395                 400

Asp Thr Tyr Asn Leu Tyr Ile Ser Asp Thr Arg Gly Val Tyr Phe Thr
            405                 410                 415

Leu Ala Leu Glu Asn Val Arg Ser Ser Arg Gly Pro Glu Gly Asn Val
        420                 425                 430

Met Ile Asp Leu Tyr Glu Val Ala Gly Ile Lys Gly Met Phe Leu Ala
    435                 440                 445

Asn Lys Lys Ile Asp Asn Gln Val Lys Thr Phe Ile Thr Tyr Asn Lys
450                 455                 460

Gly Arg Asp Trp Arg Leu Leu Gln Ala Pro Asp Ala Asp Leu Arg Gly
465                 470                 475                 480

Asp Pro Val His Cys Leu Leu Pro Tyr Cys Ser Leu His Leu His Leu
            485                 490                 495

Lys Val Ser Glu Asn Pro Tyr Thr Ser Gly Ile Ile Ala Ser Arg Asp
        500                 505                 510

Thr Ala Pro Ser Ile Ile Val Ala Ser Gly Asn Ile Gly Ser Glu Leu
    515                 520                 525

Ser Asp Ser Asp Ile Ser Met Phe Val Ser Ser Asp Ala Gly Asn Thr
530                 535                 540

Trp Arg Gln Ile Phe Glu Glu His Ser Ile Leu Tyr Leu Asp Gln
545                 550                 555                 560

Gly Gly Val Leu Val Ala Met Lys His Thr Ser Leu Pro Ile Arg His
            565                 570                 575

Leu Trp Leu Ser Phe Asp Glu Gly Arg Ser Trp Ser Lys Tyr Ser Phe
        580                 585                 590

Thr Ser Ile Pro Leu Phe Val Asp Gly Val Leu Gly Glu Pro Gly Glu
    595                 600                 605

Glu Thr Leu Ile Met Thr Val Phe Gly His Phe Ser His Arg Ser Glu
610                 615                 620

Trp Gln Leu Val Lys Val Asp Tyr Lys Ser Ile Phe Asp Arg Arg Cys
625                 630                 635                 640

Ala Glu Glu Asp Tyr Arg Pro Trp Gln Leu His Ser Gln Gly Glu Ala
            645                 650                 655

Cys Ile Met Gly Ala Lys Arg Ile Tyr Lys Lys Arg Lys Ser Glu Arg
        660                 665                 670

Lys Cys Met Gln Lys Tyr Ala Gly Ala Met Glu Ser Glu Pro Cys Val
    675                 680                 685

Cys Thr Glu Ala Asp Phe Asp Cys Asp Tyr Gly Tyr Glu Arg His Ser
    690                 695                 700

Asn Gly Gln Cys Leu Pro Ala Phe Trp Phe Asn Pro Ser Ser Leu Ser
705                 710                 715                 720

Lys Asp Cys Ser Leu Gly Gln Ser Tyr Leu Asn Ser Ala Gly Tyr Arg
            725                 730                 735

Lys Val Val Ser Asn Asn Cys Thr Asp Gly Val Arg Glu Gln Tyr Thr
        740                 745                 750

Ala Lys Pro Gln Lys Cys Pro Gly Lys Ala Pro Arg Gly Leu Arg Ile
    755                 760                 765

Val Thr Ala Asp Gly Lys Leu Thr Ala Glu Gln Gly His Asn Val Thr
    770                 775                 780

Leu Met Val Gln Leu Glu Glu Gly Asp Val Gln Arg Thr Leu Ile Gln
785                 790                 795                 800
```

Val Asp Phe Gly Asp Gly Ile Ala Val Ser Tyr Val Asn Leu Ser Ser
                805                 810                 815

Met Glu Asp Gly Ile Lys His Val Tyr Gln Asn Val Gly Ile Phe Arg
            820                 825                 830

Val Thr Val Gln Val Asp Asn Ser Leu Gly Ser Asp Ser Ala Val Leu
            835                 840                 845

Tyr Leu His Val Thr Cys Pro Leu Glu His Val His Leu Ser Leu Pro
    850                 855                 860

Phe Val Thr Thr Lys Asn Lys Glu Val Asn Ala Thr Ala Val Leu Trp
865                 870                 875                 880

Pro Ser Gln Val Gly Thr Leu Thr Tyr Val Trp Trp Tyr Gly Asn Asn
                885                 890                 895

Thr Glu Pro Leu Ile Thr Leu Glu Gly Ser Ile Ser Phe Lys Phe Thr
            900                 905                 910

Ser Glu Gly Met Asn Thr Ile Thr Val Gln Val Ser Ala Gly Asn Ala
        915                 920                 925

Ile Leu Gln Asp Thr Lys Thr Ile Ala Val Tyr Glu Glu Phe Arg Ser
    930                 935                 940

Leu Arg Leu Ala Phe Ser Pro Asn Leu Asp Asp Tyr Asn Pro Asp Ile
945                 950                 955                 960

Pro Glu Trp Arg Arg Asp Ile Ser Arg Val Ile Lys Lys Ser Leu Val
                965                 970                 975

Glu Ala Thr Gly Ile Pro Ser Gln His Ile Leu Val Ala Val Leu Pro
            980                 985                 990

Gly Leu Pro Thr Ala Ala Glu Leu Phe Val Leu Pro Tyr Gln Asp Gly
        995                 1000                1005

Thr Arg Glu Asn Lys Arg Ser Pro Glu Asp Leu Glu Gln Ile Ser
    1010                1015                1020

Glu Val Leu Ile His Lys Leu Asn Gln Asn Leu Val His Phe Glu
    1025                1030                1035

Leu Lys Pro Gly Val Gln Val Leu Val His Ala Ala His Leu Thr
    1040                1045                1050

Ala Ala Pro Leu Val Asp Leu Thr Pro Thr His Ser Gly
    1055                1060                1065

<210> SEQ ID NO 28
<211> LENGTH: 1057
<212> TYPE: PRT
<213> ORGANISM: Mus musculus
<220> FEATURE:
<221> NAME/KEY: MISC_FEATURE
<222> LOCATION: (1)..(1057)
<223> OTHER INFORMATION: mature SorCS1b, isoform 1

<400> SEQUENCE: 28

Ser Gly Thr Glu Pro Glu Lys Ile Glu Pro Gly Glu Gly Ala Ser Arg
1               5                   10                  15

Ser Arg Arg Asp Met Leu Lys Asp Gly Gln Gln Gly Leu Gly Thr
            20                  25                  30

Gly Ala Arg Asp Pro Gly Lys Ala Thr Arg Phe Arg Met Glu Glu Leu
        35                  40                  45

Arg Leu Thr Ser Thr Thr Phe Ala Leu Thr Gly Asp Ser Ala His Asn
    50                  55                  60

Gln Ala Met Val His Trp Ser Gly His Asn Ser Ser Val Ile Leu Ile
65                  70                  75                  80

Leu Thr Lys Leu Tyr Asp Tyr Asn Leu Gly Ser Ile Thr Glu Ser Ser

```
                    85                  90                  95
Leu Trp Arg Ser Thr Asp Tyr Gly Thr Thr Tyr Glu Lys Leu Asn Asp
                100                 105                 110

Lys Val Gly Leu Lys Thr Ile Leu Ser Tyr Leu Tyr Val Cys Pro Thr
            115                 120                 125

Asn Lys Cys Lys Ile Met Leu Leu Thr Asp Pro Glu Ile Glu Ser Ser
        130                 135                 140

Leu Leu Ile Ser Ser Asp Glu Gly Ala Thr Tyr Gln Lys Tyr Arg Leu
145                 150                 155                 160

Asn Phe Tyr Leu Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Ser Val Val Pro Asn Arg Phe
        195                 200                 205

Tyr Trp Ser Val Met Gly Ser Ser Lys Glu Pro Asp Leu Val His Leu
    210                 215                 220

Glu Ala Arg Thr Val Asp Gly His Ser Ile Tyr Leu Thr Cys Arg Met
225                 230                 235                 240

Gln Asn Cys Thr Glu Ala Asn Arg Asn Lys Pro Phe Pro Gly Tyr Ile
                245                 250                 255

Asp Pro Asp Ser Leu Ile Val Gln Asp Asp Tyr Val Phe Val Gln Leu
            260                 265                 270

Thr Ser Gly Gly Arg Pro His Tyr Tyr Val Ser Tyr Arg Arg Ser Pro
        275                 280                 285

Phe Ala Gln Met Lys Leu Pro Lys Tyr Ala Leu Pro Lys Asp Met His
    290                 295                 300

Val Ile Ser Thr Asp Glu Asn Gln Val Phe Ala Ala Val Gln Glu Trp
305                 310                 315                 320

Asn Gln Asn Asp Thr Tyr Asn Leu Tyr Ile Ser Asp Thr Arg Gly Val
                325                 330                 335

Tyr Phe Thr Leu Ala Leu Glu Asn Val Arg Ser Ser Arg Gly Pro Glu
            340                 345                 350

Gly Asn Val Met Ile Asp Leu Tyr Glu Val Ala Gly Ile Lys Gly Met
        355                 360                 365

Phe Leu Ala Asn Lys Lys Ile Asp Asn Gln Val Lys Thr Phe Ile Thr
    370                 375                 380

Tyr Asn Lys Gly Arg Asp Trp Arg Leu Leu Gln Ala Pro Asp Ala Asp
385                 390                 395                 400

Leu Arg Gly Asp Pro Val His Cys Leu Leu Pro Tyr Cys Ser Leu His
                405                 410                 415

Leu His Leu Lys Val Ser Glu Asn Pro Tyr Thr Ser Gly Ile Ile Ala
            420                 425                 430

Ser Arg Asp Thr Ala Pro Ser Ile Ile Val Ala Ser Gly Asn Ile Gly
        435                 440                 445

Ser Glu Leu Ser Asp Ser Asp Ile Ser Met Phe Val Ser Ser Asp Ala
    450                 455                 460

Gly Asn Thr Trp Arg Gln Ile Phe Glu Glu His Ser Ile Leu Tyr
465                 470                 475                 480

Leu Asp Gln Gly Gly Val Leu Val Ala Met Lys His Thr Ser Leu Pro
                485                 490                 495

Ile Arg His Leu Trp Leu Ser Phe Asp Glu Gly Arg Ser Trp Ser Lys
            500                 505                 510
```

```
Tyr Ser Phe Thr Ser Ile Pro Leu Phe Val Asp Gly Val Leu Gly Glu
            515                 520                 525

Pro Gly Glu Glu Thr Leu Ile Met Thr Val Phe Gly His Phe Ser His
    530                 535                 540

Arg Ser Glu Trp Gln Leu Val Lys Val Asp Tyr Lys Ser Ile Phe Asp
545                 550                 555                 560

Arg Arg Cys Ala Glu Glu Asp Tyr Arg Pro Trp Gln Leu His Ser Gln
                565                 570                 575

Gly Glu Ala Cys Ile Met Gly Ala Lys Arg Ile Tyr Lys Lys Arg Lys
                580                 585                 590

Ser Glu Arg Lys Cys Met Gln Lys Tyr Ala Gly Ala Met Glu Ser Glu
            595                 600                 605

Pro Cys Val Cys Thr Glu Ala Asp Phe Asp Cys Asp Tyr Gly Tyr Glu
            610                 615                 620

Arg His Ser Asn Gly Gln Cys Leu Pro Ala Phe Trp Phe Asn Pro Ser
625                 630                 635                 640

Ser Leu Ser Lys Asp Cys Ser Leu Gly Gln Ser Tyr Leu Asn Ser Ala
                645                 650                 655

Gly Tyr Arg Lys Val Val Ser Asn Asn Cys Thr Asp Gly Val Arg Glu
                660                 665                 670

Gln Tyr Thr Ala Lys Pro Gln Lys Cys Pro Gly Lys Ala Pro Arg Gly
            675                 680                 685

Leu Arg Ile Val Thr Ala Asp Gly Lys Leu Thr Ala Glu Gln Gly His
            690                 695                 700

Asn Val Thr Leu Met Val Gln Leu Glu Glu Gly Asp Val Gln Arg Thr
705                 710                 715                 720

Leu Ile Gln Val Asp Phe Gly Asp Gly Ile Ala Val Ser Tyr Val Asn
                725                 730                 735

Leu Ser Ser Met Glu Asp Gly Ile Lys His Val Tyr Gln Asn Val Gly
                740                 745                 750

Ile Phe Arg Val Thr Val Gln Val Asp Asn Ser Leu Gly Ser Asp Ser
            755                 760                 765

Ala Val Leu Tyr Leu His Val Thr Cys Pro Leu Glu His Val His Leu
            770                 775                 780

Ser Leu Pro Phe Val Thr Thr Lys Asn Lys Glu Val Asn Ala Thr Ala
785                 790                 795                 800

Val Leu Trp Pro Ser Gln Val Gly Thr Leu Thr Tyr Val Trp Trp Tyr
                805                 810                 815

Gly Asn Asn Thr Glu Pro Leu Ile Thr Leu Glu Gly Ser Ile Ser Phe
                820                 825                 830

Lys Phe Thr Ser Glu Gly Met Asn Thr Ile Thr Val Gln Val Ser Ala
            835                 840                 845

Gly Asn Ala Ile Leu Gln Asp Thr Lys Thr Ile Ala Val Tyr Glu Glu
            850                 855                 860

Phe Arg Ser Leu Arg Leu Ala Phe Ser Pro Asn Leu Asp Asp Tyr Asn
865                 870                 875                 880

Pro Asp Ile Pro Glu Trp Arg Arg Asp Ile Ser Arg Val Ile Lys Lys
                885                 890                 895

Ser Leu Val Glu Ala Thr Gly Ile Pro Ser Gln His Ile Leu Val Ala
                900                 905                 910

Val Leu Pro Gly Leu Pro Thr Ala Ala Glu Leu Phe Val Leu Pro Tyr
            915                 920                 925
```

```
Gln Asp Gly Thr Arg Glu Asn Lys Arg Ser Pro Glu Asp Leu Glu Gln
    930                 935                 940

Ile Ser Glu Val Leu Ile His Lys Leu Asn Gln Asn Leu Val His Phe
945                 950                 955                 960

Glu Leu Lys Pro Gly Val Gln Val Leu His Ala Ala His Leu Thr
                965                 970                 975

Ala Ala Pro Leu Val Asp Leu Thr Pro Thr His Ser Gly Ser Ala Met
            980                 985                 990

Leu Met Leu Leu Ser Val Val Phe Val Gly Leu Ala Val Phe Val Ile
                995                 1000                1005

Tyr Lys Phe Lys Arg Arg Val Ala Leu Pro Ser Pro Pro Ser Pro
    1010                1015                1020

Ser Ala Gln Pro Gly Asp Ser Ser Leu Arg Leu Gln Arg Pro Arg
    1025                1030                1035

Pro Ala Thr Pro Pro Ser Ser Pro Lys Arg Gly Ser Ala Gly Ala
    1040                1045                1050

Gln Phe Ala Ile
    1055

<210> SEQ ID NO 29
<211> LENGTH: 1037
<212> TYPE: PRT
<213> ORGANISM: Mus musculus
<220> FEATURE:
<221> NAME/KEY: MISC_FEATURE
<222> LOCATION: (1)..(1037)
<223> OTHER INFORMATION: mature SorCS1a, isoform 2

<400> SEQUENCE: 29

Ser Gly Thr Glu Pro Glu Lys Ile Glu Pro Gly Glu Gly Ala Ser Arg
1               5                   10                  15

Ser Arg Arg Asp Met Leu Lys Asp Gly Gly Gln Gln Gly Leu Gly Thr
            20                  25                  30

Gly Ala Arg Asp Pro Gly Lys Ala Thr Arg Phe Arg Met Glu Glu Leu
        35                  40                  45

Arg Leu Thr Ser Thr Thr Phe Ala Leu Thr Gly Asp Ser Ala His Asn
    50                  55                  60

Gln Ala Met Val His Trp Ser Gly His Asn Ser Ser Val Ile Leu Ile
65                  70                  75                  80

Leu Thr Lys Leu Tyr Asp Tyr Asn Leu Gly Ser Ile Thr Glu Ser Ser
                85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
        115                 120                 125

Asn Lys Cys Lys Ile Met Leu Leu Thr Asp Pro Glu Ile Glu Ser Ser
    130                 135                 140

Leu Leu Ile Ser Ser Asp Glu Gly Ala Thr Tyr Gln Lys Tyr Arg Leu
145                 150                 155                 160

Asn Phe Tyr Leu Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Ser Val Val Pro Asn Arg Phe
        195                 200                 205

Tyr Trp Ser Val Met Gly Ser Ser Lys Glu Pro Asp Leu Val His Leu
```

```
                    210                 215                 220
Glu Ala Arg Thr Val Asp Gly His Ser Ile Tyr Leu Thr Cys Arg Met
225                 230                 235                 240
Gln Asn Cys Thr Glu Ala Asn Arg Asn Lys Pro Phe Pro Gly Tyr Ile
                    245                 250                 255
Asp Pro Asp Ser Leu Ile Val Gln Asp Tyr Val Phe Val Gln Leu
                260                 265                 270
Thr Ser Gly Gly Arg Pro His Tyr Tyr Val Ser Tyr Arg Arg Ser Pro
                275                 280                 285
Phe Ala Gln Met Lys Leu Pro Lys Tyr Ala Leu Pro Lys Asp Met His
290                 295                 300
Val Ile Ser Thr Asp Glu Asn Gln Val Phe Ala Ala Val Gln Glu Trp
305                 310                 315                 320
Asn Gln Asn Asp Thr Tyr Asn Leu Tyr Ile Ser Asp Thr Arg Gly Val
                    325                 330                 335
Tyr Phe Thr Leu Ala Leu Glu Asn Val Arg Ser Ser Arg Gly Pro Glu
                340                 345                 350
Gly Asn Val Met Ile Asp Leu Tyr Glu Val Ala Gly Ile Lys Gly Met
                355                 360                 365
Phe Leu Ala Asn Lys Lys Ile Asp Asn Gln Val Lys Thr Phe Ile Thr
370                 375                 380
Tyr Asn Lys Gly Arg Asp Trp Arg Leu Leu Gln Ala Pro Asp Ala Asp
385                 390                 395                 400
Leu Arg Gly Asp Pro Val His Cys Leu Leu Pro Tyr Cys Ser Leu His
                    405                 410                 415
Leu His Leu Lys Val Ser Glu Asn Pro Tyr Thr Ser Gly Ile Ile Ala
                420                 425                 430
Ser Arg Asp Thr Ala Pro Ser Ile Ile Val Ala Ser Gly Asn Ile Gly
                435                 440                 445
Ser Glu Leu Ser Asp Ser Asp Ile Ser Met Phe Val Ser Ser Asp Ala
                450                 455                 460
Gly Asn Thr Trp Arg Gln Ile Phe Glu Glu His Ser Ile Leu Tyr
465                 470                 475                 480
Leu Asp Gln Gly Gly Val Leu Val Ala Met Lys His Thr Ser Leu Pro
                    485                 490                 495
Ile Arg His Leu Trp Leu Ser Phe Asp Glu Gly Arg Ser Trp Ser Lys
                500                 505                 510
Tyr Ser Phe Thr Ser Ile Pro Leu Phe Val Asp Gly Val Leu Gly Glu
                515                 520                 525
Pro Gly Glu Glu Thr Leu Ile Met Thr Val Phe Gly His Phe Ser His
530                 535                 540
Arg Ser Glu Trp Gln Leu Val Lys Val Asp Tyr Lys Ser Ile Phe Asp
545                 550                 555                 560
Arg Arg Cys Ala Glu Glu Asp Tyr Arg Pro Trp Gln Leu His Ser Gln
                    565                 570                 575
Gly Glu Ala Cys Ile Met Gly Ala Lys Arg Ile Tyr Lys Lys Arg Lys
                580                 585                 590
Ser Glu Arg Lys Cys Met Gln Lys Tyr Ala Gly Ala Met Glu Ser Glu
                595                 600                 605
Pro Cys Val Cys Thr Glu Ala Asp Phe Asp Cys Asp Tyr Gly Tyr Glu
                610                 615                 620
Arg His Ser Asn Gly Gln Cys Leu Pro Ala Phe Trp Phe Asn Pro Ser
625                 630                 635                 640
```

```
Ser Leu Ser Lys Asp Cys Ser Leu Gly Gln Ser Tyr Leu Asn Ser Ala
            645                 650                 655

Gly Tyr Arg Lys Val Ser Asn Asn Cys Thr Asp Gly Val Arg Glu
        660                 665                 670

Gln Tyr Thr Ala Lys Pro Gln Lys Cys Pro Gly Lys Ala Pro Arg Gly
            675                 680                 685

Leu Arg Ile Val Thr Ala Asp Gly Lys Leu Thr Ala Glu Gln Gly His
        690                 695                 700

Asn Val Thr Leu Met Val Gln Leu Glu Glu Gly Asp Val Gln Arg Thr
705                 710                 715                 720

Leu Ile Gln Val Asp Phe Gly Asp Gly Ile Ala Val Ser Tyr Val Asn
                725                 730                 735

Leu Ser Ser Met Glu Asp Gly Ile Lys His Val Tyr Gln Asn Val Gly
            740                 745                 750

Ile Phe Arg Val Thr Val Gln Val Asp Asn Ser Leu Gly Ser Asp Ser
        755                 760                 765

Ala Val Leu Tyr Leu His Val Thr Cys Pro Leu Glu His Val His Leu
        770                 775                 780

Ser Leu Pro Phe Val Thr Thr Lys Asn Lys Glu Val Asn Ala Thr Ala
785                 790                 795                 800

Val Leu Trp Pro Ser Gln Val Gly Thr Leu Thr Tyr Val Trp Trp Tyr
                805                 810                 815

Gly Asn Asn Thr Glu Pro Leu Ile Thr Leu Glu Gly Ser Ile Ser Phe
                820                 825                 830

Lys Phe Thr Ser Glu Gly Met Asn Thr Ile Thr Val Gln Val Ser Ala
            835                 840                 845

Gly Asn Ala Ile Leu Gln Asp Thr Lys Thr Ile Ala Val Tyr Glu Glu
        850                 855                 860

Phe Arg Ser Leu Arg Leu Ala Phe Ser Pro Asn Leu Asp Asp Tyr Asn
865                 870                 875                 880

Pro Asp Ile Pro Glu Trp Arg Arg Asp Ile Ser Arg Val Ile Lys Lys
                885                 890                 895

Ser Leu Val Glu Ala Thr Gly Ile Pro Ser Gln His Ile Leu Val Ala
            900                 905                 910

Val Leu Pro Gly Leu Pro Thr Ala Ala Glu Leu Phe Val Leu Pro Tyr
        915                 920                 925

Gln Asp Gly Thr Arg Glu Asn Lys Arg Ser Pro Glu Asp Leu Glu Gln
        930                 935                 940

Ile Ser Glu Val Leu Ile His Lys Leu Asn Gln Asn Leu Val His Phe
945                 950                 955                 960

Glu Leu Lys Pro Gly Val Gln Val Leu Val His Ala Ala His Leu Thr
                965                 970                 975

Ala Ala Pro Leu Val Asp Leu Thr Pro Thr His Ser Gly Ser Ala Met
            980                 985                 990

Leu Met Leu Leu Ser Val Val Phe Val Gly Leu Ala Val Phe Val Ile
                995                 1000                1005

Tyr Lys Phe Lys Arg Cys Val Phe Leu Leu Pro Ser Tyr Pro
        1010                1015                1020

Arg Pro Pro Pro Ser Ser Phe Cys Gln Val Gln Lys Gln
        1025                1030                1035

<210> SEQ ID NO 30
<211> LENGTH: 1068
```

```
<212> TYPE: PRT
<213> ORGANISM: Mus musculus
<220> FEATURE:
<221> NAME/KEY: MISC_FEATURE
<222> LOCATION: (1)..(1068)
<223> OTHER INFORMATION: mature SorCS1c, isoform 3

<400> SEQUENCE: 30
```

| | | | | | | | | | | | | | | |
|---|---|---|---|---|---|---|---|---|---|---|---|---|---|---|
|Ser|Gly|Thr|Glu|Pro|Glu|Lys|Ile|Glu|Pro|Gly|Gly|Ala|Ser|Arg|
|1| | | |5| | | |10| | | | |15| |
|Ser|Arg|Arg|Asp|Met|Leu|Lys|Asp|Gly|Gln|Gln|Gly|Leu|Gly|Thr|
| | | | |20| | | |25| | | | |30| |
|Gly|Ala|Arg|Asp|Pro|Gly|Lys|Ala|Thr|Arg|Phe|Arg|Met|Glu|Glu|Leu|
| | | | |35| | | |40| | | | |45| | |
|Arg|Leu|Thr|Ser|Thr|Thr|Phe|Ala|Leu|Thr|Gly|Asp|Ser|Ala|His|Asn|
| |50| | | | |55| | | | |60| | | | |
|Gln|Ala|Met|Val|His|Trp|Ser|Gly|His|Asn|Ser|Ser|Val|Ile|Leu|Ile|
|65| | | | |70| | | | |75| | | | |80|
|Leu|Thr|Lys|Leu|Tyr|Asp|Tyr|Asn|Leu|Gly|Ser|Ile|Thr|Glu|Ser|Ser|
| | | | |85| | | | |90| | | | |95| |
|Leu|Trp|Arg|Ser|Thr|Asp|Tyr|Gly|Thr|Thr|Tyr|Glu|Lys|Leu|Asn|Asp|
| | | |100| | | | |105| | | | |110| | |
|Lys|Val|Gly|Leu|Lys|Thr|Ile|Leu|Ser|Tyr|Leu|Tyr|Val|Cys|Pro|Thr|
| | | |115| | | | |120| | | | |125| | |
|Asn|Lys|Cys|Lys|Ile|Met|Leu|Leu|Thr|Asp|Pro|Glu|Ile|Glu|Ser|Ser|
| | | |130| | | | |135| | | | |140| | |
|Leu|Leu|Ile|Ser|Ser|Asp|Glu|Gly|Ala|Thr|Tyr|Gln|Lys|Tyr|Arg|Leu|
|145| | | | |150| | | | |155| | | | |160|
|Asn|Phe|Tyr|Leu|Gln|Ser|Leu|Leu|Phe|His|Pro|Lys|Gln|Glu|Asp|Trp|
| | | | |165| | | | |170| | | | |175| |
|Ile|Leu|Ala|Tyr|Ser|Gln|Asp|Gln|Lys|Leu|Tyr|Ser|Ser|Ala|Glu|Phe|
| | | |180| | | | |185| | | | |190| | |
|Gly|Arg|Arg|Trp|Gln|Leu|Ile|Gln|Glu|Ser|Val|Val|Pro|Asn|Arg|Phe|
| | | |195| | | | |200| | | | |205| | |
|Tyr|Trp|Ser|Val|Met|Gly|Ser|Ser|Lys|Glu|Pro|Asp|Leu|Val|His|Leu|
| | | |210| | | | |215| | | | |220| | |
|Glu|Ala|Arg|Thr|Val|Asp|Gly|His|Ser|Ile|Tyr|Leu|Thr|Cys|Arg|Met|
|225| | | | |230| | | | |235| | | | |240|
|Gln|Asn|Cys|Thr|Glu|Ala|Asn|Arg|Asn|Lys|Pro|Phe|Pro|Gly|Tyr|Ile|
| | | | |245| | | | |250| | | | |255| |
|Asp|Pro|Asp|Ser|Leu|Ile|Val|Gln|Asp|Tyr|Val|Phe|Val|Gln|Leu|
| | | | |260| | | | |265| | | | |270|
|Thr|Ser|Gly|Gly|Arg|Pro|His|Tyr|Tyr|Val|Ser|Tyr|Arg|Arg|Ser|Pro|
| | | |275| | | | |280| | | | |285| | |
|Phe|Ala|Gln|Met|Lys|Leu|Pro|Lys|Tyr|Ala|Leu|Pro|Lys|Asp|Met|His|
| | | |290| | | | |295| | | | |300| | |
|Val|Ile|Ser|Thr|Asp|Glu|Asn|Gln|Val|Phe|Ala|Ala|Val|Gln|Glu|Trp|
|305| | | | |310| | | | |315| | | | |320|
|Asn|Gln|Asn|Asp|Thr|Tyr|Asn|Leu|Tyr|Ile|Ser|Asp|Thr|Arg|Gly|Val|
| | | | |325| | | | |330| | | | |335| |
|Tyr|Phe|Thr|Leu|Ala|Leu|Glu|Asn|Val|Arg|Ser|Ser|Arg|Gly|Pro|Glu|
| | | |340| | | | |345| | | | |350| | |
|Gly|Asn|Val|Met|Ile|Asp|Leu|Tyr|Glu|Val|Ala|Gly|Ile|Lys|Gly|Met|
| | | |355| | | | |360| | | | |365| | |
|Phe|Leu|Ala|Asn|Lys|Lys|Ile|Asp|Asn|Gln|Val|Lys|Thr|Phe|Ile|Thr|

```
              370                 375                 380
Tyr Asn Lys Gly Arg Asp Trp Arg Leu Leu Gln Ala Pro Asp Ala Asp
385                 390                 395                 400

Leu Arg Gly Asp Pro Val His Cys Leu Leu Pro Tyr Cys Ser Leu His
                405                 410                 415

Leu His Leu Lys Val Ser Glu Asn Pro Tyr Thr Ser Gly Ile Ile Ala
                420                 425                 430

Ser Arg Asp Thr Ala Pro Ser Ile Ile Val Ala Ser Gly Asn Ile Gly
                435                 440                 445

Ser Glu Leu Ser Asp Ser Asp Ile Ser Met Phe Val Ser Ser Asp Ala
                450                 455                 460

Gly Asn Thr Trp Arg Gln Ile Phe Glu Glu Glu His Ser Ile Leu Tyr
465                 470                 475                 480

Leu Asp Gln Gly Gly Val Leu Val Ala Met Lys His Thr Ser Leu Pro
                485                 490                 495

Ile Arg His Leu Trp Leu Ser Phe Asp Glu Gly Arg Ser Trp Ser Lys
                500                 505                 510

Tyr Ser Phe Thr Ser Ile Pro Leu Phe Val Asp Gly Val Leu Gly Glu
                515                 520                 525

Pro Gly Glu Glu Thr Leu Ile Met Thr Val Phe Gly His Phe Ser His
                530                 535                 540

Arg Ser Glu Trp Gln Leu Val Lys Val Asp Tyr Lys Ser Ile Phe Asp
545                 550                 555                 560

Arg Arg Cys Ala Glu Glu Asp Tyr Arg Pro Trp Gln Leu His Ser Gln
                565                 570                 575

Gly Glu Ala Cys Ile Met Gly Ala Lys Arg Ile Tyr Lys Lys Arg Lys
                580                 585                 590

Ser Glu Arg Lys Cys Met Gln Lys Tyr Ala Gly Ala Met Glu Ser Glu
                595                 600                 605

Pro Cys Val Cys Thr Glu Ala Asp Phe Asp Cys Asp Tyr Gly Tyr Glu
                610                 615                 620

Arg His Ser Asn Gly Gln Cys Leu Pro Ala Phe Trp Phe Asn Pro Ser
625                 630                 635                 640

Ser Leu Ser Lys Asp Cys Ser Leu Gly Gln Ser Tyr Leu Asn Ser Ala
                645                 650                 655

Gly Tyr Arg Lys Val Val Ser Asn Asn Cys Thr Asp Gly Val Arg Glu
                660                 665                 670

Gln Tyr Thr Ala Lys Pro Gln Lys Cys Pro Gly Lys Ala Pro Arg Gly
                675                 680                 685

Leu Arg Ile Val Thr Ala Asp Gly Lys Leu Thr Ala Glu Gln Gly His
                690                 695                 700

Asn Val Thr Leu Met Val Gln Leu Glu Glu Gly Asp Val Gln Arg Thr
705                 710                 715                 720

Leu Ile Gln Val Asp Phe Gly Asp Gly Ile Ala Val Ser Tyr Val Asn
                725                 730                 735

Leu Ser Ser Met Glu Asp Gly Ile Lys His Val Tyr Gln Asn Val Gly
                740                 745                 750

Ile Phe Arg Val Thr Val Gln Val Asp Asn Ser Leu Gly Ser Asp Ser
                755                 760                 765

Ala Val Leu Tyr Leu His Val Thr Cys Pro Leu Glu His Val His Leu
                770                 775                 780

Ser Leu Pro Phe Val Thr Thr Lys Asn Lys Glu Val Asn Ala Thr Ala
785                 790                 795                 800
```

Val Leu Trp Pro Ser Gln Val Gly Thr Leu Thr Tyr Val Trp Trp Tyr
                805                 810                 815

Gly Asn Asn Thr Glu Pro Leu Ile Thr Leu Glu Gly Ser Ile Ser Phe
                820                 825                 830

Lys Phe Thr Ser Glu Gly Met Asn Thr Ile Thr Val Gln Val Ser Ala
                835                 840                 845

Gly Asn Ala Ile Leu Gln Asp Thr Lys Thr Ile Ala Val Tyr Glu Glu
                850                 855                 860

Phe Arg Ser Leu Arg Leu Ala Phe Ser Pro Asn Leu Asp Asp Tyr Asn
865                 870                 875                 880

Pro Asp Ile Pro Glu Trp Arg Arg Asp Ile Ser Arg Val Ile Lys Lys
                885                 890                 895

Ser Leu Val Glu Ala Thr Gly Ile Pro Ser Gln His Ile Leu Val Ala
                900                 905                 910

Val Leu Pro Gly Leu Pro Thr Ala Ala Glu Leu Phe Val Leu Pro Tyr
                915                 920                 925

Gln Asp Gly Thr Arg Glu Asn Lys Arg Ser Pro Glu Asp Leu Glu Gln
                930                 935                 940

Ile Ser Glu Val Leu Ile His Lys Leu Asn Gln Asn Leu Val His Phe
945                 950                 955                 960

Glu Leu Lys Pro Gly Val Gln Val Leu Val His Ala Ala His Leu Thr
                965                 970                 975

Ala Ala Pro Leu Val Asp Leu Thr Pro Thr His Ser Gly Ser Ala Met
                980                 985                 990

Leu Met Leu Leu Ser Val Val Phe Val Gly Leu Ala Val Phe Val Ile
                995                 1000                1005

Tyr Lys Phe Lys Arg Lys Ile Pro Gly Ile Asn Val Tyr Ala Gln
                1010                1015                1020

Met Gln Asn Glu Lys Glu Gln Glu Leu Ile Asn Pro Val Ser His
                1025                1030                1035

Ser Glu Ser Arg Pro Ser Val Pro His Pro Asp Leu Arg Arg Pro
                1040                1045                1050

Gly Gln Leu Val Asp Glu Lys Val Glu Ser Gln Leu Leu Gly Lys
                1055                1060                1065

<210> SEQ ID NO 31
<211> LENGTH: 1068
<212> TYPE: PRT
<213> ORGANISM: Mus musculus
<220> FEATURE:
<221> NAME/KEY: MISC_FEATURE
<222> LOCATION: (1)..(1068)
<223> OTHER INFORMATION: mature SorCS1c+, isoform 4

<400> SEQUENCE: 31

Ser Gly Thr Glu Pro Glu Lys Ile Glu Pro Gly Glu Gly Ala Ser Arg
1               5                   10                  15

Ser Arg Arg Asp Met Leu Lys Asp Gly Gly Gln Gln Gly Leu Gly Thr
                20                  25                  30

Gly Ala Arg Asp Pro Gly Lys Ala Thr Arg Phe Arg Met Glu Glu Leu
                35                  40                  45

Arg Leu Thr Ser Thr Thr Phe Ala Leu Thr Gly Asp Ser Ala His Asn
                50                  55                  60

Gln Ala Met Val His Trp Ser Gly His Asn Ser Ser Val Ile Leu Ile
65                  70                  75                  80

-continued

```
Leu Thr Lys Leu Tyr Asp Tyr Asn Leu Gly Ser Ile Thr Glu Ser Ser
                 85                  90                  95
Leu Trp Arg Ser Thr Asp Tyr Gly Thr Thr Tyr Glu Lys Leu Asn Asp
            100                 105                 110
Lys Val Gly Leu Lys Thr Ile Leu Ser Tyr Leu Tyr Val Cys Pro Thr
        115                 120                 125
Asn Lys Cys Lys Ile Met Leu Leu Thr Asp Pro Glu Ile Glu Ser Ser
    130                 135                 140
Leu Leu Ile Ser Ser Asp Glu Gly Ala Thr Tyr Gln Lys Tyr Arg Leu
145                 150                 155                 160
Asn Phe Tyr Leu Gln Ser Leu Leu Phe His Pro Lys Gln Glu Asp Trp
                165                 170                 175
Ile Leu Ala Tyr Ser Gln Asp Gln Lys Leu Tyr Ser Ser Ala Glu Phe
            180                 185                 190
Gly Arg Arg Trp Gln Leu Ile Gln Glu Ser Val Val Pro Asn Arg Phe
        195                 200                 205
Tyr Trp Ser Val Met Gly Ser Ser Lys Glu Pro Asp Leu Val His Leu
    210                 215                 220
Glu Ala Arg Thr Val Asp Gly His Ser Ile Tyr Leu Thr Cys Arg Met
225                 230                 235                 240
Gln Asn Cys Thr Glu Ala Asn Arg Asn Lys Pro Phe Pro Gly Tyr Ile
                245                 250                 255
Asp Pro Asp Ser Leu Ile Val Gln Asp Tyr Val Phe Val Gln Leu
            260                 265                 270
Thr Ser Gly Gly Arg Pro His Tyr Tyr Val Ser Tyr Arg Arg Ser Pro
        275                 280                 285
Phe Ala Gln Met Lys Leu Pro Lys Tyr Ala Leu Pro Lys Asp Met His
    290                 295                 300
Val Ile Ser Thr Asp Glu Asn Gln Val Phe Ala Ala Val Gln Glu Trp
305                 310                 315                 320
Asn Gln Asn Asp Thr Tyr Asn Leu Tyr Ile Ser Asp Thr Arg Gly Val
                325                 330                 335
Tyr Phe Thr Leu Ala Leu Glu Asn Val Arg Ser Ser Arg Gly Pro Glu
            340                 345                 350
Gly Asn Val Met Ile Asp Leu Tyr Glu Val Ala Gly Ile Lys Gly Met
        355                 360                 365
Phe Leu Ala Asn Lys Lys Ile Asp Asn Gln Val Lys Thr Phe Ile Thr
    370                 375                 380
Tyr Asn Lys Gly Arg Asp Trp Arg Leu Leu Gln Ala Pro Asp Ala Asp
385                 390                 395                 400
Leu Arg Gly Asp Pro Val His Cys Leu Leu Pro Tyr Cys Ser Leu His
                405                 410                 415
Leu His Leu Lys Val Ser Glu Asn Pro Tyr Thr Ser Gly Ile Ile Ala
            420                 425                 430
Ser Arg Asp Thr Ala Pro Ser Ile Ile Val Ala Ser Gly Asn Ile Gly
        435                 440                 445
Ser Glu Leu Ser Asp Ser Asp Ile Ser Met Phe Val Ser Ser Asp Ala
    450                 455                 460
Gly Asn Thr Trp Arg Gln Ile Phe Glu Glu His Ser Ile Leu Tyr
465                 470                 475                 480
Leu Asp Gln Gly Gly Val Leu Val Ala Met Lys His Thr Ser Leu Pro
                485                 490                 495
Ile Arg His Leu Trp Leu Ser Phe Asp Glu Gly Arg Ser Trp Ser Lys
```

```
              500                 505                 510
Tyr Ser Phe Thr Ser Ile Pro Leu Phe Val Asp Gly Val Leu Gly Glu
            515                 520                 525

Pro Gly Glu Glu Thr Leu Ile Met Thr Val Phe Gly His Phe Ser His
530                 535                 540

Arg Ser Glu Trp Gln Leu Val Lys Val Asp Tyr Lys Ser Ile Phe Asp
545                 550                 555                 560

Arg Arg Cys Ala Glu Glu Asp Tyr Arg Pro Trp Gln Leu His Ser Gln
                565                 570                 575

Gly Glu Ala Cys Ile Met Gly Ala Lys Arg Ile Tyr Lys Lys Arg Lys
                580                 585                 590

Ser Glu Arg Lys Cys Met Gln Lys Tyr Ala Gly Ala Met Glu Ser Glu
            595                 600                 605

Pro Cys Val Cys Thr Glu Ala Asp Phe Asp Cys Asp Tyr Gly Tyr Glu
610                 615                 620

Arg His Ser Asn Gly Gln Cys Leu Pro Ala Phe Trp Phe Asn Pro Ser
625                 630                 635                 640

Ser Leu Ser Lys Asp Cys Ser Leu Gly Gln Ser Tyr Leu Asn Ser Ala
                645                 650                 655

Gly Tyr Arg Lys Val Val Ser Asn Asn Cys Thr Asp Gly Val Arg Glu
                660                 665                 670

Gln Tyr Thr Ala Lys Pro Gln Lys Cys Pro Gly Lys Ala Pro Arg Gly
            675                 680                 685

Leu Arg Ile Val Thr Ala Asp Gly Lys Leu Thr Ala Glu Gln Gly His
            690                 695                 700

Asn Val Thr Leu Met Val Gln Leu Glu Glu Gly Asp Val Gln Arg Thr
705                 710                 715                 720

Leu Ile Gln Val Asp Phe Gly Asp Gly Ile Ala Val Ser Tyr Val Asn
                725                 730                 735

Leu Ser Ser Met Glu Asp Gly Ile Lys His Val Tyr Gln Asn Val Gly
                740                 745                 750

Ile Phe Arg Val Thr Val Gln Val Asp Asn Ser Leu Gly Ser Asp Ser
            755                 760                 765

Ala Val Leu Tyr Leu His Val Thr Cys Pro Leu Glu His Val His Leu
770                 775                 780

Ser Leu Pro Phe Val Thr Thr Lys Asn Lys Glu Val Asn Ala Thr Ala
785                 790                 795                 800

Val Leu Trp Pro Ser Gln Val Gly Thr Leu Thr Tyr Val Trp Trp Tyr
                805                 810                 815

Gly Asn Asn Thr Glu Pro Leu Ile Thr Leu Glu Gly Ser Ile Ser Phe
                820                 825                 830

Lys Phe Thr Ser Glu Gly Met Asn Thr Ile Thr Val Gln Val Ser Ala
            835                 840                 845

Gly Asn Ala Ile Leu Gln Asp Thr Lys Thr Ile Ala Val Tyr Glu Glu
            850                 855                 860

Phe Arg Ser Leu Arg Leu Ala Phe Ser Pro Asn Leu Asp Asp Tyr Asn
865                 870                 875                 880

Pro Asp Ile Pro Glu Trp Arg Arg Asp Ile Ser Arg Val Ile Lys Lys
                885                 890                 895

Ser Leu Val Glu Ala Thr Gly Ile Pro Ser Gln His Ile Leu Val Ala
                900                 905                 910

Val Leu Pro Gly Leu Pro Thr Ala Ala Glu Leu Phe Val Leu Pro Tyr
            915                 920                 925
```

```
Gln Asp Gly Thr Arg Glu Asn Lys Arg Ser Pro Glu Asp Leu Glu Gln
        930                 935                 940

Ile Ser Glu Val Leu Ile His Lys Leu Asn Gln Asn Leu Val His Phe
945                 950                 955                 960

Glu Leu Lys Pro Gly Val Gln Val Leu Val His Ala Ala His Leu Thr
                965                 970                 975

Ala Ala Pro Leu Val Asp Leu Thr Pro Thr His Ser Gly Ser Ala Met
                980                 985                 990

Leu Met Leu Leu Ser Val Val Phe Val Gly Leu Ala Val Phe Val Ile
            995                 1000                1005

Tyr Lys Phe Lys Arg Lys Ile Pro Gly Ile Asn Val Tyr Ala Gln
   1010                1015                1020

Met Gln Asn Glu Lys Glu Gln Glu Leu Ile Asn Pro Val Ser His
   1025                1030                1035

Ser Glu Ser Arg Ser Ser Val Pro His Pro Asp Leu Arg Arg Pro
   1040                1045                1050

Gly Gln Leu Val Asp Glu Lys Val Glu Ser Gln Leu Leu Gly Glu
   1055                1060                1065

<210> SEQ ID NO 32
<211> LENGTH: 1081
<212> TYPE: PRT
<213> ORGANISM: Mus musculus
<220> FEATURE:
<221> NAME/KEY: MISC_FEATURE
<222> LOCATION: (1)..(1081)
<223> OTHER INFORMATION: mature SorCS1d

<400> SEQUENCE: 32

Ser Gly Thr Glu Pro Glu Lys Ile Glu Pro Gly Glu Gly Ala Ser Arg
1               5                   10                  15

Ser Arg Arg Asp Met Leu Lys Asp Gly Gly Gln Gln Gly Leu Gly Thr
            20                  25                  30

Gly Ala Arg Asp Pro Gly Lys Ala Thr Arg Phe Arg Met Glu Glu Leu
        35                  40                  45

Arg Leu Thr Ser Thr Thr Phe Ala Leu Thr Gly Asp Ser Ala His Asn
50                  55                  60

Gln Ala Met Val His Trp Ser Gly His Asn Ser Ser Val Ile Leu Ile
65                  70                  75                  80

Leu Thr Lys Leu Tyr Asp Tyr Asn Leu Gly Ser Ile Thr Glu Ser Ser
                85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
        115                 120                 125

Asn Lys Cys Lys Ile Met Leu Leu Thr Asp Pro Glu Ile Glu Ser Ser
130                 135                 140

Leu Leu Ile Ser Ser Asp Glu Gly Ala Thr Tyr Gln Lys Tyr Arg Leu
145                 150                 155                 160

Asn Phe Tyr Leu Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Ser Val Val Pro Asn Arg Phe
        195                 200                 205
```

-continued

Tyr Trp Ser Val Met Gly Ser Ser Lys Glu Pro Asp Leu Val His Leu
    210                 215                 220

Glu Ala Arg Thr Val Asp Gly His Ser Ile Tyr Leu Thr Cys Arg Met
225                 230                 235                 240

Gln Asn Cys Thr Glu Ala Asn Arg Asn Lys Pro Phe Pro Gly Tyr Ile
                245                 250                 255

Asp Pro Asp Ser Leu Ile Val Gln Asp Tyr Val Phe Val Gln Leu
            260                 265                 270

Thr Ser Gly Gly Arg Pro His Tyr Tyr Val Ser Tyr Arg Arg Ser Pro
        275                 280                 285

Phe Ala Gln Met Lys Leu Pro Lys Tyr Ala Leu Pro Lys Asp Met His
    290                 295                 300

Val Ile Ser Thr Asp Glu Asn Gln Val Phe Ala Ala Val Gln Glu Trp
305                 310                 315                 320

Asn Gln Asn Asp Thr Tyr Asn Leu Tyr Ile Ser Asp Thr Arg Gly Val
                325                 330                 335

Tyr Phe Thr Leu Ala Leu Glu Asn Val Arg Ser Ser Arg Gly Pro Glu
            340                 345                 350

Gly Asn Val Met Ile Asp Leu Tyr Glu Val Ala Gly Ile Lys Gly Met
        355                 360                 365

Phe Leu Ala Asn Lys Lys Ile Asp Asn Gln Val Lys Thr Phe Ile Thr
    370                 375                 380

Tyr Asn Lys Gly Arg Asp Trp Arg Leu Leu Gln Ala Pro Asp Ala Asp
385                 390                 395                 400

Leu Arg Gly Asp Pro Val His Cys Leu Leu Pro Tyr Cys Ser Leu His
                405                 410                 415

Leu His Leu Lys Val Ser Glu Asn Pro Tyr Thr Ser Gly Ile Ile Ala
            420                 425                 430

Ser Arg Asp Thr Ala Pro Ser Ile Val Ala Ser Gly Asn Ile Gly
        435                 440                 445

Ser Glu Leu Ser Asp Ser Asp Ile Ser Met Phe Val Ser Ser Asp Ala
    450                 455                 460

Gly Asn Thr Trp Arg Gln Ile Phe Glu Glu His Ser Ile Leu Tyr
465                 470                 475                 480

Leu Asp Gln Gly Gly Val Leu Val Ala Met Lys His Thr Ser Leu Pro
                485                 490                 495

Ile Arg His Leu Trp Leu Ser Phe Asp Glu Gly Arg Ser Trp Ser Lys
            500                 505                 510

Tyr Ser Phe Thr Ser Ile Pro Leu Phe Val Asp Gly Val Leu Gly Glu
        515                 520                 525

Pro Gly Glu Glu Thr Leu Ile Met Thr Val Phe Gly His Phe Ser His
    530                 535                 540

Arg Ser Glu Trp Gln Leu Val Lys Val Asp Tyr Lys Ser Ile Phe Asp
545                 550                 555                 560

Arg Arg Cys Ala Glu Glu Asp Tyr Arg Pro Trp Gln Leu His Ser Gln
                565                 570                 575

Gly Glu Ala Cys Ile Met Gly Ala Lys Arg Ile Tyr Lys Lys Arg Lys
            580                 585                 590

Ser Glu Arg Lys Cys Met Gln Lys Tyr Ala Gly Ala Met Glu Ser Glu
        595                 600                 605

Pro Cys Val Cys Thr Glu Ala Asp Phe Asp Cys Asp Tyr Gly Tyr Glu
    610                 615                 620

Arg His Ser Asn Gly Gln Cys Leu Pro Ala Phe Trp Phe Asn Pro Ser

```
            625                 630                 635                 640
Ser Leu Ser Lys Asp Cys Ser Leu Gly Gln Ser Tyr Leu Asn Ser Ala
            645                 650                 655

Gly Tyr Arg Lys Val Val Ser Asn Asn Cys Thr Asp Gly Val Arg Glu
            660                 665                 670

Gln Tyr Thr Ala Lys Pro Gln Lys Cys Pro Gly Lys Ala Pro Arg Gly
            675                 680                 685

Leu Arg Ile Val Thr Ala Asp Gly Lys Leu Thr Ala Glu Gln Gly His
            690                 695                 700

Asn Val Thr Leu Met Val Gln Leu Glu Glu Gly Asp Val Gln Arg Thr
705                 710                 715                 720

Leu Ile Gln Val Asp Phe Gly Asp Gly Ile Ala Val Ser Tyr Val Asn
            725                 730                 735

Leu Ser Ser Met Glu Asp Gly Ile Lys His Val Tyr Gln Asn Val Gly
            740                 745                 750

Ile Phe Arg Val Thr Val Gln Val Asp Asn Ser Leu Gly Ser Asp Ser
            755                 760                 765

Ala Val Leu Tyr Leu His Val Thr Cys Pro Leu Glu His Val His Leu
            770                 775                 780

Ser Leu Pro Phe Val Thr Thr Lys Asn Lys Glu Val Asn Ala Thr Ala
785                 790                 795                 800

Val Leu Trp Pro Ser Gln Val Gly Thr Leu Thr Tyr Val Trp Trp Tyr
            805                 810                 815

Gly Asn Asn Thr Glu Pro Leu Ile Thr Leu Glu Gly Ser Ile Ser Phe
            820                 825                 830

Lys Phe Thr Ser Glu Gly Met Asn Thr Ile Thr Val Gln Val Ser Ala
            835                 840                 845

Gly Asn Ala Ile Leu Gln Asp Thr Lys Thr Ile Ala Val Tyr Glu Glu
            850                 855                 860

Phe Arg Ser Leu Arg Leu Ala Phe Ser Pro Asn Leu Asp Asp Tyr Asn
865                 870                 875                 880

Pro Asp Ile Pro Glu Trp Arg Arg Asp Ile Ser Arg Val Ile Lys Lys
            885                 890                 895

Ser Leu Val Glu Ala Thr Gly Ile Pro Ser Gln His Ile Leu Val Ala
            900                 905                 910

Val Leu Pro Gly Leu Pro Thr Ala Ala Glu Leu Phe Val Leu Pro Tyr
            915                 920                 925

Gln Asp Gly Thr Arg Glu Asn Lys Arg Ser Pro Glu Asp Leu Glu Gln
            930                 935                 940

Ile Ser Glu Val Leu Ile His Lys Leu Asn Gln Asn Leu Val His Phe
945                 950                 955                 960

Glu Leu Lys Pro Gly Val Gln Val Leu Val His Ala Ala His Leu Thr
            965                 970                 975

Ala Ala Pro Leu Val Asp Leu Thr Pro Thr His Ser Gly Ser Ala Met
            980                 985                 990

Leu Met Leu Leu Ser Val Val Phe  Val Gly Leu Ala Val  Phe Val Ile
            995                1000                1005

Tyr Lys  Phe Lys Arg Gly Trp  Arg Asp Arg Ser Ala  Val Lys Asn
           1010                1015                1020

Ile Gly  Cys Ser Cys Arg Gly  Pro Gly Phe Asn Ser  Gln His Gln
           1025                1030                1035

Gln Gly  Gly Ser Gln Ala Ser  Val Thr Ser Val Pro  Arg Asp Pro
           1040                1045                1050
```

```
Ser Pro Ser Ser Asp Leu His Gly His Gln Glu His Thr Trp Cys
    1055            1060                1065

Thr Asp Ile His Pro Gly Lys Thr Pro Ile His Ile Lys
    1070            1075            1080

<210> SEQ ID NO 33
<211> LENGTH: 989
<212> TYPE: PRT
<213> ORGANISM: Mus musculus
<220> FEATURE:
<221> NAME/KEY: MISC_FEATURE
<222> LOCATION: (1)..(989)
<223> OTHER INFORMATION: Soluble mature SorCS1

<400> SEQUENCE: 33

Ser Gly Thr Glu Pro Glu Lys Ile Glu Pro Gly Glu Gly Ala Ser Arg
1               5                   10                  15

Ser Arg Arg Asp Met Leu Lys Asp Gly Gly Gln Gln Gly Leu Gly Thr
            20                  25                  30

Gly Ala Arg Asp Pro Gly Lys Ala Thr Arg Phe Arg Met Glu Glu Leu
        35                  40                  45

Arg Leu Thr Ser Thr Thr Phe Ala Leu Thr Gly Asp Ser Ala His Asn
    50                  55                  60

Gln Ala Met Val His Trp Ser Gly His Asn Ser Ser Val Ile Leu Ile
65                  70                  75                  80

Leu Thr Lys Leu Tyr Asp Tyr Asn Leu Gly Ser Ile Thr Glu Ser Ser
                85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
        115                 120                 125

Asn Lys Cys Lys Ile Met Leu Leu Thr Asp Pro Glu Ile Glu Ser Ser
    130                 135                 140

Leu Leu Ile Ser Ser Asp Glu Gly Ala Thr Tyr Gln Lys Tyr Arg Leu
145                 150                 155                 160

Asn Phe Tyr Leu Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Ser Val Val Pro Asn Arg Phe
        195                 200                 205

Tyr Trp Ser Val Met Gly Ser Ser Lys Glu Pro Asp Leu Val His Leu
    210                 215                 220

Glu Ala Arg Thr Val Asp Gly His Ser Ile Tyr Leu Thr Cys Arg Met
225                 230                 235                 240

Gln Asn Cys Thr Glu Ala Asn Arg Asn Lys Pro Phe Pro Gly Tyr Ile
                245                 250                 255

Asp Pro Asp Ser Leu Ile Val Gln Asp Tyr Val Phe Val Gln Leu
            260                 265                 270

Thr Ser Gly Gly Arg Pro His Tyr Tyr Val Ser Tyr Arg Arg Ser Pro
        275                 280                 285

Phe Ala Gln Met Lys Leu Pro Lys Tyr Ala Leu Pro Lys Asp Met His
    290                 295                 300

Val Ile Ser Thr Asp Glu Asn Gln Val Phe Ala Ala Val Gln Glu Trp
305                 310                 315                 320
```

```
Asn Gln Asn Asp Thr Tyr Asn Leu Tyr Ile Ser Asp Thr Arg Gly Val
                325                 330                 335

Tyr Phe Thr Leu Ala Leu Glu Asn Val Arg Ser Ser Arg Gly Pro Glu
            340                 345                 350

Gly Asn Val Met Ile Asp Leu Tyr Glu Val Ala Gly Ile Lys Gly Met
        355                 360                 365

Phe Leu Ala Asn Lys Lys Ile Asp Asn Gln Val Lys Thr Phe Ile Thr
370                 375                 380

Tyr Asn Lys Gly Arg Asp Trp Arg Leu Leu Gln Ala Pro Asp Ala Asp
385                 390                 395                 400

Leu Arg Gly Asp Pro Val His Cys Leu Leu Pro Tyr Cys Ser Leu His
                405                 410                 415

Leu His Leu Lys Val Ser Glu Asn Pro Tyr Thr Ser Gly Ile Ile Ala
            420                 425                 430

Ser Arg Asp Thr Ala Pro Ser Ile Val Ala Ser Gly Asn Ile Gly
        435                 440                 445

Ser Glu Leu Ser Asp Ser Asp Ile Ser Met Phe Val Ser Ser Asp Ala
    450                 455                 460

Gly Asn Thr Trp Arg Gln Ile Phe Glu Glu His Ser Ile Leu Tyr
465                 470                 475                 480

Leu Asp Gln Gly Gly Val Leu Val Ala Met Lys His Thr Ser Leu Pro
                485                 490                 495

Ile Arg His Leu Trp Leu Ser Phe Asp Glu Gly Arg Ser Trp Ser Lys
            500                 505                 510

Tyr Ser Phe Thr Ser Ile Pro Leu Phe Val Asp Gly Val Leu Gly Glu
        515                 520                 525

Pro Gly Glu Glu Thr Leu Ile Met Thr Val Phe Gly His Phe Ser His
530                 535                 540

Arg Ser Glu Trp Gln Leu Val Lys Val Asp Tyr Lys Ser Ile Phe Asp
545                 550                 555                 560

Arg Arg Cys Ala Glu Glu Asp Tyr Arg Pro Trp Gln Leu His Ser Gln
                565                 570                 575

Gly Glu Ala Cys Ile Met Gly Ala Lys Arg Ile Tyr Lys Lys Arg Lys
            580                 585                 590

Ser Glu Arg Lys Cys Met Gln Lys Tyr Ala Gly Ala Met Glu Ser Glu
        595                 600                 605

Pro Cys Val Cys Thr Glu Ala Asp Phe Asp Cys Asp Tyr Gly Tyr Glu
610                 615                 620

Arg His Ser Asn Gly Gln Cys Leu Pro Ala Phe Trp Phe Asn Pro Ser
625                 630                 635                 640

Ser Leu Ser Lys Asp Cys Ser Leu Gly Gln Ser Tyr Leu Asn Ser Ala
                645                 650                 655

Gly Tyr Arg Lys Val Val Ser Asn Asn Cys Thr Asp Gly Val Arg Glu
            660                 665                 670

Gln Tyr Thr Ala Lys Pro Gln Lys Cys Pro Gly Lys Ala Pro Arg Gly
        675                 680                 685

Leu Arg Ile Val Thr Ala Asp Gly Lys Leu Thr Ala Glu Gln Gly His
690                 695                 700

Asn Val Thr Leu Met Val Gln Leu Glu Glu Gly Asp Val Gln Arg Thr
705                 710                 715                 720

Leu Ile Gln Val Asp Phe Gly Asp Gly Ile Ala Val Ser Tyr Val Asn
                725                 730                 735

Leu Ser Ser Met Glu Asp Gly Ile Lys His Val Tyr Gln Asn Val Gly
```

```
                    740                 745                 750
Ile Phe Arg Val Thr Val Gln Val Asp Asn Ser Leu Gly Ser Asp Ser
            755                 760                 765

Ala Val Leu Tyr Leu His Val Thr Cys Pro Leu Glu His Val His Leu
        770                 775                 780

Ser Leu Pro Phe Val Thr Lys Asn Lys Glu Val Asn Ala Thr Ala
785                 790                 795                 800

Val Leu Trp Pro Ser Gln Val Gly Thr Leu Thr Tyr Val Trp Trp Tyr
                805                 810                 815

Gly Asn Asn Thr Glu Pro Leu Ile Thr Leu Glu Gly Ser Ile Ser Phe
            820                 825                 830

Lys Phe Thr Ser Glu Gly Met Asn Thr Ile Thr Val Gln Val Ser Ala
        835                 840                 845

Gly Asn Ala Ile Leu Gln Asp Thr Lys Thr Ile Ala Val Tyr Glu Glu
    850                 855                 860

Phe Arg Ser Leu Arg Leu Ala Phe Ser Pro Asn Leu Asp Asp Tyr Asn
865                 870                 875                 880

Pro Asp Ile Pro Glu Trp Arg Asp Ile Ser Arg Val Ile Lys Lys
                885                 890                 895

Ser Leu Val Glu Ala Thr Gly Ile Pro Ser Gln His Ile Leu Val Ala
            900                 905                 910

Val Leu Pro Gly Leu Pro Thr Ala Ala Glu Leu Phe Val Leu Pro Tyr
        915                 920                 925

Gln Asp Gly Thr Arg Glu Asn Lys Arg Ser Pro Glu Asp Leu Glu Gln
    930                 935                 940

Ile Ser Glu Val Leu Ile His Lys Leu Asn Gln Asn Leu Val His Phe
945                 950                 955                 960

Glu Leu Lys Pro Gly Val Gln Val Leu Val His Ala Ala His Leu Thr
                965                 970                 975

Ala Ala Pro Leu Val Asp Leu Thr Pro Thr His Ser Gly
            980                 985

<210> SEQ ID NO 34
<211> LENGTH: 1361
<212> TYPE: PRT
<213> ORGANISM: Pan troglodytes
<220> FEATURE:
<221> NAME/KEY: MISC_FEATURE
<222> LOCATION: (1)..(1361)
<223> OTHER INFORMATION: preproSorCS1

<400> SEQUENCE: 34

Met Thr Gly Arg Phe Pro Pro Arg Asn Arg Lys Leu Pro Thr His Arg
1               5                   10                  15

Pro Leu Arg Glu Pro Gly Val Asp Arg Pro Arg Gly Gln Gly Ala Arg
            20                  25                  30

Thr Gln Arg Trp Asp Pro Arg Pro Arg Gly Arg Val Gly Gly Gly
        35                  40                  45

Glu Arg Arg Gly Glu Ala Ala Ala Pro Ala Arg Pro Arg Gly Ser
    50                  55                  60

Arg Arg Arg Arg Leu Gln Arg Pro Glu Thr Arg Ala Arg Ala Arg Ser
65                  70                  75                  80

Ala Ser Asp Phe Ser Ser Ala Pro Pro Arg Gly Gly Ser Leu
            85                  90                  95

Arg Pro Asp Pro Arg Ser Ala Gln Ala Gln Pro Gly Arg Ala Ala Ala
            100                 105                 110
```

```
Thr Cys Pro Ala Pro Pro Pro Ala Pro Thr Ala Ala Gln Leu Gly
        115                 120                 125

Trp Ser Trp Gly Pro Glu Arg Arg Pro Pro Thr Ala Ala Ser Ala Glu
        130                 135                 140

Leu Arg Ala Ala Thr Phe Val Leu Gly Pro Leu Ser Pro Leu Leu Phe
145                 150                 155                 160

Ala Pro Ala Met Gly Lys Val Gly Ala Gly Gly Ser Gln Ala Arg
                165                 170                 175

Leu Ser Ala Leu Leu Ala Gly Ala Gly Leu Leu Val Leu Cys Ala Pro
        180                 185                 190

Gly Val Cys Gly Gly Gly Ser Cys Cys Pro Pro His Pro Ser Ser
                195                 200                 205

Ala Pro Arg Ser Ala Ser Thr Pro Arg Gly Phe Ser His Gln Gly Arg
        210                 215                 220

Pro Gly Arg Ala Pro Ala Thr Pro Leu Pro Leu Val Val Arg Pro Leu
225                 230                 235                 240

Phe Ser Val Ala Pro Gly Asp Arg Ala Leu Ser Leu Glu Arg Ala Arg
                245                 250                 255

Gly Thr Gly Ala Ser Met Ala Val Ala Ala Arg Ser Gly Arg Arg Arg
                260                 265                 270

Arg Ser Gly Ala Asp Gln Glu Lys Ala Glu Arg Gly Glu Gly Ala Ser
        275                 280                 285

Arg Ser Pro Arg Gly Val Leu Arg Asp Gly Gly Gln Gln Glu Pro Gly
        290                 295                 300

Thr Leu Glu Arg Asp Pro Asp Lys Ala Thr Arg Phe Arg Met Glu Glu
305                 310                 315                 320

Leu Arg Leu Thr Ser Thr Thr Phe Ala Leu Thr Gly Asp Ser Ala His
                325                 330                 335

Asn Gln Ala Met Val His Trp Ser Gly His Asn Ser Ser Val Ile Leu
                340                 345                 350

Ile Leu Thr Lys Leu Tyr Asp Tyr Asn Leu Gly Ser Ile Thr Glu Ser
        355                 360                 365

Ser Leu Trp Arg Ser Thr Asp Tyr Gly Thr Thr Tyr Glu Lys Leu Asn
        370                 375                 380

Asp Lys Val Gly Leu Lys Thr Ile Leu Ser Tyr Leu Tyr Val Cys Pro
385                 390                 395                 400

Thr Asn Lys Arg Lys Ile Met Leu Leu Thr Asp Pro Glu Ile Glu Ser
                405                 410                 415

Ser Leu Leu Ile Ser Ser Asp Glu Gly Ala Thr Tyr Gln Lys Tyr Arg
                420                 425                 430

Leu Asn Phe Tyr Ile Gln Ser Leu Leu Phe His Pro Lys Gln Glu Asp
                435                 440                 445

Trp Ile Leu Ala Tyr Ser Gln Asp Gln Lys Leu Tyr Ser Ser Ala Glu
        450                 455                 460

Phe Gly Arg Arg Trp Gln Leu Ile Gln Glu Gly Val Val Pro Asn Arg
465                 470                 475                 480

Phe Tyr Trp Ser Val Met Gly Ser Asn Lys Glu Pro Asp Leu Val His
                485                 490                 495

Leu Glu Ala Arg Thr Val Asp Gly His Ser His Tyr Leu Thr Cys Arg
                500                 505                 510

Met Gln Asn Cys Thr Glu Ala Asn Arg Asn Gln Pro Phe Pro Gly Tyr
        515                 520                 525
```

-continued

Ile Asp Pro Asp Ser Leu Ile Val Gln Asp His Tyr Val Phe Val Gln
530                 535                 540

Leu Thr Ser Gly Gly Arg Pro His Tyr Val Ser Tyr Arg Arg Asn
545                 550                 555                 560

Ala Phe Ala Gln Met Lys Leu Pro Lys Tyr Ala Leu Pro Lys Asp Met
                565                 570                 575

His Val Ile Ser Thr Asp Glu Asn Gln Val Phe Ala Ala Val Gln Glu
            580                 585                 590

Trp Asn Gln Asn Asp Thr Tyr Asn Leu Tyr Ile Ser Asp Thr Arg Gly
        595                 600                 605

Val Tyr Phe Thr Leu Ala Leu Glu Asn Val Gln Ser Ser Arg Gly Pro
610                 615                 620

Glu Gly Asn Ile Met Ile Asp Leu Tyr Glu Val Ala Gly Ile Lys Gly
625                 630                 635                 640

Met Phe Leu Ala Asn Lys Lys Ile Asp Asn Gln Val Lys Thr Phe Ile
                645                 650                 655

Thr Tyr Asn Lys Gly Arg Asp Trp Arg Leu Leu Gln Ala Pro Asp Thr
                660                 665                 670

Asp Leu Arg Gly Asp Pro Val His Cys Leu Leu Pro Tyr Cys Ser Leu
            675                 680                 685

His Leu His Leu Lys Val Ser Glu Asn Pro Tyr Thr Ser Gly Ile Ile
690                 695                 700

Ala Ser Lys Asp Thr Ala Pro Ser Ile Ile Val Ala Ser Gly Asn Ile
705                 710                 715                 720

Gly Ser Glu Leu Ser Asp Thr Asp Ile Ser Met Phe Val Ser Ser Asp
                725                 730                 735

Ala Gly Asn Thr Trp Arg Gln Ile Phe Glu Glu His Ser Val Leu
                740                 745                 750

Tyr Leu Asp Gln Gly Gly Val Leu Val Ala Met Lys His Thr Ser Leu
            755                 760                 765

Pro Ile Arg His Leu Trp Leu Ser Phe Asp Glu Gly Arg Ser Trp Ser
770                 775                 780

Lys Tyr Ser Phe Thr Ser Ile Pro Leu Phe Val Asp Gly Val Leu Gly
785                 790                 795                 800

Glu Pro Gly Glu Glu Thr Leu Ile Met Thr Val Phe Gly His Phe Ser
                805                 810                 815

His Arg Ser Glu Trp Gln Leu Val Lys Val Asp Tyr Lys Ser Ile Phe
                820                 825                 830

Asp Arg Arg Cys Ala Glu Glu Asp Tyr Arg Pro Trp Gln Leu His Ser
            835                 840                 845

Gln Gly Glu Ala Cys Ile Met Gly Ala Lys Arg Ile Tyr Lys Lys Arg
850                 855                 860

Lys Ser Glu Arg Lys Cys Met Gln Gly Lys Tyr Ala Gly Ala Met Glu
865                 870                 875                 880

Ser Glu Pro Cys Val Cys Thr Glu Ala Asp Phe Asp Cys Asp Tyr Gly
                885                 890                 895

Tyr Glu Arg His Ser Asn Gly Gln Cys Leu Pro Ala Phe Trp Phe Asn
            900                 905                 910

Pro Ser Ser Leu Ser Lys Asp Cys Ser Leu Gly Gln Ser Tyr Leu Asn
            915                 920                 925

Ser Thr Gly Tyr Arg Lys Val Val Ser Asn Cys Thr Asp Gly Val
930                 935                 940

Arg Glu Gln Tyr Thr Ala Lys Pro Gln Lys Cys Pro Gly Lys Ala Pro

-continued

```
                945                 950                 955                 960
          Arg Gly Leu Arg Ile Val Thr Ala Asp Gly Lys Leu Thr Ala Glu Gln
                          965                 970                 975
          Gly His Asn Val Thr Leu Met Val Gln Leu Glu Glu Gly Asp Val Gln
                          980                 985                 990
          Arg Thr Leu Ile Gln Val Asp Phe Gly Asp Gly Ile Ala Val Ser Tyr
                          995                 1000                1005
          Val Asn Leu Ser Ser Met Glu Asp Gly Ile Lys His Val Tyr Gln
               1010                1015                1020
          Asn Val Gly Ile Phe Arg Val Thr Val Gln Val Asp Asn Ser Leu
               1025                1030                1035
          Gly Ser Asp Ser Ala Val Leu Tyr Leu His Val Thr Cys Pro Leu
               1040                1045                1050
          Glu His Val His Leu Ser Leu Pro Phe Val Thr Thr Lys Asn Lys
               1055                1060                1065
          Glu Val Asn Ala Thr Ala Val Leu Trp Pro Ser Gln Val Gly Thr
               1070                1075                1080
          Leu Thr Tyr Val Trp Trp Tyr Gly Asn Asn Thr Glu Pro Leu Ile
               1085                1090                1095
          Thr Leu Glu Gly Ser Ile Ser Phe Arg Phe Thr Ser Glu Gly Met
               1100                1105                1110
          Asn Thr Ile Thr Val Gln Val Ser Ala Gly Asn Ala Ile Leu Gln
               1115                1120                1125
          Asp Thr Lys Thr Ile Ala Val Tyr Glu Glu Phe Arg Ser Leu Arg
               1130                1135                1140
          Leu Ser Phe Ser Pro Asn Leu Asp Asp Tyr Asn Pro Asp Ile Pro
               1145                1150                1155
          Glu Trp Arg Arg Asp Ile Gly Arg Val Ile Lys Lys Ser Leu Val
               1160                1165                1170
          Glu Ala Thr Gly Val Pro Gly Gln His Ile Leu Val Ala Val Leu
               1175                1180                1185
          Pro Gly Leu Pro Thr Thr Ala Glu Leu Phe Val Leu Pro Tyr Gln
               1190                1195                1200
          Asp Pro Ala Gly Glu Asn Lys Arg Ser Thr Asp Asp Leu Glu Gln
               1205                1210                1215
          Ile Ser Glu Leu Leu Ile His Thr Leu Asn Gln Asn Ser Val His
               1220                1225                1230
          Phe Glu Leu Lys Pro Gly Val Arg Val Leu Val His Ala Ala His
               1235                1240                1245
          Leu Thr Ala Ala Pro Leu Val Asp Leu Thr Pro Thr His Ser Gly
               1250                1255                1260
          Ser Ala Met Leu Met Leu Leu Ser Val Val Phe Val Gly Leu Ala
               1265                1270                1275
          Val Phe Val Ile Tyr Lys Phe Lys Arg Lys Ile Pro Gly Ile Asn
               1280                1285                1290
          Val Tyr Ala Gln Met Gln Asn Glu Lys Glu Gln Glu Met Ile Ser
               1295                1300                1305
          Pro Val Ser His Phe Glu Ser Arg Pro Ser Val Pro Gln Thr Glu
               1310                1315                1320
          Leu Arg Arg Pro Gly Gln Leu Ile Asp Glu Lys Val Glu Ser Gln
               1325                1330                1335
          Leu Ile Gly Ser Ile Ser Ile Val Ala Glu Asn Gln Ser Thr Lys
               1340                1345                1350
```

-continued

```
Glu Ile Pro Thr Tyr Val Asn Val
    1355            1360
```

```
<210> SEQ ID NO 35
<211> LENGTH: 1165
<212> TYPE: PRT
<213> ORGANISM: Pan troglodytes
<220> FEATURE:
<221> NAME/KEY: MISC_FEATURE
<222> LOCATION: (1)..(1165)
<223> OTHER INFORMATION: proSorCS1

<400> SEQUENCE: 35
```

```
Gly Gly Ser Cys Cys Pro Pro His Pro Ser Ser Ala Pro Arg Ser
1               5                   10                  15

Ala Ser Thr Pro Arg Gly Phe Ser His Gln Gly Arg Pro Gly Arg Ala
            20                  25                  30

Pro Ala Thr Pro Leu Pro Leu Val Arg Pro Leu Phe Ser Val Ala
            35                  40                  45

Pro Gly Asp Arg Ala Leu Ser Leu Glu Arg Ala Arg Gly Thr Gly Ala
        50                  55                  60

Ser Met Ala Val Ala Ala Arg Ser Gly Arg Arg Arg Ser Gly Ala
65                  70                  75                  80

Asp Gln Glu Lys Ala Glu Arg Gly Glu Gly Ala Ser Arg Ser Pro Arg
                85                  90                  95

Gly Val Leu Arg Asp Gly Gly Gln Gln Glu Pro Gly Thr Leu Glu Arg
            100                 105                 110

Asp Pro Asp Lys Ala Thr Arg Phe Arg Met Glu Glu Leu Arg Leu Thr
            115                 120                 125

Ser Thr Thr Phe Ala Leu Thr Gly Asp Ser Ala His Asn Gln Ala Met
    130                 135                 140

Val His Trp Ser Gly His Asn Ser Ser Val Ile Leu Ile Leu Thr Lys
145                 150                 155                 160

Leu Tyr Asp Tyr Asn Leu Gly Ser Ile Thr Glu Ser Ser Leu Trp Arg
                165                 170                 175

Ser Thr Asp Tyr Gly Thr Thr Tyr Glu Lys Leu Asn Asp Lys Val Gly
            180                 185                 190

Leu Lys Thr Ile Leu Ser Tyr Leu Tyr Val Cys Pro Thr Asn Lys Arg
        195                 200                 205

Lys Ile Met Leu Leu Thr Asp Pro Glu Ile Glu Ser Ser Leu Leu Ile
    210                 215                 220

Ser Ser Asp Glu Gly Ala Thr Tyr Gln Lys Tyr Arg Leu Asn Phe Tyr
225                 230                 235                 240

Ile Gln Ser Leu Leu Phe His Pro Lys Gln Glu Asp Trp Ile Leu Ala
                245                 250                 255

Tyr Ser Gln Asp Gln Lys Leu Tyr Ser Ser Ala Glu Phe Gly Arg Arg
            260                 265                 270

Trp Gln Leu Ile Gln Glu Gly Val Pro Asn Arg Phe Tyr Trp Ser
        275                 280                 285

Val Met Gly Ser Asn Lys Glu Pro Asp Leu Val His Leu Glu Ala Arg
    290                 295                 300

Thr Val Asp Gly His Ser His Tyr Leu Thr Cys Arg Met Gln Asn Cys
305                 310                 315                 320

Thr Glu Ala Asn Arg Asn Gln Pro Phe Pro Gly Tyr Ile Asp Pro Asp
                325                 330                 335
```

-continued

```
Ser Leu Ile Val Gln Asp His Tyr Val Phe Val Gln Leu Thr Ser Gly
            340                 345                 350

Gly Arg Pro His Tyr Tyr Val Ser Tyr Arg Arg Asn Ala Phe Ala Gln
        355                 360                 365

Met Lys Leu Pro Lys Tyr Ala Leu Pro Lys Asp Met His Val Ile Ser
    370                 375                 380

Thr Asp Glu Asn Gln Val Phe Ala Ala Val Gln Glu Trp Asn Gln Asn
385                 390                 395                 400

Asp Thr Tyr Asn Leu Tyr Ile Ser Asp Thr Arg Gly Val Tyr Phe Thr
                405                 410                 415

Leu Ala Leu Glu Asn Val Gln Ser Ser Arg Gly Pro Glu Gly Asn Ile
            420                 425                 430

Met Ile Asp Leu Tyr Glu Val Ala Gly Ile Lys Gly Met Phe Leu Ala
        435                 440                 445

Asn Lys Lys Ile Asp Asn Gln Val Lys Thr Phe Ile Thr Tyr Asn Lys
    450                 455                 460

Gly Arg Asp Trp Arg Leu Leu Gln Ala Pro Asp Thr Asp Leu Arg Gly
465                 470                 475                 480

Asp Pro Val His Cys Leu Leu Pro Tyr Cys Ser Leu His Leu His Leu
                485                 490                 495

Lys Val Ser Glu Asn Pro Tyr Thr Ser Gly Ile Ile Ala Ser Lys Asp
            500                 505                 510

Thr Ala Pro Ser Ile Ile Val Ala Ser Gly Asn Ile Gly Ser Glu Leu
        515                 520                 525

Ser Asp Thr Asp Ile Ser Met Phe Val Ser Ser Asp Ala Gly Asn Thr
530                 535                 540

Trp Arg Gln Ile Phe Glu Glu His Ser Val Leu Tyr Leu Asp Gln
545                 550                 555                 560

Gly Gly Val Leu Val Ala Met Lys His Thr Ser Leu Pro Ile Arg His
                565                 570                 575

Leu Trp Leu Ser Phe Asp Glu Gly Arg Ser Trp Ser Lys Tyr Ser Phe
            580                 585                 590

Thr Ser Ile Pro Leu Phe Val Asp Gly Val Leu Gly Glu Pro Gly Glu
        595                 600                 605

Glu Thr Leu Ile Met Thr Val Phe Gly His Phe Ser His Arg Ser Glu
    610                 615                 620

Trp Gln Leu Val Lys Val Asp Tyr Lys Ser Ile Phe Asp Arg Arg Cys
625                 630                 635                 640

Ala Glu Glu Asp Tyr Arg Pro Trp Gln Leu His Ser Gln Gly Glu Ala
                645                 650                 655

Cys Ile Met Gly Ala Lys Arg Ile Tyr Lys Lys Arg Lys Ser Glu Arg
            660                 665                 670

Lys Cys Met Gln Gly Lys Tyr Ala Gly Ala Met Glu Ser Glu Pro Cys
        675                 680                 685

Val Cys Thr Glu Ala Asp Phe Asp Cys Asp Tyr Gly Tyr Glu Arg His
    690                 695                 700

Ser Asn Gly Gln Cys Leu Pro Ala Phe Trp Phe Asn Pro Ser Ser Leu
705                 710                 715                 720

Ser Lys Asp Cys Ser Leu Gly Gln Ser Tyr Leu Asn Ser Thr Gly Tyr
                725                 730                 735

Arg Lys Val Val Ser Asn Asn Cys Thr Asp Gly Val Arg Glu Gln Tyr
            740                 745                 750

Thr Ala Lys Pro Gln Lys Cys Pro Gly Lys Ala Pro Arg Gly Leu Arg
```

-continued

```
          755                 760                 765
Ile Val Thr Ala Asp Gly Lys Leu Thr Ala Glu Gln Gly His Asn Val
          770                 775                 780
Thr Leu Met Val Gln Leu Glu Glu Gly Asp Val Gln Arg Thr Leu Ile
785                 790                 795                 800
Gln Val Asp Phe Gly Asp Gly Ile Ala Val Ser Tyr Val Asn Leu Ser
                    805                 810                 815
Ser Met Glu Asp Gly Ile Lys His Val Tyr Gln Asn Val Gly Ile Phe
                    820                 825                 830
Arg Val Thr Val Gln Val Asp Asn Ser Leu Gly Ser Asp Ser Ala Val
                    835                 840                 845
Leu Tyr Leu His Val Thr Cys Pro Leu Glu His Val His Leu Ser Leu
          850                 855                 860
Pro Phe Val Thr Thr Lys Asn Lys Glu Val Asn Ala Thr Ala Val Leu
865                 870                 875                 880
Trp Pro Ser Gln Val Gly Thr Leu Thr Tyr Val Trp Trp Tyr Gly Asn
                    885                 890                 895
Asn Thr Glu Pro Leu Ile Thr Leu Glu Gly Ser Ile Ser Phe Arg Phe
                    900                 905                 910
Thr Ser Glu Gly Met Asn Thr Ile Thr Val Gln Val Ser Ala Gly Asn
                    915                 920                 925
Ala Ile Leu Gln Asp Thr Lys Thr Ile Ala Val Tyr Glu Glu Phe Arg
          930                 935                 940
Ser Leu Arg Leu Ser Phe Ser Pro Asn Leu Asp Asp Tyr Asn Pro Asp
945                 950                 955                 960
Ile Pro Glu Trp Arg Arg Asp Ile Gly Arg Val Ile Lys Lys Ser Leu
                    965                 970                 975
Val Glu Ala Thr Gly Val Pro Gly Gln His Ile Leu Val Ala Val Leu
                    980                 985                 990
Pro Gly Leu Pro Thr Thr Ala Glu Leu Phe Val Leu Pro Tyr Gln Asp
                    995                1000                1005
Pro Ala Gly Glu Asn Lys Arg Ser Thr Asp Asp Leu Glu Gln Ile
          1010                1015                1020
Ser Glu Leu Leu Ile His Thr Leu Asn Gln Asn Ser Val His Phe
          1025                1030                1035
Glu Leu Lys Pro Gly Val Arg Val Leu Val His Ala Ala His Leu
          1040                1045                1050
Thr Ala Ala Pro Leu Val Asp Leu Thr Pro Thr His Ser Gly Ser
          1055                1060                1065
Ala Met Leu Met Leu Leu Ser Val Val Phe Val Gly Leu Ala Val
          1070                1075                1080
Phe Val Ile Tyr Lys Phe Lys Arg Lys Ile Pro Gly Ile Asn Val
          1085                1090                1095
Tyr Ala Gln Met Gln Asn Glu Lys Glu Gln Glu Met Ile Ser Pro
          1100                1105                1110
Val Ser His Phe Glu Ser Arg Pro Ser Val Pro Gln Thr Glu Leu
          1115                1120                1125
Arg Arg Pro Gly Gln Leu Ile Asp Glu Val Glu Ser Gln Leu
          1130                1135                1140
Ile Gly Ser Ile Ser Ile Val Ala Glu Asn Gln Ser Thr Lys Glu
          1145                1150                1155
Ile Pro Thr Tyr Val Asn Val
          1160                1165
```

<210> SEQ ID NO 36
<211> LENGTH: 1088
<212> TYPE: PRT
<213> ORGANISM: Pan troglodytes
<220> FEATURE:
<221> NAME/KEY: MISC_FEATURE
<222> LOCATION: (1)..(1088)
<223> OTHER INFORMATION: mature SorCS1

<400> SEQUENCE: 36

```
Ser Gly Ala Asp Gln Glu Lys Ala Glu Arg Gly Gly Ala Ser Arg
1               5                   10                  15

Ser Pro Arg Gly Val Leu Arg Asp Gly Gln Gln Glu Pro Gly Thr
            20                  25                  30

Leu Glu Arg Asp Pro Asp Lys Ala Thr Arg Phe Arg Met Glu Glu Leu
        35                  40                  45

Arg Leu Thr Ser Thr Thr Phe Ala Leu Thr Gly Asp Ser Ala His Asn
    50                  55                  60

Gln Ala Met Val His Trp Ser Gly His Asn Ser Ser Val Ile Leu Ile
65                  70                  75                  80

Leu Thr Lys Leu Tyr Asp Tyr Asn Leu Gly Ser Ile Thr Glu Ser Ser
                85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
        115                 120                 125

Asn Lys Arg Lys Ile Met Leu Leu Thr Asp Pro Glu Ile Glu Ser Ser
    130                 135                 140

Leu Leu Ile Ser Ser Asp Glu Gly Ala Thr Tyr Gln Lys Tyr Arg Leu
145                 150                 155                 160

Asn Phe Tyr Ile Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Gly Val Val Pro Asn Arg Phe
        195                 200                 205

Tyr Trp Ser Val Met Gly Ser Asn Lys Glu Pro Asp Leu Val His Leu
    210                 215                 220

Glu Ala Arg Thr Val Asp Gly His Ser His Tyr Leu Thr Cys Arg Met
225                 230                 235                 240

Gln Asn Cys Thr Glu Ala Asn Arg Asn Gln Pro Phe Pro Gly Tyr Ile
                245                 250                 255

Asp Pro Asp Ser Leu Ile Val Gln Asp His Tyr Val Phe Val Gln Leu
            260                 265                 270

Thr Ser Gly Gly Arg Pro His Tyr Tyr Val Ser Tyr Arg Arg Asn Ala
        275                 280                 285

Phe Ala Gln Met Lys Leu Pro Lys Tyr Ala Leu Pro Lys Asp Met His
    290                 295                 300

Val Ile Ser Thr Asp Glu Asn Gln Val Phe Ala Ala Val Gln Glu Trp
305                 310                 315                 320

Asn Gln Asn Asp Thr Tyr Asn Leu Tyr Ile Ser Asp Thr Arg Gly Val
                325                 330                 335

Tyr Phe Thr Leu Ala Leu Glu Asn Val Gln Ser Ser Arg Gly Pro Glu
            340                 345                 350
```

-continued

```
Gly Asn Ile Met Ile Asp Leu Tyr Glu Val Ala Gly Ile Lys Gly Met
            355                 360                 365
Phe Leu Ala Asn Lys Lys Ile Asp Asn Gln Val Lys Thr Phe Ile Thr
        370                 375                 380
Tyr Asn Lys Gly Arg Asp Trp Arg Leu Leu Gln Ala Pro Asp Thr Asp
385                 390                 395                 400
Leu Arg Gly Asp Pro Val His Cys Leu Leu Pro Tyr Cys Ser Leu His
                405                 410                 415
Leu His Leu Lys Val Ser Glu Asn Pro Tyr Thr Ser Gly Ile Ile Ala
            420                 425                 430
Ser Lys Asp Thr Ala Pro Ser Ile Ile Val Ala Ser Gly Asn Ile Gly
        435                 440                 445
Ser Glu Leu Ser Asp Thr Asp Ile Ser Met Phe Val Ser Ser Asp Ala
    450                 455                 460
Gly Asn Thr Trp Arg Gln Ile Phe Glu Glu His Ser Val Leu Tyr
465                 470                 475                 480
Leu Asp Gln Gly Gly Val Leu Val Ala Met Lys His Thr Ser Leu Pro
                485                 490                 495
Ile Arg His Leu Trp Leu Ser Phe Asp Glu Gly Arg Ser Trp Ser Lys
            500                 505                 510
Tyr Ser Phe Thr Ser Ile Pro Leu Phe Val Asp Gly Val Leu Gly Glu
        515                 520                 525
Pro Gly Glu Glu Thr Leu Ile Met Thr Val Phe Gly His Phe Ser His
    530                 535                 540
Arg Ser Glu Trp Gln Leu Val Lys Val Asp Tyr Lys Ser Ile Phe Asp
545                 550                 555                 560
Arg Arg Cys Ala Glu Glu Asp Tyr Arg Pro Trp Gln Leu His Ser Gln
                565                 570                 575
Gly Glu Ala Cys Ile Met Gly Ala Lys Arg Ile Tyr Lys Lys Arg Lys
            580                 585                 590
Ser Glu Arg Lys Cys Met Gln Gly Lys Tyr Ala Gly Ala Met Glu Ser
        595                 600                 605
Glu Pro Cys Val Cys Thr Glu Ala Asp Phe Asp Cys Asp Tyr Gly Tyr
    610                 615                 620
Glu Arg His Ser Asn Gly Gln Cys Leu Pro Ala Phe Trp Phe Asn Pro
625                 630                 635                 640
Ser Ser Leu Ser Lys Asp Cys Ser Leu Gly Gln Ser Tyr Leu Asn Ser
                645                 650                 655
Thr Gly Tyr Arg Lys Val Val Ser Asn Asn Cys Thr Asp Gly Val Arg
            660                 665                 670
Glu Gln Tyr Thr Ala Lys Pro Gln Lys Cys Pro Gly Lys Ala Pro Arg
        675                 680                 685
Gly Leu Arg Ile Val Thr Ala Asp Gly Lys Leu Thr Ala Glu Gln Gly
    690                 695                 700
His Asn Val Thr Leu Met Val Gln Leu Glu Gly Asp Val Gln Arg
705                 710                 715                 720
Thr Leu Ile Gln Val Asp Phe Gly Asp Gly Ile Ala Val Ser Tyr Val
                725                 730                 735
Asn Leu Ser Ser Met Glu Asp Gly Ile Lys His Val Tyr Gln Asn Val
            740                 745                 750
Gly Ile Phe Arg Val Thr Val Gln Val Asp Asn Ser Leu Gly Ser Asp
        755                 760                 765
Ser Ala Val Leu Tyr Leu His Val Thr Cys Pro Leu Glu His Val His
```

```
                    770                 775                 780
Leu Ser Leu Pro Phe Val Thr Thr Lys Asn Lys Glu Val Asn Ala Thr
785                 790                 795                 800

Ala Val Leu Trp Pro Ser Gln Val Gly Thr Leu Thr Tyr Val Trp Trp
                    805                 810                 815

Tyr Gly Asn Asn Thr Glu Pro Leu Ile Thr Leu Glu Gly Ser Ile Ser
                820                 825                 830

Phe Arg Phe Thr Ser Glu Gly Met Asn Thr Ile Thr Val Gln Val Ser
            835                 840                 845

Ala Gly Asn Ala Ile Leu Gln Asp Thr Lys Thr Ile Ala Val Tyr Glu
        850                 855                 860

Glu Phe Arg Ser Leu Arg Leu Ser Phe Ser Pro Asn Leu Asp Asp Tyr
865                 870                 875                 880

Asn Pro Asp Ile Pro Glu Trp Arg Arg Asp Ile Gly Arg Val Ile Lys
                    885                 890                 895

Lys Ser Leu Val Glu Ala Thr Gly Val Pro Gly Gln His Ile Leu Val
                900                 905                 910

Ala Val Leu Pro Gly Leu Pro Thr Thr Ala Glu Leu Phe Val Leu Pro
            915                 920                 925

Tyr Gln Asp Pro Ala Gly Glu Asn Lys Arg Ser Thr Asp Asp Leu Glu
        930                 935                 940

Gln Ile Ser Glu Leu Leu Ile His Thr Leu Asn Gln Asn Ser Val His
945                 950                 955                 960

Phe Glu Leu Lys Pro Gly Val Arg Val Leu Val His Ala Ala His Leu
                    965                 970                 975

Thr Ala Ala Pro Leu Val Asp Leu Thr Pro Thr His Ser Gly Ser Ala
                980                 985                 990

Met Leu Met Leu Leu Ser Val Val Phe Val Gly Leu Ala Val Phe Val
            995                 1000                1005

Ile Tyr Lys Phe Lys Arg Lys Ile Pro Gly Ile Asn Val Tyr Ala
        1010                1015                1020

Gln Met Gln Asn Glu Lys Glu Gln Glu Met Ile Ser Pro Val Ser
        1025                1030                1035

His Phe Glu Ser Arg Pro Ser Val Pro Gln Thr Glu Leu Arg Arg
        1040                1045                1050

Pro Gly Gln Leu Ile Asp Glu Lys Val Glu Ser Gln Leu Ile Gly
        1055                1060                1065

Ser Ile Ser Ile Val Ala Glu Asn Gln Ser Thr Lys Glu Ile Pro
        1070                1075                1080

Thr Tyr Val Asn Val
        1085

<210> SEQ ID NO 37
<211> LENGTH: 990
<212> TYPE: PRT
<213> ORGANISM: Pan troglodytes
<220> FEATURE:
<221> NAME/KEY: MISC_FEATURE
<222> LOCATION: (1)..(990)
<223> OTHER INFORMATION: soluble SorCS1

<400> SEQUENCE: 37

Ser Gly Ala Asp Gln Glu Lys Ala Glu Arg Gly Glu Gly Ala Ser Arg
1               5                   10                  15

Ser Pro Arg Gly Val Leu Arg Asp Gly Gly Gln Gln Glu Pro Gly Thr
                20                  25                  30
```

```
Leu Glu Arg Asp Pro Asp Lys Ala Thr Arg Phe Arg Met Glu Glu Leu
            35                  40                  45

Arg Leu Thr Ser Thr Thr Phe Ala Leu Thr Gly Asp Ser Ala His Asn
 50                  55                  60

Gln Ala Met Val His Trp Ser Gly His Asn Ser Ser Val Ile Leu Ile
 65                  70                  75                  80

Leu Thr Lys Leu Tyr Asp Tyr Asn Leu Gly Ser Ile Thr Glu Ser Ser
                 85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
            115                 120                 125

Asn Lys Arg Lys Ile Met Leu Leu Thr Asp Pro Glu Ile Glu Ser Ser
130                 135                 140

Leu Leu Ile Ser Ser Asp Glu Gly Ala Thr Tyr Gln Lys Tyr Arg Leu
145                 150                 155                 160

Asn Phe Tyr Ile Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Gly Val Val Pro Asn Arg Phe
            195                 200                 205

Tyr Trp Ser Val Met Gly Ser Asn Lys Glu Pro Asp Leu Val His Leu
            210                 215                 220

Glu Ala Arg Thr Val Asp Gly His Ser His Tyr Leu Thr Cys Arg Met
225                 230                 235                 240

Gln Asn Cys Thr Glu Ala Asn Arg Asn Gln Pro Phe Pro Gly Tyr Ile
                245                 250                 255

Asp Pro Asp Ser Leu Ile Val Gln Asp His Tyr Val Phe Val Gln Leu
            260                 265                 270

Thr Ser Gly Gly Arg Pro His Tyr Tyr Val Ser Tyr Arg Arg Asn Ala
            275                 280                 285

Phe Ala Gln Met Lys Leu Pro Lys Tyr Ala Leu Pro Lys Asp Met His
            290                 295                 300

Val Ile Ser Thr Asp Glu Asn Gln Val Phe Ala Ala Val Gln Glu Trp
305                 310                 315                 320

Asn Gln Asn Asp Thr Tyr Asn Leu Tyr Ile Ser Asp Thr Arg Gly Val
                325                 330                 335

Tyr Phe Thr Leu Ala Leu Glu Asn Val Gln Ser Ser Arg Gly Pro Glu
            340                 345                 350

Gly Asn Ile Met Ile Asp Leu Tyr Glu Val Ala Gly Ile Lys Gly Met
            355                 360                 365

Phe Leu Ala Asn Lys Lys Ile Asp Asn Gln Val Lys Thr Phe Ile Thr
            370                 375                 380

Tyr Asn Lys Gly Arg Asp Trp Arg Leu Leu Gln Ala Pro Asp Thr Asp
385                 390                 395                 400

Leu Arg Gly Asp Pro Val His Cys Leu Leu Pro Tyr Cys Ser Leu His
                405                 410                 415

Leu His Leu Lys Val Ser Glu Asn Pro Tyr Thr Ser Gly Ile Ile Ala
            420                 425                 430

Ser Lys Asp Thr Ala Pro Ser Ile Ile Val Ala Ser Gly Asn Ile Gly
            435                 440                 445
```

```
Ser Glu Leu Ser Asp Thr Asp Ile Ser Met Phe Val Ser Ser Asp Ala
450                 455                 460

Gly Asn Thr Trp Arg Gln Ile Phe Glu Glu His Ser Val Leu Tyr
465                 470                 475                 480

Leu Asp Gln Gly Gly Val Leu Ala Met Lys His Thr Ser Leu Pro
                485                 490                 495

Ile Arg His Leu Trp Leu Ser Phe Asp Glu Gly Arg Ser Trp Ser Lys
                500                 505                 510

Tyr Ser Phe Thr Ser Ile Pro Leu Phe Val Asp Gly Val Leu Gly Glu
                515                 520                 525

Pro Gly Glu Glu Thr Leu Ile Met Thr Val Phe Gly His Phe Ser His
530                 535                 540

Arg Ser Glu Trp Gln Leu Val Lys Val Asp Tyr Lys Ser Ile Phe Asp
545                 550                 555                 560

Arg Arg Cys Ala Glu Glu Asp Tyr Arg Pro Trp Gln Leu His Ser Gln
                565                 570                 575

Gly Glu Ala Cys Ile Met Gly Ala Lys Arg Ile Tyr Lys Lys Arg Lys
                580                 585                 590

Ser Glu Arg Lys Cys Met Gln Gly Lys Tyr Ala Gly Ala Met Glu Ser
                595                 600                 605

Glu Pro Cys Val Cys Thr Glu Ala Asp Phe Asp Cys Asp Tyr Gly Tyr
610                 615                 620

Glu Arg His Ser Asn Gly Gln Cys Leu Pro Ala Phe Trp Phe Asn Pro
625                 630                 635                 640

Ser Ser Leu Ser Lys Asp Cys Ser Leu Gly Gln Ser Tyr Leu Asn Ser
                645                 650                 655

Thr Gly Tyr Arg Lys Val Val Ser Asn Asn Cys Thr Asp Gly Val Arg
                660                 665                 670

Glu Gln Tyr Thr Ala Lys Pro Gln Lys Cys Pro Gly Lys Ala Pro Arg
                675                 680                 685

Gly Leu Arg Ile Val Thr Ala Asp Gly Lys Leu Thr Ala Glu Gln Gly
                690                 695                 700

His Asn Val Thr Leu Met Val Gln Leu Glu Glu Gly Asp Val Gln Arg
705                 710                 715                 720

Thr Leu Ile Gln Val Asp Phe Gly Asp Gly Ile Ala Val Ser Tyr Val
                725                 730                 735

Asn Leu Ser Ser Met Glu Asp Gly Ile Lys His Val Tyr Gln Asn Val
                740                 745                 750

Gly Ile Phe Arg Val Thr Val Gln Val Asp Asn Ser Leu Gly Ser Asp
                755                 760                 765

Ser Ala Val Leu Tyr Leu His Val Thr Cys Pro Leu Glu His Val His
770                 775                 780

Leu Ser Leu Pro Phe Val Thr Thr Lys Asn Lys Glu Val Asn Ala Thr
785                 790                 795                 800

Ala Val Leu Trp Pro Ser Gln Val Gly Thr Leu Thr Tyr Val Trp Trp
                805                 810                 815

Tyr Gly Asn Asn Thr Glu Pro Leu Ile Thr Leu Glu Gly Ser Ile Ser
                820                 825                 830

Phe Arg Phe Thr Ser Glu Gly Met Asn Thr Ile Thr Val Gln Val Ser
                835                 840                 845

Ala Gly Asn Ala Ile Leu Gln Asp Thr Lys Thr Ile Ala Val Tyr Glu
                850                 855                 860

Glu Phe Arg Ser Leu Arg Leu Ser Phe Ser Pro Asn Leu Asp Asp Tyr
```

```
865                 870                 875                 880
Asn Pro Asp Ile Pro Glu Trp Arg Arg Asp Ile Gly Arg Val Ile Lys
                885                 890                 895

Lys Ser Leu Val Glu Ala Thr Gly Val Pro Gly Gln His Ile Leu Val
            900                 905                 910

Ala Val Leu Pro Gly Leu Pro Thr Thr Ala Glu Leu Phe Val Leu Pro
        915                 920                 925

Tyr Gln Asp Pro Ala Gly Glu Asn Lys Arg Ser Thr Asp Asp Leu Glu
    930                 935                 940

Gln Ile Ser Glu Leu Leu Ile His Thr Leu Asn Gln Asn Ser Val His
945                 950                 955                 960

Phe Glu Leu Lys Pro Gly Val Arg Val Leu Val His Ala Ala His Leu
                965                 970                 975

Thr Ala Ala Pro Leu Val Asp Leu Thr Pro Thr His Ser Gly
            980                 985                 990

<210> SEQ ID NO 38
<211> LENGTH: 997
<212> TYPE: PRT
<213> ORGANISM: Canis lupus familiaris
<220> FEATURE:
<221> NAME/KEY: MISC_FEATURE
<222> LOCATION: (1)..(997)
<223> OTHER INFORMATION: mature SorCS1

<400> SEQUENCE: 38

Met Arg Lys Val Ser Glu Ile Met Val Leu Arg Ser Trp His Ser Val
1               5                   10                  15

Ile Leu Ile Leu Thr Lys Leu Tyr Asp Tyr Asn Leu Gly Ser Ile Thr
                20                  25                  30

Glu Ser Ser Leu Trp Arg Ser Thr Asp Tyr Gly Thr Thr Tyr Glu Lys
            35                  40                  45

Leu Asn Asp Lys Val Gly Leu Lys Thr Ile Leu Ser Tyr Leu Tyr Val
        50                  55                  60

Cys Pro Thr Asn Lys Arg Lys Ile Met Leu Leu Thr Asp Pro Glu Ile
65                  70                  75                  80

Glu Ser Ser Leu Leu Ile Ser Ser Asp Glu Gly Ala Thr Tyr Gln Lys
                85                  90                  95

Tyr Arg Leu Asn Phe Tyr Ile Gln Ser Leu Leu Phe His Pro Lys Gln
            100                 105                 110

Glu Asp Trp Ile Leu Ala Tyr Ser Gln Asp Gln Lys Leu Tyr Ser Ser
        115                 120                 125

Ala Glu Phe Gly Arg Arg Trp Gln Leu Ile Gln Glu Gly Val Val Pro
    130                 135                 140

Asn Arg Phe Tyr Trp Ser Val Met Gly Ser Asn Lys Glu Pro Asp Leu
145                 150                 155                 160

Val His Leu Glu Ala Arg Thr Val Asp Gly His Ser Gln Tyr Leu Thr
                165                 170                 175

Cys Arg Met Gln Asn Cys Thr Glu Ala Asn Arg Asn Lys Pro Phe Pro
            180                 185                 190

Gly Tyr Ile Asp Pro Asp Ser Leu Ile Val Gln Asp Asp Tyr Val Phe
        195                 200                 205

Val Gln Leu Thr Ser Gly Gly Arg Pro His Tyr Tyr Val Ser Tyr Arg
    210                 215                 220

Arg Asn Ala Phe Ala Gln Met Lys Leu Pro Lys Tyr Ala Leu Pro Lys
225                 230                 235                 240
```

```
Asp Met His Val Ile Ser Thr Asp Glu Asn Gln Val Phe Ala Ala Val
                245                 250                 255
Gln Glu Trp Asn Gln Asn Asp Thr Tyr Asn Leu Tyr Ile Ser Asp Thr
                260                 265                 270
Arg Gly Val Tyr Phe Thr Leu Ala Leu Glu Asn Val Gln Ser Ser Arg
                275                 280                 285
Gly Pro Glu Gly Asn Ile Met Ile Asp Leu Tyr Glu Val Ala Gly Ile
290                 295                 300
Lys Gly Met Phe Leu Ala Asn Lys Lys Ile Asp Asn Gln Val Lys Thr
305                 310                 315                 320
Phe Ile Thr Tyr Asn Lys Gly Arg Asp Trp Arg Leu Leu Gln Ala Pro
                325                 330                 335
Asp Thr Asp Leu Arg Gly Asp Pro Val His Cys Leu Leu Pro Tyr Cys
                340                 345                 350
Ser Leu His Leu His Leu Lys Val Ser Glu Asn Pro Tyr Thr Ser Gly
                355                 360                 365
Ile Ile Ala Ser Arg Asp Thr Ala Pro Ser Ile Ile Val Ala Ser Gly
370                 375                 380
Asn Ile Gly Ser Glu Leu Ser Asp Ser Asp Ile Ser Met Phe Val Ser
385                 390                 395                 400
Ser Asp Ala Gly Asn Thr Trp Arg Gln Ile Phe Glu Glu His Ser
                405                 410                 415
Val Leu Tyr Leu Asp Gln Gly Gly Val Leu Val Ala Met Lys His Thr
                420                 425                 430
Ser Leu Pro Ile Arg His Leu Trp Leu Ser Phe Asp Glu Gly Arg Ser
                435                 440                 445
Trp Ser Lys Tyr Ser Phe Thr Ser Ile Pro Leu Phe Val Asp Gly Val
450                 455                 460
Leu Gly Glu Pro Gly Glu Glu Thr Leu Ile Met Thr Val Phe Gly His
465                 470                 475                 480
Phe Ser His Arg Ser Glu Trp Gln Leu Val Lys Val Asp Tyr Lys Ser
                485                 490                 495
Ile Phe Asp Arg Arg Cys Ala Glu Glu Asp Tyr Arg Pro Trp Gln Leu
                500                 505                 510
His Ser Gln Gly Glu Ala Cys Ile Met Gly Ala Lys Arg Ile Tyr Lys
                515                 520                 525
Lys Arg Lys Ser Glu Arg Lys Cys Met Gln Gly Lys Tyr Ala Gly Ala
                530                 535                 540
Met Glu Ser Glu Pro Cys Val Cys Thr Glu Ala Asp Phe Asp Cys Asp
545                 550                 555                 560
Tyr Gly Tyr Glu Arg His Ser Asn Gly Gln Cys Leu Pro Ala Phe Trp
                565                 570                 575
Phe Asn Pro Ser Ser Leu Ser Lys Asp Cys Ser Leu Gly Gln Ser Tyr
                580                 585                 590
Leu Asn Ser Thr Gly Tyr Arg Lys Val Val Ser Asn Asn Cys Thr Asp
                595                 600                 605
Gly Val Arg Glu Gln Tyr Thr Ala Lys Pro Gln Lys Cys Pro Gly Lys
                610                 615                 620
Ala Pro Arg Gly Leu Arg Ile Val Thr Ala Asp Gly Lys Leu Thr Ala
625                 630                 635                 640
Glu Gln Gly His Asn Val Thr Leu Met Val Gln Leu Glu Glu Gly Asp
                645                 650                 655
```

```
Val Gln Arg Thr Leu Ile Gln Val Asp Phe Gly Asp Gly Ile Ala Val
                660                 665                 670

Ser Tyr Val Asn Leu Ser Ser Met Glu Asp Gly Ile Lys His Val Tyr
            675                 680                 685

His Asn Val Gly Ile Phe Arg Val Thr Val Gln Val Asp Asn Ser Leu
        690                 695                 700

Gly Ser Asp Ser Ala Val Leu Tyr Leu His Val Thr Cys Pro Leu Glu
705                 710                 715                 720

His Val His Leu Ser Leu Pro Phe Val Thr Thr Lys Asn Lys Glu Val
                725                 730                 735

Asn Ala Thr Ala Val Leu Trp Pro Ser Gln Val Gly Thr Leu Thr Tyr
            740                 745                 750

Val Trp Trp Tyr Gly Asn Asn Thr Glu Pro Leu Ile Thr Leu Glu Gly
        755                 760                 765

Ser Ile Ser Phe Lys Phe Thr Ser Glu Gly Met Asn Thr Ile Thr Val
770                 775                 780

Gln Val Ser Ala Gly Asn Ala Ile Leu Gln Asp Thr Lys Thr Ile Ala
785                 790                 795                 800

Val Tyr Glu Glu Phe Arg Ser Leu Arg Leu Ser Phe Ser Pro Asn Leu
                805                 810                 815

Asp Asp Tyr Asn Pro Asp Ile Pro Glu Trp Arg Arg Asp Ile Ser Arg
            820                 825                 830

Val Ile Lys Lys Ser Leu Val Glu Ala Thr Gly Val Pro Gly Gln His
        835                 840                 845

Ile Leu Val Ala Val Leu Pro Gly Leu Pro Thr Ala Ala Glu Leu Phe
850                 855                 860

Val Leu Pro Tyr Gln Asp Pro Thr Gly Glu Asn Lys Arg Ser Ala Glu
865                 870                 875                 880

Asp Leu Glu Gln Ile Ser Glu Leu Leu Ile His Lys Leu Asn Gln Asn
                885                 890                 895

Ser Val His Phe Glu Leu Lys Pro Gly Val Gln Ile Leu Val His Ala
            900                 905                 910

Ala His Leu Thr Ala Ala Pro Leu Val Asp Leu Thr Pro Thr His Ser
        915                 920                 925

Gly Ser Ala Met Leu Met Leu Leu Ser Val Val Phe Val Gly Leu Ala
930                 935                 940

Val Phe Val Ile Tyr Lys Phe Lys Arg Arg Val Ala Leu Pro Ser Pro
945                 950                 955                 960

Pro Ser Pro Ser Thr Gln Pro Gly Asp Ser Ser Leu Arg Leu Gln Arg
                965                 970                 975

Ala Arg His Ala Thr Pro Pro Ser Thr Pro Lys Arg Gly Ser Ala Gly
            980                 985                 990

Ala Gln Phe Ala Ile
        995
```

<210> SEQ ID NO 39
<211> LENGTH: 929
<212> TYPE: PRT
<213> ORGANISM: Canis lupus familiaris
<220> FEATURE:
<221> NAME/KEY: MISC_FEATURE
<222> LOCATION: (1)..(929)
<223> OTHER INFORMATION: soluble SorCS1

<400> SEQUENCE: 39

Met Arg Lys Val Ser Glu Ile Met Val Leu Arg Ser Trp His Ser Val

-continued

```
1               5                   10                  15
Ile Leu Ile Leu Thr Lys Leu Tyr Asp Tyr Asn Leu Gly Ser Ile Thr
            20                  25                  30
Glu Ser Ser Leu Trp Arg Ser Thr Asp Tyr Gly Thr Thr Tyr Glu Lys
            35                  40                  45
Leu Asn Asp Lys Val Gly Leu Lys Thr Ile Leu Ser Tyr Leu Tyr Val
 50                  55                  60
Cys Pro Thr Asn Lys Arg Lys Ile Met Leu Leu Thr Asp Pro Glu Ile
 65                  70                  75                  80
Glu Ser Ser Leu Leu Ile Ser Ser Asp Glu Gly Ala Thr Tyr Gln Lys
                85                  90                  95
Tyr Arg Leu Asn Phe Tyr Ile Gln Ser Leu Leu Phe His Pro Lys Gln
                100                 105                 110
Glu Asp Trp Ile Leu Ala Tyr Ser Gln Asp Gln Lys Leu Tyr Ser Ser
            115                 120                 125
Ala Glu Phe Gly Arg Arg Trp Gln Leu Ile Gln Glu Gly Val Val Pro
 130                 135                 140
Asn Arg Phe Tyr Trp Ser Val Met Gly Ser Asn Lys Glu Pro Asp Leu
145                 150                 155                 160
Val His Leu Glu Ala Arg Thr Val Asp Gly His Ser Gln Tyr Leu Thr
                165                 170                 175
Cys Arg Met Gln Asn Cys Thr Glu Ala Asn Arg Asn Lys Pro Phe Pro
                180                 185                 190
Gly Tyr Ile Asp Pro Asp Ser Leu Ile Val Gln Asp Tyr Val Phe
            195                 200                 205
Val Gln Leu Thr Ser Gly Gly Arg Pro His Tyr Tyr Val Ser Tyr Arg
 210                 215                 220
Arg Asn Ala Phe Ala Gln Met Lys Leu Pro Lys Tyr Ala Leu Pro Lys
225                 230                 235                 240
Asp Met His Val Ile Ser Thr Asp Glu Asn Gln Val Phe Ala Ala Val
                245                 250                 255
Gln Glu Trp Asn Gln Asn Asp Thr Tyr Asn Leu Tyr Ile Ser Asp Thr
            260                 265                 270
Arg Gly Val Tyr Phe Thr Leu Ala Leu Glu Asn Val Gln Ser Ser Arg
            275                 280                 285
Gly Pro Glu Gly Asn Ile Met Ile Asp Leu Tyr Glu Val Ala Gly Ile
 290                 295                 300
Lys Gly Met Phe Leu Ala Asn Lys Lys Ile Asp Asn Gln Val Lys Thr
305                 310                 315                 320
Phe Ile Thr Tyr Asn Lys Gly Arg Asp Trp Arg Leu Leu Gln Ala Pro
                325                 330                 335
Asp Thr Asp Leu Arg Gly Asp Pro Val His Cys Leu Leu Pro Tyr Cys
            340                 345                 350
Ser Leu His Leu His Leu Lys Val Ser Glu Asn Pro Tyr Thr Ser Gly
            355                 360                 365
Ile Ile Ala Ser Arg Asp Thr Ala Pro Ser Ile Ile Val Ala Ser Gly
 370                 375                 380
Asn Ile Gly Ser Glu Leu Ser Asp Ser Asp Ile Ser Met Phe Val Ser
385                 390                 395                 400
Ser Asp Ala Gly Asn Thr Trp Arg Gln Ile Phe Glu Glu His Ser
                405                 410                 415
Val Leu Tyr Leu Asp Gln Gly Gly Val Leu Val Ala Met Lys His Thr
            420                 425                 430
```

```
Ser Leu Pro Ile Arg His Leu Trp Leu Ser Phe Asp Glu Gly Arg Ser
        435                 440                 445

Trp Ser Lys Tyr Ser Phe Thr Ser Ile Pro Leu Phe Val Asp Gly Val
450                 455                 460

Leu Gly Glu Pro Gly Glu Glu Thr Leu Ile Met Thr Val Phe Gly His
465                 470                 475                 480

Phe Ser His Arg Ser Glu Trp Gln Leu Val Lys Val Asp Tyr Lys Ser
                485                 490                 495

Ile Phe Asp Arg Arg Cys Ala Glu Asp Tyr Arg Pro Trp Gln Leu
                500                 505                 510

His Ser Gln Gly Glu Ala Cys Ile Met Gly Ala Lys Arg Ile Tyr Lys
        515                 520                 525

Lys Arg Lys Ser Glu Arg Lys Cys Met Gln Gly Lys Tyr Ala Gly Ala
        530                 535                 540

Met Glu Ser Glu Pro Cys Val Cys Thr Glu Ala Asp Phe Asp Cys Asp
545                 550                 555                 560

Tyr Gly Tyr Glu Arg His Ser Asn Gly Gln Cys Leu Pro Ala Phe Trp
                565                 570                 575

Phe Asn Pro Ser Ser Leu Ser Lys Asp Cys Ser Leu Gly Gln Ser Tyr
            580                 585                 590

Leu Asn Ser Thr Gly Tyr Arg Lys Val Val Ser Asn Asn Cys Thr Asp
        595                 600                 605

Gly Val Arg Glu Gln Tyr Thr Ala Lys Pro Gln Lys Cys Pro Gly Lys
        610                 615                 620

Ala Pro Arg Gly Leu Arg Ile Val Thr Ala Asp Gly Lys Leu Thr Ala
625                 630                 635                 640

Glu Gln Gly His Asn Val Thr Leu Met Val Gln Leu Glu Gly Asp
                645                 650                 655

Val Gln Arg Thr Leu Ile Gln Val Asp Phe Gly Asp Gly Ile Ala Val
                660                 665                 670

Ser Tyr Val Asn Leu Ser Ser Met Glu Asp Gly Ile Lys His Val Tyr
        675                 680                 685

His Asn Val Gly Ile Phe Arg Val Thr Val Gln Val Asp Asn Ser Leu
        690                 695                 700

Gly Ser Asp Ser Ala Val Leu Tyr Leu His Val Thr Cys Pro Leu Glu
705                 710                 715                 720

His Val His Leu Ser Leu Pro Phe Val Thr Lys Asn Lys Glu Val
                725                 730                 735

Asn Ala Thr Ala Val Leu Trp Pro Ser Gln Val Gly Thr Leu Thr Tyr
            740                 745                 750

Val Trp Trp Tyr Gly Asn Asn Thr Glu Pro Leu Ile Thr Leu Glu Gly
            755                 760                 765

Ser Ile Ser Phe Lys Phe Thr Ser Glu Gly Met Asn Thr Ile Thr Val
770                 775                 780

Gln Val Ser Ala Gly Asn Ala Ile Leu Gln Asp Thr Lys Thr Ile Ala
785                 790                 795                 800

Val Tyr Glu Glu Phe Arg Ser Leu Arg Leu Ser Phe Ser Pro Asn Leu
                805                 810                 815

Asp Asp Tyr Asn Pro Asp Ile Pro Glu Trp Arg Arg Asp Ile Ser Arg
            820                 825                 830

Val Ile Lys Lys Ser Leu Val Glu Ala Thr Gly Val Pro Gly Gln His
835                 840                 845
```

```
Ile Leu Val Ala Val Leu Pro Gly Leu Pro Thr Ala Ala Glu Leu Phe
            850                 855                 860

Val Leu Pro Tyr Gln Asp Pro Thr Gly Glu Asn Lys Arg Ser Ala Glu
865                 870                 875                 880

Asp Leu Glu Gln Ile Ser Glu Leu Leu Ile His Lys Leu Asn Gln Asn
            885                 890                 895

Ser Val His Phe Glu Leu Lys Pro Gly Val Gln Ile Leu Val His Ala
            900                 905                 910

Ala His Leu Thr Ala Ala Pro Leu Val Asp Leu Thr Pro Thr His Ser
            915                 920                 925

Gly

<210> SEQ ID NO 40
<211> LENGTH: 1196
<212> TYPE: PRT
<213> ORGANISM: Bos taurus
<220> FEATURE:
<221> NAME/KEY: MISC_FEATURE
<222> LOCATION: (1)..(1196)
<223> OTHER INFORMATION: preproSorCS1

<400> SEQUENCE: 40

Met Gly Lys Val Gly Ala Gly Gly Val Ser Pro Ala Gly Leu Ser Ala
1               5                   10                  15

Leu Leu Ala Gly Ala Gly Leu Leu Val Leu Cys Ala Pro Gly Ser Cys
            20                  25                  30

Gly Gly Gly Ser Cys Cys Pro Pro Arg His Pro Ser Ala Ala Pro Arg
            35                  40                  45

Trp Ala Pro Thr Pro Gly Gly Leu Pro His Gln Gly Pro Arg Gly Arg
50                  55                  60

Ala Pro Ala Thr Pro Leu Pro Gln Leu Gly Arg Pro Leu Phe Ala Val
65                  70                  75                  80

Ala Pro Gly Asp Arg Ala Leu Ser Leu Glu Arg Ala Pro Gly Thr Gly
            85                  90                  95

Ala Ser Val Ala Val Ala Pro Arg Ser Gly Arg Lys Arg Arg Ser Gly
            100                 105                 110

Glu Asp Gln Glu Lys Ala Glu Arg Gly Glu Gly Thr Ser Arg Ser Pro
            115                 120                 125

Arg Gly Val Leu Arg Asp Arg Gly Gln Leu Glu Pro Gly Thr Leu Glu
            130                 135                 140

Arg Asp Pro Asp Lys Ala Thr Arg Phe Arg Leu Glu Glu Leu Lys Leu
145                 150                 155                 160

Thr Ser Thr Thr Phe Ala Leu Thr Gly Asp Ser Ala His Asn Gln Ala
            165                 170                 175

Met Val His Trp Ser Gly His Asn Ser Ser Val Ile Leu Ile Leu Thr
            180                 185                 190

Lys Leu Phe Asp Tyr Asn Leu Gly Ser Ile Thr Glu Ser Ser Leu Trp
            195                 200                 205

Arg Ser Thr Asp Tyr Gly Thr Thr Tyr Glu Lys Leu Asn Asp Lys Val
            210                 215                 220

Gly Leu Lys Thr Ile Leu Ser Tyr Leu Tyr Val Cys Pro Thr Asn Lys
225                 230                 235                 240

Arg Lys Ile Met Leu Leu Thr Asp Pro Glu Ile Glu Ser Ser Leu Leu
            245                 250                 255

Ile Ser Ser Asp Glu Gly Ala Thr Tyr Gln Lys Tyr Arg Leu Asn Phe
            260                 265                 270
```

```
Tyr Ile Gln Ser Leu Leu Phe His Pro Lys Gln Glu Asp Trp Ile Leu
            275                 280                 285

Ala Tyr Ser Gln Asp Gln Lys Leu Tyr Ser Ser Ala Glu Phe Gly Arg
    290                 295                 300

Arg Trp Gln Leu Ile Gln Glu Ala Val Val Pro Asn Arg Phe Tyr Trp
305                 310                 315                 320

Ser Val Met Gly Ser Asn Lys Glu Pro Asp Leu Val His Leu Glu Ala
                325                 330                 335

Arg Thr Val Asp Gly His Ser Gln Tyr Leu Thr Cys Arg Met Gln Asn
                340                 345                 350

Cys Thr Glu Ala Asn Arg Asn Lys Pro Phe Pro Gly Tyr Ile Asp Pro
            355                 360                 365

Asp Ser Leu Ile Val Gln Asp Tyr Val Phe Val Gln Leu Thr Ser
            370                 375                 380

Gly Gly Arg Pro His Tyr Tyr Val Ser Tyr Arg Arg Asn Ala Phe Ala
385                 390                 395                 400

Gln Met Lys Leu Pro Lys Tyr Ala Leu Pro Lys Asp Met His Val Ile
                405                 410                 415

Ser Thr Asp Glu Asn Gln Val Phe Ala Ala Val Gln Glu Trp Asn Gln
            420                 425                 430

Asn Asp Thr Tyr Asn Leu Tyr Ile Ser Asp Thr Arg Gly Val Tyr Phe
            435                 440                 445

Thr Leu Ala Leu Glu Asn Val Gln Ser Ser Arg Gly Pro Glu Gly Asn
    450                 455                 460

Val Met Ile Asp Leu Tyr Glu Val Ala Gly Ile Lys Gly Met Phe Leu
465                 470                 475                 480

Ala Asn Lys Lys Ile Asp Asn Gln Val Lys Thr Phe Ile Thr Tyr Asn
                485                 490                 495

Lys Gly Arg Asp Trp Arg Leu Leu Gln Ala Pro Asp Thr Asp Leu Arg
                500                 505                 510

Gly Asp Pro Val His Cys Val Leu Pro Tyr Cys Ser Leu His Leu His
            515                 520                 525

Leu Lys Val Ser Glu Asn Pro Tyr Thr Ser Gly Ile Ile Ala Ser Arg
    530                 535                 540

Asp Thr Ala Pro Ser Ile Ile Val Ala Ser Gly Asn Ile Gly Ser Glu
545                 550                 555                 560

Leu Ser Asp Ser Asp Ile Ser Met Phe Val Ser Ser Asp Ala Gly Asn
                565                 570                 575

Thr Trp Arg Gln Ile Phe Glu Glu His Ser Val Leu Tyr Leu Asp
                580                 585                 590

Gln Gly Gly Val Leu Val Ala Met Lys His Thr Ser Leu Pro Ile Arg
    595                 600                 605

His Leu Trp Leu Ser Phe Asp Glu Gly Arg Ser Trp Ser Lys Tyr Ser
    610                 615                 620

Phe Thr Ser Ile Pro Leu Phe Val Asp Gly Val Leu Gly Glu Pro Gly
625                 630                 635                 640

Glu Glu Thr Leu Ile Met Thr Leu Leu Asp His Ser His Ser Asp Trp
                645                 650                 655

Leu Val Thr Ala Leu Gln Pro Cys Cys Leu Phe Leu Leu Gly Asn Glu
                660                 665                 670

Trp Glu Asp Lys Ile Ala Trp Lys Pro Gln Asp Gln Gly Glu Ala Cys
                675                 680                 685
```

-continued

```
Ile Met Gly Ala Lys Arg Ile Tyr Lys Lys Arg Lys Ser Glu Arg Lys
690                 695                 700
Cys Met Gln Gly Lys Tyr Ala Gly Ala Met Glu Ser Glu Pro Cys Val
705                 710                 715                 720
Cys Thr Glu Ala Asp Phe Asp Cys Asp Tyr Gly Tyr Glu Arg His Ser
                725                 730                 735
Asn Gly Gln Cys Leu Pro Ala Phe Trp Phe Asn Pro Ser Ser Leu Ser
                740                 745                 750
Lys Asp Cys Ser Leu Gly Gln Ser Tyr Leu Asn Ser Thr Gly Tyr Arg
                755                 760                 765
Lys Val Val Ser Asn Asn Cys Thr Asp Gly Val Arg Glu Gln Tyr Thr
770                 775                 780
Ala Lys Pro Gln Lys Cys Pro Gly Lys Ala Pro Arg Gly Leu Arg Ile
785                 790                 795                 800
Val Thr Ala Asp Gly Lys Leu Thr Ala Glu Gln Gly His Asn Val Thr
                805                 810                 815
Leu Met Val Gln Leu Glu Glu Gly Asp Val Gln Arg Thr Leu Ile Gln
                820                 825                 830
Val Asp Phe Gly Asp Gly Ile Ala Val Ser Tyr Val Asn Leu Ser Ser
                835                 840                 845
Met Glu Asp Gly Ile Lys His Val Tyr His Asn Val Gly Ile Phe Arg
850                 855                 860
Val Thr Val Gln Val Asp Asn Ser Leu Gly Ser Asp Ser Ala Val Leu
865                 870                 875                 880
Tyr Leu His Val Thr Cys Pro Leu Glu His Val His Leu Ser Leu Pro
                885                 890                 895
Phe Val Thr Thr Lys Asn Lys Glu Val Asn Ala Thr Ala Val Leu Trp
                900                 905                 910
Pro Ser Gln Val Gly Thr Leu Thr Tyr Val Trp Trp Tyr Gly Asn Asn
                915                 920                 925
Thr Glu Pro Leu Ile Thr Leu Glu Gly Ser Ile Ala Phe Lys Phe Thr
                930                 935                 940
Ser Glu Gly Met Asn Thr Ile Thr Val Gln Val Ser Ala Gly Asn Ala
945                 950                 955                 960
Ile Leu Gln Asp Thr Lys Thr Ile Ala Val Tyr Glu Glu Phe Arg Ser
                965                 970                 975
Leu Arg Leu Ser Phe Ser Pro Asn Leu Asp Asp Tyr Asn Pro Asp Ile
                980                 985                 990
Pro Glu Trp Arg Arg Asp Val Ser Arg Val Ile Lys Lys Ala Leu Val
                995                 1000                1005
Glu Ala Thr Gly Val Pro Gly Gln His Ile Leu Val Ala Val Leu
        1010                1015                1020
Pro Gly Leu Pro Thr Ala Ala Glu Leu Phe Val Leu Pro His Gln
        1025                1030                1035
Asp Pro Thr Gly Glu Asn Lys Arg Pro Ala Glu Asp Leu Glu Gln
        1040                1045                1050
Ile Ser Glu Leu Met Ile His Lys Leu Asn Gln Asn Ser Val His
        1055                1060                1065
Phe Glu Leu Lys Pro Gly Val Gln Val Leu Val His Ala Ala His
        1070                1075                1080
Leu Thr Ala Ala Pro Leu Val Asp Leu Thr Pro Thr His Ser Gly
        1085                1090                1095
Ser Ala Met Leu Met Leu Leu Ser Val Val Phe Val Gly Leu Ala
```

```
                        1100                    1105                    1110
Val Phe Val Ile Tyr Lys Phe Lys Arg Lys Ile Pro Gly Ile Asn
    1115                    1120                    1125

Val Tyr Ala Gln Met Gln Asn Glu Lys Glu Gln Glu Met Val Ser
    1130                    1135                    1140

Arg Val Ser His Pro Glu Ser Arg Pro Tyr Val Pro Gln Thr Glu
    1145                    1150                    1155

Leu Arg Arg Pro Gly Gln Leu Ile Asp Glu Lys Val Glu Ser Gln
    1160                    1165                    1170

Leu Ile Gly Ser Ile Ser Ile Val Ala Glu Asn Gln Ser Thr Lys
    1175                    1180                    1185

Glu Ile Pro Thr Tyr Val Asn Val
    1190                    1195

<210> SEQ ID NO 41
<211> LENGTH: 1163
<212> TYPE: PRT
<213> ORGANISM: Bos taurus
<220> FEATURE:
<221> NAME/KEY: MISC_FEATURE
<222> LOCATION: (1)..(1163)
<223> OTHER INFORMATION: proSorCS1

<400> SEQUENCE: 41

Gly Gly Ser Cys Cys Pro Pro Arg His Pro Ser Ala Ala Pro Arg Trp
1               5                   10                  15

Ala Pro Thr Pro Gly Gly Leu Pro His Gln Gly Pro Arg Gly Arg Ala
            20                  25                  30

Pro Ala Thr Pro Leu Pro Gln Leu Gly Arg Pro Leu Phe Ala Val Ala
        35                  40                  45

Pro Gly Asp Arg Ala Leu Ser Leu Glu Arg Ala Pro Thr Gly Ala
    50                  55                  60

Ser Val Ala Val Ala Pro Arg Ser Gly Arg Lys Arg Ser Gly Glu
65                  70                  75                  80

Asp Gln Glu Lys Ala Glu Arg Gly Glu Gly Thr Ser Arg Ser Pro Arg
                85                  90                  95

Gly Val Leu Arg Asp Arg Gly Gln Leu Glu Pro Gly Thr Leu Glu Arg
            100                 105                 110

Asp Pro Asp Lys Ala Thr Arg Phe Arg Leu Glu Glu Leu Lys Leu Thr
        115                 120                 125

Ser Thr Thr Phe Ala Leu Thr Gly Asp Ser Ala His Asn Gln Ala Met
    130                 135                 140

Val His Trp Ser Gly His Asn Ser Ser Val Ile Leu Ile Leu Thr Lys
145                 150                 155                 160

Leu Phe Asp Tyr Asn Leu Gly Ser Ile Thr Glu Ser Ser Leu Trp Arg
                165                 170                 175

Ser Thr Asp Tyr Gly Thr Thr Tyr Glu Lys Leu Asn Asp Lys Val Gly
            180                 185                 190

Leu Lys Thr Ile Leu Ser Tyr Leu Tyr Val Cys Pro Thr Asn Lys Arg
        195                 200                 205

Lys Ile Met Leu Leu Thr Asp Pro Glu Ile Glu Ser Ser Leu Leu Ile
    210                 215                 220

Ser Ser Asp Glu Gly Ala Thr Tyr Gln Lys Tyr Arg Leu Asn Phe Tyr
225                 230                 235                 240

Ile Gln Ser Leu Leu Phe His Pro Lys Gln Glu Asp Trp Ile Leu Ala
                245                 250                 255
```

```
Tyr Ser Gln Asp Gln Lys Leu Tyr Ser Ala Glu Phe Gly Arg Arg
            260                 265                 270

Trp Gln Leu Ile Gln Glu Ala Val Pro Asn Arg Phe Tyr Trp Ser
            275                 280                 285

Val Met Gly Ser Asn Lys Glu Pro Asp Leu Val His Leu Glu Ala Arg
290                 295                 300

Thr Val Asp Gly His Ser Gln Tyr Leu Thr Cys Arg Met Gln Asn Cys
305                 310                 315                 320

Thr Glu Ala Asn Arg Asn Lys Pro Phe Pro Gly Tyr Ile Asp Pro Asp
                325                 330                 335

Ser Leu Ile Val Gln Asp Tyr Val Phe Val Gln Leu Thr Ser Gly
            340                 345                 350

Gly Arg Pro His Tyr Tyr Val Ser Tyr Arg Arg Asn Ala Phe Ala Gln
                355                 360                 365

Met Lys Leu Pro Lys Tyr Ala Leu Pro Lys Asp Met His Val Ile Ser
            370                 375                 380

Thr Asp Glu Asn Gln Val Phe Ala Ala Val Gln Glu Trp Asn Gln Asn
385                 390                 395                 400

Asp Thr Tyr Asn Leu Tyr Ile Ser Asp Thr Arg Gly Val Tyr Phe Thr
                405                 410                 415

Leu Ala Leu Glu Asn Val Gln Ser Ser Arg Gly Pro Glu Gly Asn Val
            420                 425                 430

Met Ile Asp Leu Tyr Glu Val Ala Gly Ile Lys Gly Met Phe Leu Ala
            435                 440                 445

Asn Lys Lys Ile Asp Asn Gln Val Lys Thr Phe Ile Thr Tyr Asn Lys
            450                 455                 460

Gly Arg Asp Trp Arg Leu Leu Gln Ala Pro Asp Thr Asp Leu Arg Gly
465                 470                 475                 480

Asp Pro Val His Cys Val Leu Pro Tyr Cys Ser Leu His Leu His Leu
                485                 490                 495

Lys Val Ser Glu Asn Pro Tyr Thr Ser Gly Ile Ile Ala Ser Arg Asp
            500                 505                 510

Thr Ala Pro Ser Ile Ile Val Ala Ser Gly Asn Ile Gly Ser Glu Leu
            515                 520                 525

Ser Asp Ser Asp Ile Ser Met Phe Val Ser Ser Asp Ala Gly Asn Thr
530                 535                 540

Trp Arg Gln Ile Phe Glu Glu His Ser Val Leu Tyr Leu Asp Gln
545                 550                 555                 560

Gly Gly Val Leu Val Ala Met Lys His Thr Ser Leu Pro Ile Arg His
                565                 570                 575

Leu Trp Leu Ser Phe Asp Glu Gly Arg Ser Trp Ser Lys Tyr Ser Phe
            580                 585                 590

Thr Ser Ile Pro Leu Phe Val Asp Gly Val Leu Gly Glu Pro Gly Glu
            595                 600                 605

Glu Thr Leu Ile Met Thr Leu Leu Asp His Ser His Ser Asp Trp Leu
            610                 615                 620

Val Thr Ala Leu Gln Pro Cys Cys Leu Phe Leu Leu Gly Asn Glu Trp
625                 630                 635                 640

Glu Asp Lys Ile Ala Trp Lys Pro Gln Asp Gln Gly Glu Ala Cys Ile
                645                 650                 655

Met Gly Ala Lys Arg Ile Tyr Lys Arg Lys Ser Gly Arg Lys Cys
            660                 665                 670
```

```
Met Gln Gly Lys Tyr Ala Gly Ala Met Glu Ser Glu Pro Cys Val Cys
            675                 680                 685

Thr Glu Ala Asp Phe Asp Cys Asp Tyr Gly Tyr Glu Arg His Ser Asn
690                 695                 700

Gly Gln Cys Leu Pro Ala Phe Trp Phe Asn Pro Ser Ser Leu Ser Lys
705                 710                 715                 720

Asp Cys Ser Leu Gly Gln Ser Tyr Leu Asn Ser Thr Gly Tyr Arg Lys
                725                 730                 735

Val Val Ser Asn Asn Cys Thr Asp Val Arg Glu Gln Tyr Thr Ala
            740                 745                 750

Lys Pro Gln Lys Cys Pro Gly Lys Ala Pro Arg Gly Leu Arg Ile Val
            755                 760                 765

Thr Ala Asp Gly Lys Leu Thr Ala Glu Gln Gly His Asn Val Thr Leu
770                 775                 780

Met Val Gln Leu Glu Glu Gly Asp Val Gln Arg Thr Leu Ile Gln Val
785                 790                 795                 800

Asp Phe Gly Asp Gly Ile Ala Val Ser Tyr Val Asn Leu Ser Ser Met
                805                 810                 815

Glu Asp Gly Ile Lys His Val Tyr His Asn Val Gly Ile Phe Arg Val
                820                 825                 830

Thr Val Gln Val Asp Asn Ser Leu Gly Ser Asp Ser Ala Val Leu Tyr
                835                 840                 845

Leu His Val Thr Cys Pro Leu Glu His Val His Leu Ser Leu Pro Phe
850                 855                 860

Val Thr Thr Lys Asn Lys Glu Val Asn Ala Thr Ala Val Leu Trp Pro
865                 870                 875                 880

Ser Gln Val Gly Thr Leu Thr Tyr Val Trp Trp Tyr Gly Asn Asn Thr
                885                 890                 895

Glu Pro Leu Ile Thr Leu Glu Gly Ser Ile Ala Phe Lys Phe Thr Ser
                900                 905                 910

Glu Gly Met Asn Thr Ile Thr Val Gln Val Ser Ala Gly Asn Ala Ile
            915                 920                 925

Leu Gln Asp Thr Lys Thr Ile Ala Val Tyr Glu Glu Phe Arg Ser Leu
930                 935                 940

Arg Leu Ser Phe Ser Pro Asn Leu Asp Asp Tyr Asn Pro Asp Ile Pro
945                 950                 955                 960

Glu Trp Arg Arg Asp Val Ser Arg Val Ile Lys Lys Ala Leu Val Glu
                965                 970                 975

Ala Thr Gly Val Pro Gln His Ile Leu Val Ala Val Leu Pro Gly
            980                 985                 990

Leu Pro Thr Ala Ala Glu Leu Phe Val Leu Pro His Gln Asp Pro Thr
            995                 1000                1005

Gly Glu Asn Lys Arg Pro Ala Glu Asp Leu Glu Gln Ile Ser Glu
    1010                1015                1020

Leu Met Ile His Lys Leu Asn Gln Asn Ser Val His Phe Glu Leu
    1025                1030                1035

Lys Pro Gly Val Gln Val Leu Val His Ala Ala His Leu Thr Ala
    1040                1045                1050

Ala Pro Leu Val Asp Leu Thr Pro Thr His Ser Gly Ser Ala Met
    1055                1060                1065

Leu Met Leu Leu Ser Val Val Phe Val Gly Leu Ala Val Phe Val
    1070                1075                1080

Ile Tyr Lys Phe Lys Arg Lys Ile Pro Gly Ile Asn Val Tyr Ala
```

```
            1085                1090                1095
Gln Met Gln Asn Glu Lys Glu  Gln Glu Met Val Ser Arg Val Ser
    1100                1105                1110

His Pro Glu Ser Arg Pro Tyr Val Pro Gln Thr Glu Leu Arg Arg
    1115                1120                1125

Pro Gly Gln Leu Ile Asp Glu Lys Val Glu Ser Gln Leu Ile Gly
    1130                1135                1140

Ser Ile Ser Ile Val Ala Glu Asn Gln Ser Thr Lys Glu Ile Pro
    1145                1150                1155

Thr Tyr Val Asn Val
    1160

<210> SEQ ID NO 42
<211> LENGTH: 1086
<212> TYPE: PRT
<213> ORGANISM: Bos taurus
<220> FEATURE:
<221> NAME/KEY: MISC_FEATURE
<222> LOCATION: (1)..(1086)
<223> OTHER INFORMATION: mature SorCS1

<400> SEQUENCE: 42

Ser Gly Glu Asp Gln Glu Lys Ala Glu Arg Gly Glu Gly Thr Ser Arg
1               5                   10                  15

Ser Pro Arg Gly Val Leu Arg Asp Arg Gly Gln Leu Glu Pro Gly Thr
            20                  25                  30

Leu Glu Arg Asp Pro Asp Lys Ala Thr Arg Phe Arg Leu Glu Glu Leu
        35                  40                  45

Lys Leu Thr Ser Thr Thr Phe Ala Leu Thr Gly Asp Ser Ala His Asn
 50                  55                  60

Gln Ala Met Val His Trp Ser Gly His Asn Ser Ser Val Ile Leu Ile
65                  70                  75                  80

Leu Thr Lys Leu Phe Asp Tyr Asn Leu Gly Ser Ile Thr Glu Ser Ser
                85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
        115                 120                 125

Asn Lys Arg Lys Ile Met Leu Leu Thr Asp Pro Glu Ile Glu Ser Ser
    130                 135                 140

Leu Leu Ile Ser Ser Asp Glu Gly Ala Thr Tyr Gln Lys Tyr Arg Leu
145                 150                 155                 160

Asn Phe Tyr Ile Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Ala Val Val Pro Asn Arg Phe
        195                 200                 205

Tyr Trp Ser Val Met Gly Ser Asn Lys Glu Pro Asp Leu Val His Leu
    210                 215                 220

Glu Ala Arg Thr Val Asp Gly His Ser Gln Tyr Leu Thr Cys Arg Met
225                 230                 235                 240

Gln Asn Cys Thr Glu Ala Asn Arg Asn Lys Pro Phe Pro Gly Tyr Ile
                245                 250                 255

Asp Pro Asp Ser Leu Ile Val Gln Asp Asp Tyr Val Phe Val Gln Leu
            260                 265                 270
```

-continued

```
Thr Ser Gly Gly Arg Pro His Tyr Tyr Val Ser Tyr Arg Arg Asn Ala
        275                 280                 285
Phe Ala Gln Met Lys Leu Pro Lys Tyr Ala Leu Pro Lys Asp Met His
        290                 295                 300
Val Ile Ser Thr Asp Glu Asn Gln Val Phe Ala Ala Val Gln Glu Trp
305                 310                 315                 320
Asn Gln Asn Asp Thr Tyr Asn Leu Tyr Ile Ser Asp Thr Arg Gly Val
                    325                 330                 335
Tyr Phe Thr Leu Ala Leu Glu Asn Val Gln Ser Ser Arg Gly Pro Glu
                340                 345                 350
Gly Asn Val Met Ile Asp Leu Tyr Glu Val Ala Gly Ile Lys Gly Met
                355                 360                 365
Phe Leu Ala Asn Lys Lys Ile Asp Asn Gln Val Lys Thr Phe Ile Thr
        370                 375                 380
Tyr Asn Lys Gly Arg Asp Trp Arg Leu Leu Gln Ala Pro Asp Thr Asp
385                 390                 395                 400
Leu Arg Gly Asp Pro Val His Cys Val Leu Pro Tyr Cys Ser Leu His
                    405                 410                 415
Leu His Leu Lys Val Ser Glu Asn Pro Tyr Thr Ser Gly Ile Ile Ala
                420                 425                 430
Ser Arg Asp Thr Ala Pro Ser Ile Ile Val Ala Ser Gly Asn Ile Gly
                435                 440                 445
Ser Glu Leu Ser Asp Ser Asp Ile Ser Met Phe Val Ser Ser Asp Ala
        450                 455                 460
Gly Asn Thr Trp Arg Gln Ile Phe Glu Glu His Ser Val Leu Tyr
465                 470                 475                 480
Leu Asp Gln Gly Gly Val Leu Val Ala Met Lys His Thr Ser Leu Pro
                    485                 490                 495
Ile Arg His Leu Trp Leu Ser Phe Asp Glu Gly Arg Ser Trp Ser Lys
                500                 505                 510
Tyr Ser Phe Thr Ser Ile Pro Leu Phe Val Asp Gly Val Leu Gly Glu
        515                 520                 525
Pro Gly Glu Glu Thr Leu Ile Met Thr Leu Leu Asp His Ser His Ser
        530                 535                 540
Asp Trp Leu Val Thr Ala Leu Gln Pro Cys Cys Leu Phe Leu Leu Gly
545                 550                 555                 560
Asn Glu Trp Glu Asp Lys Ile Ala Trp Lys Pro Gln Asp Gln Gly Glu
                    565                 570                 575
Ala Cys Ile Met Gly Ala Lys Arg Ile Tyr Lys Arg Lys Ser Glu
                580                 585                 590
Arg Lys Cys Met Gln Gly Lys Tyr Ala Gly Ala Met Glu Ser Glu Pro
        595                 600                 605
Cys Val Cys Thr Glu Ala Asp Phe Asp Cys Asp Tyr Gly Tyr Glu Arg
        610                 615                 620
His Ser Asn Gly Gln Cys Leu Pro Ala Phe Trp Phe Asn Pro Ser Ser
625                 630                 635                 640
Leu Ser Lys Asp Cys Ser Leu Gly Gln Ser Tyr Leu Asn Ser Thr Gly
                    645                 650                 655
Tyr Arg Lys Val Val Ser Asn Asn Cys Thr Asp Gly Val Arg Glu Gln
                660                 665                 670
Tyr Thr Ala Lys Pro Gln Lys Cys Pro Gly Lys Ala Pro Arg Gly Leu
                675                 680                 685
```

-continued

```
Arg Ile Val Thr Ala Asp Gly Lys Leu Thr Ala Glu Gln Gly His Asn
    690                 695                 700

Val Thr Leu Met Val Gln Leu Glu Glu Gly Asp Val Gln Arg Thr Leu
705                 710                 715                 720

Ile Gln Val Asp Phe Gly Asp Gly Ile Ala Val Ser Tyr Val Asn Leu
                725                 730                 735

Ser Ser Met Glu Asp Gly Ile Lys His Val Tyr His Asn Val Gly Ile
            740                 745                 750

Phe Arg Val Thr Val Gln Val Asp Asn Ser Leu Gly Ser Asp Ser Ala
        755                 760                 765

Val Leu Tyr Leu His Val Thr Cys Pro Leu Glu His Val His Leu Ser
770                 775                 780

Leu Pro Phe Val Thr Thr Lys Asn Lys Glu Val Asn Ala Thr Ala Val
785                 790                 795                 800

Leu Trp Pro Ser Gln Val Gly Thr Leu Thr Tyr Val Trp Trp Tyr Gly
                805                 810                 815

Asn Asn Thr Glu Pro Leu Ile Thr Leu Glu Gly Ser Ile Ala Phe Lys
            820                 825                 830

Phe Thr Ser Glu Gly Met Asn Thr Ile Thr Val Gln Val Ser Ala Gly
        835                 840                 845

Asn Ala Ile Leu Gln Asp Thr Lys Thr Ile Ala Val Tyr Glu Glu Phe
850                 855                 860

Arg Ser Leu Arg Leu Ser Phe Ser Pro Asn Leu Asp Asp Tyr Asn Pro
865                 870                 875                 880

Asp Ile Pro Glu Trp Arg Arg Asp Val Ser Arg Val Ile Lys Lys Ala
                885                 890                 895

Leu Val Glu Ala Thr Gly Val Pro Gly Gln His Ile Leu Val Ala Val
            900                 905                 910

Leu Pro Gly Leu Pro Thr Ala Ala Glu Leu Phe Val Leu Pro His Gln
        915                 920                 925

Asp Pro Thr Gly Glu Asn Lys Arg Pro Ala Glu Asp Leu Glu Gln Ile
930                 935                 940

Ser Glu Leu Met Ile His Lys Leu Asn Gln Asn Ser Val His Phe Glu
945                 950                 955                 960

Leu Lys Pro Gly Val Gln Val Leu Val His Ala His Leu Thr Ala
                965                 970                 975

Ala Pro Leu Val Asp Leu Thr Pro Thr His Ser Gly Ser Ala Met Leu
            980                 985                 990

Met Leu Leu Ser Val Val Phe Val Gly Leu Ala Val Phe Val Ile Tyr
        995                 1000                1005

Lys Phe Lys Arg Lys Ile Pro Gly Ile Asn Val Tyr Ala Gln Met
    1010                1015                1020

Gln Asn Glu Lys Glu Gln Glu Met Val Ser Arg Val Ser His Pro
    1025                1030                1035

Glu Ser Arg Pro Tyr Val Pro Gln Thr Glu Leu Arg Arg Pro Gly
    1040                1045                1050

Gln Leu Ile Asp Glu Lys Val Glu Ser Gln Leu Ile Gly Ser Ile
    1055                1060                1065

Ser Ile Val Ala Glu Asn Gln Ser Thr Lys Glu Ile Pro Thr Tyr
    1070                1075                1080

Val Asn Val
    1085
```

<210> SEQ ID NO 43
<211> LENGTH: 988
<212> TYPE: PRT
<213> ORGANISM: Bos taurus
<220> FEATURE:
<221> NAME/KEY: MISC_FEATURE
<222> LOCATION: (1)..(988)
<223> OTHER INFORMATION: soluble SorCS1

<400> SEQUENCE: 43

```
Ser Gly Glu Asp Gln Glu Lys Ala Glu Arg Gly Glu Gly Thr Ser Arg
  1               5                  10                  15

Ser Pro Arg Gly Val Leu Arg Asp Arg Gly Gln Leu Glu Pro Gly Thr
             20                  25                  30

Leu Glu Arg Asp Pro Asp Lys Ala Thr Arg Phe Arg Leu Glu Glu Leu
         35                  40                  45

Lys Leu Thr Ser Thr Thr Phe Ala Leu Thr Gly Asp Ser Ala His Asn
 50                  55                  60

Gln Ala Met Val His Trp Ser Gly His Asn Ser Ser Val Ile Leu Ile
 65                  70                  75                  80

Leu Thr Lys Leu Phe Asp Tyr Asn Leu Gly Ser Ile Thr Glu Ser Ser
                 85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
        115                 120                 125

Asn Lys Arg Lys Ile Met Leu Leu Thr Asp Pro Glu Ile Glu Ser Ser
130                 135                 140

Leu Leu Ile Ser Ser Asp Glu Gly Ala Thr Tyr Gln Lys Tyr Arg Leu
145                 150                 155                 160

Asn Phe Tyr Ile Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Ala Val Val Pro Asn Arg Phe
        195                 200                 205

Tyr Trp Ser Val Met Gly Ser Asn Lys Glu Pro Asp Leu Val His Leu
210                 215                 220

Glu Ala Arg Thr Val Asp Gly His Ser Gln Tyr Leu Thr Cys Arg Met
225                 230                 235                 240

Gln Asn Cys Thr Glu Ala Asn Arg Asn Lys Pro Phe Pro Gly Tyr Ile
                245                 250                 255

Asp Pro Asp Ser Leu Ile Val Gln Asp Tyr Val Phe Val Gln Leu
            260                 265                 270

Thr Ser Gly Gly Arg Pro His Tyr Tyr Val Ser Tyr Arg Arg Asn Ala
        275                 280                 285

Phe Ala Gln Met Lys Leu Pro Lys Tyr Ala Leu Pro Lys Asp Met His
290                 295                 300

Val Ile Ser Thr Asp Glu Asn Gln Val Phe Ala Ala Val Gln Glu Trp
305                 310                 315                 320

Asn Gln Asn Asp Thr Tyr Asn Leu Tyr Ile Ser Asp Thr Arg Gly Val
                325                 330                 335

Tyr Phe Thr Leu Ala Leu Glu Asn Val Gln Ser Ser Arg Gly Pro Glu
            340                 345                 350

Gly Asn Val Met Ile Asp Leu Tyr Glu Val Ala Gly Ile Lys Gly Met
        355                 360                 365
```

Phe Leu Ala Asn Lys Lys Ile Asp Asn Gln Val Lys Thr Phe Ile Thr
    370                 375                 380

Tyr Asn Lys Gly Arg Asp Trp Arg Leu Leu Gln Ala Pro Asp Thr Asp
385                 390                 395                 400

Leu Arg Gly Asp Pro Val His Cys Val Leu Pro Tyr Cys Ser Leu His
            405                 410                 415

Leu His Leu Lys Val Ser Glu Asn Pro Tyr Thr Ser Gly Ile Ile Ala
            420                 425                 430

Ser Arg Asp Thr Ala Pro Ser Ile Val Ala Ser Gly Asn Ile Gly
            435                 440                 445

Ser Glu Leu Ser Asp Ser Asp Ile Ser Met Phe Val Ser Ser Asp Ala
    450                 455                 460

Gly Asn Thr Trp Arg Gln Ile Phe Glu Glu His Ser Val Leu Tyr
465                 470                 475                 480

Leu Asp Gln Gly Gly Val Leu Val Ala Met Lys His Thr Ser Leu Pro
            485                 490                 495

Ile Arg His Leu Trp Leu Ser Phe Asp Glu Gly Arg Ser Trp Ser Lys
            500                 505                 510

Tyr Ser Phe Thr Ser Ile Pro Leu Phe Val Asp Gly Val Leu Gly Glu
    515                 520                 525

Pro Gly Glu Glu Thr Leu Ile Met Thr Leu Leu Asp His Ser His Ser
530                 535                 540

Asp Trp Leu Val Thr Ala Leu Gln Pro Cys Cys Leu Phe Leu Leu Gly
545                 550                 555                 560

Asn Glu Trp Glu Asp Lys Ile Ala Trp Lys Pro Gln Asp Gln Gly Glu
            565                 570                 575

Ala Cys Ile Met Gly Ala Lys Arg Ile Tyr Lys Lys Arg Lys Ser Glu
            580                 585                 590

Arg Lys Cys Met Gln Gly Lys Tyr Ala Gly Ala Met Glu Ser Glu Pro
            595                 600                 605

Cys Val Cys Thr Glu Ala Asp Phe Asp Cys Asp Tyr Gly Tyr Glu Arg
    610                 615                 620

His Ser Asn Gly Gln Cys Leu Pro Ala Phe Trp Phe Asn Pro Ser Ser
625                 630                 635                 640

Leu Ser Lys Asp Cys Ser Leu Gly Gln Ser Tyr Leu Asn Ser Thr Gly
            645                 650                 655

Tyr Arg Lys Val Val Ser Asn Asn Cys Thr Asp Gly Val Arg Glu Gln
            660                 665                 670

Tyr Thr Ala Lys Pro Gln Lys Cys Pro Gly Lys Ala Pro Arg Gly Leu
    675                 680                 685

Arg Ile Val Thr Ala Asp Gly Lys Leu Thr Ala Glu Gln Gly His Asn
690                 695                 700

Val Thr Leu Met Val Gln Leu Glu Glu Gly Asp Val Gln Arg Thr Leu
705                 710                 715                 720

Ile Gln Val Asp Phe Gly Asp Gly Ile Ala Val Ser Tyr Val Asn Leu
            725                 730                 735

Ser Ser Met Glu Asp Gly Ile Lys His Val Tyr His Asn Val Gly Ile
            740                 745                 750

Phe Arg Val Thr Val Gln Val Asp Asn Ser Leu Gly Ser Asp Ser Ala
    755                 760                 765

Val Leu Tyr Leu His Val Thr Cys Pro Leu Glu His Val His Leu Ser
770                 775                 780

-continued

```
Leu Pro Phe Val Thr Thr Lys Asn Lys Glu Val Asn Ala Thr Ala Val
785                 790                 795                 800

Leu Trp Pro Ser Gln Val Gly Thr Leu Thr Tyr Val Trp Trp Tyr Gly
            805                 810                 815

Asn Asn Thr Glu Pro Leu Ile Thr Leu Glu Gly Ser Ile Ala Phe Lys
            820                 825                 830

Phe Thr Ser Glu Gly Met Asn Thr Ile Thr Val Gln Val Ser Ala Gly
            835                 840                 845

Asn Ala Ile Leu Gln Asp Thr Lys Thr Ile Ala Val Tyr Glu Glu Phe
850                 855                 860

Arg Ser Leu Arg Leu Ser Phe Ser Pro Asn Leu Asp Asp Tyr Asn Pro
865                 870                 875                 880

Asp Ile Pro Glu Trp Arg Arg Asp Val Ser Arg Val Ile Lys Lys Ala
            885                 890                 895

Leu Val Glu Ala Thr Gly Val Pro Gly Gln His Ile Leu Val Ala Val
            900                 905                 910

Leu Pro Gly Leu Pro Thr Ala Ala Glu Leu Phe Val Leu Pro His Gln
            915                 920                 925

Asp Pro Thr Gly Glu Asn Lys Arg Pro Ala Glu Asp Leu Glu Gln Ile
930                 935                 940

Ser Glu Leu Met Ile His Lys Leu Asn Gln Asn Ser Val His Phe Glu
945                 950                 955                 960

Leu Lys Pro Gly Val Gln Val Leu Val His Ala Ala His Leu Thr Ala
            965                 970                 975

Ala Pro Leu Val Asp Leu Thr Pro Thr His Ser Gly
            980                 985

<210> SEQ ID NO 44
<211> LENGTH: 1369
<212> TYPE: PRT
<213> ORGANISM: Rattus norvegicus
<220> FEATURE:
<221> NAME/KEY: MISC_FEATURE
<222> LOCATION: (1)..(1369)
<223> OTHER INFORMATION: preproSorCS1

<400> SEQUENCE: 44

Met Arg Ala Gln Val Phe Leu Gln Gln Ser Gly Leu Ser Glu Lys Lys
1               5                   10                  15

His Thr Asp Gly Ile Pro Thr Val Pro Ser Ile Asn Val Ile Pro Glu
            20                  25                  30

Arg Ser Lys Glu Leu Leu Val Pro Arg Gly Arg Val Leu Trp Leu Leu
        35                  40                  45

Ala Gly Thr Leu Arg Ser Leu Gly Arg Val Gly Asp Ser Thr Ala Arg
    50                  55                  60

Ala Arg Leu Pro Val His Ser Ala Ala Arg Arg Asp Ala Ala Pro
65                  70                  75                  80

Gly Ala Leu Ala Glu Pro Ala Leu Pro Pro Ala Ser Pro Arg Arg Arg
            85                  90                  95

Arg Arg Arg Trp Leu Ala Ala Pro Ser Gln Pro Ala Arg Ser Ser Gln
            100                 105                 110

Ala Gln Pro Gly Arg Ala Ala Gly Thr Cys Pro Ala Pro Pro Arg
        115                 120                 125

Ala Pro Pro Pro Asn Leu Asp Gly Val Val Leu Ser Ala His
    130                 135                 140

Pro Ala Ala Val Ser Pro Val Pro Arg Ser Ala Ala Cys Leu Arg Phe
```

```
      145                 150                 155                 160
Gly Thr Pro Ser Pro Leu Leu Ser Ala Pro Glu Met Gly Lys Val Gly
                165                 170                 175

Ala Gly Asp Gly Ser Ser Ala Ala Leu Ser Ala Leu Leu Thr Gly Ala
                180                 185                 190

Gly Leu Leu Met Leu Leu Ala Pro Gly Ile Cys Ser Ser Leu Ser Cys
            195                 200                 205

Cys Pro Pro Gln His Pro Ser Ser Thr Pro Arg Trp Thr Leu Thr Pro
        210                 215                 220

Arg Gly Phe Ser Tyr Pro Gly Pro Leu Gly Arg Ala Pro Ala Thr Pro
225                 230                 235                 240

Pro Pro Leu Phe Met Arg Pro Leu Phe Ala Val Ala Pro Gly Asp Arg
                245                 250                 255

Ala Leu Phe Leu Glu Arg Ala Gly Gly Ser Arg Val Ser Val Ala Thr
                260                 265                 270

Ala Ser Arg Ser Gly Arg Arg Arg Ser Gly Met Asp Pro Glu Lys
            275                 280                 285

Thr Glu Pro Gly Glu Gly Thr Ser Arg Ser Arg Arg Asp Met Leu Arg
        290                 295                 300

Asp Gly Gly Gln Gln Gly Pro Gly Thr Gly Ala Arg Asp Pro Asp Lys
305                 310                 315                 320

Ala Thr Arg Phe Arg Met Glu Glu Leu Arg Leu Thr Ser Thr Thr Phe
                325                 330                 335

Ala Leu Thr Gly Asp Ser Ala His Asn Gln Ala Met Val His Trp Ser
                340                 345                 350

Gly His Asn Ser Ser Val Ile Leu Ile Leu Thr Lys Leu Tyr Asp Tyr
            355                 360                 365

Asn Leu Gly Ser Ile Thr Glu Ser Ser Leu Trp Arg Ser Thr Asp Tyr
        370                 375                 380

Gly Thr Thr Tyr Glu Lys Leu Asn Asp Lys Val Gly Leu Lys Thr Ile
385                 390                 395                 400

Leu Ser Tyr Leu Tyr Val Cys Pro Thr Asn Lys Arg Lys Ile Met Leu
                405                 410                 415

Leu Thr Asp Pro Glu Ile Glu Ser Ser Leu Leu Ile Ser Ser Asp Glu
                420                 425                 430

Gly Ala Thr Tyr Gln Lys Tyr Arg Leu Asn Phe Tyr Ile Gln Ser Leu
            435                 440                 445

Leu Phe His Pro Lys Gln Glu Asp Trp Ile Leu Ala Tyr Ser Gln Asp
        450                 455                 460

Gln Lys Leu Tyr Ser Ser Ala Glu Phe Gly Arg Arg Trp Gln Leu Ile
465                 470                 475                 480

Gln Glu Ala Val Val Pro Asn Arg Phe Tyr Trp Ser Val Leu Gly Ser
                485                 490                 495

Asn Lys Glu Pro Asp Leu Val His Leu Glu Ala Arg Thr Val Asp Gly
            500                 505                 510

His Ser Ile Tyr Leu Thr Cys Arg Met Gln Asn Cys Thr Glu Ala Asn
        515                 520                 525

Arg Asn Lys Pro Phe Pro Gly Tyr Ile Asp Pro Asp Ser Leu Ile Val
530                 535                 540

Gln Asp Asp Tyr Val Phe Val Gln Leu Thr Ser Gly Gly Arg Pro His
                545 (should be 550)

Tyr Tyr Val Ser Tyr Arg Arg Asn Pro Phe Ala Gln Met Lys Leu Pro
                565                 570                 575
```

-continued

```
Lys Tyr Ala Leu Pro Lys Asp Met His Val Ile Ser Thr Asp Glu Asn
            580                 585                 590

Gln Val Phe Ala Ala Val Gln Glu Trp Asn Gln Asn Asp Thr Tyr Asn
        595                 600                 605

Leu Tyr Ile Ser Asp Thr Arg Gly Val Tyr Phe Thr Leu Ala Leu Glu
    610                 615                 620

Asn Val Gln Ser Ser Arg Gly Pro Glu Gly Asn Val Met Ile Asp Leu
625                 630                 635                 640

Tyr Glu Val Ala Gly Ile Lys Gly Met Phe Leu Ala Asn Lys Lys Ile
            645                 650                 655

Asp Asn Gln Val Lys Thr Phe Ile Thr Tyr Asn Lys Gly Arg Asp Trp
        660                 665                 670

Arg Leu Leu Gln Ala Pro Asp Ala Asp Leu Arg Gly Asp Pro Val His
    675                 680                 685

Cys Leu Leu Pro Tyr Cys Ser Leu His Leu His Leu Lys Val Ser Glu
690                 695                 700

Asn Pro Tyr Thr Ser Gly Ile Ile Ala Ser Arg Asp Thr Ala Pro Ser
705                 710                 715                 720

Ile Ile Val Ala Ser Gly Asn Ile Gly Ser Glu Leu Ser Asp Ser Asp
            725                 730                 735

Ile Ser Met Phe Val Ser Ser Asp Ala Gly Asn Thr Trp Arg Gln Ile
        740                 745                 750

Phe Glu Glu Glu His Ser Ile Leu Tyr Leu Asp Gln Gly Gly Val Leu
    755                 760                 765

Val Ala Met Lys His Thr Ser Leu Pro Ile Arg His Leu Trp Leu Ser
770                 775                 780

Phe Asp Glu Gly Arg Ser Trp Ser Lys Tyr Ser Phe Thr Ser Ile Pro
785                 790                 795                 800

Leu Phe Val Asp Gly Val Leu Gly Glu Pro Gly Glu Glu Thr Leu Ile
            805                 810                 815

Met Thr Val Phe Gly His Phe Ser His Arg Ser Glu Trp Gln Leu Val
        820                 825                 830

Lys Val Asp Tyr Lys Ser Ile Phe Asp Arg Arg Cys Ala Glu Glu Asp
    835                 840                 845

Tyr Arg Pro Trp Gln Leu His Ser Gln Gly Glu Ala Cys Ile Met Gly
850                 855                 860

Ala Lys Arg Ile Tyr Lys Lys Arg Lys Ser Glu Arg Lys Cys Met Gln
865                 870                 875                 880

Gly Thr Tyr Ala Gly Ala Met Glu Ser Glu Pro Cys Val Cys Thr Glu
            885                 890                 895

Ala Asp Phe Asp Cys Asp Tyr Gly Tyr Glu Arg His Ser Ser Gly Gln
        900                 905                 910

Cys Leu Pro Ala Phe Trp Phe Asn Pro Ser Ser Leu Ser Lys Asp Cys
    915                 920                 925

Ser Leu Gly Gln Ser Tyr Leu Asn Ser Thr Gly Tyr Arg Lys Val Val
930                 935                 940

Ser Asn Asn Cys Thr Asp Gly Val Arg Glu Gln Tyr Thr Ala Lys Pro
945                 950                 955                 960

Gln Lys Cys Pro Gly Lys Ala Pro Arg Gly Leu Arg Ile Val Thr Ala
            965                 970                 975

Asp Gly Lys Leu Thr Ala Glu Gln Gly His Asn Val Thr Leu Met Val
        980                 985                 990
```

```
Gln Leu Glu Glu Gly Asp Val Gln Arg Thr Leu Ile Gln Val Asp Phe
            995                 1000                1005

Gly Asp Gly Ile Ala Val Ser Tyr Val Asn Leu Ser Ser Met Glu
   1010                1015                1020

Asp Gly Ile Lys His Val Tyr Gln Asn Val Gly Ile Phe Arg Val
   1025                1030                1035

Thr Val Gln Val Asp Asn Ser Leu Gly Ser Asp Ser Ala Val Leu
   1040                1045                1050

Tyr Leu His Val Thr Cys Pro Leu Glu His Val His Leu Ser Leu
   1055                1060                1065

Pro Phe Val Thr Thr Lys Asn Lys Glu Val Asn Ala Thr Ala Val
   1070                1075                1080

Leu Trp Pro Ser Gln Val Gly Thr Leu Thr Tyr Val Trp Trp Tyr
   1085                1090                1095

Gly Asn Asn Thr Glu Pro Leu Ile Thr Leu Glu Gly Ser Ile Ser
   1100                1105                1110

Phe Lys Phe Thr Ser Glu Gly Met Asn Thr Ile Thr Val Gln Val
   1115                1120                1125

Ser Ala Gly Asn Ala Ile Leu Gln Asp Thr Lys Thr Ile Ala Val
   1130                1135                1140

Tyr Glu Glu Phe Arg Ser Leu Arg Leu Ala Phe Ser Pro Asn Leu
   1145                1150                1155

Asp Asp Tyr Asn Pro Asp Ile Pro Glu Trp Arg Arg Asp Ile Ser
   1160                1165                1170

Arg Val Ile Lys Lys Ser Leu Val Glu Ala Thr Gly Ile Pro Ser
   1175                1180                1185

Gln His Ile Leu Val Ala Val Leu Pro Gly Leu Pro Thr Ala Ala
   1190                1195                1200

Glu Leu Phe Val Leu Pro Tyr Gln Asp Gly Ala Arg Glu Asn Lys
   1205                1210                1215

Arg Ser Pro Glu Asp Leu Gln Ile Ser Glu Val Leu Ile His
   1220                1225                1230

Lys Leu Asn Gln Asn Leu Val His Phe Glu Leu Lys Pro Gly Val
   1235                1240                1245

Gln Val Leu Val His Ala Ala His Leu Thr Ala Ala Pro Leu Val
   1250                1255                1260

Asp Leu Thr Pro Thr His Ser Gly Ser Ala Met Leu Met Leu Leu
   1265                1270                1275

Ser Val Val Phe Val Gly Leu Ala Val Phe Val Ile Tyr Lys Phe
   1280                1285                1290

Lys Arg Lys Ile Pro Gly Ile Asn Val Tyr Ala Gln Met Gln Asn
   1295                1300                1305

Glu Lys Glu Gln Glu Leu Ile Asn Pro Val Ser His Thr Glu Ser
   1310                1315                1320

Arg Pro Thr Ala Pro His Pro Asp Leu Arg Arg Pro Gly Gln Leu
   1325                1330                1335

Val Asp Glu Lys Val Glu Ser His Leu Leu Gly Ser Ile Ser Ile
   1340                1345                1350

Val Ala Glu Asn Gln Ser Thr Lys Glu Ile Pro Thr Tyr Val Asn
   1355                1360                1365

Val

<210> SEQ ID NO 45
```

```
<211> LENGTH: 1165
<212> TYPE: PRT
<213> ORGANISM: Rattus norvegicus
<220> FEATURE:
<221> NAME/KEY: MISC_FEATURE
<222> LOCATION: (1)..(1165)
<223> OTHER INFORMATION: proSorCS1

<400> SEQUENCE: 45
```

| Ser | Leu | Ser | Cys | Cys | Pro | Pro | Gln | His | Pro | Ser | Thr | Pro | Arg | Trp |
|---|---|---|---|---|---|---|---|---|---|---|---|---|---|---|
| 1 | | | | 5 | | | | | 10 | | | | | 15 |

| Thr | Leu | Thr | Pro | Arg | Gly | Phe | Ser | Tyr | Pro | Gly | Pro | Leu | Gly | Arg | Ala |
|---|---|---|---|---|---|---|---|---|---|---|---|---|---|---|---|
| | | | | 20 | | | | 25 | | | | | 30 | | |

| Pro | Ala | Thr | Pro | Pro | Leu | Phe | Met | Arg | Pro | Leu | Phe | Ala | Val | Ala |
|---|---|---|---|---|---|---|---|---|---|---|---|---|---|---|
| | | | 35 | | | | | 40 | | | | | 45 | |

| Pro | Gly | Asp | Arg | Ala | Leu | Phe | Leu | Glu | Arg | Ala | Gly | Gly | Ser | Arg | Val |
|---|---|---|---|---|---|---|---|---|---|---|---|---|---|---|---|
| | 50 | | | | | 55 | | | | | 60 | | | | |

| Ser | Val | Ala | Thr | Ala | Ser | Arg | Ser | Gly | Arg | Arg | Arg | Ser | Gly | Met |
|---|---|---|---|---|---|---|---|---|---|---|---|---|---|---|
| 65 | | | | | 70 | | | | | 75 | | | | 80 |

| Asp | Pro | Glu | Lys | Thr | Glu | Pro | Gly | Glu | Gly | Thr | Ser | Arg | Ser | Arg | Arg |
|---|---|---|---|---|---|---|---|---|---|---|---|---|---|---|---|
| | | | | 85 | | | | | 90 | | | | | 95 | |

| Asp | Met | Leu | Arg | Asp | Gly | Gly | Gln | Gln | Gly | Pro | Gly | Thr | Gly | Ala | Arg |
|---|---|---|---|---|---|---|---|---|---|---|---|---|---|---|---|
| | | | 100 | | | | | 105 | | | | | 110 | | |

| Asp | Pro | Asp | Lys | Ala | Thr | Arg | Phe | Arg | Met | Glu | Glu | Leu | Arg | Leu | Thr |
|---|---|---|---|---|---|---|---|---|---|---|---|---|---|---|---|
| | | 115 | | | | | 120 | | | | | 125 | | | |

| Ser | Thr | Thr | Phe | Ala | Leu | Thr | Gly | Asp | Ser | Ala | His | Asn | Gln | Ala | Met |
|---|---|---|---|---|---|---|---|---|---|---|---|---|---|---|---|
| 130 | | | | | 135 | | | | | 140 | | | | | |

| Val | His | Trp | Ser | Gly | His | Asn | Ser | Ser | Val | Ile | Leu | Ile | Leu | Thr | Lys |
|---|---|---|---|---|---|---|---|---|---|---|---|---|---|---|---|
| 145 | | | | | 150 | | | | | 155 | | | | | 160 |

| Leu | Tyr | Asp | Tyr | Asn | Leu | Gly | Ser | Ile | Thr | Glu | Ser | Ser | Leu | Trp | Arg |
|---|---|---|---|---|---|---|---|---|---|---|---|---|---|---|---|
| | | | | 165 | | | | | 170 | | | | | 175 | |

| Ser | Thr | Asp | Tyr | Gly | Thr | Thr | Tyr | Glu | Lys | Leu | Asn | Asp | Lys | Val | Gly |
|---|---|---|---|---|---|---|---|---|---|---|---|---|---|---|---|
| | | | 180 | | | | | 185 | | | | | 190 | | |

| Leu | Lys | Thr | Ile | Leu | Ser | Tyr | Leu | Tyr | Val | Cys | Pro | Thr | Asn | Lys | Arg |
|---|---|---|---|---|---|---|---|---|---|---|---|---|---|---|---|
| | | 195 | | | | | 200 | | | | | 205 | | | |

| Lys | Ile | Met | Leu | Leu | Thr | Asp | Pro | Glu | Ile | Glu | Ser | Ser | Leu | Leu | Ile |
|---|---|---|---|---|---|---|---|---|---|---|---|---|---|---|---|
| | 210 | | | | | 215 | | | | | 220 | | | | |

| Ser | Ser | Asp | Glu | Gly | Ala | Thr | Tyr | Gln | Lys | Tyr | Arg | Leu | Asn | Phe | Tyr |
|---|---|---|---|---|---|---|---|---|---|---|---|---|---|---|---|
| 225 | | | | | 230 | | | | | 235 | | | | | 240 |

| Ile | Gln | Ser | Leu | Leu | Phe | His | Pro | Lys | Gln | Glu | Asp | Trp | Ile | Leu | Ala |
|---|---|---|---|---|---|---|---|---|---|---|---|---|---|---|---|
| | | | | 245 | | | | | 250 | | | | | 255 | |

| Tyr | Ser | Gln | Asp | Gln | Lys | Leu | Tyr | Ser | Ser | Ala | Glu | Phe | Gly | Arg | Arg |
|---|---|---|---|---|---|---|---|---|---|---|---|---|---|---|---|
| | | | 260 | | | | | 265 | | | | | 270 | | |

| Trp | Gln | Leu | Ile | Gln | Glu | Ala | Val | Val | Pro | Asn | Arg | Phe | Tyr | Trp | Ser |
|---|---|---|---|---|---|---|---|---|---|---|---|---|---|---|---|
| | | 275 | | | | | 280 | | | | | 285 | | | |

| Val | Leu | Gly | Ser | Asn | Lys | Glu | Pro | Asp | Leu | Val | His | Leu | Glu | Ala | Arg |
|---|---|---|---|---|---|---|---|---|---|---|---|---|---|---|---|
| | 290 | | | | | 295 | | | | | 300 | | | | |

| Thr | Val | Asp | Gly | His | Ser | Ile | Tyr | Leu | Thr | Cys | Arg | Met | Gln | Asn | Cys |
|---|---|---|---|---|---|---|---|---|---|---|---|---|---|---|---|
| 305 | | | | | 310 | | | | | 315 | | | | | 320 |

| Thr | Glu | Ala | Asn | Arg | Asn | Lys | Pro | Phe | Pro | Gly | Tyr | Ile | Asp | Pro | Asp |
|---|---|---|---|---|---|---|---|---|---|---|---|---|---|---|---|
| | | | | 325 | | | | | 330 | | | | | 335 | |

| Ser | Leu | Ile | Val | Gln | Asp | Asp | Tyr | Val | Phe | Val | Gln | Leu | Thr | Ser | Gly |
|---|---|---|---|---|---|---|---|---|---|---|---|---|---|---|---|
| | | | 340 | | | | | 345 | | | | | 350 | | |

| Gly | Arg | Pro | His | Tyr | Tyr | Val | Ser | Tyr | Arg | Arg | Asn | Pro | Phe | Ala | Gln |
|---|---|---|---|---|---|---|---|---|---|---|---|---|---|---|---|
| | | 355 | | | | | 360 | | | | | 365 | | | |

```
Met Lys Leu Pro Lys Tyr Ala Leu Pro Lys Asp Met His Val Ile Ser
    370             375             380

Thr Asp Glu Asn Gln Val Phe Ala Ala Val Gln Glu Trp Asn Gln Asn
385             390             395             400

Asp Thr Tyr Asn Leu Tyr Ile Ser Asp Thr Arg Gly Val Tyr Phe Thr
            405             410             415

Leu Ala Leu Glu Asn Val Gln Ser Ser Arg Gly Pro Glu Gly Asn Val
        420             425             430

Met Ile Asp Leu Tyr Glu Val Ala Gly Ile Lys Gly Met Phe Leu Ala
            435             440             445

Asn Lys Lys Ile Asp Asn Gln Val Lys Thr Phe Ile Thr Tyr Asn Lys
    450             455             460

Gly Arg Asp Trp Arg Leu Leu Gln Ala Pro Asp Ala Asp Leu Arg Gly
465             470             475             480

Asp Pro Val His Cys Leu Leu Pro Tyr Cys Ser Leu His Leu His Leu
                485             490             495

Lys Val Ser Glu Asn Pro Tyr Thr Ser Gly Ile Ile Ala Ser Arg Asp
            500             505             510

Thr Ala Pro Ser Ile Ile Val Ala Ser Gly Asn Ile Gly Ser Glu Leu
        515             520             525

Ser Asp Ser Asp Ile Ser Met Phe Val Ser Ser Asp Ala Gly Asn Thr
    530             535             540

Trp Arg Gln Ile Phe Glu Glu His Ser Ile Leu Tyr Leu Asp Gln
545             550             555             560

Gly Gly Val Leu Val Ala Met Lys His Thr Ser Leu Pro Ile Arg His
            565             570             575

Leu Trp Leu Ser Phe Asp Glu Gly Arg Ser Trp Ser Lys Tyr Ser Phe
        580             585             590

Thr Ser Ile Pro Leu Phe Val Asp Gly Val Leu Gly Glu Pro Gly Glu
    595             600             605

Glu Thr Leu Ile Met Thr Val Phe Gly His Phe Ser His Arg Ser Glu
    610             615             620

Trp Gln Leu Val Lys Val Asp Tyr Lys Ser Ile Phe Asp Arg Arg Cys
625             630             635             640

Ala Glu Glu Asp Tyr Arg Pro Trp Gln Leu His Ser Gln Gly Glu Ala
            645             650             655

Cys Ile Met Gly Ala Lys Arg Ile Tyr Lys Lys Arg Lys Ser Glu Arg
        660             665             670

Lys Cys Met Gln Gly Thr Tyr Ala Gly Ala Met Glu Ser Glu Pro Cys
    675             680             685

Val Cys Thr Glu Ala Asp Phe Asp Cys Asp Tyr Gly Tyr Glu Arg His
    690             695             700

Ser Ser Gly Gln Cys Leu Pro Ala Phe Trp Phe Asn Pro Ser Ser Leu
705             710             715             720

Ser Lys Asp Cys Ser Leu Gly Gln Ser Tyr Leu Asn Ser Thr Gly Tyr
            725             730             735

Arg Lys Val Val Ser Asn Asn Cys Thr Asp Gly Val Arg Glu Gln Tyr
        740             745             750

Thr Ala Lys Pro Gln Lys Cys Pro Gly Lys Ala Pro Arg Gly Leu Arg
    755             760             765

Ile Val Thr Ala Asp Gly Lys Leu Thr Ala Glu Gln Gly His Asn Val
    770             775             780

Thr Leu Met Val Gln Leu Glu Glu Gly Asp Val Gln Arg Thr Leu Ile
```

```
            785                 790                 795                 800
Gln Val Asp Phe Gly Asp Gly Ile Ala Val Ser Tyr Val Asn Leu Ser
                805                 810                 815

Ser Met Glu Asp Gly Ile Lys His Val Tyr Gln Asn Val Gly Ile Phe
                820                 825                 830

Arg Val Thr Val Gln Val Asp Asn Ser Leu Gly Ser Asp Ser Ala Val
                835                 840                 845

Leu Tyr Leu His Val Thr Cys Pro Leu Glu His Val His Leu Ser Leu
    850                 855                 860

Pro Phe Val Thr Thr Lys Asn Lys Glu Val Asn Ala Thr Ala Val Leu
865                 870                 875                 880

Trp Pro Ser Gln Val Gly Thr Leu Thr Tyr Val Trp Trp Tyr Gly Asn
                885                 890                 895

Asn Thr Glu Pro Leu Ile Thr Leu Glu Gly Ser Ile Ser Phe Lys Phe
                900                 905                 910

Thr Ser Glu Gly Met Asn Thr Ile Thr Val Gln Val Ser Ala Gly Asn
            915                 920                 925

Ala Ile Leu Gln Asp Thr Lys Thr Ile Ala Val Tyr Glu Glu Phe Arg
        930                 935                 940

Ser Leu Arg Leu Ala Phe Ser Pro Asn Leu Asp Asp Tyr Asn Pro Asp
945                 950                 955                 960

Ile Pro Glu Trp Arg Arg Asp Ile Ser Arg Val Ile Lys Lys Ser Leu
                965                 970                 975

Val Glu Ala Thr Gly Ile Pro Ser Gln His Ile Leu Val Ala Val Leu
            980                 985                 990

Pro Gly Leu Pro Thr Ala Ala Glu  Leu Phe Val Leu Pro  Tyr Gln Asp
        995                 1000                1005

Gly Ala  Arg Glu Asn Lys Arg  Ser Pro Glu Asp Leu  Glu Gln Ile
    1010                1015                1020

Ser Glu  Val Leu Ile His Lys  Leu Asn Gln Asn Leu  Val His Phe
    1025                1030                1035

Glu Leu  Lys Pro Gly Val Gln  Val Leu Val His Ala  Ala His Leu
    1040                1045                1050

Thr Ala  Ala Pro Leu Val Asp  Leu Thr Pro Thr His  Ser Gly Ser
    1055                1060                1065

Ala Met  Leu Met Leu Leu Ser  Val Val Phe Val Gly  Leu Ala Val
    1070                1075                1080

Phe Val  Ile Tyr Lys Phe Lys  Arg Lys Ile Pro Gly  Ile Asn Val
    1085                1090                1095

Tyr Ala  Gln Met Gln Asn Glu  Lys Glu Gln Glu Leu  Ile Asn Pro
    1100                1105                1110

Val Ser  His Thr Glu Ser Arg  Pro Thr Ala Pro His  Pro Asp Leu
    1115                1120                1125

Arg Arg  Pro Gly Gln Leu Val  Asp Glu Lys Val Glu  Ser His Leu
    1130                1135                1140

Leu Gly  Ser Ile Ser Ile Val  Ala Glu Asn Gln Ser  Thr Lys Glu
    1145                1150                1155

Ile Pro  Thr Tyr Val Asn Val
    1160                1165

<210> SEQ ID NO 46
<211> LENGTH: 1088
<212> TYPE: PRT
<213> ORGANISM: Rattus norvegicus
```

<220> FEATURE:
<221> NAME/KEY: MISC_FEATURE
<222> LOCATION: (1)..(1088)
<223> OTHER INFORMATION: mature SorCS1

<400> SEQUENCE: 46

```
Ser Gly Met Asp Pro Glu Lys Thr Glu Pro Gly Glu Gly Thr Ser Arg
1               5                   10                  15

Ser Arg Arg Asp Met Leu Arg Asp Gly Gly Gln Gln Gly Pro Gly Thr
            20                  25                  30

Gly Ala Arg Asp Pro Asp Lys Ala Thr Arg Phe Arg Met Glu Glu Leu
        35                  40                  45

Arg Leu Thr Ser Thr Thr Phe Ala Leu Thr Gly Asp Ser Ala His Asn
    50                  55                  60

Gln Ala Met Val His Trp Ser Gly His Asn Ser Ser Val Ile Leu Ile
65                  70                  75                  80

Leu Thr Lys Leu Tyr Asp Tyr Asn Leu Gly Ser Ile Thr Glu Ser Ser
                85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
        115                 120                 125

Asn Lys Arg Lys Ile Met Leu Leu Thr Asp Pro Glu Ile Glu Ser Ser
    130                 135                 140

Leu Leu Ile Ser Ser Asp Glu Gly Ala Thr Tyr Gln Lys Tyr Arg Leu
145                 150                 155                 160

Asn Phe Tyr Ile Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Ala Val Val Pro Asn Arg Phe
        195                 200                 205

Tyr Trp Ser Val Leu Gly Ser Asn Lys Glu Pro Asp Leu Val His Leu
    210                 215                 220

Glu Ala Arg Thr Val Asp Gly His Ser Ile Tyr Leu Thr Cys Arg Met
225                 230                 235                 240

Gln Asn Cys Thr Glu Ala Asn Arg Asn Lys Pro Phe Pro Gly Tyr Ile
                245                 250                 255

Asp Pro Asp Ser Leu Ile Val Gln Asp Tyr Val Phe Val Gln Leu
            260                 265                 270

Thr Ser Gly Gly Arg Pro His Tyr Tyr Val Ser Tyr Arg Arg Asn Pro
        275                 280                 285

Phe Ala Gln Met Lys Leu Pro Lys Tyr Ala Leu Pro Lys Asp Met His
    290                 295                 300

Val Ile Ser Thr Asp Glu Asn Gln Val Phe Ala Ala Val Gln Glu Trp
305                 310                 315                 320

Asn Gln Asn Asp Thr Tyr Asn Leu Tyr Ile Ser Asp Thr Arg Gly Val
                325                 330                 335

Tyr Phe Thr Leu Ala Leu Glu Asn Val Gln Ser Ser Arg Gly Pro Glu
            340                 345                 350

Gly Asn Val Met Ile Asp Leu Tyr Glu Val Ala Gly Ile Lys Gly Met
        355                 360                 365

Phe Leu Ala Asn Lys Lys Ile Asp Asn Gln Val Lys Thr Phe Ile Thr
    370                 375                 380
```

-continued

```
Tyr Asn Lys Gly Arg Asp Trp Arg Leu Leu Gln Ala Pro Asp Ala Asp
385                 390                 395                 400
Leu Arg Gly Asp Pro Val His Cys Leu Leu Pro Tyr Cys Ser Leu His
            405                 410                 415
Leu His Leu Lys Val Ser Glu Asn Pro Tyr Thr Ser Gly Ile Ile Ala
        420                 425                 430
Ser Arg Asp Thr Ala Pro Ser Ile Ile Val Ala Ser Gly Asn Ile Gly
    435                 440                 445
Ser Glu Leu Ser Asp Ser Asp Ile Ser Met Phe Val Ser Ser Asp Ala
450                 455                 460
Gly Asn Thr Trp Arg Gln Ile Phe Glu Glu His Ser Ile Leu Tyr
465                 470                 475                 480
Leu Asp Gln Gly Gly Val Leu Ala Met Lys His Thr Ser Leu Pro
            485                 490                 495
Ile Arg His Leu Trp Leu Ser Phe Asp Glu Gly Arg Ser Trp Ser Lys
        500                 505                 510
Tyr Ser Phe Thr Ser Ile Pro Leu Phe Val Asp Gly Val Leu Gly Glu
    515                 520                 525
Pro Gly Glu Glu Thr Leu Ile Met Thr Val Phe Gly His Phe Ser His
530                 535                 540
Arg Ser Glu Trp Gln Leu Val Lys Val Asp Tyr Lys Ser Ile Phe Asp
545                 550                 555                 560
Arg Arg Cys Ala Glu Glu Asp Tyr Arg Pro Trp Gln Leu His Ser Gln
            565                 570                 575
Gly Glu Ala Cys Ile Met Gly Ala Lys Arg Ile Tyr Lys Lys Arg Lys
        580                 585                 590
Ser Glu Arg Lys Cys Met Gln Gly Thr Tyr Ala Gly Ala Met Glu Ser
    595                 600                 605
Glu Pro Cys Val Cys Thr Glu Ala Asp Phe Asp Cys Asp Tyr Gly Tyr
610                 615                 620
Glu Arg His Ser Ser Gly Gln Cys Leu Pro Ala Phe Trp Phe Asn Pro
625                 630                 635                 640
Ser Ser Leu Ser Lys Asp Cys Ser Leu Gly Gln Ser Tyr Leu Asn Ser
            645                 650                 655
Thr Gly Tyr Arg Lys Val Val Ser Asn Asn Cys Thr Asp Gly Val Arg
        660                 665                 670
Glu Gln Tyr Thr Ala Lys Pro Gln Lys Cys Pro Gly Lys Ala Pro Arg
    675                 680                 685
Gly Leu Arg Ile Val Thr Ala Asp Gly Lys Leu Thr Ala Glu Gln Gly
690                 695                 700
His Asn Val Thr Leu Met Val Gln Leu Glu Glu Gly Asp Val Gln Arg
705                 710                 715                 720
Thr Leu Ile Gln Val Asp Phe Gly Asp Gly Ile Ala Val Ser Tyr Val
            725                 730                 735
Asn Leu Ser Ser Met Glu Asp Gly Ile Lys His Val Tyr Gln Asn Val
        740                 745                 750
Gly Ile Phe Arg Val Thr Val Gln Val Asp Asn Ser Leu Gly Ser Asp
    755                 760                 765
Ser Ala Val Leu Tyr Leu His Val Thr Cys Pro Leu Glu His Val His
770                 775                 780
Leu Ser Leu Pro Phe Val Thr Thr Lys Asn Lys Glu Val Asn Ala Thr
785                 790                 795                 800
Ala Val Leu Trp Pro Ser Gln Val Gly Thr Leu Thr Tyr Val Trp Trp
```

```
                        805                 810                 815
Tyr Gly Asn Asn Thr Glu Pro Leu Ile Thr Leu Glu Gly Ser Ile Ser
                820                 825                 830

Phe Lys Phe Thr Ser Glu Gly Met Asn Thr Ile Thr Val Gln Val Ser
            835                 840                 845

Ala Gly Asn Ala Ile Leu Gln Asp Thr Lys Thr Ile Ala Val Tyr Glu
    850                 855                 860

Glu Phe Arg Ser Leu Arg Leu Ala Phe Ser Pro Asn Leu Asp Asp Tyr
865                 870                 875                 880

Asn Pro Asp Ile Pro Glu Trp Arg Arg Asp Ile Ser Arg Val Ile Lys
                885                 890                 895

Lys Ser Leu Val Glu Ala Thr Gly Ile Pro Ser Gln His Ile Leu Val
            900                 905                 910

Ala Val Leu Pro Gly Leu Pro Thr Ala Ala Glu Leu Phe Val Leu Pro
        915                 920                 925

Tyr Gln Asp Gly Ala Arg Glu Asn Lys Arg Ser Pro Glu Asp Leu Glu
    930                 935                 940

Gln Ile Ser Glu Val Leu Ile His Lys Leu Asn Gln Asn Leu Val His
945                 950                 955                 960

Phe Glu Leu Lys Pro Gly Val Gln Val Leu Val His Ala Ala His Leu
                965                 970                 975

Thr Ala Ala Pro Leu Val Asp Leu Thr Pro Thr His Ser Gly Ser Ala
            980                 985                 990

Met Leu Met Leu Leu Ser Val Val Phe Val Gly Leu Ala Val Phe Val
        995                1000                1005

Ile Tyr Lys Phe Lys Arg Lys Ile Pro Gly Ile Asn Val Tyr Ala
    1010                1015                1020

Gln Met Gln Asn Glu Lys Glu Gln Glu Leu Ile Asn Pro Val Ser
    1025                1030                1035

His Thr Glu Ser Arg Pro Thr Ala Pro His Pro Asp Leu Arg Arg
    1040                1045                1050

Pro Gly Gln Leu Val Asp Glu Lys Val Glu Ser His Leu Leu Gly
    1055                1060                1065

Ser Ile Ser Ile Val Ala Glu Asn Gln Ser Thr Lys Glu Ile Pro
    1070                1075                1080

Thr Tyr Val Asn Val
    1085

<210> SEQ ID NO 47
<211> LENGTH: 990
<212> TYPE: PRT
<213> ORGANISM: Rattus norvegicus
<220> FEATURE:
<221> NAME/KEY: MISC_FEATURE
<222> LOCATION: (1)..(990)
<223> OTHER INFORMATION: soluble SorCS1

<400> SEQUENCE: 47

Ser Gly Met Asp Pro Glu Lys Thr Glu Pro Gly Glu Gly Thr Ser Arg
1               5                   10                  15

Ser Arg Arg Asp Met Leu Arg Asp Gly Gln Gln Gly Pro Gly Thr
            20                  25                  30

Gly Ala Arg Asp Pro Asp Lys Ala Thr Arg Phe Arg Met Glu Glu Leu
        35                  40                  45

Arg Leu Thr Ser Thr Thr Phe Ala Leu Thr Gly Asp Ser Ala His Asn
    50                  55                  60
```

-continued

```
Gln Ala Met Val His Trp Ser Gly His Asn Ser Ser Val Ile Leu Ile
 65                  70                  75                  80

Leu Thr Lys Leu Tyr Asp Tyr Asn Leu Gly Ser Ile Thr Glu Ser Ser
                 85                  90                  95

Leu Trp Arg Ser Thr Asp Tyr Gly Thr Thr Tyr Glu Lys Leu Asn Asp
            100                 105                 110

Lys Val Gly Leu Lys Thr Ile Leu Ser Tyr Leu Tyr Val Cys Pro Thr
        115                 120                 125

Asn Lys Arg Lys Ile Met Leu Leu Thr Asp Pro Glu Ile Glu Ser Ser
130                 135                 140

Leu Leu Ile Ser Ser Asp Glu Gly Ala Thr Tyr Gln Lys Tyr Arg Leu
145                 150                 155                 160

Asn Phe Tyr Ile Gln Ser Leu Leu Phe His Pro Lys Gln Glu Asp Trp
                165                 170                 175

Ile Leu Ala Tyr Ser Gln Asp Gln Lys Leu Tyr Ser Ser Ala Glu Phe
            180                 185                 190

Gly Arg Arg Trp Gln Leu Ile Gln Glu Ala Val Val Pro Asn Arg Phe
        195                 200                 205

Tyr Trp Ser Val Leu Gly Ser Asn Lys Glu Pro Asp Leu Val His Leu
210                 215                 220

Glu Ala Arg Thr Val Asp Gly His Ser Ile Tyr Leu Thr Cys Arg Met
225                 230                 235                 240

Gln Asn Cys Thr Glu Ala Asn Arg Asn Lys Pro Phe Pro Gly Tyr Ile
                245                 250                 255

Asp Pro Asp Ser Leu Ile Val Gln Asp Tyr Val Phe Val Gln Leu
            260                 265                 270

Thr Ser Gly Gly Arg Pro His Tyr Tyr Val Ser Tyr Arg Arg Asn Pro
        275                 280                 285

Phe Ala Gln Met Lys Leu Pro Lys Tyr Ala Leu Pro Lys Asp Met His
290                 295                 300

Val Ile Ser Thr Asp Glu Asn Gln Val Phe Ala Ala Val Gln Glu Trp
305                 310                 315                 320

Asn Gln Asn Asp Thr Tyr Asn Leu Tyr Ile Ser Asp Thr Arg Gly Val
                325                 330                 335

Tyr Phe Thr Leu Ala Leu Glu Asn Val Gln Ser Ser Arg Gly Pro Glu
            340                 345                 350

Gly Asn Val Met Ile Asp Leu Tyr Glu Val Ala Gly Ile Lys Gly Met
        355                 360                 365

Phe Leu Ala Asn Lys Lys Ile Asp Asn Gln Val Lys Thr Phe Ile Thr
370                 375                 380

Tyr Asn Lys Gly Arg Asp Trp Arg Leu Leu Gln Ala Pro Asp Ala Asp
385                 390                 395                 400

Leu Arg Gly Asp Pro Val His Cys Leu Leu Pro Tyr Cys Ser Leu His
                405                 410                 415

Leu His Leu Lys Val Ser Glu Asn Pro Tyr Thr Ser Gly Ile Ile Ala
            420                 425                 430

Ser Arg Asp Thr Ala Pro Ser Ile Ile Val Ala Ser Gly Asn Ile Gly
        435                 440                 445

Ser Glu Leu Ser Asp Ser Asp Ile Ser Met Phe Val Ser Ser Asp Ala
450                 455                 460

Gly Asn Thr Trp Arg Gln Ile Phe Glu Glu His Ser Ile Leu Tyr
465                 470                 475                 480
```

```
Leu Asp Gln Gly Gly Val Leu Val Ala Met Lys His Thr Ser Leu Pro
                485                 490                 495

Ile Arg His Leu Trp Leu Ser Phe Asp Glu Gly Arg Ser Trp Ser Lys
            500                 505                 510

Tyr Ser Phe Thr Ser Ile Pro Leu Phe Val Asp Gly Val Leu Gly Glu
        515                 520                 525

Pro Gly Glu Glu Thr Leu Ile Met Thr Val Phe Gly His Phe Ser His
    530                 535                 540

Arg Ser Glu Trp Gln Leu Val Lys Val Asp Tyr Lys Ser Ile Phe Asp
545                 550                 555                 560

Arg Arg Cys Ala Glu Glu Asp Tyr Arg Pro Trp Gln Leu His Ser Gln
                565                 570                 575

Gly Glu Ala Cys Ile Met Gly Ala Lys Arg Ile Tyr Lys Lys Arg Lys
            580                 585                 590

Ser Glu Arg Lys Cys Met Gln Gly Thr Tyr Ala Gly Ala Met Glu Ser
        595                 600                 605

Glu Pro Cys Val Cys Thr Glu Ala Asp Phe Asp Cys Asp Tyr Gly Tyr
    610                 615                 620

Glu Arg His Ser Ser Gly Gln Cys Leu Pro Ala Phe Trp Phe Asn Pro
625                 630                 635                 640

Ser Ser Leu Ser Lys Asp Cys Ser Leu Gly Gln Ser Tyr Leu Asn Ser
                645                 650                 655

Thr Gly Tyr Arg Lys Val Val Ser Asn Asn Cys Thr Asp Gly Val Arg
            660                 665                 670

Glu Gln Tyr Thr Ala Lys Pro Gln Lys Cys Pro Gly Lys Ala Pro Arg
        675                 680                 685

Gly Leu Arg Ile Val Thr Ala Asp Gly Lys Leu Thr Ala Glu Gln Gly
    690                 695                 700

His Asn Val Thr Leu Met Val Gln Leu Glu Glu Gly Asp Val Gln Arg
705                 710                 715                 720

Thr Leu Ile Gln Val Asp Phe Gly Asp Gly Ile Ala Val Ser Tyr Val
                725                 730                 735

Asn Leu Ser Ser Met Glu Asp Gly Ile Lys His Val Tyr Gln Asn Val
            740                 745                 750

Gly Ile Phe Arg Val Thr Val Gln Val Asp Asn Ser Leu Gly Ser Asp
        755                 760                 765

Ser Ala Val Leu Tyr Leu His Val Thr Cys Pro Leu Glu His Val His
    770                 775                 780

Leu Ser Leu Pro Phe Val Thr Thr Lys Asn Lys Glu Val Asn Ala Thr
785                 790                 795                 800

Ala Val Leu Trp Pro Ser Gln Val Gly Thr Leu Thr Tyr Val Trp Trp
                805                 810                 815

Tyr Gly Asn Asn Thr Glu Pro Leu Ile Thr Leu Glu Gly Ser Ile Ser
            820                 825                 830

Phe Lys Phe Thr Ser Glu Gly Met Asn Thr Ile Thr Val Gln Val Ser
        835                 840                 845

Ala Gly Asn Ala Ile Leu Gln Asp Thr Lys Thr Ile Ala Val Tyr Glu
    850                 855                 860

Glu Phe Arg Ser Leu Arg Leu Ala Phe Ser Pro Asn Leu Asp Asp Tyr
865                 870                 875                 880

Asn Pro Asp Ile Pro Glu Trp Arg Arg Asp Ile Ser Arg Val Ile Lys
                885                 890                 895

Lys Ser Leu Val Glu Ala Thr Gly Ile Pro Ser Gln His Ile Leu Val
```

```
                900             905             910
Ala Val Leu Pro Gly Leu Pro Thr Ala Ala Glu Leu Phe Val Leu Pro
            915             920             925

Tyr Gln Asp Gly Ala Arg Glu Asn Lys Arg Ser Pro Glu Asp Leu Glu
        930             935             940

Gln Ile Ser Glu Val Leu Ile His Lys Leu Asn Gln Asn Leu Val His
945             950             955             960

Phe Glu Leu Lys Pro Gly Val Gln Val Leu Val His Ala Ala His Leu
            965             970             975

Thr Ala Ala Pro Leu Val Asp Leu Thr Pro Thr His Ser Gly
            980             985             990

<210> SEQ ID NO 48
<211> LENGTH: 1258
<212> TYPE: PRT
<213> ORGANISM: Gallus gallus
<220> FEATURE:
<221> NAME/KEY: MISC_FEATURE
<222> LOCATION: (1)..(1258)
<223> OTHER INFORMATION: preproSorCS1

<400> SEQUENCE: 48

Met Glu Lys Val Ala Gly Trp Tyr Pro Ala Trp His Val Ala Leu Leu
1               5                   10                  15

Tyr Trp Thr Trp Leu Phe Leu Phe Thr Phe Gly Phe Thr Gly Ala Glu
            20                  25                  30

Ile Thr Cys Arg Ser Cys His Ser Gln Val Asn Pro Gln Gln His
        35                  40                  45

Pro Gln Gln Gly Leu Pro Met His Leu Lys Thr Asp Arg Gly Glu Lys
50                  55                  60

Glu Arg Trp Arg Ile Pro Gly Glu Gln Gly Glu Arg Gly Arg Gly
65                  70                  75                  80

Ala Gly Met Asp Thr Glu Asp Ala Glu Leu Gln Ala Pro Phe Asp Pro
                85                  90                  95

Ala Leu Ala Gly Thr Lys Phe Ser Gly Trp Glu Thr Arg Ser Trp Ala
            100                 105                 110

Ser Glu Pro Glu Lys Ala Pro Gly Asp Ser Arg Pro Gly Ala Ala Ala
        115                 120                 125

Ala Pro Thr Gly Glu Tyr Pro Gln Arg Gly Gln Ala Gly Gly Arg Arg
    130                 135                 140

Asn Ser Ala Arg Arg Arg Gly Arg Ser Pro Arg Gly Thr Ala Gly
145                 150                 155                 160

Pro Gly Gly Ala Ala Gly Arg Glu Pro Gly Gly Ser Gly Ala Ala Arg
                165                 170                 175

Phe Gly Leu Glu Glu Leu Arg Leu Gly Ser Thr Thr Phe Ala Leu Thr
            180                 185                 190

Gly Asp Ser Ala His Asn Gln Ala Met Val His Trp Ser Gly Gln Asn
        195                 200                 205

Ser Ser Val Ile Leu Ile Leu Thr Lys Leu Tyr Asp Tyr Asn Leu Gly
    210                 215                 220

Ser Ile Thr Glu Ser Ser Leu Trp Arg Ser Thr Asp Tyr Gly Thr Thr
225                 230                 235                 240

Tyr Glu Lys Leu Asn Asp Lys Ile Gly Leu Lys Thr Ile Leu Ser Tyr
                245                 250                 255

Leu Tyr Val Cys Pro Thr Asn Lys Arg Lys Ile Met Leu Leu Thr Asp
            260                 265                 270
```

```
Pro Glu Val Glu Ser Ser Leu Leu Ile Ser Thr Asp Glu Gly Ala Thr
            275                 280                 285

Tyr Gln Lys Tyr Arg Leu Asn Phe Tyr Ile His Ser Leu Leu Phe His
        290                 295                 300

Pro Lys Gln Glu Asp Trp Ile Leu Ala Tyr Ser Gln Asp Gln Lys Leu
305                 310                 315                 320

Phe Ser Ser Val Glu Phe Gly Arg Arg Trp Leu Leu Leu His Glu Gly
                325                 330                 335

Val Ala Pro Asn Arg Phe Tyr Trp Ser Met Met Val Ser Gly Arg Glu
            340                 345                 350

Pro Asp Leu Val His Leu Glu Ala Lys Thr Val Asp Gly His Ala Gln
            355                 360                 365

Tyr Ile Thr Cys Lys Met Gln Asn Cys Ser Glu Ala Ser Gln Asn Lys
        370                 375                 380

Pro Phe Pro Gly Tyr Ile Asp His Asn Ser Leu Ile Val Gln Asp Asp
385                 390                 395                 400

Tyr Val Phe Val Gln Leu Thr Ser Gly Gly Arg Pro His Tyr Tyr Val
                405                 410                 415

Ser Tyr Arg Arg Asn Ala Phe Thr Pro Ile Lys Leu Pro Lys Tyr Ser
            420                 425                 430

Leu Pro Lys Asp Met His Val Ile Ser Thr Asp Glu Ser Gln Val Phe
        435                 440                 445

Ala Ala Val Gln Glu Trp Asn Gln Asn Asp Thr Tyr Asn Leu Tyr Ile
        450                 455                 460

Ser Asp Thr Arg Gly Val Tyr Phe Thr Leu Ala Leu Glu Asn Val Lys
465                 470                 475                 480

Ser Ser Gln Gly Leu Asp Gly Asn Val Met Ile Asp Leu Tyr Glu Val
                485                 490                 495

Ala Gly Ile Lys Gly Met Phe Leu Ala Asn Lys Lys Ile Asp Asn Gln
            500                 505                 510

Val Lys Thr Phe Ile Thr Tyr Asn Lys Gly Arg Asp Trp Asn Leu Leu
            515                 520                 525

Gln Ala Pro Asp Thr Asp Leu Lys Gly Asn Pro Val His Cys Leu Leu
530                 535                 540

Pro Tyr Cys Ser Leu His Leu His Leu Lys Val Ser Glu Asn Pro Tyr
545                 550                 555                 560

Thr Ser Gly Asn Ile Ala Ser Arg Asp Thr Ala Pro Ser Ile Ile Val
            565                 570                 575

Ala Ser Gly Asn Ile Gly Pro Glu Leu Ser Asp Asn Asp Ile Ser Met
            580                 585                 590

Phe Val Ser Ser Asp Ala Gly Asn Thr Trp Arg Gln Ile Phe Glu Glu
            595                 600                 605

Glu His Ser Val Leu Tyr Leu Asp Gln Gly Gly Val Leu Val Ala Ile
        610                 615                 620

Lys His Thr Ser Leu Pro Ile Arg His Leu Trp Leu Ser Phe Asp Glu
625                 630                 635                 640

Gly Lys Ser Trp Ser Lys Tyr Ser Phe Thr Ser Leu Pro Leu Phe Val
                645                 650                 655

Asp Gly Ile Leu Gly Glu Pro Gly Glu Glu Thr Leu Ile Met Thr Val
            660                 665                 670

Phe Gly His Phe Ser His Arg Ser Glu Trp Gln Leu Val Lys Ile Asp
            675                 680                 685
```

```
Tyr Lys Ser Ile Phe Asp Arg Arg Cys Ala Glu Glu Asp Tyr Trp Thr
    690             695                 700

Trp Gln Leu His Ser Gln Gly Glu Ala Cys Ile Met Gly Ala Lys Arg
705             710                  715                 720

Ile Tyr Arg Lys Arg Lys Ser Glu Lys Lys Cys Met Gln Gly Lys Tyr
            725                 730                 735

Ala Gly Ala Met Thr Ser Glu Pro Cys Val Cys Thr Asp Ala Asp Phe
            740                 745                 750

Asp Cys Asp Tyr Gly Tyr Glu His Arg Asn Gly Gln Cys Leu Pro
            755                 760                 765

Ala Phe Trp Tyr Asn Pro Ser Ser Leu Ser Lys Asp Cys Ser Leu Gly
770             775                 780

Gln Ser Tyr Leu Asn Ser Thr Gly Tyr Arg Lys Val Val Ser Asn Asn
785             790                 795                 800

Cys Thr Asp Gly Val Arg Glu Gln Tyr Thr Ala Lys Pro Gln Gln Cys
            805                 810                 815

Pro Gly Lys Ala Pro Gln Gly Leu Arg Ile Ile Thr Ser Asp Gly Lys
            820                 825                 830

Leu Thr Ala Glu Gln Gly His Asn Val Thr Phe Leu Val Gln Leu Glu
            835                 840                 845

Glu Gly Asp Leu Gln Arg Ser Leu Ile Gln Val Asp Phe Gly Asp Gly
850             855                 860

Thr Ala Val Ser Tyr Ala Asn Leu Ser Ser Thr Glu Asp Gly Ile Lys
865             870                 875                 880

His Thr Tyr Gln Asn Val Gly Ile Phe Arg Val Thr Val Leu Val Glu
            885                 890                 895

Asn Ser Leu Gly Ser Asp Asn Ala Val Leu Tyr Leu His Val Thr Cys
            900                 905                 910

Pro Leu Glu His Val His Leu Ser Leu Pro Phe Val Thr Thr Lys Asn
            915                 920                 925

Lys Glu Val Asn Ala Thr Ala Val Leu Trp Pro Ser Gln Val Gly Thr
930             935                 940

Leu Thr Tyr Val Trp Trp Phe Gly Asn Asn Thr Glu Pro Leu Ile Thr
945             950                 955                 960

Leu Glu Gly Ser Ile Thr Phe Thr Phe Ser Val Glu Gly Met Asn Thr
            965                 970                 975

Ile Thr Val Gln Val Ser Ala Gly Asn Thr Ile Leu Gln Asp Thr Lys
            980                 985                 990

Thr Ile Ala Val Tyr Glu Gln Phe Arg Ser Leu Arg Leu Ser Phe Ser
            995                 1000                1005

Pro Asn Leu Asp Asp Tyr Asn Pro Asp Ile Pro Glu Trp Arg Arg
    1010            1015                1020

Asp Ile Ser Arg Val Val Lys Arg Ala Leu Val Glu Ala Thr Gly
    1025            1030                1035

Ile Ser Ser Lys His Ile Leu Val Ala Val Leu Pro Gly Leu Pro
    1040            1045                1050

Thr Ser Ala Glu Leu Phe Ile Leu Pro Tyr Gln Asp Ala Thr Gly
    1055            1060                1065

Gly Asn Lys Arg Thr Glu Asp Leu Glu Gln Ile Ser Glu Ile Leu
    1070            1075                1080

Ile Gln Lys Leu Asn Gln Asn Phe Val His Phe Glu Leu Lys Pro
    1085            1090                1095

Gly Val Arg Val Leu Val His Ala Ala His Leu Thr Ala Ala Pro
```

```
                   1100                1105                1110

Leu Val Asp Leu Thr Pro Ser His Ser Gly Ser Ala Met Leu Met
        1115                1120                1125

Leu Leu Ser Val Val Phe Val Gly Leu Ala Val Phe Val Ile Tyr
        1130                1135                1140

Lys Phe Lys Arg Lys Ile Pro Gly Leu Asn Ile Tyr Ala Gln Met
        1145                1150                1155

Gln Asn Glu Lys Asp Gln Glu Met Val Ser Pro Val Ser Gln Arg
        1160                1165                1170

Glu Ser Ile Pro Asn Val Pro Gln Ser Glu Leu Met Ser Pro Glu
        1175                1180                1185

Gln Leu Val Asp Glu Lys Leu Asp Val Gln Pro Ile Glu Gln Pro
        1190                1195                1200

Gln Ala Thr Val Gln Asn Pro Arg Lys Gly Asn Ala Ala Lys Val
        1205                1210                1215

Val Trp Thr Glu Asp Phe Gln Lys Ala Cys Gly Ser Pro Arg Gly
        1220                1225                1230

Phe Lys Pro Arg Pro Gly Ala Glu Val Phe Pro Gln Leu Leu Ser
        1235                1240                1245

Pro Arg Ala Gln Lys Lys Ser Leu Pro Met
        1250                1255

<210> SEQ ID NO 49
<211> LENGTH: 1200
<212> TYPE: PRT
<213> ORGANISM: Gallus gallus
<220> FEATURE:
<221> NAME/KEY: MISC_FEATURE
<222> LOCATION: (1)..(1200)
<223> OTHER INFORMATION: proSorCS1

<400> SEQUENCE: 49

Thr Asp Arg Gly Glu Lys Glu Arg Trp Arg Ile Pro Gly Gln Gly
1               5                  10                  15

Gly Glu Arg Gly Arg Gly Ala Gly Met Asp Thr Glu Asp Ala Glu Leu
            20                  25                  30

Gln Ala Pro Phe Asp Pro Ala Leu Ala Gly Thr Lys Phe Ser Gly Trp
        35                  40                  45

Glu Thr Arg Ser Trp Ala Ser Glu Pro Glu Lys Ala Pro Gly Asp Ser
    50                  55                  60

Arg Pro Gly Ala Ala Ala Ala Pro Thr Gly Glu Tyr Pro Gln Arg Gly
65                  70                  75                  80

Gln Ala Gly Gly Arg Arg Asn Ser Ala Arg Arg Arg Gly Arg Ser
            85                  90                  95

Pro Arg Gly Thr Ala Gly Pro Gly Gly Ala Ala Gly Arg Glu Pro Gly
        100                 105                 110

Gly Ser Gly Ala Ala Arg Phe Gly Leu Glu Glu Leu Arg Leu Gly Ser
    115                 120                 125

Thr Thr Phe Ala Leu Thr Gly Asp Ser Ala His Asn Gln Ala Met Val
130                 135                 140

His Trp Ser Gly Gln Asn Ser Ser Val Ile Leu Ile Leu Thr Lys Leu
145                 150                 155                 160

Tyr Asp Tyr Asn Leu Gly Ser Ile Thr Glu Ser Ser Leu Trp Arg Ser
                165                 170                 175

Thr Asp Tyr Gly Thr Thr Tyr Glu Lys Leu Asn Asp Lys Ile Gly Leu
            180                 185                 190
```

```
Lys Thr Ile Leu Ser Tyr Leu Tyr Val Cys Pro Thr Asn Lys Arg Lys
        195                 200                 205

Ile Met Leu Leu Thr Asp Pro Glu Val Glu Ser Ser Leu Leu Ile Ser
    210                 215                 220

Thr Asp Glu Gly Ala Thr Tyr Gln Lys Tyr Arg Leu Asn Phe Tyr Ile
225                 230                 235                 240

His Ser Leu Leu Phe His Pro Lys Gln Glu Asp Trp Ile Leu Ala Tyr
                245                 250                 255

Ser Gln Asp Gln Lys Leu Phe Ser Ser Val Glu Phe Gly Arg Arg Trp
            260                 265                 270

Leu Leu Leu His Glu Gly Val Ala Pro Asn Arg Phe Tyr Trp Ser Met
        275                 280                 285

Met Val Ser Gly Arg Glu Pro Asp Leu Val His Leu Glu Ala Lys Thr
    290                 295                 300

Val Asp Gly His Ala Gln Tyr Ile Thr Cys Lys Met Gln Asn Cys Ser
305                 310                 315                 320

Glu Ala Ser Gln Asn Lys Pro Phe Pro Gly Tyr Ile Asp His Asn Ser
                325                 330                 335

Leu Ile Val Gln Asp Asp Tyr Val Phe Val Gln Leu Thr Ser Gly Gly
            340                 345                 350

Arg Pro His Tyr Tyr Val Ser Tyr Arg Arg Asn Ala Phe Thr Pro Ile
        355                 360                 365

Lys Leu Pro Lys Tyr Ser Leu Pro Lys Asp Met His Val Ile Ser Thr
    370                 375                 380

Asp Glu Ser Gln Val Phe Ala Ala Val Gln Glu Trp Asn Gln Asn Asp
385                 390                 395                 400

Thr Tyr Asn Leu Tyr Ile Ser Asp Thr Arg Gly Val Tyr Phe Thr Leu
                405                 410                 415

Ala Leu Glu Asn Val Lys Ser Ser Gln Gly Leu Asp Gly Asn Val Met
            420                 425                 430

Ile Asp Leu Tyr Glu Val Ala Gly Ile Lys Gly Met Phe Leu Ala Asn
        435                 440                 445

Lys Lys Ile Asp Asn Gln Val Lys Thr Phe Ile Thr Tyr Asn Lys Gly
    450                 455                 460

Arg Asp Trp Asn Leu Leu Gln Ala Pro Asp Thr Asp Leu Lys Gly Asn
465                 470                 475                 480

Pro Val His Cys Leu Leu Pro Tyr Cys Ser Leu His Leu His Leu Lys
                485                 490                 495

Val Ser Glu Asn Pro Tyr Thr Ser Gly Asn Ile Ala Ser Arg Asp Thr
            500                 505                 510

Ala Pro Ser Ile Ile Val Ala Ser Gly Asn Ile Gly Pro Glu Leu Ser
        515                 520                 525

Asp Asn Asp Ile Ser Met Phe Val Ser Ser Asp Ala Gly Asn Thr Trp
    530                 535                 540

Arg Gln Ile Phe Glu Glu His Ser Val Leu Tyr Leu Asp Gln Gly
545                 550                 555                 560

Gly Val Leu Val Ala Ile Lys His Thr Ser Leu Pro Ile Arg His Leu
                565                 570                 575

Trp Leu Ser Phe Asp Glu Gly Lys Ser Trp Ser Lys Tyr Ser Phe Thr
            580                 585                 590

Ser Leu Pro Leu Phe Val Asp Gly Ile Leu Gly Glu Pro Gly Glu Glu
        595                 600                 605
```

```
Thr Leu Ile Met Thr Val Phe Gly His Phe Ser His Arg Ser Glu Trp
610                 615                 620

Gln Leu Val Lys Ile Asp Tyr Lys Ser Ile Phe Asp Arg Arg Cys Ala
625                 630                 635                 640

Glu Glu Asp Tyr Trp Thr Trp Gln Leu His Ser Gln Gly Ala Cys
                645                 650                 655

Ile Met Gly Ala Lys Arg Ile Tyr Arg Lys Arg Lys Ser Glu Lys Lys
                660                 665                 670

Cys Met Gln Gly Lys Tyr Ala Gly Ala Met Thr Ser Glu Pro Cys Val
            675                 680                 685

Cys Thr Asp Ala Asp Phe Asp Cys Asp Tyr Gly Tyr Glu Arg His Arg
        690                 695                 700

Asn Gly Gln Cys Leu Pro Ala Phe Trp Tyr Asn Pro Ser Ser Leu Ser
705                 710                 715                 720

Lys Asp Cys Ser Leu Gly Gln Ser Tyr Leu Asn Ser Thr Gly Tyr Arg
                725                 730                 735

Lys Val Val Ser Asn Asn Cys Thr Asp Gly Val Arg Glu Gln Tyr Thr
            740                 745                 750

Ala Lys Pro Gln Gln Cys Pro Gly Lys Ala Pro Gln Gly Leu Arg Ile
        755                 760                 765

Ile Thr Ser Asp Gly Lys Leu Thr Ala Glu Gln Gly His Asn Val Thr
770                 775                 780

Phe Leu Val Gln Leu Glu Glu Gly Asp Leu Gln Arg Ser Leu Ile Gln
785                 790                 795                 800

Val Asp Phe Gly Asp Gly Thr Ala Val Ser Tyr Ala Asn Leu Ser Ser
                805                 810                 815

Thr Glu Asp Gly Ile Lys His Thr Tyr Gln Asn Val Gly Ile Phe Arg
            820                 825                 830

Val Thr Val Leu Val Glu Asn Ser Leu Gly Ser Asp Asn Ala Val Leu
        835                 840                 845

Tyr Leu His Val Thr Cys Pro Leu Glu His Val His Leu Ser Leu Pro
850                 855                 860

Phe Val Thr Thr Lys Asn Lys Glu Val Asn Ala Thr Ala Val Leu Trp
865                 870                 875                 880

Pro Ser Gln Val Gly Thr Leu Thr Tyr Val Trp Trp Phe Gly Asn Asn
                885                 890                 895

Thr Glu Pro Leu Ile Thr Leu Glu Gly Ser Ile Thr Phe Thr Phe Ser
            900                 905                 910

Val Glu Gly Met Asn Thr Ile Thr Val Gln Val Ser Ala Gly Asn Thr
        915                 920                 925

Ile Leu Gln Asp Thr Lys Thr Ile Ala Val Tyr Glu Gln Phe Arg Ser
930                 935                 940

Leu Arg Leu Ser Phe Ser Pro Asn Leu Asp Asp Tyr Asn Pro Asp Ile
945                 950                 955                 960

Pro Glu Trp Arg Arg Asp Ile Ser Arg Val Val Lys Arg Ala Leu Val
                965                 970                 975

Glu Ala Thr Gly Ile Ser Ser Lys His Ile Leu Val Ala Val Leu Pro
            980                 985                 990

Gly Leu Pro Thr Ser Ala Glu Leu Phe Ile Leu Pro Tyr Gln Asp Ala
        995                 1000                1005

Thr Gly Gly Asn Lys Arg Thr Glu Asp Leu Glu Gln Ile Ser Glu
        1010                1015                1020

Ile Leu Ile Gln Lys Leu Asn Gln Asn Phe Val His Phe Glu Leu
```

-continued

Lys Pro Gly Val Arg Val Leu Val His Ala Ala His Leu Thr Ala
         1040                1045                1050

Ala Pro Leu Val Asp Leu Thr Pro Ser His Ser Gly Ser Ala Met
    1055                1060                1065

Leu Met Leu Leu Ser Val Val Phe Val Gly Leu Ala Val Phe Val
    1070                1075                1080

Ile Tyr Lys Phe Lys Arg Lys Ile Pro Gly Leu Asn Ile Tyr Ala
    1085                1090                1095

Gln Met Gln Asn Glu Lys Asp Gln Glu Met Val Ser Pro Val Ser
    1100                1105                1110

Gln Arg Glu Ser Ile Pro Asn Val Pro Gln Ser Glu Leu Met Ser
    1115                1120                1125

Pro Glu Gln Leu Val Asp Glu Lys Leu Asp Val Gln Pro Ile Glu
    1130                1135                1140

Gln Pro Gln Ala Thr Val Gln Asn Pro Arg Lys Gly Asn Ala Ala
    1145                1150                1155

Lys Val Val Trp Thr Glu Asp Phe Gln Lys Ala Cys Gly Ser Pro
    1160                1165                1170

Arg Gly Phe Lys Pro Arg Pro Gly Ala Glu Val Phe Pro Gln Leu
    1175                1180                1185

Leu Ser Pro Arg Ala Gln Lys Lys Ser Leu Pro Met
    1190                1195                1200

<210> SEQ ID NO 50
<211> LENGTH: 1121
<212> TYPE: PRT
<213> ORGANISM: Gallus gallus
<220> FEATURE:
<221> NAME/KEY: MISC_FEATURE
<222> LOCATION: (1)..(1121)
<223> OTHER INFORMATION: mature SorCS1

<400> SEQUENCE: 50

Gly Gln Ala Gly Gly Arg Arg Asn Ser Ala Arg Arg Arg Gly Arg
1               5                   10                  15

Ser Pro Arg Gly Thr Ala Gly Pro Gly Ala Ala Gly Arg Glu Pro
            20                  25                  30

Gly Gly Ser Gly Ala Ala Arg Phe Gly Leu Glu Glu Leu Arg Leu Gly
        35                  40                  45

Ser Thr Thr Phe Ala Leu Thr Gly Asp Ser Ala His Asn Gln Ala Met
    50                  55                  60

Val His Trp Ser Gly Gln Asn Ser Ser Val Ile Leu Ile Leu Thr Lys
65                  70                  75                  80

Leu Tyr Asp Tyr Asn Leu Gly Ser Ile Thr Glu Ser Ser Leu Trp Arg
                85                  90                  95

Ser Thr Asp Tyr Gly Thr Thr Tyr Glu Lys Leu Asn Asp Lys Ile Gly
            100                 105                 110

Leu Lys Thr Ile Leu Ser Tyr Leu Tyr Val Cys Pro Thr Asn Lys Arg
        115                 120                 125

Lys Ile Met Leu Leu Thr Asp Pro Glu Val Glu Ser Ser Leu Leu Ile
    130                 135                 140

Ser Thr Asp Glu Gly Ala Thr Tyr Gln Lys Tyr Arg Leu Asn Phe Tyr
145                 150                 155                 160

Ile His Ser Leu Leu Phe His Pro Lys Gln Glu Asp Trp Ile Leu Ala
                165                 170                 175

-continued

```
Tyr Ser Gln Asp Gln Lys Leu Phe Ser Ser Val Glu Phe Gly Arg Arg
            180                 185                 190

Trp Leu Leu Leu His Glu Gly Val Ala Pro Asn Arg Phe Tyr Trp Ser
        195                 200                 205

Met Met Val Ser Gly Arg Glu Pro Asp Leu Val His Leu Glu Ala Lys
    210                 215                 220

Thr Val Asp Gly His Ala Gln Tyr Ile Thr Cys Lys Met Gln Asn Cys
225                 230                 235                 240

Ser Glu Ala Ser Gln Asn Lys Pro Phe Pro Gly Tyr Ile Asp His Asn
                245                 250                 255

Ser Leu Ile Val Gln Asp Tyr Val Phe Val Gln Leu Thr Ser Gly
            260                 265                 270

Gly Arg Pro His Tyr Tyr Val Ser Tyr Arg Arg Asn Ala Phe Thr Pro
        275                 280                 285

Ile Lys Leu Pro Lys Tyr Ser Leu Pro Lys Asp Met His Val Ile Ser
    290                 295                 300

Thr Asp Glu Ser Gln Val Phe Ala Ala Val Gln Glu Trp Asn Gln Asn
305                 310                 315                 320

Asp Thr Tyr Asn Leu Tyr Ile Ser Asp Thr Arg Gly Val Tyr Phe Thr
                325                 330                 335

Leu Ala Leu Glu Asn Val Lys Ser Ser Gln Gly Leu Asp Gly Asn Val
            340                 345                 350

Met Ile Asp Leu Tyr Glu Val Ala Gly Ile Lys Gly Met Phe Leu Ala
        355                 360                 365

Asn Lys Lys Ile Asp Asn Gln Val Lys Thr Phe Ile Thr Tyr Asn Lys
    370                 375                 380

Gly Arg Asp Trp Asn Leu Leu Gln Ala Pro Asp Thr Asp Leu Lys Gly
385                 390                 395                 400

Asn Pro Val His Cys Leu Leu Pro Tyr Cys Ser Leu His Leu His Leu
                405                 410                 415

Lys Val Ser Glu Asn Pro Tyr Thr Ser Gly Asn Ile Ala Ser Arg Asp
            420                 425                 430

Thr Ala Pro Ser Ile Val Ala Ser Gly Asn Ile Gly Pro Glu Leu
        435                 440                 445

Ser Asp Asn Asp Ile Ser Met Phe Val Ser Ser Asp Ala Gly Asn Thr
    450                 455                 460

Trp Arg Gln Ile Phe Glu Glu His Ser Val Leu Tyr Leu Asp Gln
465                 470                 475                 480

Gly Gly Val Leu Val Ala Ile Lys His Thr Ser Leu Pro Ile Arg His
                485                 490                 495

Leu Trp Leu Ser Phe Asp Glu Gly Lys Ser Trp Ser Tyr Ser Phe
            500                 505                 510

Thr Ser Leu Pro Leu Phe Val Asp Gly Ile Leu Gly Glu Pro Gly Glu
        515                 520                 525

Glu Thr Leu Ile Met Thr Val Phe Gly His Phe Ser His Arg Ser Glu
    530                 535                 540

Trp Gln Leu Val Lys Ile Asp Tyr Lys Ser Ile Phe Asp Arg Arg Cys
545                 550                 555                 560

Ala Glu Glu Asp Tyr Trp Thr Trp Gln Leu His Ser Gln Gly Glu Ala
                565                 570                 575

Cys Ile Met Gly Ala Lys Arg Ile Tyr Arg Lys Arg Lys Ser Glu Lys
            580                 585                 590
```

```
Lys Cys Met Gln Gly Lys Tyr Ala Gly Ala Met Thr Ser Glu Pro Cys
            595                 600                 605

Val Cys Thr Asp Ala Asp Phe Asp Cys Asp Tyr Gly Tyr Glu Arg His
610                 615                 620

Arg Asn Gly Gln Cys Leu Pro Ala Phe Trp Tyr Asn Pro Ser Ser Leu
625                 630                 635                 640

Ser Lys Asp Cys Ser Leu Gly Gln Ser Tyr Leu Asn Ser Thr Gly Tyr
                645                 650                 655

Arg Lys Val Val Ser Asn Asn Cys Thr Asp Gly Val Arg Glu Gln Tyr
            660                 665                 670

Thr Ala Lys Pro Gln Gln Cys Pro Gly Lys Ala Pro Gln Gly Leu Arg
        675                 680                 685

Ile Ile Thr Ser Asp Gly Lys Leu Thr Ala Glu Gln Gly His Asn Val
    690                 695                 700

Thr Phe Leu Val Gln Leu Glu Glu Gly Asp Leu Gln Arg Ser Leu Ile
705                 710                 715                 720

Gln Val Asp Phe Gly Asp Gly Thr Ala Val Ser Tyr Ala Asn Leu Ser
                725                 730                 735

Ser Thr Glu Asp Gly Ile Lys His Thr Tyr Gln Asn Val Gly Ile Phe
            740                 745                 750

Arg Val Thr Val Leu Val Glu Asn Ser Leu Gly Ser Asp Asn Ala Val
        755                 760                 765

Leu Tyr Leu His Val Thr Cys Pro Leu Glu His Val His Leu Ser Leu
    770                 775                 780

Pro Phe Val Thr Thr Lys Asn Lys Glu Val Asn Ala Thr Ala Val Leu
785                 790                 795                 800

Trp Pro Ser Gln Val Gly Thr Leu Thr Tyr Val Trp Trp Phe Gly Asn
                805                 810                 815

Asn Thr Glu Pro Leu Ile Thr Leu Glu Gly Ser Ile Thr Phe Thr Phe
            820                 825                 830

Ser Val Glu Gly Met Asn Thr Ile Thr Val Gln Val Ser Ala Gly Asn
        835                 840                 845

Thr Ile Leu Gln Asp Thr Lys Thr Ile Ala Val Tyr Glu Gln Phe Arg
    850                 855                 860

Ser Leu Arg Leu Ser Phe Ser Pro Asn Leu Asp Asp Tyr Asn Pro Asp
865                 870                 875                 880

Ile Pro Glu Trp Arg Arg Asp Ile Ser Arg Val Val Lys Arg Ala Leu
                885                 890                 895

Val Glu Ala Thr Gly Ile Ser Ser Lys His Ile Leu Val Ala Val Leu
            900                 905                 910

Pro Gly Leu Pro Thr Ser Ala Glu Leu Phe Ile Leu Pro Tyr Gln Asp
        915                 920                 925

Ala Thr Gly Gly Asn Lys Arg Thr Glu Asp Leu Glu Gln Ile Ser Glu
    930                 935                 940

Ile Leu Ile Gln Lys Leu Asn Gln Asn Phe Val His Phe Glu Leu Lys
945                 950                 955                 960

Pro Gly Val Arg Val Leu Val His Ala Ala His Leu Thr Ala Ala Pro
                965                 970                 975

Leu Val Asp Leu Thr Pro Ser His Ser Gly Ser Ala Met Leu Met Leu
            980                 985                 990

Leu Ser Val Val Phe Val Gly Leu Ala Val Phe Val Ile Tyr Lys Phe
        995                 1000                1005

Lys Arg Lys Ile Pro Gly Leu Asn Ile Tyr Ala Gln Met Gln Asn
```

```
                    1010                1015                1020

Glu Lys Asp Gln Glu Met Val Ser Pro Val Ser Gln Arg Glu Ser
        1025                1030                1035

Ile Pro Asn Val Pro Gln Ser Glu Leu Met Ser Pro Glu Gln Leu
        1040                1045                1050

Val Asp Glu Lys Leu Asp Val Gln Pro Ile Glu Gln Pro Gln Ala
        1055                1060                1065

Thr Val Gln Asn Pro Arg Lys Gly Asn Ala Ala Lys Val Val Trp
        1070                1075                1080

Thr Glu Asp Phe Gln Lys Ala Cys Gly Ser Pro Arg Gly Phe Lys
        1085                1090                1095

Pro Arg Pro Gly Ala Glu Val Phe Pro Gln Leu Leu Ser Pro Arg
        1100                1105                1110

Ala Gln Lys Lys Ser Leu Pro Met
        1115                1120

<210> SEQ ID NO 51
<211> LENGTH: 986
<212> TYPE: PRT
<213> ORGANISM: Gallus gallus
<220> FEATURE:
<221> NAME/KEY: MISC_FEATURE
<222> LOCATION: (1)..(986)
<223> OTHER INFORMATION: soluble SorCS1

<400> SEQUENCE: 51

Gly Gln Ala Gly Gly Arg Arg Asn Ser Ala Arg Arg Arg Gly Arg
1               5                   10                  15

Ser Pro Arg Gly Thr Ala Gly Pro Gly Gly Ala Ala Gly Arg Glu Pro
            20                  25                  30

Gly Gly Ser Gly Ala Ala Arg Phe Gly Leu Glu Glu Leu Arg Leu Gly
            35                  40                  45

Ser Thr Thr Phe Ala Leu Thr Gly Asp Ser Ala His Asn Gln Ala Met
    50                  55                  60

Val His Trp Ser Gly Gln Asn Ser Ser Val Ile Leu Ile Leu Thr Lys
65                  70                  75                  80

Leu Tyr Asp Tyr Asn Leu Gly Ser Ile Thr Glu Ser Ser Leu Trp Arg
                85                  90                  95

Ser Thr Asp Tyr Gly Thr Thr Tyr Glu Lys Leu Asn Asp Lys Ile Gly
            100                 105                 110

Leu Lys Thr Ile Leu Ser Tyr Leu Tyr Val Cys Pro Thr Asn Lys Arg
        115                 120                 125

Lys Ile Met Leu Leu Thr Asp Pro Glu Val Glu Ser Ser Leu Leu Ile
    130                 135                 140

Ser Thr Asp Glu Gly Ala Thr Tyr Gln Lys Tyr Arg Leu Asn Phe Tyr
145                 150                 155                 160

Ile His Ser Leu Leu Phe His Pro Lys Gln Glu Asp Trp Ile Leu Ala
                165                 170                 175

Tyr Ser Gln Asp Gln Lys Leu Phe Ser Ser Val Glu Phe Gly Arg Arg
            180                 185                 190

Trp Leu Leu Leu His Glu Gly Val Ala Pro Asn Arg Phe Tyr Trp Ser
        195                 200                 205

Met Met Val Ser Gly Arg Glu Pro Asp Leu Val His Leu Glu Ala Lys
    210                 215                 220

Thr Val Asp Gly His Ala Gln Tyr Ile Thr Cys Lys Met Gln Asn Cys
225                 230                 235                 240
```

```
Ser Glu Ala Ser Gln Asn Lys Pro Phe Pro Gly Tyr Ile Asp His Asn
                245                 250                 255

Ser Leu Ile Val Gln Asp Asp Tyr Val Phe Val Gln Leu Thr Ser Gly
                260                 265                 270

Gly Arg Pro His Tyr Tyr Val Ser Tyr Arg Arg Asn Ala Phe Thr Pro
                275                 280                 285

Ile Lys Leu Pro Lys Tyr Ser Leu Pro Lys Asp Met His Val Ile Ser
                290                 295                 300

Thr Asp Glu Ser Gln Val Phe Ala Ala Val Gln Glu Trp Asn Gln Asn
305                 310                 315                 320

Asp Thr Tyr Asn Leu Tyr Ile Ser Asp Thr Arg Gly Val Tyr Phe Thr
                325                 330                 335

Leu Ala Leu Glu Asn Val Lys Ser Ser Gln Gly Leu Asp Gly Asn Val
                340                 345                 350

Met Ile Asp Leu Tyr Glu Val Ala Gly Ile Lys Gly Met Phe Leu Ala
                355                 360                 365

Asn Lys Lys Ile Asp Asn Gln Val Lys Thr Phe Ile Thr Tyr Asn Lys
                370                 375                 380

Gly Arg Asp Trp Asn Leu Leu Gln Ala Pro Asp Thr Asp Leu Lys Gly
385                 390                 395                 400

Asn Pro Val His Cys Leu Leu Pro Tyr Cys Ser Leu His Leu His Leu
                405                 410                 415

Lys Val Ser Glu Asn Pro Tyr Thr Ser Gly Asn Ile Ala Ser Arg Asp
                420                 425                 430

Thr Ala Pro Ser Ile Ile Val Ala Ser Gly Asn Ile Gly Pro Glu Leu
                435                 440                 445

Ser Asp Asn Asp Ile Ser Met Phe Val Ser Ser Asp Ala Gly Asn Thr
                450                 455                 460

Trp Arg Gln Ile Phe Glu Glu His Ser Val Leu Tyr Leu Asp Gln
465                 470                 475                 480

Gly Gly Val Leu Val Ala Ile Lys His Thr Ser Leu Pro Ile Arg His
                485                 490                 495

Leu Trp Leu Ser Phe Asp Glu Gly Lys Ser Trp Ser Tyr Ser Phe
                500                 505                 510

Thr Ser Leu Pro Leu Phe Val Asp Gly Ile Leu Gly Glu Pro Gly Glu
                515                 520                 525

Glu Thr Leu Ile Met Thr Val Phe Gly His Phe Ser His Arg Ser Glu
530                 535                 540

Trp Gln Leu Val Lys Ile Asp Tyr Lys Ser Ile Phe Asp Arg Arg Cys
545                 550                 555                 560

Ala Glu Glu Asp Tyr Trp Thr Trp Gln Leu His Ser Gln Gly Glu Ala
                565                 570                 575

Cys Ile Met Gly Ala Lys Arg Ile Tyr Arg Lys Arg Lys Ser Glu Lys
                580                 585                 590

Lys Cys Met Gln Gly Lys Tyr Ala Gly Ala Met Thr Ser Glu Pro Cys
                595                 600                 605

Val Cys Thr Asp Ala Asp Phe Asp Cys Asp Tyr Gly Tyr Glu Arg His
                610                 615                 620

Arg Asn Gly Gln Cys Leu Pro Ala Phe Trp Tyr Asn Pro Ser Ser Leu
625                 630                 635                 640

Ser Lys Asp Cys Ser Leu Gly Gln Ser Tyr Leu Asn Ser Thr Gly Tyr
                645                 650                 655
```

```
Arg Lys Val Val Ser Asn Asn Cys Thr Asp Gly Val Arg Glu Gln Tyr
            660                 665                 670

Thr Ala Lys Pro Gln Gln Cys Pro Gly Lys Ala Pro Gln Gly Leu Arg
            675                 680                 685

Ile Ile Thr Ser Asp Gly Lys Leu Thr Ala Glu Gln Gly His Asn Val
            690                 695                 700

Thr Phe Leu Val Gln Leu Glu Glu Gly Asp Leu Gln Arg Ser Leu Ile
705                 710                 715                 720

Gln Val Asp Phe Gly Asp Gly Thr Ala Val Ser Tyr Ala Asn Leu Ser
            725                 730                 735

Ser Thr Glu Asp Gly Ile Lys His Thr Tyr Gln Asn Val Gly Ile Phe
            740                 745                 750

Arg Val Thr Val Leu Val Glu Asn Ser Leu Gly Ser Asp Asn Ala Val
            755                 760                 765

Leu Tyr Leu His Val Thr Cys Pro Leu Glu His Val His Leu Ser Leu
            770                 775                 780

Pro Phe Val Thr Thr Lys Asn Lys Glu Val Asn Ala Thr Ala Val Leu
785                 790                 795                 800

Trp Pro Ser Gln Val Gly Thr Leu Thr Tyr Val Trp Trp Phe Gly Asn
            805                 810                 815

Asn Thr Glu Pro Leu Ile Thr Leu Glu Gly Ser Ile Thr Phe Thr Phe
            820                 825                 830

Ser Val Glu Gly Met Asn Thr Ile Thr Val Gln Val Ser Ala Gly Asn
            835                 840                 845

Thr Ile Leu Gln Asp Thr Lys Thr Ile Ala Val Tyr Glu Gln Phe Arg
850                 855                 860

Ser Leu Arg Leu Ser Phe Ser Pro Asn Leu Asp Asp Tyr Asn Pro Asp
865                 870                 875                 880

Ile Pro Glu Trp Arg Arg Asp Ile Ser Arg Val Val Lys Arg Ala Leu
            885                 890                 895

Val Glu Ala Thr Gly Ile Ser Ser Lys His Ile Leu Val Ala Val Leu
            900                 905                 910

Pro Gly Leu Pro Thr Ser Ala Glu Leu Phe Ile Leu Pro Tyr Gln Asp
            915                 920                 925

Ala Thr Gly Gly Asn Lys Arg Thr Glu Asp Leu Glu Gln Ile Ser Glu
            930                 935                 940

Ile Leu Ile Gln Lys Leu Asn Gln Asn Phe Val His Phe Glu Leu Lys
945                 950                 955                 960

Pro Gly Val Arg Val Leu Val His Ala Ala His Leu Thr Ala Ala Pro
            965                 970                 975

Leu Val Asp Leu Thr Pro Ser His Ser Gly
            980                 985

<210> SEQ ID NO 52
<211> LENGTH: 831
<212> TYPE: PRT
<213> ORGANISM: Homo sapiens
<220> FEATURE:
<221> NAME/KEY: MISC_FEATURE
<222> LOCATION: (1)..(831)
<223> OTHER INFORMATION: preproSortilin

<400> SEQUENCE: 52

Met Glu Arg Pro Trp Gly Ala Ala Asp Gly Leu Ser Arg Trp Pro His
1               5                   10                  15

Gly Leu Gly Leu Leu Leu Leu Gln Leu Leu Pro Pro Ser Thr Leu
```

```
                20                  25                  30
Ser Gln Asp Arg Leu Asp Ala Pro Pro Pro Ala Ala Pro Leu Pro
         35                  40                  45
Arg Trp Ser Gly Pro Ile Gly Val Ser Trp Gly Leu Arg Ala Ala
 50                  55                  60
Ala Gly Gly Ala Phe Pro Arg Gly Gly Arg Trp Arg Ser Ala Pro
 65                  70                  75                  80
Gly Glu Asp Glu Glu Cys Gly Arg Val Arg Asp Phe Val Ala Lys Leu
                 85                  90                  95
Ala Asn Asn Thr His Gln His Val Phe Asp Asp Leu Arg Gly Ser Val
             100                 105                 110
Ser Leu Ser Trp Val Gly Asp Ser Thr Gly Val Ile Leu Val Leu Thr
             115                 120                 125
Thr Phe His Val Pro Leu Val Ile Met Thr Phe Gly Gln Ser Lys Leu
             130                 135                 140
Tyr Arg Ser Glu Asp Tyr Gly Lys Asn Phe Lys Asp Ile Thr Asp Leu
145                 150                 155                 160
Ile Asn Asn Thr Phe Ile Arg Thr Glu Phe Gly Met Ala Ile Gly Pro
             165                 170                 175
Glu Asn Ser Gly Lys Val Val Leu Thr Ala Glu Val Ser Gly Gly Ser
             180                 185                 190
Arg Gly Gly Arg Ile Phe Arg Ser Ser Asp Phe Ala Lys Asn Phe Val
             195                 200                 205
Gln Thr Asp Leu Pro Phe His Pro Leu Thr Gln Met Met Tyr Ser Pro
             210                 215                 220
Gln Asn Ser Asp Tyr Leu Leu Ala Leu Ser Thr Glu Asn Gly Leu Trp
225                 230                 235                 240
Val Ser Lys Asn Phe Gly Gly Lys Trp Glu Glu Ile His Lys Ala Val
             245                 250                 255
Cys Leu Ala Lys Trp Gly Ser Asp Asn Thr Ile Phe Phe Thr Thr Tyr
             260                 265                 270
Ala Asn Gly Ser Cys Lys Ala Asp Leu Gly Ala Leu Glu Leu Trp Arg
             275                 280                 285
Thr Ser Asp Leu Gly Lys Ser Phe Lys Thr Ile Gly Val Lys Ile Tyr
             290                 295                 300
Ser Phe Gly Leu Gly Gly Arg Phe Leu Phe Ala Ser Val Met Ala Asp
305                 310                 315                 320
Lys Asp Thr Thr Arg Arg Ile His Val Ser Thr Asp Gln Gly Asp Thr
             325                 330                 335
Trp Ser Met Ala Gln Leu Pro Ser Val Gly Gln Glu Gln Phe Tyr Ser
             340                 345                 350
Ile Leu Ala Ala Asn Asp Asp Met Val Phe Met His Val Asp Glu Pro
             355                 360                 365
Gly Asp Thr Gly Phe Gly Thr Ile Phe Thr Ser Asp Asp Arg Gly Ile
             370                 375                 380
Val Tyr Ser Lys Ser Leu Asp Arg His Leu Tyr Thr Thr Thr Gly Gly
385                 390                 395                 400
Glu Thr Asp Phe Thr Asn Val Thr Ser Leu Arg Gly Val Tyr Ile Thr
             405                 410                 415
Ser Val Leu Ser Glu Asp Asn Ser Ile Gln Thr Met Ile Thr Phe Asp
             420                 425                 430
Gln Gly Gly Arg Trp Thr His Leu Arg Lys Pro Glu Asn Ser Glu Cys
             435                 440                 445
```

```
Asp Ala Thr Ala Lys Asn Lys Asn Glu Cys Ser Leu His Ile His Ala
        450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
        755                 760                 765

Val Thr Val Val Ala Gly Val Leu Ile Val Lys Lys Tyr Val Cys Gly
    770                 775                 780

Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
                805                 810                 815

Asn Lys Ser Gly Tyr His Asp Asp Ser Asp Glu Asp Leu Leu Glu
            820                 825                 830

<210> SEQ ID NO 53
<211> LENGTH: 2214
<212> TYPE: PRT
<213> ORGANISM: Homo sapiens
<220> FEATURE:
```

<220> NAME/KEY: MISC_FEATURE
<222> LOCATION: (1)..(2214)
<223> OTHER INFORMATION: preproSorLA

<400> SEQUENCE: 53

```
Met Ala Thr Arg Ser Ser Arg Arg Glu Ser Arg Leu Pro Phe Leu Phe
1               5                   10                  15

Thr Leu Val Ala Leu Leu Pro Pro Gly Ala Leu Cys Glu Val Trp Thr
            20                  25                  30

Gln Arg Leu His Gly Gly Ser Ala Pro Leu Pro Gln Asp Arg Gly Phe
        35                  40                  45

Leu Val Val Gln Gly Asp Pro Arg Glu Leu Arg Leu Trp Ala Arg Gly
    50                  55                  60

Asp Ala Arg Gly Ala Ser Arg Ala Asp Glu Lys Pro Leu Arg Arg Lys
65                  70                  75                  80

Arg Ser Ala Ala Leu Gln Pro Glu Pro Ile Lys Val Tyr Gly Gln Val
                85                  90                  95

Ser Leu Asn Asp Ser His Asn Gln Met Val Val His Trp Ala Gly Glu
            100                 105                 110

Lys Ser Asn Val Ile Val Ala Leu Ala Arg Asp Ser Leu Ala Leu Ala
        115                 120                 125

Arg Pro Lys Ser Ser Asp Val Tyr Val Ser Tyr Asp Tyr Gly Lys Ser
    130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
            180                 185                 190

Phe Cys Asn Thr Leu Gln Gly Phe Ser Ile Pro Phe Arg Ala Ala Asp
        195                 200                 205

Leu Leu Leu His Ser Lys Ala Ser Asn Leu Leu Gly Phe Asp Arg
    210                 215                 220

Ser His Pro Asn Lys Gln Leu Trp Lys Ser Asp Asp Phe Gly Gln Thr
225                 230                 235                 240

Trp Ile Met Ile Gln Glu His Val Lys Ser Phe Ser Trp Gly Ile Asp
                245                 250                 255

Pro Tyr Asp Lys Pro Asn Thr Ile Tyr Ile Glu Arg His Glu Pro Ser
            260                 265                 270

Gly Tyr Ser Thr Val Phe Arg Ser Thr Asp Phe Phe Gln Ser Arg Glu
        275                 280                 285

Asn Gln Glu Val Ile Leu Glu Glu Val Arg Asp Phe Gln Leu Arg Asp
    290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                325                 330                 335

Ala Ala Gln Phe Val Thr Arg His Pro Ile Asn Glu Tyr Tyr Ile Ala
            340                 345                 350

Asp Ala Ser Glu Asp Gln Val Phe Val Cys Val Ser His Ser Asn Asn
        355                 360                 365

Arg Thr Asn Leu Tyr Ile Ser Glu Ala Glu Gly Leu Lys Phe Ser Leu
    370                 375                 380

Ser Leu Glu Asn Val Leu Tyr Tyr Ser Pro Gly Gly Ala Gly Ser Asp
```

```
                    385                 390                 395                 400
            Thr Leu Val Arg Tyr Phe Ala Asn Glu Pro Phe Ala Asp Phe His Arg
                            405                 410                 415

Val Glu Gly Leu Gln Gly Val Tyr Ile Ala Thr Leu Ile Asn Gly Ser
                            420                 425                 430

Met Asn Glu Glu Asn Met Arg Ser Val Ile Thr Phe Asp Lys Gly Gly
                        435                 440                 445

Thr Trp Glu Phe Leu Gln Ala Pro Ala Phe Thr Gly Tyr Gly Glu Lys
                        450                 455                 460

Ile Asn Cys Glu Leu Ser Gln Gly Cys Ser Leu His Leu Ala Gln Arg
            465                 470                 475                 480

Leu Ser Gln Leu Leu Asn Leu Gln Leu Arg Arg Met Pro Ile Leu Ser
                                485                 490                 495

Lys Glu Ser Ala Pro Gly Leu Ile Ile Ala Thr Gly Ser Val Gly Lys
                            500                 505                 510

Asn Leu Ala Ser Lys Thr Asn Val Tyr Ile Ser Ser Ala Gly Ala
                            515                 520                 525

Arg Trp Arg Glu Ala Leu Pro Gly Pro His Tyr Tyr Thr Trp Gly Asp
                            530                 535                 540

His Gly Gly Ile Ile Thr Ala Ile Ala Gln Gly Met Glu Thr Asn Glu
            545                 550                 555                 560

Leu Lys Tyr Ser Thr Asn Glu Gly Glu Thr Trp Lys Thr Phe Ile Phe
                                565                 570                 575

Ser Glu Lys Pro Val Phe Val Tyr Gly Leu Leu Thr Glu Pro Gly Glu
                            580                 585                 590

Lys Ser Thr Val Phe Thr Ile Phe Gly Ser Asn Lys Glu Asn Val His
                        595                 600                 605

Ser Trp Leu Ile Leu Gln Val Asn Ala Thr Asp Ala Leu Gly Val Pro
                        610                 615                 620

Cys Thr Glu Asn Asp Tyr Lys Leu Trp Ser Pro Ser Asp Glu Arg Gly
            625                 630                 635                 640

Asn Glu Cys Leu Leu Gly His Lys Thr Val Phe Lys Arg Arg Thr Pro
                                645                 650                 655

His Ala Thr Cys Phe Asn Gly Glu Asp Phe Asp Arg Pro Val Val Val
                            660                 665                 670

Ser Asn Cys Ser Cys Thr Arg Glu Asp Tyr Glu Cys Asp Phe Gly Phe
                        675                 680                 685

Lys Met Ser Glu Asp Leu Ser Leu Glu Val Cys Val Pro Asp Pro Glu
                        690                 695                 700

Phe Ser Gly Lys Ser Tyr Ser Pro Val Pro Cys Pro Val Gly Ser
            705                 710                 715                 720

Thr Tyr Arg Arg Thr Arg Gly Tyr Arg Lys Ile Ser Gly Asp Thr Cys
                                725                 730                 735

Ser Gly Gly Asp Val Glu Ala Arg Leu Glu Gly Glu Leu Val Pro Cys
                            740                 745                 750

Pro Leu Ala Glu Glu Asn Glu Phe Ile Leu Tyr Ala Val Arg Lys Ser
                        755                 760                 765

Ile Tyr Arg Tyr Asp Leu Ala Ser Gly Ala Thr Glu Gln Leu Pro Leu
                        770                 775                 780

Thr Gly Leu Arg Ala Ala Val Ala Leu Asp Phe Asp Tyr Glu His Asn
            785                 790                 795                 800

Cys Leu Tyr Trp Ser Asp Leu Ala Leu Asp Val Ile Gln Arg Leu Cys
                                805                 810                 815
```

```
Leu Asn Gly Ser Thr Gly Gln Glu Val Ile Ile Asn Ser Gly Leu Glu
            820                 825                 830

Thr Val Glu Ala Leu Ala Phe Glu Pro Leu Ser Gln Leu Leu Tyr Trp
            835                 840                 845

Val Asp Ala Gly Phe Lys Lys Ile Glu Val Ala Asn Pro Asp Gly Asp
850                 855                 860

Phe Arg Leu Thr Ile Val Asn Ser Ser Val Leu Asp Arg Pro Arg Ala
865                 870                 875                 880

Leu Val Leu Val Pro Gln Glu Gly Val Met Phe Trp Thr Asp Trp Gly
                885                 890                 895

Asp Leu Lys Pro Gly Ile Tyr Arg Ser Asn Met Asp Gly Ser Ala Ala
            900                 905                 910

Tyr His Leu Val Ser Glu Asp Val Lys Trp Pro Asn Gly Ile Ser Val
            915                 920                 925

Asp Asp Gln Trp Ile Tyr Trp Thr Asp Ala Tyr Leu Glu Cys Ile Glu
        930                 935                 940

Arg Ile Thr Phe Ser Gly Gln Gln Arg Ser Val Ile Leu Asp Asn Leu
945                 950                 955                 960

Pro His Pro Tyr Ala Ile Ala Val Phe Lys Asn Glu Ile Tyr Trp Asp
                965                 970                 975

Asp Trp Ser Gln Leu Ser Ile Phe Arg Ala Ser Lys Tyr Ser Gly Ser
            980                 985                 990

Gln Met Glu Ile Leu Ala Asn Gln Leu Thr Gly Leu Met Asp Met Lys
            995                 1000                1005

Ile Phe Tyr Lys Gly Lys Asn Thr Gly Ser Asn Ala Cys Val Pro
            1010                1015                1020

Arg Pro Cys Ser Leu Leu Cys Leu Pro Lys Ala Asn Asn Ser Arg
        1025                1030                1035

Ser Cys Arg Cys Pro Glu Asp Val Ser Ser Ser Val Leu Pro Ser
        1040                1045                1050

Gly Asp Leu Met Cys Asp Cys Pro Gln Gly Tyr Gln Leu Lys Asn
        1055                1060                1065

Asn Thr Cys Val Lys Glu Glu Asn Thr Cys Leu Arg Asn Gln Tyr
        1070                1075                1080

Arg Cys Ser Asn Gly Asn Cys Ile Asn Ser Ile Trp Trp Cys Asp
        1085                1090                1095

Phe Asp Asn Asp Cys Gly Asp Met Ser Asp Glu Arg Asn Cys Pro
        1100                1105                1110

Thr Thr Ile Cys Asp Leu Asp Thr Gln Phe Arg Cys Gln Glu Ser
        1115                1120                1125

Gly Thr Cys Ile Pro Leu Ser Tyr Lys Cys Asp Leu Glu Asp Asp
        1130                1135                1140

Cys Gly Asp Asn Ser Asp Glu Ser His Cys Glu Met His Gln Cys
        1145                1150                1155

Arg Ser Asp Glu Tyr Asn Cys Ser Ser Gly Met Cys Ile Arg Ser
        1160                1165                1170

Ser Trp Val Cys Asp Gly Asp Asn Asp Cys Arg Asp Trp Ser Asp
        1175                1180                1185

Glu Ala Asn Cys Thr Ala Ile Tyr His Thr Cys Glu Ala Ser Asn
        1190                1195                1200

Phe Gln Cys Arg Asn Gly His Cys Ile Pro Gln Arg Trp Ala Cys
        1205                1210                1215
```

```
Asp Gly Asp Thr Asp Cys Gln Asp Gly Ser Asp Glu Asp Pro Val
    1220                1225                1230

Asn Cys Glu Lys Lys Cys Asn Gly Phe Arg Cys Pro Asn Gly Thr
    1235                1240                1245

Cys Ile Pro Ser Ser Lys His Cys Asp Gly Leu Arg Asp Cys Ser
    1250                1255                1260

Asp Gly Ser Asp Glu Gln His Cys Glu Pro Leu Cys Thr His Phe
    1265                1270                1275

Met Asp Phe Val Cys Lys Asn Arg Gln Gln Cys Leu Phe His Ser
    1280                1285                1290

Met Val Cys Asp Gly Ile Ile Gln Cys Arg Asp Gly Ser Asp Glu
    1295                1300                1305

Asp Ala Ala Phe Ala Gly Cys Ser Gln Asp Pro Glu Phe His Lys
    1310                1315                1320

Val Cys Asp Glu Phe Gly Phe Gln Cys Gln Asn Gly Val Cys Ile
    1325                1330                1335

Ser Leu Ile Trp Lys Cys Asp Gly Met Asp Asp Cys Gly Asp Tyr
    1340                1345                1350

Ser Asp Glu Ala Asn Cys Glu Asn Pro Thr Glu Ala Pro Asn Cys
    1355                1360                1365

Ser Arg Tyr Phe Gln Phe Arg Cys Glu Asn Gly His Cys Ile Pro
    1370                1375                1380

Asn Arg Trp Lys Cys Asp Arg Glu Asn Asp Cys Gly Asp Trp Ser
    1385                1390                1395

Asp Glu Lys Asp Cys Gly Asp Ser His Ile Leu Pro Phe Ser Thr
    1400                1405                1410

Pro Gly Pro Ser Thr Cys Leu Pro Asn Tyr Tyr Arg Cys Ser Ser
    1415                1420                1425

Gly Thr Cys Val Met Asp Thr Trp Val Cys Asp Gly Tyr Arg Asp
    1430                1435                1440

Cys Ala Asp Gly Ser Asp Glu Glu Ala Cys Pro Leu Leu Ala Asn
    1445                1450                1455

Val Thr Ala Ala Ser Thr Pro Thr Gln Leu Gly Arg Cys Asp Arg
    1460                1465                1470

Phe Glu Phe Glu Cys His Gln Pro Lys Thr Cys Ile Pro Asn Trp
    1475                1480                1485

Lys Arg Cys Asp Gly His Gln Asp Cys Gln Asp Gly Arg Asp Glu
    1490                1495                1500

Ala Asn Cys Pro Thr His Ser Thr Leu Thr Cys Met Ser Arg Glu
    1505                1510                1515

Phe Gln Cys Glu Asp Gly Glu Ala Cys Ile Val Leu Ser Glu Arg
    1520                1525                1530

Cys Asp Gly Phe Leu Asp Cys Ser Asp Glu Ser Asp Glu Lys Ala
    1535                1540                1545

Cys Ser Asp Glu Leu Thr Val Tyr Lys Val Gln Asn Leu Gln Trp
    1550                1555                1560

Thr Ala Asp Phe Ser Gly Asp Val Thr Leu Thr Trp Met Arg Pro
    1565                1570                1575

Lys Lys Met Pro Ser Ala Ser Cys Val Tyr Asn Val Tyr Tyr Arg
    1580                1585                1590

Val Val Gly Glu Ser Ile Trp Lys Thr Leu Glu Thr His Ser Asn
    1595                1600                1605

Lys Thr Asn Thr Val Leu Lys Val Leu Lys Pro Asp Thr Thr Tyr
```

-continued

```
            1610                1615                1620
Gln Val Lys Val Gln Val Gln Cys Leu Ser Lys Ala His Asn Thr
        1625                1630                1635
Asn Asp Phe Val Thr Leu Arg Thr Pro Glu Gly Leu Pro Asp Ala
    1640                1645                1650
Pro Arg Asn Leu Gln Leu Ser Leu Pro Arg Glu Ala Glu Gly Val
1655                1660                1665
Ile Val Gly His Trp Ala Pro Pro Ile His Thr His Gly Leu Ile
1670                1675                1680
Arg Glu Tyr Ile Val Glu Tyr Ser Arg Ser Gly Ser Lys Met Trp
1685                1690                1695
Ala Ser Gln Arg Ala Ala Ser Asn Phe Thr Glu Ile Lys Asn Leu
1700                1705                1710
Leu Val Asn Thr Leu Tyr Thr Val Arg Val Ala Ala Val Thr Ser
1715                1720                1725
Arg Gly Ile Gly Asn Trp Ser Asp Ser Lys Ser Ile Thr Thr Ile
1730                1735                1740
Lys Gly Lys Val Ile Pro Pro Asp Ile His Ile Asp Ser Tyr
1745                1750                1755
Gly Glu Asn Tyr Leu Ser Phe Thr Leu Thr Met Glu Ser Asp Ile
1760                1765                1770
Lys Val Asn Gly Tyr Val Val Asn Leu Phe Trp Ala Phe Asp Thr
1775                1780                1785
His Lys Gln Glu Arg Arg Thr Leu Asn Phe Arg Gly Ser Ile Leu
1790                1795                1800
Ser His Lys Val Gly Asn Leu Thr Ala His Thr Ser Tyr Glu Ile
1805                1810                1815
Ser Ala Trp Ala Lys Thr Asp Leu Gly Asp Ser Pro Leu Ala Phe
1820                1825                1830
Glu His Val Met Thr Arg Gly Val Arg Pro Pro Ala Pro Ser Leu
1835                1840                1845
Lys Ala Lys Ala Ile Asn Gln Thr Ala Val Glu Cys Thr Trp Thr
1850                1855                1860
Gly Pro Arg Asn Val Val Tyr Gly Ile Phe Tyr Ala Thr Ser Phe
1865                1870                1875
Leu Asp Leu Tyr Arg Asn Pro Lys Ser Leu Thr Thr Ser Leu His
1880                1885                1890
Asn Lys Thr Val Ile Val Ser Lys Asp Glu Gln Tyr Leu Phe Leu
1895                1900                1905
Val Arg Val Val Val Pro Tyr Gln Gly Pro Ser Ser Asp Tyr Val
1910                1915                1920
Val Val Lys Met Ile Pro Asp Ser Arg Leu Pro Pro Arg His Leu
1925                1930                1935
His Val Val His Thr Gly Lys Thr Ser Val Val Ile Lys Trp Glu
1940                1945                1950
Ser Pro Tyr Asp Ser Pro Asp Gln Asp Leu Leu Tyr Ala Ile Ala
1955                1960                1965
Val Lys Asp Leu Ile Arg Lys Thr Asp Arg Ser Tyr Lys Val Lys
1970                1975                1980
Ser Arg Asn Ser Thr Val Glu Tyr Thr Leu Asn Lys Leu Glu Pro
1985                1990                1995
Gly Gly Lys Tyr His Ile Ile Val Gln Leu Gly Asn Met Ser Lys
2000                2005                2010
```

```
Asp Ser Ser Ile Lys Ile Thr Thr Val Ser Leu Ser Ala Pro Asp
    2015                2020                2025

Ala Leu Lys Ile Ile Thr Glu Asn Asp His Val Leu Leu Phe Trp
    2030                2035                2040

Lys Ser Leu Ala Leu Lys Glu Lys His Phe Asn Glu Ser Arg Gly
    2045                2050                2055

Tyr Glu Ile His Met Phe Asp Ser Ala Met Asn Ile Thr Ala Tyr
    2060                2065                2070

Leu Gly Asn Thr Thr Asp Asn Phe Phe Lys Ile Ser Asn Leu Lys
    2075                2080                2085

Met Gly His Asn Tyr Thr Phe Thr Val Gln Ala Arg Cys Leu Phe
    2090                2095                2100

Gly Asn Gln Ile Cys Gly Glu Pro Ala Ile Leu Leu Tyr Asp Glu
    2105                2110                2115

Leu Gly Ser Gly Ala Asp Ala Ser Ala Thr Gln Ala Ala Arg Ser
    2120                2125                2130

Thr Asp Val Ala Ala Val Val Val Pro Ile Leu Phe Leu Ile Leu
    2135                2140                2145

Leu Ser Leu Gly Val Gly Phe Ala Ile Leu Tyr Thr Lys His Arg
    2150                2155                2160

Arg Leu Gln Ser Ser Phe Thr Ala Phe Ala Asn Ser His Tyr Ser
    2165                2170                2175

Ser Arg Leu Gly Ser Ala Ile Phe Ser Ser Gly Asp Asp Leu Gly
    2180                2185                2190

Glu Asp Asp Glu Asp Ala Pro Met Ile Thr Gly Phe Ser Asp Asp
    2195                2200                2205

Val Pro Met Val Ile Ala
    2210
```

<210> SEQ ID NO 54
<211> LENGTH: 1159
<212> TYPE: PRT
<213> ORGANISM: Homo sapiens
<220> FEATURE:
<221> NAME/KEY: MISC_FEATURE
<222> LOCATION: (1)..(1159)
<223> OTHER INFORMATION: preproSorCS2

<400> SEQUENCE: 54

```
Met Ala His Arg Gly Pro Ser Arg Ala Ser Lys Gly Pro Gly Pro Thr
1               5                   10                  15

Ala Arg Ala Pro Ser Pro Gly Ala Pro Pro Pro Arg Ser Pro Arg
            20                  25                  30

Ser Arg Pro Leu Leu Leu Leu Leu Leu Leu Gly Ala Cys Gly Ala
        35                  40                  45

Ala Gly Arg Ser Pro Glu Pro Gly Arg Leu Gly Pro His Ala Gln Leu
    50                  55                      60

Thr Arg Val Pro Arg Ser Pro Ala Gly Arg Ala Glu Pro Gly Gly
65                  70                  75                  80

Gly Glu Asp Arg Gln Ala Arg Gly Thr Glu Pro Gly Ala Pro Gly Pro
                85                  90                      95

Ser Pro Gly Pro Ala Pro Gly Pro Gly Glu Asp Gly Ala Pro Ala Ala
            100                 105                 110

Gly Tyr Arg Arg Trp Glu Arg Ala Ala Pro Leu Ala Gly Val Ala Ser
        115                 120                 125
```

```
Arg Ala Gln Val Ser Leu Ile Ser Thr Ser Phe Val Leu Lys Gly Asp
    130                 135                 140
Ala Thr His Asn Gln Ala Met Val His Trp Thr Gly Glu Asn Ser Ser
145                 150                 155                 160
Val Ile Leu Ile Leu Thr Lys Tyr Tyr His Ala Asp Met Gly Lys Val
                165                 170                 175
Leu Glu Ser Ser Leu Trp Arg Ser Ser Asp Phe Gly Thr Ser Tyr Thr
            180                 185                 190
Lys Leu Thr Leu Gln Pro Gly Val Thr Val Ile Asp Asn Phe Tyr
        195                 200                 205
Ile Cys Pro Thr Asn Lys Arg Lys Val Ile Leu Val Ser Ser Ser Leu
210                 215                 220
Ser Asp Arg Asp Gln Ser Leu Phe Leu Ser Ala Asp Glu Gly Ala Thr
225                 230                 235                 240
Phe Gln Lys Gln Pro Ile Pro Phe Val Glu Thr Leu Ile Phe His
                245                 250                 255
Pro Lys Glu Glu Asp Lys Val Leu Ala Tyr Thr Lys Gly Ser Lys Leu
            260                 265                 270
Tyr Val Ser Ser Asp Leu Gly Lys Lys Trp Thr Leu Leu Gln Glu Arg
        275                 280                 285
Val Thr Lys Asp His Val Phe Trp Ser Val Ser Gly Val Asp Ala Asp
    290                 295                 300
Pro Asp Leu Val His Val Glu Ala Gln Asp Leu Gly Gly Asp Phe Arg
305                 310                 315                 320
Tyr Val Thr Cys Ala Ile His Asn Cys Ser Glu Lys Met Leu Thr Ala
                325                 330                 335
Pro Phe Ala Gly Pro Ile Asp His Gly Ser Leu Thr Val Gln Asp Asp
            340                 345                 350
Tyr Ile Phe Phe Lys Ala Thr Ser Ala Asn Gln Thr Lys Tyr Tyr Val
        355                 360                 365
Ser Tyr Arg Arg Asn Glu Phe Val Leu Met Lys Leu Pro Lys Tyr Ala
    370                 375                 380
Leu Pro Lys Asp Leu Gln Ile Ile Ser Thr Asp Glu Ser Gln Val Phe
385                 390                 395                 400
Val Ala Val Gln Glu Trp Tyr Gln Met Asp Thr Tyr Asn Leu Tyr Gln
                405                 410                 415
Ser Asp Pro Arg Gly Val Arg Tyr Ala Leu Val Leu Gln Asp Val Arg
            420                 425                 430
Ser Ser Arg Gln Ala Glu Glu Ser Val Leu Ile Asp Ile Leu Glu Val
        435                 440                 445
Arg Gly Val Lys Gly Val Phe Leu Ala Asn Gln Lys Ile Asp Gly Lys
    450                 455                 460
Val Met Thr Leu Ile Thr Tyr Asn Lys Gly Arg Asp Trp Asp Tyr Leu
465                 470                 475                 480
Arg Pro Pro Ser Met Asp Met Asn Gly Lys Pro Thr Asn Cys Lys Pro
                485                 490                 495
Pro Asp Cys His Leu His Leu His Leu Arg Trp Ala Asp Asn Pro Tyr
            500                 505                 510
Val Ser Gly Thr Val His Thr Lys Asp Thr Ala Pro Gly Leu Ile Met
        515                 520                 525
Gly Ala Gly Asn Leu Gly Ser Gln Leu Val Glu Tyr Lys Glu Glu Met
    530                 535                 540
Tyr Ile Thr Ser Asp Cys Gly His Thr Trp Arg Gln Val Phe Glu Glu
```

```
            545                 550                 555                 560
        Glu His His Ile Leu Tyr Leu Asp His Gly Gly Val Ile Val Ala Ile
                        565                 570                 575

Lys Asp Thr Ser Ile Pro Leu Lys Ile Leu Lys Phe Ser Val Asp Glu
                        580                 585                 590

Gly Leu Thr Trp Ser Thr His Asn Phe Thr Ser Thr Ser Val Phe Val
                        595                 600                 605

Asp Gly Leu Leu Ser Glu Pro Gly Asp Glu Thr Leu Val Met Thr Val
                        610                 615                 620

Phe Gly His Ile Ser Phe Arg Ser Asp Trp Glu Leu Val Lys Val Asp
        625                 630                 635                 640

Phe Arg Pro Ser Phe Ser Arg Gln Cys Gly Glu Asp Tyr Ser Ser
                        645                 650                 655

Trp Glu Leu Ser Asn Leu Gln Gly Asp Arg Cys Ile Met Gly Gln Gln
                        660                 665                 670

Arg Ser Phe Arg Lys Arg Lys Ser Thr Ser Trp Cys Ile Lys Gly Arg
                        675                 680                 685

Ser Phe Thr Ser Ala Leu Thr Ser Arg Val Cys Glu Cys Arg Asp Ser
                        690                 695                 700

Asp Phe Leu Cys Asp Tyr Gly Phe Glu Arg Ser Pro Ser Ser Glu Ser
        705                 710                 715                 720

Ser Thr Asn Lys Cys Ser Ala Asn Phe Trp Phe Asn Pro Leu Ser Pro
                        725                 730                 735

Pro Asp Asp Cys Ala Leu Gly Gln Thr Tyr Thr Ser Ser Leu Gly Tyr
                        740                 745                 750

Arg Lys Val Val Ser Asn Val Cys Glu Gly Gly Val Asp Met Gln Gln
                        755                 760                 765

Ser Gln Val Gln Leu Gln Cys Pro Leu Thr Pro Arg Gly Leu Gln
                        770                 775                 780

Val Ser Ile Gln Gly Glu Ala Val Ala Val Arg Pro Gly Glu Asp Val
        785                 790                 795                 800

Leu Phe Val Val Arg Gln Glu Gln Gly Asp Val Leu Thr Thr Lys Tyr
                        805                 810                 815

Gln Val Asp Leu Gly Asp Gly Phe Lys Ala Met Tyr Val Asn Leu Thr
                        820                 825                 830

Leu Thr Gly Glu Pro Ile Arg His Arg Tyr Glu Ser Pro Gly Ile Tyr
                        835                 840                 845

Arg Val Ser Val Arg Ala Glu Asn Thr Ala Gly His Asp Glu Ala Val
                        850                 855                 860

Leu Phe Val Gln Val Asn Ser Pro Leu Gln Ala Leu Tyr Leu Glu Val
        865                 870                 875                 880

Val Pro Val Ile Gly Leu Asn Gln Glu Val Asn Leu Thr Ala Val Leu
                        885                 890                 895

Leu Pro Leu Asn Pro Asn Leu Thr Val Phe Tyr Trp Trp Ile Gly His
                        900                 905                 910

Ser Leu Gln Pro Leu Leu Ser Leu Asp Asn Ser Val Thr Thr Arg Phe
                        915                 920                 925

Ser Asp Thr Gly Asp Val Arg Val Thr Val Gln Ala Ala Cys Gly Asn
                        930                 935                 940

Ser Val Leu Gln Asp Ser Arg Val Leu Arg Val Leu Asp Gln Phe Gln
        945                 950                 955                 960

Val Met Pro Leu Gln Phe Ser Lys Glu Leu Asp Ala Tyr Asn Pro Asn
                        965                 970                 975
```

```
Thr Pro Glu Trp Arg Glu Asp Val Gly Leu Val Val Thr Arg Leu Leu
            980                 985                 990

Ser Lys Glu Thr Ser Val Pro Gln Glu Leu Leu Val Thr Val Val Lys
        995                1000                1005

Pro Gly Leu Pro Thr Leu Ala Asp Leu Tyr Val Leu Leu Pro Pro
    1010                1015                1020

Pro Arg Pro Thr Arg Lys Arg Ser Leu Ser Ser Asp Lys Arg Leu
    1025                1030                1035

Ala Ala Ile Gln Gln Val Leu Asn Ala Gln Lys Ile Ser Phe Leu
    1040                1045                1050

Leu Arg Gly Gly Val Arg Val Leu Val Ala Leu Arg Asp Thr Gly
    1055                1060                1065

Thr Gly Ala Glu Gln Leu Gly Gly Gly Gly Gly Tyr Trp Ala Val
    1070                1075                1080

Val Val Leu Phe Val Ile Gly Leu Phe Ala Ala Gly Ala Phe Ile
    1085                1090                1095

Leu Tyr Lys Phe Lys Arg Lys Arg Pro Gly Arg Thr Val Tyr Ala
    1100                1105                1110

Gln Met His Asn Glu Lys Glu Gln Glu Met Thr Ser Pro Val Ser
    1115                1120                1125

His Ser Glu Asp Val Gln Gly Ala Val Gln Gly Asn His Ser Gly
    1130                1135                1140

Val Val Leu Ser Ile Asn Ser Arg Glu Met His Ser Tyr Leu Val
    1145                1150                1155

Ser

<210> SEQ ID NO 55
<211> LENGTH: 1222
<212> TYPE: PRT
<213> ORGANISM: Homo sapiens
<220> FEATURE:
<221> NAME/KEY: MISC_FEATURE
<222> LOCATION: (1)..(1222)
<223> OTHER INFORMATION: preproSorCS3

<400> SEQUENCE: 55

Met Glu Ala Ala Arg Thr Glu Arg Pro Ala Gly Arg Pro Gly Ala Pro
1               5                   10                  15

Leu Val Arg Thr Gly Leu Leu Leu Ser Thr Trp Val Leu Ala Gly
            20                  25                  30

Ala Glu Ile Thr Trp Asp Ala Thr Gly Pro Gly Arg Pro Ala Ala
        35                  40                  45

Pro Ala Ser Arg Pro Pro Ala Leu Ser Pro Leu Ser Pro Arg Ala Val
    50                  55                  60

Ala Ser Gln Trp Pro Glu Glu Leu Ala Ser Ala Arg Arg Ala Ala Val
65                  70                  75                  80

Leu Gly Arg Arg Ala Gly Pro Glu Leu Leu Pro Gln Gln Gly Gly
            85                  90                  95

Arg Gly Gly Glu Met Gln Val Glu Ala Gly Gly Thr Ser Pro Ala Gly
        100                 105                 110

Glu Arg Arg Gly Arg Gly Ile Pro Ala Pro Ala Lys Leu Gly Gly Ala
        115                 120                 125

Arg Arg Ser Arg Arg Ala Gln Pro Pro Ile Thr Gln Glu Arg Gly Asp
        130                 135                 140

Ala Trp Ala Thr Ala Pro Ala Asp Gly Ser Arg Gly Ser Arg Pro Leu
```

```
            145                 150                 155                 160
        Ala Lys Gly Ser Arg Glu Glu Val Lys Ala Pro Arg Ala Gly Gly Ser
                        165                 170                 175

Ala Ala Glu Asp Leu Arg Leu Pro Ser Thr Ser Phe Ala Leu Thr Gly
                        180                 185                 190

Asp Ser Ala His Asn Gln Ala Met Val His Trp Ser Gly His Asn Ser
                        195                 200                 205

Ser Val Ile Leu Ile Leu Thr Lys Leu Tyr Asp Phe Asn Leu Gly Ser
                        210                 215                 220

Val Thr Glu Ser Ser Leu Trp Arg Ser Thr Asp Tyr Gly Thr Thr Tyr
        225                 230                 235                 240

Glu Lys Leu Asn Asp Lys Val Gly Leu Lys Thr Val Leu Ser Tyr Leu
                        245                 250                 255

Tyr Val Asn Pro Thr Asn Lys Arg Lys Ile Met Leu Leu Ser Asp Pro
                        260                 265                 270

Glu Met Glu Ser Ser Ile Leu Ile Ser Ser Asp Glu Gly Ala Thr Tyr
                        275                 280                 285

Gln Lys Tyr Arg Leu Thr Phe Tyr Ile Gln Ser Leu Leu Phe His Pro
                        290                 295                 300

Lys Gln Glu Asp Trp Val Leu Ala Tyr Ser Leu Asp Gln Lys Leu Tyr
        305                 310                 315                 320

Ser Ser Met Asp Phe Gly Arg Arg Trp Gln Leu Met His Glu Arg Ile
                        325                 330                 335

Thr Pro Asn Arg Phe Tyr Trp Ser Val Ala Gly Leu Asp Lys Glu Ala
                        340                 345                 350

Asp Leu Val His Met Glu Val Arg Thr Thr Asp Gly Tyr Ala His Tyr
                        355                 360                 365

Leu Thr Cys Arg Ile Gln Glu Cys Ala Glu Thr Thr Arg Ser Gly Pro
                        370                 375                 380

Phe Ala Arg Ser Ile Asp Ile Ser Ser Leu Val Val Gln Asp Glu Tyr
        385                 390                 395                 400

Ile Phe Ile Gln Val Thr Thr Ser Gly Arg Ala Ser Tyr Tyr Val Ser
                        405                 410                 415

Tyr Arg Arg Glu Ala Phe Ala Gln Ile Lys Leu Pro Lys Tyr Ser Leu
                        420                 425                 430

Pro Lys Asp Met His Ile Ile Ser Thr Asp Glu Asn Gln Val Phe Ala
                        435                 440                 445

Ala Val Gln Glu Trp Asn Gln Asn Asp Thr Tyr Asn Leu Tyr Ile Ser
        450                 455                 460

Asp Thr Arg Gly Ile Tyr Phe Thr Leu Ala Met Glu Asn Ile Lys Ser
        465                 470                 475                 480

Ser Arg Gly Leu Met Gly Asn Ile Ile Glu Leu Tyr Glu Val Ala
                        485                 490                 495

Gly Ile Lys Gly Ile Phe Leu Ala Asn Lys Lys Val Asp Asp Gln Val
                        500                 505                 510

Lys Thr Tyr Ile Thr Tyr Asn Lys Gly Arg Asp Trp Arg Leu Leu Gln
                        515                 520                 525

Ala Pro Asp Val Asp Leu Arg Gly Ser Pro Val His Cys Leu Leu Pro
                        530                 535                 540

Phe Cys Ser Leu His Leu His Leu Gln Leu Ser Glu Asn Pro Tyr Ser
        545                 550                 555                 560

Ser Gly Arg Ile Ser Ser Lys Glu Thr Ala Pro Gly Leu Val Val Ala
                        565                 570                 575
```

```
Thr Gly Asn Ile Gly Pro Glu Leu Ser Tyr Thr Asp Ile Gly Val Phe
            580                 585                 590

Ile Ser Ser Asp Gly Gly Asn Thr Trp Arg Gln Ile Phe Asp Glu Glu
            595                 600                 605

Tyr Asn Val Trp Phe Leu Asp Trp Gly Gly Ala Leu Val Ala Met Lys
610                 615                 620

His Thr Pro Leu Pro Val Arg His Leu Trp Val Ser Phe Asp Glu Gly
625                 630                 635                 640

His Ser Trp Asp Lys Tyr Gly Phe Thr Ser Val Pro Leu Phe Val Asp
                645                 650                 655

Gly Ala Leu Val Glu Ala Gly Met Glu Thr His Ile Met Thr Val Phe
            660                 665                 670

Gly His Phe Ser Leu Arg Ser Glu Trp Gln Leu Val Lys Val Asp Tyr
            675                 680                 685

Lys Ser Ile Phe Ser Arg His Cys Thr Lys Glu Asp Tyr Gln Thr Trp
            690                 695                 700

His Leu Leu Asn Gln Gly Glu Pro Cys Val Met Gly Glu Arg Lys Ile
705                 710                 715                 720

Phe Lys Lys Arg Lys Pro Gly Ala Gln Cys Ala Leu Gly Arg Asp His
                725                 730                 735

Ser Gly Ser Val Val Ser Glu Pro Cys Val Cys Ala Asn Trp Asp Phe
            740                 745                 750

Glu Cys Asp Tyr Gly Tyr Glu Arg His Gly Glu Ser Gln Cys Val Pro
            755                 760                 765

Ala Phe Trp Tyr Asn Pro Ala Ser Pro Ser Lys Asp Cys Ser Leu Gly
            770                 775                 780

Gln Ser Tyr Leu Asn Ser Thr Gly Tyr Arg Arg Ile Val Ser Asn Asn
785                 790                 795                 800

Cys Thr Asp Gly Leu Arg Glu Lys Tyr Thr Ala Lys Ala Gln Met Cys
                805                 810                 815

Pro Gly Lys Ala Pro Arg Gly Leu His Val Val Thr Thr Asp Gly Arg
            820                 825                 830

Leu Val Ala Glu Gln Gly His Asn Ala Thr Phe Ile Ile Leu Met Glu
            835                 840                 845

Glu Gly Asp Leu Gln Arg Thr Asn Ile Gln Leu Asp Phe Gly Asp Gly
850                 855                 860

Ile Ala Val Ser Tyr Ala Asn Phe Ser Pro Ile Glu Asp Gly Ile Lys
865                 870                 875                 880

His Val Tyr Lys Ser Ala Gly Ile Phe Gln Val Thr Ala Tyr Ala Glu
                885                 890                 895

Asn Asn Leu Gly Ser Asp Thr Ala Val Leu Phe Leu His Val Val Cys
            900                 905                 910

Pro Val Glu His Val His Leu Arg Val Pro Phe Val Ala Ile Arg Asn
            915                 920                 925

Lys Glu Val Asn Ile Ser Ala Val Val Trp Pro Ser Gln Leu Gly Thr
            930                 935                 940

Leu Thr Tyr Phe Trp Trp Phe Gly Asn Ser Thr Lys Pro Leu Ile Thr
945                 950                 955                 960

Leu Asp Ser Ser Ile Ser Phe Thr Phe Leu Ala Glu Gly Thr Asp Thr
                965                 970                 975

Ile Thr Val Gln Val Ala Ala Gly Asn Ala Leu Ile Gln Asp Thr Lys
            980                 985                 990
```

-continued

Glu Ile Ala Val His Glu Tyr Phe Gln Ser Gln Leu Leu Ser Phe Ser
        995                 1000                1005

Pro Asn Leu Asp Tyr His Asn Pro Asp Ile Pro Glu Trp Arg Lys
    1010                1015                1020

Asp Ile Gly Asn Val Ile Lys Arg Ala Leu Val Lys Val Thr Ser
    1025                1030                1035

Val Pro Glu Asp Gln Ile Leu Ile Ala Val Phe Pro Gly Leu Pro
    1040                1045                1050

Thr Ser Ala Glu Leu Phe Ile Leu Pro Pro Lys Asn Leu Thr Glu
    1055                1060                1065

Arg Arg Lys Gly Asn Glu Gly Asp Leu Glu Gln Ile Val Glu Thr
    1070                1075                1080

Leu Phe Asn Ala Leu Asn Gln Asn Leu Val Gln Phe Glu Leu Lys
    1085                1090                1095

Pro Gly Val Gln Val Ile Val Tyr Val Thr Gln Leu Thr Leu Ala
    1100                1105                1110

Pro Leu Val Asp Ser Ser Ala Gly His Ser Ser Ser Ala Met Leu
    1115                1120                1125

Met Leu Leu Ser Val Val Phe Val Gly Leu Ala Val Phe Leu Ile
    1130                1135                1140

Tyr Lys Phe Lys Arg Lys Ile Pro Trp Ile Asn Ile Tyr Ala Gln
    1145                1150                1155

Val Gln His Asp Lys Glu Gln Glu Met Ile Gly Ser Val Ser Gln
    1160                1165                1170

Ser Glu Asn Ala Pro Lys Ile Thr Leu Ser Asp Phe Thr Glu Pro
    1175                1180                1185

Glu Glu Leu Leu Asp Lys Glu Leu Asp Thr Arg Val Ile Gly Gly
    1190                1195                1200

Ile Ala Thr Ile Ala Asn Ser Glu Ser Thr Lys Glu Ile Pro Asn
    1205                1210                1215

Cys Thr Ser Val
    1220

<210> SEQ ID NO 56
<211> LENGTH: 1382
<212> TYPE: PRT
<213> ORGANISM: Homo sapiens
<220> FEATURE:
<221> NAME/KEY: MISC_FEATURE
<222> LOCATION: (1)..(1382)
<223> OTHER INFORMATION: Human Insulin Receptor

<400> SEQUENCE: 56

Met Gly Thr Gly Gly Arg Arg Gly Ala Ala Ala Ala Pro Leu Leu Val
1               5                   10                  15

Ala Val Ala Ala Leu Leu Leu Gly Ala Ala Gly His Leu Tyr Pro Gly
                20                  25                  30

Glu Val Cys Pro Gly Met Asp Ile Arg Asn Asn Leu Thr Arg Leu His
            35                  40                  45

Glu Leu Glu Asn Cys Ser Val Ile Glu Gly His Leu Gln Ile Leu Leu
        50                  55                  60

Met Phe Lys Thr Arg Pro Glu Asp Phe Arg Asp Leu Ser Phe Pro Lys
65                  70                  75                  80

Leu Ile Met Ile Thr Asp Tyr Leu Leu Leu Phe Arg Val Tyr Gly Leu
                85                  90                  95

Glu Ser Leu Lys Asp Leu Phe Pro Asn Leu Thr Val Ile Arg Gly Ser

-continued

```
                100                 105                 110
Arg Leu Phe Phe Asn Tyr Ala Leu Val Ile Phe Glu Met Val His Leu
            115                 120                 125

Lys Glu Leu Gly Leu Tyr Asn Leu Met Asn Ile Thr Arg Gly Ser Val
130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn Tyr Ile Val Leu Asn Lys
                165                 170                 175

Asp Asp Asn Glu Glu Cys Gly Asp Ile Cys Pro Gly Thr Ala Lys Gly
            180                 185                 190

Lys Thr Asn Cys Pro Ala Thr Val Ile Asn Gly Gln Phe Val Glu Arg
        195                 200                 205

Cys Trp Thr His Ser His Cys Gln Lys Val Cys Pro Thr Ile Cys Lys
    210                 215                 220

Ser His Gly Cys Thr Ala Glu Gly Leu Cys Cys His Ser Glu Cys Leu
225                 230                 235                 240

Gly Asn Cys Ser Gln Pro Asp Asp Pro Thr Lys Cys Val Ala Cys Arg
                245                 250                 255

Asn Phe Tyr Leu Asp Gly Arg Cys Val Glu Thr Cys Pro Pro Pro Tyr
            260                 265                 270

Tyr His Phe Gln Asp Trp Arg Cys Val Asn Phe Ser Phe Cys Gln Asp
        275                 280                 285

Leu His His Lys Cys Lys Asn Ser Arg Arg Gln Gly Cys His Gln Tyr
    290                 295                 300

Val Ile His Asn Asn Lys Cys Ile Pro Glu Cys Pro Ser Gly Tyr Thr
305                 310                 315                 320

Met Asn Ser Ser Asn Leu Leu Cys Thr Pro Cys Leu Gly Pro Cys Pro
                325                 330                 335

Lys Val Cys His Leu Glu Gly Glu Lys Thr Ile Asp Ser Val Thr
            340                 345                 350

Ser Ala Gln Glu Leu Arg Gly Cys Thr Val Ile Asn Gly Ser Leu Ile
        355                 360                 365

Ile Asn Ile Arg Gly Gly Asn Asn Leu Ala Ala Glu Leu Glu Ala Asn
    370                 375                 380

Leu Gly Leu Ile Glu Glu Ile Ser Gly Tyr Leu Lys Ile Arg Arg Ser
385                 390                 395                 400

Tyr Ala Leu Val Ser Leu Ser Phe Phe Arg Lys Leu Arg Leu Ile Arg
                405                 410                 415

Gly Glu Thr Leu Glu Ile Gly Asn Tyr Ser Phe Tyr Ala Leu Asp Asn
            420                 425                 430

Gln Asn Leu Arg Gln Leu Trp Asp Trp Ser Lys His Asn Leu Thr Ile
        435                 440                 445

Thr Gln Gly Lys Leu Phe Phe His Tyr Asn Pro Lys Leu Cys Leu Ser
    450                 455                 460

Glu Ile His Lys Met Glu Glu Val Ser Gly Thr Lys Gly Arg Gln Glu
465                 470                 475                 480

Arg Asn Asp Ile Ala Leu Lys Thr Asn Gly Asp Gln Ala Ser Cys Glu
                485                 490                 495

Asn Glu Leu Leu Lys Phe Ser Tyr Ile Arg Thr Ser Phe Asp Lys Ile
            500                 505                 510

Leu Leu Arg Trp Glu Pro Tyr Trp Pro Pro Asp Phe Arg Asp Leu Leu
        515                 520                 525
```

```
Gly Phe Met Leu Phe Tyr Lys Glu Ala Pro Tyr Gln Asn Val Thr Glu
        530                 535                 540

Phe Asp Gly Gln Asp Ala Cys Gly Ser Asn Ser Trp Thr Val Val Asp
545                 550                 555                 560

Ile Asp Pro Pro Leu Arg Ser Asn Asp Pro Lys Ser Gln Asn His Pro
                565                 570                 575

Gly Trp Leu Met Arg Gly Leu Lys Pro Trp Thr Gln Tyr Ala Ile Phe
                580                 585                 590

Val Lys Thr Leu Val Thr Phe Ser Asp Glu Arg Arg Thr Tyr Gly Ala
                595                 600                 605

Lys Ser Asp Ile Ile Tyr Val Gln Thr Asp Ala Thr Asn Pro Ser Val
        610                 615                 620

Pro Leu Asp Pro Ile Ser Val Ser Asn Ser Ser Ser Gln Ile Ile Leu
625                 630                 635                 640

Lys Trp Lys Pro Pro Ser Asp Pro Asn Gly Asn Ile Thr His Tyr Leu
                645                 650                 655

Val Phe Trp Glu Arg Gln Ala Glu Asp Ser Glu Leu Phe Glu Leu Asp
                660                 665                 670

Tyr Cys Leu Lys Gly Leu Lys Leu Pro Ser Arg Thr Trp Ser Pro Pro
                675                 680                 685

Phe Glu Ser Glu Asp Ser Gln Lys His Asn Gln Ser Glu Tyr Glu Asp
690                 695                 700

Ser Ala Gly Glu Cys Cys Ser Cys Pro Lys Thr Asp Ser Gln Ile Leu
705                 710                 715                 720

Lys Glu Leu Glu Glu Ser Ser Phe Arg Lys Thr Phe Glu Asp Tyr Leu
                725                 730                 735

His Asn Val Val Phe Val Pro Arg Lys Thr Ser Ser Gly Thr Gly Ala
                740                 745                 750

Glu Asp Pro Arg Pro Ser Arg Lys Arg Arg Ser Leu Gly Asp Val Gly
                755                 760                 765

Asn Val Thr Val Ala Val Pro Thr Val Ala Ala Phe Pro Asn Thr Ser
        770                 775                 780

Ser Thr Ser Val Pro Thr Ser Pro Glu Glu His Arg Pro Phe Glu Lys
785                 790                 795                 800

Val Val Asn Lys Glu Ser Leu Val Ile Ser Gly Leu Arg His Phe Thr
                805                 810                 815

Gly Tyr Arg Ile Glu Leu Gln Ala Cys Asn Gln Asp Thr Pro Glu Glu
                820                 825                 830

Arg Cys Ser Val Ala Ala Tyr Val Ser Ala Arg Thr Met Pro Glu Ala
                835                 840                 845

Lys Ala Asp Asp Ile Val Gly Pro Val Thr His Glu Ile Phe Glu Asn
850                 855                 860

Asn Val Val His Leu Met Trp Gln Glu Pro Lys Glu Pro Asn Gly Leu
865                 870                 875                 880

Ile Val Leu Tyr Glu Val Ser Tyr Arg Arg Tyr Gly Asp Glu Glu Leu
                885                 890                 895

His Leu Cys Val Ser Arg Lys His Phe Ala Leu Glu Arg Gly Cys Arg
                900                 905                 910

Leu Arg Gly Leu Ser Pro Gly Asn Tyr Ser Val Arg Ile Arg Ala Thr
                915                 920                 925

Ser Leu Ala Gly Asn Gly Ser Trp Thr Glu Pro Thr Tyr Phe Tyr Val
                930                 935                 940
```

```
Thr Asp Tyr Leu Asp Val Pro Ser Asn Ile Ala Lys Ile Ile Ile Gly
945                 950                 955                 960

Pro Leu Ile Phe Val Phe Leu Phe Ser Val Val Ile Gly Ser Ile Tyr
            965                 970                 975

Leu Phe Leu Arg Lys Arg Gln Pro Asp Gly Pro Leu Gly Pro Leu Tyr
                980                 985                 990

Ala Ser Ser Asn Pro Glu Tyr Leu Ser Ala Ser Asp Val Phe Pro Cys
        995                 1000                1005

Ser Val Tyr Val Pro Asp Glu Trp Glu Val Ser Arg Glu Lys Ile
    1010                1015                1020

Thr Leu Leu Arg Glu Leu Gly Gln Gly Ser Phe Gly Met Val Tyr
    1025                1030                1035

Glu Gly Asn Ala Arg Asp Ile Ile Lys Gly Ala Glu Thr Arg
    1040                1045                1050

Val Ala Val Lys Thr Val Asn Glu Ser Ala Ser Leu Arg Glu Arg
    1055                1060                1065

Ile Glu Phe Leu Asn Glu Ala Ser Val Met Lys Gly Phe Thr Cys
    1070                1075                1080

His His Val Val Arg Leu Leu Gly Val Val Ser Lys Gly Gln Pro
    1085                1090                1095

Thr Leu Val Val Met Glu Leu Met Ala His Gly Asp Leu Lys Ser
    1100                1105                1110

Tyr Leu Arg Ser Leu Arg Pro Glu Ala Glu Asn Asn Pro Gly Arg
    1115                1120                1125

Pro Pro Pro Thr Leu Gln Glu Met Ile Gln Met Ala Ala Glu Ile
    1130                1135                1140

Ala Asp Gly Met Ala Tyr Leu Asn Ala Lys Lys Phe Val His Arg
    1145                1150                1155

Asp Leu Ala Ala Arg Asn Cys Met Val Ala His Asp Phe Thr Val
    1160                1165                1170

Lys Ile Gly Asp Phe Gly Met Thr Arg Asp Ile Tyr Glu Thr Asp
    1175                1180                1185

Tyr Tyr Arg Lys Gly Gly Lys Gly Leu Leu Pro Val Arg Trp Met
    1190                1195                1200

Ala Pro Glu Ser Leu Lys Asp Gly Val Phe Thr Thr Ser Ser Asp
    1205                1210                1215

Met Trp Ser Phe Gly Val Val Leu Trp Glu Ile Thr Ser Leu Ala
    1220                1225                1230

Glu Gln Pro Tyr Gln Gly Leu Ser Asn Glu Gln Val Leu Lys Phe
    1235                1240                1245

Val Met Asp Gly Gly Tyr Leu Asp Gln Pro Asp Asn Cys Pro Glu
    1250                1255                1260

Arg Val Thr Asp Leu Met Arg Met Cys Trp Gln Phe Asn Pro Lys
    1265                1270                1275

Met Arg Pro Thr Phe Leu Glu Ile Val Asn Leu Leu Lys Asp Asp
    1280                1285                1290

Leu His Pro Ser Phe Pro Glu Val Ser Phe Phe His Ser Glu Glu
    1295                1300                1305

Asn Lys Ala Pro Glu Ser Glu Glu Leu Glu Met Glu Phe Glu Asp
    1310                1315                1320

Met Glu Asn Val Pro Leu Asp Arg Ser Ser His Cys Gln Arg Glu
    1325                1330                1335

Glu Ala Gly Gly Arg Asp Gly Gly Ser Ser Leu Gly Phe Lys Arg
```

```
            1340                1345                1350
Ser Tyr Glu Glu His Ile Pro Tyr Thr His Met Asn Gly Gly Lys
            1355                1360                1365

Lys Asn Gly Arg Ile Leu Thr Leu Pro Arg Ser Asn Pro Ser
            1370                1375                1380
```

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      SorCS (ex24), forward primer

<400> SEQUENCE: 57
aagtctctgc tgggaacgcc atactgcaag                               30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      SorCS (ex24), reverse primer

<400> SEQUENCE: 58
gtggacaaga acttggacgc caggcttcag                               30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      SorCS-a (ex25), forward primer

<400> SEQUENCE: 59
aagtctctgc tgggaacgcc atactgcaag                               30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      SorCS-a (ex25), reverse primer

<400> SEQUENCE: 60
tattgcttct gaacctggca gaaagaggag                               30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      SorCS-b (ex27), forward primer

<400> SEQUENCE: 61
aagtctctgc tgggaacgcc atactgcaag                               30

<210> SEQ ID NO 62
<211> LENGTH: 30
<212> TYPE: DNA
<213> ORGANISM: Artificial Sequence
<220> FEATURE:

```
<223> OTHER INFORMATION: Description of Artificial Sequence: Synthetic
      SorCS-b (ex27), reverse primer

<400> SEQUENCE: 62
gctttggcga tgaaggtgga gttgctggct                                          30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      SorCS-c (ex26), forward primer

<400> SEQUENCE: 63
aagtctctgc tgggaacgcc atactgcaag                                          30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      SorCS-c (ex26), reverse primer

<400> SEQUENCE: 64
cagggtgagg gacactgggc ctgctttcag                                          30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      SorCS-d (ex28), forward primer

<400> SEQUENCE: 65
aagtctctgc tgggaacgcc atactgcaag                                          30

<210> SEQ ID NO 66
<211> LENGTH: 33
<212> TYPE: DNA
<213> ORGANISM: Artificial Sequence
<220> FEATURE:
<223> OTHER INFORMATION: Description of Artificial Sequence: Synthetic
      SorCS-d (ex28), reverse primer

<400> SEQUENCE: 66
cggatctctt ggaactgaag ttacagatgc ttg                                      33

<210> SEQ ID NO 67
<211> LENGTH: 22
<212> TYPE: PRT
<213> ORGANISM: Homo sapiens

<400> SEQUENCE: 67

Ala Arg Ser Gly Arg Arg Arg Ser Gly Ala Asp Gln Glu Lys Ala
1               5                   10                  15
Glu Arg Gly Glu Gly Ala
            20

<210> SEQ ID NO 68
<211> LENGTH: 19
<212> TYPE: PRT
<213> ORGANISM: Homo sapiens
```

<400> SEQUENCE: 68

Ser Arg Ser Pro Arg Gly Val Leu Arg Asp Gly Gln Gln Glu Pro
1               5                   10                  15

Gly Thr Arg

<210> SEQ ID NO 69
<211> LENGTH: 19
<212> TYPE: PRT
<213> ORGANISM: Homo sapiens

<400> SEQUENCE: 69

Glu Arg Asp Pro Asp Lys Ala Thr Arg Phe Arg Met Glu Glu Leu Arg
1               5                   10                  15

Leu Thr Ser

<210> SEQ ID NO 70
<211> LENGTH: 22
<212> TYPE: PRT
<213> ORGANISM: Homo sapiens

<400> SEQUENCE: 70

Tyr Asn Leu Gly Ser Ile Thr Glu Ser Ser Leu Trp Arg Ser Thr Asp
1               5                   10                  15

Tyr Gly Thr Thr Tyr Glu
            20

<210> SEQ ID NO 71
<211> LENGTH: 19
<212> TYPE: PRT
<213> ORGANISM: Homo sapiens

<400> SEQUENCE: 71

Tyr Val Ser Tyr Arg Arg Asn Ala Phe Ala Gln Met Lys Leu Pro Lys
1               5                   10                  15

Tyr Ala Leu

<210> SEQ ID NO 72
<211> LENGTH: 24
<212> TYPE: PRT
<213> ORGANISM: Homo sapiens

<400> SEQUENCE: 72

Val Lys Val Asp Tyr Lys Ser Ile Phe Asp Arg Arg Cys Ala Glu Glu
1               5                   10                  15

Asp Tyr Arg Pro Trp Gln Leu His
            20

<210> SEQ ID NO 73
<211> LENGTH: 21
<212> TYPE: PRT
<213> ORGANISM: Homo sapiens

<400> SEQUENCE: 73

Tyr Leu Asn Ser Thr Gly Tyr Arg Lys Val Val Ser Asn Asn Cys Thr
1               5                   10                  15

Asp Gly Val Arg Glu
            20

<210> SEQ ID NO 74
<211> LENGTH: 18
<212> TYPE: PRT

<213> ORGANISM: Homo sapiens

<400> SEQUENCE: 74

Tyr Gln Asn Val Gly Ile Phe Arg Val Thr Val Gln Val Asp Asn Ser
1               5                   10                  15

Leu Gly

<210> SEQ ID NO 75
<211> LENGTH: 29
<212> TYPE: PRT
<213> ORGANISM: Mus musculus

<400> SEQUENCE: 75

Tyr Lys Phe Lys Arg Cys Val Phe Leu Leu Pro Ser Tyr Pro Arg
1               5                   10                  15

Pro Pro Pro Pro Ser Ser Phe Cys Gln Val Gln Lys Gln
            20                  25

<210> SEQ ID NO 76
<211> LENGTH: 49
<212> TYPE: PRT
<213> ORGANISM: Mus musculus

<400> SEQUENCE: 76

Tyr Lys Phe Lys Arg Arg Val Ala Leu Pro Ser Pro Ser Pro Ser
1               5                   10                  15

Ala Gln Pro Gly Asp Ser Ser Leu Arg Leu Gln Arg Pro Arg Pro Ala
            20                  25                  30

Thr Pro Pro Ser Ser Pro Lys Arg Gly Ser Ala Gly Gln Phe Ala
        35                  40                  45

Ile

<210> SEQ ID NO 77
<211> LENGTH: 60
<212> TYPE: PRT
<213> ORGANISM: Mus musculus

<400> SEQUENCE: 77

Tyr Lys Phe Lys Arg Lys Ile Pro Gly Ile Asn Val Tyr Ala Gln Met
1               5                   10                  15

Gln Asn Glu Lys Glu Gln Glu Leu Ile Asn Pro Val Ser His Ser Glu
            20                  25                  30

Ser Arg Pro Ser Val Pro His Pro Asp Leu Arg Arg Pro Gly Gln Leu
        35                  40                  45

Val Asp Glu Lys Val Glu Ser Gln Leu Leu Gly Lys
    50                  55                  60

<210> SEQ ID NO 78
<211> LENGTH: 60
<212> TYPE: PRT
<213> ORGANISM: Mus musculus

<400> SEQUENCE: 78

Tyr Lys Phe Lys Arg Lys Ile Pro Gly Ile Asn Val Tyr Ala Gln Met
1               5                   10                  15

Gln Asn Glu Lys Glu Gln Glu Leu Ile Asn Pro Val Ser His Ser Glu
            20                  25                  30

Ser Arg Pro Ser Val Pro His Pro Asp Leu Arg Arg Pro Gly Gln Leu
        35                  40                  45

Val Asp Glu Lys Val Glu Ser Gln Leu Leu Gly Gln
 50                  55                  60

<210> SEQ ID NO 79
<211> LENGTH: 73
<212> TYPE: PRT
<213> ORGANISM: Mus musculus

<400> SEQUENCE: 79

Tyr Lys Phe Lys Arg Gly Trp Arg Asp Arg Ser Ala Val Lys Asn Ile
1               5                   10                  15

Gly Cys Ser Cys Arg Gly Pro Gly Phe Asn Ser Gln His Gln Gln Gly
            20                  25                  30

Gly Ser Gln Ala Ser Val Thr Ser Val Pro Arg Asp Pro Ser Pro Ser
        35                  40                  45

Ser Asp Leu His Gly His Gln Glu His Thr Trp Cys Thr Asp Ile His
 50                  55                  60

Pro Gly Lys Thr Pro Ile His Ile Lys
65                  70

<210> SEQ ID NO 80
<211> LENGTH: 1198
<212> TYPE: PRT
<213> ORGANISM: Homo sapiens

<400> SEQUENCE: 80

Met Gly Lys Val Gly Ala Gly Gly Gly Ser Gln Ala Arg Leu Ser Ala
1               5                   10                  15

Leu Leu Ala Gly Ala Gly Leu Leu Ile Leu Cys Ala Pro Gly Val Cys
            20                  25                  30

Gly Gly Gly Ser Cys Cys Pro Ser Pro His Pro Ser Ser Ala Pro Arg
        35                  40                  45

Ser Ala Ser Thr Pro Arg Gly Phe Ser His Gln Gly Arg Pro Gly Arg
 50                  55                  60

Ala Pro Ala Thr Pro Leu Pro Leu Val Val Arg Pro Leu Phe Ser Val
65                  70                  75                  80

Ala Pro Gly Asp Arg Ala Leu Ser Leu Glu Arg Ala Arg Gly Thr Gly
            85                  90                  95

Ala Ser Met Ala Val Ala Ala Arg Ser Gly Arg Arg Arg Ser Gly
            100                 105                 110

Ala Asp Gln Glu Lys Ala Glu Arg Gly Glu Gly Ala Ser Arg Ser Pro
        115                 120                 125

Arg Gly Val Leu Arg Asp Gly Gln Gln Glu Pro Gly Thr Arg Glu
130                 135                 140

Arg Asp Pro Asp Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
            165                 170                 175

Met Val His Trp Ser Gly His Asn Ser Ser Val Ile Leu Ile Leu Thr
        180                 185                 190

Lys Leu Tyr Asp Tyr Asn Leu Gly Ser Ile Thr Glu Ser Ser Leu Trp
    195                 200                 205

Arg Ser Thr Asp Tyr Gly Thr Thr Tyr Glu Lys Leu Asn Asp Lys Val
 210                 215                 220

Gly Leu Lys Thr Ile Leu Ser Tyr Leu Tyr Val Cys Pro Thr Asn Lys
225                 230                 235                 240

-continued

```
Arg Lys Ile Met Leu Leu Thr Asp Pro Glu Ile Glu Ser Ser Leu Leu
                245                 250                 255

Ile Ser Ser Asp Glu Gly Ala Thr Tyr Gln Lys Tyr Arg Leu Asn Phe
            260                 265                 270

Tyr Ile Gln Ser Leu Leu Phe His Pro Lys Gln Glu Asp Trp Ile Leu
        275                 280                 285

Ala Tyr Ser Gln Asp Gln Lys Leu Tyr Ser Ser Ala Glu Phe Gly Arg
    290                 295                 300

Arg Trp Gln Leu Ile Gln Gly Val Val Pro Asn Arg Phe Tyr Trp
305                 310                 315                 320

Ser Val Met Gly Ser Asn Lys Glu Pro Asp Leu Val His Leu Glu Ala
                325                 330                 335

Arg Thr Val Asp Gly His Ser His Tyr Leu Thr Cys Arg Met Gln Asn
            340                 345                 350

Cys Thr Glu Ala Asn Arg Asn Gln Pro Phe Pro Gly Tyr Ile Asp Pro
        355                 360                 365

Asp Ser Leu Ile Val Gln Asp His Tyr Val Phe Val Gln Leu Thr Ser
    370                 375                 380

Gly Gly Arg Pro His Tyr Tyr Val Ser Tyr Arg Arg Asn Ala Phe Ala
385                 390                 395                 400

Gln Met Lys Leu Pro Lys Tyr Ala Leu Pro Lys Asp Met His Val Ile
                405                 410                 415

Ser Thr Asp Glu Asn Gln Val Phe Ala Ala Val Gln Glu Trp Asn Gln
            420                 425                 430

Asn Asp Thr Tyr Asn Leu Tyr Ile Ser Asp Thr Arg Gly Val Tyr Phe
        435                 440                 445

Thr Leu Ala Leu Glu Asn Val Gln Ser Ser Arg Gly Pro Glu Gly Asn
    450                 455                 460

Ile Met Ile Asp Leu Tyr Glu Val Ala Gly Ile Lys Gly Met Phe Leu
465                 470                 475                 480

Ala Asn Lys Lys Ile Asp Asn Gln Val Lys Thr Phe Ile Thr Tyr Asn
                485                 490                 495

Lys Gly Arg Asp Trp Arg Leu Leu Gln Ala Pro Asp Thr Asp Leu Arg
            500                 505                 510

Gly Asp Pro Val His Cys Leu Leu Pro Tyr Cys Ser Leu His Leu His
        515                 520                 525

Leu Lys Val Ser Glu Asn Pro Tyr Thr Ser Gly Ile Ile Ala Ser Lys
    530                 535                 540

Asp Thr Ala Pro Ser Ile Ile Val Ala Ser Gly Asn Ile Gly Ser Glu
545                 550                 555                 560

Leu Ser Asp Thr Asp Ile Ser Met Phe Val Ser Ser Asp Ala Gly Asn
                565                 570                 575

Thr Trp Arg Gln Ile Phe Glu Glu Glu His Ser Val Leu Tyr Leu Asp
            580                 585                 590

Gln Gly Gly Val Leu Val Ala Met Lys His Thr Ser Leu Pro Ile Arg
        595                 600                 605

His Leu Trp Leu Ser Phe Asp Glu Gly Arg Ser Trp Ser Lys Tyr Ser
    610                 615                 620

Phe Thr Ser Ile Pro Leu Phe Val Asp Gly Val Leu Gly Glu Pro Gly
625                 630                 635                 640

Glu Glu Thr Leu Ile Met Thr Val Phe Gly His Phe Ser His Arg Ser
                645                 650                 655

Glu Trp Gln Leu Val Lys Val Asp Tyr Lys Ser Ile Phe Asp Arg Arg
```

```
                    660             665             670
Cys Ala Glu Glu Asp Tyr Arg Pro Trp Gln Leu His Ser Gln Gly Glu
                675             680             685
Ala Cys Ile Met Gly Ala Lys Arg Ile Tyr Lys Arg Lys Ser Glu
    690             695             700
Arg Lys Cys Met Gln Gly Lys Tyr Ala Gly Met Glu Ser Glu Pro
705             710             715             720
Cys Val Cys Thr Glu Ala Asp Phe Asp Cys Asp Tyr Gly Tyr Glu Arg
                725             730             735
His Ser Asn Gly Gln Cys Leu Pro Ala Phe Trp Phe Asn Pro Ser Ser
                740             745             750
Leu Ser Lys Asp Cys Ser Leu Gly Gln Ser Tyr Leu Asn Ser Thr Gly
                755             760             765
Tyr Arg Lys Val Val Ser Asn Asn Cys Thr Asp Gly Val Arg Glu Gln
                770             775             780
Tyr Thr Ala Lys Pro Gln Lys Cys Pro Gly Lys Ala Pro Arg Gly Leu
785             790             795             800
Arg Ile Val Thr Ala Asp Gly Lys Leu Thr Ala Glu Gln His Asn
                805             810             815
Val Thr Leu Met Val Gln Leu Glu Glu Gly Asp Val Gln Arg Thr Leu
                820             825             830
Ile Gln Val Asp Phe Gly Asp Gly Ile Ala Val Ser Tyr Val Asn Leu
                835             840             845
Ser Ser Met Glu Asp Gly Ile Lys His Val Tyr Gln Asn Val Gly Ile
                850             855             860
Phe Arg Val Thr Val Gln Val Asp Asn Ser Leu Gly Ser Asp Ser Ala
865             870             875             880
Val Leu Tyr Leu His Val Thr Cys Pro Leu Glu His Val His Leu Ser
                885             890             895
Leu Pro Phe Val Thr Thr Lys Asn Lys Glu Val Asn Ala Thr Ala Val
                900             905             910
Leu Trp Pro Ser Gln Val Gly Thr Leu Thr Tyr Val Trp Trp Tyr Gly
                915             920             925
Asn Asn Thr Glu Pro Leu Ile Thr Leu Glu Gly Ser Ile Ser Phe Arg
                930             935             940
Phe Thr Ser Glu Gly Met Asn Thr Ile Thr Val Gln Val Ser Ala Gly
945             950             955             960
Asn Ala Ile Leu Gln Asp Thr Lys Thr Ile Ala Val Tyr Glu Glu Phe
                965             970             975
Arg Ser Leu Arg Leu Ser Phe Ser Pro Asn Leu Asp Asp Tyr Asn Pro
                980             985             990
Asp Ile Pro Glu Trp Arg Arg Asp Ile Gly Arg Val Ile Lys Lys Ser
                995             1000            1005
Leu Val Glu Ala Thr Gly Val Pro Gly Gln His Ile Leu Val Ala
                1010            1015            1020
Val Leu Pro Gly Leu Pro Thr Thr Ala Glu Leu Phe Val Leu Pro
                1025            1030            1035
Tyr Gln Asp Pro Ala Gly Glu Asn Lys Arg Ser Thr Asp Asp Leu
                1040            1045            1050
Glu Gln Ile Ser Glu Leu Leu Ile His Thr Leu Asn Gln Asn Ser
                1055            1060            1065
Val His Phe Glu Leu Lys Pro Gly Val Arg Val Leu Val His Ala
                1070            1075            1080
```

Ala His Leu Thr Ala Ala Pro Leu Val Asp Leu Thr Pro Thr His
    1085                1090                1095

Ser Gly Ser Ala Met Leu Met Leu Leu Ser Val Phe Val Gly
    1100                1105                1110

Leu Ala Val Phe Val Ile Tyr Lys Phe Lys Arg Lys Ile Pro Gly
    1115                1120                1125

Ile Asn Val Tyr Ala Gln Met Gln Asn Glu Lys Glu Gln Glu Met
    1130                1135                1140

Ile Ser Pro Val Ser His Ser Glu Ser Arg Pro Asn Val Pro Gln
    1145                1150                1155

Thr Glu Leu Arg Arg Pro Gly Gln Leu Ile Asp Glu Lys Val Glu
    1160                1165                1170

Ser Gln Leu Ile Gly Ser Ile Ser Ile Val Ala Glu Asn Gln Ser
    1175                1180                1185

Thr Lys Glu Ile Pro Thr Tyr Val Asn Val
    1190                1195

<210> SEQ ID NO 81
<211> LENGTH: 21
<212> TYPE: PRT
<213> ORGANISM: Mus musculus

<400> SEQUENCE: 81

Lys Asp Leu Phe Pro Asn Leu Thr Val Ile Arg Gly Ser Arg Leu Phe
1               5                   10                  15

Phe Asn Tyr Ala Leu
            20

<210> SEQ ID NO 82
<211> LENGTH: 24
<212> TYPE: PRT
<213> ORGANISM: Mus musculus

<400> SEQUENCE: 82

His Leu Lys Glu Leu Gly Leu Tyr Asn Leu Met Asn Ile Thr Arg Gly
1               5                   10                  15

Ser Val Arg Ile Glu Lys Asn Asn
            20

<210> SEQ ID NO 83
<211> LENGTH: 27
<212> TYPE: PRT
<213> ORGANISM: Mus musculus

<400> SEQUENCE: 83

Ser Phe Cys Gln Asp Leu His His Lys Cys Lys Asn Ser Arg Arg Gln
1               5                   10                  15

Gly Cys His Gln Tyr Val Ile His Asn Asn Lys
            20                  25

<210> SEQ ID NO 84
<211> LENGTH: 18
<212> TYPE: PRT
<213> ORGANISM: Mus musculus

<400> SEQUENCE: 84

Val Ile Asn Gly Ser Leu Ile Ile Asn Ile Arg Gly Gly Asn Asn Leu
1               5                   10                  15

Ala Ala

<210> SEQ ID NO 85
<211> LENGTH: 18
<212> TYPE: PRT
<213> ORGANISM: Mus musculus

<400> SEQUENCE: 85

Val Lys Thr Leu Val Thr Phe Ser Asp Glu Arg Arg Thr Tyr Gly Ala
1               5                   10                  15

Lys Ser

<210> SEQ ID NO 86
<211> LENGTH: 24
<212> TYPE: PRT
<213> ORGANISM: Mus musculus

<400> SEQUENCE: 86

Ile Ser Val Ser Asn Ser Ser Gln Ile Ile Leu Lys Trp Lys Pro
1               5                   10                  15

Pro Ser Asp Pro Asn Gly Asn Ile
            20

<210> SEQ ID NO 87
<211> LENGTH: 24
<212> TYPE: PRT
<213> ORGANISM: Mus musculus

<400> SEQUENCE: 87

Gly Thr Gly Ala Glu Asp Pro Arg Pro Ser Arg Lys Arg Ser Leu
1               5                   10                  15

Gly Asp Val Gly Asn Val Thr Val
            20

<210> SEQ ID NO 88
<211> LENGTH: 21
<212> TYPE: PRT
<213> ORGANISM: Homo sapiens

<400> SEQUENCE: 88

Ala Arg Ser Gly Arg Arg Arg Ser Gly Ala Asp Gln Glu Lys Ala
1               5                   10                  15

Glu Arg Gly Glu Gly
            20

<210> SEQ ID NO 89
<211> LENGTH: 18
<212> TYPE: PRT
<213> ORGANISM: Homo sapiens

<400> SEQUENCE: 89

Ala Ser Arg Ser Pro Arg Gly Val Leu Arg Asp Gly Gly Gln Gln Glu
1               5                   10                  15

Pro Gly

<210> SEQ ID NO 90
<211> LENGTH: 18
<212> TYPE: PRT
<213> ORGANISM: Homo sapiens

<400> SEQUENCE: 90

Thr Arg Glu Arg Asp Pro Asp Lys Ala Thr Arg Phe Arg Met Glu Glu
1               5                   10                  15

Leu Arg

<210> SEQ ID NO 91
<211> LENGTH: 21
<212> TYPE: PRT
<213> ORGANISM: Homo sapiens

<400> SEQUENCE: 91

Gln Asp Gln Lys Leu Tyr Ser Ser Ala Glu Phe Gly Arg Arg Trp Gln
1               5                   10                  15

Leu Ile Gln Glu Gly
            20

<210> SEQ ID NO 92
<211> LENGTH: 18
<212> TYPE: PRT
<213> ORGANISM: Homo sapiens

<400> SEQUENCE: 92

Tyr Val Ser Tyr Arg Arg Asn Ala Phe Ala Gln Met Lys Leu Pro Lys
1               5                   10                  15

Tyr Ala

<210> SEQ ID NO 93
<211> LENGTH: 24
<212> TYPE: PRT
<213> ORGANISM: Homo sapiens

<400> SEQUENCE: 93

Val Lys Val Asp Tyr Lys Ser Ile Phe Asp Arg Arg Cys Ala Glu Glu
1               5                   10                  15

Asp Tyr Arg Pro Trp Gln Leu His
            20

<210> SEQ ID NO 94
<211> LENGTH: 21
<212> TYPE: PRT
<213> ORGANISM: Homo sapiens

<400> SEQUENCE: 94

Tyr Leu Asn Ser Thr Gly Tyr Arg Lys Val Val Ser Asn Asn Cys Thr
1               5                   10                  15

Asp Gly Val Arg Glu
            20

<210> SEQ ID NO 95
<211> LENGTH: 17
<212> TYPE: PRT
<213> ORGANISM: Homo sapiens

<400> SEQUENCE: 95

Tyr Gln Asn Gly Ile Phe Arg Val Thr Val Gln Val Asp Asn Ser Leu
1               5                   10                  15

Gly

<210> SEQ ID NO 96
<211> LENGTH: 21
<212> TYPE: PRT
<213> ORGANISM: Homo sapiens

<400> SEQUENCE: 96

```
Lys Asp Leu Phe Pro Asn Leu Thr Val Ile Arg Gly Ser Arg Leu Phe
1               5                   10                  15

Phe Asn Tyr Ala Leu
            20
```

<210> SEQ ID NO 97
<211> LENGTH: 24
<212> TYPE: PRT
<213> ORGANISM: Homo sapiens

<400> SEQUENCE: 97

```
His Leu Lys Glu Leu Gly Leu Tyr Asn Leu Met Asn Ile Thr Arg Gly
1               5                   10                  15

Ser Val Arg Ile Glu Lys Asn Asn
            20
```

<210> SEQ ID NO 98
<211> LENGTH: 27
<212> TYPE: PRT
<213> ORGANISM: Homo sapiens

<400> SEQUENCE: 98

```
Ser Phe Cys Gln Asp Leu His His Lys Cys Lys Asn Ser Arg Arg Gln
1               5                   10                  15

Gly Cys His Gln Tyr Val Ile His Asn Asn Lys
            20                  25
```

<210> SEQ ID NO 99
<211> LENGTH: 18
<212> TYPE: PRT
<213> ORGANISM: Homo sapiens

<400> SEQUENCE: 99

```
Val Ile Asn Gly Ser Leu Ile Ile Asn Ile Arg Gly Gly Asn Asn Leu
1               5                   10                  15

Ala Ala
```

<210> SEQ ID NO 100
<211> LENGTH: 18
<212> TYPE: PRT
<213> ORGANISM: Homo sapiens

<400> SEQUENCE: 100

```
Val Lys Thr Leu Val Thr Phe Ser Asp Glu Arg Arg Thr Tyr Gly Ala
1               5                   10                  15

Lys Ser
```

<210> SEQ ID NO 101
<211> LENGTH: 24
<212> TYPE: PRT
<213> ORGANISM: Homo sapiens

<400> SEQUENCE: 101

```
Ile Ser Val Ser Asn Ser Ser Ser Gln Ile Ile Leu Lys Trp Lys Pro
1               5                   10                  15

Pro Ser Asp Pro Asn Gly Asn Ile
            20
```

<210> SEQ ID NO 102
<211> LENGTH: 24
<212> TYPE: PRT
<213> ORGANISM: Homo sapiens

```
<400> SEQUENCE: 102

Gly Thr Gly Ala Glu Asp Pro Arg Pro Ser Arg Lys Arg Arg Ser Leu
1               5                   10                  15

Gly Asp Val Gly Asn Val Thr Val
            20
```

SORCS1 FOR THE TREATMENT OF OBESITY

This application is a Continuation in Part of U.S. application Ser. No. 13/377,277 filed Dec. 9, 2011 which is the U.S. National Stage of PCT/DK2010/050131 filed Jun. 10, 2010 which in turn claims priority to U.S. Provisional Application No. 61/213,455, filed Jun. 10, 2009, and Denmark Patent Application No. PA 2009 70024, filed Jun. 10, 2009. The entire contents of all of the above related applications are incorporated herein by reference in their entireties.

SEQUENCE LISTING

The instant application contains a Sequence Listing which has been submitted electronically in ASCII format via EFS-Web and is hereby incorporated by reference in its entirety.

FIELD OF INVENTION

The present invention relates to a method of treating obesity by administering SorCS1-like agents, preferably SorCS1 polypeptides and fragments and variants thereof.

BACKGROUND OF THE INVENTION

The Insulin Resistance Syndrome.

The prevalence of metabolic disturbance, collectively known as metabolic syndrome or insulin resistance syndrome, has reached an epidemic proportion in industrialized countries. The insulin resistance syndrome refers to a constellation of findings, including glucose intolerance, obesity, an altered lipid profile (dyslipidemia) and hypertension, that promote the development of type 2 diabetes, cardiovascular disease, cancer, polycystic ovarian disease, and other disorders. In all of these disorders, a central component of the pathophysiology is insulin resistance. The underlying causes of this syndrome are overweight/obesity, physical inactivity and a series of currently not yet well-defined genetic polymorphisms (reviewed in 1+2). Lifestyle interventions and pharmacological treatment of the pathologies of the syndrome are only partially efficient and new therapeutic approaches are urgently needed.

Insulin and Insulin Resistance.

Insulin is a hormone produced by β-cells in the islets of Langerhans in the pancreas. Insulin release is stimulated as blood glucose levels rise and glucose is removed from the blood by insulin dependent stimulation of glucose transporters located in the cell membranes of target tissue, in particular in adipose tissue, skeletal muscle and liver. Insulin exerts its biological effects by binding to and activating the membrane-bound insulin receptor (IR), thereby initiating a cascade of intracellular signaling events, which regulates multiple biological processes such as glucose and lipid metabolism, gene expression, protein synthesis, and non-metabolic processes such as cell growth and differentiation. The diverse effects of IR activation are mediated through a multicomponent signaling complex that assembles upon binding of insulin. Thus, the intrinsic protein-tyrosine kinase activity of IR results in autophosphorylation of several tyrosine residues followed by recruitment and phosphorylation of several intracellular protein substrates including IR substrate (IRS) proteins and Scr-homolgy-2 containing (Shc) proteins. This initiates the activation of two main signalling pathways: the phosphatidylinositol 3-kinase (PI3K)-AKT/protein kinase B (PKB) pathway, which is responsible for most of the metabolic actions, including translocation of the glucose transporter GLUT4 to the cell membrane and stimulation of glycogen synthesis, and the Ras-mitogen-activated protein kinase (MAPK) pathway, which regulates expression of some genes and cooperates with the (PI3K)-AKT pathway to control cell growth and differentiation (reviewed in 3-8).

The ability of insulin to stimulate glucose disposal vary continuously throughout a population of apparently healthy persons, and a difference of ≥600% exists between the most insulin-sensitive and the most insulin resistive persons. However, the third of the population that is the most insulin resistant is at a much greater risk of developing several abnormalities and clinical syndromes, including type 2 diabetes, cardiovascular diseases, hypertension, stroke, non-alcoholic fatty liver, polycystic ovary disease, and certain forms of cancer (reviewed in 9) Individuals are said to be 'insulin resistant', because their tissues behave as if there was insufficient insulin in the bloodstream as reflected by decreased insulin response and glucose uptake in liver, adipose tissue, and skeletal muscle. The first response to insulin resistance is a compensatory production and secretion of insulin to compensate for the body's decreased sensitivity, leading to hyperinsulinaemia. Thus, high insulin levels and a decreased responsiveness of tissue to the clearance of glucose from the bloodstream characterize insulin resistance. Insulin resistance is the primary event leading to a series of metabolic changes including compensatory hyperinsulinemia, dyslipidemia, decompensation of pancreatic beta-cells, and hyperglycemia (reviewed in 6-8).

Type 2 Diabetes and Insulin Resistance.

Type-2 diabetes (non-insulin-dependent diabetes) is a complex and heterogeneous disorder associated with an increased risk for mortality as well as morbidity. The incidence is steadily increasing and the disease presently affects more than 150 million people worldwide making it a major public concern. The disorder is a prototypic complex polygenic disease with a strong heritable component but is also heavily influenced by environmental factors such as e.g. obesity. The pathogenesis of type 2 diabetes involves progressive development of insulin resistance in liver and peripheral tissue accompanied by defective insulin secretion from pancreatic beta cells leading to overt hyperglycaemia (an abnormally high amount of glucose levels in blood). The first response to insulin resistance is a compensatory production and secretion of insulin to compensate for the body's decreased sensitivity, leading to hyperinsulinaemia and rendering the individual prediabetic. However, when the pancreas of an insulin resistant individual is unable to produce sufficient hormone to compensate for the increased demand, the β-cell mass will ultimately be exhausted and degenerate leading to hyperglycemia and overt type-2 diabetes (reviewed in 4 and 5). Thus, type 2 diabetes only develops in subjects that are unable to sustain the β-cell compensatory insulin response. These subjects have "susceptible" as opposed to "robust" islets—a condition determined by genetic and/or acquired factors, ex obesity (FIG. 14).

Identification of a peptide/protein that could restore glucose metabolism and treat insulin resistance hold great promise as new therapeutic targets in the potentially combined treatment of type 2 diabetes, metabolic syndrome and other diseases characterised by insulin resistance.

Obesity

Obesity is a medical condition in which body fat has accumulated to an extent that it may have adverse effects on health. Clinically, obesity is defined by the World health Organization (WHO) as having a Body Mass Index (BMI) over 30. Within the obese population, three distinct subclasses can be defined, based on the severity of obesity, ranging from class I obesity (BMI 30.0-34.9), class II obesity (BMI 35.0-39.9) and class III obesity (BMI over 40), which are also cumulative issues for public health action. It is estimated that up to 15% of all adults in Denmark suffer from obesity (BMI>30).

Adverse consequences of obesity are, a negative social image, cardiovascular disease and type 2 diabetes (Darvall et al., Eur J Vasc Endovasc Surg 2007, Haslam & James, Lancet 2005, Vernochet et al., FEBS J 2009, Yusuf et al., Lancet 2004), as well as several cancers (Roberts et al., Annu Rev Med 2009). In addition to these adverse effects, obesity is also associated with a number of other co-morbidities such as psychiatric- and neurological disorders (Beydoun et al., Obes Rev 2008, Harney et al., Pain Med 2007).

Currently, obesity is one of the most important risk factors attributing to disease-burden worldwide, and the second leading preventable cause of death (after smoking) in the US (Mokdad et al., JAMA 2004). In 2005, 1.1 billion adults and 10% of children were classified as overweight or obese (Haslam & James, Lancet 2005). In Europe, the incidence of obesity is increasing, and maybe of even more concern; childhood obesity is becoming more and more prevalent (Livingstone, Public Health Nutr 2011).

SUMMARY OF THE INVENTION

SorCS1 is a receptor that is expressed in the brain, pancreas, fatty tissue and muscles. Genetic studies have shown that polymorphisms in the SORCS1 gene in humans (Nat Genet. 2006 June; 38(6):688-93), rats (Genetics. 2006 November; 174(3):1565-72) and mice (Diabetes. 2007 July; 56(7):1922-9) are strongly associated to risk of development of type-2 diabetes.

SorCS1 is one of five members of the mammalian Vps10p-domain (Vps10p-D) receptor family, which also comprises Sortilin, SorLA, SorCS2, and SorCS3. They are all type-1 transmembrane receptors sharing the characteristic structural feature of an N-terminal Vps10p-D with high homology to Vps10p, a sorting protein in yeast (10). At present the physiological function(s) of the receptor family is unclear, but recent findings indicate that both Sortilin and SorLA play a crucial role as regulators of neuronal survival and death (11, 12). Interestingly, Sortilin has also been associated with insulin-regulated glucose up-take as it may facilitate translocation of the glucose transporter GLUT4 from an intracellular compartment to the plasma membrane (13,14).

SorCS1 is unique among the Vps10p-D receptors as it exists in several distinct splice variants, denoted SorCS1-a, b, c, c+, and d, that encode identical extracellular and transmembrane parts, and cytoplasmic domains that differ in length and sequence (10, 11). The present inventors, have found that SorCS1, in addition to in the nervous system, is expressed in adipose tissue, skeletal muscle and β-cells of the pancreas; all tissues involved in glucose metabolism. Moreover, each splice variant exhibit a distinct tissue distribution as well as subcellular expression pattern suggesting that the tail-variants might be implicated in different biological activities (15-17).

The present inventors have found that SorCS1 can bind to the insulin receptor (IR) and stabilize its expression in muscle- and fat tissue, hereby ensuring the ability to respond to insulin. To support this notion, treatment with the extracellular domain of SorCS1 (soluble SorCS1) results in a marked reduction in both plasma glucose and insulin levels in db/db mice (obesity dependent type-2 diabetic mice).

Furthermore, the inventors have found that the extracellular domain of SorCS1 also results in a significant weight reduction. Sixteen days treatment with hepatic adenoviral overexpression of soluble SorCS1 (extracellular domain) results in a weight reduction of about 23% compared to mice treated with a control virus. The weight reduction is likely due to appetite suppression as food intake in the same period also was reduced compared to control mice.

In conjunction with the present studies the inventors also found that even high overexpression of SorCS1 does not cause hypoglycemia in euglycemic mice.

Accordingly SorCS1 can be used to treat overweight and/or obese patients who are not afflicted with diabetes.

The present inventors have studied the effect of SorCS1 and its different splice variants on the treatment of insulin resistance in mice, and the effect of SorCS1 and the different splice variants on insulin receptor expression using cell studies, and consequently in a main aspect the present invention relates to a method of treatment of obesity and/or overweight, said method comprising administering to an individual in need thereof a therapeutically effective amount of an agent selected from the group consisting of:

a) an isolated SorCS1 polypeptide selected from the group consisting of
   i) an amino acid sequence consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 51, 52, 53 and 54;
   ii) a biologically active sequence variant of the amino acid sequence of i) wherein the variant has at least 95% sequence identity to said SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 and 54; or
   iii) a biologically active fragment of any of i or ii wherein said fragment comprises at least 5 contiguous amino acids, and having at least 95% sequence identity to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 51, 52, 53 and 54 in a range of overlap of at least 5 amino acids, b) a nucleic acid sequence encoding a polypeptide as defined in a);

c) a vector comprising the nucleic acid molecule as defined in b), d) an isolated host cell transformed or transduced with the nucleic acid of b) or the vector of c).

The present invention additionally relates to a SorCS1-like agent for use in treating insulin resistance and/or a disease associated with insulin resistance in an individual, wherein said agent is capable of binding to the insulin receptor (IR) at a SorCS1 binding site and being capable of sensitization of an insulin receptor.

SorCS1 is one of five members of the mammalian Vps10p-domain (Vps10p-D) receptor family, which also comprises Sortilin, SorLA, SorCS2, and SorCS3 (FIG. 1). Murine SorCS1 is unique among the Vps10p-D receptors as it exists in several distinct splice variants, denoted mSorCS1-a, b, c, c+, and d (FIG. 2)

In brief, the inventors have demonstrated that in knockout mice lacking all splice variants of mSorCS1 the old male mice are hyperinsulimic but prediabetic, whereas old SorCS1 knockout female mice are hyperglycaemic and hyperinsulimic, thus both becoming diabetic with age, as a consequence of insulin resistance in the transgenic mice. Furthermore, the inventors have shown that murine SorCS1 binds the insulin receptor and that mSorCS1 regulates the expression of the insulin receptor.

Furthermore, the invention relates to a nucleic acid sequence encoding a polypeptide as defined above for use in the treatment of insulin resistance or diseases associated with insulin resistance in an individual, as well as a vector, a host cell and a packaging cell line comprising the nucleic acid for treatment purposes.

In a further aspect the invention relates to a pharmaceutical composition comprising one or more of the agent as defined above; or the isolated nucleic acid sequence as defined above; or the expression vector as defined above; or a composition of host cells as defined above; or a packaging cell line as defined above, or a combination thereof.

Furthermore, in another aspect the present invention relates to a method of treatment of insulin resistance or diseases associated with insulin resistance, said method comprising administering to an individual in need thereof a therapeutically effective amount of the agent as defined above; or the isolated nucleic acid sequence as defined above; or the expression vector as defined above; or a composition of host cells as defined above; or a packaging cell line as defined above, or a combination thereof.

In another aspect, the present invention relates to a method of upregulating an insulin receptor or a fragment or variant thereof, in a patient in need thereof, said method comprising administering to an individual in need thereof a therapeutically effective amount of the agent as defined above; or the isolated nucleic acid sequence as defined above; or the expression vector as defined above; or a composition of host cells as defined above; or a packaging cell line as defined above, or a combination thereof.

In another aspect, the present invention relates to a method of sensitizing an insulin receptor, said method comprising administering a Vps10p-domain receptor selected from the group consisting of:
  a) SorCS1
  b) SorCS2
  c) SorCS3
  d) Sortilin and
  e) SorLA,
thus being useful in a method of treatment of insulin resistance or diseases associated with insulin resistance (e.g. obesity).

The diseases associated with insulin resistance are in particular selected from the group consisting of insulin resistance syndrome, Type 2 diabetes mellitus, impaired glucose tolerance, the metabolic syndrome, hyperglycemia, hyperinsulinemia, arteriosclerosis, hypercholesterolemia, hypertriglyceridemia, hyperlipidemia, dyslipidemia, obesity, central obesity, polycystic ovarian syndrome, hypercoagulability, hypertension, microalbuminuria, insulin resistance syndrome (IRS), Type 2 diabetes mellitus, impaired glucose tolerance, the metabolic syndrome, hyperglycemia, and hyperinsulinemia.

In yet another aspect the present invention relates to a kit in parts comprising:
  a pharmaceutical composition as defined herein,
  a medical instrument or other means for administering said pharmaceutical composition,
  instructions on how to use the kit in parts.

In a further aspect, the present invention relates to a transgenic knock-out mouse in which the endogenous Vps10p-domain receptor SorCS1 genes have been disrupted to abolish expression of a functional SorCS1 receptor, and wherein said mouse exhibits a reduced response to insulin relative to a non-transgenic control mouse.

In a further important aspect, the invention relates to a method for screening for the ability of the SorCS1-like agent to reduce blood glucose levels, said method comprising the steps of:
  a) providing a first and a second transgenic mouse as defined herein;
  b) administering to said first transgenic mouse a candidate agent, and
  c) administering to said second transgenic mouse a physiological solution, and
  d) taking blood samples from the mouse of b) and c) respectively, at predetermined time intervals, such as at 15 minutes, 30 minutes, 60 minutes, 2 and 4 hours, subsequent to administration of said agent, and
  e) comparing blood glucose levels in the samples of d); wherein a reduction in blood glucose level of said first transgenic mouse administered said candidate agent relative to said second transgenic mouse not administered said candidate agent indicates that the candidate agent reduces blood glucose levels.

In a further important aspect, the invention relates to a method for screening for the ability of the SorCS1-like agent to reduce blood glucose levels, said method comprising the steps of:
  a) providing a first and a second wild-type mouse; and
  b) administering to said first mouse the agent as defined herein, and
  c) administering to said second mouse a physiological solution, and
  d) taking blood samples from the two mice of b) and c) respectively, at predetermined time intervals, such as at 15 minutes, 30 minutes, 60 minutes, 2 and 4 hours, subsequent to administration of said agent, and
  e) comparing plasma glucose levels in the samples of d); wherein a reduction in blood glucose level of said first wild-type mouse administered said agent relative to said second wild type mouse not administered said candidate agent, indicates that the agent reduces blood glucose levels.

In a further aspect the invention relates to a transgenic mouse capable of encoding soluble and/or full length SorCS1 in a tissue specific manner, upon activation of expression.

In yet a further aspect the invention relates to the use of an agent capable of enhancing binding activity between SorCS1 or a fragment or variant thereof, and an insulin receptor for the treatment of insulin resistance and/or diseases associated with insulin resistance.

The invention also relates to methods of promoting or enhancing weight loss in a subject comprising administration of one or more agents disclosed herein (e.g. SorCS1 or active fragments thereof).

BRIEF DESCRIPTION OF THE DRAWINGS

FIG. 2A) Organization of the murine SorCS1 gene leading to the generation of different cytoplasmic tails. FIG. 2B) Amino acid sequences of the mSorCS1 cytoplasmic domains SEQ ID NO75: Mouse preproSorCS1b (isoform 1), SEQ ID NO 76: Mouse preproSorCS1a (isoform 2), SEQ ID NO 77: Mouse preproSorCS1c (isoform 3), SEQ ID NO 78: Mouse preproSorCS1c+(isoform 4), SEQ ID NO 79: Mouse preproSorCS1d.

FIG. 4A) Strategy used to generate mSorCS1 knockout mice by homologous recombination in embryonic stem cells. FIG. 4B) Analysis of mSorCS1 mRNA expression, showing lack of transcription of all mSorCS1 splice variant. FIG. 4C) Western blot analysis of cortex showing lack of mSorCS1 protein in the mSorCS1 knockout (KO) mice.

FIGS. 9A and 9B: Abdominal adipose tissue in wild-type and knockout mice fed a western type diet.

Female FIG. 9A) and male FIG. 9B) wild type and SorCS1 knockout mice were fed a high calorie Western type diet (WD) from 10 weeks of age to 50 weeks of age. At the end of the study the animals were killed and the abdominal fat (adipose tissue) was separated and weighed. Data are means±SEM for 4 to 10 mice in each group.

FIGS. 10A and 10B: Expression of IR, phosphorylated IR (pY-IR) and Glut4 in muscle and adipose tissue. Female SorCS1 knockout (−/−) mice and wild-type (+/+) control mice 50 weeks of age were fasted overnight, injected intraperitoneally with insulin (10 units/kg body weight) in sterile saline, and killed 15 min later. FIG. 10A) Adipose and FIG. 10B) muscle tissue (100 µg) were analysed by western blotting with anti-IR, anti-IR-pY, anti-Glut, and anti-actin as a loading control.

FIGS. 11A and 11B: Physical interaction between SorCS1 and insulin receptor. FIG. 11A) CHO cells transfected with the indicated receptors (only transient transfected with IR$_A$ and IR$_B$) were stimulated with insulin and immunoprecipitated with IR, and analysed by western blotting using α-SorCS1-leu and α-IR, respectively. FIG. 11B) Surface plasmon resonance experiment (BIAcore) showing the direct interaction of soluble full-length extracellular part of SorCS1 with immobilized soluble insulin receptor (IR). The K$_d$ is estimated to approximately 5 nM.

Figure 12:
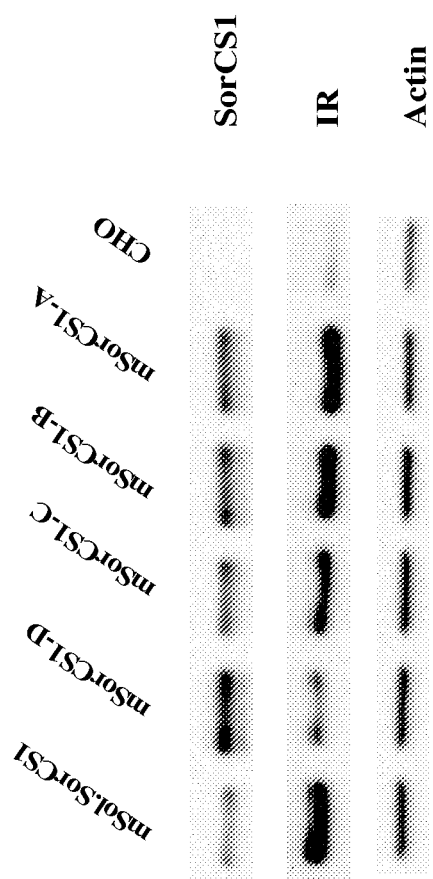

FIG. 12: Insulin receptor expression in CHO cells transfected with SorCS1. Cell lysat from CHO cells and CHO cells stably expressing mSorCS1-A, mSorCS1-B, mSorCS1-C, mSorCS1-D, and msol.SorCS1 (the extracellular part of SorCS1) were subjected to SDS-PAGE and Western blot analysis using anti-IR, anti-SorCS1-leu and anti-actin as a loading control.

Figure 13:
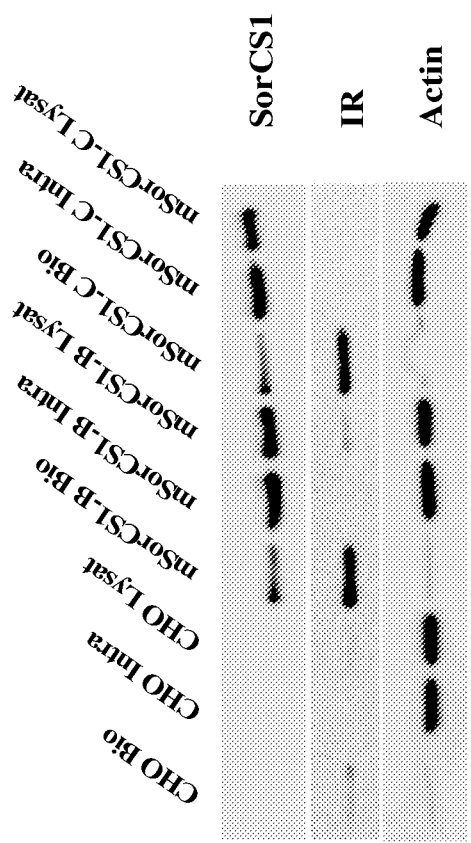

FIG. 13: Expression of IR and SorCS1 on the cell membrane. CHO cells and CHO cells stably expressing mSorCS1-B and mSorCS1-C were subjected to surface biotinylation followed by SDS-PAGE and Western blot analysis using anti-IR, anti-SorCS1-leu and anti-actin as a loading control. The Bio lanes contain biotinylated surface proteins, the Intra lanes contain intracellular proteins, and cell lysates (lysat) were used as input control.

Figure 14:
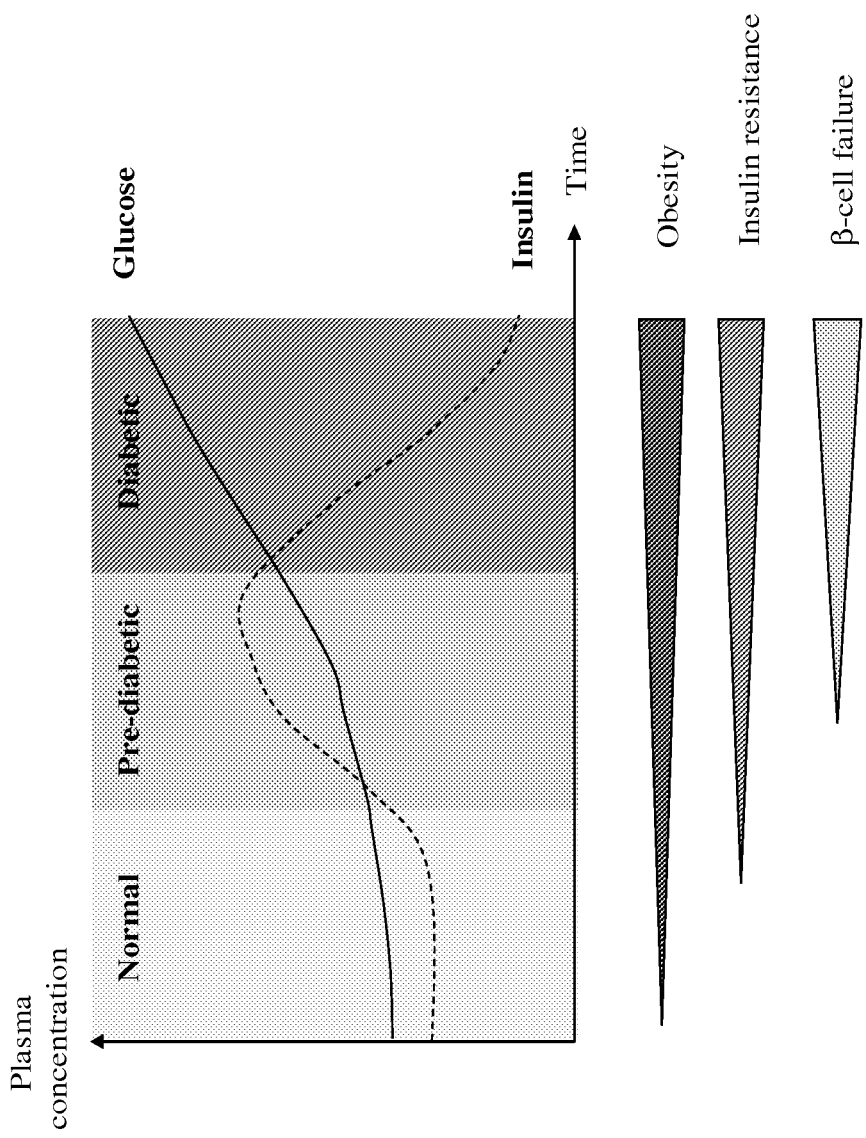

FIG. 14: Development stages towards type 2 diabetes in human. Increases in blood glucose concentration during the development of T2D are illustrated on the graph (black line) showing the change from normal to pre-diabetic, before the onset of frank diabetes. Furthermore, the level of insulin during development of T2D is revealed on the same graph (dashed line), showing an increase of insulin during the pre-diabetic state as compensation to insulin resistance and a severe decline in insulin release at onset of frank diabetes as a consequence of β cell failure.

FIG. 15: Insulin immunostaining of pancreatic islets in wild-type and knockout mice 20 days of age. Pancreata were removed, fixed in paraformaldehyde, cryosectioned, and immunostained with anti-insulin antibody. Representative images are shown.

FIG. 16: Alignment of SorCS1 Sequence alignment of SorCS1 from Human (*homo sapiens*) (SEQ ID NO: 80), Chimpanzee (*Pan troglodytes*) (SEQ ID NO: 34), Cow (*Bos Taurus*) (SEQ ID NO: 40), Mouse (*Mus musculus*) (SEQ ID NO: 16), Rat (*Rattus norvegicus*) (SEQ ID NO: 44), Dog (*Canis lupus familiaris*) (SEQ ID NO: 38) and Chicken (*Gallus gallus*) (SEQ ID NO: 48) origin. The sequence identity is as demonstrated in table 2.

TABLE 2

| | Sequence identity to human SorCS1 | |
|---|---|---|
| Species | Protein (% identity) | DNA (% identity) |
| Human | 100 | 100 |
| Chimpanzee | 99.6 | 99.4 |
| Dog | 97.6 | 92.5 |
| Cow | 92.9 | 89.8 |
| Mouse | 93.2 | 87.7 |
| Rat | 93.2 | 88.0 |
| Chicken | 85.3 | 79.7 |

FIG. 17: Decreased plasma glucose levels in female wild-type and SorCS1 knockout mice after hepatic overexpression of soluble SorCS1.

SorCS1 knockout or wild-type female mice were injected with an adenovirus for hepatic expression of soluble human SorCS1 or with a control virus encoding LacZ. A) Plasmid map of the adenoviral shuttle vector containing the CMV (cytomegalovirus) promoter and the soluble human SorCS1 for hepatic over-expression of soluble SorCS1 are shown.

B) At the day of injection (0d) as well as 7 days after virus administration (7d) plasma glucose was determined in mice fasted 16 hrs. The figure shows relative plasma glucose after normalization to the values obtained at day 0. (n=4). The figure shows that overexpression of soluble SorCS1 (the extracellular domain) reduces plasma glucose in both wild-type and SorCS1 knockout mice.

FIGS. 18A and 18B: Expression of IR, phosphorylated IR, and Glut4 in muscle and adipose tissue from SorCS1 knockout female mice over-expressing soluble SorCS1.

Female SorCS1 knockout (−/−) mice 40 weeks of age were injected with an adenoviral vector expressing either human soluble SorCS1 or LacZ as a control. Twelve days after virus injection, the mice were fasted overnight, injected intraperitoneally with insulin (10 units/kg body weight) in sterile saline, and killed 15 min later. 50 µg lysates from muscle (FIG. 18A) and adipose tissue (FIG. 18B) were analysed by western blotting with anti-IR, anti-IR-pY, and anti-Glut4. The figure shows that treatment with SorCS1-encoding virus increases IR expression, IR phosphorylation as well as Glut4 expression.

FIGS. 19A and 19B: Decreased plasma glucose and insulin levels in diabetic db/db female mice over-expressing soluble SorCS1.

Obese type-2 diabetic female db/db mice 10 weeks of age were injected with adenovirus expressing either human soluble SorCS1 or LacZ as a control. At day 0 (d0) prior to virus infection and 7 days after (d7), blood samples from mice fasted overnight (16 hrs) were obtained by retroorbital bleeding and blood glucose (FIG. 19A) and plasma insulin (FIG. 19B) levels were measured. Data are means±SEM for 5 mice in each group and are presented as relative values compared to day 0. Mice treated with SorCS1 virus, but not LacZ virus, exhibit increased insulin sensitivity as reflected by reduced plasma glucose and insulin levels. The increase in both plasma glucose and insulin from day 0 to 7 in the LacZ group reflects that the animals are in the process of developing diabetes.

Figure 20:
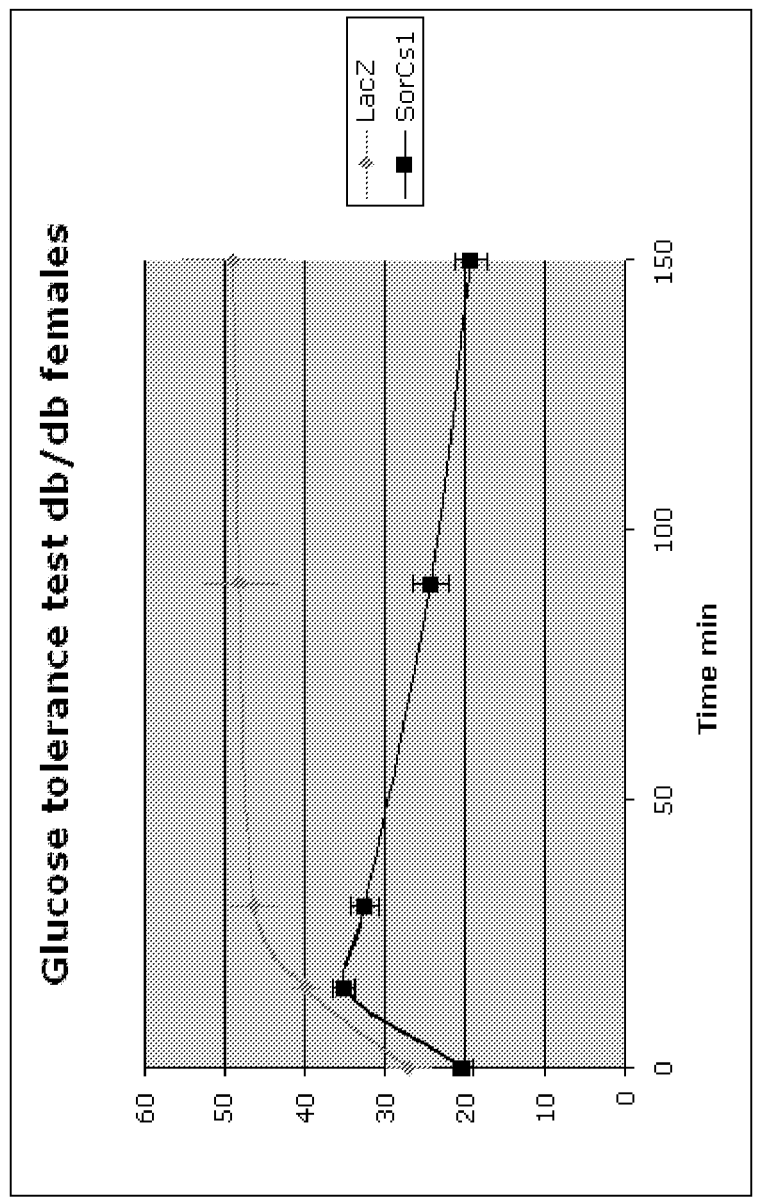

FIG. 20: Glucose tolerance test in diabetic db/db female mice with over-expression of soluble SorCS1.

Fasted female db/db mice were 3 days post-infection with adenovira expressing either soluble SorCS1 or LacZ fasted injected intraperitoneally with a bolus of glucose (2 mg/g body weight) in sterile saline. Blood samples were obtained by retroorbital bleeding at times 0, 15, 30, 90, and 150 min after injection, and blood glucose levels were measured. Values are means±SEM for 5 mice in each group. The experiment shows that baseline blood glucose is restored at 150 min in mice that received the sol-SorCS1 virus, whereas hyperglycemia is maintained in mice treated with LacZ-virus.

FIGS. 21A and 21B: Plasma glucose and insulin levels in diabetic db/db male mice over-expressing soluble SorCS1.

Obese male db/db mice 6 weeks of age were injected with adenovirus expressing either human soluble SorCS1 or LacZ as a control. At day 0 and 7, mice were fasted overnight (16 h), blood samples were obtained by retroorbital bleeding and blood glucose (FIG. 19A) and plasma insulin (FIG. 19B) levels were measured. Data are means±SEM for 5 mice in each group and are presented as relative change to day 0. The figure show that treatment with SorCS1 virus increases glucose sensitivity as plasma glucose decreases while insulin levels are similar to that of mice receiving LacZ virus. The increase in plasma insulin from day 0 to 7 in both groups reflects that the animals are in the process of developing diabetes. During the course of the experiment they can still compensate a reduction in insulin sensitivity by increasing insulin production.

Figure 22:
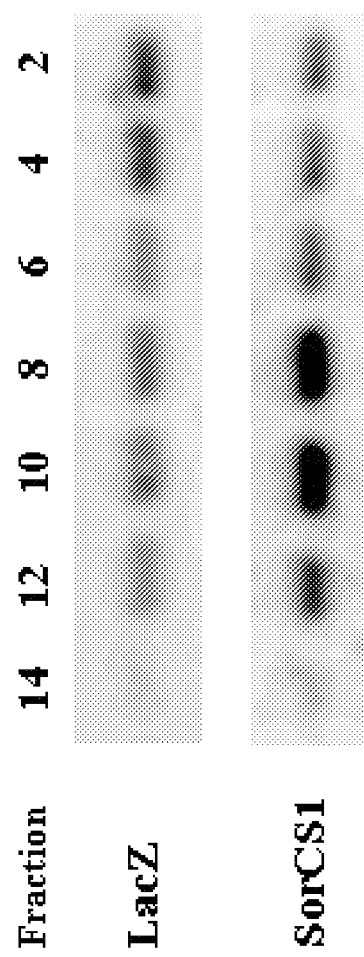

FIG. 22: Subcellular localization of Glut4 in muscle tissue from db/db male mice over-expressing soluble SorCS1.

Light microsomes isolated by subcellular fractionation from muscle tissue of five db/db male mice after over-expression of soluble SorCS1 or lacZ were fractionated in a 0.8 M to 1.6 M sucrose velocity gradient. Gradient fractions were subjected to gel electrophoresis and blotted with a Glut4 antibody, thus identifying the location of Glut4 in the different fractions. The experiment shows that SorCS1 expression changes the subcellular localization of Glut4, in line an important role of SorCS1 in regulating glucose uptake.

Figure 23B:
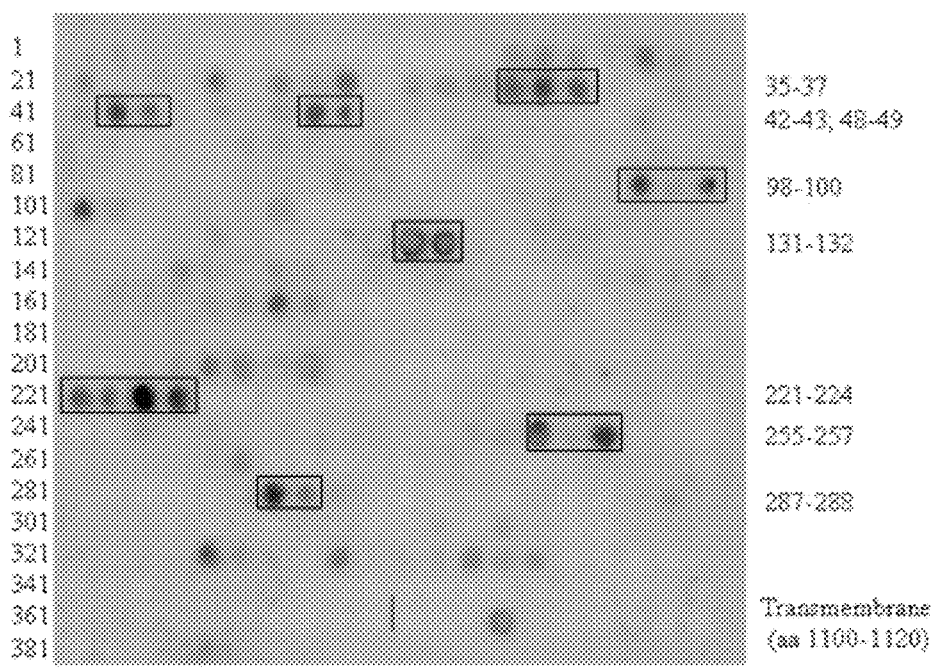

FIGS. 23A and 23B: Analysis of SorCS1/IR contact sequences by SPOT analysis.

FIG. 23A) Consecutive 16-mer amino acid peptides (SEQ ID NOs: 81-87, respectively, in order of appearance) overlapping by three residues of the human insulin receptor were spotted on to filters. The filters were subsequently incubated with the radiolabelled extracellular domains of murine SorCS1, and binding was detected by autoradiography. Possible SorCS1 binding sites in the insulin receptor are indicated. FIG. 23B) Consecutive 16-mer amino acid peptides (SEQ ID NOs: 88-95, respectively, in order of appearance) overlapping by three residues of human SorCS1-a were spotted on to filters and probed for insulin receptor binding using his-tagged soluble receptor. Peptides capable of SorCS1-a binding were visualized by Western blotting using an antibody against the histidine tag. Possible binding sequences in SorCS1-a are indicated.

FIGS. 24A and 23B: Gene expression profiling of adipose tissue from SorCS1 knockout mice by PCR arrays.

The gene expression in SorCS1 knockout adipose tissue as compared to wild-type adipose tissue was examined for FIG. 24A) 84 genes related to the mouse insulin signalling pathway and FIG. 24B) 84 genes related to mouse lipoprotein signalling & cholesterol metabolism. Genes in the SorCS1 knockouts that are either 3 times higher or lower than that of wild-type mice are listed and their putative functions indicated.

Figure 25:
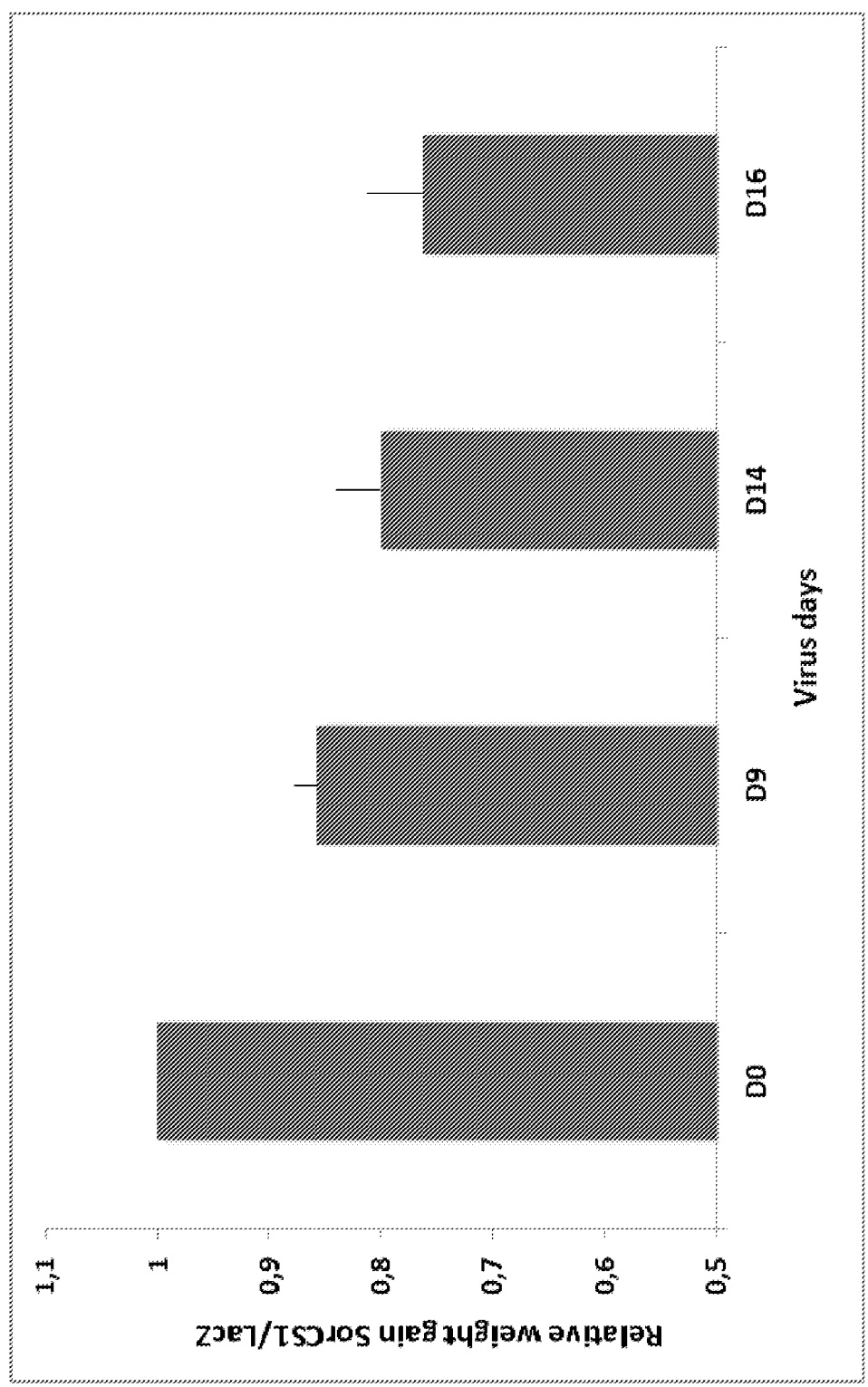

FIG. 25: Reduced weight in diabetic db/db mice after overexpression of soluble SorCS1. Db/db mice 6 weeks of age, with spontaneous type-2 diabetes, were injected i.v with adenovirus encoding the soluble extra-cellular domain of SorCS1 or LacZ (control). Day 0, 9, 14 and 16 after virus injection the mice were weighed. The change in weight after treatment with SorCS1 virus is shown relative to the LacZ control group (N=5 in both groups). The conclusion is that over-expression of soluble SorCS1 leads to a time-dependent reduction in weight.

Figure 26:
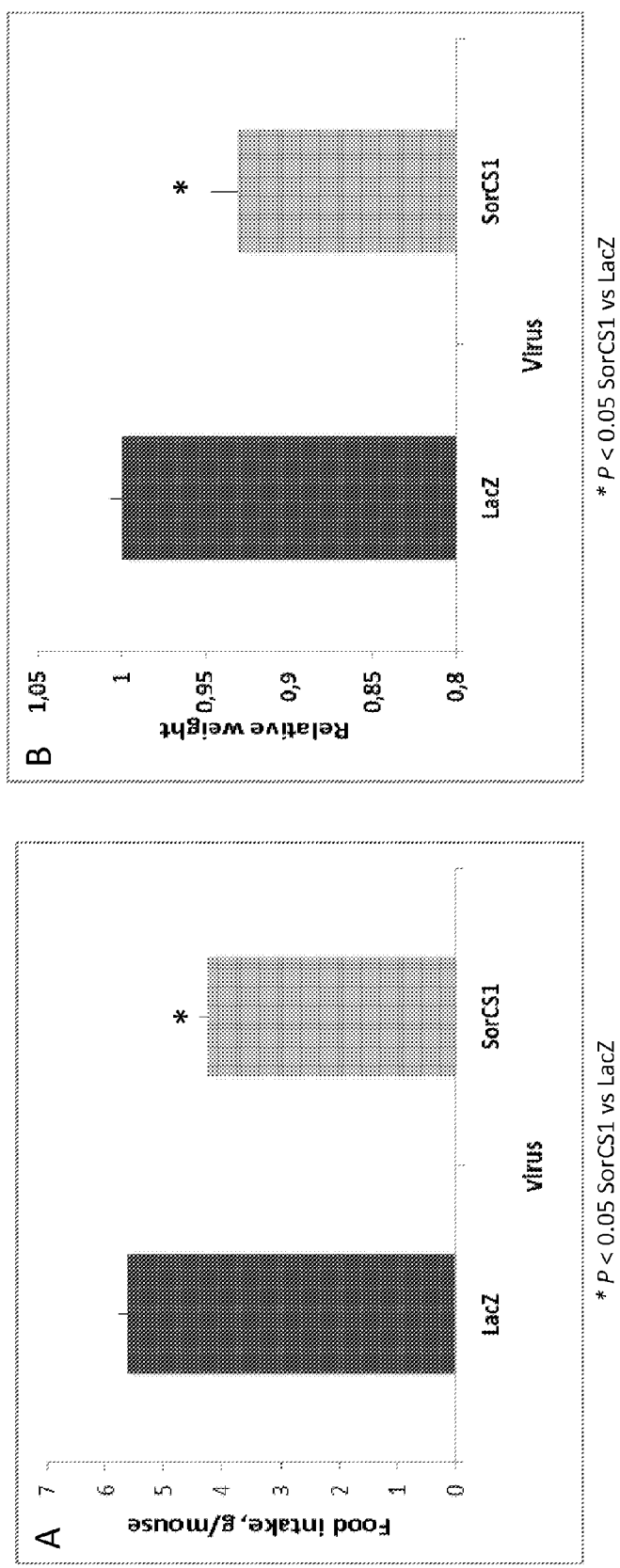

FIG. 26: Reduced food intake and weight in diabetic db/db mice after over-expression of soluble SorCS1.

Db/db mice 6 weeks of age, with spontaneous type-2 diabetes, were injected i.v with adenovirus encoding the soluble extra-cellular domain of SorCS1 or LacZ (control). A) At day 9 the mice were placed in metabolic cages and the food intake over the following 24 hours was measured. Mice with over-expression of soluble SorCS1 ingested significant less than the control mice expressing LacZ. B) At day 0 and 11 after virus treatment the mice were weighed. The relative weight changes over the time period are shown. In conclusion overexpression of soluble SorCS1 leads to a significant weight reduction.

DETAILED DESCRIPTION ON THE INVENTION

Definitions

Unless specifically indicated otherwise, all technical and scientific terms used herein have the same meaning as commonly understood by those of ordinary skill in the art to which this invention belongs. For purposes of the present invention, the following terms are defined.

Adjuvant: Any substance whose admixture with an administered immunogenic determinant/antigen increases or otherwise modifies the immune response to said determinant.

Affinity: The interaction of most ligands with their binding sites can be characterized in terms of a binding affinity. In general, high affinity ligand binding results from greater intermolecular force between the ligand and its receptor while low affinity ligand binding involves less intermolecular force between the ligand and its receptor. In general, high affinity binding involves a longer residence time for the ligand at its receptor binding site than is the case for low affinity binding. High affinity binding of ligands to receptors is often physiologically important when some of the binding energy can be used to cause a conformational change in the receptor, resulting in altered behavior of an associated ion channel or enzyme.

A ligand that can bind to a receptor, alter the function of the receptor and trigger a physiological response is called an agonist for that receptor. Agonist binding to a receptor can be characterized both in terms of how much physiological response can be triggered and the concentration of the agonist that is required to produce the physiological response. High affinity ligand binding implies that a relatively low concentration of a ligand is adequate to maximally occupy a ligand binding site and trigger a physiological response. Low affinity binding implies that a relatively high concentration of a ligand is required before the binding site is maximally occupied and the maximum physiological response to the ligand is achieved. Ligand binding is often characterized in terms of the concentration of ligand at which half of the receptor binding sites are occupied, known as the dissociation constant ($k_d$). Affinity is also the strength of binding between receptors and their ligands, for example between an antibody and its antigen.

Alcohol: A class of organic compounds containing one or more hydroxyl groups (OH). In this context a saturated or unsaturated, branched or unbranched hydrocarbon group sitting as a substituent on a larger molecule.

Alicyclic group: the term "alicyclic group" means a cyclic hydrocarbon group having properties resembling those of aliphatic groups.

Aliphatic group: in the context of the present invention, the term "aliphatic group" means a saturated or unsaturated linear or branched hydrocarbon group. This term is used to encompass alkyl, alkenyl, and alkynyl groups, for example.

Alkyl group: the term "alkyl group" means a saturated linear or branched hydrocarbon group including, for example, methyl, ethyl, isopropyl, t-butyl, heptyl, dodecyl, octadecyl, amyl, 2-ethylhexyl, and the like.

Alkenyl group: the term "alkenyl group" means an unsaturated, linear or branched hydrocarbon group with one or more carbon-carbon double bonds, such as a vinyl group.

Alkynyl group: the term "alkynyl group" means an unsaturated, linear or branched hydrocarbon group with one or more carbon-carbon triple bonds.

Amphiphil: substance containing both polar, water-soluble and nonpolar, water-insoluble groups.

Agonist: An agonist is a compound capable of increasing or effecting the activity of a receptor. Specifically, a Vps10p-domain receptor agonist is a compound capable of binding to one or more of binding sites of a Vps10p-domain receptor thereby inducing the same physiological response as a given endogenous agonist ligand compound.

Antagonist: An antagonist is in this case synonymous with an inhibitor. An antagonist is a compound capable of decreasing the activity of an effector such as a receptor. Specifically, a Vps10p-domain receptor antagonist is a compound capable of binding to one or more of binding sites of Vps10p-domain receptor thereby inhibiting binding of another ligand thus inhibiting a physiological response.

Antibody: The term "antibody" as referred to herein includes whole antibodies and any antigen binding fragment (i.e., "antigen-binding portion") or single chain thereof.

Polyclonal antibody: Polyclonal antibodies are a mixture of antibody molecules recognising a specific given antigen, hence polyclonal antibodies may recognise different epitopes within said antigen.

Aromatic group: the term "aromatic group" or "aryl group" means a mono- or polycyclic aromatic hydrocarbon group.

Binding: The term "binding" refers to a condition of proximity between chemical entities or compounds, or portions thereof. The binding may be non-covalent-wherein the juxtaposition is energetically favoured by hydrogen bonding or van der Waals or electrostatic interactions-or it may be covalent. The agents according to the invention are capable of binding to the insulin receptor. An assay for binding may be the Biocore assay discussed in relation to FIG. 11B as well as the co.IP assay discussed in relation to FIG. 11A.

Binding site: The term "binding site" or "binding pocket", as used herein, refers to a region of a molecule or molecular complex that, as a result of its shape, favourably associates with another molecule, molecular complex, chemical entity or compound. As used herein, the pocket comprises at least a deep cavity and, optionally a shallow cavity.

Bioreactive agent or biologically active or biological activity: The terms are as used herein refers to effect of any a substance which may be used in connection with an application that is therapeutic or otherwise useful according to this invention. The biological activity refers to the biological effect in vitro and/or in vivo. In the present context the biological activity of an agent according to this invention is the capability of binding to the insulin receptor and/or enhancing binding of a SorCS1-like agent to the insulin receptor, and in a more preferred embodiment the biological activity includes sensitization of the insulin receptor. The bioactive agents may be neutral, positively or negatively charged. Suitable bioactive agents include, for example, prodrugs, diagnostic agents, therapeutic agents, pharmaceutical agents, drugs, oxygen delivery agents, blood substitutes, synthetic organic molecules, polypeptides, peptides, vitamins, steroids, steroid analogues and genetic determinants, including nucleosides, nucleotides and polynucleotides.

Cationic group: A chemical group capable of functioning as a proton donor when a compound comprising the chemical group is dissolved in a solvent, preferably when dissolved in water.

Complex: As used herein the term "complex" refers to the combination of a molecule or a protein, conservative analogues or truncations thereof bound to a chemical entity.

Cyclic group: the term "cyclic group" means a closed ring hydrocarbon group that is classified as an alicyclic group, aromatic group, or heterocyclic group.

Cycloalkenyl: means a monovalent unsaturated carbocyclic radical consisting of one, two or three rings, of three to eight carbons per ring, which can optionally be substituted with one or two substituents selected from the group consisting of hydroxy, cyano, lower alkenyl, lower alkoxy, lower haloalkoxy, alkenylthio, halo, haloalkenyl, hydroxyalkenyl, nitro, alkoxycarbonenyl, amino, alkenylamino, alkenylsulfonyl, arylsulfonyl, alkenylaminosulfonyl, arylaminosulfonyl, alkylsulfonylamino, arylsulfonylamino, alkenylaminocarbonyl, arylaminocarbonyl, alkenylcarbonylamino and arylcarbonylamino.

Cycloalkyl: means a monovalent saturated carbocyclic radical consisting of one, two or three rings, of three to eight carbons per ring, which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino and arylcarbonylamino.

Electrostatic interaction: The term "electrostatic interaction" as used herein refers to any interaction occurring between charged components, molecules or ions, due to attractive forces when components of opposite electric charge are attracted to each other. Examples include, but are not limited to: ionic interactions, covalent interactions, interactions between a ion and a dipole (ion and polar molecule), interactions between two dipoles (partial charges of polar molecules), hydrogen bonds and London dispersion bonds (induced dipoles of polarizable molecules). Thus, for example, "ionic interaction" or "electrostatic interaction" refers to the attraction between a first, positively charged molecule and a second, negatively charged molecule. Ionic or electrostatic interactions include, for example, the attraction between a negatively charged bioactive agent.

Form a ring: means that the atoms mentioned are connected through a bond when the ring structure is formed.

Fragments: The polypeptide fragments according to the present invention, including any functional equivalents thereof, may in one embodiment comprise less than 500 amino acid residues, such as less than 450 amino acid residues, for example less than 400 amino acid residues, such as less than 350 amino acid residues, for example less than 300 amino acid residues, for example less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues, such as less than 45 amino acid residues, for example less than 40 amino acid residues, such as 35 amino acid residues, for example 30 amino acid residues, such as 25 amino acid residues, such as 20 amino acid residues, for example 15 amino acid residues, such as 10 amino acid residues, for example 5 contiguous amino acid residues of an amino acid sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 and 51 or a variant thereof being at least 70% (e.g. at least 85%, 90%, 95%, 97%, 98%, or 99%) identical to said sequences. Also, the polypeptide fragments according to the present invention, including any functional equivalents thereof, may in one embodiment comprise more than 5 amino acid residues, such as more than 10 amino acid residues, for example more than 15 amino acid residues, such as more than 20 amino acid residues, for example more than 25 amino acid residues, for example more than 50 amino acid residues, such as more than 75 amino acid residues, for example more than 100 amino acid residues, such as more than 125 amino acid residues, for example more than 150 amino acid residues, such as more than 175 amino acid residues, for example more than 200 amino acid residues, such as more than 225 amino acid residues, for example more than 250 amino acid residues, such as more than 275 amino acid residues, for example more than 300 amino acid residues, such as more than 325 amino acid residues, for example more than 350 amino acid residues, such as more than 375 amino acid residues, for example more than 400 amino acid residues, such as more than 425 amino acid residues, for example more than 450 amino acid residues, such as more than 475 amino acid residues, for example more than 500 amino acid residues, such as more than 525 amino acid residues, for example more than 550 amino acid residues, such as more than 575 amino acid residues, for example more than 600 amino acid residues, such as 625 amino acid residues, for example 650 amino acid residues, such as 675 amino acid residues, such as 700 amino acid residues of an amino acid sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 and 51 or a variant thereof being at least 70% (e.g. at least 85%, 90%, 95%, 97%, 98%, or 99%) identical to said sequences. Examples of active fragments include one or more of the following: SEQ ID NO: 1 aa 103-124, SEQ ID NO: 1 aa 125-143, SEQ ID NO: 1 aa 144-162, SEQ ID NO: 1 aa 197-218, SEQ ID NO: 1 aa 391-409, SEQ ID NO: 1 aa 661-684, SEQ ID NO: 1 aa 763-783, or SEQ ID NO: 1 aa 859-876. The fragments may be from 5 to 50 amino acids in length, for example, 15 to 50, 5 to 15, 7 to 15, 10 to 25, 10 to 20, and 7 to 25 amino acids in length.

Functional equivalency: "Functional equivalency" as used in the present invention is, according to one preferred embodiment, established by means of reference to the corresponding functionality of a predetermined fragment of the sequence.

Functional equivalents or variants of a SorCS1 polypeptide, or a fragment thereof will be understood to exhibit amino acid sequences gradually differing from the preferred predetermined SorCS1 polypeptide or the SorCS1 fragment sequence respectively, as the number and scope of insertions, deletions and substitutions including conservative substitutions increase, while retaining the biological activity of a SorCS1 polypeptide in this context. This difference is measured as a reduction in homology between the preferred predetermined sequence and the fragment or functional equivalent.

A functional variant obtained by substitution may well exhibit some form or degree of native SorCS1 activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity is not a principal measure of a fragment being a variant or functional equivalent of a preferred predetermined fragment according to the present invention.

Gene "silencing": a process leading to reduced expression of endogenous genes. Gene silencing is preferably the result of post-transcriptional reduction of gene expression.

Group: (Moiety/substitution) as is well understood in this technical area, a large degree of substitution is not only tolerated, but is often advisable. Substitution is anticipated on the materials of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like. The same definitions apply to "alkenyl group" and "alkenyl moiety"; to "alkynyl group" and "alkynyl moiety"; to "cyclic group" and "cyclic moiety; to "alicyclic group" and "alicyclic moiety"; to "aromatic group" or "aryl group" and to "aromatic moiety" or "aryl moiety"; as well as to "heterocyclic group" and "heterocyclic moiety".

Heterocyclic group: the term "heterocyclic group" means a closed ring hydrocarbon in which one or more of the atoms in the ring is an element other than carbon (e.g., nitrogen, oxygen, sulphur, etc.).

Heterocyclyl means a monovalent saturated cyclic radical, consisting of one to two rings, of three to eight atoms per ring, incorporating one or two ring heteroatoms (chosen from N, O or $S(O)_{0-2}$, and which can optionally be substituted with one or two substituents selected from the group consisting of hydroxyl, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminofarbonyl, arylaminocarbonyl, alkylcarbonylamino, or arylcarbonylamino.

Heteroaryl means a monovalent aromatic cyclic radical having one to three rings, of four to eight atoms per ring, incorporating one or two heteroatoms (chosen from nitrogen, oxygen, or sulphur) within the ring which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonlamino and arylcarbonylamino.

Homology: The homology between amino acid sequences may be calculated using well known scoring matrices such as any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Fragments sharing homology with fragments of SEQ ID NOs: SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 and 51, respectively, are to be considered as falling within the scope of the present invention when they are preferably at least about 60 percent homologous, for example at least 65 percent homologous, for example at least 70 percent homologous, for example at least 75 percent homologous, for example at least 80 percent homologous, for example at least 85 percent homologous, for example at least 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with said predetermined fragment sequences, respectively. According to one embodiment of the invention, the homology percentages refer to identity percentages.

A further suitably adaptable method for determining structure and function relationships of peptide fragments is described in U.S. Pat. No. 6,013,478, which is herein incorporated by reference. Also, methods of assaying the binding of an amino acid sequence to a receptor moiety are known to the skilled artisan.

In addition to conservative substitutions introduced into any position of a preferred predetermined SorCS1 polypeptide, or a fragment thereof, it may also be desirable to introduce non-conservative substitutions in any one or more positions of such a SorCS1 polypeptide, or a fragment thereof.

A non-conservative substitution leading to the formation of a functionally equivalent fragment of a SorCS1 polypeptide, or a fragment thereof would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Variants obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same or other SorCS1 polypeptides, or fragment thereof, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Covalent or aggregative functional equivalents and derivatives thereof are useful as reagents in immunoassays or for affinity purification procedures. For example, a fragment of a SorCS1 polypeptide according to the present invention may be insolubilized by covalent bonding to cyanogen bromide-activated Sepharose by methods known per se or adsorbed to polyolefin surfaces, either with or without glutaraldehyde cross-linking, for use in an assay or purification of anti-SorCS1 activity modulator antibodies or cell surface receptors. Fragments may also be labelled with a detectable group, e.g., radioiodinated by the chloramine T procedure, covalently bound to rare earth chelates or conjugated to another fluorescent moiety for use in e.g. diagnostic assays.

Mutagenesis of a preferred predetermined SorCS1 polypeptide, or a fragment thereof, can be conducted by making amino acid insertions, usually on the order of about from 1 to 10 amino acid residues, preferably from about 1 to 5 amino acid residues, or deletions of from about from 1 to 10 residues, such as from about 2 to 5 residues.

In one embodiment the ligand of binding site 1, 2 or 3 is an oligopeptide synthesised by automated synthesis. Any of the commercially available solid-phase techniques may be employed, such as the Merrifield solid phase synthesis method, in which amino acids are sequentially added to a growing amino acid chain (see Merrifield, J. Am. Chem. Soc. 85:2149-2146, 1963).

Equipment for automated synthesis of polypeptides is commercially available from suppliers such as Applied Biosystems, Inc. of Foster City, Calif., and may generally be operated according to the manufacturer's instructions. Solid phase synthesis will enable the incorporation of desirable amino acid substitutions into any fragment of SorCS1 according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Oligomers including dimers including homodimers and heterodimers of fragments of sortilin inhibitors according to the invention are also provided and fall under the scope of the invention. SorCS1 polypeptides and fragments, functional equivalents and variants thereof can be produced as homodimers or heterodimers with other amino acid sequences or with native sortilin inhibitor sequences. Heterodimers include dimers containing immunoreactive sortilin inhibiting fragments as well as sortilin inhibiting fragments that need not have or exert any biological activity.

SorCS1 polypeptides, or fragments and variants thereof may be synthesised both in vitro and in vivo. Methods for in vitro synthesis are well known, and methods being suitable or suitably adaptable to the synthesis in vivo of sortilin inhibitors are also described in the prior art. When synthesized in vivo, a host cell is transformed with vectors containing DNA encoding a sortilin peptide inhibitor or a fragment thereof. A vector is defined as a replicable nucleic acid construct. Vectors are used to mediate expression of SorCS1 polypeptides, and/or fragments and variants. An expression vector is a replicable DNA construct in which a nucleic acid sequence encoding the predetermined sortilin inhibiting fragment, or any functional equivalent thereof that can be expressed in vivo, is operably linked to suitable control sequences capable of effecting the expression of the fragment or equivalent in a suitable host. Such control sequences are well known in the art. Both prokaryotic and eukaryotic cells may be used for synthesising ligands. Cultures of cells derived from multicellular organisms however represent preferred host cells. In principle, any higher eukaryotic cell culture is workable, whether from vertebrate or invertebrate culture. Examples of useful host cell lines are VERO and HeLa cells, Chinese hamster ovary (CHO) cell lines, and WI38, BHK, COS-7, 293 and MDCK cell lines. Preferred host cells are eukaryotic cells known to synthesize endogenous sortilin inhibitors. Cultures of such host cells may be isolated and used as a source of the fragment, or used in therapeutic methods of treatment, including therapeutic methods aimed at promoting or inhibiting a growth state, or diagnostic methods carried out on the human or animal body.

Hydrophobic bond: The term "hydrogen bond" as used herein refers to an attractive force, or bridge, which may occur between a hydrogen atom which is bonded covalently to an electronegative atom, for example, oxygen, sulphur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

Hydrophobic interaction: The term "hydrophobic interaction" as used herein refers to any interaction occurring between essentially non-polar (hydrophobic) components located within attraction range of one another in a polar environment (e.g. water). As used herein, attraction range is on the scale of from 0.1 up to 2 nm. A particular type of hydrophobic interaction is exerted by "Van der Waal's forces", i.e. the attractive forces between non-polar molecules that are accounted for by quantum mechanics. Van der Waal's forces are generally associated with momentary dipole moments which are induced by neighbouring molecules and which involve changes in electron distribution.

Insulin: Insulin is a hormone that is produced by the beta cells of the pancreas. The insulin produced is released into the blood stream and is transported throughout the body. Insulin is an important hormone that has many actions within the body. Most of the actions of insulin are directed at metabolism (control) of carbohydrates (sugars and starches), lipids (fats), and proteins. Insulin also is important in regulating the cells of the body including their growth.

Insulin resistance: Insulin resistance (IR) is a condition in which the cells of the body become resistant to the effects of insulin, that is, the normal response to a given amount of insulin is reduced. As a result, higher levels of insulin are needed in order for insulin to have its effects. Insulin resistance precedes the development of type 2 diabetes, sometimes by several years. In individuals who will ultimately develop type 2 diabetes, it is believed that blood glucose and insulin levels are normal for many years; then at some point in time, insulin resistance develops. Accordingly, the treatment of the cause of insulin resistance is preferred over treatment of the symptoms of diabetes. The present invention is primarily aimed at providing a medicament for use in the treatment of insulin resistance.

In vitro/in vivo: the terms are used in their normal meaning.

Ligand: a substance, compound or biomolecule such as a protein including receptors, that is able to bind to and form a complex with (a second) biomolecule to serve a biological purpose. In a narrower sense, it is a signal triggering molecule binding to a site on a target protein, by intermolecular forces such as ionic bonds, hydrogen bonds and Van der Waals forces. The docking (association) is usually reversible (dissociation). Actual irreversible covalent binding between a ligand and its target molecule is rare in biological systems. As opposed to the meaning in metalorganic and inorganic chemistry, it is irrelevant, whether or not the ligand actually binds at a metal site, as it is the case in hemoglobin. Ligand binding to receptors may alter the chemical conformation, i.e. the three dimensional shape of the receptor protein. The conformational state of a receptor protein determines the functional state of a receptor. The tendency or strength of binding is called affinity. Ligands include substrates, inhibitors, activators, non-self receptors, co-receptors and neurotransmitters.

Pharmaceutical agent: The terms "pharmaceutical agent" or "drug" or "medicament" refer to any therapeutic or prophylactic use of an agent according to the invention, which agent may be used in the treatment (including the prevention, diagnosis, alleviation, or cure) of a malady, affliction, condition, disease or injury in a patient. Therapeutically useful genetic determinants, peptides, polypeptides and polynucleotides may be included within the meaning of the term pharmaceutical or drug. As defined herein, a "therapeutic agent", "pharmaceutical agent" or "drug" or "medicament" is a type of bioactive agent.

Pharmaceutical composition: or drug, medicament or agent refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical composition" and "medicament" preferably encompass an active agent as such or an inactive drug and the active metabolite.

Polypeptide: The term "polypeptide" as used herein refers to a molecule comprising at least two amino acids. The amino acids may be natural or synthetic. "Oligopeptides" are defined herein as being polypeptides of length not more than 100 amino acids. The term "polypeptide" is also intended to include proteins, i.e. functional biomolecules comprising at least one polypeptide; when comprising at least two polypeptides, these may form complexes, be covalently linked or may be non-covalently linked. The polypeptides in a protein can be glycosylated and/or lipidated and/or comprise prosthetic groups.

Polynucleotide: "Polynucleotide" as used herein refers to a molecule comprising at least two nucleic acids. The nucleic acids may be naturally occurring or modified, such as locked nucleic acids (LNA), or peptide nucleic acids (PNA). Polynucleotide as used herein generally pertains to i) a polynucleotide comprising a predetermined coding sequence, or
ii) a polynucleotide encoding a predetermined amino acid sequence, or
iii) a polynucleotide encoding a fragment of a polypeptide encoded by polynucleotides (i) or (ii), wherein said fragment has at least one predetermined activity as specified herein; and
iv) a polynucleotide the complementary strand of which hybridizes under stringent conditions with a polynucleotide as defined in any one of (i), (ii) and (iii), and encodes a polypeptide, or a fragment thereof, having at least one predetermined activity as specified herein; and
v) a polynucleotide comprising a nucleotide sequence which is degenerate to the nucleotide sequence of polynucleotides (iii) or (iv);

or the complementary strand of such a polynucleotide.

Prediabetes: Prediabetes refers to the intermediate metabolic states between normal and diabetic glucose homeostasis. It comprises of two distinct states, those of impaired fasting glucose (IFG) and impaired glucose tolerance (IGT) or a combination of both but by itself is not diabetes. Thus, it is a condition in which blood glucose level is higher than normal, but not high enough to be classified as type 2 diabetes.

Purified antibody: The term a "purified antibody" is an antibody at least 60 weight percent of which is free from the polypeptides and naturally-occurring organic molecules with which it is naturally associated. Preferably, the preparation comprises antibody in an amount of at least 75 weight percent, more preferably at least 90 weight percent, and most preferably at least 99 weight percent.

Root mean square deviation: The term "root mean square deviation" (RMSD) is used as a mean of comparing two closely related structures and relates to a deviation in the distance between related atoms of the two structures after structurally minimizing this distance in an alignment. Related proteins with closely related structures will be characterized by relatively low RMSD values whereas larger differences will result in an increase of the RMSD value.

Sensitization of the insulin receptor: the term "sensitization of the insulin receptor" is used to explain that the agents according to the invention are preferred to be able to stabilise the insulin receptor, and preferably also to increase the amount of insulin receptors. Sensitization of the insulin receptor may be measured by administering an agent according to the invention and then performing a glucose tolerance test, as discussed in relation to FIG. 20. Furthermore, the sensitization may be assessed by assessing the amount of insulin receptors before and after administration of the agent according to the invention, whereby an increase is indicative of sensitization of the insulin receptor. Also, the sensitization may be assessed by assessing the amount of activated insulin receptors, ie. phosphorylated insulin receptors. Furthermore, the sensitization may also be assessed by measuring the affinity between insulin and the insulin receptor, in that an increase in affinity is an indication of sensitization.

Sequence identity: Sequence identity is determined in one embodiment by utilising fragments of SorCS1 polypeptides comprising at least 25 contiguous amino acids and having an amino acid sequence which is at least 80%, such as 85%, for example 90%, such as 95%, for example 99% identical to the amino acid sequence of any of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 and 51 as well as SEQ ID NO: 1 aa 103-124, SEQ ID NO: 1 aa 125-143, SEQ ID NO: 1 aa 144-162, SEQ ID NO: 1 aa 197-218, SEQ ID NO: 1 aa 391-409, SEQ ID NO: 1 aa 661-684, SEQ ID NO: 1 aa 763-783 and SEQ ID NO: 1 aa 859-876.

respectively, wherein the percent identity is determined with the algorithm GAP, BESTFIT, or FASTA in the Wisconsin Genetics Software Package Release 7.0, using default gap weights.

The following terms are used to describe the sequence relationships between two or more polynucleotides: "predetermined sequence", "comparison window", "sequence identity", "percentage of sequence identity", and "substantial identity".

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

As applied to polypeptides, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

An "unrelated" or "non-homologous" sequence shares less than 40% identity, though preferably less than 25% identity, with one of the SorCS1 polypeptide sequences of the present invention. The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:

i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)

xii) Hydrophilic, acidic amino acids (Gln, Asn, Glu, Asp), and
xiii) Hydrophobic amino acids (Leu, Ile, Val)

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

SorCS1-like agent: The expression "a SorCS1-like agent" as used herein refers to any agent capable of structurally imitating the Vps10p-domain receptor SorCS1 thus having the same or similar biological effect on the insulin receptor, as the effect demonstrated herein by the present inventors. Accordingly, as SorCS1-like agent may be a peptide, a polypeptide, a small organic molecule, siRNA, siDNA, nucleic acid molecules encoding a polypeptide. In a preferred embodiment, the SorCS1-like agent is a SorCS1 fragment, preferably human soluble SorCS1 (SEQ ID NO: 15) or a precursor thereof.

Substituted lower alkyl means a lower alkyl having one to three substituents selected from the group consisting of hydroxyl, alkoxy, amino, amido, carboxyl, acyl, halogen, cyano, nitro and thiol.

Treatment: The term "treatment" as used herein refers to a method involving therapy including surgery of a clinical condition in an individual including a human or animal body. The therapy may be ameliorating, curative or prophylactic, i.e. reducing mental and behavioural symptoms.

Variants: The term "variants" as used herein refers to amino acid sequence variants said variants preferably having at least 60% identity, for example at least 63% identity, such as at least 66% identity, for example at least 70% sequence identity, for example at least 72% sequence identity, for example at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with any of the predetermined sequences.

The variants preferably include the fragments shown to bind to the insulin receptor, see for example FIG. 23B and/or parts of the SorCS1 sequence conserved from one species to other, see for example FIG. 13.

Up-regulation of expression: a process leading to increased expression of genes, preferably of endogenous genes.

Insulin Resistance

Insulin resistance (IR) is a condition in which the cells of the body become resistant to the effects of insulin, that is, the normal response to a given amount of insulin is reduced. As a result, higher levels of insulin are needed in order for insulin to have its effects. The resistance is seen with both the body's own insulin (endogenous) and if insulin is given through injection (exogenous).

There are probably several causes of insulin resistance and as described herein above there is a strong genetic factor. Drug-induced IR may be a further cause. In addition, insulin resistance is seen often in the following conditions: the metabolic syndrome, obesity, pregnancy, infection or severe illness and stress during steroid use. Treatments of insulin resistance in these conditions are aspects of the present invention.

The relationship between insulin resistance and diabetes is as follows. Type 2 diabetes, is the type of diabetes that normally occurs later in life. Insulin resistance precedes the development of type 2 diabetes, sometimes by several years. In individuals who will ultimately develop type 2 diabetes, it is believed that blood glucose and insulin levels are normal for many years; then at some point in time, insulin resistance develops most likely caused by overweight/obesity, physical inactivity and/or a series of currently not yet well-defined genetic polymorphisms. Accordingly, the treatment of the cause of insulin resistance is preferred over treatment of the symptoms of diabetes. The present invention is primarily aimed at providing a medicament for use in the treatment of insulin resistance.

As is well known by those skilled in the art, one of the actions of insulin is to cause the cells of the body, particularly hepatocytes and other cells of the liver, the muscle and fat cells, to remove and use glucose from the blood. In this way insulin controls the blood glucose level. Insulin has this effect on the cells by binding to insulin receptors on the cell surface and to allow influx of glucose into the cells, to be used as energy by the cell. With insulin resistance, the cells do not react appropriately to the insulin (they are resistant), and a signal is sent to the pancreas that more insulin needs to be produced, which in turn results in increased level of insulin in the blood resulting in an even stronger signal through the insulin receptors. In this manner the insulin resistance of the cells increases over time. As long as the pancreas is able to produce enough insulin to overcome this resistance, blood glucose levels remain normal. When the pancreas can no longer produce enough insulin, the blood glucose levels begin to rise, initially after meals when glucose levels are at their highest and more insulin is needed, but eventually in the fasting state as well. At this point, insulin resistance has resulted in a number of medical conditions, including type 2 diabetes, fatty liver, atherosclerosis wherein the latter in turn may result in coronary artery disease (angina pectoris and heart attack), stroke and peripheral vascular disease.

A further medical condition associated with insulin resistance includes skin lesions, *acanthosis nigricans* (a cosmetic condition involving darkening of the skin in areas where there are creases such as the neck and arm pits). Further conditions associated with IR are skin tags, reproductive abnormalities in women, polycystic ovary disease, hyperandrogenism, high male hormone levels and growth abnormalities.

Growth abnormalities as a result of insulin resistance are caused by the high levels of circulating insulin that may be present in the blood. While insulin's effects on glucose metabolism may be impaired, it's effects on other mechanisms may be intact (or at least less impaired). Insulin, which is an anabolic, can exert effects on growth, through a medicator known as insulin-like growth factor-1. Patients may have actual linear growth and a noticeable coarsening of features. The increase incidence of skin tags mentioned above may be through this mechanism as well.

The ability of insulin to stimulate glucose disposal vary continuously throughout a population of apparently healthy persons, and a difference of 600% exists between the most insulin-sensitive and the most insulin resistance persons. Approximately 50% of this variability can be attributed to adiposisty (25%) and physical fitness (25%), with the remaining 50% likely of genetic origin. The third of the population that is the most insulin resistant is at a much greater risk of developing several abnormalities and clinical syndromes, including type 2 diabetes, cardio vascular diseases, hypertension, stroke, non-alcoholic fatty liver, polycystic ovary disease, and certain forms of cancer Insulin resistance can be diagnosed by a physician who can identify individuals that are likely to have insulin resistance with a detailed patient history, patient physical examination, and laboratory testing utilizing the risk factors. Tests for diagnosing IR includes but are not limited to euglycemic insulin clamping and intravenous tolerance testing. However, these are expensive or complicated and are not necessary for managing patients.

In general clinical practice, glucose levels in conjunction with fasting insulin levels can give the physician a clue as to whether insulin resistance is present or not in patients without diabetes.

Insulin resistance can be treated by attempting to reduce the need for insulin, in combination with increasing the sensitivity of the cells to the action of insulin can be increased.

To decrease the need for insulin the individual suffering from insulin resistance can alter his/her diet, and particularly the intake of carbohydrates through the diet.

As described herein, the present invention addresses methods for sensitizing the cells (insulin receptors) to increase the action of insulin.

In one aspect the agent according to the present invention may be used to treat diseases and disorders associated with insulin resistance wherein said diseases and disorders are selected from the group consisting of insulin resistance syndrome, Type 2 diabetes mellitus, impaired glucose tolerance, the metabolic syndrome, hyperglycemia, hyperinsulinemia, arteriosclerosis, hypercholesterolemia, hypertriglyceridemia, hyperlipidemia, dyslipidemia, obesity, central obesity, polycystic ovarian syndrome, hypercoagulability, hypertension, microalbuminuria, and any combinations thereof. In one aspect the agent according to the present invention may be used to treat or prevent obesity.

Other conditions treatable by the present invention include but are not limited to insulin resistance syndrome (IRS), Type 2 diabetes mellitus, impaired glucose tolerance, the metabolic syndrome, hyperglycemia, and hyperinsulinemia.

Agent of the Invention

The present inventors have found that SorCS1 physically interacts with the insulin receptor (FIG. 11), and have furthermore shown by cell biological experiments that the expression of the insulin receptor is elevated in cells stably overexpressing soluble SorCS1 or the different SorCS1 splice variants (FIG. 12), and the elevated amount of insulin receptor is still located on the cell surface (FIG. 13).

Figure 17A:
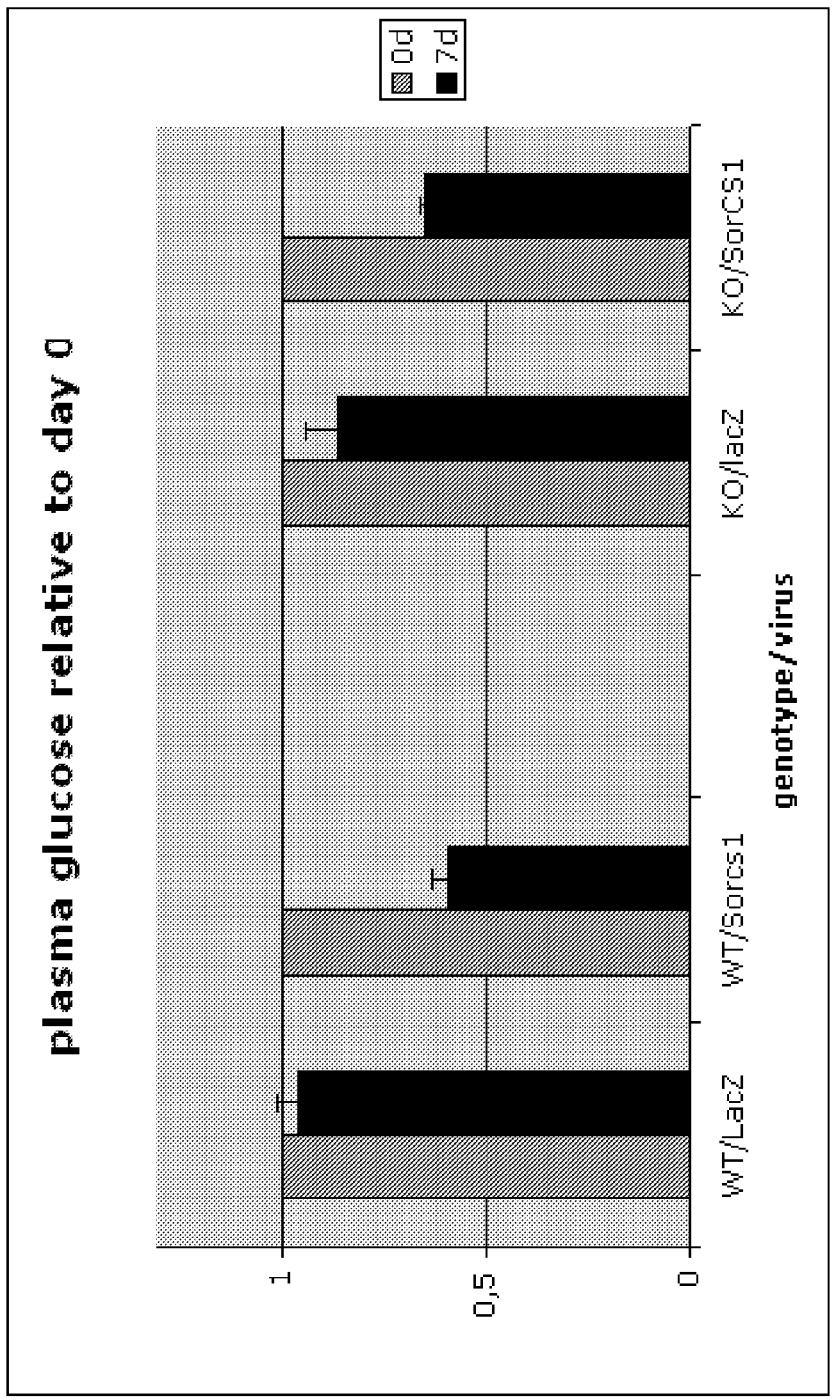
Figure 17B:
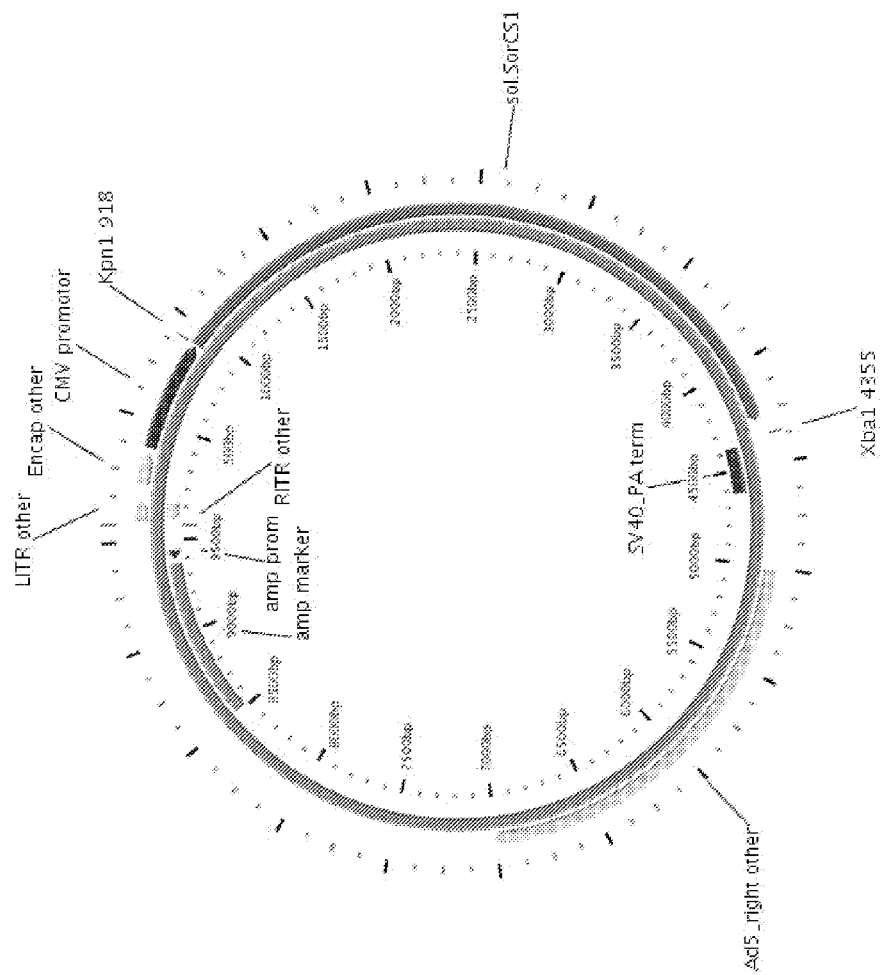
Figure 18:
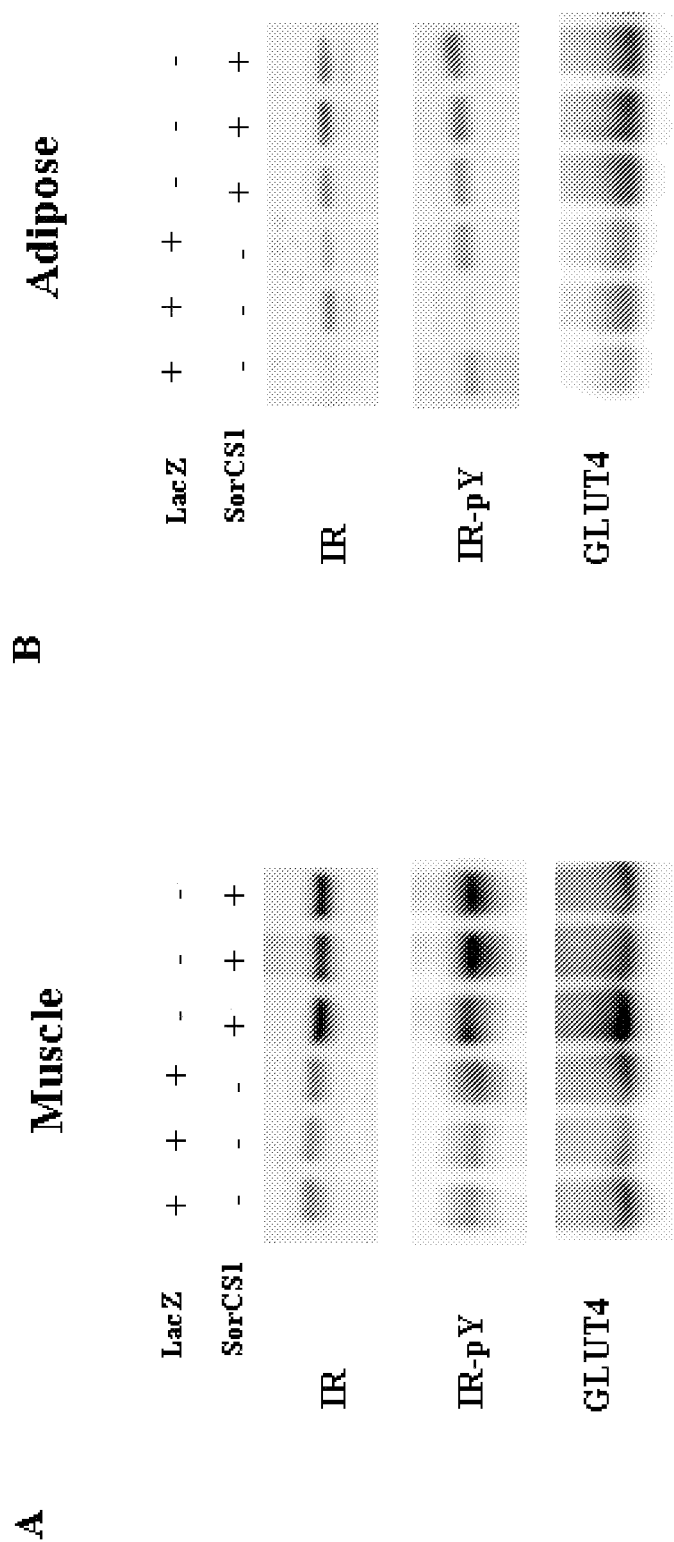

Also, the inventors have found that overexpression of soluble SorCS1 in SorCS1 knockout mice as well as administration of SorCS1 decreases the plasma glucose level (FIG. 17) and increases expression and phosphorylation of the insulin receptor as well as the glucose transporter type 4 (Glut4) protein (FIG. 18). Moreover, overexpression of soluble SorCS1 in type 2 diabetic female mice decreases the plasma glucose and insulin levels (FIG. 19) and changes the subcellular localization of Glut4, which may consequently regulate glucose uptake.

Therefore, in a main aspect, the present invention relates to a SorCS1-like agent for use in the treatment of insulin resistance and/or a disease associated with insulin resistance in an individual, wherein said agent is capable of binding to the insulin receptor (IR) at a SorCS1 binding site and being capable of sensitization of an insulin receptor. The insulin receptor may be any insulin receptor, but preferably the insulin receptor is a human insulin receptor having the sequence of SEQ ID NO: 56.

The present inventors have found that SorCS1 binds to the insulin receptor through at least one binding site, and that one or more of the following parts of SorCS1 takes part in the binding:

SEQ ID NO: 1 aa 103-124 (SEQ ID NO: 67)
SEQ ID NO: 1 aa 125-143 (SEQ ID NO: 68)
SEQ ID NO: 1 aa 144-162 (SEQ ID NO: 69)
SEQ ID NO: 1 aa 197-218 (SEQ ID NO: 70)
SEQ ID NO: 1 aa 391-409 (SEQ ID NO: 71)
SEQ ID NO: 1 aa 661-684 (SEQ ID NO: 72)
SEQ ID NO: 1 aa 763-783 (SEQ ID NO: 73)
SEQ ID NO: 1 aa 859-876 (SEQ ID NO: 74)

Accordingly, the SorCS1-like agent preferably binds to a binding site on the insulin receptor, which binding site is characterised in that one or more of the shown parts of SorCS1 bind(s) to said binding site.

In a preferred embodiment the binding site on the insulin receptor comprises one or more of the sequences defined as follows:

SEQ ID NO: 56 aa 100-120 (SEQ ID NO: 96)
SEQ ID NO: 56 aa 127-150 (SEQ ID NO: 97)
SEQ ID NO: 56 aa 284-310 (SEQ ID NO: 98)
SEQ ID NO: 56 aa 362-379 (SEQ ID NO: 99)
SEQ ID NO: 56 aa 593-610 (SEQ ID NO: 100)
SEQ ID NO: 56 aa 629-652 (SEQ ID NO: 101)
SEQ ID NO: 56 aa 749-772 (SEQ ID NO: 102).

In one preferred embodiment, the agent as defined herein above is selected from the group consisting of
a) an isolated SorCS1 polypeptide selected from the group consisting of
    i) an amino acid sequence consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 51, 52, 53 and 54;
    ii) a biologically active sequence variant of the amino acid sequence of a) wherein the variant has at least 70% (e.g. 95%) sequence identity to said SEQ ID NO: 1; or
    iii) a biologically active fragment of any of i or ii wherein said fragment comprises at least 5 contiguous amino acids of any of a) through b), and having at least 70% (e.g. 95%) sequence identity to SEQ ID NO: 1 in a range of overlap of at least 5 amino acids wherein the biological activity is sensitization of an insulin receptor,
or a pharmaceutically acceptable salt thereof.

In one embodiment, the polypeptide is a naturally occurring allelic variant of the sequence selected from the group consisting of SEQ ID NO: SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 and 54 and preferably the polypeptide comprises an amino acid sequence selected from the group consisting of SEQ ID NOs: 5, 10, 15, 21, 27, 33, 37, 39, 43 and 47.

In a further embodiment the polypeptide is a variant polypeptide described therein, wherein any amino acid specified in the selected sequence is altered to provide a conservative substitution as defined above. Accordingly, the polypeptide preferably has at least 70%, e.g. 75%, such as 80%, e.g. 85%, such as 90%, e.g. 95%, such as 98%, e.g. 99% sequence identity to a protein having a sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 and 54.

In one embodiment the polypeptide is glycosylated, such as a polypeptide being selected from the group consisting of SEQ ID NOs: 1, 2, 3, 4, 6, 7, 8, 9, 11, 12, 13, 14, wherein the polypeptide may be glycosylated in one or more of the following amino acid residue positions 184, 352, 433, 765, 776, 816, 847, 908 and 929, and/or wherein the polypeptide is selected from the group consisting of SEQ ID NOs: 16, 17, 18, 19, 20, 22, 26, 28, 29, 30, 31 and 32, wherein the polypeptide may be glycosylated in one or more of the following amino acid residue positions 184, 352, 433, 765, 776, 816, 847, 908 and 929, and in another embodiment the glycosylated fragment has the sequence selected from the group consisting of SEQ ID NO: 5, 10 and 15, or the glycosylated polypeptide fragment has the sequence selected from the group consisting of SEQ ID NO: 21, 27 and 33.

In some embodiments, however, it is preferred that the polypeptide is deglycosylated.

The SorCS1-like agent may comprise a soluble fragment of a polypeptide as defined herein or a fragment of a variant, and accordingly, in one embodiment the polypeptide is a soluble polypeptide being a fragment of the sequences selected from the group consisting of SEQ ID NOs: 1, 2, 3, 4, 6, 7, 8, 9, 11, 12, 13, 14, or the polypeptide is a soluble polypeptide being a fragment of the sequences as defined herein.

It is preferred that the polypeptide is capable of forming at least one intramolecular cystine bridge, and more preferably that the polypeptide as defined herein above comprises a dimer of said polypeptide linked through at least one intermolecular cystine bridge.

In one embodiment the polypeptide according to the present invention further comprises an affinity tag, such as a polyhis tag, a GST tag, a HA tag, a Flag tag, a C-myc tag, a HSV tag, a V5 tag, a maltose binding protein tag, a cellulose binding domain tag.

Nucleic Acid, Vectors and Host Cells

In one aspect, the invention relates to a nucleic acid sequence capable of encoding the polypeptide as defined herein above, wherein the encoded polypeptide has at least 70%%, e.g. 75%, such as 80%, e.g. 85%, such as 90%, e.g. 95%, such as 98%, e.g. 99% sequence identity to a sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 and 54 or to a fragment thereof.

In a preferred aspect the invention relates to a vector, said vector comprising at least one nucleic acid molecule as defined herein above, for use in the treatment of insulin resistance or diseases associated with insulin resistance in an individual.

The vector of the invention may further comprise a promoter which may be operably linked to the nucleic acid molecule of the invention.

The promoter may be, but is not limited to the group consisting of: CMV, human UbiC, RSV, Tet-regulatable promoter, Mo-MLV-LTR, Mx1, EF-1alpha, PDGF beta and CaMK II.

The vector of the invention may be selected from the group consisting of vectors derived from the Retroviridae family including lentivirus, HIV, SIV, FIV, EAIV, CIV.

Other vectors of the invention are selected from the group consisting of alphavirus, adenovirus, adeno associated virus, baculovirus, HSV, coronavirus, Bovine papilloma virus, Mo-MLV, preferably adeno associated virus.

In another preferred embodiment, the invention also relates to a host cell comprising the nucleic acid as described above, and even more preferred an isolated host cell of the invention is transformed or transduced with at least one vector as defined herein above, for use in the treatment of insulin resistance or diseases associated with insulin resistance in an individual.

The isolated host may be selected from the group consisting of *Saccharomyces cerevisiae*, *E. coli*, *Aspergillus* and Sf9 insect cells and of mammalian cells selected from the group consisting of human, feline, porcine, simian, canine, murine and rat cells, wherein the mammalian cell may be selected from, but is not limited to the group consisting of muscle cells, hepatocytes, adipocytes and cells of the pancreas such as α cells, β cells and δ cells.

In one embodiment the isolated host cell is selected from the group consisting of CHO, CHO-K1, HEI193T, HEK293, COS, PC12, HiB5, RN33b and BHK cells.

In another aspect the invention relates to a packaging cell line as defined herein above, wherein said packaging cell line is capable of producing an infective virus particle for use in the treatment of insulin resistance or diseases associated with insulin resistance in an individual, said virus particle comprising a Retroviridae derived genome comprising a 5' retroviral LTR, a tRNA binding site, a packaging signal, a promoter operably linked to a polynucleotide sequence encoding the polypeptide as defined herein above, an origin of second strand DNA synthesis, and a 3' retroviral LTR.

In one embodiment the genome of the packaging cell line is lentivirally derived and the LTRs are lentiviral.

As discussed above the SorCS1-like agent is any agent having the biological activity of SorCS1 in relation to the insulin receptor, i.e. an agent which is capable a binding to the insulin receptor, and more preferably the agent is also capable of sensitizing the insulin receptor whereby it is possible to lower the blood glucose concentration in the individual being administered with the SorCS1-like agent by treating insulin resistance and diseases associated with insulin resistance.

The agent may be any type of compound, such as polypeptides, antibodies as well as small organic molecules, wherein the antibody may be selected from the group consisting of: polyclonal antibodies, monoclonal antibodies, humanised antibodies, single chain antibodies, recombinant antibodies directed towards the insulin receptor.

Furthermore, as discussed herein administration of nucleic acids either naked, or in host cells or packaging cells, wherein the nucleic acid is capable of encoding the polypeptide as discussed herein, for the treatment of insulin resistance and diseases associated with insulin resistance is also an aspect of the invention.

Antibodies

As mentioned above, the agent of the present invention may be an antibody, in particularly an antibody directed against the insulin receptor, or more preferred against one or more of the binding sites on the insulin receptor shown in FIG. 23A.

Antibodies may furthermore be used as research tool for screening various aspects of the invention. Such methods are well known by those skilled in the art but is nevertheless described in further detail below. The antibodies for used for research tools are both antibodies directed towards the insulin receptor as well as directed towards the Vps10p-domain receptor, including SorCS1.

It is an aspect of the present invention to provide antibodies or functional equivalents thereof specifically recognising and binding epitopes of the Vps10p-domain receptors and insulin receptors.

The antibody or functional equivalent thereof may be any antibody known in the art, for example a polyclonal or a monoclonal antibody derived from a mammal or a synthetic antibody, such as a single chain antibody or hybrids comprising antibody fragments. Furthermore, the antibody may be mixtures of monoclonal antibodies or artificial polyclonal antibodies. In addition functional equivalents of antibodies may be antibody fragments, in particular epitope binding fragments.

Furthermore, antibodies or functional equivalent thereof may be a small molecule mimicking an antibody. Naturally occurring antibodies are immunoglobulin molecules consisting of heavy and light chains. In preferred embodiments of the invention, the antibody is a monoclonal antibody.

The antibodies according to the present invention may also be recombinant antibodies. Recombinant antibodies are antibodies or fragments thereof or functional equivalents thereof produced using recombinant technology. For example recombinant antibodies may be produced using a synthetic library or by phage display. Recombinant antibodies may be produced according to any conventional method for example the methods outlined in "Recombinant Antibodies", Frank Breitling, Stefan DUbel, Jossey-Bass, September 1999.

The antibodies according to the present invention may also be bispecific antibodies, i.e. antibodies specifically recognising two different epitopes. Bispecific antibodies may in general be prepared starting from monoclonal antibodies, or from recombinant antibodies, for example by fusing two hybridoma's in order to combine their specificity, by Chemical crosslinking or using recombinant technologies. Antibodies according to the present invention may also be tri-specific antibodies.

Functional equivalents of antibodies may in one preferred embodiment be a fragment of an antibody, preferably an antigen binding fragment or a variable region. Examples of antibody fragments useful with the present invention include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Preferred antibody fragments retain some or essential all the ability of an antibody to selectively binding with its antigen or receptor. Some preferred fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule and can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

In one embodiment of the present invention the antibody is a single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "scFv" antibody fragments. Generally, the Fv polypeptide further comprises a polypeptide linker between the VH and VL domains that enables the scFv to form the desired structure for antigen binding.

Procedures for Making Antibodies

Polyclonal and monoclonal antibodies directed against a specific antigen, or epitope of an antigen, can be produced according to standard procedures (see e.g. Antibodies—A laboratory Manual by Ed Harlow and David Lane, Cold Spring Harbor Laboratory 1998, ISBN 0-87969-314-2). The procedure for subsequent generation of humanized antibodies or fragments thereof has also been described (e.g. A. M. Scott et al, Cancer Research 60:3254-3261, 2000; A. Nissim and Y. Chernajovsky, Handb. Exp. Pharmacol. 181:3-18, 2008; A. Mountain and J. R. Adair, Biotechnol. Genet. Eng. Rev. 10:1-142, 1992).

Humanised Antibody Framework

It is not always desirable to use non-human antibodies for human therapy, since the non-human "foreign" epitopes may elicit immune response in the individual to be treated. To eliminate or minimize the problems associated with non-human antibodies, it is desirable to engineer chimeric antibody derivatives, i.e., "humanized" antibody molecules that combine the non-human Fab variable region binding determinants with a human constant region (Fc). Such antibodies are characterized by equivalent antigen specificity and affinity of the monoclonal and polyclonal antibodies described above, and are less immunogenic when administered to humans, and therefore more likely to be tolerated by the individual to be treated.

Accordingly, in one embodiment the binding polypeptide has a binding domain carried on a humanised antibody framework, also called a humanised antibody.

Human Antibodies

Human monoclonal antibodies of the invention can be produced by a variety of techniques, including conventional monoclonal antibody methodology, e.g., the standard somatic cell hybridization technique of Kohler and Milstein, *Nature* 256:495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes.

To generate fully human monoclonal antibodies to the epitopes of interest to the present invention, transgenic or transchromosomal mice containing human immunoglobulin genes (e.g., HCo12, HCo7 or KM mice) can be immunized with an enriched preparation of the antigen and/or cells expressing the epitopes of the receptor targets of the present invention, as described, for example, by Lonberg et al. (1994), supra; Fishwild et al. (1996), supra, and WO 98/24884. Alternatively, mice can be immunized with DNA encoding the CaOU-1 epitope. Preferably, the mice will be 6-16 weeks of age upon the first infusion.

Monovalent Antibodies

The monospecific binding polypeptide may be monovalent, i.e having only one binding domain.

For a monovalent antibody, the immunoglobulin constant domain amino acid residue sequences comprise the structural portions of an antibody molecule known in the art as CH1, CH2, CH3 and CH4. Preferred are those binding polypeptides which are known in the art as $C_L$. Preferred $C_L$ polypeptides are selected from the group consisting of $C_{kappa}$ and $C_{lambda}$.

Furthermore, insofar as the constant domain can be either a heavy or light chain constant domain ($C_H$ or $C_L$, respectively), a variety of monovalent binding polypeptide compositions are contemplated by the present invention. For example, light chain constant domains are capable of disulfide bridging to either another light chain constant domain, or to a heavy chain constant domain. In contrast, a heavy chain constant domain can form two independent disulfide bridges, allowing for the possibility of bridging to both another heavy chain and to a light chain, or to form polymers of heavy chains.

Thus, in another embodiment, the invention contemplates an isolated monovalent binding polypeptide wherein the constant chain domain C has a cysteine residue capable of forming at least one disulfide bridge, and where at least two monovalent polypeptides are covalently linked by said disulfide bridge.

In preferred embodiments, the constant chain domain C can be either $C_L$ or $C_H$. Where C is $C_L$, the $C_L$ polypeptide is preferably selected from the group consisting of $C_{kappa}$ and $C_{lambda}$.

In another embodiment, the invention contemplates a binding polypeptide composition comprising a monovalent polypeptide as above except where C is $C_L$ having a cysteine residue capable of forming a disulfide bridge, such that the composition contains two monovalent polypeptides covalently linked by said disulfide bridge.

Multispecificity, Including Bispecificity

In a preferred embodiment the present invention relates to multispecific binding polypeptides, which have affinity for and are capable of binding at least two different entities. Multispecific binding polypeptides can include bispecific binding polypeptides.

In one embodiment the multispecific molecule is a bispecific antibody (BsAb), which carries at least two different binding domains, where preferably at least one of which is of antibody origin.

A bispecific molecule of the invention can also be a single chain bispecific molecule, such as a single chain bispecific antibody, a single chain bispecific molecule comprising one single chain antibody and a binding domain, or a single chain bispecific molecule comprising two binding domains. Multispecific molecules can also be single chain molecules or may comprise at least two single chain molecules.

The multispecific, including bispecific, antibodies may be produced by any suitable manner known to the person skilled in the art.

The traditional approach to generate bispecific whole antibodies was to fuse two hybridoma cell lines each producing an antibody having the desired specificity. Because of the random association of immunoglobulin heavy and light chains, these hybrid hybridomas produce a mixture of up to 10 different heavy and light chain combinations, only one of which is the bispecific antibody. Therefore, these bispecific antibodies have to be purified with cumbersome procedures, which considerably decrease the yield of the desired product.

By using a bispecific or multispecific binding polypeptide according to the invention the invention offers several advantages as compared to monospecific/monovalent binding polypeptides.

While human monoclonal antibodies are preferred, other antibodies which can be employed in the bispecific or multispecific molecules of the invention are murine, chimeric and humanized monoclonal antibodies. Such murine, chimeric and humanized monoclonal antibodies can be prepared by methods known in the art.

The inventors of this application have raised antibodies against several parts of the Vps10p-domain receptors. The present invention is directed to antibodies against the unifying feature of this receptor family—the Vps10p domain. The below sequence alignment of the Vps10p-domain demonstrate the conservation within this receptor family.

TABLE 1

Antibodies against Vps10p-domain receptors

| Receptor | Name | Antigen | Species | Western | IH/IC | Ref. |
|---|---|---|---|---|---|---|
| SorLA | SORLA goat | extracellular domain | goat | X | X | Schmidt et. al., J. Biol. Chem. 282: 32956-67, 2007 |
| | Hale SORLA | Cytoplasmic domain | rabbit | X | | |
| | SORLA LA | Complement type repeat | rabbit | X | | |

TABLE 1-continued

Antibodies against Vps10p-domain receptors

| Receptor | Name | Antigen | Species | Western | IH/IC | Ref. |
|---|---|---|---|---|---|---|
|  | Sol SORLA | extracellular domain | rabbit | X | X | Andersen et al., PNAS 103: 13461-6, 2005 |
|  | SORLA tail | Cytoplasmic domain | rabbit | X |  |  |
|  | SORLA VPS | VPS10p domain | rabbit | X |  |  |
|  | #606870 | Peptide seq. in Vps10p-domain | rabbit | X |  |  |
|  | #642739 | C-terminal | rabbit | X |  |  |
|  | #643739 | Cytoplasmic tail | rabbit | X |  |  |
|  | 20C11 | Extracellular domain | mouse | X | X |  |
|  | AG4 | Extracellular domain | mouse | X |  |  |
| Sortilin | #5264 | Extracellular domain | rabbit | X | X | Munck Petersen et al, EMBO J. 18: 595-604, 1999 |
|  | #5448 | Cytoplasmic domain | rabbit | X | X | Jansen et al, Nature Neurosci. 10: 1449-1457, 2007 |
|  | #5287 | Cytoplasmic domain | rabbit | X |  |  |
|  | CP 96 334 SR 96 204 | propeptide | Rabbit | X |  | Munck Petersen et al, EMBO J. 18: 595-604, 1999 |
|  | #5438 | Vps10p | rabbit | X |  |  |
|  | Sortilin goat/Laika | Extracellular domain | goat | X |  |  |
|  | F9 | Extracellular domain | mouse | X | X |  |
|  | F11 | Extracellular domain | mouse | X | X |  |
|  | AF2934 | Extracellular domain | goat | X | X | R&D Systems, Jansen et al, Nature Neurosci. 10: 1449-1457, 2007 |
|  | AF3154 | Extracellular domain | goat | X | X | R&D Systems; Jansen et al, Nature Neurosci. 10: 1449-1457, 2007 |
|  | anti-NTR3 | Extracellular domain | mouse | X | X | BD Transduction Laboratories, |
|  | ANT-009 | Extracellular domain | mouse | X | X | Alomone Labs; Nykjaer et al, Nature 427: 843-848, 2004 |
| SorCS1 | AF3457 | Extracellular domain | goat | X | X | BD Transduction Laboratories |
|  | SorCS1 goat | Extracellular domain | goat | X |  |  |
|  | L-SorCS1 | Extracellular domain | rabbit | X | X | Hermey et al, J. Biol. Chem. 279: 50221-50229, 2003 |

TABLE 1-continued

Antibodies against Vps10p-domain receptors

| Receptor | Name | Antigen | Species | Western | IH/IC | Ref. |
|---|---|---|---|---|---|---|
| | Leu-SorCS1 | Leucine-rich domain | rabbit | X | X | Hermey et al, J. Biol. Chem. 279: 50221-50229, 2003 |
| | #5466 | Extracellular domain | rabbit | X | X | |
| | 1D | Extracellular domain | mouse | X | | |
| | 4H | Extracellular domain | mouse | X | | |
| | 6B | Extracellular domain | mouse | X | | |
| | 4A | Extracellular domain | mouse | X | | |
| SorCS2 | AF4237 | Extracellular domain | sheep | X | | BD Transduction Laboratories |
| | SorCS2 goat | Extracellular domain | goat | X | X | |
| | #5422 | Extracellular domain | rabbit | X | X | Hermey et al, Biochem. J., 395: 285-93, 2006 |
| | #5431 | 28 C-terminal amino acids | rabbit | X | X | |
| | SorCS2-prp | propeptide | rabbit | X | | Schousboe Sjoegaard, Dissertation, Aarhus University, 2005 |
| | M1 | Extracellular domain | mouse | | X | Roland Holst, Master of Science Thesis, Aarhus University, 2006 |
| | M3 | Extracellular domain | mouse | | X | Roland Holst, Master of Science Thesis, Aarhus University, 2006 |
| | M4 | Extracellular domain | mouse | | X | Roland Holst, Master of Science Thesis, Aarhus University, 2006 |
| | M7 | Extracellular domain | mouse | | X | Roland Holst, Master of Science Thesis, Aarhus University, 2006 |
| | M9 | Extracellular domain | mouse | | X | Roland Holst, Master of Science Thesis, Aarhus University, 2006 |
| | M10 | Extracellular domain | mouse | | X | Roland Holst, Master of Science Thesis, Aarhus University, 2006 |

TABLE 1-continued

Antibodies against Vps10p-domain receptors

| Receptor | Name | Antigen | Species | Western | IH/IC | Ref. |
|---|---|---|---|---|---|---|
| | M13 | Extracellular domain | mouse | X | | Roland Holst, Master of Science Thesis, Aarhus University, 2006 |
| | M15 | Extracellular domain | mouse | | X | Roland Holst, Master of Science Thesis, Aarhus University, 2006 |
| | M18 | Extracellular domain | mouse | X | X | Roland Holst, Master of Science Thesis, Aarhus University, 2006 |
| | M19 | Extracellular domain | mouse | X | X | Roland Holst, Master of Science Thesis, Aarhus University, 2006 |
| | S21 | Extracellular domain | mouse | X | | Roland Holst, Master of Science Thesis, Aarhus University, 2006 |
| | SorCS2-GST-73aa | Extracellular domain | rabbit | X | | |
| | SorCS2-GST-100aa | Extracellular domain | rabbit | X | | |
| | SorCS2-GST-172aa | Extracellular domain | rabbit | X | | |
| SorCS3 | SorCS3-N | extracellular domain | rabbit | X | | |
| | SorCS3-C | 15 C-terminal aa | rabbit | X | | |
| | Sort3 N Term #5389 | N-terminal domain | rabbit | X | X | Westergaard et al, FEBS Lett. 579: 1172-6, 2005 |
| | #5432 | Extracellular domain | rabbit | X | X | |
| | MAB3067 | Extracellular domain | mouse | X | | BD Transduction Laboratories |
| | MAB30671 | Extracellular domain | mouse | X | | BD Transduction Laboratories |
| | AF3326 | Extracellular domain | goat | X | | BD Transduction Laboratories |
| | SorCS3 goat | Extracellular domain | goat | X | | |

Successful Clinical Use of Antibodies

A number of therapeutic antibodies are in clinical use. Examples include Genentech's Rituxan, an antibody directed against the CD20 receptor (used in rheumatoid arthritis), Johnson & Johnson's Remicade, an antibody directed against TNF alpha receptor (in Psoriasis), Roche's Avastin, an anti-VEGF antibody used for treatment of colorectal and lung cancer, as well as Herceptin, an antibody against the receptor HRE2 used in breast cancer therapy.

Assessing binding to a receptor is routine work for the person skilled in the bio-technical field. In this regard it has to be mentioned that the Vps10p-domain receptor family were known at the priority date of this invention and binding assays involving.

In one embodiment, the agent of the present invention is an anti-Insulin Receptor polyclonal or monoclonal antibody.

Transgenic SorCS1 Mice

Figure 3:
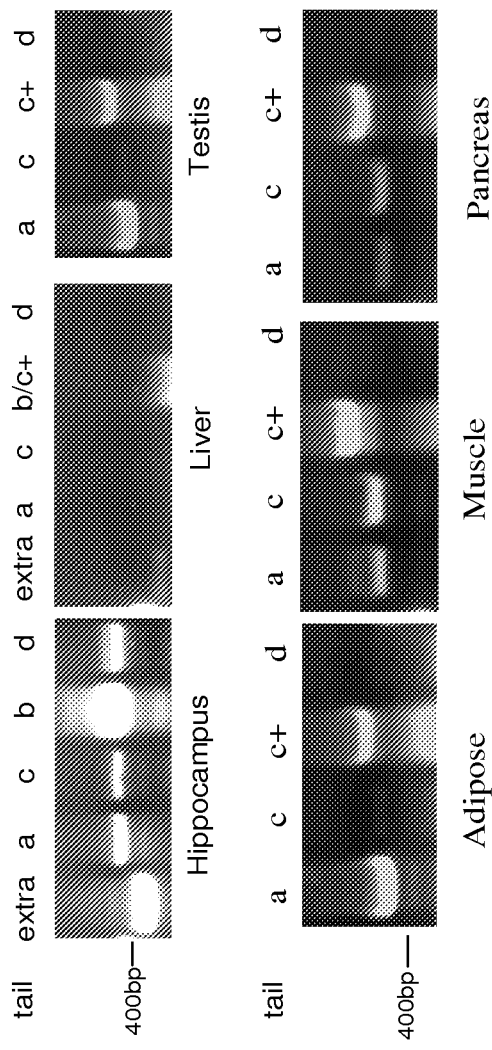
FIG. 3: Expression of the different mSorCS1 splice variants. Fragments obtained by RT-PCR on mRNA from different tissue with specific primer pairs used to identify the extracellular part of SorCS1 (extra) or each of the five tail variants (a, b, c, c$^+$, and d).
Figure 4:
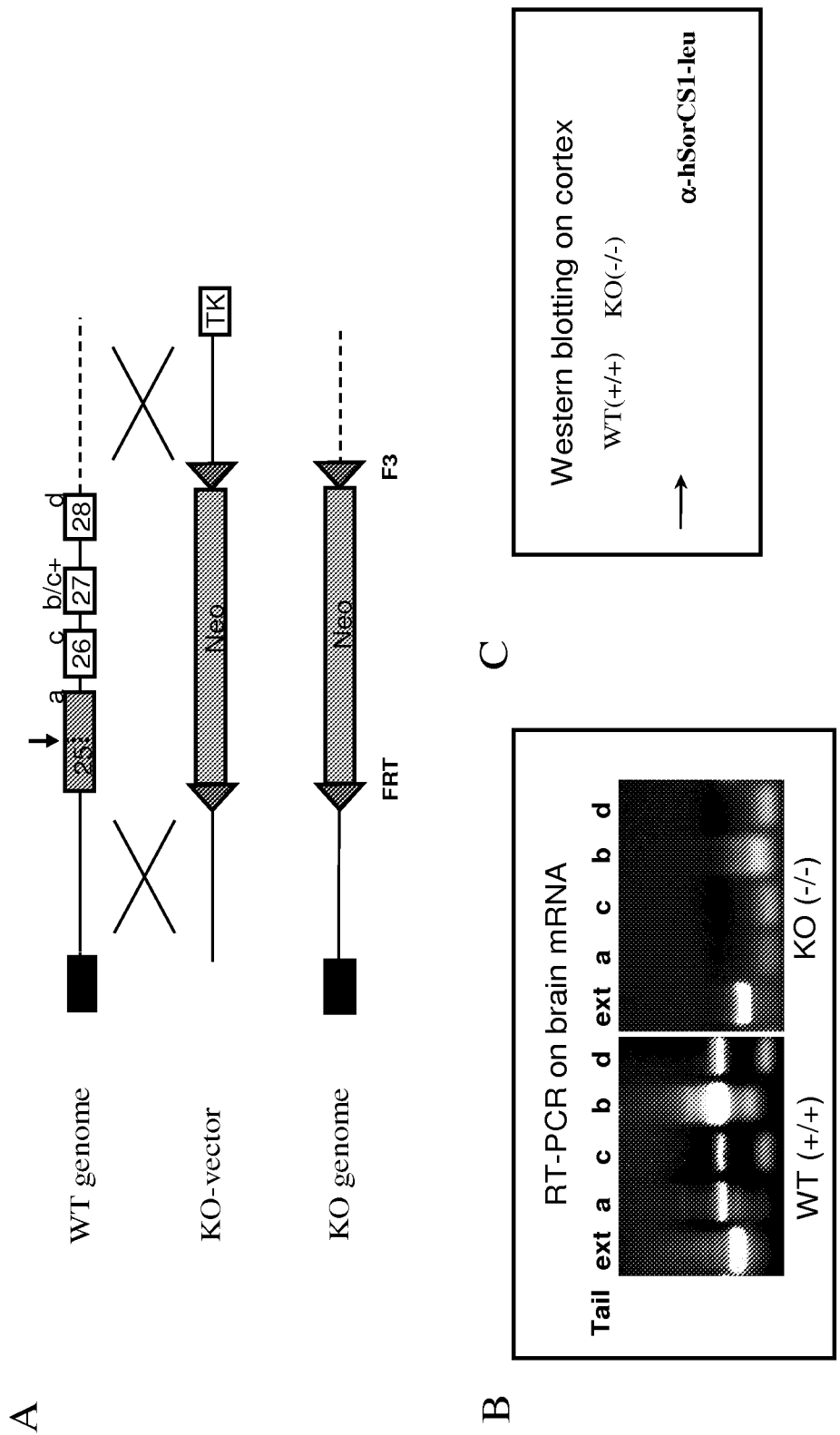
FIGS. 4A-4C: Generation of the mSorCS1 knockout mouse.
Figure 5:
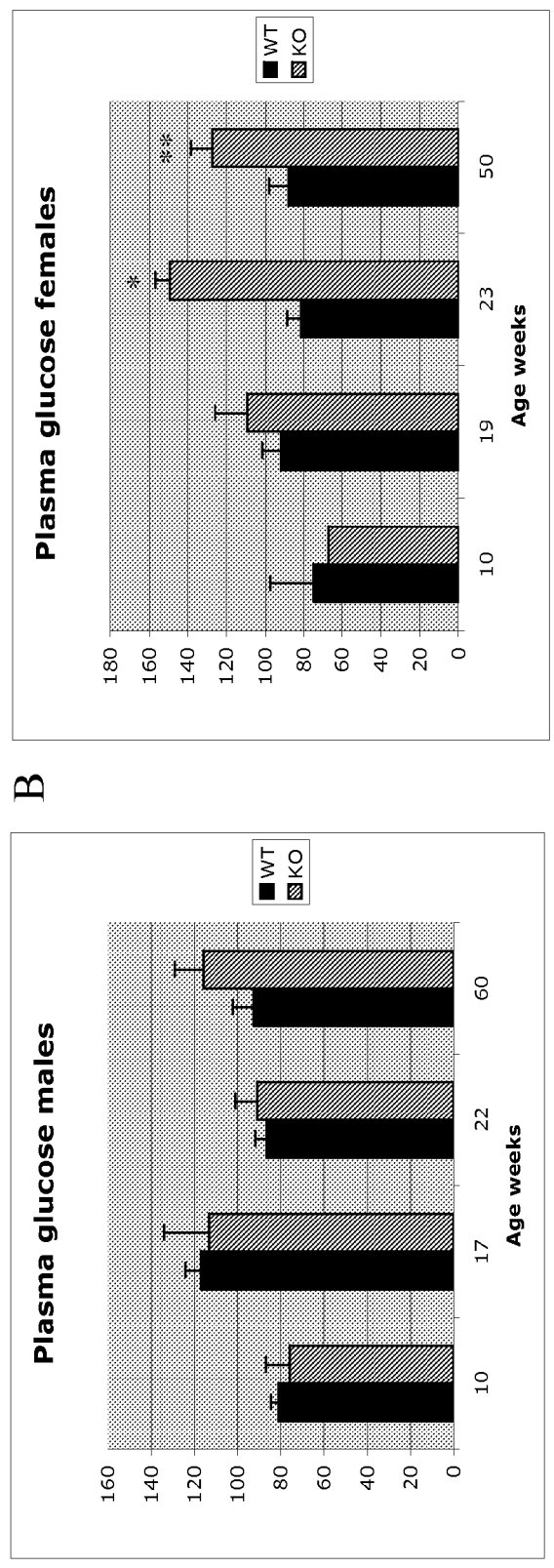
FIGS. 5A and 5B: Average blood glucose in FIG. 5A) male and FIG. 5B) female mice at different age. Animals were fasted overnight (16 h). Blood samples were obtained by retroorbital bleeding and plasma glucose was measured immediately on an automatic monitor.
Figure 6:
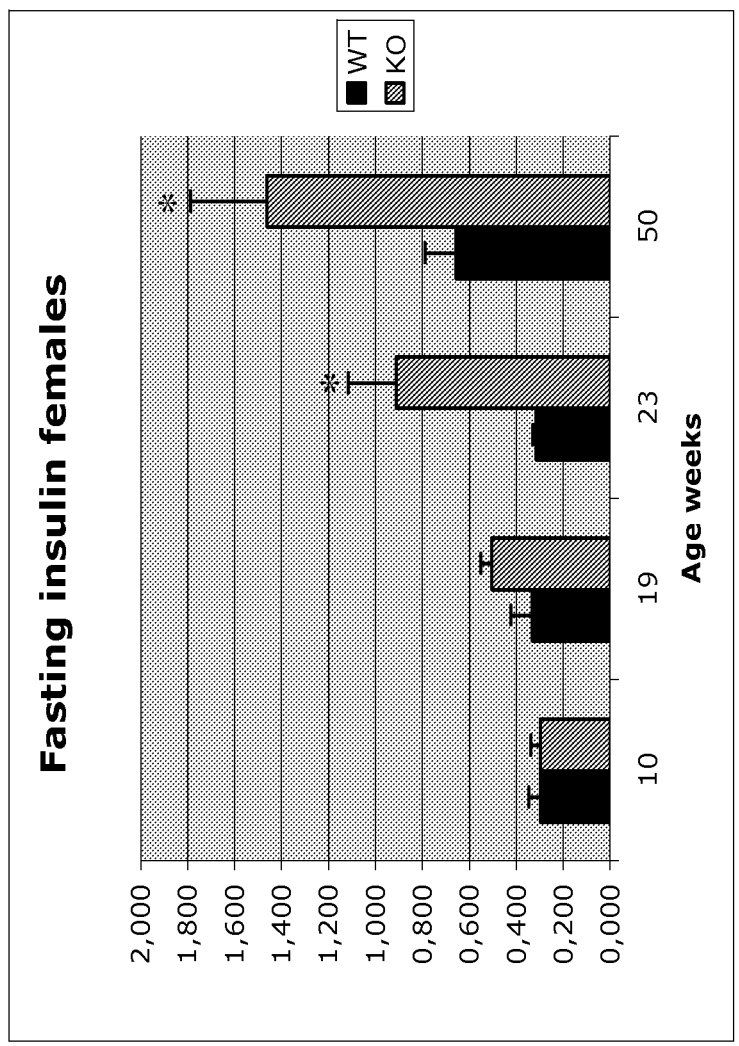
FIG. 6: Plasma insulin levels in female wild-type and SorCS1 knockout mice from 10 to 50 weeks of age. Animals were fasted overnight (16 h). Blood samples were obtained by retroorbital bleeding and plasma insulin levels were determined using an ultrasensitive mouse insulin enzyme-linked immunosorbent assay kit.

The present inventors have found that SorCS1 is expressed in adipose tissue, skeletal muscle and β-cells of the pancreas; all tissues involved in glucose metabolism (FIG. 3). In order to examine the function of SorCS1 and its different splice variants the inventors generated a conditional knockout mouse using a new developed targeting strategy based on FLP recombination and an insertion technique called 'recombinase-mediated cassette exchange'. The model was used to generate a 'full' knockout mouse lacking all splice forms of SorCS1 whereby expression of all the splice variants have been disrupted (FIG. 4). SorCS1 mice deficient in all splice variants ('full' knockout) show no gross abnormalities or signs of changed behaviour, they are fertile and they exhibit a normal life span (unpublished). However, the SorCS1 knockout mouse was phenotypically characterized with respect to glucose metabolism and development of type-2 diabetes, and preliminary results support an important role of the receptor in development of diabetes. Whereas blood glucose levels in fasting male mice at 17 and 50 weeks of age were similar to that of control littermates, female mice at the age of 50 weeks showed a dramatic elevation in blood glucose as compared to age-matched control mice (FIG. 5). However, both genders exhibited elevated levels of insulin at 50 weeks of age (FIG. 6 female only). In agreement, their pancreatic islets were up to 3-fold enlarged as determined by immunostaining for a □-cell marker (FIG. 15). The results indicate that old SorCS1 knockout male mice are hyperinsulimic but prediabetic, whereas old SorCS1 knockout female mice are hyperglycaemic and hyperinsulimic, thus becoming diabetic.

Figure 8:
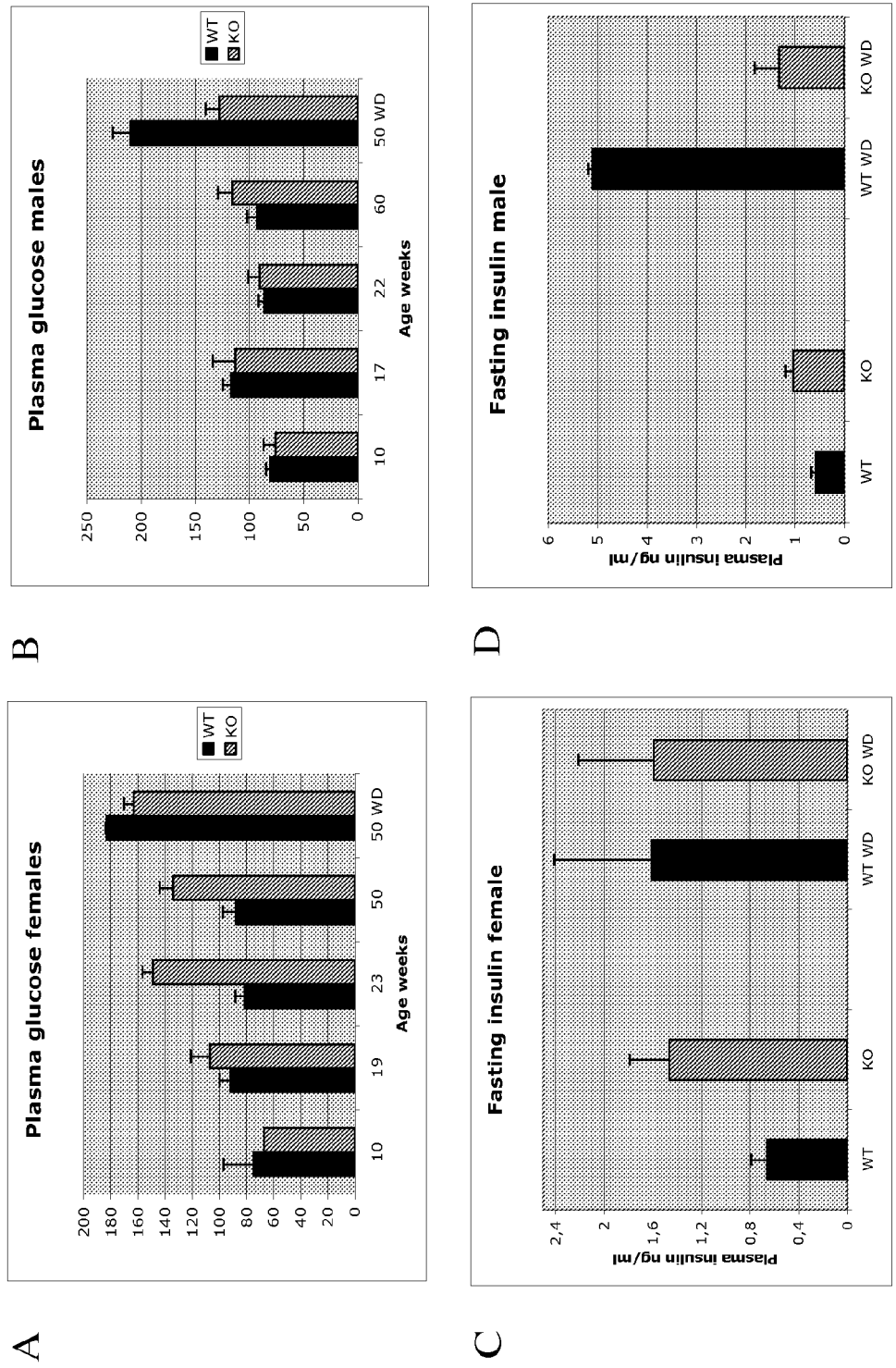
FIGS. 8A-8D: Elevated levels of fasting plasma glucose and insulin in wild type mice on Western type diet. Female FIG. 8A)+FIG. 8C) and male FIG. 8B)+FIG. 8D) wild type and SorCS1 knockout mice were fed a high calorie Western type diet (WD) from 10 weeks of age to 50 weeks of age. At 50 weeks of age the animals were fasted overnight (16 h), blood samples were obtained by retroorbital bleeding and plasma glucose FIG. 8A)+FIG. 8B) and plasma insulin levels FIG. 8C)+FIG. 8D) were measured. Data are means±SEM for 4 to 10 mice in each group.

Furthermore, the inventors have also found that both male and female SorCS1 knockout mice have normal body weight. The absence of obesity in the knockout mice makes it possible to dissociate the effect of obesity on the prediabetic or diabetic phenotype, which complicates analysis in several existing animal models of diabetes. However, because obesity is a significant risk factor for type-2 diabetes, SorCS1 deficient animals were also fed a high calorie Western type diet to study the impact of obesity on disease progression. Physiological measurements revealed increases in plasma glucose and insulin levels and in abdominal fat for the wild type mice on high calorie diet compared to wild type mice on normal diet (FIG. 8+9). In contrast, the SorCS1 knockout mice showed no significant changes on Western type diet compared to normal diet, thus showing no aggravation of the diabetic status. The lower amount of abdominal fat in the knockout mice on western diet compared to the wild type mice confirm the insulin resistance of the knockout mice as it leads to reduced uptake of glucose in the adipose tissue and thereby less production of abdominal fat.

Accordingly, the present inventors have shown that the SorCS1 knockout mouse is a unique animal model for studying insulin resistance and diseases related to insulin resistance, in particularly diabetes because the SorCS1 knockout mouse develops the symptoms normally related to insulin resistance and diabetes, including the late symptoms of diabetes, such as neuropathic symptoms.

In addition, the inventors have shown that 50 weeks old male and female SorCS1−/− mice exhibit elevated amount of phosphorylated IR as compared to age-matched controls (FIG. 10) suggesting that SorCS1 may partake in insulin signalling in peripheral tissues. Alternatively, a signal derived from SorCS1 that convert on the insulin signalling pathways may be missing, resulting in compensatory upregulation of phosphorylated a. Since SorCS1 is also engaged in cellular sorting, the receptor may also regulate the subcellular distribution of IR.

Therefore, one important aspect of the present invention relates to a transgenic knock-out mouse in which the endogenous Vps10p-domain receptor SorCS1 genes have been disrupted to abolish expression of a functional SorCS1 receptor, and wherein said mouse exhibits a reduced response to insulin relative to a non-transgenic control mouse.

In a further embodiment the invention relates to the transgenic mouse as defined herein above, wherein said disruption comprises a deletion of the SorCS1 receptor gene nucleotide sequences encoding the start codon or a region of the mouse SorCS1 receptor from the extracellular domain, transmembrane domain, or the cytoplasmic domain.

In one aspect, the invention relates to a transgenic mouse capable of encoding soluble and/or full length SorCS1 in a tissue specific manner, upon activation of expression. The procedure for preparing said mouse is described in example 12. The tissue to be specifically activated may be selected from, but is not limited to, the group consisting of liver, muscle, pancreas and adipose tissue.

Methods of Screening for Agents of the Invention

The present invention provides specific targets and methods for screening and evaluating further candidate agents including SorCS1 peptide and polypeptide fragments and mutant and variants thereof.

While the screening of a large number of peptides for a certain physiological activity may be a laborious undertaking, the exact disclosures of the assay herein to be carried out enables the skilled person to reproduce the present invention without undue burden of experimentation and without needing inventive skill.

For this purpose screening libraries of candidate agents are readily available for purchase on the market. Whether a library is a peptide library or a chemical library does not have any impact in the present situation since screening of chemical libraries is also routine work. In fact screening of chemical libraries is a service offered by commercial companies, and it is clear from their presentation material that they do not consider the screening work as such to be inventive.

Initially in the process of screening for SorCs1-like agents it is relevant to perform binding studies as discussed herein, in particularly in relation to the Figures and the Examples to verify that the agent binds to the insulin receptor. Furthermore, it may be relevant to show that the agent in fact also sensitizes the insulin receptor. As discussed above, this may be done indirectly by showing that administration of the SorCS1-like agent in fact reduces the blood glucose concentration by for example performing a glucose tolerance test (GTT), and preferably also showing that the insulin concentration is lowered, if it initially was increased. Furthermore, sensitisation of the insulin receptor may also be measured by measuring the amount of insulin receptor, since administration of soluble SorCS1 leads to an increase of insulin receptors.

Accordingly, in one embodiment the present invention relates to a method for screening for the ability of the SorCS1-like agent as defined herein above to reduce blood glucose levels, said method comprising the steps of
 a) providing a first and a second transgenic mouse as defined herein;
 b) administering to said first transgenic mouse a candidate agent, and
 c) administering to said second transgenic mouse a physiological solution, and d) taking blood samples from the mouse of b) and c) respectively, at predetermined time intervals, such as at 15 minutes, 30 minutes, 60 minutes, 2 and 4 hours, subsequent to administration of said agent, and e) comparing blood glucose levels in the samples of d); wherein a reduction in blood glucose level of said first transgenic mouse administered said candidate agent relative to said second transgenic mouse not administered said candidate agent indicates that the candidate agent reduces blood glucose levels.

In another embodiment, the invention relates to a method for screening for the ability of the SorCS1-like agent of the invention to reduce blood glucose levels, said method comprising the steps of a) providing a first and a second wild-type mouse; and b) administering to said first mouse the agent as defined herein, and c) administering to said second mouse a physiological solution, and d) taking blood samples from the two mice of b) and c) respectively, at predetermined time intervals, such as at 15 minutes, 30 minutes, 60 minutes, 2 and 4 hours, subsequent to administration of said agent, and e) comparing plasma glucose levels in the samples of d); wherein a reduction in blood glucose level of said first wild-type mouse administered said agent relative to said second wild type mouse not administered said candidate agent, indicates that the agent reduces blood glucose levels.

Pharmaceutical Composition and Administration Forms

The present invention also encompasses pharmaceutical compositions comprising the agent as defined herein. In the present context the term agent and compound is considered synonyms when discussing the pharmaceutical composition.

The main routes of drug delivery according to this invention are parenteral, oral or enteral, and topical in order to introduce the agent into the blood stream to ultimately target the sites of the insulin receptors.

The agent may be administered to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth.

The agents may be administered orally or parenterally.

Compounds of the invention may also be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. The compounds may also be administered by inhalation, which is by intranasal and oral inhalation administration. Appropriate dosage forms for such administration, such as an aerosol formulation or a metered dose inhaler, may be prepared by conventional techniques.

The compounds according to the invention may be administered with at least one other compound, such as for example insulin. The compounds may be administered simultaneously, either as separate formulations or combined in a unit dosage form, or administered sequentially.

In one embodiment of the present invention, the dosage of the active ingredient of the pharmaceutical composition as defined herein above, is between 10 µg to 500 mg per kg body mass, such as between 20 µg and 400 mg, e.g. between 30 µg and 300 mg, such as between 40 µg and 200 mg, e.g. between 50 µg and 100 mg, such as between 60 µg and 90 µg, e.g. between 70 µg and 80 µg.

Furthermore, the dosage may be administered as a bolus administration or as a continuous administration. In relation to bolus administration the pharmaceutical composition may be administered at intervals of 30 minutes to 24 hours, such as at intervals of 1 to 6 hours. When the administration is continuous it is administered over an interval of time that normally is from 6 hours to 7 days. However, normally the dosage will be administered as a bolus 1-3 times per day.

In one important aspect of the present invention the duration of the treatment is life long.

Formulations

Whilst it is possible for the compounds or salts of the present invention to be administered as the raw chemical, it is preferred to present them in the form of a pharmaceutical formulation. Accordingly, the present invention further provides a pharmaceutical formulation, for medicinal application, which comprises a compound of the present invention or a pharmaceutically acceptable salt thereof, as herein defined, and a pharmaceutically acceptable carrier therefore.

The agents of the present invention may be formulated into a wide variety dosage forms, suitable for the various administration forms discussed above.

The pharmaceutical compositions and dosage forms may comprise the agents of the invention or its pharmaceutically acceptable salt or a crystal form thereof as the active component.

Furthermore, the pharmaceutical compositions may comprise pharmaceutically acceptable carriers that can be either solid or liquid.

Solid form preparations are normally provided for oral or enteral administration, such as powders, tablets, pills, capsules, cachets, suppositories, and dispersible granules. A solid carrier can be one or more substances which may also act as diluents, flavoring agents, solubilizers, lubricants, suspending agents, binders, preservatives, wetting agents, tablet disintegrating agents, or an encapsulating material.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. Powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentrifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavours, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkyl-imidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The compounds of the invention can also be delivered topically for transdermal or transmucosal administration. Regions for topical administration include the skin surface and also mucous membrane tissues of the vagina, rectum, nose, mouth, and throat. Compositions for topical administration via the skin and mucous membranes should not give rise to signs of irritation, such as swelling or redness. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, such as a sublingual tablet, capsule, dry powder, syrup, balm or lozenge, for example. Methods for preparing such compositions are well known in the pharmaceutical industry.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Transdermal delivery may be accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

The compounds of the present invention may also be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The active compound may be formulated into a suppository comprising, for example, about 0.5% to about 50% of a compound of the invention, disposed in a polyethylene glycol (PEG) carrier (e.g., PEG 1000 [96%] and PEG 4000 [4%].

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Pharmaceutically Acceptable Salts

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

In one embodiment the pharmaceutical composition as defined herein above comprises a pharmaceutically acceptable carrier.

In one embodiment of the present invention the pH of the pharmaceutical composition as defined herein above is between pH 4 and pH 9.

Kit of Parts

In one aspect the present invention relates to a kit in parts comprising:
   a pharmaceutical composition as defined herein above
   a medical instrument or other means for administering the medicament
   instructions on how to use the kit in parts.
   optionally a second active ingredient as defined herein above In a further embodiment the instrument as defined herein above is also called insulin pen described in US Pat. No. 5,462,535, U.S. Pat. No. 5,999,323 and U.S. Pat. No. 5,984,906.

The second ingredient may be any suitable active ingredient normally administered to individuals suffering from insulin resistance and diseases associated with insulin resistance such as insulin. By sensitizing the insulin receptor due to administration of a pharmaceutical composition as defined herein it is believed that the need for insulin is reduced.

Treatments

As discussed above the present invention also relates to the treatment of insulin resistance or diseases associated with insulin resistance, said method comprising administering to an individual in need thereof a therapeutically effective amount of the agent as defined above; or the isolated nucleic acid sequence as defined above; or the expression vector as defined above; or a composition of host cells as defined above; or a packaging cell line as defined above, or a combination thereof The diseases associated with insulin resistance are in particular selected from the group consisting of insulin resistance syndrome, Type 2 diabetes mellitus, impaired glucose tolerance, the metabolic syndrome, hyperglycemia, hyperinsulinemia, arteriosclerosis, hypercholesterolemia, hypertriglyceridemia, hyperlipidemia, dyslipidemia, obesity, central obesity, polycystic ovarian syndrome, hypercoagulability, hypertension, microalbuminuria, insulin resistance syndrome (IRS), Type 2 diabetes mellitus, impaired glucose tolerance, the metabolic syndrome, hyperglycemia, and hyperinsulinemia.

The present invention have found that administration of a SorCS1-like agent sensitizes the insulin receptor, in that it stabilises the insulin receptor, increases the amount of insulin receptors, and/or increases the amount of activated insulin receptors (phosphorylated insulin receptors are measured). Therefore, in another aspect, the present invention relates to a method of sensitizing an insulin receptor, said method comprising administering a Vps10p-domain receptor selected from the group consisting of:
   a) SorCS1 (SEQ ID NO: 1-51)
   b) SorCS2 (SEQ ID NO: 54)
   c) SorCS3 (SEQ ID NO: 55)
   d) Sortilin (SEQ ID NO: 52) and
   e) SorLA, (SEQ ID NO: 53)
thus being useful in a method of treatment of insulin resistance or diseases associated with insulin resistance.

Furthermore, the inventors have found that when administering a SorCS1-like agent then the insulin receptors may be upregulated, and accordingly, the present invention relates to a method of upregulating an insulin receptor or a fragment or variant thereof, in a patient in need thereof, said method comprising administering to an individual in need thereof a therapeutically effective amount of the agent as defined above; or the isolated nucleic acid sequence as defined above; or the expression vector as defined above; or a composition of host cells as defined above; or a packaging cell line as defined above, or a combination thereof.

Furthermore, it has been found that a SorCS1-like agent increases the insulin sensitivity, and accordingly the present invention also relates to a method for increasing insulin sensitivity comprising administering to an individual in need thereof a therapeutically effective amount of the agent as defined above; or the isolated nucleic acid sequence as defined above; or the expression vector as defined above; or a composition of host cells as defined above; or a packaging cell line as defined above, or a combination thereof. This individual is typically an individual suffering from any of the diseases mentioned above, more likely an individual suffering from diabetes type 1 or type 2.

DETAILED DESCRIPTION OF THE DRAWINGS

Figure 1:
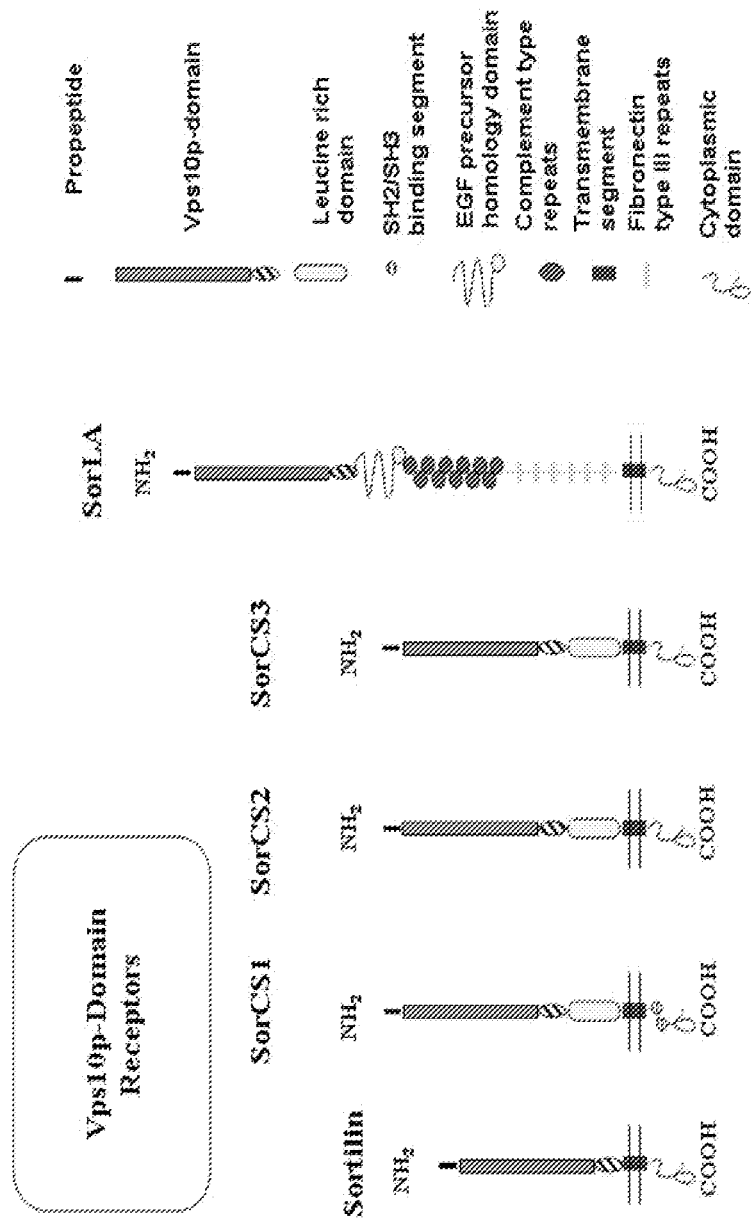
FIG. 1: The Vps10p-domain receptor family. Their structural organization is indicated.

FIG. 1: The Vps10p-domain receptor family. Their structural organization is indicated.

Figure 2:
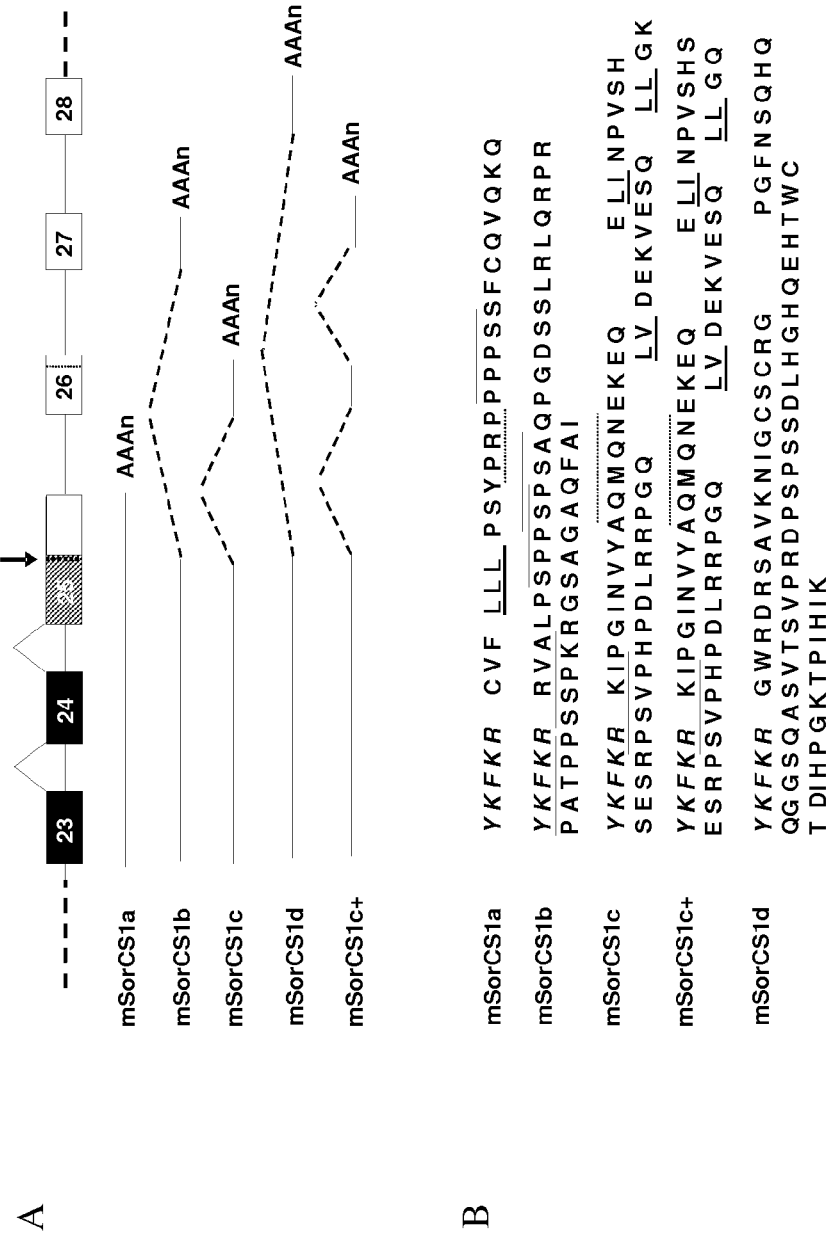
FIGS. 2A and 2B: Splice variants of mSorCS1.

FIGS. 2A and 2B: Splice variants of mSorCS1. FIG. 2A) Organization of the murine SorCS1 gene leading to the generation of different cytoplasmic tails. The black boxes represent exon 23 and 24 with typical splice sites. In the composite internal/terminal exon 25 (grey) and 26 (white), the dotted line indicates a potential splice site. The alternative used terminal exons 25, 26, 27, and 28 are shown in white. FIG. 2B) Amino acid sequences of the mSorCS1 cytoplasmic domains (SEQ ID NOS 75-79, respectively, in order of appearance). Dileucine motifs are underlined, SH3 domain-binding motifs are overlined, SH2 domain-binding motifs are underlined by dashed lines, and YXXØ motifs are overlined by dashed lines.

FIG. 3: Expression of the different mSorCS1 splice variants. Expression of the extracellular part of SorCS1 (SorCS1.ex) and the five tail splice variants SorCS1-a, -b, -c, e and -d were determined in tissue from adult mice by reverse transcription-PCR (RT-PCR) with specific primer pairs. The SorCS1.ex specific primers are spanning the exon 21 to 24 junctions giving a 390 bp product. The SorCS1-a specific primers are spanning the exon 21 to 25 junctions giving a 586 bp product. The SorCS1-b specific primers are spanning the exon 21 to 25 junctions and the exon 25 to 27 junctions giving a 621 bp product. The SorCS1-c specific primers are spanning the exon 21 to 26 junctions giving a 626 bp product. The SorCS1-d specific primers are spanning the exon 21 to 25 junctions and the exon 25 to 28 junction giving a 636 bp product. Total RNA preparations were made from hippocampus, liver, adipose tissue (fat), muscle, pancreas and testis isolated from wild type and hippocampus and liver from SorCS1-KO mice of about 8 weeks of age using the RNA purification kit sold under the trademark Versagene. Briefly, tissues were surgically removed and frozen on dry ice. Frozen tissue samples were disrupted and homogenized for up to 60 sec using a rotor stator (Ultra-Turrax, IKA-Werke) in 800 µl lysis buffer containing 5 mM Tris (2-carboxyethyl) phosphine (TCEP) and the total RNA was purified according to the manufacturers protocol for the kit. RT-PCR were performed with 0.75 µg to 1 µg total RNA from each sample using the TITANIUM One-step RT-PCR kit (Clontech). All reactions were performed in 50 µl volume containing 1× One-step buffer (40 mM tricine, 20 mM KCl, 3 mM $MgCl_2$, 3.75 µg/µl BSA), 0.2 mM of each dNTP, 25 µl Thermostabilizing reagent, 10 µl GC-melt, 20 µM Oligo(dT)primer, 20 units Recombinant RNase inhibitor, 1×RT-TITANIUM™ Taq enzyme mix (all supplied with the kit) and 45 µM of each primer. PCR conditions were: 50° C. for 1 hour, 94° C. for 5 min, 35 cycles at 94° C. for 30 sec, 64° C. for 30 sec, 68° C. for 1 min, and 68° C. for 2 min.

FIGS. 4A-4C: Generation of the mSorCS1 knockout mouse. FIG. 4A) Strategy used to generate mSorCS1 knockout mice by homologous recombination in embryonic stem cells. A schematic representation of the wild-type murine SorCS1 locus (top), the targeting vector (middle), and the homologous recombinant genome (bottom) are shown. FIG. 4B) Analysis of mSorCS1 mRNA expression, showing lack of transcription of all mSorCS1 splice variant. Fragments are obtained by RT-PCR on mRNA from hippocampus of wild-type (WT) and SorCS1 knockout (KO) mice using specific primer pairs to identify the extracellular part of SorCS1 (ext) or each of the five tail variants (a, b, c, c$^+$, and d) (see FIG. 3). FIG. 4C) Western blot analysis of cortex showing lack of mSorCS1 protein in the mSorCS1 knockout (KO) mice. Proteins were extracted as lysates from cortex obtained at E14.5. The tissue was dissolved in 100 THE-buffer (10 mM Tris-HCl, 150 mM NaCl, 1 mM EDTA, 1% nonidet P-40 (Sigma Aldrich) pH. 8) containing protease inhibitors (CompleteMini) by vigorous vortexing. After freezing ON at 20° C., the lysates were vortexed and centrifuged 10 min at 1000×g. The lysates (supernatant) were transferred to a new tube and Bio-Rad Protein Assay measured the protein concentration. Lysates (200 µg) were resolved on SDS-PAGE and transferred to nitrocellulose. The blot was then probed with a rabbit polyclonal antibody against the leucine-rich part of SorCS1 (α-hSorCS1-leu). Arrow indicates band of SorCS1. Neo; neomycin, TK; thymidine kinase, FRT/F3; Flp recombinase target sites.

FIG. 5: Average blood glucose in FIG. 5A) male and FIG. 5B) female mice at different age. Animals were fasted overnight (16 h). Wild type (wt) and SorCS1 knockout (KO) mice were anesthetized with diethyl ether, blood samples were obtained by retroorbital bleeding and plasma glucose was measured immediately on an automatic monitor (Ascensia Contour from Bayer). Statistically significant increases in blood glucose levels from knockout relative to wild type mice are indicated with stars. Error bars indicate SEM.

FIG. 6: Plasma insulin levels in female wild-type and SorCS1 knockout mice from 10 to 50 weeks of age. Animals were fasted overnight (16 h). Mice were anesthetized with diethyl ether, blood samples were obtained by retroorbital bleeding and plasma insulin levels were determined using an ultrasensitive mouse insulin enzyme-linked immunosorbent assay kit (DRG Diagnostics, Marburg, Germany). Data are means±SEM for 4 to 10 mice in each group. Statistically significant increases in blood glucose levels from knockout relative to wild type mice are indicated with stars.

Figure 7:
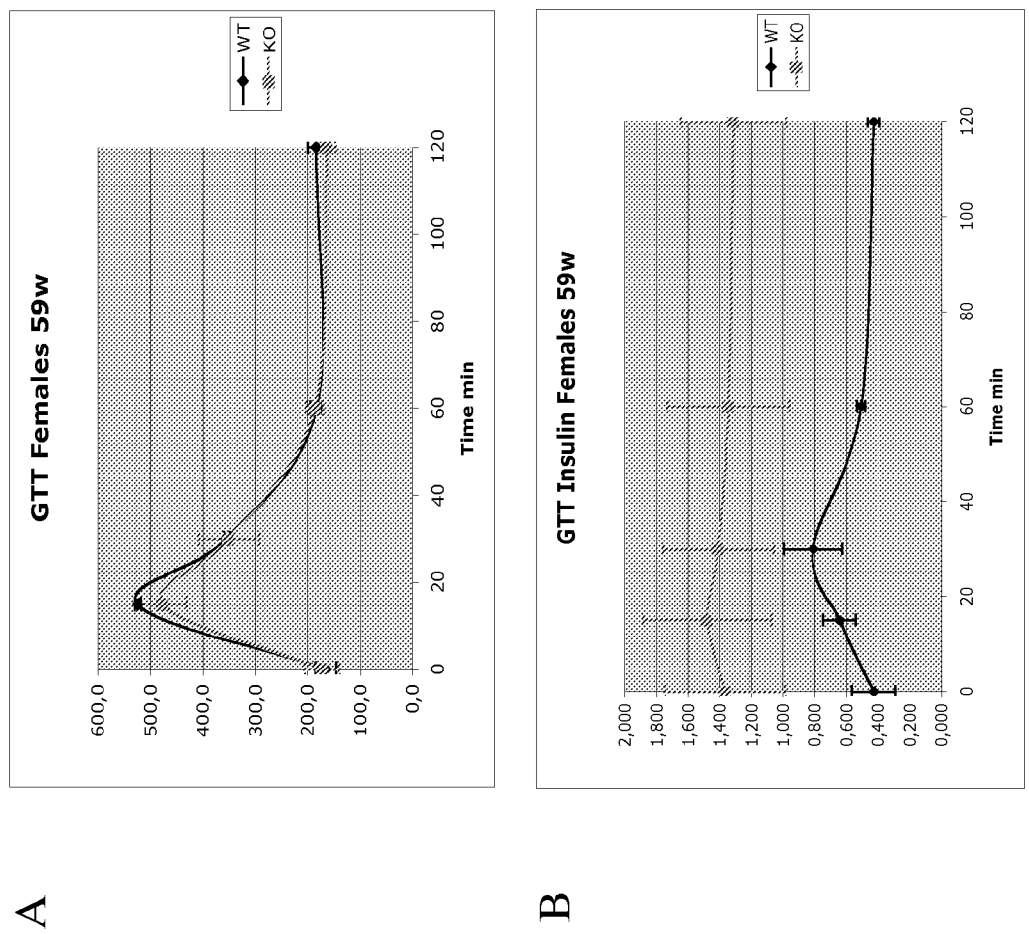
FIGS. 7A and 7B: Glucose tolerance test in SorCS1 knockout mice and wild type littermates. Mice 59 weeks of age were fasted overnight (16 h) and injected intraperitoneally with a bolus of glucose (2 mg/g body weight) in sterile saline. Blood samples were obtained by retroorbital bleeding at times 0, 15, 30, 60, and 120 min after injection, and plasma FIG. 7A) glucose and FIG. 7B) insulin levels were measured. Data are means±SEM for four mice in each group.

FIGS. 7A and 7B: Glucose tolerance test in SorCS1 knockout mice and wild type littermates. Female wild type (wt) and SorCS1 knockout (KO) mice 59 weeks of age were fasted overnight (16 h) and injected intraperitoneally with a bolus of D-glucose (Sigma) (2 mg/g body weight) in sterile saline. Mice were anesthetized with diethyl ether, blood samples were obtained by retroorbital bleeding at times 0, 15, 30, 60, and 120 min after injection, and plasma FIG. 7A) glucose and FIG. 7B) insulin levels were measured. Plasma glucose was measured immediately after sampling on an automatic monitor (Ascensia Contour from Bayer). Insulin levels were determined using an ultrasensitive mouse insulin enzyme-linked immunosorbent assay kit (DRG Diagnostics, Marburg, Germany). Data are means±SEM for four mice in each group.

FIGS. 8A-8D: Elevated plasma glucose- and insulin levels in wild type mice on Western type diet. Female FIG. 8A)+FIG. 8C) and male FIG. 8B)+FIG. 8D) wild type (wt) and SorCS1 knockout (KO) mice were fed a high calorie Western type diet (WD) (24% protein, 41% carbohydrate, 24% fat) (Research Diets. D12451) from 10 weeks of age to 50 weeks of age. At 50 weeks of age the animals were fasted overnight (16 h), anesthetized with diethyl ether and blood samples were obtained by retroorbital bleeding. Plasma glucose levels FIG. 8A)+FIG. 8B) were measured immediately after sampling on an automatic monitor (Ascensia Contour from Bayer), whereas plasma insulin levels FIG. 8C)+FIG. 8D) were determined using an ultrasensitive mouse insulin enzyme-linked immunosorbent assay kit (DRG Diagnostics, Marburg, Germany). Data are means±SEM for 4 to 10 mice in each group.

FIGS. 9A-9B: Abdominal adipose tissue in wild-type and knockout mice on western type diet. Female FIG. 9A) and male FIG. 9B) wild type and SorCS1 knockout mice were fed a high calorie Western type diet (WD) (24% protein, 41% carbohydrate, 24% fat) (Research Diets. D12451) from 10 weeks of age to 50 weeks of age. At the end of the study the animals were killed and the abdominal fat (adipose tissue) was separated and weighed. Data are means±SEM for 4 to 10 mice in each group.

FIGS. 10A-10B: Expression of IR, phosphorylated IR (pY-IR) and Glut4 in muscle and adipose tissue. Female SorCS1 knockout (−/−) mice and wild-type (+/+) control mice 50 weeks of age were fasted overnight, injected intraperitoneally with insulin (Novorapid, Novo Nordisk A/S) (10 units/kg body weight) in sterile saline, and killed 15 min later. FIG. 10A) Adipose and FIG. 10B) muscle tissue were removed and homogenized in lysis buffer THE-buffer (10 mM Tris-HCl, 150 mM NaCl, 1 mM EDTA, 1% nonidet P-40 (Sigma Aldrich) pH. 8) containing protease inhibitors (CompleteMini). The lysates were cleared by centrifugation 10 min at 1000×g, and protein concentrations were determined by Bio-Rad Protein Assay. Equal amounts of total protein for different samples (100 µg) were separated on a 4-16% SDS-PAGE gel and transferred onto polyvinylidene difluoride (PVDF) membranes (Amersham Pharmacia). Membrane was analysed by western blotting with anti-IR (Santa Cruz Biotechnology, sc-711), anti-IR-pY (R&D systems, AF2507), anti-Glut4 (Abcam, ab654), and anti-β-actin (Sigma, AF5441) as a loading control. Bound antibodies were developed by SuperSignal West Pico reagent (Pierce) and a Fuji film LAS3000.

Figure 11:
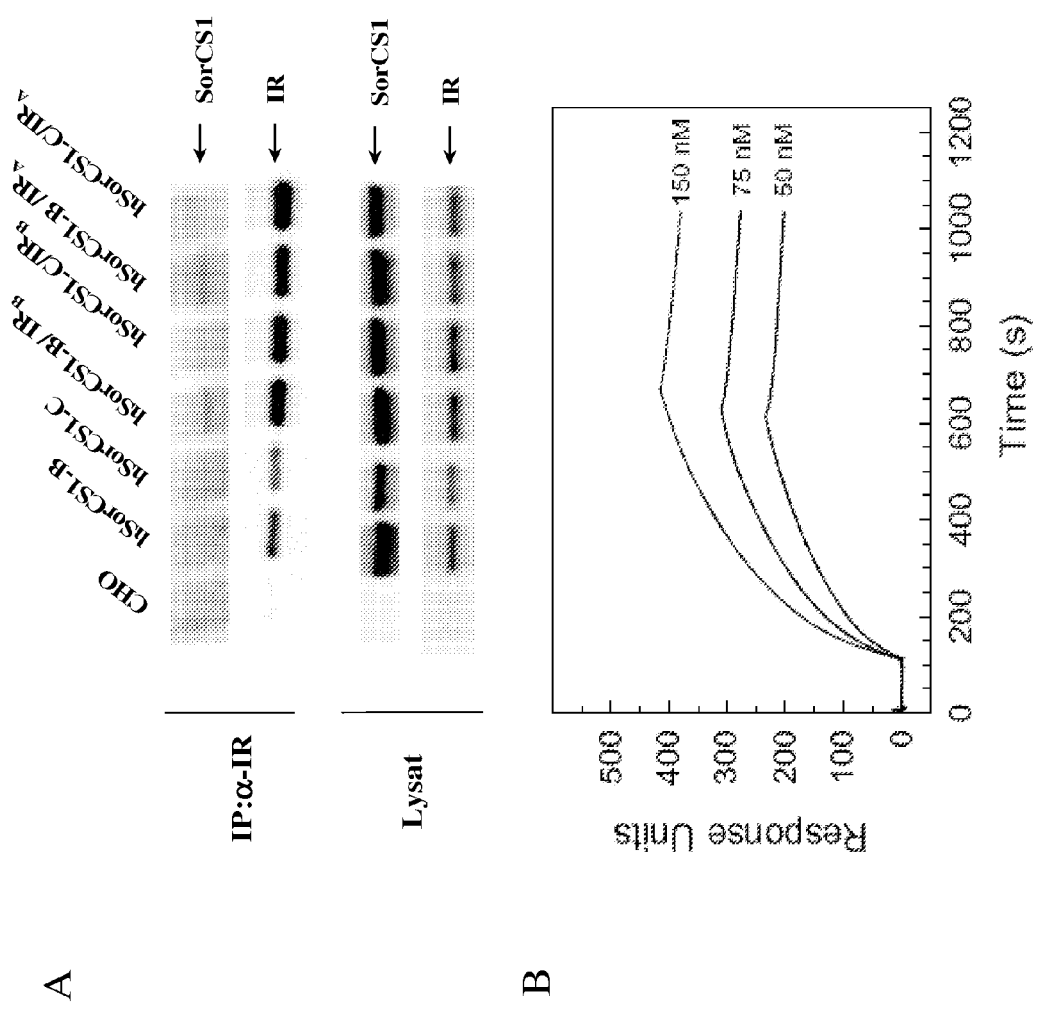

FIG. 11: Physical interaction between SorCS1 and insulin receptor. A) CHO cells transfected with the indicated receptors (only transient transfected with $IR_A$ and $IR_B$) were stimulated with insulin for 30 min followed by crosslinking with 5 nM DSP (Pierce) and subsequently lysed. The cell lysates was incubated with antibody against IR (Santa Cruz Biotechnology, sc-711) bound to Gammabind beads (GE Healthcare). The precipitated complexes were eluted from the washed beads with SDS loading buffer. The eluate was subjected to SDS-PAGE and Western blot analysis using α-SorCS1-leu and α-IR to reveal the presence of a SorCS1:IR complex. Crude lysates subjected to Western blot analysis using α-SorCS1-leu and α-IR were included to assess the transfection efficiency. B) Surface plasmon resonance experiment (BIAcore) showing the direct interaction of soluble full-length extracellular part of SorCS1 with immobilized soluble insulin receptor (IR) (R&D systems). The soluble SorCS1 concentrations used were 50 nM, 75 nM, and 150 nM. The $K_d$ is estimated to approximately 5 nM.

FIG. 12: Insulin receptor expression in CHO cells transfected with SorCS1. Chinese hamster ovary (CHO) cells stably transfected with the four murine SorCS1 splice variants (SorCS1-a,-b,-c,-d) and msol.SorCS1 (the extracellular part of SorCS1) were grown to confluency in serum-free HyQ-CCM5 CHO medium (HyClone) supplemented with antibiotics (50 U/ml penicillin/50 µg/ml streptomycin). The cells were washed with PBS and lysed in lysis-buffer (1% Triton X-100, 20 mM Tris-HCl, 10 mM EDTA, pH 8.0), supplemented with proteinase inhibitors (CompleteMini, Roche Molecular Biochemicals). Aliquots of the lysates, corresponding to 10 µg protein, were dissolved in SDS sample buffer and subjected to reducing SDS-PAGE using 4-16% acrylamide gels. For immunoblotting, proteins were electrophoretically transferred onto polyvinylidene difluoride (PVDF) membranes (Amersham Pharmacia) and probed with anti-IR (Santa Cruz Biotechnology, sc-711), anti-SorCS1-leu and anti-β-actin (Sigma, AF5441) as a loading control. Bound antibodies were developed by SuperSignal West Pico reagent (Pierce) and a Fuji film LAS3000.

FIG. 13: Expression of IR and SorCS1 on the cell membrane. Cell surface expression of the insulin receptor and SorCS1 was determined by cell surface biotinylation. CHO cells and CHO cells stably expressing mSorCS1-B and mSorCS1-C were subjected to surface biotinylation using the membrane impermeable biotinylation reagent NHS-SS-biotin (Pierce). Cells were grown to confluency, following which cells were washed with phosphate-buffered saline (PBS). Biotinylation was carried out using 0.5 mg/ml NHS-SS-biotin in PBS for 90 min at 4° C. with gentle shaking. After labeling, cells were washed twice with ice-cold PBS to remove the residual NHS-SS-biotin. Subsequently, cells were solubilized in lysis buffer (10 mM Tris-HCl, 150 mM NaCl, 1 mM EDTA, 1% nonidet P-40 (Sigma Aldrich) pH. 8) containing protease inhibitors (CompleteMini) by gently shaking on ice for approximately 10 min. The lysate were clarified by centrifugation at 14,000×g for 5 min at 4° C., 20 µl of the cleared lysate was saved (lysate fraction) and the rest of the lysate was incubated overnight with 100 µl of streptavidin-agarose beads (Sigma) at 4° C. with gentle agitation. After incubation, the lysate/beads mixture was separated by centrifugation at 14,000×g for 5 min at 4° C. The lysate fraction contains the intracellular proteins of the cells (Intra). The beads were washed twice with PBS and the captured biotinylated proteins (Bio) were eluted from the beads with 150 µl of SDS sample buffer. Finally, a portion of the biotinylated (Bio) (30 µl), the intracellular (Intra) (25 µl), and the crude lysates (Lysate) was subjected to SDS-PAGE and Western blot analysis using anti-IR (Santa Cruz Biotechnology, sc-711), anti-IR-pY (R&D systems, AF2507), anti-Glut4 (Abcam, ab654), and anti-β-actin (Sigma, AF5441) as a loading control. Bound antibodies were developed by SuperSignal West Pico reagent (Pierce) and a Fuji film LAS3000.

FIG. 14: Development stages towards type 2 diabetes in human. Type 2 diabetes (T2D) develops in response to obesity in subjects that have underlying genetic and acquired predispositions to both insulin resistance and β cell dysfunction. Over time, islet β cell compensation for the insulin resistance fails, resulting in progressive decline in β cell function. As a consequence, subject's progress from normal glucose tolerance to impaired glucose tolerance (pre-diabetes) and finally to established T2D. Increases in blood glucose concentration during the development of T2D are illustrated on the graph (black line) showing the change from normal to pre-diabetic, before the onset of frank diabetes. Furthermore, the level of insulin during development of T2D is revealed on the same graph (dashed line), showing an increase of insulin during the pre-diabetic state as compensation to insulin resistance and a severe decline in insulin release at onset of frank diabetes as a consequence of 13 cell failure.

FIG. 15: Insulin immunostaining of pancreatic islets in wild-type and knockout mice 20 days of age. Pancreata were removed and fixed with 4% paraformaldehyde, freshly prepared in PBS. Samples were embedded in Tissue-Tek (Sakura). Cryosections (10 µm) were obtained from several positions throughout the pancreas, and stored in −80° C. For immunostaining, the slide were placed in PBS for 2×5 min, blocked in 0.2% hydrogen peroxid ($H_2O_2$) in methanol for 15 min at −20° C., washed with PBS (1×5 min) and PBS+0.1% TritonX-100 (2×10 min) before preincubation with 10% fetal calf serum (FCS) in PBS for 30 min. Slides were subsequently rinsed in PBS (3×2 min) and incubated overnight at 4° C. in primary antibody guinea pig anti-insulin (1-8510, Sigma) diluted in PBS+10% FCS (1:500). Slides were washed with PBS (3×15 min), incubated with secondary antibody Cy3-conjugated anti-guinea pig (706-165-148, Jackson ImmunoResearch) diluted in PBS+FCS (1:500) in the dark for 1 hr at RT, and subsequently washed in PBS (3×15 min) and allowed to air-dry. Finally, the slides were mounted with Vectashield with DAPI (H-1200, Vector Labs) and analysed by confocal scanning laser microscopy (LMS 510, Carl Zeiss).

FIG. 16: Alignment of SorCS1 Sequence alignment of SorCS1 from Human (*homo sapiens*) (SEQ ID NO: 80), Chimpanzee (*Pan troglodytes*) (SEQ ID NO: 34), Cow (*Bos Taurus*) (SEQ ID NO: 40), Mouse (*Mus musculus*) (SEQ ID NO: 16), Rat (*Rattus norvegicus*) (SEQ ID NO: 44), Dog (*Canis lupus familiaris*) (SEQ ID NO: 38) and Chicken (*Gallus gallus*) (SEQ ID NO: 48) origin. The sequence identity is as demonstrated in table 2.

TABLE 2

Sequence identity to human SorCS1

| Species | Protein (% identity) | DNA (% identity) |
|---|---|---|
| Human | 100 | 100 |
| Chimpanzee | 99.6 | 99.4 |
| Dog | 97.6 | 92.5 |
| Cow | 92.9 | 89.8 |
| Mouse | 93.2 | 87.7 |
| Rat | 93.2 | 88.0 |
| Chicken | 85.3 | 79.7 |

FIGS. 17A-17B: Decreased plasma glucose levels in female wild-type and SorCS1 knockout mice after hepatic overexpression of soluble SorCS1.

Wild-type and SorCS1 knockout female mice were injected with an adenovirus over-expressing soluble SorCS1 or an adenovirus over-expressing lacZ as a negative control. The recombinant adenovirus for expression of human soluble SorCS1 (hsol.SorCS1) was generated as follows: pcDNA3.1/Zeo(−)/hsol.SorCS1 encoding the human soluble SorCS1 cDNA (amino acids 1-1100) was digested with Pme1 and Apa1 and the fragment encoding hsol.SorCS1 inserted into the shuttle plasmid pVQpacAd5CMVK-NpA (ViraQuest Inc, North Liberty, Iowa) generating the plasmid pVQAd5CMVK-NpA-sol.SorCS1. The vector map of this plasmid is shown in FIG. 17A. The plasmid was sent to ViraQuest Inc, North Liberty, Iowa, that used this shuttle plasmid for generation and propagation of adenovirus overexpressing hso1. SorCS1. The virus VQAd5 CMV ntLacZ that over-express LacZ as a negative control was also purchased from ViraQuest. The blood glucose of SorCS1 knockout and wild-type mice were measured before and after hepatic over-expression of soluble SorCS1 or lacZ. Thus, female SorCS1 knockout and wild-type mice 40 weeks of age were fasted overnight. In the morning, on day 0, blood samples were obtained by retroorbital bleeding and plasma glucose was measured immediately on an automatic monitor (Ascentia Contour from Bayer). Then, the mice were injected in the tail vein with 2E9 pfu's of the adenoviral vector with either hsol.SorCS1 or LacZ as a negative control (from ViraQuest Inc, North Liberty, Iowa). On day 7, measurements of plasma glucose were repeated on overnight fasted mice to evaluate the effect of the SorCS1 and LacZ protein. In FIG. 17B is shown the relative plasma glucose after normalization to the values obtained at day 0. The data are means±SEM for 4 mice in each group. Mice with over-expression of soluble SorCS1 exhibited a significant decrease in plasma glucose (≈40%) both in SorCS1 knockout mice and wild-type mice. This increase was not seen in the mice that received the control virus LacZ.

FIG. 18: Expression of IR, phosphorylated IR, and Glut4 in muscle and adipose tissue from SorCS1 knockout female mice over-expressing soluble SorCS1.

Female SorCS1 knockout (−/−) mice 40 weeks of age were injected with a adenoviral vector expressing either hsol.SorCS1 or LacZ as a negative control (see detailed protocol in FIG. 17). On day 12 after virus injection, the mice were fasted overnight, injected intraperitoneally with insulin (Novorapid, Novo Nordisk A/S) (10 units/kg body weight) in sterile saline, and killed 15 min later. A) Muscle and B) adipose tissue were removed and homogenized in lysis buffer TNE-buffer (10 mM Tris-HCl, 150 mM NaCl, 1 mM EDTA, 1% nonidet P-40, pH. 8) containing protease inhibitors (Complete Mini, Roche) and phosphatase inhibitors (cocktail 1, Sigma Aldrich). The lysates were cleared by centrifugation 10 min at 10,000×g, and protein concentration were determined by Bio-Rad Protein Assay. Equal amount of total protein (50 µs) for different samples were separated on a 4-12% Bis-tris gel (Nupage, Invitrogen) and transferred onto polyvinylidene difluoride (PVDF) membranes (Amersham Pharmacia). Membranes were analysed by western blotting with anti-IR (Santa Cruz Biotechnology, sc-711), anti-IR-pY (R&D systems, AF2507) and anti-Glut4 (Abcam, ab654). Bound antibodies were developed by Super-Signal West Pico reagent (Pierce) and a Fuji film LAS3000. In both A) muscle and B) adipose tissue from SorCS1 knockout mice overexpressing soluble SorCS1 there are elevated amount of IR, phosphorylated IR (IR-pY) and glut4 compared to mice expressing the LacZ control protein, suggesting increased insulin sensitivity in mice which received the hsol.SorCS1 virus.

FIGS. 19A and 19B: Decreased plasma glucose and insulin levels in diabetic db/db female mice over-expressing soluble SorCS1.

To evaluate the effect of soluble SorCS1 in an obese mouse model that spontaneously develops type 2 diabetes we used the db/db mouse strain (BKS.Cg-m+/+Lpr$^{db}$/BomTac from Taconic). These mice lack the leptin receptor consequently the mice become obese and develop insulin resistance and finally severe diabetes at the age of 6-8 weeks. We injected adenovirus expressing either hsol.SorCS1 or LacZ as a control (as described in FIG. 17), to examine the effect on plasma glucose and insulin levels. In detail, db/db female mice 10 weeks of age were fasted overnight. In the morning, on day 0, the mice were anesthetized with diethyl ether and blood samples were obtained by retroorbital bleeding. FIG. 19A) Blood glucose was measured immediately on an automatic monitor (Ascentia Contour from Bayer), whereas FIG. 19B) plasma insulin levels were determined using an ultrasensitive mouse insulin enzyme-linked immunoabsorbent assay kit (DRG Diagnostics). Thereafter the mice were injected in the tail vein with 2E9 pfu's of an adenoviral vector with either hsol.SorCS1 or LacZ (from ViraQuest Inc, North Liberty, Iowa) as a negative control virus. On day 7, measurements of blood glucose and plasma insulin were repeated on overnight fasted mice to evaluate the effect of the SorCS1 and LacZ protein. Data are means±SEM for 5 mice in each group. On day 7, db/db female mice with over-expression of soluble SorCS1 exhibited a significant decrease in blood glucose (≈35%) compared to the mice that received the control LacZ virus. Furthermore, on day 7 there was also a significant decrease in the plasma insulin levels in the db/db female mice over-expressing soluble SorCS1 compared to mice that express the control virus. Thus, over-expression of soluble SorCS1 improves the diabetic status in this type 2 diabetic mouse model.

FIG. 20: Glucose tolerance test in diabetic db/db female mice with over-expression of soluble SorCS1.

Female db/db mice injected with adenoviruses expressing either soluble SorCS1 or LacZ (see FIG. 17) where on day 3 fasted over-night (16 hrs). On day 4 the mice were injected intraperitoneally with a bolus of glucose (2 mg/g body weight) in sterile saline. The animals were anesthetized with diethyl ether and blood samples were obtained by retroorbital bleeding at times 0, 15, 30, 90, and 150 min after injection.

Blood glucose levels were measured immediately after sampling on an automatic monitor (Ascentia Contour from Bayer). Data are means±SEM for 5 mice in each group. The results show, that over-expression of soluble SorCS1 renders the mice more sensitive to insulin as the level of blood glucose returns to baseline after 150 min. By contrast, blood glucose in mice expressing LacZ stays elevated during the course of the experiments. In conclusion, db/db female mice with over-expression of soluble SorCS1 are less insulin resistant.

FIGS. 21A and 21B: Plasma glucose and insulin levels in diabetic db/db male mice over-expressing soluble SorCS1.

To evaluate the effect of soluble SorCS1 in an obese mouse model that spontaneously develops type 2 diabetes we used the db/db mouse strain (BKS.Cg-m+/+Lpr$^{db}$/BomTac from Taconic). These mice lack the leptin receptor consequently the mice become obese and develop insulin resistance and finally severe diabetes at the age of 6-8 weeks. We injected adenovirus expressing either hsol.SorCS1 or LacZ as a control (as described in FIG. 17), to examine the effect on plasma glucose and insulin levels. In detail, db/db male mice 6 weeks of age were fasted overnight. In the morning, on day 0, the mice were anesthetized with diethyl ether and blood samples were obtained by retroorbital bleeding. FIG. 19A) Blood glucose was measured immediately on an automatic monitor (Ascentia Contour from Bayer), whereas FIG. 19B) plasma insulin levels were determined using an ultrasensitive mouse insulin enzyme-linked immunoabsorbent assay kit (DRG Diagnostics). Thereafter the mice were injected in the tail vein with 2E9 pfu's of an adenoviral vector with either hsol.SorCS1 or LacZ (from ViraQuest Inc, North Liberty, Iowa) as a negative control virus. On day 7, measurements of blood glucose and plasma insulin were repeated on overnight fasted mice to evaluate the effect of the SorCS1 and LacZ protein. Data are means±SEM for 5 mice in each group. On day 7, db/db male mice with over-expression of soluble SorCS1 exhibited a significant decrease in blood glucose (≈35%) compared to the mice that received the control LacZ virus. Because the decline in glucose levels were not accounted by an increased insulin concentration as compared to LacZ treated animals, we conclude that over-expression of soluble SorCS1 improves the diabetic status in male type 2 diabetic db/db mice.

FIG. 22: Subcellular localization of Glut4 in muscle tissue from db/db male mice over-expressing soluble SorCS1.

To evaluate if over-expression of soluble SorCS1 might change the distribution of Glut4 we conducted subcellular fractionation on muscle tissue from db/db male mice over-expressing soluble SorCS1. In detail, db/db male mice 6 weeks of age were injected in the tail vein with a adenoviral vector expressing either hsol.SorCS1 or LacZ as a control as described in FIG. 17. On day 7 after virus injection, the mice were fasted overnight, injected intraperitoneally with insulin (Novorapid, Novo Nordisk A/S) (10 units/kg body weight) in sterile saline, and killed 15 min later. Muscle tissue from 5 mice injected with the same virus was removed, pooled and transferred to 5 ml of HEPES-buffered sucrose (0.25 M sucrose, 1 mM EDTA, 20 mM HEPES-KOH, pH. 7.4), homogenized by 10 strokes up and down using a Teflon pestle, and centrifuged at 1000×g for 10 min. Thus, heavy mitochondrial, light mitochondrial, and microsomal fraction were obtained by several round of centrifugation. First, the supernatant was centrifuged at 3,000×g for 10 min, then the resulting supernatant was centrifuged at 16,000×g for 10 min, and finally the resulting supernatant was centrifuged a 100,000×g for 45 min giving a pellet containing the microsomal fraction. The microsomal fractions were resuspended in 0.5 ml HEPES-buffered solution and subjected to sucrose (velocity) gradient centrifugation. The 0.5 ml microsomal samples were loaded onto a 12 ml linear 0.8 M to 1.6 M sucrose gradient in 1 M HEPES, pH 7.2, and centrifuged 18 h in a swinging bucket rotor (SW41 Ti) at 84,000×g. Each gradient was separated into 24 fractions starting from the top of the tube. Finally, gel electrophoresis and Western blotting analyzed the expression of Glut4 in the different fractions. The result shows that the sedimentation distribution of Glut4 in muscle tissue over-expressing SorCS1 is different from muscle tissue expressing the control protein lacZ. Thus, accumulation of glut4 shifted from fractions 2-4 after LacZ treatment to fractions 8-12 in the SorCS1 group.

This indicate that over-expression of soluble SorCS1 might change the distribution of Glut4 and thereby modulate glucose uptake.

FIG. 23 A+B: Analysis of SorCS1/IR contact sequences by SPOT analyses.

Co-immunoprecipitation and BIAcore (surface Plasmon resonance) experiments showed SorCS1 can physically associate with the insulin receptor. We here used SPOT synthesis analysis to identify linear amino acid sequences in either of the two receptors that may partake in the protein-protein interaction. In practice filters were spotted with consecutive 15-mer peptides overlapping by three amino acids from the N- to the C-terminus of SorCS1 (B) and IR (A), and the filters were subsequently probed with (A) $^{125}$I-labelled soluble human SorCS1 or (B) histidine-tagged insulin receptor (R&D systems, no1544-IR/CF). The filters were then washed and bound proteins visualized. The binding assay was performed directly on the peptide membrane through immunodetection or radiography of bound protein. In detail, the membrane was washed 1×10 min in 96% ethanol, followed by 3×10 min washing with 1×TBS (500 mM Tris-HCl, 1500 mM NaCl), pH.8.0 and 3 hrs incubation in membrane blocking buffer (BB; 1×Blocking buffer (B6429, Sigma), 1×TBS, 5% sucrose). The blocked IR-membrane was incubated overnight with $^{125}$I-sol.SorCS1 (400.000 cpm/ml BB) and the SorCS1-membrane with his-IR (10 µg/ml BB). Both membrane were washed 3×10 min with 1×TBS. A) Bound his-IR on the SorCS1 membrane was detected by immunodetection using primary anti-body against the histidine tag, α-histidine (Invitrogen) (Mouse monoclonal) followed by an HRP-tagged secondary anti-mouse antibody (Sigma). Bound antibody was visualized using the enhanced chemiluminescence (ECL) Western blotting Detection reagent (Amersham biosciences) and a Fuji film LAS1000). Bound radiolabelled SorCS1 to the IR-membrane was detected by radiography using a Fuji image plate, and after 12 hrs exposure subsequently developed using a Fujifilm FLA3000. A signal (SPOT) indicates that the ligand binds to a peptide. Overlapping linear binding epitopes are represented by signals from neighbouring spots. The SPOT's are framed on the membrane figures and key sequences corresponding to the SPOT's are indicated beneath the membrane. FIGS. 23A and 23B disclose SEQ ID NOS 81-95, respectively, in order of appearance.

FIG. 24 A+B: Gene expression profiling of adipose tissue from SorCS1 knockout mice by PCR arrays.

Using gene array analysis of adipose tissue from SorCS1 knockout wild-type adipose mice we tested expression of FIG. 24A) 84 genes related to the mouse insulin signalling pathway and FIG. 24B) 84 genes related to mouse lipoprotein signalling & cholesterol metabolism. In practice, first strand cDNA was synthesized from total RNA (Applied Biosystems) from SorCS1 knockout (−/−) and wild-type (+/+) adipose tissue from female mice 50 weeks of age (n=3). Then superarray of FIG. 24A) Mouse Insulin Signalling Pathway (PAMM-030A RT2 Profiler PCR arrays) or FIG. 24B) the type Mouse Lipoprotein Signalling & Cholesterol Metabolism (PAMM-080-A RT2 Profiler PCR arrays) were processed using an AB17900 platform (Applied Biosystems) and SYBR Green/Rox PCR (SABiosciences). AROS Applied Biotechnology, Aarhus, Denmark, did the expression analyses. Genes showing an expression more than 3 times up- or down-regulated in the SorCS1 knockout mice when compared to wild-type mice are listed in the upper tables and their known functions are indicated in the table below. Several genes in FIG. 24A and FIG. 24B show changed expression in the SorCS1 knockout mice compared to the wild-type mice indicating that insulin and cholesterol signalling pathways and metabolism are altered in SorCS1 knockout mice.

FIG. 25: Reduced weight in diabetic db/db mice after over-expression of soluble SorCS1. To evaluate the effect of soluble SorCS1 on weight in an obese mouse model that spontaneously develops type 2 diabetes, we used the db/db mouse strain (BKS.Cg-m+/+Lpr$^{db}$/BomTac from Taconic). These mice lack the leptin receptor and consequently the mice become obese and develop insulin resistance and finally severe diabetes at the age of 6-8 weeks. We injected adenovirus expressing either human soluble (hsol.) SorCS1 or LacZ as a control (as described in FIG. 17), to examine the effect on weight. In detail, db/db female mice 6 weeks of age were injected in the tail vein with 2E9 pfu's of an adenoviral vector with either hsol.SorCS1 or LacZ (from ViraQuest Inc, North Liberty, Iowa) as a negative control virus. In the morning, on day 0, 9, 14 and day 16, the mice were weighed on a scale. Data are means±SEM for 5 mice in each group. On day 9 to 16, the db/db female mice with over-expression of soluble SorCS1 exhibited a significant decrease in weight compared to the mice that received the control LacZ virus. Thus, over-expression of soluble SorCS1 improves the obese status in this obese mouse model.

FIGS. 26A and 26B Reduced food intake and weight in diabetic db/db mice after over-expression of soluble SorCS1.

To evaluate the effect of soluble SorCS1 on weight in an obese mouse model that spontaneously develops type 2 diabetes, we used the db/db mouse strain (BKS.Cg-m+/+Lpr$^{db}$/BomTac from Taconic). These mice lack the leptin receptor and consequently the mice become obese and develop insulin resistance and finally severe diabetes at the age of 6-8 weeks. We injected adenovirus expressing either hsol.SorCS1 or LacZ as a control (as described in FIG. 17), to examine the effect on weight. In detail, db/db female mice 6 weeks of age were injected in the tail vein with 2E9 pfu's of an adenoviral vector with either hsol.SorCS1 or LacZ (from ViraQuest Inc, North Liberty, Iowa) as a negative control virus. FIG. 26A) In the morning of day 9 after virus treatment each mouse was moved to a metabolic cage with a measured amount of food. 24 hours later the mouse was moved back to a normal mouse cage and the food in the metabolic cage was weighed to determine the food intake. The amount of ingested food over 24 hours is shown. Data are means±SEM for 4 mice in each group. Mice with over-expression of soluble SorCS1 ate significant less than the control mice expressing LacZ. FIG. 26B) In the morning, on day 0 and 11 after virus treatment, the mice were weighed on a scale. The relative weight changes over the time period are shown. Data are means±SEM for 4 mice in each group. On day 11, the db/db female mice with over-expression of soluble SorCS1 exhibited a significant decrease in body weight compared to the mice that received the control LacZ virus.

EXAMPLES

Example 1

Expression of mSorCS1 Splice Variants in Tissues from Mice

Expression of the extracellular part of SorCS1 (SorCS1.ex) and the five tail splice variants SorCS1-a, -b, -c, c$^+$ and -d were determined in various tissues from adult mice (see FIG. 3). The organization of the SorCS1 gene and the amino acid sequences of the cytoplasmic domains of the splice variants are shown in FIGS. 2A and 2B, respectively.

Expression of the extracellular part of SorCS1 (SorCS1.ex) and splice variants were determined by reverse transcription-PCR (RT-PCR) with specific primer pairs. The SorCS1.ex specific primers (SEQ ID NO: 57 and SEQ ID NO: 58) are spanning the exon 21 to 24 junctions giving a 390 bp product. The SorCS1-a specific primers (SEQ ID NO: 59 and SEQ ID NO: 60) are spanning the exon 21 to 25 junctions giving a 586 bp product. The SorCS1-b specific primers (SEQ ID NO: 61 and SEQ ID NO: 62) are spanning the exon 21 to 25 junctions and the exon 25 to 27 junctions giving a 621 bp product. The SorCS1-c (SEQ ID NO: 63 and SEQ ID NO: 64) specific primers are spanning the exon 21 to 26 junctions giving a 626 bp product. The SorCS1-d specific primers (SEQ ID NO: 65 and SEQ ID NO: 66) are spanning the exon 21 to 25 junctions and the exon 25 to 28 junction giving a 636 bp product. Total RNA preparations were made from hippocampus, liver, adipose tissue (fat), muscle, pancreas and testis isolated from wild type and hippocampus and liver from SorCS1-KO mice of about 8 weeks of age using the Versagene Total RNA purification Kit (Gentra Systems). Briefly, tissues were surgically removed and frozen on dry ice. Frozen tissue samples were disrupted and homogenized for up to 60 sec using a rotor stator (Ultra-Turrax, IKA-Werke) in 800 µl lysis buffer containing 5 mM Tris (2-carboxyethyl) phosphine (TCEP) and the total RNA was purified according to the manufacturers protocol for the kit. RT-PCR were performed with 0.75 µg to 1 µg total RNA from each sample using the TITANIUM One-step RT-PCR kit (Clontech). All reactions were performed in 50 µl volume containing 1×One-step buffer (40 mM tricine, 20 mM KCl, 3 mM MgCl$_2$, 3.75 µg/ml BSA), 0.2 mM of each dNTP, 25 µl Thermostabilizing reagent, 10 µl GC-melt, 20 µM Oligo(dT)primer, 20 units Recombinant RNase inhibitor, 1×RT-TITANIUM Taq enzyme mix (all supplied with the kit) and 45 µM of each primer. PCR conditions were: 50° C. for 1 hour, 94° C. for 5 min, 35 cycles at 94° C. for 30 sec, 64° C. for 30 sec, 68° C. for 1 min, and 68° C. for 2 min.

Example 2

Generation of the mSorCS1 Knockout Mouse

To investigate the function of SorCS1 and its different splice variants, a conditional knockout mouse was generated by homologous recombination in embryonic stem cells. The homologous recombination was initiated by the site-specific FLP recombinase at a FRT-site, which results in "recombinase-mediated cassette exchange". The recombination event is illustrated in FIG. 4A, where the SorCS1 gene is "exchanged" with the Neo gene thereby generating a full knockout mouse where all SorCS1 splice variants are disrupted.

Expression of SorCS1 was tested in wild-type and SorCS1 knockout mice by RT-PCR on mRNA from hippocampus of wild-type (WT) and SorCS1 knockout (KO) mice using specific primer pairs to identify the extracellular part of SorCS1 (ext) or each of the five tail variants (a, b, c, c$^+$, and d). The results shown in FIG. 4B reveal that transcription of all mSorCS1 splice variants are disrupted in the SorCS1 knockout mouse.

Western blot analysis of cortex revealed the lack of mSorCS1 protein in the mSorCS1 knockout (KO) mice (FIG. 4C). Proteins were extracted as lysates from cortex obtained at E14.5. The tissue was dissolved in 100 µl THE-buffer (10 mM Tris-HCl, 150 mM NaCl, 1 mM EDTA, 1% nonidet P-40 (Sigma Aldrich) pH. 8) containing protease inhibitors (CompleteMini) by vigorous vortexing. After freezing ON at 20° C., the lysates were vortexed and centrifuged 10 min at 1000×g. The lysates (supernatant) were transferred to a new tube and Bio-Rad Protein Assay measured the protein concentration. Lysates (200 µg) were resolved on SDS-PAGE and transferred to nitrocellulose. The blot was then probed with a rabbit polyclonal antibody against the leucine-rich part of SorCS1 (α-hSorCS1-leu).

Example 3

Plasma Glucose Levels in SorCS1 Knockout Mice

Type 2 diabetes (T2D) develops in response to obesity in subjects that have underlying genetic and acquired predispositions to both insulin resistance and β cell dysfunction. Over time, islet β cell compensation for the insulin resistance fails, resulting in progressive decline in β cell function. As a consequence, subject's progress from normal glucose tolerance to impaired glucose tolerance (pre-diabetes) and finally to established T2D. Increases in blood glucose concentration during the development of T2D are illustrated on the graph (black line) showing the change from normal to pre-diabetic, before the onset of frank diabetes. Furthermore, the level of insulin during development of T2D is revealed on the same graph (dashed line), showing an increase of insulin during the pre-diabetic state as compensation to insulin resistance and a severe decline in insulin release at onset of frank diabetes as a consequence of β cell failure (FIG. 14)

To examine the SorCS1 knockout mouse with respect to glucose metabolism, the plasma glucose levels were determined in male (FIG. 5A) and female mice (FIG. 5B) at different age. Animals were fasted overnight (16 h). Mice were anesthetized with diethyl ether, blood samples were obtained by retroorbital bleeding and plasma glucose was measured immediately on an automatic monitor (Ascensia Contour from Bayer). The results in FIG. 5B shows a statistically significant increase in plasma glucose levels of female SorCS1 knockout mice at an age of 23 and 50 weeks relative to wild type mice.

Example 4

Plasma Insulin Levels in Female SorCS1 Knockout Mice

To further examine the SorCS1 knockout mouse with respect to glucose metabolism, the plasma insulin levels were determined in female SorCS1 knockout mice from 10 to 20 weeks of age (FIG. 6). Animals were fasted overnight (16 h). Mice were anesthetized with diethyl ether, blood samples were obtained by retroorbital bleeding and plasma insulin levels were determined using an ultrasensitive mouse insulin enzyme-linked immunosorbent assay kit (DRG Diagnostics, Marburg, Germany). Data are means±SEM for 4 to 10 mice in each group. In agreement with the results shown in FIG. 5B, the results in FIG. 6 shows a statistically significant increase plasma insulin levels of female SorCS1 knockout mice at an age of 23 and 50 weeks relative to wild type mice.

Insulin levels were further investigated by immunostaining of tissues from wild-type and SorCS1 knockout mice 20 days of age.

Pancreata were removed and fixed with 4% paraformaldehyde, freshly prepared in PBS. Samples were embedded in Tissue-Tek (Sakura). Cryosections (10 µm) were obtained from several positions throughout the pancreas, and stored in −80° C. For immunostaining, the slide were placed in PBS for 2×5 min, blocked in 0.2% hydrogen peroxid ($H_2O_2$) in methanol for 15 min at −20° C., washed with PBS (1×5 min) and PBS+0.1% TritonX-100 (2×10 min) before preincubation with 10% fetal calf serum (FCS) in PBS for 30 min. Thereafter rinsed in PBS (3×2 min) and incubated overnight at 4° C. in primary antibody guinea pig anti-insulin (1-8510, Sigma) diluted in PBS+10% FCS (1:500). Slides were washed with PBS (3×15 min), incubated with secondary antibody Cy3-conjugated anti-guinea pig (706-165-148, Jackson ImmunoResearch) diluted in PBS+FCS (1:500) in the dark for 1 hr at RT, and subsequently washed in PBS (3×15 min) and allowed to air-dry. Finally, the slides were mounted with Vectashield with DAPI (H-1200, Vector Labs) and analysed by confocal scanning laser microscopy (LMS 510, Carl Zeiss). This data suggest that the pancreas strives to compensate the decreased insulin sensitivity by increasing the size of beta-cell islets and insulin production.

Example 5

Glucose Tolerance Test in Female SorCS1 Knockout Mice

The glucose tolerance of female SorCS1 knockout mice was tested by measuring glucose and insulin levels at different time points after injection with glucose (FIG. 8) Female mice 59 weeks of age were fasted overnight (16 h) and injected intraperitoneally with a bolus of D-glucose (Sigma) (2 mg/g body weight) in sterile saline. Mice were anesthetized with diethyl ether, blood samples were obtained by retroorbital bleeding at times 0, 15, 30, 60, and 120 min after injection, and plasma glucose levels (FIG. 8A) and insulin levels (FIG. 8B) were measured. Plasma glucose levels were measured immediately after sampling on an automatic monitor (Ascensia Contour from Bayer). Insulin levels were determined using an ultrasensitive mouse insulin enzyme-linked immunosorbent assay kit (DRG Diagnostics, Marburg, Germany). The results in FIG. 7B show increased insulin levels in female SorCS1 knockout mice at all time points (0-120 min) after injection.

Example 6

Elevated Levels of Plasma Glucose and Insulin in Wild Type Mice on Western Type Diet Female (FIG. 8A+8C) and male (FIG. 8B+8D) wild type and SorCS1 knockout mice were fed a high calorie Western type diet (WD) (24% protein, 41% carbohydrate, 24% fat) (Research Diets. D12451) from 10 weeks of age to 50 weeks of age. At 50 weeks of age the animals were fasted overnight (16 h), anesthetized with diethyl ether and blood samples were obtained by retroorbital bleeding. Plasma glucose levels (FIG. 8A+8B) were measured immediately after sampling on an automatic monitor (Ascensia Contour from Bayer), whereas plasma insulin levels (FIG. 8C+8D) were determined using an ultrasensitive mouse insulin enzyme-linked immunosorbent assay kit (DRG Diagnostics, Marburg, Germany). The results depicted in FIG. 6 shows plasma glucose and insulin levels are elevated in wild type mice on Western type diet.

Example 7

Figure 10:
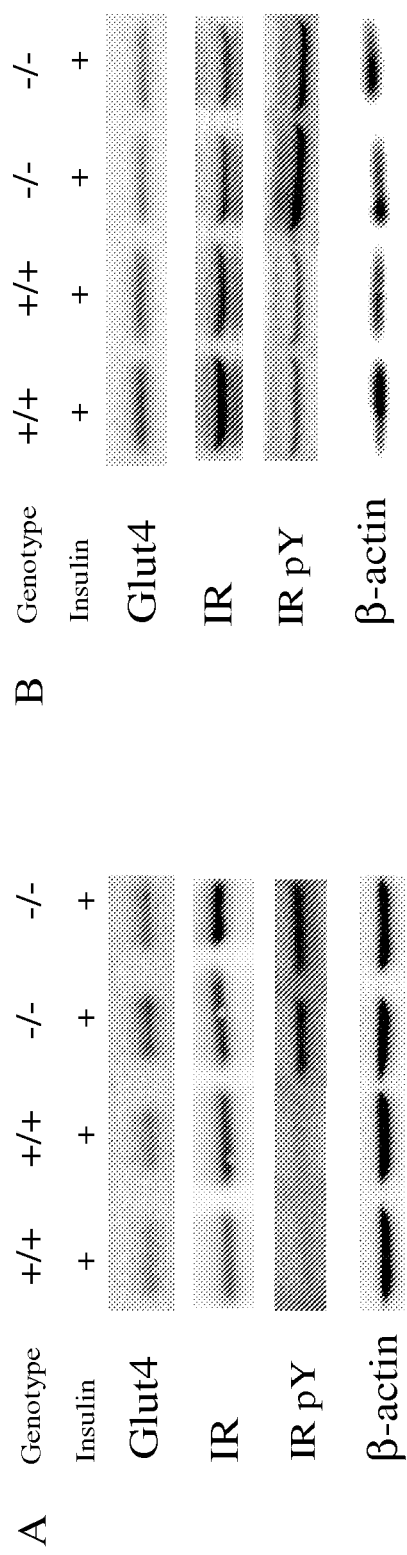

Demonstration of Increased Insulin Receptor Phosphorylation in SorCS1 Knockout Mice Female SorCS1 knockout (−/−) mice and wild-type (+/+) control mice 40 and 50 weeks of age were fasted overnight, injected intraperitoneally with insulin (10 units/kg body weight) in sterile saline, and killed 15 min later. Muscle tissue were removed and homogenized in lysis buffer THE-buffer (10 mM Tris-HCl, 150 mM NaCl, 1 mM EDTA, 1% nonidet P-40 (Sigma Aldrich), pH=8.0 containing protease (CompleteMini, Roche) and phosphatase inhibitors (Cocktail 1, Sigma Aldrich). The lysates were cleared by centrifugation 10 min at 1000×g, and protein concentration were determined by Bio-Rad Protein Assay. Equal amounts of total protein from different samples (100 µg) were separated on a 4-16% SDS-PAGE gel and transferred onto polyvinylidene difluoride (PVDF) membranes (Amersham Pharmacia). Membrane were subjected to Western blotting with anti-IR (Santa Cruz Biotechnology, sc-711), anti-IR-pY (R&D, AF 2507), and anti-β-actin (Sigma Aldrich, AF5441) as a loading control. Furthermore, tyrosine phosphorylation of IR were also analysed by immunoprecipitation with an anti-phosphotyrosine antibody (4G10). The immunoprecipitation was conducted as follows. 100 µg protein from muscle tissue was incubated with Gammabind G-Sepharose beads (Amersham Bioscience) coated with anti-phosphotyrosine (4G10, Upstate/Millipore) overnight at 4° C. The beads were subsequently washed 4×5 min, and finally resuspended in reducing sample buffer (20 mM DTE, 2.5% SDS) and boiled. The supernatant of the boiled samples, containing precipitated proteins, were analyzed by Western blotting using anti-IR (Santa Cruz Biotechnology, sc-711). All bound antibodies were developed by Super Signal West Pico reagent (Pierce) and a Fuji film LAS3000. FIG. 10 shows an increased expression of insulin receptor and a decreased phosphorylation of the insulin receptor in SorCS1 knockout mice aged 50 weeks suggesting that IR accumulates in a compartment in SorCS1 knockout mice thereby precluding the receptor from phosphorylation and activation. The results suggest that SorCS1 plays a role in insulin signalling and activation of the insulin receptor.

Example 8

Physical Interaction Between SorCS1 and Insulin Receptor

To examine the interaction between SorCS1 an the insulin receptor (IR), Chinese hamster ovary (CHO) cells stably transfected with the four murine SorCS1 splice variants (SorCS1-a,-b,-c,-d) and msol.SorCS1 (the extracellular part of SorCS1) were grown to confluency in serum-free HyQ-CCM5 CHO medium (HyClone) supplemented with antibiotics (50 U/ml penicillin/50 µg/ml streptomycin). The cells were washed with PBS and lysed in lysis-buffer (1% Triton X-100, 20 mM Tris-HCl, 10 mM EDTA, pH 8.0), supplemented with proteinase inhibitors (CompleteMini, Roche Molecular Biochemicals). Aliquots of the lysates, corresponding to 10 µg protein, were dissolved in SDS sample buffer and subjected to reducing SDS-PAGE using 4-16% acrylamide gels. For immunoblotting, proteins were electrophoretically transferred onto polyvinylidene difluoride (PVDF) membranes (Amersham Pharmacia) and probed with anti-IR (Santa Cruz Biotechnology, sc-711), anti-SorCS1-leu and anti-β-actin (Sigma, AF5441) as a loading control. Bound antibodies were developed by SuperSignal West Pico reagent (Pierce) and a Fuji film LAS3000. Cell lines stably transfected with the different splice variants of SorCS1 showed elevated expression of the IR compared to CHO cells without SorCS1 expression (FIG. 12). To identify the cellular localisation of the elevated amount of IR in the SorCS1 transfected cells surface biotinylation were conducted. CHO cells and CHO cells stably expressing mSorCS1-B and mSorCS1-C were subjected to surface biotinylation using the membrane impermeable biotinylation reagent NHS-SS-biotin (Pierce). Confluent cell monolayers were washed in phosphate-buffered saline (PBS) and biotinylation was carried out using 0.5 mg/ml NHS-SS-biotin in PBS for 90 min at 4° C. with gentle shaking. After labeling, cells were washed twice with ice-cold PBS to remove the residual NHS-SS-biotin. Subsequently, cells were solubilized in lysis buffer (10 mM Tris-HCl, 150 mM NaCl, 1 mM EDTA, 1% nonidet P-40 (Sigma Aldrich) pH. 8) containing protease inhibitors (CompleteMini) by gently shaking on ice for approximately 10 min. The lysate were clarified by centrifugation at 14,000×g for 5 min at 4° C., 20 µl of the cleared lysate was saved (lysate fraction) and the rest of the lysate was incubated overnight with 100 µl of streptavidin-agarose beads (Sigma) at 4° C. with gentle agitation. After incubation, the lysate/beads mixture was separated by centrifugation at 14,000×g for 5 min at 4° C. The lysate fraction contains the intracellular proteins of the cells (Intra). The beads were washed twice with PBS and the captured biotinylated proteins (Bio) were eluted from the beads with 150 µl of SDS sample buffer. Finally, a portion of the biotinylated (Bio) (30 µl), the intracellular (Intra) (25 µl), and the crude lysates (Lysate) was subjected to SDS-PAGE and Western blot analysis using anti-IR (Santa Cruz Biotechnology, sc-711), anti-IR-pY (R&D systems, AF2507), anti-Glut4 (Abcam, ab654), and anti-β-actin (Sigma, AF5441) as a loading control. The elevated amount of the insulin receptor in SorCS1-B and SorCS1-C cells were located on the cell surface (in the Bio fraction), co-localising with a portion of the SorCS1 proteins (FIG. 13), indicating that SorCS1 regulates the expression of IR by physical interaction and/or by lowering the turn over of the IR protein.

Example 9

Demonstration of SorCS1:IR Complex Formation

To examine the potential physical interaction between SorCS1 and IR, CHO cell stably transfected with plasmids encoding SorCS1-B and -C and subsequently transiently transfected with $IR_A$ and $IR_B$ were used for immunoprecipitation. The cells were transfected with plasmids encoding $IR_A$ and $IR_B$ using the HiFect kit (Amaxa) according to the supplier's protocol. After two days of growth and at 80% confluency the cells were crosslinked with DSP (Peirce) and subsequently lysed. The cell lysates was incubated with antibody against IR (Santa Cruz Biotechnology, sc-711) bound to Gammabind beads (GE Healthcare). The precipitated complexes were eluted from the washed beads with SDS loading buffer and subjected to SDS-PAGE and Western blot analysis using anti-SorCS1-leu and anti-IR (Santa Cruz Biotechnology, sc-711). Western blot analysis revealed the presence of a SorCS1:IR complex (FIG. 11A). The direct interaction of the extracellular domains of SorCS1 and IR was also demonstrated using surface plasmon resonance (Biacore, Sweden) using CaHBS as standard running buffer (10 mM HEPES, pH 7.4, 140 mM NaCl, 2 mM $CaCl_2$, 1 mM EGTA, 0.005% tween-20). A biosensor chip from Biacore (CM5, cat.no. BR-1000-14) was activated using the NHS/EDC method as described by the supplier followed by coating with soluble IR (R&D systems, 28-956). Soluble SorCS1 showed strong binding to soluble insulin receptor with a $K_d$ estimated to approximately 5 nM (FIG. 11B).

Example 10

Analysis of SorCS1/IR Contact Sites Based on SPOT Synthesis

The co-immunoprecipitation and the Biacore experiments showed protein interaction at whole molecular level. However, the SPOT synthesis method is used to identify the protein interaction at amino acid level using a protein-derived scan of overlapping peptides either from SorCS1 or IR, thereby identifying small SorCS1 peptide agonists. The SPOT synthesis maps linear epitopes (protein chain involved in interaction) using overlapping peptides derived from the entire primary sequence of either human SorCS1-a (FIG. 23A) or human IR-β (FIG. 23B). In detail, the SorCS1 and IR sequence is fragmented and synthesized on cellulose with short overlapping peptides (15 amino acids in length and shifted by 3 amino acid) from C-terminus to N-terminus, which is subsequently probed for binding to the respective partner protein, IR-protein (histidine-tagged) (R&D systems, no1544-IR/CF) and soluble mouse SorCS1 protein ($I^{125}$-tagged). The binding assay is performed directly on the peptide membrane through immunodetection or radiography of bound protein. In detail, the membrane is washed 1×10 min in 96% ethanol, followed by 3×10 min wash with 1×TBS (500 mM Tris-HCl, 1500 mM NaCl), pH.8.0 and 3 hrs incubation in membrane blocking buffer (BB; 1× Blocking buffer (B6429, Sigma), 1×TBS, 5% sucrose). The blocked IR-membrane is incubated overnight with $I^{125}$-sol.SorCS1 (400.000 cpm/ml BB) and the SorCS1-membrane with his-IR (10 μg/ml BB). Both membrane are washed 3×10 min with 1×TBS. In FIG. 23A, the bound protein on the SorCS1 membrane was detected by immunodetection using primary antibody against the histidine tag, α-histidine (Invitrogen) (Mouse monoclonal) followed by an HRP-tagged secondary anti-mouse antibody (Sigma). Bound antibody was visualized by using the enhanced chemiluminescence (ECL) Western blotting Detection reagent (Amersham biosciences) and a Fuli film LAS1000. In FIG. 23B, the bound protein on the IR-membrane was detected by radiography as the membrane was exposed to a fuji image plate for 12 hrs, which was subsequently developed using a Fujifilm FLA3000. A specific signal (SPOT) indicates that the peptide interacts with the applied ligand. Linear binding epitopes are present in neighbouring peptides on the SPOT membrane and represent the binding site.

Example 11

Binding of Specific Peptides to Either SorCS1 or IR

The SPOT analysis identified synthetic SorCS1 or IR candidate peptides binding to their ligand protein (IR and SorCS1). The binding was further confirmed by surface plasmon resonance (Biacore, Sweden) analysis (FIG. 11B) using CaHBS as standard running buffer (10 mM HEPES, pH 7.4, 140 mM NaCl, 2 mM $CaCl_2$, 1 mM EGTA, 0.005% tween-20). A biosensor chip from Biacore (CM5, cat.no. BR-1000-14) was activated using the NHS/EDC method as described by the supplier followed by coating with soluble IR (R&D systems, 28-956). Full-length SorCS1 was tested for binding to IR by passage over the biosensor chip, showing a positive sigmoid binding curve, indicating direct interaction of soluble full-length extracellular part of SorCS1 with immobilized soluble insulin receptor (IR)

Example 12

Competition Studies. The Synthetic SorCS1 and IR Peptides that Bind to the ligands protein are used in competitions studies to establish their influence on the interaction between SorCS1 and IR in the SorCS1:IR complex. A biosensor chip from Biacore (CM5, cat.no. BR-1000-14) was activated using the NHS/EDC method as described by the supplier followed by coating with soluble IR (R&D systems, 28-956) or soluble SorCS1. The chips were incubated with samples of pure soluble SorCS1 or soluble IR (R&D systems, 28-956) (300 nM, 400 in the absence of competing peptide to determine the maximal binding capacity set to represent 100% binding (see example 11). In subsequent experiments, a similar amount of soluble SorCS1 or IR are injected to the ligand ship, but in the presence of competing peptides at different concentrations to determine their ability to diminish or destroy the interaction between SorCS1 and IR.

Example 13

Competition Studies

The synthetic SorCS1 and IR peptides that bind to the ligands protein are used in competitions studies in cells to establish their influence on the interaction between SorCS1 and IR in the SorCS1:IR complex. A) CHO cell stably transfected with plasmids encoding the different splice variants of SorCS1 and subsequently transiently transfected with $IR_A$ and $IR_B$ were used for immunoprecipitation. The cells are transfected with plasmids encoding IR using the Hifect kit (Amaxa) according to the supplier's protocol. The cells are grown two days in media without or with competing synthetic SorCS1 or IR peptide in different concentrations and at 80% confluency the cells are crosslinked with DSP and subsequently lysed. The cell lysates was incubated with antibody against IR (Santa Cruz Biotechnology, sc-711) bound to Gammabind beads (GE Healthcare). The precipitated complexes are eluted from the washed beads with SDS loading buffer and subjected to SDS-PAGE and Western blot analysis using anti-SorCS1-leu and anti-IR (Santa Cruz Biotechnology, sc-711). Western blot analyses are used to reveal the presence or absence of a SorCS1:IR complex, and thereby establish the ability of the synthetic peptide to diminish or destroy the interaction between SorCS1 and IR. B) Expression of endogene IR in the absence or presence of synthetic SorCS1 peptide(s) is examined in CHO cells and CHO cells stably transfected with the four murine SorCS1 splice variants (SorCS1-a,-b,-c,-d) and msol.SorCS1 (the extracellular part of SorCS1). The cells are grown to 80% confluency in serum-free HyQ-CCM5 CHO medium (HyClone) and in serum-free HyQ-CCM5 CHO medium supplemented with different concentration of synthetic SorCC1 peptide. The cells were washed with PBS and lysed in lysis-buffer and aliquots of the lysates are subjected to reducing SDS-PAGE and Western blot analysis using anti-SorCS1-leu and anti-IR (Santa Cruz Biotechnology, sc-711). Western blot analyses are used to reveal the influence of the synthetic SorCS1 peptide on the expression of IR in cells without or with stably expression of SorCS1, and thereby establish the ability of the synthetic peptide to diminish or destroy the up-regulation of IR in cells expressing SorCS1.

Example 14

Administering of Soluble SorCS1 or SorCS1 Peptides for the Treatment of Insulin Resistance The soluble domain of mouse SorCS1 peptide(s) able to bind to IR (see example 5) is expressed recombinantly at a large scale in a mammalian cell culture and is subsequently purified by for example immunoaffinity chromatography. The protein/peptid is administered by peritoneal, intraveneous, intramuscular or subcutaneous injection to e.g. SorCS1 knockout mice or another diabetic animal model showing insulin resistance (1 mg to 1 g/kg body weight each day or every week) in parallel with a wild type reference mouse. Good effect is obtained, and the same methods using human SorCS1 are applied for patient with insulin resistance.

Example 15

The Application of DNA Encoding Soluble SorCS1 or SorCS1 Peptides for the Treatment of Insulin Resistance Gene Therapy in a Clinical Setting Gene therapy is defined as the introduction of exogenous genetic material into cells or tissue in order to cure a disease or to avoid associated symptoms, in this case insulin resistance. The genetic material can be introduced into living cells/patients using different delivery methods/compounds: a) as naked therapeutic genetic molecules (DNA), where the genetic material itself is introduced directly into the tissue/patient (example 9), b) as specialized gene delivery vehicles, where the gene is inserted into different biological entities suited for gene delivery before introduction into the patient (example 10), and c) as virus, where the gene is inserted into a viral vector before introduction into the patient. Proteins might have a short life-time when introduced into the mouse or patient, so an additional treatment is applied were plasmid DNA encoding soluble SorCS1 or SorCS1 peptides are delivered to the SorCS1 knockout mice either by peritoneal injection, oral administration or injection directly into muscle or adipose tissue. The DNA encoding soluble SorCS1 or specific SorCS1 fragments are transcribed into protein in the organism restoring the level of SorCS1 and thereby treating the insulin resistance. The same method is used in humans lacking SorCS1 or showing insulin resistance treating the symptoms of the patient.

Example 16

The Application of Gene Delivery Vehicles Containing Soluble SorCS1 or Specific SorCS1 Fragments for the Treatment of Insulin Resistance To overcome any limitations of using plasmid DNA or adenovirus for expression of SorCS1 (soluble or specific fragments) specialized gene delivery vehicles (GDVs) are used which improve delivery efficiency and cell specificity whilst protecting against immune recognition. Several different GDVs will be produced: A) Strains of bacteria with desirable properties are transformed with plasmid cargo containing SorCS1 and amplified to generate GDVs. B) the phagemid, a modified bacterial plasmid with phage sequence within, is used as the cargo of SorCS1 and transformed into bacteria. The bacteria is infected with a replication-defective helper phage that produces essential gene for the packing of the phagemid vector into bacteriophage GDVs. C) Virus surface proteins are produced in cell culture and purified as capsid monomers. The genetic cargo containing SorCS1 is then packaged into a virion as the monomers are transferred to a buffer that promotes assembly of the virion. D) Erythrocytes are harvested from the patient and lysed to produce erythrocyte ghosts. The ghosts are then loaded, through osmotic pressure, with the genetic cargo containing SorCS1 before being reintroduced into the patients. E) Patients-derived primary cells are harvested and stimulated to produce exosomes, which are then purified and loaded, by electroporation, with the genetic cargo containing SorCS1 before being reintroduced into the patient.

Example 17

The Application of Adenovirus Expressing Soluble SorCS1 or Specific SorCS1 Fragments for the Treatment of Insulin Resistance Genetic material expressing soluble SorCS1 or specific peptides of SorCS1 is inserted into an adeno-associated viral vector. The adeno-associated viral vector is chosen because, unlike first-generation adenoviruses that contain a full complement of viral proteins, this vector encodes no viral proteins and has negligible toxicity. Furthermore, this virus gives prolonged and stable transgene (SorCS1) expression, which lower the need of repeated injection of virus to the patient. In detail, a DNA construct encoding either soluble SorCS1 or fragments of SorCS1 is inserted into an adeno-associated viral vector. The adeno-associated virus is together with a helper plasmid introduced into a cell culture and a large amount of adeno-associated virus produced. Finally, $1 \times 10^{11}$ adeno-associated virus particles is injected into SorCS1 knockout mice. The viral-expressed SorCS1 cures the insulin resistance of the knockout mice and the same method is used to treat patients with insulin resistance.

Example 18

Generation of Mouse Overexpressing SorCS1

For tissue-specific induction of SorCS1 expression in the mouse, an expression construct containing a CAAG promoter (chicken beta-actin/minimal CMV) upstream of a lox-STOP-lox cassette, followed by the cDNA of full-length SorCS1 (all splice variants) or soluble SorCS1 is introduced by homologous recombination into the ROSA gene locus. To drive expression, the stop cassette is excised by cross-breeding with transgenic mice that express Cre-recombinase in a tissue specific manner. Alternatively, recombinant virus expressing Cre may be subjected to the mice containing the CAAG promoter (chicken beta-actin/minimal CMV), lox-STOP-lox cassette, followed by the cDNA of full-length SorCS1 (all splice variants) or soluble SorCS1 to induce expression of full-length or soluble SorCS1, respectively. Thus, liver expression is achieved by injecting Cre-expressing adenovirus into e.g. the tail vein.

Example 19

Decreased Plasma Glucose Levels in Mice Overexpressing Soluble SorCS1

To examine the use of SorCS1 for treatment of insulin resistance, wild-type and SorCS1 knockout female mice were injected with an adenovirus over-expressing soluble SorCS1. The recombinant adenovirus for expression of human soluble SorCS1 (hsol.SorCS1) was generated as follows: pcDNA3.1/Zeo(-)/hsol.SorCS1 encoding the human soluble SorCS1 cDNA (amino acids 1-1100) was digested with Pme1 and Apa1 and the fragment encoding hsol.SorCS1 inserted into the shuttle plasmid pVQpacAd5CMVK-NpA (ViraQuest Inc, North Liberty, Iowa). ViraQuest Inc, North Liberty, Iowa, then used this shuttle plasmid for generation and propagation of adenovirus over-expressing hsol. SorCS1. Female SorCS1 knockout and wild-type mice 40 weeks of age were fasted overnight. In the morning, on day 0, blood samples were obtained by retroorbital bleeding and plasma glucose was measured immediately on an automatic monitor (Ascentia Contour from Bayer). The mice were subsequently injected in the tail vein with 2E9 pfu's of an adenoviral vector with either hsol. SorCS1 or LacZ as a negative control (from ViraQuest Inc, North Liberty, Iowa). On day 7, measurements of plasma glucose were repeated on overnight fasted mice to evaluate the effect of the SorCS1 and LacZ protein. As shown in FIG. 17, wild-type and SorCS1 knockout mice, which over-expressed soluble SorCS1 protein, exhibited a significant decrease in plasma glucose levels ($\approx$40%) both in. As expected, a significant decrease in glucose levels was not observed in mice that received the LacZ control virus.

Example 20

Expression and Phosphorylation of IR and Expression of Glut4 in SorCS1 Knockout Mice Over-Expressing Soluble SorCS1

To further examine the effect of SorCS1 on insulin resistance, the expression of insulin receptor (IR), phosphorylation of IR and the expression of glucose transporter type 4 (Glut4) was determined in mice overexpressing SorCS1. Female SorCS1 knockout (-/-) mice 40 weeks of age were injected with an adenoviral vector expressing either hsol. SorCS1 or LacZ as a negative control (see example 19). On day 12 after virus injection, the mice were fasted overnight, injected intraperitoneally with insulin (Novorapid, Novo Nordisk A/S) (10 units/kg body weight) in sterile saline, and killed 15 min later. Muscle and adipose tissue were removed and homogenized in lysis buffer THE-buffer (10 mM Tris-HCl, 150 mM NaCl, 1 mM EDTA, 1% nonidet P-40, pH. 8) containing protease inhibitors (Complete Mini, Roche) and phosphatase inhibitors (cocktail 1, Sigma Aldrich). The lysates were cleared by centrifugation 10 min at 10.000×g, and protein concentration were determined by Bio-Rad Protein Assay. Equal amount of total protein (50 μg) for different samples were separated on a 4-12% Bis-tris gel (Nupage, Invitrogen) and transferred onto polyvinylidene difluoride (PVDF) membranes (Amersham Pharmacia). Membranes were analysed by western blotting with anti-IR (Santa Cruz Biotechnology, sc-711), anti-IR-pY (R&D systems, AF2507) and anti-Glut4 (Abcam, ab654). Bound antibodies were developed by Super-Signal West Pico reagent (Pierce) and a Fuji film LAS3000. Elevated amounts of IR, phosphorylated IR (IR-pY) and glut4 were observed in both muscle (FIG. 18A) and adipose (FIG. 18B) tissue from SorCS1 knockout mice over-expressing soluble SorCS1 when compared to mice expressing the LacZ control protein, suggesting increased insulin sensitivity in mice overexpressing SorCS1.

Example 21

Decreased Plasma Glucose and Insulin Levels in Diabetic Db/Db Female Mice Over-Expressing Soluble SorCS1

Figure 19:
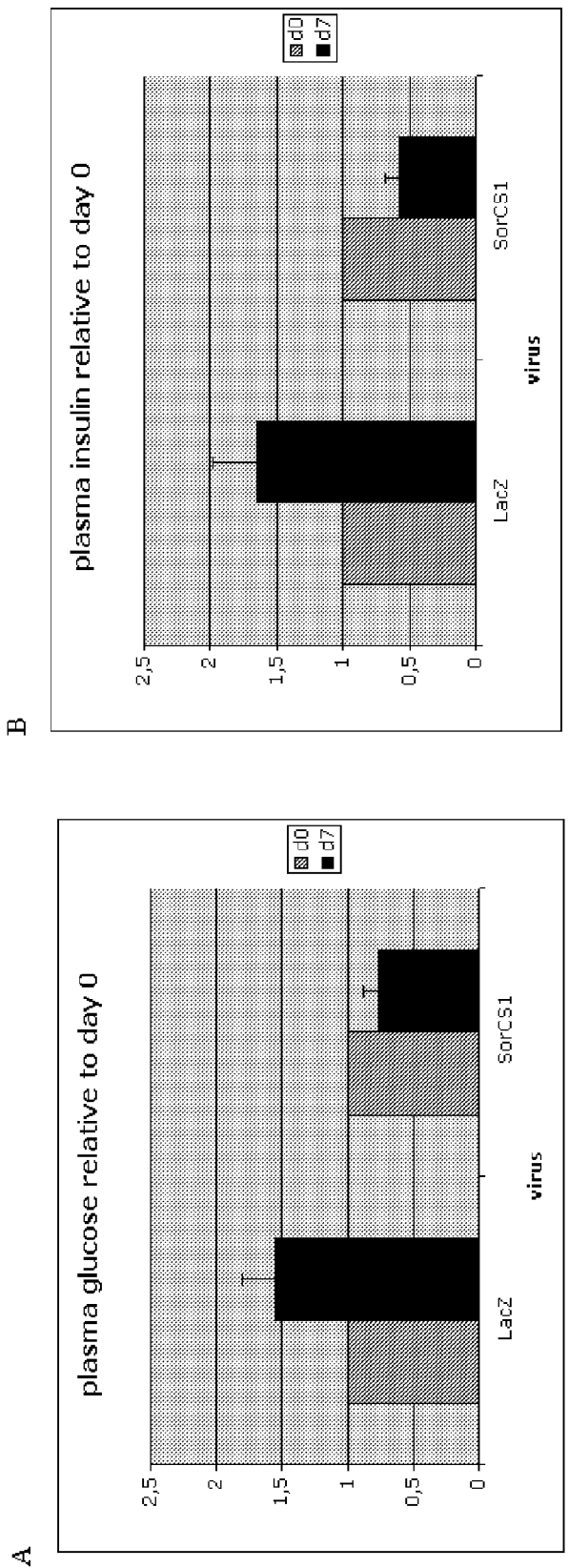

To evaluate the effect of soluble SorCS1 in an obese mouse model that spontaneously develops type 2 diabetes we used the db/db mouse strain (BKS.Cg-m+/+Lpr$^{db}$/BomTac from Taconic). These mice lack the leptin receptor consequently the mice become obese and develop insulin resistance and finally severe diabetes at the age of 6-8 weeks. To examine the effect on plasma glucose and insulin levels, mice were injected with adenovirus expressing either hsol.SorCS1 or LacZ as a control (see example 13). In detail, db/db female mice 10 weeks of age were fasted overnight. In the morning, on day 0, the mice were anesthetized with diethyl ether and blood samples were obtained by retroorbital bleeding. Blood glucose was measured immediately on an automatic monitor (Ascentia Contour from Bayer), whereas plasma insulin levels were determined using an ultrasensitive mouse insulin enzyme-linked immunoabsorbent assay kit (DRG Diagnostics). Thereafter the mice were injected in the tail vein with 2E9 pfu's of an adenoviral vector with either hsol.SorCS1 or LacZ (from ViraQuest Inc, North Liberty, Iowa) as a negative control virus. On day 7, measurements of blood glucose and plasma insulin were repeated on overnight fasted mice to evaluate the effect of the SorCS1 and LacZ protein. Data shown in FIG. 19 are means±SEM for 5 mice in each group. On day 7, db/db female mice with over-expression of soluble SorCS1 exhibited a significant decrease in blood glucose ($\approx$35%) compared to the mice that received the control LacZ virus (FIG. 19A). Furthermore, on day 7 there was also a significant decrease in the plasma insulin levels in the db/db female mice over-expressing soluble SorCS1 compared to mice that express the control virus (FIG. 19B). Thus, over-expression of soluble SorCS1 improves the diabetic status in the type 2 diabetic (db/db) mouse model.

Example 22

Glucose Tolerance Test in Diabetic Db/Db Female Mice with Over-Expression of Soluble SorCS1

To examine the effect of SorCS1 on glucose tolerance, female db/db mice injected with adenoviruses expressing either soluble SorCS1 or LacZ (see example 13) where on day 3 fasted over-night (16 hrs). On day 4 the mice were injected intraperitoneally with a bolus of glucose (2 mg/g body weight) in sterile saline. The animals were anesthetized with diethyl ether and blood samples were obtained by retroorbital bleeding at times 0, 15, 30, 90, and 150 minutes after injection. Blood glucose levels were measured immediately after sampling on an automatic monitor (Ascentia Contour from Bayer). Data shown in FIG. 20 are means±SEM for 5 mice in each group. The results in FIG. 20 show that over-expression of soluble SorCS1 renders the mice more sensitive to insulin as the level of blood glucose becomes normal (i.e. the same as before glucose injection) after 150 min. By contrast, the blood glucose level in mice expressing the control protein LacZ remains elevated during the 150 minutes. In conclusion, these results show that db/db female mice over-expressing soluble SorCS1 are less insulin resistant.

Example 23

Plasma Glucose and Insulin Levels in Diabetic Db/Db Male Mice Over-Expressing Soluble SorCS1

Figure 21:
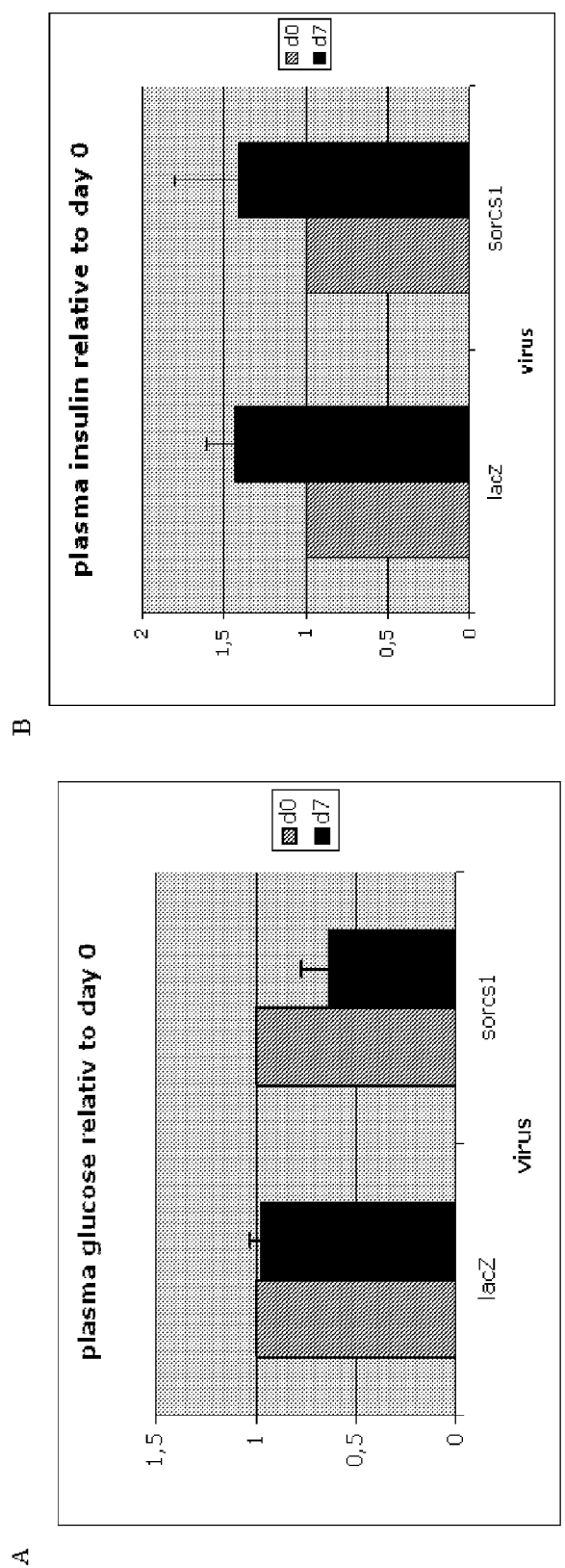

To evaluate the effect of soluble SorCS1 in an obese mouse model that spontaneously develops type 2 diabetes, we used the db/db mouse strain (BKS.Cg-m+/+Lpr$^{db}$/BomTac from Taconic). Mice were injected with adenovirus expressing either hsol.SorCS1 or LacZ as a control (see example 13), to examine the effect on plasma glucose and insulin levels. In detail, db/db male mice 6 weeks of age were fasted overnight. In the morning, on day 0, the mice were anesthetized with diethyl ether and blood samples were obtained by retroorbital bleeding. Blood glucose was measured immediately on an automatic monitor (Ascentia Contour from Bayer), whereas plasma insulin levels were determined using an ultrasensitive mouse insulin enzyme-linked immunoabsorbent assay kit (DRG Diagnostics). The mice were subsequently injected in the tail vein with 2E9 pfu's of an adenoviral vector with either hsol.SorCS1 or LacZ (from ViraQuest Inc, North Liberty, Iowa) as a negative control. On day 7, measurements of blood glucose and plasma insulin were repeated on overnight fasted mice to evaluate the effect of the SorCS1 and LacZ protein. The data shown in FIG. 21 are means±SEM for 5 mice in each group. On day 7, db/db male mice with over-expression of soluble SorCS1 exhibited a significant decrease in blood glucose (≈35%) compared to the mice that received the control LacZ virus (FIG. 21A). Because the decline in glucose levels were not accounted by an increased insulin concentration in mice overexpressing SorCS1 (FIG. 21B), we conclude that over-expression of soluble SorCS1 improves the diabetic status in male type 2 diabetic db/db mice.

Example 24

Subcellular Localization of Glut4 in Muscle Tissue from Db/Db Male Mice Over-Expressing Soluble SorCS1

To evaluate if over-expression of soluble SorCS1 might change the distribution of Glut4 we conducted subcellular fractionation on muscle tissue from db/db male mice over-expressing soluble SorCS1. In detail, db/db male mice 6 weeks of age were injected in the tail vein with an adenoviral vector expressing either hsol.SorCS1 or LacZ as a control (see example 13). On day 7 after virus injection, the mice were fasted overnight, injected intraperitoneally with insulin (Novorapid, Novo Nordisk A/S) (10 units/kg body weight) in sterile saline, and killed 15 min later. Muscle tissue from 5 mice injected with the same virus was removed, pooled and transferred to 5 ml of HEPES-buffered sucrose (0.25 M sucrose, 1 mM EDTA, 20 mM HEPES-KOH, pH. 7.4), homogenized by 10 strokes up and down using a Teflon pestle, and centrifuged at 1000×g for 10 min. Thus, heavy mitochondrial, light mitochondrial, and microsomal fraction were obtained by several round of centrifugation. First, the supernatant was centrifuged at 3.000×g for 10 min, then the resulting supernatant was centrifuged at 16.000×g for 10 min, and finally the resulting supernatant was centrifuged a 100.000×g for 45 min giving a pellet containing the microsomal fraction. The microsomal fractions were resuspended in 0.5 ml HEPES-buffered solution and subjected to sucrose (velocity) gradient centrifugation. The 0.5 ml microsomal samples were loaded onto a 12 ml linear 0.8 M to 1.6 M sucrose gradient in 1 M HEPES, pH 7.2, and centrifuged 18 h in a swinging bucket rotor (SW41 Ti) at 84.000×g. Each gradient was separated into 24 fractions starting from the top of the tube. Finally, gel electrophoresis and Western blotting analyzed the expression of Glut4 in the different fractions. The results in FIG. 22 show that the sedimentation distribution of Glut4 in muscle tissue over-expressing SorCS1 (lower panel) is different from muscle tissue expressing the control protein LacZ (upper panel). Thus, over-expression of soluble SorCS1 in db/db male mice may change the distribution of Glut4 and thereby modulate glucose uptake.

Example 25

Gene Expression Profiling of Adipose Tissue from SorCS1 Knockout Mice by PCR Arrays To examine the gene expression profile of SorCS1 knockout mice, the expression of 84 genes related to the mouse insulin signalling pathway and 84 genes related to mouse lipoprotein signalling & cholesterol metabolism was determined using microarray analysis. The microarray analyses were performed using RNA from adipose tissue of SorCS1 knockout wild-type adipose mice. In practice, first strand cDNA was synthesized from total RNA (Applied Biosystems) from SorCS1 knockout (−/−) and wild-type (+/+) adipose tissue from female mice 50 weeks of age (n=3). The superarray of Mouse Insulin Signalling Pathway (PAMM-030A RT2 Profiler PCR arrays) or B) the type Mouse Lipoprotein Signalling & Cholesterol Metabolism (PAMM-080-A RT2 Profiler PCR arrays) were processed using an ABI7900 platform (Applied Biosystems) and SYBR Green/Rox PCR (SABiosciences). AROS Applied Biotechnology, Aarhus, Denmark, did the expression analyses. Genes showing an expression more than 3 times up- or down-regulated in the SorCS1 knockout mice when compared to wild-type mice are listed in the upper tables and their known functions are indicated in the table below. The data in FIGS. 24A and 24B shows that the expression of several genes are changed in the SorCS1 knockout mice compared to the wild-type mice, indicating that insulin and cholesterol signalling pathways and metabolism are altered in SorCS1 knockout mice.

Example 26

Reduced Weight in Diabetic Db/Db Mice after Over-Expression of Soluble SorCS1

To evaluate the effect of soluble SorCS1 on weight in an obese mouse model that spontaneously develops type 2 diabetes, we used the db/db mouse strain (BKS.Cg-m+/+Lpr$^{db}$/BomTac from Taconic). These mice lack the leptin receptor and consequently the mice become obese and develop insulin resistance and finally severe diabetes at the age of 6-8 weeks. We injected adenovirus expressing either human soluble (hsol.) SorCS1 or LacZ as a control (as described in FIGS. 17A and 17B), to examine the effect on weight. In detail, db/db female mice 6 weeks of age were injected in the tail vein with 2E9 pfu's of an adenoviral vector with either hsol.SorCS1 or LacZ (from ViraQuest Inc, North Liberty, Iowa) as a negative control virus. In the morning, on day 0, 9, 14 and day 16, the mice were weighed on a scale. Data are means±SEM for 5 mice in each group. On day 9 to 16, the db/db female mice with over-expression of soluble SorCS1 exhibited a significant decrease in weight compared to the mice that received the control LacZ virus. Thus, over-expression of soluble SorCS1 improves the obese status in this obese mouse model. The results are illustrated in FIG. 25.

Example 27

Reduced Food Intake and Weight in Diabetic Db/Db Mice after Over-Expression of Soluble SorCS1

To evaluate the effect of soluble SorCS1 on weight in an obese mouse model that spontaneously develops type 2 diabetes, we used the db/db mouse strain (BKS.Cg-m+/+Lpr$^{db}$/BomTac from Taconic). These mice lack the leptin receptor and consequently the mice become obese and develop insulin resistance and finally severe diabetes at the age of 6-8 weeks. We injected adenovirus expressing either hsol.SorCS1 or LacZ as a control (see FIG. 17), to examine the effect on weight. In detail, db/db female mice 6 weeks of age were injected in the tail vein with 2E9 pfu's of an adenoviral vector with either hsol.SorCS1 or LacZ (from ViraQuest Inc, North Liberty, Iowa) as a negative control virus. A) In the morning of day 9 after virus treatment each mouse was moved to a metabolic cage with a measured amount of food. 24 hours later the mouse was moved back to a normal mouse cage and the food in the metabolic cage was weighed to determine the food intake. The amount of ingested food over 24 hours is shown in FIG. 26. Data are means±SEM for 4 mice in each group. Mice with over-expression of soluble SorCS1 ate significantly less than the control mice expressing LacZ. B) In the morning, on day 0 and 11 after virus treatment, the mice were weighed on a scale. The relative weight changes over the time period are shown. Data are means±SEM for 4 mice in each group. On day 11, the db/db female mice with over-expression of soluble SorCS1 exhibited a significant decrease in body weight compared to the mice that received the control LacZ virus. The results are illustrated in FIG. 26.

Example 28

Administering of Soluble SorCS1 or SorCS1 Peptides for the Treatment of Obesity

The soluble domain of mouse SorCS1 peptide(s) which is capable of binding to IR (see example 9 and 11) is expressed recombinantly in large scale, in a mammalian cell culture and is subsequently purified by for example immune-affinity chromatography. The protein or peptide is administered by peritoneal, intravenous, intramuscular or subcutaneous injection to e.g. an obese animal model (ob/ob or db/db mouse model) showing massive obesity (1 mg to 1 g/kg body weight each day or every week) in parallel with a wild type reference mouse. Good effect is obtained, and the same methods using human SorCS1 are applied for patients with obesity.

Example 29

Studies in Isolated Primary Adipocytes from Obese Mice

Primary cultures of adipocytes are isolated from obese mice (db/db or ob/ob) and treated with soluble SorCS1 or a control protein (delivered either as a virus or directly as a protein). Morphology and amount of adipokines are studied, and tested for $^3$H-glucose uptake in the different cell lines. Studies are undertaken of the insulin receptor and GLUT4 (stability, subcellular location, turnover), intracellular signaling cascades, and differentiation of primary cultures of adipocytes.

Example 30

Expression of Different Variants of SorCS1 in Human Adipose Tissue

Expression of SorCS1 polymorphisms and splice variants are investigated using quantitative PCR in adipose tissue from humans with obesity and/or type II diabetes.

Example 31

Fat Distribution in Obese Mice Treated with SorCS1 Using NMRI

Fat distribution is investigated in obese mice treated with either soluble SorCS1 or a control protein (delivered either as a virus or directly as a protein). The investigation is undertaken using NMR imaging (e.g. Siemens 3 Tesla or a custom-build 7 Tesla scanner available at the Department of Chemistry, Aarhus University, Denmark.

Example 32

Screening Assay for Identification of Active Polypeptides

The present assay is used to identify SorCS1 like agents having similar activity as the agents tested herein above. Such SorCS1 like agents include but is not limited to the other Vps10p-D receptors Sortilin (SEQ ID NO: 52), SorLA (SEQ ID NO: 53), SorCS2 (SEQ ID NO: 54) and SorCS3 (SEQ ID NO: 55).

Expression vectors containing nucleic acid sequences encoding candidate polypeptides such as fragments of sortilin, SorLA, SorCS2 and SorCS3 or other polypeptide and transfected into NIH 3T3-L1 mouse embryonic fibroblast cells. The pre-adipocyte 3T3-L1 cells differentiate into mature adipocytes when cultured in the presence of 0.5 M methylisobutylxanthine, 1 µM dexamethasone, 5 µg/ml insulin and 10% fetal bovine serum for 2 days. Cells are fed every 2 days with standard media without any additive for about 10 days. At that time, lipid droplets are visible by phase-contrast microscopy and the amount of the lipid droplets are measured and quantified to find the effect of the peptide on fat deposits and obesity development. Furthermore, Western Blot using antibodies against different differentiation markers, such as CCAAT/enhancer-binding proteins (C/EBPs) and peroxisome proliferator-activated receptors (PPARs), measures the effect of the different peptides on differentiation of the fibroblast into mature adipocytes. Peptide fragments having an effect on the adipocytes differentiation and fat deposits are then used for the mice studies as outlined in example 32.

Example 33

Investigation of Similar Effect of Other Vps10p Domain Receptors on Fat Distribution, Food Intake and Weight Development To examine the effect of peptide fragments of sortilin (SEQ ID NO: 52), SorLA (SEQ ID NO: 53), SorCS2 (SEQ ID NO: 54) and SorCS3 (SEQ ID NO: 55) on weight gain and food intake, female db/db mice are injected with adenoviruses expressing either soluble peptide fragments of a candidate polypeptide such as sortilin/SorLA/SorCS2/SorCS3 or LacZ (see example 27). In detail, db/db female mice 6 weeks of age are injected in the tail vein with 2E9 pfu's of an adenoviral vector with either of the above mentioned VPS10P domain receptor fragments (which are found to have an effect on 3T3-L1 cells in example 31) or LacZ (from ViraQuest Inc, North Liberty, Iowa) as a negative control virus. In the morning of day 9 after virus treatment each mouse is moved to a metabolic cage with a measured amount of food. 24 hours later the mouse is moved back to a normal mouse cage and the food in the metabolic cage is weighed to determine the food intake. In the morning, on day 0 and 11 after virus treatment, the mice is weighed on a scale. The relative weight changes over the time period are measured. Fat distribution in the body in the mice is determined as described in example 30 using NMRI and an evaluation of the candidate polypeptide as a drug is performed.

REFERENCES

1. P. Zimmet et al. (2005) The metabolic syndrome: A global public health problem and a new definition. *J. Arthero. Thromb.* 12(6) pp. 295-300
2. K. Srinivasan and P. Ramarao (2007) Animal models in type 2 diabetes research: An overview. *Indian J. Med. Res.* 125, pp 451-472
3. L. Plum et al. (2004) Transgenic and knockout mice in diabetes research: Novel insights into pathophysiology, limitations, and perspectives. *Physiology* 20 pp. 152-61
4. P. C. Champe and R. A. Harvey (2005) Diabetes Mellitus. *Biochemistry* 3$^{rd}$ Chapter 25
5. M. A. Herman and B. B. Kahn (2006) Glucose transport and sensing in them maintenance of glucose homeostasis and metabolic harmony. *J. Cli. Invest.* 116 pp. 1767-75 *Pharm. Res.* 57 pp 6-18
6. S. Koren and G. Fantus (2007) Inhibition of the protein tyrosine phosphatase PTP1B: potential therapy for obesity, insulin resistance and type-2 diabetes mellitus. *Prac. Res. Clin. Endo. Meta.* 21(4) pp 621-640
7. J. C. Hou and J. E. Pessin (2007) Ins (endocytosis) and outs (exocytosis) of GLUT4 trafficking. *Cur. Opin. Cell. Biol.* 19 pp 466-473
8. T. E. Graham and B. B. Kahn (2007) Tissue-specific alterations of glucose transport and molecular mechanisms of intertissue communication in obesity and type 2 diabetes. *Horm. Metab. Res.* 39 pp 717-721
9. C. Guerra et al. (2001) Brown adipose tissue-specific insulin receptor knockout shows diabetic phenotype without insulin resistance. *J. Clin. Invest.* 108(8) pp 1205-1213
10. G. Hermey et al. (1999) Identification and characterization of SorCS, a third member of a novel receptor family. *Biochem. Biophys. Res. Commun.* 266(2) pp. 347-51
11. A. Nykjaer et al. (2004) Sortilin is essential for proNGF-induced neuronal death. *Nature* 427(6977) pp. 843-8
12. O. M. Andersen et al. (2005) Neuronal sorting protein-related receptor SorLA/LR11 regulates processing of the amyloid precursor protein. *Proc. Natl. Acad Sci. USA.* 102 (38) pp. 13461-13466
13. N. J. Morris et al. (1998) Sortilin is the major 110-kDa protein in GLUT4 vesicles from adipocytes. *J. Biol. Chem.* 273(6) pp. 3582-7
14. J. Shi and V. Kandror (2005) Sortilin is essential and sufficient for the formation of Glut4 storage vesicles in 3T3-L1 adipocytes. *Dev. Cell* 9 pp 99-108
15. G. Hermey and H. C. Schaller (2000) Alternative splicing of murine SorCS leads to two forms of the receptor that differ completely in their cytoplasmic tails. *Biochim. Biophys. Acta.* 1491(1-3) pp. 350-54
16. G. Hermey et al. (2003) Characterization of SorCS1, an alternatively spliced receptor with completely different cytoplasmic domains that mediate different trafficking in cells. *J. Biol. Chem.* 278 pp. 7390-96
17. M. S. Nielsen et al. (2008) Different motifs regulate trafficking of SorCS1 isoforms. *Traffic* 9 pp. 980-94
18. S. M. Clee et al. (2006) Positional of SorCS1, a type 2 diabetes quantitative trait locus. *Nature genetics* 6 pp. 688-93
19. M. O. Goodarzi et al. (2007) SorCS1: A novel human type 2 diabetes susceptibility gene suggested by the mouse. *Diabetes* 56(7) pp. 1922-9
20. WO 2004/022719 (Attie et al.)

OVERVIEW OF SEQUENCES

SEQ ID NO 1: *Homo sapiens* preproSorCS1b (Isoform 1)
SEQ ID NO 2: *Homo sapiens* preproSorCS1 (Isoform 2)
SEQ ID NO 3: *Homo sapiens* preproSorCS1c (Isoform 3)
SEQ ID NO 4: *Homo sapiens* preproSorCS1a (Isoform 4)
SEQ ID NO 5: Soluble *Homo sapiens* preproSorCS1
SEQ ID NO 6: *Homo sapiens* proSorCS1b (Isoform 1)
SEQ ID NO 7: *Homo sapiens* proSorCS1 (Isoform 2)
SEQ ID NO 8: *Homo sapiens* proSorCS1c (Isoform 3)
SEQ ID NO 9: *Homo sapiens* proSorCS1a (Isoform 4)
SEQ ID NO 10: Soluble *Homo sapiens* proSorCS1
SEQ ID NO 11: *Homo sapiens* mature SorCS1b (Isoform 1)
SEQ ID NO 12: *Homo sapiens* mature SorCS1 (Isoform 2)
SEQ ID NO 13: *Homo sapiens* mature SorCS1c (Isoform 3)
SEQ ID NO 14: *Homo sapiens* mature SorCS1a (Isoform 4)
SEQ ID NO 15: Soluble *Homo sapiens* mature SorCS1
SEQ ID NO 16: Mouse preproSorCS1b (isoform 1)
SEQ ID NO 17: Mouse preproSorCS1a (isoform 2)
SEQ ID NO 18: Mouse preproSorCS1c (isoform 3)
SEQ ID NO 19: Mouse preproSorCS1c+(isoform 4)
SEQ ID NO 20: Mouse preproSorCS1d
SEQ ID NO 21: Soluble mouse preproSorCS1
SEQ ID NO 22: Mouse proSorCS1b (isoform 1)
SEQ ID NO 23: Mouse proSorCS1a (isoform 2)
SEQ ID NO 24: Mouse proSorCS1c (isoform 3)
SEQ ID NO 25: Mouse proSorCS1c+(isoform 4)
SEQ ID NO 26: Mouse proSorCS1d
SEQ ID NO 27: Soluble mouse proSorCS1
SEQ ID NO 28: Mouse mature SorCS1b (isoform 1)
SEQ ID NO 29: Mouse mature SorCS1a (isoform 2)
SEQ ID NO 30: Mouse mature SorCS1c (isoform 3)
SEQ ID NO 31: Mouse mature SorCS1c+(isoform 4)
SEQ ID NO 32: Mouse mature SorCS1d
SEQ ID NO 33: Soluble mouse mature SorCS1
SEQ ID NO 34: Chimpanzee preproSorCS1
SEQ ID NO 35: Chimpanzee proSorCS1
SEQ ID NO 36: Chimpanzee mature SorCS1
SEQ ID NO 37: Chimpanzee soluble SorCS1
SEQ ID NO 38: Dog mature SorCS1
SEQ ID NO 39: Dog soluble SorCS1
SEQ ID NO 40: Cow preproSorCS1
SEQ ID NO 41: Cow proSorCS1
SEQ ID NO 42: Cow mature SorCS1
SEQ ID NO 43: Cow soluble SorCS1
SEQ ID NO 44: Rat preproSorSC1
SEQ ID NO 45: Rat proSorCS1
SEQ ID NO 46: Rat mature SorCS1
SEQ ID NO 47: Rat soluble SorCS1
SEQ ID NO 48: Chicken preproSorCS1
SEQ ID NO 49: Chicken proSorCS1
SEQ ID NO 50: Chicken mature SorCS1
SEQ ID NO 51: Chicken soluble SorCS1
SEQ ID NO 52: *Homo sapiens* Sortilin
SEQ ID NO 53: *Homo sapiens* SorLA SEQ ID NO 54: *Homo sapiens* SorCS2
SEQ ED NO 55: *Homo sapiens* SorCS3
SEQ ID NO 56: *Homo sapiens* Human Insulin Receptor (IR)

SorCS1 (ex24), forward primer
SEQ ID NO: 57
5'-AAGTCTCTGCTGGGAACGCCATACTGCAAG-3

SorCS1 (ex24), reverse primer
SEQ ID NO: 58
5'-GTGGACAAGAACTTGGACGCCAGGCTTCAG-3

SorCS1-a (ex25), forward primer
SEQ ID NO: 59
5'-AAGTCTCTGCTGGGAACGCCATACTGCAAG-3

SorCS1-a (ex25), reverse primer
SEQ ID NO: 60
5'-TATTGCTTCTGAACCTGGCAGAAAGAGGAG-3'

SorCS1-b (ex27), forward primer
SEQ ID NO: 61
5'-AAGTCTCTGCTGGGAACGCCATACTGCAAG-3

SorCS1-b (ex27), reverse primer
SEQ ID NO: 62
5'-GCTTTGGCGATGAAGGTGGAGTTGCTGGCT-3'

SorCS1-c (ex26), forward primer
SEQ ID NO: 63
5'-AAGTCTCTGCTGGGAACGCCATACTGCAAG-3

SorCS1-c (ex26), reverse primer
SEQ ID NO: 64
5'-CAGGGTGAGGGACACTGGGCCTGCTTTCAG-3

SorCS1-d (ex28), forward primer
SEQ ID NO: 65
5'-AAGTCTCTGCTGGGAACGCCATACTGCAAG-3

SorCS1-d (ex28), reverse primer
SEQ ID NO: 66
5'-CGGATCTCTTGGAACTGAAGTTACAGATGCTTG-3

The invention claimed is:

1. A method of treatment of obesity and/or promoting weight loss in a subject, said method comprising administering to an individual in need thereof a therapeutically effective amount of an isolated soluble Vps10p domain-containing receptor SorCS1 (SorCS1) polypeptide selected from the group consisting of
   (i) an amino acid sequence consisting of SEQ ID NO: 15; and
   (ii) a biologically active mammalian homolog of the amino acid sequence of wherein the homolog has at least 90% sequence identity to said SEQ ID NO: 15, and wherein said homolog competes for binding with the polypeptide of (i) to a SorCS1 binding site of an insulin receptor.

2. The method according to claim 1, wherein said polypeptide consists of an amino acid sequence selected from the group consisting of: SEQ ID NOs: 5, 10, 21, 27, 33, 37, 39, 43, and 47.

3. The method according to claim 1, wherein any amino acid specified in the sequence of a homolog is altered to provide a conservative substitution.

4. The method according to claim 1, wherein said polypeptide has at least 98% sequence identity to SEQ ID NO: 15.

5. The method according to claim 1, wherein said polypeptide has at least 99% sequence identity to SEQ ID NO: 15.

6. The method according to claim 1 wherein the polypeptide is glycosylated.

7. The method according to claim 6, wherein the polypeptide is glycosylated in amino acid residue positions corresponding to 74, 242, 323, 655, 666, 706, 737, 798 and 819 of SEQ ID NO: 15.

8. The method according to claim 1, wherein the polypeptide is capable of forming at least one intramolecular cysteine bridge.

9. The method according to claim 1, comprising a dimer of said polypeptide linked through at least one intermolecular cysteine bridge.

10. The method according to claim 1, wherein said polypeptide further comprises an affinity tag, such as a polyhis tag, a GST tag, a HA tag, a Flag tag, a C-myc tag, a HSV tag, a V5 tag, a maltose binding protein tag, a cellulose binding domain tag.

11. The method of claim 1, wherein said individual is suffering from insulin resistance and/or diabetes mellitus type 2.

12. The method of claim 11 wherein the agent is administered as a pharmaceutical composition further comprising a pharmaceutically acceptable carrier.

13. The method of claim 12 wherein the pH of the composition is between pH 4 and pH 10.

14. The method of claim 13, wherein the injection is intravenous, intramuscular, intraspinal, intraperitoneal, subcutaneous, a bolus or a continuous administration.

15. The method of claim 13, wherein administration occurs at intervals of 30 minutes to 24 hours, such as at intervals of 1 to 6 hours.

16. The method of claim 12 wherein the composition is formulated for administration by injection, suppository, oral administration, sublingual tablet or spray, cutaneous administration or inhalation or for local administration by implantation.

17. The method of claim 11, wherein the duration of the treatment is from 6 to 72 hours.

18. The method of claim 11, wherein the duration of the treatment is lifelong.

19. The method of claim 11, wherein the dosage of the active ingredient is between 10 μg to 500 mg per kg body mass.

* * * * *